US009090889B2

(12) United States Patent
Nunn, Jr. et al.

(10) Patent No.: US 9,090,889 B2
(45) Date of Patent: Jul. 28, 2015

(54) XYLOSE ISOMERASES AND THEIR USES

(71) Applicants: David Neal Nunn, Jr., Carlsbad, CA (US); Peter Luginbuhl, San Diego, CA (US); Ling Li, San Diego, CA (US); Adam Martin Burja, San Diego, CA (US); Jon Peter Flash Bartnek, San Diego, CA (US)

(72) Inventors: David Neal Nunn, Jr., Carlsbad, CA (US); Peter Luginbuhl, San Diego, CA (US); Ling Li, San Diego, CA (US); Adam Martin Burja, San Diego, CA (US); Jon Peter Flash Bartnek, San Diego, CA (US)

(73) Assignee: BP Corporation North America Inc., Houston, TX (US)

( * ) Notice: Subject to any disclaimer, the term of this patent is extended or adjusted under 35 U.S.C. 154(b) by 0 days.

(21) Appl. No.: 13/948,956

(22) Filed: Jul. 23, 2013

(65) Prior Publication Data

US 2014/0186884 A1 Jul. 3, 2014

Related U.S. Application Data

(60) Provisional application No. 61/675,241, filed on Jul. 24, 2012.

(51) Int. Cl.

| | |
|---|---|
| ***C12N 9/90*** | (2006.01) |
| ***C12Q 1/14*** | (2006.01) |
| ***C12P 7/16*** | (2006.01) |
| ***C12P 17/18*** | (2006.01) |
| ***C12P 35/06*** | (2006.01) |
| ***C12P 7/06*** | (2006.01) |
| ***C12P 7/18*** | (2006.01) |
| ***C12P 7/20*** | (2006.01) |
| ***C12P 7/40*** | (2006.01) |
| ***C12P 7/64*** | (2006.01) |
| ***C12P 13/04*** | (2006.01) |
| ***C12N 9/92*** | (2006.01) |

(52) U.S. Cl.

CPC .. *C12N 9/90* (2013.01); *C12N 9/92* (2013.01); *C12P 7/06* (2013.01); *C12P 7/16* (2013.01); *C12P 7/18* (2013.01); *C12P 7/20* (2013.01); *C12P 7/40* (2013.01); *C12P 7/649* (2013.01); *C12P 13/04* (2013.01); *C12P 17/184* (2013.01); *C12P 35/06* (2013.01); *C12Y 503/01005* (2013.01); *C12P 2203/00* (2013.01); *Y02E 50/10* (2013.01); *Y02E 50/13* (2013.01); *Y02E 50/16* (2013.01); *Y02E 50/17* (2013.01); *Y02E 50/343* (2013.01)

(58) Field of Classification Search

None

See application file for complete search history.

(56) References Cited

U.S. PATENT DOCUMENTS

2012/0142067 A1 6/2012 Desfourgadas et al.

FOREIGN PATENT DOCUMENTS

| | | |
|---|---|---|
| CN | 102 174 549 | 9/2011 |
| WO | WO 03/062430 | 7/2003 |
| WO | WO 2009/109634 | 11/2009 |
| WO | WO 2010/074577 | 7/2010 |
| WO | WO 2011/090731 | 7/2011 |

OTHER PUBLICATIONS

Accession AEL74969. Aug. 10, 2011.*

Chica et al. Curr Opin Biotechnol. Aug. 2005;16(4):378-84.*

Sen et al. Appl Biochem Biotechnol. Dec. 2007;143(3):212-23.*

Ethanol Production Related Xylose Isomerase, XP002714606 Nov. 10, 2011, 1 page.

Sequence 18 from Patent WO 2010/074577, XP002714607 Aug. 3, 2010, 1 page.

Sequence 19 from Patent WO 2010/074577, XP002714608, Aug. 3, 2010, 1 page.

Sequence 20 from Patent WO 2010/074577, XP 002714609, Aug. 3, 2010, 1 page.

Kuyper et al., High-level functional expression of a fungal xylose isomerase:, vol. 4, Oct. 1, 2013, pp. 69-78.

Harhangi H.R. et al. "Xylos metabolism in the anaerobic fungus *Piromyces sp.* Strain E2 follows the bacterial pathway", Springer, DE, vol. 180, No. 2, Jun. 13, 2003, pp. 134-141.

"RecName: Full=Xylose Isomerase": XP002714610, Mar. 23, 2010, 1 page.

"RecName: Full=Xylose Isomerase": XP002714611 Oct. 19, 2011, 1 page.

Hector et al. "Growth and fermentation of D-xylose by *Saacharomyces cerevisiae* expressing a novel D-xylose isomerase originating from the bacterium Provotella ruminicola TC2-24", Biotechnology for Biofuels, Ltd. May 30, 2013.

* cited by examiner

*Primary Examiner* — Christian Fronda

(74) *Attorney, Agent, or Firm* — DLA Piper LLP (US)

(57) ABSTRACT

This disclosure relates to novel xylose isomerases and their uses, particularly in fermentation processes that employ xylose-containing media.

39 Claims, 13 Drawing Sheets

SEQUENCE LISTING

<160> NUMBER OF SEQ ID NOS: 237

<210> SEQ ID NO 1
<211> LENGTH: 1314
<212> TYPE: DNA
<213> ORGANISM: Unknown
<220> FEATURE:
<223> OTHER INFORMATION: Obtained from environmental sample

<400> SEQUENCE: 1
atggcagtta aagaatattt cccggagata ggcaagatcg cctttgaagg aaaggagtcc 60
aagaacccta tggcattcca ctactacaat ccagagcagg tagtagccgg aaagaaaatg 120
aaagattggt tcaagttcgc tatggcatgg tggcacaccc tctgcgctga aggtggcgac 180
cagttcggtc ctggtaccaa gaaattccct tggaacacag gtgcaactgc actcgaaaga 240
gcaaagaaca aaatggacgc aggtttcgag atcatgagca agctcggtat cgagtatttc 300
tgcttccacg atgttgacct tatcgacgag gctgacactg ttgaagagta cgaggctaac 360
atgaaggcta tcacagctta cgcaaaggag aaaatggccg ctactggcat caaactcctc 420
tggggaacag ccaatgtatt cggcaacaag agatatatga acggcgcttc taccaaccct 480
gacttcaacg tggctgcacg cgctatgctc cagatcaaga acgctatcga cgcaactatc 540
gctctcggtg gtgactgcta tgtattctgg ggcggccgtg agggttacat gagccttctc 600
aacaccgata tgaagagaga gaaagagcac atggctacca tgcttaccat ggcacgcgac 660
tatgctcgtt ctaagggctt caagggtacc ttccttatcg agcctaagcc aatggagccg 720
atgaagcacc agtacgatgt cgatactgag actgtcgtag gtttcctccg cgcccatggt 780
cttgacaagg acttcaaggt aaacatcgag gttaaccacg ctactctcgc aggccacacc 840
ttcgagcacg agctccagtg cgccgttgac gcaggcatgc tcggaagcat cgacgccaac 900
cgtggtgact accagaacgg ctgggatacc gaccagttcc ctatcgacct ctatgagctc 960
gtacaggcta tgatggttat catcaagggc ggcggtctcg tcggcggtac caacttcgac 1020
gccaagaccc gtcgtaactc aacagacctc gaggatatct tcatcgctca tgtatccggc 1080
atggatgtca tggcacgcgc tctcctcatc gctgctgacc ttctcgagaa atctcctatt 1140
cctgcaatgg tcaaggagcg ttacgcttcc tacgactcag gcatgggcaa ggacttcgag 1200
aacggcaagc ttactctcga gcaggttgtc gatttcgcaa gaaagaacgg cgagcctaag 1260
agcaccagcg gaaagcagga gctctacgag tctatcgtca atctctacat ctaa 1314

<210> SEQ ID NO 2
<211> LENGTH: 437
<212> TYPE: PRT
<213> ORGANISM: Unknown
<220> FEATURE:
<223> OTHER INFORMATION: Obtained from environmental sample

<400> SEQUENCE: 2

-continued

```
Met Ala Val Lys Glu Tyr Phe Pro Glu Ile Gly Lys Ile Ala Phe Glu
1               5                   10                  15

Gly Lys Glu Ser Lys Asn Pro Met Ala Phe His Tyr Tyr Asn Pro Glu
            20                  25                  30

Gln Val Val Ala Gly Lys Lys Met Lys Asp Trp Phe Lys Phe Ala Met
        35                  40                  45

Ala Trp Trp His Thr Leu Cys Ala Glu Gly Gly Asp Gln Phe Gly Pro
    50                  55                  60

Gly Thr Lys Lys Phe Pro Trp Asn Thr Gly Ala Thr Ala Leu Glu Arg
65                  70                  75                  80

Ala Lys Asn Lys Met Asp Ala Gly Phe Glu Ile Met Ser Lys Leu Gly
                85                  90                  95

Ile Glu Tyr Phe Cys Phe His Asp Val Asp Leu Ile Asp Glu Ala Asp
            100                 105                 110

Thr Val Glu Glu Tyr Glu Ala Asn Met Lys Ala Ile Thr Ala Tyr Ala
        115                 120                 125

Lys Glu Lys Met Ala Ala Thr Gly Ile Lys Leu Leu Trp Gly Thr Ala
    130                 135                 140

Asn Val Phe Gly Asn Lys Arg Tyr Met Asn Gly Ala Ser Thr Asn Pro
145                 150                 155                 160

Asp Phe Asn Val Ala Ala Arg Ala Met Leu Gln Ile Lys Asn Ala Ile
                165                 170                 175

Asp Ala Thr Ile Ala Leu Gly Gly Asp Cys Tyr Val Phe Trp Gly Gly
            180                 185                 190

Arg Glu Gly Tyr Met Ser Leu Leu Asn Thr Asp Met Lys Arg Glu Lys
        195                 200                 205

Glu His Met Ala Thr Met Leu Thr Met Ala Arg Asp Tyr Ala Arg Ser
    210                 215                 220

Lys Gly Phe Lys Gly Thr Phe Leu Ile Glu Pro Lys Pro Met Glu Pro
225                 230                 235                 240

Met Lys His Gln Tyr Asp Val Asp Thr Glu Thr Val Val Gly Phe Leu
                245                 250                 255

Arg Ala His Gly Leu Asp Lys Asp Phe Lys Val Asn Ile Glu Val Asn
            260                 265                 270

His Ala Thr Leu Ala Gly His Thr Phe Glu His Glu Leu Gln Cys Ala
        275                 280                 285

Val Asp Ala Gly Met Leu Gly Ser Ile Asp Ala Asn Arg Gly Asp Tyr
    290                 295                 300

Gln Asn Gly Trp Asp Thr Asp Gln Phe Pro Ile Asp Leu Tyr Glu Leu
305                 310                 315                 320

Val Gln Ala Met Met Val Ile Ile Lys Gly Gly Gly Leu Val Gly Gly
                325                 330                 335

Thr Asn Phe Asp Ala Lys Thr Arg Arg Asn Ser Thr Asp Leu Glu Asp
            340                 345                 350

Ile Phe Ile Ala His Val Ser Gly Met Asp Val Met Ala Arg Ala Leu
        355                 360                 365

Leu Ile Ala Ala Asp Leu Leu Glu Lys Ser Pro Ile Pro Ala Met Val
    370                 375                 380

Lys Glu Arg Tyr Ala Ser Tyr Asp Ser Gly Met Gly Lys Asp Phe Glu
385                 390                 395                 400

Asn Gly Lys Leu Thr Leu Glu Gln Val Val Asp Phe Ala Arg Lys Asn
                405                 410                 415

Gly Glu Pro Lys Ser Thr Ser Gly Lys Gln Glu Leu Tyr Glu Ser Ile
```

```
            420                 425                 430

Val Asn Leu Tyr Ile
        435


<210> SEQ ID NO 3
<211> LENGTH: 1314
<212> TYPE: DNA
<213> ORGANISM: Unknown
<220> FEATURE:
<223> OTHER INFORMATION: Obtained from environmental sample

<400> SEQUENCE: 3

atggcaaaca aagagtactt cccggagatc gggaaaatca aattcgaagg caaggattcc      60

aagaacccgc ttgcattcca ttattacaat cctgagcagg tcgtctgcgg caagccgatg     120

aaggactggc tcaagttcgc tatggcatgg tggcacaccc tctgcgcaga gggtagcgac     180

cagttcggcg gacccaccaa gtcattccct tggaacaaag cttcggatcc catcgcaaag     240

gccaagcaga aagtcgacgc cggtttcgag atcatgcaga agctcggtat cggatactat     300

tgcttccacg atgtagacct catcgacgag cccgccacca tcgaggagta tgaggccgat     360

ctcaaggaga tcgtcgctta cctcaaggag aagcaggccc agaccggcat caagctcctt     420

tggggcaccg ccaacgtctt cggtcacaag cggtacatga acggcgcctc caccaaccct     480

gatttcgacg tcgcagcccg cgccatggtc cagatcaaga acgccatgga cgccaccatc     540

gagctcggcg gcgagtgcta tgtcttctgg ggcggccgcg agggctacat gagcctcctc     600

aacaccgaca tgaagcgtga gaagcagcat atggccacca tgctcggcat ggcccgcgac     660

tatgcacgcg gcaagggctt caagggcacc ttcctcatcg agcccaagcc catggagccg     720

accaagcacc agtatgacgt cgacaccgag accgtcatcg gtttcctccg tgccaacggt     780

cttgacaagg acttcaaggt caacatcgag gtcaatcacg ccaccctcgc cggccacacc     840

ttcgagcatg agctccagtg cgccgccgat gccggtctcc tcggatccat cgacgccaac     900

cgcggcgact atcagaacgg ctgggatacc gaccagttcc cgatcgacct ctatgagctc     960

acccaggcca tgatggtcat cctcaagaat ggcggcctcg tcggcggtac caacttcgac    1020

gccaagaccc gtcgcaactc caccgacctg gacgacatca tcatcgccca cgtcagcggt    1080

atggacatca tggcacgcgc actcctcgtc gctgccgacg tcctcaccaa gtccgagctt    1140

cccaagatgc tcaaggagcg ttacgcttcc ttcgactccg gcaagggcaa ggagttcgaa    1200

gagggcaagc tcactctcga gcaggtcgta gagtacgcca agaccaaggg cgagcccaag    1260

gccaccagcg gcaagcagga gctctacgag accatcgtca acatgtacat ctaa          1314


<210> SEQ ID NO 4
<211> LENGTH: 437
<212> TYPE: PRT
<213> ORGANISM: Unknown
<220> FEATURE:
<223> OTHER INFORMATION: Obtained from environmental sample

<400> SEQUENCE: 4

Met Ala Asn Lys Glu Tyr Phe Pro Glu Ile Gly Lys Ile Lys Phe Glu
1               5                   10                  15

Gly Lys Asp Ser Lys Asn Pro Leu Ala Phe His Tyr Tyr Asn Pro Glu
            20                  25                  30

Gln Val Val Cys Gly Lys Pro Met Lys Asp Trp Leu Lys Phe Ala Met
        35                  40                  45

Ala Trp Trp His Thr Leu Cys Ala Glu Gly Ser Asp Gln Phe Gly Gly
```

-continued

```
    50                  55                  60

Pro Thr Lys Ser Phe Pro Trp Asn Lys Ala Ser Asp Pro Ile Ala Lys
65                  70                  75                  80

Ala Lys Gln Lys Val Asp Ala Gly Phe Glu Ile Met Gln Lys Leu Gly
                85                  90                  95

Ile Gly Tyr Tyr Cys Phe His Asp Val Asp Leu Ile Asp Glu Pro Ala
            100                 105                 110

Thr Ile Glu Glu Tyr Glu Ala Asp Leu Lys Glu Ile Val Ala Tyr Leu
        115                 120                 125

Lys Glu Lys Gln Ala Gln Thr Gly Ile Lys Leu Leu Trp Gly Thr Ala
    130                 135                 140

Asn Val Phe Gly His Lys Arg Tyr Met Asn Gly Ala Ser Thr Asn Pro
145                 150                 155                 160

Asp Phe Asp Val Ala Ala Arg Ala Met Val Gln Ile Lys Asn Ala Met
                165                 170                 175

Asp Ala Thr Ile Glu Leu Gly Gly Glu Cys Tyr Val Phe Trp Gly Gly
            180                 185                 190

Arg Glu Gly Tyr Met Ser Leu Leu Asn Thr Asp Met Lys Arg Glu Lys
        195                 200                 205

Gln His Met Ala Thr Met Leu Gly Met Ala Arg Asp Tyr Ala Arg Gly
    210                 215                 220

Lys Gly Phe Lys Gly Thr Phe Leu Ile Glu Pro Lys Pro Met Glu Pro
225                 230                 235                 240

Thr Lys His Gln Tyr Asp Val Asp Thr Glu Thr Val Ile Gly Phe Leu
                245                 250                 255

Arg Ala Asn Gly Leu Asp Lys Asp Phe Lys Val Asn Ile Glu Val Asn
            260                 265                 270

His Ala Thr Leu Ala Gly His Thr Phe Glu His Glu Leu Gln Cys Ala
        275                 280                 285

Ala Asp Ala Gly Leu Leu Gly Ser Ile Asp Ala Asn Arg Gly Asp Tyr
    290                 295                 300

Gln Asn Gly Trp Asp Thr Asp Gln Phe Pro Ile Asp Leu Tyr Glu Leu
305                 310                 315                 320

Thr Gln Ala Met Met Val Ile Leu Lys Asn Gly Gly Leu Val Gly Gly
                325                 330                 335

Thr Asn Phe Asp Ala Lys Thr Arg Arg Asn Ser Thr Asp Leu Asp Asp
            340                 345                 350

Ile Ile Ile Ala His Val Ser Gly Met Asp Ile Met Ala Arg Ala Leu
        355                 360                 365

Leu Val Ala Ala Asp Val Leu Thr Lys Ser Glu Leu Pro Lys Met Leu
    370                 375                 380

Lys Glu Arg Tyr Ala Ser Phe Asp Ser Gly Lys Gly Lys Glu Phe Glu
385                 390                 395                 400

Glu Gly Lys Leu Thr Leu Glu Gln Val Val Glu Tyr Ala Lys Thr Lys
                405                 410                 415

Gly Glu Pro Lys Ala Thr Ser Gly Lys Gln Glu Leu Tyr Glu Thr Ile
            420                 425                 430

Val Asn Met Tyr Ile
        435
```

<210> SEQ ID NO 5
<211> LENGTH: 1329
<212> TYPE: DNA
<213> ORGANISM: Unknown

-continued

<220> FEATURE:
<223> OTHER INFORMATION: Obtained from environmental sample

<400> SEQUENCE: 5

```
atgaatttt ataaaggcga aaaagaattc ttccccggaa taggaaagat tcagtttgaa      60

ggacgcgagt caaagaaccc gatggcgttt cattattatg acgaaaacaa ggtggtgatg    120

ggtaaaacac tgaaggatca tcttcgtttt gcaatggctt actggcatac gctttgtgcc    180

gaagggggcg accagtttgg cggtggtacg aaaacattcc cctggaatgc tgctgccgac    240

ccgatcagcc gtgccaaata taagatggat gcagcgttcg agtttatgac aaaatgcagc    300

atcccttatt actgtttcca tgatgtggac gtggtggacg aagctcccac gctggctcag    360

tttgaaaaag accttcatac gatggtaggc catgccaaag ggcttcagca ggcaaccgga    420

aaaaaactgt tatggtctac tgccaacgtg ttcagcaaca aacgctatat gaacggggct    480

gccactaatc ctgacttctc ggccgtggct tgtgccggta cgcagatcaa gaatgcgatc    540

gatgcctgta tcgcgctgga cggtgaaaac tatgtgttct ggggcggacg tgaaggatat    600

atgggcttgc tcaataccga tatgaaacgc gaaaaagacc atctggccat gatgctgacg    660

atggcacgcg actatggccg caagaacggt ttcaaaggta ctttcctgat cgagccgaaa    720

ccgatggaac cgaccaagca tcaatatgat gtcgactcgg aaactgtaat cggcttccta    780

cgtcattatg gcctggataa agacttcgcc ctgaatatcg aagtaaatca tgcaaccctg    840

gccggacata cgttcgagca cgaattgcag gctgctgtcg atgccggtat gctgtgcagt    900

atcgatgcca accgtggtga ctaccagaat ggctgggata ccgaccaatt cccgatggac    960

atctacgaac tgactcaggc ttggctggtc attctgcaag gtggtggtct gacaaccggc   1020

ggaacgaact tcgatgccaa gacccgccgc aactcgaccg acctggacga tatcttcctg   1080

gctcatatag gtggtatgga tgcgtttgcc cgtgccctga tcacggctgc tgccatcctt   1140

gaaaactccg attacacgaa gatgcgtgcc gaacgttaca ccagcttcga tggtggcgaa   1200

ggcaaagcgt ttgaagacgg taaactttct ctggaagacc tgcgtacgat cgctctccgc   1260

gacggagaac cgaagatggt cagcggcaaa caggaattat atgagatgat tctcaattta   1320

tacatataa                                                           1329
```

<210> SEQ ID NO 6
<211> LENGTH: 442
<212> TYPE: PRT
<213> ORGANISM: Unknown
<220> FEATURE:
<223> OTHER INFORMATION: Obtained from environmental sample

<400> SEQUENCE: 6

```
Met Asn Phe Tyr Lys Gly Glu Lys Glu Phe Phe Pro Gly Ile Gly Lys
1               5                   10                  15

Ile Gln Phe Glu Gly Arg Glu Ser Lys Asn Pro Met Ala Phe His Tyr
            20                  25                  30

Tyr Asp Glu Asn Lys Val Val Met Gly Lys Thr Leu Lys Asp His Leu
        35                  40                  45

Arg Phe Ala Met Ala Tyr Trp His Thr Leu Cys Ala Glu Gly Gly Asp
    50                  55                  60

Gln Phe Gly Gly Gly Thr Lys Thr Phe Pro Trp Asn Ala Ala Ala Asp
65                  70                  75                  80

Pro Ile Ser Arg Ala Lys Tyr Lys Met Asp Ala Ala Phe Glu Phe Met
                85                  90                  95
```

-continued

```
Thr Lys Cys Ser Ile Pro Tyr Tyr Cys Phe His Asp Val Asp Val Val
            100                 105                 110

Asp Glu Ala Pro Thr Leu Ala Gln Phe Glu Lys Asp Leu His Thr Met
        115                 120                 125

Val Gly His Ala Lys Gly Leu Gln Gln Ala Thr Gly Lys Lys Leu Leu
    130                 135                 140

Trp Ser Thr Ala Asn Val Phe Ser Asn Lys Arg Tyr Met Asn Gly Ala
145                 150                 155                 160

Ala Thr Asn Pro Asp Phe Ser Ala Val Ala Cys Ala Gly Thr Gln Ile
                165                 170                 175

Lys Asn Ala Ile Asp Ala Cys Ile Ala Leu Asp Gly Glu Asn Tyr Val
            180                 185                 190

Phe Trp Gly Gly Arg Glu Gly Tyr Met Gly Leu Leu Asn Thr Asp Met
        195                 200                 205

Lys Arg Glu Lys Asp His Leu Ala Met Met Leu Thr Met Ala Arg Asp
    210                 215                 220

Tyr Gly Arg Lys Asn Gly Phe Lys Gly Thr Phe Leu Ile Glu Pro Lys
225                 230                 235                 240

Pro Met Glu Pro Thr Lys His Gln Tyr Asp Val Asp Ser Glu Thr Val
                245                 250                 255

Ile Gly Phe Leu Arg His Tyr Gly Leu Asp Lys Asp Phe Ala Leu Asn
            260                 265                 270

Ile Glu Val Asn His Ala Thr Leu Ala Gly His Thr Phe Glu His Glu
        275                 280                 285

Leu Gln Ala Ala Val Asp Ala Gly Met Leu Cys Ser Ile Asp Ala Asn
    290                 295                 300

Arg Gly Asp Tyr Gln Asn Gly Trp Asp Thr Asp Gln Phe Pro Met Asp
305                 310                 315                 320

Ile Tyr Glu Leu Thr Gln Ala Trp Leu Val Ile Leu Gln Gly Gly Gly
                325                 330                 335

Leu Thr Thr Gly Gly Thr Asn Phe Asp Ala Lys Thr Arg Arg Asn Ser
            340                 345                 350

Thr Asp Leu Asp Asp Ile Phe Leu Ala His Ile Gly Gly Met Asp Ala
        355                 360                 365

Phe Ala Arg Ala Leu Ile Thr Ala Ala Ala Ile Leu Glu Asn Ser Asp
    370                 375                 380

Tyr Thr Lys Met Arg Ala Glu Arg Tyr Thr Ser Phe Asp Gly Gly Glu
385                 390                 395                 400

Gly Lys Ala Phe Glu Asp Gly Lys Leu Ser Leu Glu Asp Leu Arg Thr
                405                 410                 415

Ile Ala Leu Arg Asp Gly Glu Pro Lys Met Val Ser Gly Lys Gln Glu
            420                 425                 430

Leu Tyr Glu Met Ile Leu Asn Leu Tyr Ile
        435                 440
```

```
<210> SEQ ID NO 7
<211> LENGTH: 1329
<212> TYPE: DNA
<213> ORGANISM: Unknown
<220> FEATURE:
<223> OTHER INFORMATION: Obtained from environmental sample

<400> SEQUENCE: 7

atgaattact ttaaaggtga gaaagagttc ttcccgggaa tcgggaaaat agagtttgaa      60

ggacgtgaat cgaagaatcc gatggctttt cattactatg acgagaacaa ggttgtcatg     120
```

-continued

```
gggaagacct tgaaggacca tctgcgtttt gcgatggctt attggcatac gctgtgtgcg    180
gaaggcgccg accagttcgg cggcgggacg aaggcatttc cctggaatac cggggcggat    240
cgtatttccc gtgccaagta taagatggat gctgcttttg agtttatgac gaaatgtaac    300
atcccgtact attgtttcca tgatgtggat gtggtggatg aagctccgac actggccgaa    360
tttgaaaaag acttgcatac gatggtcgaa tatgccaagc agcatcagga ggcaaccggg    420
aaaaaactgt tgtggtctac cgccaatgtg ttcagcaata aacgttatat gaacggggct    480
gccacaaatc cgtatttccc tgctgtcgct tgtgcgggta cgcagatcaa gaatgctatc    540
gacgcttgta ttgccctggg cggcgaaaac tatgtgttct ggggcggtcg tgaagggtat    600
atgagcttgt tgaacaccaa tatgaaacgc gaaaaggaac atctcgccat gatgttgacg    660
atggctcgcg attatgcgcg taagaacggc ttcaaaggta ctttcctggt agagcctaaa    720
ccgatggaac cgaccaaaca tcagtatgat gtggacacag aaactgttat cggcttcctg    780
cgtcattacg gccttgacaa ggactttgcc atcaacatcg aagtgaatca tgctacattg    840
gctggacata cattcgaaca tgagcttcag gcggctgccg atgccggtat gctgtgcagc    900
atcgacgcca accgcggcga ttaccagaat ggttgggaca cggatcagtt cccggtcgac    960
atctacgaac tgacacaggc gtggctggtt atcctcgaag cgggtggcct gactaccggt   1020
ggtacgaact tcgacgccaa gacgcgccgc aactcgactg acctggacga tatcttcctg   1080
gcacacatcg gtggtatgga ttcgtttgcc cgtgctttga tggcggctgc cgatatattg   1140
gaacactccg attacaaaaa gatgcgtgcc gaacgttatg ccagcttcga tcaaggcgac   1200
ggcaagaagt tcgaagatgg taaactcctt ctcgaggacc tccgcaccat cgctcttgcc   1260
tccggcgaac cgaagcaaat cagcgggaaa caggaattgt atgaaatgat tatcaaccag   1320
tacatttaa                                                            1329
```

<210> SEQ ID NO 8
<211> LENGTH: 442
<212> TYPE: PRT
<213> ORGANISM: Unknown
<220> FEATURE:
<223> OTHER INFORMATION: Obtained from environmental sample

<400> SEQUENCE: 8

```
Met Asn Tyr Phe Lys Gly Glu Lys Glu Phe Phe Pro Gly Ile Gly Lys
1               5                   10                  15

Ile Glu Phe Glu Gly Arg Glu Ser Lys Asn Pro Met Ala Phe His Tyr
            20                  25                  30

Tyr Asp Glu Asn Lys Val Val Met Gly Lys Thr Leu Lys Asp His Leu
        35                  40                  45

Arg Phe Ala Met Ala Tyr Trp His Thr Leu Cys Ala Glu Gly Ala Asp
    50                  55                  60

Gln Phe Gly Gly Gly Thr Lys Ala Phe Pro Trp Asn Thr Gly Ala Asp
65                  70                  75                  80

Arg Ile Ser Arg Ala Lys Tyr Lys Met Asp Ala Ala Phe Glu Phe Met
                85                  90                  95

Thr Lys Cys Asn Ile Pro Tyr Tyr Cys Phe His Asp Val Asp Val Val
            100                 105                 110

Asp Glu Ala Pro Thr Leu Ala Glu Phe Glu Lys Asp Leu His Thr Met
        115                 120                 125

Val Glu Tyr Ala Lys Gln His Gln Glu Ala Thr Gly Lys Lys Leu Leu
    130                 135                 140
```

-continued

Trp Ser Thr Ala Asn Val Phe Ser Asn Lys Arg Tyr Met Asn Gly Ala
145 150 155 160

Ala Thr Asn Pro Tyr Phe Pro Ala Val Ala Cys Ala Gly Thr Gln Ile
165 170 175

Lys Asn Ala Ile Asp Ala Cys Ile Ala Leu Gly Gly Glu Asn Tyr Val
180 185 190

Phe Trp Gly Gly Arg Glu Gly Tyr Met Ser Leu Leu Asn Thr Asn Met
195 200 205

Lys Arg Glu Lys Glu His Leu Ala Met Met Leu Thr Met Ala Arg Asp
210 215 220

Tyr Ala Arg Lys Asn Gly Phe Lys Gly Thr Phe Leu Val Glu Pro Lys
225 230 235 240

Pro Met Glu Pro Thr Lys His Gln Tyr Asp Val Asp Thr Glu Thr Val
245 250 255

Ile Gly Phe Leu Arg His Tyr Gly Leu Asp Lys Asp Phe Ala Ile Asn
260 265 270

Ile Glu Val Asn His Ala Thr Leu Ala Gly His Thr Phe Glu His Glu
275 280 285

Leu Gln Ala Ala Ala Asp Ala Gly Met Leu Cys Ser Ile Asp Ala Asn
290 295 300

Arg Gly Asp Tyr Gln Asn Gly Trp Asp Thr Asp Gln Phe Pro Val Asp
305 310 315 320

Ile Tyr Glu Leu Thr Gln Ala Trp Leu Val Ile Leu Glu Ala Gly Gly
325 330 335

Leu Thr Thr Gly Gly Thr Asn Phe Asp Ala Lys Thr Arg Arg Asn Ser
340 345 350

Thr Asp Leu Asp Asp Ile Phe Leu Ala His Ile Gly Gly Met Asp Ser
355 360 365

Phe Ala Arg Ala Leu Met Ala Ala Ala Asp Ile Leu Glu His Ser Asp
370 375 380

Tyr Lys Lys Met Arg Ala Glu Arg Tyr Ala Ser Phe Asp Gln Gly Asp
385 390 395 400

Gly Lys Lys Phe Glu Asp Gly Lys Leu Leu Leu Glu Asp Leu Arg Thr
405 410 415

Ile Ala Leu Ala Ser Gly Glu Pro Lys Gln Ile Ser Gly Lys Gln Glu
420 425 430

Leu Tyr Glu Met Ile Ile Asn Gln Tyr Ile
435 440

<210> SEQ ID NO 9
<211> LENGTH: 1329
<212> TYPE: DNA
<213> ORGANISM: Unknown
<220> FEATURE:
<223> OTHER INFORMATION: Obtained from environmental sample

<400> SEQUENCE: 9
atgaattatt ttaaaggtga aaaagagttt ttccctggaa tcgggaaaat agagtttgaa 60
ggacgtgagt cgaagaatcc gatggctttt cattattatg atgaaaacaa ggtcgtaatg 120
ggcaagacct tgaaagatca cctccgcttt gcaatggctt actggcatac gttgtgcgcg 180
gaaggcgcag accagtttgg cggtggcaca aaatcattcc cctggaatac cgcagcggat 240
cgtatttccc gcgctaaata taaaatggat gctgctttcg agtttatgac caagtgcagt 300
atcccgtact attgtttcca tgatgtggac gtggtggacg aagctccggc actggccgaa 360

```
tttgaaaagg acctgcatac gatggtggga ttcgccaaac aacaccagga agcaaccgga    420

aagaaactgt tgtggtctac agccaatgta ttcgggcata aacgttatat gaacggagcg    480

gctaccaatc cttatttccc ggctgtcgct tgtgccggta cgcagatcaa gaatgcaatc    540

gacgcctgta tcgagctggg tggagagaac tatgtattct ggggcggacg cgaaggctac    600

atgagcctgc tgaacaccaa tatgaaacgt gaaaaggatc atttggccat gatgctgaca    660

atggcacgcg attatgcccg caagaatggt ttcaagggta ctttcctggt ggaatctaag    720

ccgatggaac cgaccaaaca tcagtatgac gcagatacgg aaaccgtgat cggcttcctg    780

cgccactatg gcctcgacaa ggatttcgct atcaacattg aagtgaacca tgctacattg    840

gccggccata cattcgaaca tgaacttcag gctgctgccg atgccggtat gctgtgcagc    900

atcgatgcaa atagaggcga ctatcagaat ggttgggata cggatcagtt ccccgtagac    960

atttacgaac tgacacaggc ctggctggtt atcctggaag cgggcggact gacaaccgga   1020

ggtacgaact tcgatgcgaa gacccgtcgt aactcgactg acctcgacga tatcttcctg   1080

gcccatatcg gcggtatgga ttcgtttgca cgtgccttga tggcagctgc cgatatcctg   1140

gaacattctg attacaagaa gatgcgtgcc gaacgttacg ccagcttcga ccagggcgac   1200

ggcaagaagt tcgaagacgg caaactcctt ctcgaagacc tgcgcacaat tgcccttgcc   1260

ggcgacgaac cgaagcagat cagcggcaag caggagttgt atgagatgat tatcaatcag   1320

tatatttaa                                                           1329

<210> SEQ ID NO 10
<211> LENGTH: 442
<212> TYPE: PRT
<213> ORGANISM: Unknown
<220> FEATURE:
<223> OTHER INFORMATION: Obtained from environmental sample

<400> SEQUENCE: 10

Met Asn Tyr Phe Lys Gly Glu Lys Glu Phe Phe Pro Gly Ile Gly Lys
1               5                   10                  15

Ile Glu Phe Glu Gly Arg Glu Ser Lys Asn Pro Met Ala Phe His Tyr
            20                  25                  30

Tyr Asp Glu Asn Lys Val Val Met Gly Lys Thr Leu Lys Asp His Leu
        35                  40                  45

Arg Phe Ala Met Ala Tyr Trp His Thr Leu Cys Ala Glu Gly Ala Asp
    50                  55                  60

Gln Phe Gly Gly Gly Thr Lys Ser Phe Pro Trp Asn Thr Ala Ala Asp
65                  70                  75                  80

Arg Ile Ser Arg Ala Lys Tyr Lys Met Asp Ala Ala Phe Glu Phe Met
                85                  90                  95

Thr Lys Cys Ser Ile Pro Tyr Tyr Cys Phe His Asp Val Asp Val Val
            100                 105                 110

Asp Glu Ala Pro Ala Leu Ala Glu Phe Glu Lys Asp Leu His Thr Met
        115                 120                 125

Val Gly Phe Ala Lys Gln His Gln Glu Ala Thr Gly Lys Lys Leu Leu
    130                 135                 140

Trp Ser Thr Ala Asn Val Phe Gly His Lys Arg Tyr Met Asn Gly Ala
145                 150                 155                 160

Ala Thr Asn Pro Tyr Phe Pro Ala Val Ala Cys Ala Gly Thr Gln Ile
                165                 170                 175

Lys Asn Ala Ile Asp Ala Cys Ile Glu Leu Gly Gly Glu Asn Tyr Val
```

```
            180                 185                 190

Phe Trp Gly Gly Arg Glu Gly Tyr Met Ser Leu Leu Asn Thr Asn Met
        195                 200                 205

Lys Arg Glu Lys Asp His Leu Ala Met Met Leu Thr Met Ala Arg Asp
    210                 215                 220

Tyr Ala Arg Lys Asn Gly Phe Lys Gly Thr Phe Leu Val Glu Ser Lys
225                 230                 235                 240

Pro Met Glu Pro Thr Lys His Gln Tyr Asp Ala Asp Thr Glu Thr Val
                245                 250                 255

Ile Gly Phe Leu Arg His Tyr Gly Leu Asp Lys Asp Phe Ala Ile Asn
            260                 265                 270

Ile Glu Val Asn His Ala Thr Leu Ala Gly His Thr Phe Glu His Glu
        275                 280                 285

Leu Gln Ala Ala Ala Asp Ala Gly Met Leu Cys Ser Ile Asp Ala Asn
    290                 295                 300

Arg Gly Asp Tyr Gln Asn Gly Trp Asp Thr Asp Gln Phe Pro Val Asp
305                 310                 315                 320

Ile Tyr Glu Leu Thr Gln Ala Trp Leu Val Ile Leu Glu Ala Gly Gly
                325                 330                 335

Leu Thr Thr Gly Gly Thr Asn Phe Asp Ala Lys Thr Arg Arg Asn Ser
            340                 345                 350

Thr Asp Leu Asp Asp Ile Phe Leu Ala His Ile Gly Gly Met Asp Ser
        355                 360                 365

Phe Ala Arg Ala Leu Met Ala Ala Ala Asp Ile Leu Glu His Ser Asp
    370                 375                 380

Tyr Lys Lys Met Arg Ala Glu Arg Tyr Ala Ser Phe Asp Gln Gly Asp
385                 390                 395                 400

Gly Lys Lys Phe Glu Asp Gly Lys Leu Leu Leu Glu Asp Leu Arg Thr
                405                 410                 415

Ile Ala Leu Ala Gly Asp Glu Pro Lys Gln Ile Ser Gly Lys Gln Glu
            420                 425                 430

Leu Tyr Glu Met Ile Ile Asn Gln Tyr Ile
        435                 440
```

<210> SEQ ID NO 11
<211> LENGTH: 1308
<212> TYPE: DNA
<213> ORGANISM: Unknown
<220> FEATURE:
<223> OTHER INFORMATION: Obtained from environmental sample

<400> SEQUENCE: 11

```
atgaaacagt atttcccgaa catctccgcc atcaagtttg agggcgtcga gagcaagaat      60

cccctggctt accgctacta cgaccgcgac cgcgtcgtca tgggtaagaa gatgagcgaa     120

tggtttaagt tcgctatgtg ctggtggcac accctctgcg ccgagggctc cgatcagttc     180

ggtcccggca caaagacctt cccctggaac gccgccgccg accccgtgca ggctgccaag     240

gacaaggccg acgctggctt cgagatcatg cagaaactcg gcatcgagta ctactgcttc     300

cacgacgttg acctcgtggc cgaggctccc gacgtggaga cctacgagaa gaacctcaag     360

gagatcgtgg cttatctcaa gcagaaacag gctgagacgg gcatcaagct gctctggggc     420

actgccaacg tcttcggaca caagcgctac atgaacggag cctccacgaa ccccgacttc     480

gatgtcgtgg cacgcgctat cgtgcagatc aagaacgcca tcgatgctac catcgagctg     540

ggcggcacca actacgtctt ctggggcggt cgcgaaggct acatgagcct gctcaacacc     600
```

```
gatatgaagc gcgagaagga gcacatggct acgatgttga cgatggcacg cgactatgcc    660

cgttctaagg gattcaaggg cacgttcctc atcgaaccca aacccatgga acccacgaag    720

catcagtacg atgcggacac cgagacggtc atcggattcc tccgtgctca tggtctcgac    780

aaggatttca aggtcaacat cgaggtcaac cacgccacgc tggccggaca cacgttcgag    840

catgagctgg cctgcgccgt agacgccgat atgctcggca gcatcgatgc caatcgcggc    900

gactatcaga acggatggga caccgaccag ttccccatcg accactacga actcacgcag    960

gctatgctgc agatcatccg caacggaggt ttcaaggacg gtggcaccaa ttttgacgct   1020

aagacgcgcc gcaacagcac cgacctcgag gatatcttca tcgctcacgt agcagccatg   1080

gacgccatgg cccacgccct gttgtcggct gccgatatca tcgagaagtc gcccatctgc   1140

acgatggtca aggagcgtta cgccagcttc gatgccggcg aaggcaagcg cttcgaagaa   1200

ggcaagatga ccctcgagga agcctacgag tatggcaaga aggtcgggga gcccaagcag   1260

accagcggaa agcaggagct ctacgaagcc attgtcaata tgtattga                1308
```

```
<210> SEQ ID NO 12
<211> LENGTH: 435
<212> TYPE: PRT
<213> ORGANISM: Unknown
<220> FEATURE:
<223> OTHER INFORMATION: Obtained from environmental sample

<400> SEQUENCE: 12

Met Lys Gln Tyr Phe Pro Asn Ile Ser Ala Ile Lys Phe Glu Gly Val
1               5                   10                  15

Glu Ser Lys Asn Pro Leu Ala Tyr Arg Tyr Tyr Asp Arg Asp Arg Val
            20                  25                  30

Val Met Gly Lys Lys Met Ser Glu Trp Phe Lys Phe Ala Met Cys Trp
        35                  40                  45

Trp His Thr Leu Cys Ala Glu Gly Ser Asp Gln Phe Gly Pro Gly Thr
    50                  55                  60

Lys Thr Phe Pro Trp Asn Ala Ala Ala Asp Pro Val Gln Ala Ala Lys
65                  70                  75                  80

Asp Lys Ala Asp Ala Gly Phe Glu Ile Met Gln Lys Leu Gly Ile Glu
                85                  90                  95

Tyr Tyr Cys Phe His Asp Val Asp Leu Val Ala Glu Ala Pro Asp Val
            100                 105                 110

Glu Thr Tyr Glu Lys Asn Leu Lys Glu Ile Val Ala Tyr Leu Lys Gln
        115                 120                 125

Lys Gln Ala Glu Thr Gly Ile Lys Leu Leu Trp Gly Thr Ala Asn Val
    130                 135                 140

Phe Gly His Lys Arg Tyr Met Asn Gly Ala Ser Thr Asn Pro Asp Phe
145                 150                 155                 160

Asp Val Val Ala Arg Ala Ile Val Gln Ile Lys Asn Ala Ile Asp Ala
                165                 170                 175

Thr Ile Glu Leu Gly Gly Thr Asn Tyr Val Phe Trp Gly Gly Arg Glu
            180                 185                 190

Gly Tyr Met Ser Leu Leu Asn Thr Asp Met Lys Arg Glu Lys Glu His
        195                 200                 205

Met Ala Thr Met Leu Thr Met Ala Arg Asp Tyr Ala Arg Ser Lys Gly
    210                 215                 220

Phe Lys Gly Thr Phe Leu Ile Glu Pro Lys Pro Met Glu Pro Thr Lys
225                 230                 235                 240
```

```
His Gln Tyr Asp Ala Asp Thr Glu Thr Val Ile Gly Phe Leu Arg Ala
                245                 250                 255

His Gly Leu Asp Lys Asp Phe Lys Val Asn Ile Glu Val Asn His Ala
            260                 265                 270

Thr Leu Ala Gly His Thr Phe Glu His Glu Leu Ala Cys Ala Val Asp
        275                 280                 285

Ala Asp Met Leu Gly Ser Ile Asp Ala Asn Arg Gly Asp Tyr Gln Asn
    290                 295                 300

Gly Trp Asp Thr Asp Gln Phe Pro Ile Asp His Tyr Glu Leu Thr Gln
305                 310                 315                 320

Ala Met Leu Gln Ile Ile Arg Asn Gly Gly Phe Lys Asp Gly Gly Thr
                325                 330                 335

Asn Phe Asp Ala Lys Thr Arg Arg Asn Ser Thr Asp Leu Glu Asp Ile
            340                 345                 350

Phe Ile Ala His Val Ala Ala Met Asp Ala Met Ala His Ala Leu Leu
        355                 360                 365

Ser Ala Ala Asp Ile Ile Glu Lys Ser Pro Ile Cys Thr Met Val Lys
    370                 375                 380

Glu Arg Tyr Ala Ser Phe Asp Ala Gly Glu Gly Lys Arg Phe Glu Glu
385                 390                 395                 400

Gly Lys Met Thr Leu Glu Glu Ala Tyr Glu Tyr Gly Lys Lys Val Gly
                405                 410                 415

Glu Pro Lys Gln Thr Ser Gly Lys Gln Glu Leu Tyr Glu Ala Ile Val
            420                 425                 430

Asn Met Tyr
        435
```

<210> SEQ ID NO 13
<211> LENGTH: 1317
<212> TYPE: DNA
<213> ORGANISM: Unknown
<220> FEATURE:
<223> OTHER INFORMATION: Obtained from environmental sample

<400> SEQUENCE: 13

```
atggcaacaa aagagtattt tcccggaata ggaaagatta aattcgaagg taaagagagt      60

atgaacccga tggcatatcg ttactacgat gctgagaagg taatcatggg taagaagatg     120

aaagattggt tgaagtttgc tatggcttgg tggcacactc tctgcgcaga aggtggtgac     180

caattcggtg gcggaacgaa acaattccct tggaatggtg actctgacgc tttgcaagca     240

gctaaaaata aattggatgc aggtttcgaa ttcatgcaga agatgggtat cgaatactat     300

tgcttccacg atgtagacct gatttctgaa ggtgcaagca tcgaagaata cgaagctaac     360

ttgaaagcta tcgtagctta tgcaaaagaa aaacaggctg aaactggtat caagctgttg     420

tggggtactg ctaacgtatt cggtcatgca cgttatatga acggtgctgc taccaatcct     480

gatttcgacg ttgtagcacg cgctgctgtt cagatcaaga acgctattga cgctactatc     540

gaactgggtg gttcaaacta tgtattctgg ggcggtcgcg aaggttacat gtctttgctg     600

aacactgacc agaaacgtga aaaagaacac cttgcaaaga tgttgactat cgctcgtgac     660

tatgcacgtg ctcgtggctt caaaggtact ttcctgattg agccgaaacc gatggaaccg     720

acaaaacatc agtatgatgt agatactgaa acagttatcg gcttcctgaa agctcacggt     780

ttggataagg atttcaaagt aaacatcgag gttaatcacg caactttggc tggccatact     840

ttcgaacacg aactggctgt agctgttgac aacggcatgt taggttctat cgacgctaac     900
```

```
cgtggtgact accagaacgg ttgggatact gaccaattcc ctatcgataa ctacgaactg    960

actcaagcta tgatgcagat catccgcaac ggtggtttgg gtaatggcgg tactaacttc   1020

gacgctaaga cccgtcgtaa ctctaccgac ctggaagata tcttcatcgc tcacattgca   1080

ggtatggatg ctatggcacg tgctctggaa agtgcagcta aattactgga agaatctcct   1140

tataagaaaa tgttggctga tcgttacgca tcattcgacg gtggcaaggg taaggaattc   1200

gaagaaggca aattgtcttt ggaagatgtt gtagcttatg cgaaagctaa cggcgaaccg   1260

aagcaaacca gcggcaagca agaattgtat gaagcaatcg tgaatatgta ttgctaa      1317
```

```
<210> SEQ ID NO 14
<211> LENGTH: 438
<212> TYPE: PRT
<213> ORGANISM: Unknown
<220> FEATURE:
<223> OTHER INFORMATION: Obtained from environmental sample

<400> SEQUENCE: 14

Met Ala Thr Lys Glu Tyr Phe Pro Gly Ile Gly Lys Ile Lys Phe Glu
1               5                   10                  15

Gly Lys Glu Ser Met Asn Pro Met Ala Tyr Arg Tyr Tyr Asp Ala Glu
            20                  25                  30

Lys Val Ile Met Gly Lys Lys Met Lys Asp Trp Leu Lys Phe Ala Met
        35                  40                  45

Ala Trp Trp His Thr Leu Cys Ala Glu Gly Gly Asp Gln Phe Gly Gly
    50                  55                  60

Gly Thr Lys Gln Phe Pro Trp Asn Gly Asp Ser Asp Ala Leu Gln Ala
65                  70                  75                  80

Ala Lys Asn Lys Leu Asp Ala Gly Phe Glu Phe Met Gln Lys Met Gly
                85                  90                  95

Ile Glu Tyr Tyr Cys Phe His Asp Val Asp Leu Ile Ser Glu Gly Ala
            100                 105                 110

Ser Ile Glu Glu Tyr Glu Ala Asn Leu Lys Ala Ile Val Ala Tyr Ala
        115                 120                 125

Lys Glu Lys Gln Ala Glu Thr Gly Ile Lys Leu Leu Trp Gly Thr Ala
    130                 135                 140

Asn Val Phe Gly His Ala Arg Tyr Met Asn Gly Ala Ala Thr Asn Pro
145                 150                 155                 160

Asp Phe Asp Val Val Ala Arg Ala Ala Val Gln Ile Lys Asn Ala Ile
                165                 170                 175

Asp Ala Thr Ile Glu Leu Gly Gly Ser Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Leu Ala Lys Met Leu Thr Ile Ala Arg Asp Tyr Ala Arg Ala
    210                 215                 220

Arg Gly Phe Lys Gly Thr Phe Leu Ile Glu Pro Lys Pro Met Glu Pro
225                 230                 235                 240

Thr Lys His Gln Tyr Asp Val Asp Thr Glu Thr Val Ile Gly Phe Leu
                245                 250                 255

Lys Ala His Gly Leu Asp Lys Asp Phe Lys Val Asn Ile Glu Val Asn
            260                 265                 270

His Ala Thr Leu Ala Gly His Thr Phe Glu His Glu Leu Ala Val Ala
        275                 280                 285
```

```
Val Asp Asn Gly Met Leu Gly Ser Ile Asp Ala Asn Arg Gly Asp Tyr
    290                 295                 300

Gln Asn Gly Trp Asp Thr Asp Gln Phe Pro Ile Asp Asn Tyr Glu Leu
305                 310                 315                 320

Thr Gln Ala Met Met Gln Ile Ile Arg Asn Gly Gly Leu Gly Asn Gly
                325                 330                 335

Gly Thr Asn Phe Asp Ala Lys Thr Arg Arg Asn Ser Thr Asp Leu Glu
            340                 345                 350

Asp Ile Phe Ile Ala His Ile Ala Gly Met Asp Ala Met Ala Arg Ala
        355                 360                 365

Leu Glu Ser Ala Ala Lys Leu Leu Glu Glu Ser Pro Tyr Lys Lys Met
    370                 375                 380

Leu Ala Asp Arg Tyr Ala Ser Phe Asp Gly Gly Lys Gly Lys Glu Phe
385                 390                 395                 400

Glu Glu Gly Lys Leu Ser Leu Glu Asp Val Val Ala Tyr Ala Lys Ala
                405                 410                 415

Asn Gly Glu Pro Lys Gln Thr Ser Gly Lys Gln Glu Leu Tyr Glu Ala
            420                 425                 430

Ile Val Asn Met Tyr Cys
        435


<210> SEQ ID NO 15
<211> LENGTH: 1314
<212> TYPE: DNA
<213> ORGANISM: Unknown
<220> FEATURE:
<223> OTHER INFORMATION: Obtained from environmental sample

<400> SEQUENCE: 15

atggcaaaag agtattttcc tggcgtgaaa aaaatccagt tcgagggtaa ggacagtaag     60

aatccaatgg cttaccgtta ttatgatgca gagaaggtca tcatgggtaa gaagatgaag    120

gattggttga agttcgctat ggcttggtgg cacactttgt gcgctgaggg cgcagaccag    180

ttcggtggcg gtactaagac tttcccttgg aacgaaggtg caaacgcttt ggaagttgct    240

aagaataagg ctgatgctgg tttcgagatt atggagaagc ttggcatcga gtactactgt    300

ttccacgatg tagacctcgt tgaggaggct gcaactatcg aggagtatga ggctaacatg    360

aaggctatcg ttgcttatct taaggagaag caggctgcta ctggcaagaa gcttctttgg    420

ggtactgcta acgtattcgg caacaagcgc tatatgaacg gtgcttctac aaaccctgac    480

ttcgacgttg ttgctcgcgc ttgtgttcag attaagaacg ctatcgacgc tactatcgaa    540

cttggtggta caaactacgt attctggggt ggccgcgagg gttatatgag ccttcttaac    600

acagatatga agcgtgagaa ggagcacatg gcaactatgc ttactaaggc tcgcgactac    660

gctcgttcaa agggctttac tggtacattc cttatcgagc caaagccaat ggaaccatca    720

aagcatcagt atgatgttga tactgagact gtttgtggtt tcttgagggc tcacggtctt    780

gacaaggact tcaaggtaaa catcgaggtt aaccacgcta ctttggctgg tcacacattc    840

gagcacgagt tggctgctgc tgttgataac ggtatgcttg gctctatcga cgctaaccgc    900

ggtgactacc agaacggttg ggatactgac cagttcccta tcgacaactt cgagcttatt    960

caggctatga tgcagattat ccgcaacggt ggtcttggca acggtggtac aaacttcgac   1020

gctaagactc gtcgtaactc aactgacctt gaggatatct tcatcgcaca catcgctggt   1080

atggatgcaa tggctcgcgc tcttgagaac gcagcagacc ttttggagaa ctctccaatc   1140

aagaagatgg ttgctgagcg ttacgcttca ttcgacagcg gcaagggtaa ggagttcgag   1200
```

gaaggcaagt tgagccttgg ggacatcgtt gcttatgcta agcagaacgg tgagcctaag 1260
cagacaagcg gtaagcagga gctttacgag gctatcgtaa acatgtactg ctaa 1314

<210> SEQ ID NO 16
<211> LENGTH: 437
<212> TYPE: PRT
<213> ORGANISM: Unknown
<220> FEATURE:
<223> OTHER INFORMATION: Obtained from environmental sample

<400> SEQUENCE: 16

Met Ala Lys Glu Tyr Phe Pro Gly Val Lys Lys Ile Gln Phe Glu Gly
1 5 10 15

Lys Asp Ser Lys Asn Pro Met Ala Tyr Arg Tyr Tyr Asp Ala Glu Lys
20 25 30

Val Ile Met Gly Lys Lys Met Lys Asp Trp Leu Lys Phe Ala Met Ala
35 40 45

Trp Trp His Thr Leu Cys Ala Glu Gly Ala Asp Gln Phe Gly Gly Gly
50 55 60

Thr Lys Thr Phe Pro Trp Asn Glu Gly Ala Asn Ala Leu Glu Val Ala
65 70 75 80

Lys Asn Lys Ala Asp Ala Gly Phe Glu Ile Met Glu Lys Leu Gly Ile
85 90 95

Glu Tyr Tyr Cys Phe His Asp Val Asp Leu Val Glu Glu Ala Ala Thr
100 105 110

Ile Glu Glu Tyr Glu Ala Asn Met Lys Ala Ile Val Ala Tyr Leu Lys
115 120 125

Glu Lys Gln Ala Ala Thr Gly Lys Lys Leu Leu Trp Gly Thr Ala Asn
130 135 140

Val Phe Gly Asn Lys Arg Tyr Met Asn Gly Ala Ser Thr Asn Pro Asp
145 150 155 160

Phe Asp Val Val Ala Arg Ala Cys Val Gln Ile Lys Asn Ala Ile Asp
165 170 175

Ala Thr Ile Glu Leu Gly Gly Thr Asn Tyr Val Phe Trp Gly Gly Arg
180 185 190

Glu Gly Tyr Met Ser Leu Leu Asn Thr Asp Met Lys Arg Glu Lys Glu
195 200 205

His Met Ala Thr Met Leu Thr Lys Ala Arg Asp Tyr Ala Arg Ser Lys
210 215 220

Gly Phe Thr Gly Thr Phe Leu Ile Glu Pro Lys Pro Met Glu Pro Ser
225 230 235 240

Lys His Gln Tyr Asp Val Asp Thr Glu Thr Val Cys Gly Phe Leu Arg
245 250 255

Ala His Gly Leu Asp Lys Asp Phe Lys Val Asn Ile Glu Val Asn His
260 265 270

Ala Thr Leu Ala Gly His Thr Phe Glu His Glu Leu Ala Ala Ala Val
275 280 285

Asp Asn Gly Met Leu Gly Ser Ile Asp Ala Asn Arg Gly Asp Tyr Gln
290 295 300

Asn Gly Trp Asp Thr Asp Gln Phe Pro Ile Asp Asn Phe Glu Leu Ile
305 310 315 320

Gln Ala Met Met Gln Ile Ile Arg Asn Gly Gly Leu Gly Asn Gly Gly
325 330 335

Thr Asn Phe Asp Ala Lys Thr Arg Arg Asn Ser Thr Asp Leu Glu Asp

```
            340                 345                 350

Ile Phe Ile Ala His Ile Ala Gly Met Asp Ala Met Ala Arg Ala Leu
        355                 360                 365

Glu Asn Ala Ala Asp Leu Leu Glu Asn Ser Pro Ile Lys Lys Met Val
    370                 375                 380

Ala Glu Arg Tyr Ala Ser Phe Asp Ser Gly Lys Gly Lys Glu Phe Glu
385                 390                 395                 400

Glu Gly Lys Leu Ser Leu Gly Asp Ile Val Ala Tyr Ala Lys Gln Asn
                405                 410                 415

Gly Glu Pro Lys Gln Thr Ser Gly Lys Gln Glu Leu Tyr Glu Ala Ile
            420                 425                 430

Val Asn Met Tyr Cys
        435
```

<210> SEQ ID NO 17
<211> LENGTH: 1317
<212> TYPE: DNA
<213> ORGANISM: Unknown
<220> FEATURE:
<223> OTHER INFORMATION: Obtained from environmental sample

<400> SEQUENCE: 17

```
atggcgacaa aagaatactt tcccggaata gggaaaatca agtttgaggg tgtgaatagc     60

tataatccgc tggcatacag atattacgat gccgagcgca tagtccttgg caagccgatg    120

aaggagtggc tcaagtttgc catggcatgg tggcacacac tctgcgcaga gggtggcgac    180

cagtttggcg gcggtacgaa gaattttccc tggaatggag atcccgatcc ggtacaggcc    240

gcaaaaaaca aagtagacgc cggcttcgaa ttcatgacca agatgggaat agagtatttc    300

tgtttccacg acgtggatct cgtcagcgag gcagcaacca tcgaggagta tgaggccaac    360

ctgaaggaag tggtgggcta catcaaggaa aagcaggccg agacggggat caaaaacctc    420

tggggcactg ccaacgtgtt cagccacgcg cgctacatga acggagccgc caccaacccc    480

gacttcgatg tagtggcccg cgcagccgtg cagatcaaga atgctatcga cgccacgata    540

gccttaggtg gcaccaacta cgtgttctgg ggtggccgtg aaggttacat gagcctgctc    600

aacaccgacc agaagcgcga gaaggagcat ctggcaatga tgctccgcat ggcccgcgac    660

tatgcgcgtg caaaaggctt caccggcacc ttccttatcg agcccaagcc gatggagccc    720

accaagcacc agtatgatgt agacaccgag actgtgatag gcttcctccg tgcccacggc    780

ctcgacaagg acttcaaggt caacatagag gtgaaccacg ccaccctggc cggccatacc    840

ttcgagcatg agctggcagt ggccgtggac aacggtatgc tcggcagcat cgacgccaac    900

cgcggtgact accagaacgg ctgggatacc gaccagttcc ccatcgacaa ctacgagctg    960

acccaggcca tgatgcagat aatacgcaac ggcggcttcg gcaacggcgg atgcaacttc   1020

gacgccaaga cacgccgcaa ctccaccgac ctggaggata tcttcatagc ccacatagca   1080

ggcatggacg ccatggcccg cgccctgctc agcgcagcag aagtgctgga gaaatcgccc   1140

tacaggaaga tgctcgccga gcgctacgca ccgtttgatg ccggccaggg aaaggcattt   1200

gaagagggcg caatgtcgct caccgacctt gtggagtatg ccaaggagca tggcgagccc   1260

acacagactt ccggcaagca ggaactctat gaggcaatcg tcaatatgta ttgctaa      1317
```

<210> SEQ ID NO 18
<211> LENGTH: 438
<212> TYPE: PRT
<213> ORGANISM: Unknown

-continued

<220> FEATURE:
<223> OTHER INFORMATION: Obtained from environmental sample

<400> SEQUENCE: 18

```
Met Ala Thr Lys Glu Tyr Phe Pro Gly Ile Gly Lys Ile Lys Phe Glu
1               5                   10                  15

Gly Val Asn Ser Tyr Asn Pro Leu Ala Tyr Arg Tyr Tyr Asp Ala Glu
            20                  25                  30

Arg Ile Val Leu Gly Lys Pro Met Lys Glu Trp Leu Lys Phe Ala Met
        35                  40                  45

Ala Trp Trp His Thr Leu Cys Ala Glu Gly Gly Asp Gln Phe Gly Gly
    50                  55                  60

Gly Thr Lys Asn Phe Pro Trp Asn Gly Asp Pro Asp Pro Val Gln Ala
65                  70                  75                  80

Ala Lys Asn Lys Val Asp Ala Gly Phe Glu Phe Met Thr Lys Met Gly
                85                  90                  95

Ile Glu Tyr Phe Cys Phe His Asp Val Asp Leu Val Ser Glu Ala Ala
            100                 105                 110

Thr Ile Glu Glu Tyr Glu Ala Asn Leu Lys Glu Val Val Gly Tyr Ile
        115                 120                 125

Lys Glu Lys Gln Ala Glu Thr Gly Ile Lys Asn Leu Trp Gly Thr Ala
    130                 135                 140

Asn Val Phe Ser His Ala Arg Tyr Met Asn Gly Ala Ala Thr Asn Pro
145                 150                 155                 160

Asp Phe Asp Val Val Ala Arg Ala Ala Val Gln Ile Lys Asn Ala Ile
                165                 170                 175

Asp Ala Thr Ile Ala Leu Gly Gly Thr Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Leu Ala Met Met Leu Arg Met Ala Arg Asp Tyr Ala Arg Ala
    210                 215                 220

Lys Gly Phe Thr Gly Thr Phe Leu Ile Glu Pro Lys Pro Met Glu Pro
225                 230                 235                 240

Thr Lys His Gln Tyr Asp Val Asp Thr Glu Thr Val Ile Gly Phe Leu
                245                 250                 255

Arg Ala His Gly Leu Asp Lys Asp Phe Lys Val Asn Ile Glu Val Asn
            260                 265                 270

His Ala Thr Leu Ala Gly His Thr Phe Glu His Glu Leu Ala Val Ala
        275                 280                 285

Val Asp Asn Gly Met Leu Gly Ser Ile Asp Ala Asn Arg Gly Asp Tyr
    290                 295                 300

Gln Asn Gly Trp Asp Thr Asp Gln Phe Pro Ile Asp Asn Tyr Glu Leu
305                 310                 315                 320

Thr Gln Ala Met Met Gln Ile Ile Arg Asn Gly Gly Phe Gly Asn Gly
                325                 330                 335

Gly Cys Asn Phe Asp Ala Lys Thr Arg Arg Asn Ser Thr Asp Leu Glu
            340                 345                 350

Asp Ile Phe Ile Ala His Ile Ala Gly Met Asp Ala Met Ala Arg Ala
        355                 360                 365

Leu Leu Ser Ala Ala Glu Val Leu Glu Lys Ser Pro Tyr Arg Lys Met
    370                 375                 380

Leu Ala Glu Arg Tyr Ala Pro Phe Asp Ala Gly Gln Gly Lys Ala Phe
385                 390                 395                 400
```

Glu Glu Gly Ala Met Ser Leu Thr Asp Leu Val Glu Tyr Ala Lys Glu
405 410 415

His Gly Glu Pro Thr Gln Thr Ser Gly Lys Gln Glu Leu Tyr Glu Ala
420 425 430

Ile Val Asn Met Tyr Cys
435

<210> SEQ ID NO 19
<211> LENGTH: 1320
<212> TYPE: DNA
<213> ORGANISM: Unknown
<220> FEATURE:
<223> OTHER INFORMATION: Obtained from environmental sample

<400> SEQUENCE: 19
atggcaacaa aggaatattt tccccatata gggaagatcc agttcaaagg cacggaatcg 60
tacgatccga tgtcgtatcg ttactatgac gccgagcgcg tagttctggg caagcccatg 120
aaggaatggc tgaaattcgc catggcatgg tggcacacat tgtgcgccga gggcggcgac 180
cagttcggcg gcggaacgaa gaagttcccc tggaacgagg gcgaggacgc catgaccatc 240
gccaagcaga aggctgacgc cggcttcgag atcatgcaga agctcggcat cgagtatttc 300
tgcttccacg acatcgacct gatcggcgac ctgggcgacg acatcgagga ctatgagaac 360
cgtatgcacg aaatcaccgc acacctgaag gagaagatgg ccgccacggg catcaagaac 420
ctgtggggca ctgccaacgt gttcggccac gcacgctata tgaacggcgc cgccaccaac 480
cccgacttcg acgttgtggc acgcgcatgt gtgcagatca agaacgccat cgacgccacc 540
atcgctctag gcggtacaaa ctatgtattc tggggcggcc gcgagggcta catgagcctg 600
ctgaacaccg accagaagcg cgagaaagag cacttggcta ccatgctgac catggcacgc 660
gactatgccc gcgccaatgg cttcaccgga acgttcctga tcgagcccaa acccatggag 720
cccagcaagc atcagtatga tgtggatacc gagaccgtaa tcggcttcct gaaggcccac 780
aacctggaca aggacttcaa ggtgaacatc gaggtgaacc atgccactct ggccggccac 840
acattcgagc atgagctggc agtagccgtg gacaacggca tgctgggcag catcgacgcc 900
aaccgcggcg actatcagaa cggctgggac accgaccagt tccccatcga caactatgag 960
ctgacccagg ccatgatgca gataatccgc aacggtggcc tcggcaacgg cggtaccaac 1020
ttcgacgcca agacacgtcg caactccacc gacctggacg acatcttcat cgctcacatc 1080
gccggtatgg acgctatggc ccgcgctccg ctcagcgcag ccgacgtgct tgagaagtcg 1140
ccttacaaga agatgctggc cgaccgctac gcttcattcg acagcggcga gggcaagaag 1200
ttcgaggaag gcaagatgac tctggaggat gtcgtggcct acgccaagaa gaatcccgaa 1260
cccgctcaga ccagcggcaa gcaggaactc tacgaggcca tcatcaacat gtacgcctga 1320

<210> SEQ ID NO 20
<211> LENGTH: 439
<212> TYPE: PRT
<213> ORGANISM: Unknown
<220> FEATURE:
<223> OTHER INFORMATION: Obtained from environmental sample

<400> SEQUENCE: 20

Met Ala Thr Lys Glu Tyr Phe Pro His Ile Gly Lys Ile Gln Phe Lys
1 5 10 15

Gly Thr Glu Ser Tyr Asp Pro Met Ser Tyr Arg Tyr Tyr Asp Ala Glu
20 25 30

-continued

Arg Val Val Leu Gly Lys Pro Met Lys Glu Trp Leu Lys Phe Ala Met
        35                  40                  45

Ala Trp Trp His Thr Leu Cys Ala Glu Gly Gly Asp Gln Phe Gly Gly
    50                  55                  60

Gly Thr Lys Lys Phe Pro Trp Asn Glu Gly Glu Asp Ala Met Thr Ile
65                  70                  75                  80

Ala Lys Gln Lys Ala Asp Ala Gly Phe Glu Ile Met Gln Lys Leu Gly
                85                  90                  95

Ile Glu Tyr Phe Cys Phe His Asp Ile Asp Leu Ile Gly Asp Leu Gly
            100                 105                 110

Asp Asp Ile Glu Asp Tyr Glu Asn Arg Met His Glu Ile Thr Ala His
        115                 120                 125

Leu Lys Glu Lys Met Ala Ala Thr Gly Ile Lys Asn Leu Trp Gly Thr
    130                 135                 140

Ala Asn Val Phe Gly His Ala Arg Tyr Met Asn Gly Ala Ala Thr Asn
145                 150                 155                 160

Pro Asp Phe Asp Val Val Ala Arg Ala Cys Val Gln Ile Lys Asn Ala
                165                 170                 175

Ile Asp Ala Thr Ile Ala Leu Gly Gly Thr Asn Tyr Val Phe Trp Gly
            180                 185                 190

Gly Arg Glu Gly Tyr Met Ser Leu Leu Asn Thr Asp Gln Lys Arg Glu
        195                 200                 205

Lys Glu His Leu Ala Thr Met Leu Thr Met Ala Arg Asp Tyr Ala Arg
    210                 215                 220

Ala Asn Gly Phe Thr Gly Thr Phe Leu Ile Glu Pro Lys Pro Met Glu
225                 230                 235                 240

Pro Ser Lys His Gln Tyr Asp Val Asp Thr Glu Thr Val Ile Gly Phe
                245                 250                 255

Leu Lys Ala His Asn Leu Asp Lys Asp Phe Lys Val Asn Ile Glu Val
            260                 265                 270

Asn His Ala Thr Leu Ala Gly His Thr Phe Glu His Glu Leu Ala Val
        275                 280                 285

Ala Val Asp Asn Gly Met Leu Gly Ser Ile Asp Ala Asn Arg Gly Asp
    290                 295                 300

Tyr Gln Asn Gly Trp Asp Thr Asp Gln Phe Pro Ile Asp Asn Tyr Glu
305                 310                 315                 320

Leu Thr Gln Ala Met Met Gln Ile Ile Arg Asn Gly Gly Leu Gly Asn
                325                 330                 335

Gly Gly Thr Asn Phe Asp Ala Lys Thr Arg Arg Asn Ser Thr Asp Leu
            340                 345                 350

Asp Asp Ile Phe Ile Ala His Ile Ala Gly Met Asp Ala Met Ala Arg
        355                 360                 365

Ala Pro Leu Ser Ala Ala Asp Val Leu Glu Lys Ser Pro Tyr Lys Lys
    370                 375                 380

Met Leu Ala Asp Arg Tyr Ala Ser Phe Asp Ser Gly Glu Gly Lys Lys
385                 390                 395                 400

Phe Glu Glu Gly Lys Met Thr Leu Glu Asp Val Val Ala Tyr Ala Lys
                405                 410                 415

Lys Asn Pro Glu Pro Ala Gln Thr Ser Gly Lys Gln Glu Leu Tyr Glu
            420                 425                 430

Ala Ile Ile Asn Met Tyr Ala
        435

<210> SEQ ID NO 21
<211> LENGTH: 1320
<212> TYPE: DNA
<213> ORGANISM: Unknown
<220> FEATURE:
<223> OTHER INFORMATION: Obtained from environmental sample

<400> SEQUENCE: 21

```
atggcaacaa aagaattttt tcccgagatt ggtaaaatca agtttgaggg ccgcgaaagc      60

cgcaatcccc tcgcattccg ctactacggc cccgagaaag tcgttcttgg caagaagatg     120

aaagactggt tcaagtttgc gatggcttgg tggcacacac tgtgcgccca gggcaccgac     180

cagtttggtg gcgacaccaa gcagtttccg tggaacactg ccagtgaccc catgcaggcc     240

gccaaggata aggtggatgc cggatttgaa ttcatgacca agatgggcat tgagtacttc     300

tgcttccacg atgtggatct cgtcgccgag gccgccactg tcgaggagta tgaggctaac     360

ctcaagacca tcgtcgccta catcaaagag aaacaagccg agaccggcat caagaacctg     420

tggggcacag ccaacgtatt cggacacaaa cgctacatga acggtgccgc caccaacccc     480

gactttgatg tcgtggcacg cgccatcgtg caaatcaaga acgccatcga cgccaccatc     540

gagttgggcg gcacgagtta cgtcttttgg ggcggccgcg agggccacat gagcctgctc     600

aacaccgacc agaagcgcga gaaggagcac cttgcacgca tgctgaccat ggcacgcgac     660

tatgcccgcg cacgtggttt caacggcacc ttcctcatcg agcccaagcc catggagccg     720

accaagcacc aatatgatgt ggacaccgag accgtcatcg gtttcctgcg tgcccatggt     780

ctggacaagg acttcaaggt caacatcgag gtgaaccacg ctacactggc cggacacacc     840

ttcgagcgcg aactggcagt ggccgtcgac aacggtctac tcggctcaat cgacgccaac     900

cgtggtgact atcagaatgg ttgggacacc gatcagttcc ccatcgacca ctatgagttg     960

gttcagggca tgttgcagat tatccgcaat ggtggtttca ccgacggtgg caccaacttc    1020

gatgccaaga cccgccgcaa ctcgaccgac ctcgaggaca tcttcatcgc ccacatcgcc    1080

gcgatggatg ccatggctca tgcgctggag agtgctgcct ccatcatcga ggagtcgccc    1140

tactgccaga tggtcaagga tcgctatgcc tcatttgact ccggcatcgg caaggacttt    1200

gaggacggca agttgacact ggaacaagcc tacgagtacg gtaagcaagt gggcgaaccc    1260

aagcagacca gtggcaagca agaactgtac gagtcaatca tcaatatgta ttccatttaa    1320
```

<210> SEQ ID NO 22
<211> LENGTH: 439
<212> TYPE: PRT
<213> ORGANISM: Unknown
<220> FEATURE:
<223> OTHER INFORMATION: Obtained from environmental sample

<400> SEQUENCE: 22

```
Met Ala Thr Lys Glu Phe Phe Pro Glu Ile Gly Lys Ile Lys Phe Glu
1               5                   10                  15

Gly Arg Glu Ser Arg Asn Pro Leu Ala Phe Arg Tyr Tyr Gly Pro Glu
            20                  25                  30

Lys Val Val Leu Gly Lys Lys Met Lys Asp Trp Phe Lys Phe Ala Met
        35                  40                  45

Ala Trp Trp His Thr Leu Cys Ala Gln Gly Thr Asp Gln Phe Gly Gly
    50                  55                  60

Asp Thr Lys Gln Phe Pro Trp Asn Thr Ala Ser Asp Pro Met Gln Ala
65                  70                  75                  80
```

-continued

```
Ala Lys Asp Lys Val Asp Ala Gly Phe Glu Phe Met Thr Lys Met Gly
                85                  90                  95

Ile Glu Tyr Phe Cys Phe His Asp Val Asp Leu Val Ala Glu Ala Ala
            100                 105                 110

Thr Val Glu Glu Tyr Glu Ala Asn Leu Lys Thr Ile Val Ala Tyr Ile
        115                 120                 125

Lys Glu Lys Gln Ala Glu Thr Gly Ile Lys Asn Leu Trp Gly Thr Ala
    130                 135                 140

Asn Val Phe Gly His Lys Arg Tyr Met Asn Gly Ala Ala Thr Asn Pro
145                 150                 155                 160

Asp Phe Asp Val Val Ala Arg Ala Ile Val Gln Ile Lys Asn Ala Ile
                165                 170                 175

Asp Ala Thr Ile Glu Leu Gly Gly Thr Ser Tyr Val Phe Trp Gly Gly
            180                 185                 190

Arg Glu Gly His Met Ser Leu Leu Asn Thr Asp Gln Lys Arg Glu Lys
        195                 200                 205

Glu His Leu Ala Arg Met Leu Thr Met Ala Arg Asp Tyr Ala Arg Ala
    210                 215                 220

Arg Gly Phe Asn Gly Thr Phe Leu Ile Glu Pro Lys Pro Met Glu Pro
225                 230                 235                 240

Thr Lys His Gln Tyr Asp Val Asp Thr Glu Thr Val Ile Gly Phe Leu
                245                 250                 255

Arg Ala His Gly Leu Asp Lys Asp Phe Lys Val Asn Ile Glu Val Asn
            260                 265                 270

His Ala Thr Leu Ala Gly His Thr Phe Glu Arg Glu Leu Ala Val Ala
        275                 280                 285

Val Asp Asn Gly Leu Leu Gly Ser Ile Asp Ala Asn Arg Gly Asp Tyr
    290                 295                 300

Gln Asn Gly Trp Asp Thr Asp Gln Phe Pro Ile Asp His Tyr Glu Leu
305                 310                 315                 320

Val Gln Gly Met Leu Gln Ile Ile Arg Asn Gly Gly Phe Thr Asp Gly
                325                 330                 335

Gly Thr Asn Phe Asp Ala Lys Thr Arg Arg Asn Ser Thr Asp Leu Glu
            340                 345                 350

Asp Ile Phe Ile Ala His Ile Ala Ala Met Asp Ala Met Ala His Ala
        355                 360                 365

Leu Glu Ser Ala Ala Ser Ile Ile Glu Glu Ser Pro Tyr Cys Gln Met
    370                 375                 380

Val Lys Asp Arg Tyr Ala Ser Phe Asp Ser Gly Ile Gly Lys Asp Phe
385                 390                 395                 400

Glu Asp Gly Lys Leu Thr Leu Glu Gln Ala Tyr Glu Tyr Gly Lys Gln
                405                 410                 415

Val Gly Glu Pro Lys Gln Thr Ser Gly Lys Gln Glu Leu Tyr Glu Ser
            420                 425                 430

Ile Ile Asn Met Tyr Ser Ile
        435
```

<210> SEQ ID NO 23
<211> LENGTH: 1317
<212> TYPE: DNA
<213> ORGANISM: Unknown
<220> FEATURE:
<223> OTHER INFORMATION: Obtained from environmental sample

<400> SEQUENCE: 23

-continued

```
atggcaacaa aagagtattt tcctggtata ggaaagatta aatttgaagg taaagagagt      60
aagaatccga tggcattccg ctattatgat gccaataaag taatcatggg caagaagatg     120
agcgagtggc tgaagtttgc catggcttgg tggcacacat tgtgcgccga aggtggtgac     180
cagtttggtg gtggaacaaa gactttcccg tggaacgatt cggacaacgc cgtagaagca     240
gccaaccata aagtagatgc cggttttgaa tttatgcaga aaatgggcat cgaatactat     300
tgcttccatg atgtagacct ctgcactgaa gctgctacca ttgaagaata tgaagccaat     360
ctgaaggaaa tagtagccta tccgaaacag aaacaggctg aaacaggtat caaacttctg     420
tggggtacgg caaatgtatt tggtcacaaa cgctatatga atggtgctgc taccaatccg     480
gattttgatg tagtggctcg tgctgctgta cagattaaga atgcgataga cgctacaatt     540
gaactcggtg gtagcaacta cgtgttctgg ggcggccgtg aaggttatat gagcttgctc     600
aatacagacc agaaacgtga gaaagagcat ttggcacaaa tgttgaccat ggctcgtgac     660
tatgctcgtg ccaaaggatt caagggtacc ttcctggttg aacccaaacc gatggaacca     720
actaaacacc agtatgatgt agatacggaa actgtaatcg gcttcctcaa ggctcataat     780
ttggataagg atttcaaggt aaatattgaa gtaaaccatg ctacattggc cggtcatact     840
tttgaacacg aattggctgt tgccgtagac aacgatatgc ttggctctat cgatgccaac     900
cgcggtgact atcagaacgg ttgggatact gaccagttcc ccattgacaa cttcgagctt     960
atccaagcca tgatgcagat tattcgcggt ggtggcttca aagatggtgg tacaaacttc    1020
gacgctaaga ctcgtcgtaa ctctaccgac ctggaagata ttttcattgc acacatcgct    1080
ggtatggatg ctatggcacg tgctttggaa agtgcagcca agttgcttga ggaatctcct    1140
tataagaaaa tgttggctga ccgctatgca tcgttcgata gtggcaaagg taaggagttt    1200
gaagaaggca agctgacatt ggaagacgtt gtagtttatg ccaagcagaa tggcgagcct    1260
aaacagacca gcggtaagca ggaattgtat gaggcaattg taaatatgta tgcctga       1317
```

```
<210> SEQ ID NO 24
<211> LENGTH: 438
<212> TYPE: PRT
<213> ORGANISM: Unknown
<220> FEATURE:
<223> OTHER INFORMATION: Obtained from environmental sample

<400> SEQUENCE: 24

Met Ala Thr Lys Glu Tyr Phe Pro Gly Ile Gly Lys Ile Lys Phe Glu
1               5                   10                  15

Gly Lys Glu Ser Lys Asn Pro Met Ala Phe Arg Tyr Tyr Asp Ala Asn
            20                  25                  30

Lys Val Ile Met Gly Lys Lys Met Ser Glu Trp Leu Lys Phe Ala Met
        35                  40                  45

Ala Trp Trp His Thr Leu Cys Ala Glu Gly Gly Asp Gln Phe Gly Gly
    50                  55                  60

Gly Thr Lys Thr Phe Pro Trp Asn Asp Ser Asp Asn Ala Val Glu Ala
65                  70                  75                  80

Ala Asn His Lys Val Asp Ala Gly Phe Glu Phe Met Gln Lys Met Gly
                85                  90                  95

Ile Glu Tyr Tyr Cys Phe His Asp Val Asp Leu Cys Thr Glu Ala Ala
            100                 105                 110

Thr Ile Glu Glu Tyr Glu Ala Asn Leu Lys Glu Ile Val Ala Tyr Pro
        115                 120                 125

Lys Gln Lys Gln Ala Glu Thr Gly Ile Lys Leu Leu Trp Gly Thr Ala
```

130 135 140

Asn Val Phe Gly His Lys Arg Tyr Met Asn Gly Ala Ala Thr Asn Pro
145 150 155 160

Asp Phe Asp Val Val Ala Arg Ala Ala Val Gln Ile Lys Asn Ala Ile
165 170 175

Asp Ala Thr Ile Glu Leu Gly Gly Ser Asn Tyr Val Phe Trp Gly Gly
180 185 190

Arg Glu Gly Tyr Met Ser Leu Leu Asn Thr Asp Gln Lys Arg Glu Lys
195 200 205

Glu His Leu Ala Gln Met Leu Thr Met Ala Arg Asp Tyr Ala Arg Ala
210 215 220

Lys Gly Phe Lys Gly Thr Phe Leu Val Glu Pro Lys Pro Met Glu Pro
225 230 235 240

Thr Lys His Gln Tyr Asp Val Asp Thr Glu Thr Val Ile Gly Phe Leu
245 250 255

Lys Ala His Asn Leu Asp Lys Asp Phe Lys Val Asn Ile Glu Val Asn
260 265 270

His Ala Thr Leu Ala Gly His Thr Phe Glu His Glu Leu Ala Val Ala
275 280 285

Val Asp Asn Asp Met Leu Gly Ser Ile Asp Ala Asn Arg Gly Asp Tyr
290 295 300

Gln Asn Gly Trp Asp Thr Asp Gln Phe Pro Ile Asp Asn Phe Glu Leu
305 310 315 320

Ile Gln Ala Met Met Gln Ile Ile Arg Gly Gly Gly Phe Lys Asp Gly
325 330 335

Gly Thr Asn Phe Asp Ala Lys Thr Arg Arg Asn Ser Thr Asp Leu Glu
340 345 350

Asp Ile Phe Ile Ala His Ile Ala Gly Met Asp Ala Met Ala Arg Ala
355 360 365

Leu Glu Ser Ala Ala Lys Leu Leu Glu Glu Ser Pro Tyr Lys Lys Met
370 375 380

Leu Ala Asp Arg Tyr Ala Ser Phe Asp Ser Gly Lys Gly Lys Glu Phe
385 390 395 400

Glu Glu Gly Lys Leu Thr Leu Glu Asp Val Val Val Tyr Ala Lys Gln
405 410 415

Asn Gly Glu Pro Lys Gln Thr Ser Gly Lys Gln Glu Leu Tyr Glu Ala
420 425 430

Ile Val Asn Met Tyr Ala
435

<210> SEQ ID NO 25
<211> LENGTH: 1317
<212> TYPE: DNA
<213> ORGANISM: Unknown
<220> FEATURE:
<223> OTHER INFORMATION: Obtained from environmental sample

<400> SEQUENCE: 25
atggcaacaa aagagtattt tcctggaata ggaaagatta aatttgaagg aaaagagagt 60
aagaacccga tggcattccg ttgctacgat gcagaaaaag ttatcatggg taagagaatg 120
aaagattggt tgaagtttgc aatggcgtgg tggcatacac tttgtgcaga aggcggtgac 180
caattcggtg gcggtacaaa gagtttcccc cggaacgact atactgataa aattcaggct 240
gctaaaaaca agatggatgc cggttttgag tttatgcaga agatggggat cgaatactat 300

-continued

```
tgttttcacg atgtagacct ctgcacggaa gctgatacca ttgaagaata cgaagctaat    360

ttgaaagaaa tcgtagttta cgcaaagcaa aagcaggtag aaacaggtat caaattattg    420

tggggtactg ccaatgtatt cggtcatgaa cgctatatga atggtgcggc taccaaccca    480

gattttgatg ttgtagcccg tgctgctgtt cagattaaga atgcaattga tgctaccatt    540

gaactaggtg gcttaaacta tgtgttctgg ggtggacgcg aaggttatat gtctttgctg    600

aacactgatc agaaacgtga gaaagaacat cttgcacaaa tgctgaccat tgcccgtgac    660

tatgcccgtg cccgtggctt caaaggtaca ttcttggttg aaccgaaacc gatggaacca    720

accaaacatc aatatgacgt agatacagaa acagttatcg gtttttgaa agctcatgct    780

ttggataaag actttaaagt aaatattgaa gtaaatcatg caacattagc cggtcataca    840

tttgaacacg aactggcagt ggctgtcgac aacggtatgc tgggttctat tgacgctaat    900

cgtggtgatt gtcaaaacgg ttgggataca gaccaatttc ccattgataa ctatgaactg    960

actcaagcca tgatgcagat tattcgtaac ggtggtttgg gcaatggtgg tacgaatttt   1020

gacgctaaaa ctcgccgtaa ttctactgat cttggagata tcttcattgc tcacatcgca   1080

ggtatggatg ctatggcacg tgcattggaa agtgcggcca agttgttgga agaatctccc   1140

tataagaaga tgctggcaga acgttatgca tcctttgaca gcggtaaggg taaagagttt   1200

gaagagggta agttgacctt ggaggatctt gttgcttatg caaaagtcaa tggcgaaccg   1260

aaacaaatca gtggtaaaca agaattgtat gaggcaattg tgaatatgta ttgctaa      1317
```

<210> SEQ ID NO 26
<211> LENGTH: 438
<212> TYPE: PRT
<213> ORGANISM: Unknown
<220> FEATURE:
<223> OTHER INFORMATION: Obtained from environmental sample

<400> SEQUENCE: 26

```
Met Ala Thr Lys Glu Tyr Phe Pro Gly Ile Gly Lys Ile Lys Phe Glu
1               5                   10                  15

Gly Lys Glu Ser Lys Asn Pro Met Ala Phe Arg Cys Tyr Asp Ala Glu
            20                  25                  30

Lys Val Ile Met Gly Lys Arg Met Lys Asp Trp Leu Lys Phe Ala Met
        35                  40                  45

Ala Trp Trp His Thr Leu Cys Ala Glu Gly Gly Asp Gln Phe Gly Gly
    50                  55                  60

Gly Thr Lys Ser Phe Pro Arg Asn Asp Tyr Thr Asp Lys Ile Gln Ala
65                  70                  75                  80

Ala Lys Asn Lys Met Asp Ala Gly Phe Glu Phe Met Gln Lys Met Gly
                85                  90                  95

Ile Glu Tyr Tyr Cys Phe His Asp Val Asp Leu Cys Thr Glu Ala Asp
            100                 105                 110

Thr Ile Glu Glu Tyr Glu Ala Asn Leu Lys Glu Ile Val Val Tyr Ala
        115                 120                 125

Lys Gln Lys Gln Val Glu Thr Gly Ile Lys Leu Leu Trp Gly Thr Ala
    130                 135                 140

Asn Val Phe Gly His Glu Arg Tyr Met Asn Gly Ala Ala Thr Asn Pro
145                 150                 155                 160

Asp Phe Asp Val Val Ala Arg Ala Ala Val Gln Ile Lys Asn Ala Ile
                165                 170                 175

Asp Ala Thr Ile Glu Leu Gly Gly Leu Asn Tyr Val Phe Trp Gly Gly
            180                 185                 190
```

```
Arg Glu Gly Tyr Met Ser Leu Leu Asn Thr Asp Gln Lys Arg Glu Lys
        195                 200                 205

Glu His Leu Ala Gln Met Leu Thr Ile Ala Arg Asp Tyr Ala Arg Ala
    210                 215                 220

Arg Gly Phe Lys Gly Thr Phe Leu Val Glu Pro Lys Pro Met Glu Pro
225                 230                 235                 240

Thr Lys His Gln Tyr Asp Val Asp Thr Glu Thr Val Ile Gly Phe Leu
                245                 250                 255

Lys Ala His Ala Leu Asp Lys Asp Phe Lys Val Asn Ile Glu Val Asn
            260                 265                 270

His Ala Thr Leu Ala Gly His Thr Phe Glu His Glu Leu Ala Val Ala
        275                 280                 285

Val Asp Asn Gly Met Leu Gly Ser Ile Asp Ala Asn Arg Gly Asp Cys
    290                 295                 300

Gln Asn Gly Trp Asp Thr Asp Gln Phe Pro Ile Asp Asn Tyr Glu Leu
305                 310                 315                 320

Thr Gln Ala Met Met Gln Ile Ile Arg Asn Gly Gly Leu Gly Asn Gly
                325                 330                 335

Gly Thr Asn Phe Asp Ala Lys Thr Arg Arg Asn Ser Thr Asp Leu Gly
            340                 345                 350

Asp Ile Phe Ile Ala His Ile Ala Gly Met Asp Ala Met Ala Arg Ala
        355                 360                 365

Leu Glu Ser Ala Ala Lys Leu Leu Glu Glu Ser Pro Tyr Lys Lys Met
    370                 375                 380

Leu Ala Glu Arg Tyr Ala Ser Phe Asp Ser Gly Lys Gly Lys Glu Phe
385                 390                 395                 400

Glu Glu Gly Lys Leu Thr Leu Glu Asp Leu Val Ala Tyr Ala Lys Val
                405                 410                 415

Asn Gly Glu Pro Lys Gln Ile Ser Gly Lys Gln Glu Leu Tyr Glu Ala
            420                 425                 430

Ile Val Asn Met Tyr Cys
        435
```

<210> SEQ ID NO 27
<211> LENGTH: 1317
<212> TYPE: DNA
<213> ORGANISM: Unknown
<220> FEATURE:
<223> OTHER INFORMATION: Obtained from environmental sample

<400> SEQUENCE: 27

```
atggcaacaa aagagtattt tcccggaata ggaaagatta aattcgaagg taaagagagc      60

aagaacccga tggcattccg ttattacgat gccgataaag taatcatggg taagaaaatg     120

agcgaatggc tgaagttcgc catggcatgg tggcacactc tttgcgcaga aggtggtgac     180

cagttcggtg gcggaacaaa gaaattcccc tggaacggtg aggctgacaa ggttcaggct     240

gccaagaaca aaatggacgc cggctttgaa ttcatgcaga aaatgggtat cgaatactac     300

tgcttccacg atgtagacct ctgcgaagaa gccgagacca ttgaagaata cgaagccaac     360

ttgaaggaaa tcgtagcgta tgccaagcag aaacaagcag aaaccggcat caagctgttg     420

tggggtactg ccaacgtatt cggccatgcc cgctacatga atggtgcagc caccaacccc     480

gatttcgatg ttgtggcacg tgcagccgtc caaatcaaaa gcgccatcga cgctactatc     540

gagctgggag gttcgaacta tgtgttctgg ggcggtcgcg aaggctacat gtcattgctg     600
```

aatacagacc agaagcgtga gaaagagcac ctcgcacaga tgttgaccat cgcccgcgac 660
tatgcccgtg cccgtggctt caaaggtacc ttcctgattg aaccgaaacc gatggaacct 720
acaaaacacc agtatgatgt agacaccgaa accgttatcg gcttcttgaa ggcccacaat 780
ctggacaaag atttcaaggt aaacatcgaa gtgaaccacg ctactttggc gggccacacc 840
ttcgagcacg aactcgcagt agccgtagac aacggtatgc tcggctccat cgatgccaac 900
cgtggtgact accagaacgg ctgggataca gaccagttcc ccattgacaa cttcgaactg 960
acccaggcaa tgatgcaaat catccgtaac ggcggctttg gcaatggcgg tacaaacttc 1020
gatgccaaga cccgtcgtaa ctccaccgac ctggaagaca tcttcattgc ccacatcgcc 1080
ggtatggacg tgatggcacg tgcactggaa agtgcagcca aattgcttga agagtctcct 1140
tacaagaaga tgcttgccga ccgctatgct tccttcgaca gtggtaaagg caaggaattc 1200
gaagacggca agctgacact ggaggatttg gcagcttacg caaaagccaa cggtgagccg 1260
aaacagacca gcggcaagca gggattgtat gaggcaatcg taaatatgta ctgctga 1317

<210> SEQ ID NO 28
<211> LENGTH: 438
<212> TYPE: PRT
<213> ORGANISM: Unknown
<220> FEATURE:
<223> OTHER INFORMATION: Obtained from environmental sample

<400> SEQUENCE: 28

Met Ala Thr Lys Glu Tyr Phe Pro Gly Ile Gly Lys Ile Lys Phe Glu
1 5 10 15

Gly Lys Glu Ser Lys Asn Pro Met Ala Phe Arg Tyr Tyr Asp Ala Asp
20 25 30

Lys Val Ile Met Gly Lys Lys Met Ser Glu Trp Leu Lys Phe Ala Met
35 40 45

Ala Trp Trp His Thr Leu Cys Ala Glu Gly Gly Asp Gln Phe Gly Gly
50 55 60

Gly Thr Lys Lys Phe Pro Trp Asn Gly Glu Ala Asp Lys Val Gln Ala
65 70 75 80

Ala Lys Asn Lys Met Asp Ala Gly Phe Glu Phe Met Gln Lys Met Gly
85 90 95

Ile Glu Tyr Tyr Cys Phe His Asp Val Asp Leu Cys Glu Glu Ala Glu
100 105 110

Thr Ile Glu Glu Tyr Glu Ala Asn Leu Lys Glu Ile Val Ala Tyr Ala
115 120 125

Lys Gln Lys Gln Ala Glu Thr Gly Ile Lys Leu Leu Trp Gly Thr Ala
130 135 140

Asn Val Phe Gly His Ala Arg Tyr Met Asn Gly Ala Ala Thr Asn Pro
145 150 155 160

Asp Phe Asp Val Val Ala Arg Ala Ala Val Gln Ile Lys Ser Ala Ile
165 170 175

Asp Ala Thr Ile Glu Leu Gly Gly Ser Asn Tyr Val Phe Trp Gly Gly
180 185 190

Arg Glu Gly Tyr Met Ser Leu Leu Asn Thr Asp Gln Lys Arg Glu Lys
195 200 205

Glu His Leu Ala Gln Met Leu Thr Ile Ala Arg Asp Tyr Ala Arg Ala
210 215 220

Arg Gly Phe Lys Gly Thr Phe Leu Ile Glu Pro Lys Pro Met Glu Pro
225 230 235 240

```
Thr Lys His Gln Tyr Asp Val Asp Thr Glu Thr Val Ile Gly Phe Leu
                245                 250                 255

Lys Ala His Asn Leu Asp Lys Asp Phe Lys Val Asn Ile Glu Val Asn
            260                 265                 270

His Ala Thr Leu Ala Gly His Thr Phe Glu His Glu Leu Ala Val Ala
        275                 280                 285

Val Asp Asn Gly Met Leu Gly Ser Ile Asp Ala Asn Arg Gly Asp Tyr
    290                 295                 300

Gln Asn Gly Trp Asp Thr Asp Gln Phe Pro Ile Asp Asn Phe Glu Leu
305                 310                 315                 320

Thr Gln Ala Met Met Gln Ile Ile Arg Asn Gly Gly Phe Gly Asn Gly
                325                 330                 335

Gly Thr Asn Phe Asp Ala Lys Thr Arg Arg Asn Ser Thr Asp Leu Glu
            340                 345                 350

Asp Ile Phe Ile Ala His Ile Ala Gly Met Asp Val Met Ala Arg Ala
        355                 360                 365

Leu Glu Ser Ala Ala Lys Leu Leu Glu Glu Ser Pro Tyr Lys Lys Met
    370                 375                 380

Leu Ala Asp Arg Tyr Ala Ser Phe Asp Ser Gly Lys Gly Lys Glu Phe
385                 390                 395                 400

Glu Asp Gly Lys Leu Thr Leu Glu Asp Leu Ala Ala Tyr Ala Lys Ala
                405                 410                 415

Asn Gly Glu Pro Lys Gln Thr Ser Gly Lys Gln Gly Leu Tyr Glu Ala
            420                 425                 430

Ile Val Asn Met Tyr Cys
        435
```

<210> SEQ ID NO 29
<211> LENGTH: 1314
<212> TYPE: DNA
<213> ORGANISM: Unknown
<220> FEATURE:
<223> OTHER INFORMATION: Obtained from environmental sample

<400> SEQUENCE: 29

```
atgacaaaag agtattttcc aaccattggt aaaattcagt ttgaaggtaa agagagtaag     60

aatccattag catatcgtta ttacgatgct aacaaagtaa taatgggtaa aaagatgagc    120

gaatggctca agtttgcaat ggcatggtgg cacactttgt gtgctgaggg tagcgaccag    180

tttggtcctg gcaccaagtc attcccatgg aacgcatcaa ccgaccgtat gcaggctgca    240

aaagataagg ctgacgcagg cttcgaaatc atgcaaaaac tgggcatcga atactactgt    300

ttccatgatg ttgacctcat cgacccagca gacgatattc caacatacga aaagaatctc    360

aaggaaatcg ttgcatacct caagcaaaaa caggccgaga caggtatcaa attgctatgg    420

ggtacagcta acgtatttgg ccacaagcgt tatatgaacg gtgcatctac caatcctgac    480

tttgacgttg ttgcacgagc tatcgtgcaa atcaagaatg ctatcgatgc aacaatcgaa    540

ctgggcggca cgaactacgt attctggggt ggtcgcgaag gttacatgtc actgctcaac    600

accgaccaaa agcgcgagaa agagcacatg gctaccatgt taggaatggc acgtgactat    660

gcacgttcta aaggctttac tggtactctc cttatcgagc caaagcctat ggaaccaact    720

aagcatcaat acgacgtcga tacagaaact gttattggtt tcctcaaagc tcacggatta    780

gacaaggact tcaaggtaaa tatcgaagtg aaccacgcta cattggctgg ccataccttc    840

gaacatgaat tagcatgtgc tgttgatgca ggtatgcttg gttccatcga tgctaaccgt    900
```

-continued ggtgatatgc agaatggctg ggatacagat cagttcccta tcaacaatta cgagctcgtt 960
caggccatga tgcagattat ccgcaatggt ggtttcggta acggtggtac aaacttcgac 1020
gctaagacac gtcgtaattc aaccgatttg gaagacatca tcattgctca cgtttcagct 1080
atggatgcta tggcacgtgc tcttgaatgt gctgcagaca ttcttcaaaa ctcacctatt 1140
ccacagatgg tggccaaccg ttatgcaagt tttgacaagg gtataggtaa agatttcgaa 1200
gacggcaagc tcaccctcga gcaagtatac gaatatggta agaccgtcgg cgaaccagct 1260
attacaagcg gcaaacagga gctctacgaa gctatcgtta atatgtattg ctga 1314

<210> SEQ ID NO 30
<211> LENGTH: 437
<212> TYPE: PRT
<213> ORGANISM: Unknown
<220> FEATURE:
<223> OTHER INFORMATION: Obtained from environmental sample

<400> SEQUENCE: 30

Met Thr Lys Glu Tyr Phe Pro Thr Ile Gly Lys Ile Gln Phe Glu Gly
1 5 10 15

Lys Glu Ser Lys Asn Pro Leu Ala Tyr Arg Tyr Tyr Asp Ala Asn Lys
20 25 30

Val Ile Met Gly Lys Lys Met Ser Glu Trp Leu Lys Phe Ala Met Ala
35 40 45

Trp Trp His Thr Leu Cys Ala Glu Gly Ser Asp Gln Phe Gly Pro Gly
50 55 60

Thr Lys Ser Phe Pro Trp Asn Ala Ser Thr Asp Arg Met Gln Ala Ala
65 70 75 80

Lys Asp Lys Ala Asp Ala Gly Phe Glu Ile Met Gln Lys Leu Gly Ile
85 90 95

Glu Tyr Tyr Cys Phe His Asp Val Asp Leu Ile Asp Pro Ala Asp Asp
100 105 110

Ile Pro Thr Tyr Glu Lys Asn Leu Lys Glu Ile Val Ala Tyr Leu Lys
115 120 125

Gln Lys Gln Ala Glu Thr Gly Ile Lys Leu Leu Trp Gly Thr Ala Asn
130 135 140

Val Phe Gly His Lys Arg Tyr Met Asn Gly Ala Ser Thr Asn Pro Asp
145 150 155 160

Phe Asp Val Val Ala Arg Ala Ile Val Gln Ile Lys Asn Ala Ile Asp
165 170 175

Ala Thr Ile Glu Leu Gly Gly Thr Asn Tyr Val Phe Trp Gly Gly Arg
180 185 190

Glu Gly Tyr Met Ser Leu Leu Asn Thr Asp Gln Lys Arg Glu Lys Glu
195 200 205

His Met Ala Thr Met Leu Gly Met Ala Arg Asp Tyr Ala Arg Ser Lys
210 215 220

Gly Phe Thr Gly Thr Leu Leu Ile Glu Pro Lys Pro Met Glu Pro Thr
225 230 235 240

Lys His Gln Tyr Asp Val Asp Thr Glu Thr Val Ile Gly Phe Leu Lys
245 250 255

Ala His Gly Leu Asp Lys Asp Phe Lys Val Asn Ile Glu Val Asn His
260 265 270

Ala Thr Leu Ala Gly His Thr Phe Glu His Glu Leu Ala Cys Ala Val
275 280 285

Asp Ala Gly Met Leu Gly Ser Ile Asp Ala Asn Arg Gly Asp Met Gln

-continued

```
    290                 295                 300

Asn Gly Trp Asp Thr Asp Gln Phe Pro Ile Asn Asn Tyr Glu Leu Val
305                 310                 315                 320

Gln Ala Met Met Gln Ile Ile Arg Asn Gly Gly Phe Gly Asn Gly Gly
                325                 330                 335

Thr Asn Phe Asp Ala Lys Thr Arg Arg Asn Ser Thr Asp Leu Glu Asp
            340                 345                 350

Ile Ile Ile Ala His Val Ser Ala Met Asp Ala Met Ala Arg Ala Leu
        355                 360                 365

Glu Cys Ala Ala Asp Ile Leu Gln Asn Ser Pro Ile Pro Gln Met Val
    370                 375                 380

Ala Asn Arg Tyr Ala Ser Phe Asp Lys Gly Ile Gly Lys Asp Phe Glu
385                 390                 395                 400

Asp Gly Lys Leu Thr Leu Glu Gln Val Tyr Glu Tyr Gly Lys Thr Val
                405                 410                 415

Gly Glu Pro Ala Ile Thr Ser Gly Lys Gln Glu Leu Tyr Glu Ala Ile
            420                 425                 430

Val Asn Met Tyr Cys
        435
```

<210> SEQ ID NO 31
<211> LENGTH: 1317
<212> TYPE: DNA
<213> ORGANISM: Unknown
<220> FEATURE:
<223> OTHER INFORMATION: Obtained from environmental sample

<400> SEQUENCE: 31

```
atggctaaca aagaattttt ccccggtatt ggtaaaatca aattcgaagg taaagagagc     60

aagaacccca tggcatatcg ttactacgat gctgagaagg tagtccttgg caagaatatg    120

aaagactggt tcaagtttgc gatggcttgg tggcacacat tgtgcgccga gggtagcgac    180

cagtttggtc ccggcactaa gtctttcccc tggaacaccg cagagtgccc catgcaggca    240

gctaaggaca aggttgacgc tggcttcgag ttcatgacca agatgggtat tgaatacttc    300

tgcttccacg atgtagacct cgttgccgag gccgacactg ttgaggagta cgaggctcgc    360

atgaaggaaa tcgttgctta catcaaggag aaggtggccg agactggcat caagaacctg    420

tggggtacag ctaacgtatt tggcaacaag cgctacatga acggtgctgc tactaacccc    480

gactttgacg ttgtggctcg cgctatcgtt caaatcaaga acgctatcga cgctactatc    540

gagctcggtg gtacgtcata cgtattctgg ggcggccgcg agggttacat gagcctcttg    600

aacaccgacc agaagcgtga gaaagagcac ctggctacta tgctcactat ggcacgcgac    660

tacgctcgcg ctaagggttt caagggtaca ttcctcatcg agcccaagcc catggagccc    720

acaaagcacc agtacgatgt tgacactgag actgtaatcg gcttccttaa ggcacacaac    780

cttgacaagg acttcaaggt taacattgag gttaaccacg caactctcgc tggtcacaca    840

tttgagcacg agctcgcttg tgctgttgac gctggcatgc ttggcagcat cgacgctaac    900

cgcggtgact accagaacgg ctgggatact gaccaattcc ccatcgacaa cttcgacctc    960

actcaagcta tgctcgagat catccgcaac gatggtttca aggatggtgg tacaaacttc   1020

gacgctaaga ctcgccgcaa cagcaccgac ctcgaggata tcttcatcgc acacatcgct   1080

gctatggacg ctatggcacg tgctctcgag agcgctgctg cagtactcga ggagtcagct   1140

ctgccccaaa tgaagaagga ccgctatgca tcgttcgacg ctggcatggg taaggacttc   1200
```

gaggacggca agctcaccct ggagcaagtt tacgagtatg gtaagaaggt gggcgagccc 1260
aagcagacta gcggcaagca agagctgtat gaggctatcc tcaacatgta cgtataa 1317

<210> SEQ ID NO 32
<211> LENGTH: 438
<212> TYPE: PRT
<213> ORGANISM: Unknown
<220> FEATURE:
<223> OTHER INFORMATION: Obtained from environmental sample

<400> SEQUENCE: 32

Met Ala Asn Lys Glu Phe Phe Pro Gly Ile Gly Lys Ile Lys Phe Glu
1 5 10 15

Gly Lys Glu Ser Lys Asn Pro Met Ala Tyr Arg Tyr Tyr Asp Ala Glu
20 25 30

Lys Val Val Leu Gly Lys Asn Met Lys Asp Trp Phe Lys Phe Ala Met
35 40 45

Ala Trp Trp His Thr Leu Cys Ala Glu Gly Ser Asp Gln Phe Gly Pro
50 55 60

Gly Thr Lys Ser Phe Pro Trp Asn Thr Ala Glu Cys Pro Met Gln Ala
65 70 75 80

Ala Lys Asp Lys Val Asp Ala Gly Phe Glu Phe Met Thr Lys Met Gly
85 90 95

Ile Glu Tyr Phe Cys Phe His Asp Val Asp Leu Val Ala Glu Ala Asp
100 105 110

Thr Val Glu Glu Tyr Glu Ala Arg Met Lys Glu Ile Val Ala Tyr Ile
115 120 125

Lys Glu Lys Val Ala Glu Thr Gly Ile Lys Asn Leu Trp Gly Thr Ala
130 135 140

Asn Val Phe Gly Asn Lys Arg Tyr Met Asn Gly Ala Ala Thr Asn Pro
145 150 155 160

Asp Phe Asp Val Val Ala Arg Ala Ile Val Gln Ile Lys Asn Ala Ile
165 170 175

Asp Ala Thr Ile Glu Leu Gly Gly Thr Ser Tyr Val Phe Trp Gly Gly
180 185 190

Arg Glu Gly Tyr Met Ser Leu Leu Asn Thr Asp Gln Lys Arg Glu Lys
195 200 205

Glu His Leu Ala Thr Met Leu Thr Met Ala Arg Asp Tyr Ala Arg Ala
210 215 220

Lys Gly Phe Lys Gly Thr Phe Leu Ile Glu Pro Lys Pro Met Glu Pro
225 230 235 240

Thr Lys His Gln Tyr Asp Val Asp Thr Glu Thr Val Ile Gly Phe Leu
245 250 255

Lys Ala His Asn Leu Asp Lys Asp Phe Lys Val Asn Ile Glu Val Asn
260 265 270

His Ala Thr Leu Ala Gly His Thr Phe Glu His Glu Leu Ala Cys Ala
275 280 285

Val Asp Ala Gly Met Leu Gly Ser Ile Asp Ala Asn Arg Gly Asp Tyr
290 295 300

Gln Asn Gly Trp Asp Thr Asp Gln Phe Pro Ile Asp Asn Phe Asp Leu
305 310 315 320

Thr Gln Ala Met Leu Glu Ile Ile Arg Asn Asp Gly Phe Lys Asp Gly
325 330 335

Gly Thr Asn Phe Asp Ala Lys Thr Arg Arg Asn Ser Thr Asp Leu Glu
340 345 350

```
Asp Ile Phe Ile Ala His Ile Ala Ala Met Asp Ala Met Ala Arg Ala
        355                 360                 365

Leu Glu Ser Ala Ala Ala Val Leu Glu Glu Ser Ala Leu Pro Gln Met
    370                 375                 380

Lys Lys Asp Arg Tyr Ala Ser Phe Asp Ala Gly Met Gly Lys Asp Phe
385                 390                 395                 400

Glu Asp Gly Lys Leu Thr Leu Glu Gln Val Tyr Glu Tyr Gly Lys Lys
                405                 410                 415

Val Gly Glu Pro Lys Gln Thr Ser Gly Lys Gln Glu Leu Tyr Glu Ala
            420                 425                 430

Ile Leu Asn Met Tyr Val
        435


<210> SEQ ID NO 33
<211> LENGTH: 1317
<212> TYPE: DNA
<213> ORGANISM: Unknown
<220> FEATURE:
<223> OTHER INFORMATION: Obtained from environmental sample

<400> SEQUENCE: 33

atggctaaca aagaattttt cccaggtatt ggtaaaatca aattcgaagg caaagaaagc      60

aagaacccca tggcatatcg tcactacgat gccgagaagg tagtccttgg taagaagatg     120

aaggactggt tcaagtttgc gatggcttgg tggcacactc tgtgcgccga gggtagcgac     180

cagttcggcc ccgtgaccaa gtctttcccc tggaaccagg ccgagtgccc catgcaggct     240

gctaaggaca aggttgacgc cggcttcgag ttcatgacca agatgggtat cgaatacttc     300

tgtttccacg atgtagacct cgttgccgag gccgacaccg ttgaggagta cgaagctcgc     360

atgaaggaaa tcgtggctta catcaaggag aagatggccg agaccggcat caagaacctg     420

tggggtacag ccaacgtatt cggcaacaag cgctacatga acggtgctgc caccaacccc     480

gactttgacg ttgtggctcg cgcaatcgtt cagatcaaga acgccatcga cgctactatc     540

gagctcggcg gtacctctta cgtgttctgg ggcggccgcg agggttacat gactctcttg     600

aacaccgacc agaagcgcga gaaggagcac ctggctacca tgctcaccat ggctcgcgac     660

tatgctcgcg ctaagggctt caagggtaca ttccttatcg agcccaagcc catggagccc     720

accaagcacc agtatgacgt ggataccgag accgttatcg gcttcctcaa ggctcacggc     780

ctggacaagg acttcaaggt gaacatcgag gttaaccatg caactctcgc cggccacaca     840

ttcgagcacg aactcgcttg cgctgttgac gctggcatgc tgggcagcat cgacgctaac     900

cgcggcgact accagaacgg ctgggatacc gaccagttcc ccatcgacaa cttcgacctc     960

actcaggcta tgctcgagat catccgcaac ggtggtttca aggacggtgg tacaaacttc    1020

gacgctaaga cccgtcgcaa cagcaccgat cttgaggaca tcttcatcgc tcacatcgct    1080

gctatggacg caatggcacg cgcgctcgag agcgctgccg ctgtgctcga gcagagcccc    1140

cttccccaga tgaagaaaga ccgctacgca tcgttcgatg ccggcatggg caaggacttc    1200

gaggacggca agctcactct ggagcaggtt tacgagtatg gtaagaaggt aggcgagccc    1260

aagcagacca gcggcaagca ggaactgtac gaggctatcc tcaacatgta tgtataa       1317


<210> SEQ ID NO 34
<211> LENGTH: 438
<212> TYPE: PRT
<213> ORGANISM: Unknown
<220> FEATURE:
```

<223> OTHER INFORMATION: Obtained from environmental sample

<400> SEQUENCE: 34

```
Met Ala Asn Lys Glu Phe Phe Pro Gly Ile Gly Lys Ile Lys Phe Glu
1               5                   10                  15

Gly Lys Glu Ser Lys Asn Pro Met Ala Tyr Arg His Tyr Asp Ala Glu
            20                  25                  30

Lys Val Val Leu Gly Lys Lys Met Lys Asp Trp Phe Lys Phe Ala Met
        35                  40                  45

Ala Trp Trp His Thr Leu Cys Ala Glu Gly Ser Asp Gln Phe Gly Pro
    50                  55                  60

Val Thr Lys Ser Phe Pro Trp Asn Gln Ala Glu Cys Pro Met Gln Ala
65                  70                  75                  80

Ala Lys Asp Lys Val Asp Ala Gly Phe Glu Phe Met Thr Lys Met Gly
                85                  90                  95

Ile Glu Tyr Phe Cys Phe His Asp Val Asp Leu Val Ala Glu Ala Asp
            100                 105                 110

Thr Val Glu Glu Tyr Glu Ala Arg Met Lys Glu Ile Val Ala Tyr Ile
        115                 120                 125

Lys Glu Lys Met Ala Glu Thr Gly Ile Lys Asn Leu Trp Gly Thr Ala
    130                 135                 140

Asn Val Phe Gly Asn Lys Arg Tyr Met Asn Gly Ala Ala Thr Asn Pro
145                 150                 155                 160

Asp Phe Asp Val Val Ala Arg Ala Ile Val Gln Ile Lys Asn Ala Ile
                165                 170                 175

Asp Ala Thr Ile Glu Leu Gly Gly Thr Ser Tyr Val Phe Trp Gly Gly
            180                 185                 190

Arg Glu Gly Tyr Met Thr Leu Leu Asn Thr Asp Gln Lys Arg Glu Lys
        195                 200                 205

Glu His Leu Ala Thr Met Leu Thr Met Ala Arg Asp Tyr Ala Arg Ala
    210                 215                 220

Lys Gly Phe Lys Gly Thr Phe Leu Ile Glu Pro Lys Pro Met Glu Pro
225                 230                 235                 240

Thr Lys His Gln Tyr Asp Val Asp Thr Glu Thr Val Ile Gly Phe Leu
                245                 250                 255

Lys Ala His Gly Leu Asp Lys Asp Phe Lys Val Asn Ile Glu Val Asn
            260                 265                 270

His Ala Thr Leu Ala Gly His Thr Phe Glu His Glu Leu Ala Cys Ala
        275                 280                 285

Val Asp Ala Gly Met Leu Gly Ser Ile Asp Ala Asn Arg Gly Asp Tyr
    290                 295                 300

Gln Asn Gly Trp Asp Thr Asp Gln Phe Pro Ile Asp Asn Phe Asp Leu
305                 310                 315                 320

Thr Gln Ala Met Leu Glu Ile Ile Arg Asn Gly Gly Phe Lys Asp Gly
                325                 330                 335

Gly Thr Asn Phe Asp Ala Lys Thr Arg Arg Asn Ser Thr Asp Leu Glu
            340                 345                 350

Asp Ile Phe Ile Ala His Ile Ala Ala Met Asp Ala Met Ala Arg Ala
        355                 360                 365

Leu Glu Ser Ala Ala Ala Val Leu Glu Gln Ser Pro Leu Pro Gln Met
    370                 375                 380

Lys Lys Asp Arg Tyr Ala Ser Phe Asp Ala Gly Met Gly Lys Asp Phe
385                 390                 395                 400
```

```
Glu Asp Gly Lys Leu Thr Leu Glu Gln Val Tyr Glu Tyr Gly Lys Lys
                405                 410                 415

Val Gly Glu Pro Lys Gln Thr Ser Gly Lys Gln Glu Leu Tyr Glu Ala
            420                 425                 430

Ile Leu Asn Met Tyr Val
        435


<210> SEQ ID NO 35
<211> LENGTH: 1320
<212> TYPE: DNA
<213> ORGANISM: Unknown
<220> FEATURE:
<223> OTHER INFORMATION: Obtained from environmental sample

<400> SEQUENCE: 35

atgaaagaat attttcctat gacaaaaaaa gttgaatatg agggcgcagc atctaaaaat     60

ccatttgcgt ttaaatacta tgatgccgaa agaattatag caggcaagcc tatgaaagaa    120

catcttaaat ttgctatgag ttggtggcat acactttgtg cgggcggtgc agacccattt    180

ggcacaacaa ctatggacag aacatacggc ggacttaccg acccaatgga aattgcaaag    240

gcaaaagtag atgcaggctt tgagtttatg caaaaactcg gtatagagta tttttgtttt    300

cacgatgcgg atattgcacc ggaaggaagc agttttgttg aaacaaagaa aaacttttgg    360

gaaatagtag attatataca gcaaaagatg aatgaaacag gcataaagtt gctttggggt    420

actgcaaact gctttaatgc tccacgttat atgcacggtg caggaacatc atgcaatgcg    480

cacagttttg catatgcagc cgcacagata aaaaatgcaa ttgaagctac cgttaaactg    540

ggtggaaaag gctatgtttt ctggggcgga agagagggtt atgaaacact tctcaatacg    600

gatatggcac ttgaacttga caatatggca agacttatgc atatggcagt tgattatggc    660

agaagcattg gttttgacgg tgatttttat atcgaaccaa agccaaagga accaacaaaa    720

catcaatatg actttgactc ggcaactgtt ttgggatttt tgagaaagta cggtttagat    780

aaggatttta aacttaatat agaggcaaat catgcgacac ttgcaggtca tacatttgaa    840

catgaattga ctgtagcgcg tataaacggt gcatttggca gcatagatgc aaatagcggc    900

gatcccaatc ttggctggga taccgaccaa ttcccaacag atgtttattc ggcaacccct    960

tgtatgcttg aagtgataag agcaggcggc tttacaaacg gaggtcttaa ttttgatgca   1020

aaggtcagaa gaggctcatt tacgtttgat gacattgttt atgcatatat cagcggtatg   1080

gacacttttg cgctgggttt tataaaggca tatgaaataa ttgaggacgg cagaatagat   1140

gaatttgtaa aagaaagata cgcaagctat aatacaggca taggcaaaga tattatagat   1200

ggaaaggcaa gccttgaaag tttggaagaa tatattcttt caaatgataa tgttgtaatg   1260

caaagcggca gacaggaata tcttgaaaca gttttgaata atattttgtt taaagcataa   1320


<210> SEQ ID NO 36
<211> LENGTH: 439
<212> TYPE: PRT
<213> ORGANISM: Unknown
<220> FEATURE:
<223> OTHER INFORMATION: Obtained from environmental sample

<400> SEQUENCE: 36

Met Lys Glu Tyr Phe Pro Met Thr Lys Lys Val Glu Tyr Glu Gly Ala
1               5                   10                  15

Ala Ser Lys Asn Pro Phe Ala Phe Lys Tyr Tyr Asp Ala Glu Arg Ile
            20                  25                  30
```

-continued

```
Ile Ala Gly Lys Pro Met Lys Glu His Leu Lys Phe Ala Met Ser Trp
        35                  40                  45

Trp His Thr Leu Cys Ala Gly Gly Ala Asp Pro Phe Gly Thr Thr Thr
    50                  55                  60

Met Asp Arg Thr Tyr Gly Gly Leu Thr Asp Pro Met Glu Ile Ala Lys
65                  70                  75                  80

Ala Lys Val Asp Ala Gly Phe Glu Phe Met Gln Lys Leu Gly Ile Glu
                85                  90                  95

Tyr Phe Cys Phe His Asp Ala Asp Ile Ala Pro Glu Gly Ser Ser Phe
            100                 105                 110

Val Glu Thr Lys Lys Asn Phe Trp Glu Ile Val Asp Tyr Ile Gln Gln
        115                 120                 125

Lys Met Asn Glu Thr Gly Ile Lys Leu Leu Trp Gly Thr Ala Asn Cys
    130                 135                 140

Phe Asn Ala Pro Arg Tyr Met His Gly Ala Gly Thr Ser Cys Asn Ala
145                 150                 155                 160

His Ser Phe Ala Tyr Ala Ala Ala Gln Ile Lys Asn Ala Ile Glu Ala
                165                 170                 175

Thr Val Lys Leu Gly Gly Lys Gly Tyr Val Phe Trp Gly Gly Arg Glu
            180                 185                 190

Gly Tyr Glu Thr Leu Leu Asn Thr Asp Met Ala Leu Glu Leu Asp Asn
        195                 200                 205

Met Ala Arg Leu Met His Met Ala Val Asp Tyr Gly Arg Ser Ile Gly
    210                 215                 220

Phe Asp Gly Asp Phe Tyr Ile Glu Pro Lys Pro Lys Glu Pro Thr Lys
225                 230                 235                 240

His Gln Tyr Asp Phe Asp Ser Ala Thr Val Leu Gly Phe Leu Arg Lys
                245                 250                 255

Tyr Gly Leu Asp Lys Asp Phe Lys Leu Asn Ile Glu Ala Asn His Ala
            260                 265                 270

Thr Leu Ala Gly His Thr Phe Glu His Glu Leu Thr Val Ala Arg Ile
        275                 280                 285

Asn Gly Ala Phe Gly Ser Ile Asp Ala Asn Ser Gly Asp Pro Asn Leu
    290                 295                 300

Gly Trp Asp Thr Asp Gln Phe Pro Thr Asp Val Tyr Ser Ala Thr Leu
305                 310                 315                 320

Cys Met Leu Glu Val Ile Arg Ala Gly Gly Phe Thr Asn Gly Gly Leu
                325                 330                 335

Asn Phe Asp Ala Lys Val Arg Arg Gly Ser Phe Thr Phe Asp Asp Ile
            340                 345                 350

Val Tyr Ala Tyr Ile Ser Gly Met Asp Thr Phe Ala Leu Gly Phe Ile
        355                 360                 365

Lys Ala Tyr Glu Ile Ile Glu Asp Gly Arg Ile Asp Glu Phe Val Lys
    370                 375                 380

Glu Arg Tyr Ala Ser Tyr Asn Thr Gly Ile Gly Lys Asp Ile Ile Asp
385                 390                 395                 400

Gly Lys Ala Ser Leu Glu Ser Leu Glu Glu Tyr Ile Leu Ser Asn Asp
                405                 410                 415

Asn Val Val Met Gln Ser Gly Arg Gln Glu Tyr Leu Glu Thr Val Leu
            420                 425                 430

Asn Asn Ile Leu Phe Lys Ala
        435
```

<210> SEQ ID NO 37
<211> LENGTH: 1323
<212> TYPE: DNA
<213> ORGANISM: Unknown
<220> FEATURE:
<223> OTHER INFORMATION: Obtained from environmental sample

<400> SEQUENCE: 37
atgaaagaaa ttttcccaaa tattcctgag attaaattcg aaggaaaaga cagcaaaaat 60
ccttttgctt tccattacta caacccagac caaatcatct taggcaaacc aatgaaagaa 120
cacctcccat tcgctatggc ttggtggcac aatcttggtg caacaggtgt tgatatgttt 180
ggcgctggcc cagctgataa gagtttcggt gctaaagttg gcacaatgga acacgctaag 240
gccaaagtcg atgccggttt cgaattcatg aagaaactcg gtatcagata tttctgcttc 300
catgatgttg acttagttcc agaatgtgca gatatcaaag atacaaacaa agaattagat 360
gaaatcagtg actacatctt agaaaagatg aaaggcacag atattaagtg tttatggggc 420
accgccaata tgttctctaa cccacgcttc tgcaatggtg cgggttccac aaacagtgcg 480
gatgtcttcg ctttcgccgc tgctcaagtt aagaaagcct tagatatcac cgttaaatta 540
ggtggtaggg gttacgtctt ctggggtggt cgtgaaggtt acgaaacatt actcaataca 600
gacgttaaat tcgaacaaga aaacattgct cgtttaatga agatggctgt tgaatatggc 660
cgttccatcg gtttcaaagg cgatttctat atcgaaccaa aaccaaaaga accaatgaaa 720
caccaatatg acttcgacgc cgctacagct attggcttct taagagccca cggcttagac 780
aaagacttca agttgaacat cgaagctaac cacgctacat tagcgggtca tacattccaa 840
cacgatttaa gaatctccgc cattaatggt atgttaggtt ctatcgatgc taaccaaggc 900
gatatgctct taggttggga tacagacgaa ttcccatttg atgtctacag tgcgacacaa 960
tgtatgtacg aagtcttaaa gaatggtggt cttacaggtg gtttcaactt tgactccaaa 1020
acacgtcgtc catcctacac aatggaagat atgttcttag cctatatctt aggtatggat 1080
acattcgctt taggtttaat caaagctgct caaatcatcg aagatggccg tattgatcaa 1140
ttcatcgaaa agaaatattc ttccttccgt gaaacagaaa tcggtcaaaa gatcttaaac 1200
aacaagacaa gcttaaaaga attatccgat tacgcttgca agatgggtgc tccagaactt 1260
ccaggtagtg gtcgtcaaga aatgctcgaa gccatcgtta acgatgtctt attcggcaag 1320
taa 1323

<210> SEQ ID NO 38
<211> LENGTH: 440
<212> TYPE: PRT
<213> ORGANISM: Unknown
<220> FEATURE:
<223> OTHER INFORMATION: Obtained from environmental sample

<400> SEQUENCE: 38

Met Lys Glu Ile Phe Pro Asn Ile Pro Glu Ile Lys Phe Glu Gly Lys
1 5 10 15

Asp Ser Lys Asn Pro Phe Ala Phe His Tyr Tyr Asn Pro Asp Gln Ile
20 25 30

Ile Leu Gly Lys Pro Met Lys Glu His Leu Pro Phe Ala Met Ala Trp
35 40 45

Trp His Asn Leu Gly Ala Thr Gly Val Asp Met Phe Gly Ala Gly Pro
50 55 60

Ala Asp Lys Ser Phe Gly Ala Lys Val Gly Thr Met Glu His Ala Lys
65 70 75 80

```
Ala Lys Val Asp Ala Gly Phe Glu Phe Met Lys Lys Leu Gly Ile Arg
                85                  90                  95

Tyr Phe Cys Phe His Asp Val Asp Leu Val Pro Glu Cys Ala Asp Ile
            100                 105                 110

Lys Asp Thr Asn Lys Glu Leu Asp Glu Ile Ser Asp Tyr Ile Leu Glu
        115                 120                 125

Lys Met Lys Gly Thr Asp Ile Lys Cys Leu Trp Gly Thr Ala Asn Met
    130                 135                 140

Phe Ser Asn Pro Arg Phe Cys Asn Gly Ala Gly Ser Thr Asn Ser Ala
145                 150                 155                 160

Asp Val Phe Ala Phe Ala Ala Ala Gln Val Lys Lys Ala Leu Asp Ile
                165                 170                 175

Thr Val Lys Leu Gly Gly Arg Gly Tyr Val Phe Trp Gly Gly Arg Glu
            180                 185                 190

Gly Tyr Glu Thr Leu Leu Asn Thr Asp Val Lys Phe Glu Gln Glu Asn
        195                 200                 205

Ile Ala Arg Leu Met Lys Met Ala Val Glu Tyr Gly Arg Ser Ile Gly
    210                 215                 220

Phe Lys Gly Asp Phe Tyr Ile Glu Pro Lys Pro Lys Glu Pro Met Lys
225                 230                 235                 240

His Gln Tyr Asp Phe Asp Ala Ala Thr Ala Ile Gly Phe Leu Arg Ala
                245                 250                 255

His Gly Leu Asp Lys Asp Phe Lys Leu Asn Ile Glu Ala Asn His Ala
            260                 265                 270

Thr Leu Ala Gly His Thr Phe Gln His Asp Leu Arg Ile Ser Ala Ile
        275                 280                 285

Asn Gly Met Leu Gly Ser Ile Asp Ala Asn Gln Gly Asp Met Leu Leu
    290                 295                 300

Gly Trp Asp Thr Asp Glu Phe Pro Phe Asp Val Tyr Ser Ala Thr Gln
305                 310                 315                 320

Cys Met Tyr Glu Val Leu Lys Asn Gly Gly Leu Thr Gly Gly Phe Asn
                325                 330                 335

Phe Asp Ser Lys Thr Arg Arg Pro Ser Tyr Thr Met Glu Asp Met Phe
            340                 345                 350

Leu Ala Tyr Ile Leu Gly Met Asp Thr Phe Ala Leu Gly Leu Ile Lys
        355                 360                 365

Ala Ala Gln Ile Ile Glu Asp Gly Arg Ile Asp Gln Phe Ile Glu Lys
    370                 375                 380

Lys Tyr Ser Ser Phe Arg Glu Thr Glu Ile Gly Gln Lys Ile Leu Asn
385                 390                 395                 400

Asn Lys Thr Ser Leu Lys Glu Leu Ser Asp Tyr Ala Cys Lys Met Gly
                405                 410                 415

Ala Pro Glu Leu Pro Gly Ser Gly Arg Gln Glu Met Leu Glu Ala Ile
            420                 425                 430

Val Asn Asp Val Leu Phe Gly Lys
        435                 440
```

<210> SEQ ID NO 39
<211> LENGTH: 1323
<212> TYPE: DNA
<213> ORGANISM: Unknown
<220> FEATURE:
<223> OTHER INFORMATION: Obtained from environmental sample

<400> SEQUENCE: 39

```
atgaaagaaa ttttcccaaa tattcctgag attaaattcg aaggaaaaga cagcaaaaat     60
ccttttgctt tccattacta caacccagac caaatcatct taggtaaacc aatgaaagaa    120
cacctcccat tcgctatggc ttggtggcac aatcttggtg caacaggtgt tgatatgttt    180
ggcgctggcc cagctgataa gagtttcggt gctaaagttg gcacaatgga acacgctaag    240
gccaaagtcg atgccggttt cgaattcatg aagaaacttg gtatcagata tttctgcttc    300
catgatgttg acttagttcc agaatgtgca gatatcaaag atacaaacaa agaattagat    360
gaaatcagtg actacatctt agaaaagatg aaaggcacag atatcaagtg tttatggggc    420
accgccaata tgttctctaa cccacgtttc tgcaatggtg cgggttccac aaacagtgcg    480
gatgtcttcg ctttcgccgc tgctcaagtt aagaaagcct tagatatcac cgttaaatta    540
ggtggtaggg gttacgtctt ctggggtggt cgtgaaggtt acgaaacatt actcaataca    600
gacgttaaat tcgaacaaga aaacattgct cgtttaatga agatggctgt tgaatatggc    660
cgttccatcg gtttcaaagg cgatttctat atcgaaccaa aaccaaaaga accaatgaaa    720
caccaatatg acttcgacgc cgctacagct attggcttct taagagccca cggcttagac    780
aaagacttca agttgaacat cgaagctaac cacgctacat tagcgggtca tacattccaa    840
cacgatttaa gaatctccgc cattaatggt atgttaggtt ctatcgatgc taaccaaggc    900
gatatgctct taggttggga tacagacgaa ttcccatttg atgtctacag tgcgacacaa    960
tgtatgtacg aagtcttaaa gaatggtggt cttacaggtg gtttcaactt tgactccaaa   1020
acacgtcgtc catcctacac aatggaagat atgttcttag cctatatctt aggtatggat   1080
acattcgctt taggtttaat caaagctgct caaatcatcg aagatggccg tattgatcaa   1140
ttcatcgaaa agaaatattc ttccttccgt gaaacagaaa tcggtcaaaa gatcttaaac   1200
aacaagacaa gcttaaaaga attatccgat tacgcttgca agatgggtgc tccagaactt   1260
ccaggtagtg gtcgtcaaga aatgctcgaa gccatcgtta acgatgtctt attcggcaag   1320
taa                                                                 1323
```

<210> SEQ ID NO 40
<211> LENGTH: 440
<212> TYPE: PRT
<213> ORGANISM: Unknown
<220> FEATURE:
<223> OTHER INFORMATION: Obtained from environmental sample

<400> SEQUENCE: 40

```
Met Lys Glu Ile Phe Pro Asn Ile Pro Glu Ile Lys Phe Glu Gly Lys
1               5                   10                  15

Asp Ser Lys Asn Pro Phe Ala Phe His Tyr Tyr Asn Pro Asp Gln Ile
            20                  25                  30

Ile Leu Gly Lys Pro Met Lys Glu His Leu Pro Phe Ala Met Ala Trp
        35                  40                  45

Trp His Asn Leu Gly Ala Thr Gly Val Asp Met Phe Gly Ala Gly Pro
    50                  55                  60

Ala Asp Lys Ser Phe Gly Ala Lys Val Gly Thr Met Glu His Ala Lys
65                  70                  75                  80

Ala Lys Val Asp Ala Gly Phe Glu Phe Met Lys Lys Leu Gly Ile Arg
                85                  90                  95

Tyr Phe Cys Phe His Asp Val Asp Leu Val Pro Glu Cys Ala Asp Ile
            100                 105                 110

Lys Asp Thr Asn Lys Glu Leu Asp Glu Ile Ser Asp Tyr Ile Leu Glu
```

```
        115                 120                 125

Lys Met Lys Gly Thr Asp Ile Lys Cys Leu Trp Gly Thr Ala Asn Met
    130                 135                 140

Phe Ser Asn Pro Arg Phe Cys Asn Gly Ala Gly Ser Thr Asn Ser Ala
145                 150                 155                 160

Asp Val Phe Ala Phe Ala Ala Ala Gln Val Lys Lys Ala Leu Asp Ile
                165                 170                 175

Thr Val Lys Leu Gly Gly Arg Gly Tyr Val Phe Trp Gly Gly Arg Glu
            180                 185                 190

Gly Tyr Glu Thr Leu Leu Asn Thr Asp Val Lys Phe Glu Gln Glu Asn
        195                 200                 205

Ile Ala Arg Leu Met Lys Met Ala Val Glu Tyr Gly Arg Ser Ile Gly
    210                 215                 220

Phe Lys Gly Asp Phe Tyr Ile Glu Pro Lys Pro Lys Glu Pro Met Lys
225                 230                 235                 240

His Gln Tyr Asp Phe Asp Ala Ala Thr Ala Ile Gly Phe Leu Arg Ala
                245                 250                 255

His Gly Leu Asp Lys Asp Phe Lys Leu Asn Ile Glu Ala Asn His Ala
            260                 265                 270

Thr Leu Ala Gly His Thr Phe Gln His Asp Leu Arg Ile Ser Ala Ile
        275                 280                 285

Asn Gly Met Leu Gly Ser Ile Asp Ala Asn Gln Gly Asp Met Leu Leu
    290                 295                 300

Gly Trp Asp Thr Asp Glu Phe Pro Phe Asp Val Tyr Ser Ala Thr Gln
305                 310                 315                 320

Cys Met Tyr Glu Val Leu Lys Asn Gly Gly Leu Thr Gly Gly Phe Asn
                325                 330                 335

Phe Asp Ser Lys Thr Arg Arg Pro Ser Tyr Thr Met Glu Asp Met Phe
            340                 345                 350

Leu Ala Tyr Ile Leu Gly Met Asp Thr Phe Ala Leu Gly Leu Ile Lys
        355                 360                 365

Ala Ala Gln Ile Ile Glu Asp Gly Arg Ile Asp Gln Phe Ile Glu Lys
    370                 375                 380

Lys Tyr Ser Ser Phe Arg Glu Thr Glu Ile Gly Gln Lys Ile Leu Asn
385                 390                 395                 400

Asn Lys Thr Ser Leu Lys Glu Leu Ser Asp Tyr Ala Cys Lys Met Gly
                405                 410                 415

Ala Pro Glu Leu Pro Gly Ser Gly Arg Gln Glu Met Leu Glu Ala Ile
            420                 425                 430

Val Asn Asp Val Leu Phe Gly Lys
        435                 440
```

<210> SEQ ID NO 41
<211> LENGTH: 1326
<212> TYPE: DNA
<213> ORGANISM: Unknown
<220> FEATURE:
<223> OTHER INFORMATION: Obtained from environmental sample

<400> SEQUENCE: 41

```
atggaatatt tccctttcgt caaatcggtc caatacaagg gaccaacctc aactgaacca      60

ttcgctttca agtactacga tgccaaccgt gtcgttcttg gaaaaccaat gaaagaatgg     120

atgccattcg ctatggcttg gtggcacaac ctcggcgctg ccggtaccga catgttcggc     180

ggcaacacca tggacaagtc ctggggagtc gataaagaaa aagacccaat gggctatgcc     240
```

-continued

```
aaagccaaag ttgatgccgg cttcgaattc atgcagaaga tgggcatcga atactactgc    300

ttccacgatg tcgacctcgt cccagagtgc gacgacatca ccgttatgta ccagagactc    360

gatgagatcg gtgattacct tctcaagaaa cagaaggaaa ccggtatcaa gcttctttgg    420

tcaaccgcca atgccttcgg acaccgccgt ttcatgaacg gtgctggttc cagcaactcc    480

gccgaagtct attgcttcgc cgccgcccag atcaagaaag ctcttgagct ctgcgtcaaa    540

ctcggtggca aaggctatgt cttctggggt ggacgtgaag gctacgaaac ccttctcaac    600

accgacatga agttcgaaca agagaacatc gccaacctta tgagatgcgc ccgtgactac    660

ggccgcaaga tcggtttcaa aggcgacttc tacatcgaac caaaaccaaa agagccaaca    720

aagcatcagt atgacttcga cgccgctacc gccatcggat tcctccgtca gtacggtctc    780

gacaaagact tcaagatgaa catcgaagcc aaccacgcta ccttagctgg ccacaccttc    840

gaacacgaac tccgcgtctc cgccatgaac ggcatgctcg gttccatcga cgccaacgaa    900

ggcgatatgc tcctcggatg ggatgtcgac cgtttcccag ccaacgtcta tagcgccacc    960

ttcgccatgc tcgaagtcat caaagccggt ggacttaccg gtggcttcaa cttcgacgcc   1020

aagacccgcc gcgcttccaa cacctatgaa gatatgttca aggctttcgt ccttggtatg   1080

gataccttcg ctttaggtct tctcaatgcc gaagccatca tcaaagacgg ccgcatcgac   1140

aagttcgtcg aggatagata tgccagcttc aagaccggca tcggtgctaa ggtccgcgat   1200

cactccgcta cccttgagga tttagctgcc cacgcccttg agaccaaggt ttgcccagat   1260

ccaggcagcg gcgacgagga agaactccag gaaatcctca accagttaat gttcggtaag   1320

aaataa                                                              1326
```

<210> SEQ ID NO 42
<211> LENGTH: 441
<212> TYPE: PRT
<213> ORGANISM: Unknown
<220> FEATURE:
<223> OTHER INFORMATION: Obtained from environmental sample

<400> SEQUENCE: 42

```
Met Glu Tyr Phe Pro Phe Val Lys Ser Val Gln Tyr Lys Gly Pro Thr
1               5                   10                  15

Ser Thr Glu Pro Phe Ala Phe Lys Tyr Tyr Asp Ala Asn Arg Val Val
            20                  25                  30

Leu Gly Lys Pro Met Lys Glu Trp Met Pro Phe Ala Met Ala Trp Trp
        35                  40                  45

His Asn Leu Gly Ala Ala Gly Thr Asp Met Phe Gly Gly Asn Thr Met
    50                  55                  60

Asp Lys Ser Trp Gly Val Asp Lys Glu Lys Asp Pro Met Gly Tyr Ala
65                  70                  75                  80

Lys Ala Lys Val Asp Ala Gly Phe Glu Phe Met Gln Lys Met Gly Ile
                85                  90                  95

Glu Tyr Tyr Cys Phe His Asp Val Asp Leu Val Pro Glu Cys Asp Asp
            100                 105                 110

Ile Thr Val Met Tyr Gln Arg Leu Asp Glu Ile Gly Asp Tyr Leu Leu
        115                 120                 125

Lys Lys Gln Lys Glu Thr Gly Ile Lys Leu Leu Trp Ser Thr Ala Asn
    130                 135                 140

Ala Phe Gly His Arg Arg Phe Met Asn Gly Ala Gly Ser Ser Asn Ser
145                 150                 155                 160
```

-continued

```
Ala Glu Val Tyr Cys Phe Ala Ala Ala Gln Ile Lys Lys Ala Leu Glu
                165                 170                 175

Leu Cys Val Lys Leu Gly Gly Lys Gly Tyr Val Phe Trp Gly Gly Arg
            180                 185                 190

Glu Gly Tyr Glu Thr Leu Leu Asn Thr Asp Met Lys Phe Glu Gln Glu
        195                 200                 205

Asn Ile Ala Asn Leu Met Arg Cys Ala Arg Asp Tyr Gly Arg Lys Ile
    210                 215                 220

Gly Phe Lys Gly Asp Phe Tyr Ile Glu Pro Lys Pro Lys Glu Pro Thr
225                 230                 235                 240

Lys His Gln Tyr Asp Phe Asp Ala Ala Thr Ala Ile Gly Phe Leu Arg
                245                 250                 255

Gln Tyr Gly Leu Asp Lys Asp Phe Lys Met Asn Ile Glu Ala Asn His
            260                 265                 270

Ala Thr Leu Ala Gly His Thr Phe Glu His Glu Leu Arg Val Ser Ala
        275                 280                 285

Met Asn Gly Met Leu Gly Ser Ile Asp Ala Asn Glu Gly Asp Met Leu
    290                 295                 300

Leu Gly Trp Asp Val Asp Arg Phe Pro Ala Asn Val Tyr Ser Ala Thr
305                 310                 315                 320

Phe Ala Met Leu Glu Val Ile Lys Ala Gly Gly Leu Thr Gly Gly Phe
                325                 330                 335

Asn Phe Asp Ala Lys Thr Arg Arg Ala Ser Asn Thr Tyr Glu Asp Met
            340                 345                 350

Phe Lys Ala Phe Val Leu Gly Met Asp Thr Phe Ala Leu Gly Leu Leu
        355                 360                 365

Asn Ala Glu Ala Ile Ile Lys Asp Gly Arg Ile Asp Lys Phe Val Glu
    370                 375                 380

Asp Arg Tyr Ala Ser Phe Lys Thr Gly Ile Gly Ala Lys Val Arg Asp
385                 390                 395                 400

His Ser Ala Thr Leu Glu Asp Leu Ala Ala His Ala Leu Glu Thr Lys
                405                 410                 415

Val Cys Pro Asp Pro Gly Ser Gly Asp Glu Glu Glu Leu Gln Glu Ile
            420                 425                 430

Leu Asn Gln Leu Met Phe Gly Lys Lys
        435                 440
```

<210> SEQ ID NO 43
<211> LENGTH: 1323
<212> TYPE: DNA
<213> ORGANISM: Unknown
<220> FEATURE:
<223> OTHER INFORMATION: Obtained from environmental sample

<400> SEQUENCE: 43

```
atgagcgaat tttttaagaa tattccagag attaaattcg aaggaaaaga tagtaaaaat      60

ccatgggcat tcaagtatta caatcctgaa ttgaccatta tgggtaaaaa aatgtctgaa     120

catcttcctt ttgcaatggc ctggtggcat aaccttggcg caaatggagt tgatatgttc     180

ggttcgggaa ccgccgataa atctttcggt caggctccgg gaactatgga gcacgcaaag     240

gctaaggtag atgcaggtat cgagtttatg aagaaactcg gaatcaagta ctactgctgg     300

catgatgtag accttgttcc tgaagatcca aacgatatca acgtaacaaa caagcgcctt     360

gatgagattt cagattatat ccttgaaaaa acaaagggaa ctgacatcaa gtgtctctgg     420

ggaactgcta acatgttcag taatccccgc tttatgaacg gggcaggctc aacaaactct     480
```

```
gctgacgttt actgctttgc agctgcccag gttaaaaagg ctcttgagat taccgtaaag    540

cttggtggcc gcggttatgt attctggggt ggacgcgaag gttatgaaac tcttcttaat    600

acagatgtaa agcttgaaca ggaaaatatt gcaaacctta tgcacatggc agttgattat    660

ggccgttcaa tcggtttcaa gggagacttc tacatcgagc ctaagccaaa ggagccgatg    720

agtcatcagt atgattttga tgccgcaact gcaatcggct tcctccgcca gtatggcctc    780

gacaaagact ttaagatgaa cattgaggct aaccacgctt ctcttgcaaa tcataccttc    840

cagcatgagc tttatatcag ccgcattaac ggaatgcttg gttctgtaga tgctaaccag    900

ggaaatccaa ttctcggctg ggatacagat aacttccctt ggaatgtcta cgacgcaact    960

cttgcaatgt acgaagtact caaggctggt ggacttacag gtggcttcaa ctttgactca   1020

aagaaccgcc gcccatcaaa tacatttgaa gatatgttcc acgcttacat catgggaatg   1080

gacacttttg ctcttggtct tattaaggct gcagaaatta ttgaagacgg aagaatcgat   1140

ggcttcatta aagaaaagta ttcaagctac gaaagtggaa ttggtaagaa gatccgcgac   1200

aagcagacaa ctttggaaga gcttgctgcc cgtgccgcag aaatgaaaaa gccatctgat   1260

ccaggttcag gccgcgagga atatctggaa ggagttgtta acaatatcct ctttcgcgga   1320

taa                                                                 1323
```

<210> SEQ ID NO 44
<211> LENGTH: 440
<212> TYPE: PRT
<213> ORGANISM: Unknown
<220> FEATURE:
<223> OTHER INFORMATION: Obtained from environmental sample

<400> SEQUENCE: 44

```
Met Ser Glu Phe Phe Lys Asn Ile Pro Glu Ile Lys Phe Glu Gly Lys
1               5                   10                  15

Asp Ser Lys Asn Pro Trp Ala Phe Lys Tyr Tyr Asn Pro Glu Leu Thr
            20                  25                  30

Ile Met Gly Lys Lys Met Ser Glu His Leu Pro Phe Ala Met Ala Trp
        35                  40                  45

Trp His Asn Leu Gly Ala Asn Gly Val Asp Met Phe Gly Ser Gly Thr
    50                  55                  60

Ala Asp Lys Ser Phe Gly Gln Ala Pro Gly Thr Met Glu His Ala Lys
65                  70                  75                  80

Ala Lys Val Asp Ala Gly Ile Glu Phe Met Lys Lys Leu Gly Ile Lys
                85                  90                  95

Tyr Tyr Cys Trp His Asp Val Asp Leu Val Pro Glu Asp Pro Asn Asp
            100                 105                 110

Ile Asn Val Thr Asn Lys Arg Leu Asp Glu Ile Ser Asp Tyr Ile Leu
        115                 120                 125

Glu Lys Thr Lys Gly Thr Asp Ile Lys Cys Leu Trp Gly Thr Ala Asn
    130                 135                 140

Met Phe Ser Asn Pro Arg Phe Met Asn Gly Ala Gly Ser Thr Asn Ser
145                 150                 155                 160

Ala Asp Val Tyr Cys Phe Ala Ala Ala Gln Val Lys Lys Ala Leu Glu
                165                 170                 175

Ile Thr Val Lys Leu Gly Gly Arg Gly Tyr Val Phe Trp Gly Gly Arg
            180                 185                 190

Glu Gly Tyr Glu Thr Leu Leu Asn Thr Asp Val Lys Leu Glu Gln Glu
        195                 200                 205
```

```
Asn Ile Ala Asn Leu Met His Met Ala Val Asp Tyr Gly Arg Ser Ile
    210                 215                 220

Gly Phe Lys Gly Asp Phe Tyr Ile Glu Pro Lys Pro Lys Glu Pro Met
225                 230                 235                 240

Ser His Gln Tyr Asp Phe Asp Ala Ala Thr Ala Ile Gly Phe Leu Arg
                245                 250                 255

Gln Tyr Gly Leu Asp Lys Asp Phe Lys Met Asn Ile Glu Ala Asn His
            260                 265                 270

Ala Ser Leu Ala Asn His Thr Phe Gln His Glu Leu Tyr Ile Ser Arg
        275                 280                 285

Ile Asn Gly Met Leu Gly Ser Val Asp Ala Asn Gln Gly Asn Pro Ile
    290                 295                 300

Leu Gly Trp Asp Thr Asp Asn Phe Pro Trp Asn Val Tyr Asp Ala Thr
305                 310                 315                 320

Leu Ala Met Tyr Glu Val Leu Lys Ala Gly Gly Leu Thr Gly Gly Phe
                325                 330                 335

Asn Phe Asp Ser Lys Asn Arg Arg Pro Ser Asn Thr Phe Glu Asp Met
            340                 345                 350

Phe His Ala Tyr Ile Met Gly Met Asp Thr Phe Ala Leu Gly Leu Ile
        355                 360                 365

Lys Ala Ala Glu Ile Ile Glu Asp Gly Arg Ile Asp Gly Phe Ile Lys
    370                 375                 380

Glu Lys Tyr Ser Ser Tyr Glu Ser Gly Ile Gly Lys Lys Ile Arg Asp
385                 390                 395                 400

Lys Gln Thr Thr Leu Glu Glu Leu Ala Ala Arg Ala Ala Glu Met Lys
                405                 410                 415

Lys Pro Ser Asp Pro Gly Ser Gly Arg Glu Glu Tyr Leu Glu Gly Val
            420                 425                 430

Val Asn Asn Ile Leu Phe Arg Gly
        435                 440
```

<210> SEQ ID NO 45
<211> LENGTH: 1323
<212> TYPE: DNA
<213> ORGANISM: Unknown
<220> FEATURE:
<223> OTHER INFORMATION: Obtained from environmental sample

<400> SEQUENCE: 45

```
atgagcgagt tttttaagaa tattcctcaa ataaaatacg aaggaaaaga tagcaaaaat      60

ccctgggcat tcaagtatta caatcctgaa ttgacaatca tgggtaaaaa gatgagcgaa     120

catcttccat tcgcaatggc atggtggcat aaccttggcg caaacggcgt tgatatgttt     180

ggtcagggaa cagcagacaa gtctttcgga cagattcctg gaactatgga gcatgcaaag     240

gctaaggttg atgctggtat agagtttatg aagaagctcg gaatcaaata ttactgctgg     300

cacgatgttg accttgttcc tgaggatcca aacgatatca acgtaactaa caaacgtctg     360

gacgaaattt cagattacat ccttgaaaag acaaaaggaa cagacattaa gtgtctctgg     420

ggaactgcaa acatgttcgg taaccctcgc tttatgaacg gtgcaggctc tacaaactct     480

gctgacgttt actgttttgc tgccgctcag gtaaaaaagg ctcttgagat tactgtaaag     540

cttggtggcc gaggttatgt tttctggggt ggccgcgaag gttacgaaac tcttctcaat     600

acagacgtaa aacttgaaca ggaaaatatc gcaaacctca tgcatatggc tgttgattat     660

ggccgctcaa tcggtttcaa gggagacttc tacatcgagc ctaagccaaa ggagccaatg     720
```

agccatcagt atgattttga tgctgcaaca gcaatcggct tcctccgcca gtatggcctc 780
gacaaagatt ttaagatgaa catcgaagct aaccatgcct cacttgcaaa tcacaccttc 840
cagcacgagc tttgtatcag ccgcataaac ggaatgcttg gttctgtaga tgcaaatcag 900
ggaaatccaa ttcttggctg ggatacagat aacttcccat ggaatgttta cgatgcaact 960
ctggcaatgt acgaagttct caaggctggc ggtctaacag gtggcttcaa ctttgactca 1020
aagaaccgtc gcccatcaaa tacttttgaa gatatgttcc acgcttatat catgggtatg 1080
gatacttttg cccttggcct tattaaggct gcagaaatta ttgaagacgg cagaattgac 1140
ggcttcatca aagaaaagta ttcaagcttt gaaagtggaa ttggtaagaa gattcgtgac 1200
aagcagacaa gtttggaaga gcttgcagct cgtgccgctg aaatgaaaaa gccatctgat 1260
ccaggttcag gccgcgagga atacctcgaa ggagttgtta acaacatcct ctttcgcgga 1320
taa 1323

<210> SEQ ID NO 46
<211> LENGTH: 440
<212> TYPE: PRT
<213> ORGANISM: Unknown
<220> FEATURE:
<223> OTHER INFORMATION: Obtained from environmental sample

<400> SEQUENCE: 46

Met Ser Glu Phe Phe Lys Asn Ile Pro Gln Ile Lys Tyr Glu Gly Lys
1 5 10 15

Asp Ser Lys Asn Pro Trp Ala Phe Lys Tyr Tyr Asn Pro Glu Leu Thr
20 25 30

Ile Met Gly Lys Lys Met Ser Glu His Leu Pro Phe Ala Met Ala Trp
35 40 45

Trp His Asn Leu Gly Ala Asn Gly Val Asp Met Phe Gly Gln Gly Thr
50 55 60

Ala Asp Lys Ser Phe Gly Gln Ile Pro Gly Thr Met Glu His Ala Lys
65 70 75 80

Ala Lys Val Asp Ala Gly Ile Glu Phe Met Lys Lys Leu Gly Ile Lys
85 90 95

Tyr Tyr Cys Trp His Asp Val Asp Leu Val Pro Glu Asp Pro Asn Asp
100 105 110

Ile Asn Val Thr Asn Lys Arg Leu Asp Glu Ile Ser Asp Tyr Ile Leu
115 120 125

Glu Lys Thr Lys Gly Thr Asp Ile Lys Cys Leu Trp Gly Thr Ala Asn
130 135 140

Met Phe Gly Asn Pro Arg Phe Met Asn Gly Ala Gly Ser Thr Asn Ser
145 150 155 160

Ala Asp Val Tyr Cys Phe Ala Ala Ala Gln Val Lys Lys Ala Leu Glu
165 170 175

Ile Thr Val Lys Leu Gly Gly Arg Gly Tyr Val Phe Trp Gly Gly Arg
180 185 190

Glu Gly Tyr Glu Thr Leu Leu Asn Thr Asp Val Lys Leu Glu Gln Glu
195 200 205

Asn Ile Ala Asn Leu Met His Met Ala Val Asp Tyr Gly Arg Ser Ile
210 215 220

Gly Phe Lys Gly Asp Phe Tyr Ile Glu Pro Lys Pro Lys Glu Pro Met
225 230 235 240

Ser His Gln Tyr Asp Phe Asp Ala Ala Thr Ala Ile Gly Phe Leu Arg

-continued

```
                245                 250                 255

Gln Tyr Gly Leu Asp Lys Asp Phe Lys Met Asn Ile Glu Ala Asn His
            260                 265                 270

Ala Ser Leu Ala Asn His Thr Phe Gln His Glu Leu Cys Ile Ser Arg
        275                 280                 285

Ile Asn Gly Met Leu Gly Ser Val Asp Ala Asn Gln Gly Asn Pro Ile
    290                 295                 300

Leu Gly Trp Asp Thr Asp Asn Phe Pro Trp Asn Val Tyr Asp Ala Thr
305                 310                 315                 320

Leu Ala Met Tyr Glu Val Leu Lys Ala Gly Gly Leu Thr Gly Gly Phe
                325                 330                 335

Asn Phe Asp Ser Lys Asn Arg Arg Pro Ser Asn Thr Phe Glu Asp Met
            340                 345                 350

Phe His Ala Tyr Ile Met Gly Met Asp Thr Phe Ala Leu Gly Leu Ile
        355                 360                 365

Lys Ala Ala Glu Ile Ile Glu Asp Gly Arg Ile Asp Gly Phe Ile Lys
    370                 375                 380

Glu Lys Tyr Ser Ser Phe Glu Ser Gly Ile Gly Lys Lys Ile Arg Asp
385                 390                 395                 400

Lys Gln Thr Ser Leu Glu Glu Leu Ala Ala Arg Ala Ala Glu Met Lys
                405                 410                 415

Lys Pro Ser Asp Pro Gly Ser Gly Arg Glu Glu Tyr Leu Glu Gly Val
            420                 425                 430

Val Asn Asn Ile Leu Phe Arg Gly
        435                 440
```

```
<210> SEQ ID NO 47
<211> LENGTH: 1311
<212> TYPE: DNA
<213> ORGANISM: Unknown
<220> FEATURE:
<223> OTHER INFORMATION: Obtained from environmental sample

<400> SEQUENCE: 47

atgatatttg aaaatattcc cgcaattcct tatgagggtc cgaagagcac aaatccgctg      60

gcgtttaaat tctatgatcc ggacaagatc gttatgggaa agcccatgaa ggagcatctg     120

ccctttgcaa tggcctggtg gcacaacctt ggcgcggccg gaaccgatat gttcgggcgc     180

gataccgccg acaaatcctt cggtgcggta aaaggcacaa tggagcatgc caaagcgaaa     240

gtcgatgccg gctttgagtt catgcagaag ctggggatcc gctatttctg cttccatgat     300

gtggatcttg ttccggaggc ggatgatata aaggagacca accgccgtct ggacgagatc     360

agcgattaca tccttgaaaa gatgaagggc accgatatca agtgcctttg ggcacggcc      420

aatatgttct caaatccgcg ctttatgaac ggcgcaggct cctccaattc tgccgatgta     480

ttcgcttttg cggcagcaca ggccaagaag gccttggatc tgaccgtcaa actcggcggg     540

cgcggctatg tcttctgggg cggacgtgag ggctatgaga cacttctcaa taccgacatg     600

aagttcgagc aggagaatat cgcgaagctc atgcatatgg ctgtcgatta cggccgcagc     660

ataggcttta ccggtgattt ctatatcgag cccaaaccga aagagccgat gaaacaccag     720

tatgatttcg atgcagccac tgcgataggc ttcctccgcc agtacggact cgataaggac     780

ttcaagctca acatcgaggc aaaccacgcc acactggcag gtcacacttt ccagcacgat     840

ctgcgtgttt ccgcaataaa cggaatgctg ggcagcattg acgccaacca gggcgatatg     900

ctcctcggct gggataccga cgagttcccg ttcaatgtat atgatgcgac catgtgcatg     960
```

-continued tatgaggtgc tcaagtcaga cgggctcacc ggcggcttta acttcgactc caaatcacgc 1020
cgcccgagct atacggtcga ggatatgttt acaagctata tcctcggcat ggacactttt 1080
gccctcggcc ttctgaaagc ggccgagctt atcgaagacg gaaggcttga cgccttcgtc 1140
aaagaacgct attcaagcta tgagagcggc atcggcgcaa agatccgcag cggagaaacc 1200
gatttgaagg aattggcgga atatgcggac tccctcggag cccccgaact tccgggcagc 1260
ggaaaacagg aacagctcga gagcatagta aatcagatac ttttcggata a 1311

<210> SEQ ID NO 48
<211> LENGTH: 436
<212> TYPE: PRT
<213> ORGANISM: Unknown
<220> FEATURE:
<223> OTHER INFORMATION: Obtained from environmental sample

<400> SEQUENCE: 48

Met Ile Phe Glu Asn Ile Pro Ala Ile Pro Tyr Glu Gly Pro Lys Ser
1 5 10 15

Thr Asn Pro Leu Ala Phe Lys Phe Tyr Asp Pro Asp Lys Ile Val Met
20 25 30

Gly Lys Pro Met Lys Glu His Leu Pro Phe Ala Met Ala Trp Trp His
35 40 45

Asn Leu Gly Ala Ala Gly Thr Asp Met Phe Gly Arg Asp Thr Ala Asp
50 55 60

Lys Ser Phe Gly Ala Val Lys Gly Thr Met Glu His Ala Lys Ala Lys
65 70 75 80

Val Asp Ala Gly Phe Glu Phe Met Gln Lys Leu Gly Ile Arg Tyr Phe
85 90 95

Cys Phe His Asp Val Asp Leu Val Pro Glu Ala Asp Asp Ile Lys Glu
100 105 110

Thr Asn Arg Arg Leu Asp Glu Ile Ser Asp Tyr Ile Leu Glu Lys Met
115 120 125

Lys Gly Thr Asp Ile Lys Cys Leu Trp Gly Thr Ala Asn Met Phe Ser
130 135 140

Asn Pro Arg Phe Met Asn Gly Ala Gly Ser Ser Asn Ser Ala Asp Val
145 150 155 160

Phe Ala Phe Ala Ala Ala Gln Ala Lys Lys Ala Leu Asp Leu Thr Val
165 170 175

Lys Leu Gly Gly Arg Gly Tyr Val Phe Trp Gly Gly Arg Glu Gly Tyr
180 185 190

Glu Thr Leu Leu Asn Thr Asp Met Lys Phe Glu Gln Glu Asn Ile Ala
195 200 205

Lys Leu Met His Met Ala Val Asp Tyr Gly Arg Ser Ile Gly Phe Thr
210 215 220

Gly Asp Phe Tyr Ile Glu Pro Lys Pro Lys Glu Pro Met Lys His Gln
225 230 235 240

Tyr Asp Phe Asp Ala Ala Thr Ala Ile Gly Phe Leu Arg Gln Tyr Gly
245 250 255

Leu Asp Lys Asp Phe Lys Leu Asn Ile Glu Ala Asn His Ala Thr Leu
260 265 270

Ala Gly His Thr Phe Gln His Asp Leu Arg Val Ser Ala Ile Asn Gly
275 280 285

Met Leu Gly Ser Ile Asp Ala Asn Gln Gly Asp Met Leu Leu Gly Trp
290 295 300

```
Asp Thr Asp Glu Phe Pro Phe Asn Val Tyr Asp Ala Thr Met Cys Met
305                 310                 315                 320

Tyr Glu Val Leu Lys Ser Asp Gly Leu Thr Gly Gly Phe Asn Phe Asp
                325                 330                 335

Ser Lys Ser Arg Arg Pro Ser Tyr Thr Val Glu Asp Met Phe Thr Ser
            340                 345                 350

Tyr Ile Leu Gly Met Asp Thr Phe Ala Leu Gly Leu Leu Lys Ala Ala
        355                 360                 365

Glu Leu Ile Glu Asp Gly Arg Leu Asp Ala Phe Val Lys Glu Arg Tyr
    370                 375                 380

Ser Ser Tyr Glu Ser Gly Ile Gly Ala Lys Ile Arg Ser Gly Glu Thr
385                 390                 395                 400

Asp Leu Lys Glu Leu Ala Glu Tyr Ala Asp Ser Leu Gly Ala Pro Glu
                405                 410                 415

Leu Pro Gly Ser Gly Lys Gln Glu Gln Leu Glu Ser Ile Val Asn Gln
            420                 425                 430

Ile Leu Phe Gly
        435


<210> SEQ ID NO 49
<211> LENGTH: 1317
<212> TYPE: DNA
<213> ORGANISM: Unknown
<220> FEATURE:
<223> OTHER INFORMATION: Obtained from environmental sample

<400> SEQUENCE: 49

atgagcgagt tttttgccag cattcccaaa attccctttg aaggcaagga cagcgccaat      60

cccctggcgt tcaaatacta cgacgccgac aggatgatac tgggcaagcc catgaaggag     120

caccttccct tcgccatggc ctggtggcac aacctgtgcg ccgcgggcac cgatatgttt     180

ggccgggaca ccgccgacaa gtccttcggc caggtcaagg gcaccatgga acacgccaag     240

gccaaggtgg acgcgggctt tgagttcatg aagaagctgg gcatccgcta cttctgcttc     300

cacgacgtgg acatcgtgcc cgaagccgac gacatcaagg aaaccaaccg ccgtctggac     360

gagatctccg actatatcct ggagaaaatg aaaggcaccg acatccagtg cctgtggggc     420

accgccaaca tgttcggcaa cccccgctat atgaacggcg cgggcagctc caactccgcc     480

gacgtatact gcttcgccgc ggcccagatc aaaaaggccc tggacatcac cgtgaagctg     540

ggcggcaagg gctacgtgtt ctggggcggc cgcgagggct acgagaccct gctgaacacc     600

gatatgaagt tcgagcagga gaacatcgcc cgcctgatgc acatggccgt ggactacggc     660

cgcagcatcg gcttcaccgg cgatttctac atcgagccca agcccaagga gcccatgaag     720

caccagtacg acttcgacgc cgccaccgcc ataggctttt tgcgccagta cggcctggac     780

aaggatttca agctgaacat cgagtccaac cacgccaccc tggcgggcca taccttccag     840

cacgacctgc gcgtttccgc catcaacggc atgctgggct ccatcgacgc caaccagggc     900

gactacctgc tgggctggga taccgacgag ttcccctaca gcgtatacga gaccaccatg     960

tgcatgtacg aggtgctcaa ggccggaggt ctcaccggcg gcttcaattt cgacgccaag    1020

aaccgccgtc ccagctacac ccccgaggat atgttccacg cctacatcct tgggatggac    1080

agcttcgccc tgggcctgat caaggccgcc gagctcatcg aggacggtcg cctggacgcc    1140

ttcgtccggg accgctacca gagctgggag accggcatcg gcgataagat ccgcaagggc    1200

gagaccacac tggccgagct ggccgagtac gccgcccgga tgggcgcgcc cgcgctgccc    1260
```

ggcagcggcc gccaggaata cctggagggc gtggtcaaca atatcctgtt caaataa 1317

<210> SEQ ID NO 50
<211> LENGTH: 438
<212> TYPE: PRT
<213> ORGANISM: Unknown
<220> FEATURE:
<223> OTHER INFORMATION: Obtained from environmental sample

<400> SEQUENCE: 50

Met Ser Glu Phe Phe Ala Ser Ile Pro Lys Ile Pro Phe Glu Gly Lys
1 5 10 15

Asp Ser Ala Asn Pro Leu Ala Phe Lys Tyr Tyr Asp Ala Asp Arg Met
20 25 30

Ile Leu Gly Lys Pro Met Lys Glu His Leu Pro Phe Ala Met Ala Trp
35 40 45

Trp His Asn Leu Cys Ala Ala Gly Thr Asp Met Phe Gly Arg Asp Thr
50 55 60

Ala Asp Lys Ser Phe Gly Gln Val Lys Gly Thr Met Glu His Ala Lys
65 70 75 80

Ala Lys Val Asp Ala Gly Phe Glu Phe Met Lys Lys Leu Gly Ile Arg
85 90 95

Tyr Phe Cys Phe His Asp Val Asp Ile Val Pro Glu Ala Asp Asp Ile
100 105 110

Lys Glu Thr Asn Arg Arg Leu Asp Glu Ile Ser Asp Tyr Ile Leu Glu
115 120 125

Lys Met Lys Gly Thr Asp Ile Gln Cys Leu Trp Gly Thr Ala Asn Met
130 135 140

Phe Gly Asn Pro Arg Tyr Met Asn Gly Ala Gly Ser Ser Asn Ser Ala
145 150 155 160

Asp Val Tyr Cys Phe Ala Ala Ala Gln Ile Lys Lys Ala Leu Asp Ile
165 170 175

Thr Val Lys Leu Gly Gly Lys Gly Tyr Val Phe Trp Gly Gly Arg Glu
180 185 190

Gly Tyr Glu Thr Leu Leu Asn Thr Asp Met Lys Phe Glu Gln Glu Asn
195 200 205

Ile Ala Arg Leu Met His Met Ala Val Asp Tyr Gly Arg Ser Ile Gly
210 215 220

Phe Thr Gly Asp Phe Tyr Ile Glu Pro Lys Pro Lys Glu Pro Met Lys
225 230 235 240

His Gln Tyr Asp Phe Asp Ala Ala Thr Ala Ile Gly Phe Leu Arg Gln
245 250 255

Tyr Gly Leu Asp Lys Asp Phe Lys Leu Asn Ile Glu Ser Asn His Ala
260 265 270

Thr Leu Ala Gly His Thr Phe Gln His Asp Leu Arg Val Ser Ala Ile
275 280 285

Asn Gly Met Leu Gly Ser Ile Asp Ala Asn Gln Gly Asp Tyr Leu Leu
290 295 300

Gly Trp Asp Thr Asp Glu Phe Pro Tyr Ser Val Tyr Glu Thr Thr Met
305 310 315 320

Cys Met Tyr Glu Val Leu Lys Ala Gly Gly Leu Thr Gly Gly Phe Asn
325 330 335

Phe Asp Ala Lys Asn Arg Arg Pro Ser Tyr Thr Pro Glu Asp Met Phe
340 345 350

```
His Ala Tyr Ile Leu Gly Met Asp Ser Phe Ala Leu Gly Leu Ile Lys
        355                 360                 365

Ala Ala Glu Leu Ile Glu Asp Gly Arg Leu Asp Ala Phe Val Arg Asp
    370                 375                 380

Arg Tyr Gln Ser Trp Glu Thr Gly Ile Gly Asp Lys Ile Arg Lys Gly
385                 390                 395                 400

Glu Thr Thr Leu Ala Glu Leu Ala Glu Tyr Ala Ala Arg Met Gly Ala
                405                 410                 415

Pro Ala Leu Pro Gly Ser Gly Arg Gln Glu Tyr Leu Glu Gly Val Val
            420                 425                 430

Asn Asn Ile Leu Phe Lys
        435


<210> SEQ ID NO 51
<211> LENGTH: 1320
<212> TYPE: DNA
<213> ORGANISM: Unknown
<220> FEATURE:
<223> OTHER INFORMATION: Obtained from environmental sample

<400> SEQUENCE: 51

atgaagacct atttcaaaaa aatccccgtg atcccctacg agggaccgaa gtcccagaat     60

ccgctgtcgt tcaaattcta tgacgcggac cgcatcgttc tcggcaagcc catgaaggag    120

catctgccct tcgccatggc ctggtggcac aatctgggtg ctgccggaac ggacatgttc    180

ggccgcgata ccgccgacaa gtccttcgga gcggagaagg gcaccatgga gcatgccaag    240

gccaaggtgg acgctggctt cgagtttatg aagaaggtgg gcatccggta tttctgcttc    300

catgacgtgg atctggtccc ggaagcggac gacatcaagg agaccaaccg ccgtctcgat    360

gagatcagcg actacatcct caagaagatg aagggcacgg atatcaagtg cctctggggc    420

accgccaaca tgttcggcaa tccccggttc atgaacggcg cgggcagctc caacagcgcg    480

gacgtgttct gctttgccgc ggcccaggtg aagaaggcct tggacatcac cgtcaagctg    540

ggcggccggg gctatgtgtt ctggggcggc cgtgaggggt atgagtccct gctgaacacg    600

gacgtgaagt ttgagcagga gaacatcgcc aagctcatgc accttgccgt ggactacggc    660

cgcagcatcg gcttcaccgg cgatttctac atcgagccca agcccaagga gcccatgaag    720

caccagtacg acttcgatgc cgccaccgcc atcggcttcc tcaggcagta cggcctcgat    780

aaggacttca agatgaacat tgaagccaac cacgcgaccc tggccggcca caccttccag    840

cacgacctca ggatcagcgc catcaacggg atgctgggct ccatcgacgc caaccagggc    900

gacctcctgc tgggatggga caccgacgaa ttccccttca acgtctatga ggccaccatg    960

tgcatgtacg aggtcctcaa ggccggcggc ctcaccggcg gcttcaactt cgactcaaag   1020

aaccgccgtc cctcctacac catggaggat atgttccacg cctacatcct gggcatggac   1080

accttcgccc tgggtcttct caaggccgcg gagctcatcg aggacggtcg gatcgacaaa   1140

ttcgtggagg agcgctacgc cagctacaag accggcatcg gcgccaagat ccgttccggc   1200

gagaccacgc ttcaggagct ggccgcctat gccgacaagt tgggcgcgcc tgcccttccc   1260

ggcagcggcc gtcaggagta cctggagagc atcgtcaacc aggtgctctt cgggatgtga   1320


<210> SEQ ID NO 52
<211> LENGTH: 439
<212> TYPE: PRT
<213> ORGANISM: Unknown
<220> FEATURE:
<223> OTHER INFORMATION: Obtained from environmental sample
```

<400> SEQUENCE: 52

Met Lys Thr Tyr Phe Lys Lys Ile Pro Val Ile Pro Tyr Glu Gly Pro
1 5 10 15

Lys Ser Gln Asn Pro Leu Ser Phe Lys Phe Tyr Asp Ala Asp Arg Ile
20 25 30

Val Leu Gly Lys Pro Met Lys Glu His Leu Pro Phe Ala Met Ala Trp
35 40 45

Trp His Asn Leu Gly Ala Ala Gly Thr Asp Met Phe Gly Arg Asp Thr
50 55 60

Ala Asp Lys Ser Phe Gly Ala Glu Lys Gly Thr Met Glu His Ala Lys
65 70 75 80

Ala Lys Val Asp Ala Gly Phe Glu Phe Met Lys Lys Val Gly Ile Arg
85 90 95

Tyr Phe Cys Phe His Asp Val Asp Leu Val Pro Glu Ala Asp Asp Ile
100 105 110

Lys Glu Thr Asn Arg Arg Leu Asp Glu Ile Ser Asp Tyr Ile Leu Lys
115 120 125

Lys Met Lys Gly Thr Asp Ile Lys Cys Leu Trp Gly Thr Ala Asn Met
130 135 140

Phe Gly Asn Pro Arg Phe Met Asn Gly Ala Gly Ser Ser Asn Ser Ala
145 150 155 160

Asp Val Phe Cys Phe Ala Ala Ala Gln Val Lys Lys Ala Leu Asp Ile
165 170 175

Thr Val Lys Leu Gly Gly Arg Gly Tyr Val Phe Trp Gly Gly Arg Glu
180 185 190

Gly Tyr Glu Ser Leu Leu Asn Thr Asp Val Lys Phe Glu Gln Glu Asn
195 200 205

Ile Ala Lys Leu Met His Leu Ala Val Asp Tyr Gly Arg Ser Ile Gly
210 215 220

Phe Thr Gly Asp Phe Tyr Ile Glu Pro Lys Pro Lys Glu Pro Met Lys
225 230 235 240

His Gln Tyr Asp Phe Asp Ala Ala Thr Ala Ile Gly Phe Leu Arg Gln
245 250 255

Tyr Gly Leu Asp Lys Asp Phe Lys Met Asn Ile Glu Ala Asn His Ala
260 265 270

Thr Leu Ala Gly His Thr Phe Gln His Asp Leu Arg Ile Ser Ala Ile
275 280 285

Asn Gly Met Leu Gly Ser Ile Asp Ala Asn Gln Gly Asp Leu Leu Leu
290 295 300

Gly Trp Asp Thr Asp Glu Phe Pro Phe Asn Val Tyr Glu Ala Thr Met
305 310 315 320

Cys Met Tyr Glu Val Leu Lys Ala Gly Gly Leu Thr Gly Gly Phe Asn
325 330 335

Phe Asp Ser Lys Asn Arg Arg Pro Ser Tyr Thr Met Glu Asp Met Phe
340 345 350

His Ala Tyr Ile Leu Gly Met Asp Thr Phe Ala Leu Gly Leu Leu Lys
355 360 365

Ala Ala Glu Leu Ile Glu Asp Gly Arg Ile Asp Lys Phe Val Glu Glu
370 375 380

Arg Tyr Ala Ser Tyr Lys Thr Gly Ile Gly Ala Lys Ile Arg Ser Gly
385 390 395 400

Glu Thr Thr Leu Gln Glu Leu Ala Ala Tyr Ala Asp Lys Leu Gly Ala

-continued

```
                405                 410                 415

Pro Ala Leu Pro Gly Ser Gly Arg Gln Glu Tyr Leu Glu Ser Ile Val
            420                 425                 430

Asn Gln Val Leu Phe Gly Met
        435
```

<210> SEQ ID NO 53
<211> LENGTH: 1314
<212> TYPE: DNA
<213> ORGANISM: Unknown
<220> FEATURE:
<223> OTHER INFORMATION: Obtained from environmental sample

<400> SEQUENCE: 53

```
atggctaaag agtattttcc agagattggc aaaatcaagt ttgaaggcaa ggacagcaaa      60

aacccaatgg ctttccacta ctatgacccc gagaaggtga tcatgggcaa gcctatgaaa     120

gactggctcc gcttcgctat ggcatggtgg cacaccctct gcgcagaagg tggcgaccag     180

ttcggtggcg gcactaagaa gttcccttgg aacaacggcg ctgacgctgt agaaatcgca     240

aaacagaagg ctgacgcagg tttcgaaatc atgcagaagc tcggcatccc atatttctgc     300

ttccacgacg tggacctcgt gtctgagggc gcatctgtag aagagtatga ggctaacctc     360

aaggctatca cagactacct cgctgtgaag atgaaggaaa caggcatcaa gctcctgtgg     420

tctactgcca acgtattcgg caacggccgc tacatgaacg gtgcttctac caaccctgac     480

ttcgacgtcg ttgctcgcgc tatcgtgcag attaagaacg ctatcgacgc tggtatcaag     540

ctcggcgctg agaactacgt gttctggggc ggacgcgaag gctacatgag cctcctcaac     600

accgaccaga agcgtgagaa ggagcacatg gccactatgc tcactatggc tcgcgactac     660

gctcgcgcta agggcttcaa gggcacattc ctcatcgagc ctaagccaat ggagccttct     720

aagcaccagt atgacgttga cactgagact gtcatcggct tcctcaaggc acacaacctc     780

gacaaggact tcaaggtgaa catcgaggtg aaccacgcaa ctctcgctgg ccacaccttc     840

gagcacgagc tcgcagtggc agtggacaac aacatgctcg gctctatcga cgctaaccgt     900

ggtgactacc agaatggctg ggatactgac cagttcccaa tcgaccagta cgaactcgtt     960

caggcttgga tggaaatcat ccgtggcggc ggtctcggca ctggcggcac gaacttcgac    1020

gctaagactc gtcgtaactc taccgacctc gaagacatct tcatcgcaca catcgcaggc    1080

atggacgcta tggcacgcgc actcgaatca gctgctaagc tcctcgaaga gtctccatac    1140

aaggcaatga aggcagctcg ctacgcttca ttcgacaacg gtatcggtaa ggacttcgaa    1200

gatggcaagc tcactctcga gcaggcttac gaatacggta agaaggttgg tgagcctaag    1260

cagacttctg gcaagcagga gctctacgaa gccatcgttg caatgtacgc ttaa          1314
```

<210> SEQ ID NO 54
<211> LENGTH: 437
<212> TYPE: PRT
<213> ORGANISM: Unknown
<220> FEATURE:
<223> OTHER INFORMATION: Obtained from environmental sample

<400> SEQUENCE: 54

```
Met Ala Lys Glu Tyr Phe Pro Glu Ile Gly Lys Ile Lys Phe Glu Gly
1               5                   10                  15

Lys Asp Ser Lys Asn Pro Met Ala Phe His Tyr Tyr Asp Pro Glu Lys
            20                  25                  30

Val Ile Met Gly Lys Pro Met Lys Asp Trp Leu Arg Phe Ala Met Ala
```

```
        35                  40                  45

Trp Trp His Thr Leu Cys Ala Glu Gly Gly Asp Gln Phe Gly Gly Gly
    50                  55                  60

Thr Lys Lys Phe Pro Trp Asn Asn Gly Ala Asp Ala Val Glu Ile Ala
65                  70                  75                  80

Lys Gln Lys Ala Asp Ala Gly Phe Glu Ile Met Gln Lys Leu Gly Ile
                85                  90                  95

Pro Tyr Phe Cys Phe His Asp Val Asp Leu Val Ser Glu Gly Ala Ser
            100                 105                 110

Val Glu Glu Tyr Glu Ala Asn Leu Lys Ala Ile Thr Asp Tyr Leu Ala
        115                 120                 125

Val Lys Met Lys Glu Thr Gly Ile Lys Leu Leu Trp Ser Thr Ala Asn
    130                 135                 140

Val Phe Gly Asn Gly Arg Tyr Met Asn Gly Ala Ser Thr Asn Pro Asp
145                 150                 155                 160

Phe Asp Val Val Ala Arg Ala Ile Val Gln Ile Lys Asn Ala Ile Asp
                165                 170                 175

Ala Gly Ile Lys Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Thr Met Leu Thr Met Ala Arg Asp Tyr Ala Arg Ala Lys
    210                 215                 220

Gly Phe Lys Gly Thr Phe Leu Ile Glu Pro Lys Pro Met Glu Pro Ser
225                 230                 235                 240

Lys His Gln Tyr Asp Val Asp Thr Glu Thr Val Ile Gly Phe Leu Lys
                245                 250                 255

Ala His Asn Leu Asp Lys Asp Phe Lys Val Asn Ile Glu Val Asn His
            260                 265                 270

Ala Thr Leu Ala Gly His Thr Phe Glu His Glu Leu Ala Val Ala Val
        275                 280                 285

Asp Asn Asn Met Leu Gly Ser Ile Asp Ala Asn Arg Gly Asp Tyr Gln
    290                 295                 300

Asn Gly Trp Asp Thr Asp Gln Phe Pro Ile Asp Gln Tyr Glu Leu Val
305                 310                 315                 320

Gln Ala Trp Met Glu Ile Ile Arg Gly Gly Gly Leu Gly Thr Gly Gly
                325                 330                 335

Thr Asn Phe Asp Ala Lys Thr Arg Arg Asn Ser Thr Asp Leu Glu Asp
            340                 345                 350

Ile Phe Ile Ala His Ile Ala Gly Met Asp Ala Met Ala Arg Ala Leu
        355                 360                 365

Glu Ser Ala Ala Lys Leu Leu Glu Glu Ser Pro Tyr Lys Ala Met Lys
    370                 375                 380

Ala Ala Arg Tyr Ala Ser Phe Asp Asn Gly Ile Gly Lys Asp Phe Glu
385                 390                 395                 400

Asp Gly Lys Leu Thr Leu Glu Gln Ala Tyr Glu Tyr Gly Lys Lys Val
                405                 410                 415

Gly Glu Pro Lys Gln Thr Ser Gly Lys Gln Glu Leu Tyr Glu Ala Ile
            420                 425                 430

Val Ala Met Tyr Ala
        435
```

<210> SEQ ID NO 55

-continued

<211> LENGTH: 1314
<212> TYPE: DNA
<213> ORGANISM: Unknown
<220> FEATURE:
<223> OTHER INFORMATION: Obtained from environmental sample

<400> SEQUENCE: 55

```
atggctaaag aatttttccc agagattggt aaaatcaagt tcgaaggcaa ggattcaaag      60
aatccaatgg ctttccatta ctatgatgca gagaaggtaa tcatgggcaa acccatgaag     120
gactggctcc gtttcgctat ggcatggtgg cacacactct gtgcagaggg cggcgaccag     180
ttcggtggcg gtacgaagaa gttcccttgg aacgagggtg ctaatgctgt cgagattgct     240
aagcagaagg ctgacgctgg tttcgaaatc atgcagaagc ttggcattcc ttacttctgc     300
ttccacgatg ttgacctcgt ttctgaaggc gcatctgttg aggagtatga ggccaacctc     360
aaggctatca ctgactatct cgcggtgaag atgaaggaga ctggcattaa gctcctgtgg     420
tctactgcca acgtgttcgg caatggccgt tacatgaatg gtgcttccac caaccctgac     480
ttcgacgttg ttgctcgcgc catcgttcag attaagaacg ctatcgatgc aggtatcaag     540
ctcggtgctg agaactatgt gttctggggc ggtcgtgaag gttacatgag cctcctgaac     600
acagaccaga agcgtgagaa ggagcacatg gctactatgc tcactatggc tcgcgactac     660
gctcgcagca agggcttcaa gggtactttc ctcatcgagc ctaagccaat ggagccatct     720
aagcaccagt acgacgttga cacagagact gttatcggct tcctgaaggc acacaacctt     780
gacaaggact tcaaggtgaa catcgaggtg aaccacgcaa cactcgctgg tcacaccttc     840
gagcacgagc tcgctgtggc tgtcgacaac aatatgcttg gttctatcga tgctaaccgc     900
ggtgactacc agaatggttg ggatacggac cagttcccaa ttgaccagta cgagctcgtt     960
caggcttgga tggagatcat ccgtggtggc ggtctcggca caggtggtac aaacttcgac    1020
gctaagactc gtcgtaactc taccgacctc gaggacattt tcattgctca catcgctggt    1080
atggacgcta tggctcgcgc tcttgagtca gcagctaagc tccttgagga gtctccatac    1140
aagaagatga aggctgcccg ttatgcttct ttcgacagcg gcatgggtaa ggactttgag    1200
aacggcaagc tcacactcga acaggtttat gagtatggta agaaggtagg tgagcccaag    1260
cagacttctg gcaagcagga gctcttcgag gcaatcgtgg ccatgtacgc ataa          1314
```

<210> SEQ ID NO 56
<211> LENGTH: 437
<212> TYPE: PRT
<213> ORGANISM: Unknown
<220> FEATURE:
<223> OTHER INFORMATION: Obtained from environmental sample

<400> SEQUENCE: 56

```
Met Ala Lys Glu Phe Phe Pro Glu Ile Gly Lys Ile Lys Phe Glu Gly
1               5                   10                  15

Lys Asp Ser Lys Asn Pro Met Ala Phe His Tyr Tyr Asp Ala Glu Lys
            20                  25                  30

Val Ile Met Gly Lys Pro Met Lys Asp Trp Leu Arg Phe Ala Met Ala
        35                  40                  45

Trp Trp His Thr Leu Cys Ala Glu Gly Gly Asp Gln Phe Gly Gly Gly
    50                  55                  60

Thr Lys Lys Phe Pro Trp Asn Glu Gly Ala Asn Ala Val Glu Ile Ala
65                  70                  75                  80

Lys Gln Lys Ala Asp Ala Gly Phe Glu Ile Met Gln Lys Leu Gly Ile
                85                  90                  95
```

```
Pro Tyr Phe Cys Phe His Asp Val Asp Leu Val Ser Glu Gly Ala Ser
            100                 105                 110

Val Glu Glu Tyr Glu Ala Asn Leu Lys Ala Ile Thr Asp Tyr Leu Ala
        115                 120                 125

Val Lys Met Lys Glu Thr Gly Ile Lys Leu Leu Trp Ser Thr Ala Asn
    130                 135                 140

Val Phe Gly Asn Gly Arg Tyr Met Asn Gly Ala Ser Thr Asn Pro Asp
145                 150                 155                 160

Phe Asp Val Val Ala Arg Ala Ile Val Gln Ile Lys Asn Ala Ile Asp
                165                 170                 175

Ala Gly Ile Lys Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Thr Met Leu Thr Met Ala Arg Asp Tyr Ala Arg Ser Lys
    210                 215                 220

Gly Phe Lys Gly Thr Phe Leu Ile Glu Pro Lys Pro Met Glu Pro Ser
225                 230                 235                 240

Lys His Gln Tyr Asp Val Asp Thr Glu Thr Val Ile Gly Phe Leu Lys
                245                 250                 255

Ala His Asn Leu Asp Lys Asp Phe Lys Val Asn Ile Glu Val Asn His
            260                 265                 270

Ala Thr Leu Ala Gly His Thr Phe Glu His Glu Leu Ala Val Ala Val
        275                 280                 285

Asp Asn Asn Met Leu Gly Ser Ile Asp Ala Asn Arg Gly Asp Tyr Gln
    290                 295                 300

Asn Gly Trp Asp Thr Asp Gln Phe Pro Ile Asp Gln Tyr Glu Leu Val
305                 310                 315                 320

Gln Ala Trp Met Glu Ile Ile Arg Gly Gly Gly Leu Gly Thr Gly Gly
                325                 330                 335

Thr Asn Phe Asp Ala Lys Thr Arg Arg Asn Ser Thr Asp Leu Glu Asp
            340                 345                 350

Ile Phe Ile Ala His Ile Ala Gly Met Asp Ala Met Ala Arg Ala Leu
        355                 360                 365

Glu Ser Ala Ala Lys Leu Leu Glu Glu Ser Pro Tyr Lys Lys Met Lys
    370                 375                 380

Ala Ala Arg Tyr Ala Ser Phe Asp Ser Gly Met Gly Lys Asp Phe Glu
385                 390                 395                 400

Asn Gly Lys Leu Thr Leu Glu Gln Val Tyr Glu Tyr Gly Lys Lys Val
                405                 410                 415

Gly Glu Pro Lys Gln Thr Ser Gly Lys Gln Glu Leu Phe Glu Ala Ile
            420                 425                 430

Val Ala Met Tyr Ala
        435
```

<210> SEQ ID NO 57
<211> LENGTH: 1314
<212> TYPE: DNA
<213> ORGANISM: Unknown
<220> FEATURE:
<223> OTHER INFORMATION: Obtained from environmental sample

<400> SEQUENCE: 57
atggctaaag agtattttcc agagattggt aaaatcaagt ttgaaggcaa ggattccaag     60

-continued

```
aatccaatgg cattccacta ttatgatgca gagaaagtga ttatgggtaa gcctatgaag    120
gagtggctcc gctttgcaat ggcatggtgg cacacactct gtgcagaggg tggcgaccag    180
tttggtggtg gcactaagaa attcccatgg aacgagggca ctgacgctgt gacgattgct    240
aagcagaagg ctgatgcagg tttcgaaatc atgcagaaac tcggtttccc atatttttgc    300
ttccacgaca ttgacctcgt ttccgaaggc aacagcattg aagagtatga ggctaacctc    360
caggcaatca ctgattatct gaaagtgaag atggaagaga caggcatcaa actcttgtgg    420
tcaactgcca acgtattcgg caatggtcgc tacatgaatg gtgcttccac aaacccagac    480
tttgacgtgg tggctcgtgc catcgttcag attaagaacg caattgacgc tggtatcaaa    540
ctcggtgctg agaactatgt attctggggc ggtcgcgaag gctacatgag ccttctgaac    600
actgaccaga agcgtgagaa ggagcacatg gcaaccatgc tcactatggc tcgcgactac    660
gctcgcagca agggtttcaa gggcactttc ctcattgagc caaagccaat ggagccatct    720
aagcaccagt atgacgttga cacggagact gtcatcggct tcctcaaggc acacaacctc    780
gacaaggatt tcaaggtgaa catcgaagtg aaccacgcta cacttgcagg tcatactttc    840
gagcacgaac ttgctgtggc tgttgacaat ggcatgctcg gttctatcga cgctaaccgt    900
ggtgactatc agaacggttg ggacactgac cagttcccaa tcgaccagta cgaactcgtt    960
caggcttgga tggaaatcat ccgtggtggt ggtctcggca caggtggtac taacttcgat   1020
gctaagactc gtcgtaactc aactgacctc gaggacatct tcatcgcaca catctctggt   1080
atggatgcaa tggcacgtgc tctcgaatcg gcggctaaac ttcttgagga gtctccatac   1140
tgcgctatga agaaggctcg ttacgcttcc ttcgacagcg gcatcggtaa ggacttcgag   1200
gacggcaaac tcacgctcga gcaggcttac gagtacggca agaaagtcgg cgaacccaag   1260
cagacttctg gcaagcagga actctacgag gcaatcgttg ccatgtacgc ataa         1314
```

<210> SEQ ID NO 58
<211> LENGTH: 437
<212> TYPE: PRT
<213> ORGANISM: Unknown
<220> FEATURE:
<223> OTHER INFORMATION: Obtained from environmental sample

<400> SEQUENCE: 58

```
Met Ala Lys Glu Tyr Phe Pro Glu Ile Gly Lys Ile Lys Phe Glu Gly
1               5                   10                  15

Lys Asp Ser Lys Asn Pro Met Ala Phe His Tyr Tyr Asp Ala Glu Lys
            20                  25                  30

Val Ile Met Gly Lys Pro Met Lys Glu Trp Leu Arg Phe Ala Met Ala
        35                  40                  45

Trp Trp His Thr Leu Cys Ala Glu Gly Gly Asp Gln Phe Gly Gly Gly
    50                  55                  60

Thr Lys Lys Phe Pro Trp Asn Glu Gly Thr Asp Ala Val Thr Ile Ala
65                  70                  75                  80

Lys Gln Lys Ala Asp Ala Gly Phe Glu Ile Met Gln Lys Leu Gly Phe
                85                  90                  95

Pro Tyr Phe Cys Phe His Asp Ile Asp Leu Val Ser Glu Gly Asn Ser
            100                 105                 110

Ile Glu Glu Tyr Glu Ala Asn Leu Gln Ala Ile Thr Asp Tyr Leu Lys
        115                 120                 125

Val Lys Met Glu Glu Thr Gly Ile Lys Leu Leu Trp Ser Thr Ala Asn
    130                 135                 140
```

Val Phe Gly Asn Gly Arg Tyr Met Asn Gly Ala Ser Thr Asn Pro Asp
145 150 155 160

Phe Asp Val Val Ala Arg Ala Ile Val Gln Ile Lys Asn Ala Ile Asp
165 170 175

Ala Gly Ile Lys Leu Gly Ala Glu Asn Tyr Val Phe Trp Gly Gly Arg
180 185 190

Glu Gly Tyr Met Ser Leu Leu Asn Thr Asp Gln Lys Arg Glu Lys Glu
195 200 205

His Met Ala Thr Met Leu Thr Met Ala Arg Asp Tyr Ala Arg Ser Lys
210 215 220

Gly Phe Lys Gly Thr Phe Leu Ile Glu Pro Lys Pro Met Glu Pro Ser
225 230 235 240

Lys His Gln Tyr Asp Val Asp Thr Glu Thr Val Ile Gly Phe Leu Lys
245 250 255

Ala His Asn Leu Asp Lys Asp Phe Lys Val Asn Ile Glu Val Asn His
260 265 270

Ala Thr Leu Ala Gly His Thr Phe Glu His Glu Leu Ala Val Ala Val
275 280 285

Asp Asn Gly Met Leu Gly Ser Ile Asp Ala Asn Arg Gly Asp Tyr Gln
290 295 300

Asn Gly Trp Asp Thr Asp Gln Phe Pro Ile Asp Gln Tyr Glu Leu Val
305 310 315 320

Gln Ala Trp Met Glu Ile Ile Arg Gly Gly Gly Leu Gly Thr Gly Gly
325 330 335

Thr Asn Phe Asp Ala Lys Thr Arg Arg Asn Ser Thr Asp Leu Glu Asp
340 345 350

Ile Phe Ile Ala His Ile Ser Gly Met Asp Ala Met Ala Arg Ala Leu
355 360 365

Glu Ser Ala Ala Lys Leu Leu Glu Glu Ser Pro Tyr Cys Ala Met Lys
370 375 380

Lys Ala Arg Tyr Ala Ser Phe Asp Ser Gly Ile Gly Lys Asp Phe Glu
385 390 395 400

Asp Gly Lys Leu Thr Leu Glu Gln Ala Tyr Glu Tyr Gly Lys Lys Val
405 410 415

Gly Glu Pro Lys Gln Thr Ser Gly Lys Gln Glu Leu Tyr Glu Ala Ile
420 425 430

Val Ala Met Tyr Ala
435

<210> SEQ ID NO 59
<211> LENGTH: 1317
<212> TYPE: DNA
<213> ORGANISM: Unknown
<220> FEATURE:
<223> OTHER INFORMATION: Obtained from environmental sample

<400> SEQUENCE: 59
atggcaaaag agtatttccc tacgatcggt aagatcgttt atgaaggacc ggagtccaag 60
aaccctatgg catttcatta ctatgacgca gagcgcgtag tagctggtaa aaaaatgaaa 120
gattggatgc gtttcgctat ggcatggtgg cacaccctct gtgcagaagg tgcagaccag 180
ttcggtggag gcaccaaaca cttcccgtgg agtgaaggtc ccgatgccgt aaccatcgcc 240
aagcagaaag cagacgcagg ttttgagatc atgcagaaac tcggcttccc gtatttctgt 300
ttccatgacg tggatctggt cagcgaaggc agcagcgtag aagagtacga ggcgaacctc 360

```
gcagccatca ccgattatct caagcagaaa atggacgagt cgggtatcaa actcctttgg    420

tccactgcta acgtattcgg tcacgcccgt tacatgaacg gtgccagcac caatcctgac    480

tttgatgtcg ttgcccgtgc gattgtgcag atcaagaatg ctatcgacgc aggtatcaaa    540

ctcggcgcag agaactacgt cttctggggc ggtcgtgaag gttatatgag cctgctcaat    600

accgaccaga aacgcgagaa agagcatacg gcaatgatgc tgcgtatggc gcgtgactat    660

gcccgcagca aaggtttcaa aggtaccttc ctcatcgaac ccaaacccat ggagccgtcc    720

aagcaccagt atgacgtaga taccgagacg gtgataggtt tcctcaaagc acacggtttg    780

gagaaagact ttaaggtaaa catcgaagtg aaccacgcta ccctcgccgg tcacactttc    840

gagcacgaac tggcagtagc cgtagataac ggcatgctcg gttcgatcga tgccaaccgc    900

ggtgactatc agaacggatg ggataccgac cagttcccca tcgataactt cgaactgacc    960

caagcatgga tgcagatcgt acgtaacggt ggtctcggca caggcggaac gaacttcgac   1020

tccaagaccc gtcgtaactc caccgatctc gaggatatct tcatcgctca catcagtggt   1080

atggacgctt gtgcccgtgc cctattgaat gccgtagaga tcatggagaa atcaccgatc   1140

cctgctatgc tcaaagagcg ttacgcttcc ttcgatagcg gtctgggtaa agatttcgag   1200

gacggcaaac tgacccttga gcaagtctat gagtacggta agaaagtagg cgaacccaaa   1260

caaaccagcg gcaaacaaga actctatgag gctatcgttg ccctctacgc taaataa      1317


<210> SEQ ID NO 60
<211> LENGTH: 438
<212> TYPE: PRT
<213> ORGANISM: Unknown
<220> FEATURE:
<223> OTHER INFORMATION: Obtained from environmental sample

<400> SEQUENCE: 60

Met Ala Lys Glu Tyr Phe Pro Thr Ile Gly Lys Ile Val Tyr Glu Gly
1               5                   10                  15

Pro Glu Ser Lys Asn Pro Met Ala Phe His Tyr Tyr Asp Ala Glu Arg
            20                  25                  30

Val Val Ala Gly Lys Lys Met Lys Asp Trp Met Arg Phe Ala Met Ala
        35                  40                  45

Trp Trp His Thr Leu Cys Ala Glu Gly Ala Asp Gln Phe Gly Gly Gly
    50                  55                  60

Thr Lys His Phe Pro Trp Ser Glu Gly Pro Asp Ala Val Thr Ile Ala
65                  70                  75                  80

Lys Gln Lys Ala Asp Ala Gly Phe Glu Ile Met Gln Lys Leu Gly Phe
                85                  90                  95

Pro Tyr Phe Cys Phe His Asp Val Asp Leu Val Ser Glu Gly Ser Ser
            100                 105                 110

Val Glu Glu Tyr Glu Ala Asn Leu Ala Ala Ile Thr Asp Tyr Leu Lys
        115                 120                 125

Gln Lys Met Asp Glu Ser Gly Ile Lys Leu Leu Trp Ser Thr Ala Asn
    130                 135                 140

Val Phe Gly His Ala Arg Tyr Met Asn Gly Ala Ser Thr Asn Pro Asp
145                 150                 155                 160

Phe Asp Val Val Ala Arg Ala Ile Val Gln Ile Lys Asn Ala Ile Asp
                165                 170                 175

Ala Gly Ile Lys Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
```

```
        195                 200                 205

His Thr Ala Met Met Leu Arg Met Ala Arg Asp Tyr Ala Arg Ser Lys
    210                 215                 220

Gly Phe Lys Gly Thr Phe Leu Ile Glu Pro Lys Pro Met Glu Pro Ser
225                 230                 235                 240

Lys His Gln Tyr Asp Val Asp Thr Glu Thr Val Ile Gly Phe Leu Lys
                245                 250                 255

Ala His Gly Leu Glu Lys Asp Phe Lys Val Asn Ile Glu Val Asn His
            260                 265                 270

Ala Thr Leu Ala Gly His Thr Phe Glu His Glu Leu Ala Val Ala Val
        275                 280                 285

Asp Asn Gly Met Leu Gly Ser Ile Asp Ala Asn Arg Gly Asp Tyr Gln
    290                 295                 300

Asn Gly Trp Asp Thr Asp Gln Phe Pro Ile Asp Asn Phe Glu Leu Thr
305                 310                 315                 320

Gln Ala Trp Met Gln Ile Val Arg Asn Gly Gly Leu Gly Thr Gly Gly
                325                 330                 335

Thr Asn Phe Asp Ser Lys Thr Arg Arg Asn Ser Thr Asp Leu Glu Asp
            340                 345                 350

Ile Phe Ile Ala His Ile Ser Gly Met Asp Ala Cys Ala Arg Ala Leu
        355                 360                 365

Leu Asn Ala Val Glu Ile Met Glu Lys Ser Pro Ile Pro Ala Met Leu
    370                 375                 380

Lys Glu Arg Tyr Ala Ser Phe Asp Ser Gly Leu Gly Lys Asp Phe Glu
385                 390                 395                 400

Asp Gly Lys Leu Thr Leu Glu Gln Val Tyr Glu Tyr Gly Lys Lys Val
                405                 410                 415

Gly Glu Pro Lys Gln Thr Ser Gly Lys Gln Glu Leu Tyr Glu Ala Ile
            420                 425                 430

Val Ala Leu Tyr Ala Lys
        435


<210> SEQ ID NO 61
<211> LENGTH: 1314
<212> TYPE: DNA
<213> ORGANISM: Unknown
<220> FEATURE:
<223> OTHER INFORMATION: Obtained from environmental sample

<400> SEQUENCE: 61

atgaaagagt atttccctga gatcggtaag atccaatttg aaggcccgga gtccaagaac      60

ccgatggcat ttcactacta tgacgcagag cgcgtcgtag ccggtaaaac aatgaaagag     120

tggatgcgtt tcgctatggc ttggtggcac accctctgtg cggaaggcgg cgaccagttc     180

ggaggcggaa cgaagaagtt cccctggaac gaaggcgcta acgctttgga gatcgccaag     240

cacaaagccg atgcgggatt tgagatcatg cagaaactcg gcatccctta tttctgtttc     300

catgacgtgg atctcatcgc cgagggcggt tcggtagaag agtacgaagc caacctcgct     360

gccatcaccg attacctcaa acagaaaatg gacgagactg gcatcaaact gctgtggtcc     420

acggcgaacg tcttcagcaa cccccgttat atgaacggcg ccagcacgaa ccccgatttc     480

gatgtagtag cgcgtgccat cgtccagatc aagaacgcta tcgacgccgg tatcaaactc     540

ggagcagaga actatgtctt ctggggtggt cgcgagggct atatgagcct cctcaacact     600

gaccagcgcc gagagaaaga gcatatggct accatgctcc gtatggcgcg tgactacgcg     660
```

```
cgtgccaaag gattcaaggg caccttcctc atcgaaccca aaccatgtga gccgtccaaa    720

catcagtatg atgtcgatac cgagaccgtc atcggtttcc tcaaagcgca tggactcgac    780

aaggatttca aagtcaatat cgaggtcaac cacgccaccc tcgcaggcca cacgttcgaa    840

cacgaactgg cttgcgctgt agatgccggc atgctcggtt cgattgacgc caaccgcggt    900

gacgcccaga acggatggga caccgaccag ttccctattg ataacttcga actcacacag    960

gctttcatgc agatcgtccg caacggcggt ttcggaacag gcggtacgaa cttcgacgcc   1020

aagacacgcc gtaactccac cgacttggag gacatcttca tcgcccatat cagcggcatg   1080

gacgcttgcg cacgtgcgtt actcaatgct gtcgaaatcc tcgagaagag cccgattccg   1140

gcgatgctca aagagcgtta tgcttccttt gacggcggca tcggaaagga cttcgaggag   1200

ggaaaactga ctttcgagca ggtctatgag tacggcaaga aagtcggcga acccaaacag   1260

accagcggca aacaggagct ctacgaaacc atcgtcgccc tctatgccaa atag         1314
```

```
<210> SEQ ID NO 62
<211> LENGTH: 437
<212> TYPE: PRT
<213> ORGANISM: Unknown
<220> FEATURE:
<223> OTHER INFORMATION: Obtained from environmental sample

<400> SEQUENCE: 62

Met Lys Glu Tyr Phe Pro Glu Ile Gly Lys Ile Gln Phe Glu Gly Pro
1               5                   10                  15

Glu Ser Lys Asn Pro Met Ala Phe His Tyr Tyr Asp Ala Glu Arg Val
            20                  25                  30

Val Ala Gly Lys Thr Met Lys Glu Trp Met Arg Phe Ala Met Ala Trp
        35                  40                  45

Trp His Thr Leu Cys Ala Glu Gly Gly Asp Gln Phe Gly Gly Gly Thr
    50                  55                  60

Lys Lys Phe Pro Trp Asn Glu Gly Ala Asn Ala Leu Glu Ile Ala Lys
65                  70                  75                  80

His Lys Ala Asp Ala Gly Phe Glu Ile Met Gln Lys Leu Gly Ile Pro
                85                  90                  95

Tyr Phe Cys Phe His Asp Val Asp Leu Ile Ala Glu Gly Gly Ser Val
            100                 105                 110

Glu Glu Tyr Glu Ala Asn Leu Ala Ala Ile Thr Asp Tyr Leu Lys Gln
        115                 120                 125

Lys Met Asp Glu Thr Gly Ile Lys Leu Leu Trp Ser Thr Ala Asn Val
    130                 135                 140

Phe Ser Asn Pro Arg Tyr Met Asn Gly Ala Ser Thr Asn Pro Asp Phe
145                 150                 155                 160

Asp Val Val Ala Arg Ala Ile Val Gln Ile Lys Asn Ala Ile Asp Ala
                165                 170                 175

Gly Ile Lys Leu Gly Ala Glu Asn Tyr Val Phe Trp Gly Gly Arg Glu
            180                 185                 190

Gly Tyr Met Ser Leu Leu Asn Thr Asp Gln Arg Arg Glu Lys Glu His
        195                 200                 205

Met Ala Thr Met Leu Arg Met Ala Arg Asp Tyr Ala Arg Ala Lys Gly
    210                 215                 220

Phe Lys Gly Thr Phe Leu Ile Glu Pro Lys Pro Cys Glu Pro Ser Lys
225                 230                 235                 240

His Gln Tyr Asp Val Asp Thr Glu Thr Val Ile Gly Phe Leu Lys Ala
                245                 250                 255
```

```
His Gly Leu Asp Lys Asp Phe Lys Val Asn Ile Glu Val Asn His Ala
            260                 265                 270

Thr Leu Ala Gly His Thr Phe Glu His Glu Leu Ala Cys Ala Val Asp
        275                 280                 285

Ala Gly Met Leu Gly Ser Ile Asp Ala Asn Arg Gly Asp Ala Gln Asn
    290                 295                 300

Gly Trp Asp Thr Asp Gln Phe Pro Ile Asp Asn Phe Glu Leu Thr Gln
305                 310                 315                 320

Ala Phe Met Gln Ile Val Arg Asn Gly Gly Phe Gly Thr Gly Gly Thr
                325                 330                 335

Asn Phe Asp Ala Lys Thr Arg Arg Asn Ser Thr Asp Leu Glu Asp Ile
            340                 345                 350

Phe Ile Ala His Ile Ser Gly Met Asp Ala Cys Ala Arg Ala Leu Leu
        355                 360                 365

Asn Ala Val Glu Ile Leu Glu Lys Ser Pro Ile Pro Ala Met Leu Lys
    370                 375                 380

Glu Arg Tyr Ala Ser Phe Asp Gly Gly Ile Gly Lys Asp Phe Glu Glu
385                 390                 395                 400

Gly Lys Leu Thr Phe Glu Gln Val Tyr Glu Tyr Gly Lys Lys Val Gly
                405                 410                 415

Glu Pro Lys Gln Thr Ser Gly Lys Gln Glu Leu Tyr Glu Thr Ile Val
            420                 425                 430

Ala Leu Tyr Ala Lys
        435


<210> SEQ ID NO 63
<211> LENGTH: 1317
<212> TYPE: DNA
<213> ORGANISM: Unknown
<220> FEATURE:
<223> OTHER INFORMATION: Obtained from environmental sample

<400> SEQUENCE: 63

atggcaaaag agtatttccc tacgatcggt aagatcgttt atgaaggacc ggaatccaag      60

aaccctatgg catttcatta ctatgacgca gagcgcgtag tagctggtaa aaaaatgaaa     120

gattggatgc gtttcgctat ggcatggtgg cacaccctct gtgcagaagg tgcagaccag     180

ttcggtggag gcaccaaaca cttcccgtgg aatgaaggtc ccgatgccgt aaccatcgcc     240

aagcagaaag cagacgcagg ttttgagatc atgcagaaac tcggcttccc gtatttctgt     300

ttccatgacg tggatctggt cggcgaaggc agcagcgtag aagagtacga ggcgaacctc     360

gcagccatca ccgattatct caagcagaaa atggacgagt cgggtatcaa actcctttgg     420

tccactgcta acgtattcgg tcacgcccgt tacatgaacg gtgccagcac caatcctgac     480

tttgatgtcg ttgcccgtgc gattgtgcag atcaagaatg ctatcgacgc aggtatcaaa     540

ctcggcgcag agaactacgt cttctggggc ggtcgtgaag gttatatgag cctgctcaac     600

accgaccaga aacgcgagaa agagcatacg gcaatgatgc tgcgtatggc gcgtgactat     660

gcccgcagca aaggtttcaa aggtaccttc ctcatcgaac ccaaacccat ggagccgtcc     720

aagcaccagt atgacgtaga taccgagacg gtgataggtt tcctcaaagc acacggtttg     780

gagaaagact ttaaggtaaa catcgaagtg aaccacgcta ccctcgccgg tcacactttc     840

gagcacgaac tggcagtagc cgtagataac ggcatgctcg gttcgatcga tgccaaccgc     900

ggtgactatc agaacggatg ggataccgac cagttcccca tcgataactt cgaactgacc     960
```

```
caagcatgga tgcagatcgt acgtaacggt ggtctcggca caggcggaac gaacttcgac   1020

tccaagaccc gtcgtaactc caccgatctc gaggatatct tcatcgctca catcagtggt   1080

atggacgctt gtgcccgtgc cctattgaat gccgtagaga tcatggagaa atcaccgatc   1140

cctgctatgc tcaaagagcg ttacgcttcc ttcgatagcg gtctgggtaa agatttcgag   1200

gacggcaaac tgacccttga gcaagtctat gagtacggta agaaagtagg cgaacccaaa   1260

caaaccagcg gcaaacaaga actctatgag gctatcgttg ccctctacgc taaataa      1317
```

```
<210> SEQ ID NO 64
<211> LENGTH: 438
<212> TYPE: PRT
<213> ORGANISM: Unknown
<220> FEATURE:
<223> OTHER INFORMATION: Obtained from environmental sample

<400> SEQUENCE: 64

Met Ala Lys Glu Tyr Phe Pro Thr Ile Gly Lys Ile Val Tyr Glu Gly
1               5                   10                  15

Pro Glu Ser Lys Asn Pro Met Ala Phe His Tyr Tyr Asp Ala Glu Arg
            20                  25                  30

Val Val Ala Gly Lys Lys Met Lys Asp Trp Met Arg Phe Ala Met Ala
        35                  40                  45

Trp Trp His Thr Leu Cys Ala Glu Gly Ala Asp Gln Phe Gly Gly Gly
    50                  55                  60

Thr Lys His Phe Pro Trp Asn Glu Gly Pro Asp Ala Val Thr Ile Ala
65                  70                  75                  80

Lys Gln Lys Ala Asp Ala Gly Phe Glu Ile Met Gln Lys Leu Gly Phe
                85                  90                  95

Pro Tyr Phe Cys Phe His Asp Val Asp Leu Val Gly Glu Gly Ser Ser
            100                 105                 110

Val Glu Glu Tyr Glu Ala Asn Leu Ala Ala Ile Thr Asp Tyr Leu Lys
        115                 120                 125

Gln Lys Met Asp Glu Ser Gly Ile Lys Leu Leu Trp Ser Thr Ala Asn
    130                 135                 140

Val Phe Gly His Ala Arg Tyr Met Asn Gly Ala Ser Thr Asn Pro Asp
145                 150                 155                 160

Phe Asp Val Val Ala Arg Ala Ile Val Gln Ile Lys Asn Ala Ile Asp
                165                 170                 175

Ala Gly Ile Lys Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Thr Ala Met Met Leu Arg Met Ala Arg Asp Tyr Ala Arg Ser Lys
    210                 215                 220

Gly Phe Lys Gly Thr Phe Leu Ile Glu Pro Lys Pro Met Glu Pro Ser
225                 230                 235                 240

Lys His Gln Tyr Asp Val Asp Thr Glu Thr Val Ile Gly Phe Leu Lys
                245                 250                 255

Ala His Gly Leu Glu Lys Asp Phe Lys Val Asn Ile Glu Val Asn His
            260                 265                 270

Ala Thr Leu Ala Gly His Thr Phe Glu His Glu Leu Ala Val Ala Val
        275                 280                 285

Asp Asn Gly Met Leu Gly Ser Ile Asp Ala Asn Arg Gly Asp Tyr Gln
    290                 295                 300
```

```
Asn Gly Trp Asp Thr Asp Gln Phe Pro Ile Asp Asn Phe Glu Leu Thr
305                 310                 315                 320

Gln Ala Trp Met Gln Ile Val Arg Asn Gly Gly Leu Gly Thr Gly Gly
                325                 330                 335

Thr Asn Phe Asp Ser Lys Thr Arg Arg Asn Ser Thr Asp Leu Glu Asp
            340                 345                 350

Ile Phe Ile Ala His Ile Ser Gly Met Asp Ala Cys Ala Arg Ala Leu
        355                 360                 365

Leu Asn Ala Val Glu Ile Met Glu Lys Ser Pro Ile Pro Ala Met Leu
    370                 375                 380

Lys Glu Arg Tyr Ala Ser Phe Asp Ser Gly Leu Gly Lys Asp Phe Glu
385                 390                 395                 400

Asp Gly Lys Leu Thr Leu Glu Gln Val Tyr Glu Tyr Gly Lys Lys Val
                405                 410                 415

Gly Glu Pro Lys Gln Thr Ser Gly Lys Gln Glu Leu Tyr Glu Ala Ile
            420                 425                 430

Val Ala Leu Tyr Ala Lys
        435
```

<210> SEQ ID NO 65
<211> LENGTH: 1314
<212> TYPE: DNA
<213> ORGANISM: Unknown
<220> FEATURE:
<223> OTHER INFORMATION: Obtained from environmental sample

<400> SEQUENCE: 65

```
atgaaagagt atttccctga ggtcggtaag atccaatttg aaggcccgga gtctaagaac     60
ccgatggcat ttcactacta tgacgcagag cgcgtcgtag ccggtaaaac aatgaaagag    120
tggatgcgtt tcgctatggc ttggtggcac accctctgtg cagaaggcgg cgaccagttc    180
ggaggcggaa cgaagcattt cccgtggaat gaaggcgcta acgctttgga gatcgccaaa    240
cacaaagccg atgcgggatt cgagatcatg cagaaactcg gcatccccta tttctgtttc    300
catgacgtgg atctcatcgc cgagggcggt tcggtagaag agtacgaaac caacctcgct    360
gctatcaccg actacctcaa gcagaaaatg gacgagaccg gcatcaaact gctgtggtcc    420
acggcgaacg tgttcagcaa cccccgttat atgaacggcg cgagcacgaa ccccgatttc    480
gatgtagtag cgcgtgccat cgtgcagatc aagaatgcca tcgacgccgg catcaaactg    540
ggcgcagaga actatgtctt ctggggcggt cgcgagggct acatgagcct gctcaacacc    600
gaccagcgcc gcgagaaaga gcatatggct actatgctcc gtatggcgcg tgactacgcg    660
cgtgccaaag gattcaaggg cacctttctc atcgaaccca aaccgtgtga gccgtccaaa    720
catcagtatg atgtcgatac cgagaccgtc atcggtttcc tcaaagcgca tggactcgac    780
aaggatttca aggttaatat cgaggtcaac cacgccaccc tcgcaggcca cacgttcgaa    840
cacgaactgg cttgcgctgt agatgccggc atgctcggtt cgattgacgc caaccgcggt    900
gacgcccaga acggatggga caccgaccag ttccctattg ataacttcga actcacacag    960
gctttcatgc agatcgtccg caacggcggt ttcggaacag gcggtacgaa cttcgacgcc   1020
aagacacgcc gtaactccac cgacttggag gacatcttca tcgcccatat cagcggcatg   1080
gacgcttgcg cacgtgcgtt gctcaacgcc atcgaaatcc tcgagaagag cccgatcccg   1140
gctatgctca aagaccgtta tgcctccttt gatggcggca tcggaaagga ctttgaggag   1200
ggcaaactga ctttcgagca ggtctatgag tacggcaaga aggtcggaga acccaaacag   1260
```

accagcggca aacaggagct ctacgaaacc atcgtcgccc tctatgccaa atag 1314

<210> SEQ ID NO 66
<211> LENGTH: 437
<212> TYPE: PRT
<213> ORGANISM: Unknown
<220> FEATURE:
<223> OTHER INFORMATION: Obtained from environmental sample

<400> SEQUENCE: 66

```
Met Lys Glu Tyr Phe Pro Glu Val Gly Lys Ile Gln Phe Glu Gly Pro
1               5                   10                  15

Glu Ser Lys Asn Pro Met Ala Phe His Tyr Tyr Asp Ala Glu Arg Val
            20                  25                  30

Val Ala Gly Lys Thr Met Lys Glu Trp Met Arg Phe Ala Met Ala Trp
        35                  40                  45

Trp His Thr Leu Cys Ala Glu Gly Gly Asp Gln Phe Gly Gly Gly Thr
    50                  55                  60

Lys His Phe Pro Trp Asn Glu Gly Ala Asn Ala Leu Glu Ile Ala Lys
65                  70                  75                  80

His Lys Ala Asp Ala Gly Phe Glu Ile Met Gln Lys Leu Gly Ile Pro
                85                  90                  95

Tyr Phe Cys Phe His Asp Val Asp Leu Ile Ala Glu Gly Gly Ser Val
            100                 105                 110

Glu Glu Tyr Glu Thr Asn Leu Ala Ala Ile Thr Asp Tyr Leu Lys Gln
        115                 120                 125

Lys Met Asp Glu Thr Gly Ile Lys Leu Leu Trp Ser Thr Ala Asn Val
    130                 135                 140

Phe Ser Asn Pro Arg Tyr Met Asn Gly Ala Ser Thr Asn Pro Asp Phe
145                 150                 155                 160

Asp Val Val Ala Arg Ala Ile Val Gln Ile Lys Asn Ala Ile Asp Ala
                165                 170                 175

Gly Ile Lys Leu Gly Ala Glu Asn Tyr Val Phe Trp Gly Gly Arg Glu
            180                 185                 190

Gly Tyr Met Ser Leu Leu Asn Thr Asp Gln Arg Arg Glu Lys Glu His
        195                 200                 205

Met Ala Thr Met Leu Arg Met Ala Arg Asp Tyr Ala Arg Ala Lys Gly
    210                 215                 220

Phe Lys Gly Thr Phe Leu Ile Glu Pro Lys Pro Cys Glu Pro Ser Lys
225                 230                 235                 240

His Gln Tyr Asp Val Asp Thr Glu Thr Val Ile Gly Phe Leu Lys Ala
                245                 250                 255

His Gly Leu Asp Lys Asp Phe Lys Val Asn Ile Glu Val Asn His Ala
            260                 265                 270

Thr Leu Ala Gly His Thr Phe Glu His Glu Leu Ala Cys Ala Val Asp
        275                 280                 285

Ala Gly Met Leu Gly Ser Ile Asp Ala Asn Arg Gly Asp Ala Gln Asn
    290                 295                 300

Gly Trp Asp Thr Asp Gln Phe Pro Ile Asp Asn Phe Glu Leu Thr Gln
305                 310                 315                 320

Ala Phe Met Gln Ile Val Arg Asn Gly Gly Phe Gly Thr Gly Gly Thr
                325                 330                 335

Asn Phe Asp Ala Lys Thr Arg Arg Asn Ser Thr Asp Leu Glu Asp Ile
            340                 345                 350

Phe Ile Ala His Ile Ser Gly Met Asp Ala Cys Ala Arg Ala Leu Leu
```

-continued

```
        355                 360                 365

Asn Ala Ile Glu Ile Leu Glu Lys Ser Pro Ile Pro Ala Met Leu Lys
    370                 375                 380

Asp Arg Tyr Ala Ser Phe Asp Gly Gly Ile Gly Lys Asp Phe Glu Glu
385                 390                 395                 400

Gly Lys Leu Thr Phe Glu Gln Val Tyr Glu Tyr Gly Lys Lys Val Gly
                405                 410                 415

Glu Pro Lys Gln Thr Ser Gly Lys Gln Glu Leu Tyr Glu Thr Ile Val
            420                 425                 430

Ala Leu Tyr Ala Lys
        435
```

<210> SEQ ID NO 67
<211> LENGTH: 1314
<212> TYPE: DNA
<213> ORGANISM: Unknown
<220> FEATURE:
<223> OTHER INFORMATION: Obtained from environmental sample

<400> SEQUENCE: 67

```
atgaaagagt atttccctga gatcggtaag atccaatttg aaggcccgga gtccaagaac      60

ccgatggcgt ttcactacta tgacgctgag cgcgtcgtag ccggtaaaac aatgaaagag     120

tggatgcgtt tcgctatggc ttggtggcac accctctgtg cggaaggcgg cgaccagttc     180

ggaggaggaa cgaagaaatt cccctggaac gaaggggcaa acgctttgga gatcgccaag     240

cacaaagccg atgcgggatt cgagatcatg cagaaactcg gcatcccttta tttctgtttc     300

catgacgtgg atctcatcgc cgagggcgaa tcggtagaag agtacgaagc caacctcgct     360

gccatcaccg attacctcaa acagaaaatg gacgagaccg gcatcaaact gctgtggtcc     420

acggcgaacg tgttcagcaa cccccgttat atgaacggcg ccagcacgaa ccccgatttc     480

gatgtagtgg cacgcgctat cgtacaaatc aagaacgcta tcgacgccgg tatcaaactc     540

ggagcagaga actatgtctt ctggggcggt cgcgagggct atatgtcgct cctcaacacc     600

gaccagcgcc gagagaaaga gcatatggct actatgctcc gtatggcgcg tgactacgcg     660

cgttccaaag gattcaaggg caccttcctc atcgaaccca aaccgtgtga gccgtccaaa     720

catcagtacg atgtggacac agagaccgtc atcggtttcc ttaaagcgca tggactcgac     780

aaggatttca aagtcaatat cgaggtcaac cacgccaccc tcgcaggcca cacgttcgaa     840

cacgaactgg cttgcgctgt agatgccggc atgctcggtt cgattgacgc caaccgcggt     900

gacgcccaga acggatggga caccgaccaa ttccctattg ataacttcga actcactcag     960

gctttcatgc agatcgtccg caacggcggt ttcggaacag gcggtacgaa cttcgacgcc    1020

aagacacgcc gtaactccac cgacttggag gacatcttca tcgcccatat cagcggcatg    1080

gacgcttgcg ctcgtgcgtt gctcaatgct gtcgaaatcc tcgagaagag cccgatcccg    1140

gctatgctca aagagcgtta tgcttccttt gacggcggca tcggaaagga ctttgaggag    1200

ggcaaactga ctttcgagca ggtctatgag tacggcaaga aggtcggaga acccaaacag    1260

accagcggca aacaggagct ctacgaaacc atcgtcgccc tctatgccaa atga          1314
```

<210> SEQ ID NO 68
<211> LENGTH: 437
<212> TYPE: PRT
<213> ORGANISM: Unknown
<220> FEATURE:
<223> OTHER INFORMATION: Obtained from environmental sample

<400> SEQUENCE: 68

```
Met Lys Glu Tyr Phe Pro Glu Ile Gly Lys Ile Gln Phe Glu Gly Pro
1               5                   10                  15

Glu Ser Lys Asn Pro Met Ala Phe His Tyr Tyr Asp Ala Glu Arg Val
            20                  25                  30

Val Ala Gly Lys Thr Met Lys Glu Trp Met Arg Phe Ala Met Ala Trp
        35                  40                  45

Trp His Thr Leu Cys Ala Glu Gly Gly Asp Gln Phe Gly Gly Gly Thr
    50                  55                  60

Lys Lys Phe Pro Trp Asn Glu Gly Ala Asn Ala Leu Glu Ile Ala Lys
65                  70                  75                  80

His Lys Ala Asp Ala Gly Phe Glu Ile Met Gln Lys Leu Gly Ile Pro
                85                  90                  95

Tyr Phe Cys Phe His Asp Val Asp Leu Ile Ala Glu Gly Glu Ser Val
            100                 105                 110

Glu Glu Tyr Glu Ala Asn Leu Ala Ala Ile Thr Asp Tyr Leu Lys Gln
        115                 120                 125

Lys Met Asp Glu Thr Gly Ile Lys Leu Leu Trp Ser Thr Ala Asn Val
    130                 135                 140

Phe Ser Asn Pro Arg Tyr Met Asn Gly Ala Ser Thr Asn Pro Asp Phe
145                 150                 155                 160

Asp Val Val Ala Arg Ala Ile Val Gln Ile Lys Asn Ala Ile Asp Ala
                165                 170                 175

Gly Ile Lys Leu Gly Ala Glu Asn Tyr Val Phe Trp Gly Gly Arg Glu
            180                 185                 190

Gly Tyr Met Ser Leu Leu Asn Thr Asp Gln Arg Arg Glu Lys Glu His
        195                 200                 205

Met Ala Thr Met Leu Arg Met Ala Arg Asp Tyr Ala Arg Ser Lys Gly
    210                 215                 220

Phe Lys Gly Thr Phe Leu Ile Glu Pro Lys Pro Cys Glu Pro Ser Lys
225                 230                 235                 240

His Gln Tyr Asp Val Asp Thr Glu Thr Val Ile Gly Phe Leu Lys Ala
                245                 250                 255

His Gly Leu Asp Lys Asp Phe Lys Val Asn Ile Glu Val Asn His Ala
            260                 265                 270

Thr Leu Ala Gly His Thr Phe Glu His Glu Leu Ala Cys Ala Val Asp
        275                 280                 285

Ala Gly Met Leu Gly Ser Ile Asp Ala Asn Arg Gly Asp Ala Gln Asn
    290                 295                 300

Gly Trp Asp Thr Asp Gln Phe Pro Ile Asp Asn Phe Glu Leu Thr Gln
305                 310                 315                 320

Ala Phe Met Gln Ile Val Arg Asn Gly Gly Phe Gly Thr Gly Gly Thr
                325                 330                 335

Asn Phe Asp Ala Lys Thr Arg Arg Asn Ser Thr Asp Leu Glu Asp Ile
            340                 345                 350

Phe Ile Ala His Ile Ser Gly Met Asp Ala Cys Ala Arg Ala Leu Leu
        355                 360                 365

Asn Ala Val Glu Ile Leu Glu Lys Ser Pro Ile Pro Ala Met Leu Lys
    370                 375                 380

Glu Arg Tyr Ala Ser Phe Asp Gly Gly Ile Gly Lys Asp Phe Glu Glu
385                 390                 395                 400

Gly Lys Leu Thr Phe Glu Gln Val Tyr Glu Tyr Gly Lys Lys Val Gly
                405                 410                 415
```

Glu Pro Lys Gln Thr Ser Gly Lys Gln Glu Leu Tyr Glu Thr Ile Val
420 425 430

Ala Leu Tyr Ala Lys
435

<210> SEQ ID NO 69
<211> LENGTH: 1314
<212> TYPE: DNA
<213> ORGANISM: Unknown
<220> FEATURE:
<223> OTHER INFORMATION: Obtained from environmental sample

<400> SEQUENCE: 69
atgaaagagt atttccctga gatcggtaag atccaatttg aaggcccgga gtccaagaac 60
ccgatggcgt ttcactacta tgacgcagag cgcgtagtag ccggtaaaac aatgaaagaa 120
tggatgcgtt tcgccatggc atggtggcac accctctgtg cagaaggcgg cgaccagttc 180
ggaggaggaa cgaagcattt cccgtggaat gaaggcgcta acgctttgga gatcgccaaa 240
cacaaagccg atgcgggatt cgagatcatg cagaaactcg gcatccccta tttctgtttc 300
catgacgtgg atctcatcgc cgagggcgat tcggtggagg agtacgaagc taaccccgct 360
gccatcaccg attacctcaa acagaaaatg gacgagaccg gcatcaaact gctgtggtcc 420
acggcgaacg tcttcagcaa cccccgttac atgaacggtg cgagcacgaa cccggatttc 480
gatgtagtgg cacgcgctat cgtacaaatc aagaacgcta tcgacgccgg tatcaaactc 540
ggagcagaga actatgtctt ctggggcggt cgcgagggct atatgtcgct cctcaacacc 600
gaccagcgtc gcgagaaaga gcatatggct actatgctcc gtatggcgcg tgactacgcg 660
cgtgccaaag gattcaaggg caccttcctc atcgaaccca aaccatgtga gccgtccaaa 720
catcagtacg atgtggacac agagactgtc atcggtttcc tcaaagcgca tggactcgac 780
aaggatttca aagtcaacat cgaggtcaac cacgccaccc tcgcaggtca cacgttcgaa 840
cacgaactgg cttgcgctgt agatgccggc atgctcggtt cgattgacgc caaccgcggt 900
gacgcccaga acggatggga cactgaccag ttccctattg ataacttcga actcacacag 960
gctttcatgc agatcgtccg caacggcggt ttcggaacag gcggtacgaa cttcgacgcc 1020
aagacacgcc gtaactccac cgacttggag gacatcttca tcgcccatat cagcggcatg 1080
gacgcttgtg tccgtgcgtt gctcaacgcc atcgaaatcc tcgagaagag cccgatcccg 1140
gctatgctca aagagcgtta cgcttccttt gacggcggca tcggaaagga ctttgaggat 1200
ggtaaactga ctttcgagca ggtctatgag tacggcaaga aggtcggaga acccaaacag 1260
accagcggca aacaggagct ctacgaaacc atcgtcgccc tctatgccaa gtaa 1314

<210> SEQ ID NO 70
<211> LENGTH: 437
<212> TYPE: PRT
<213> ORGANISM: Unknown
<220> FEATURE:
<223> OTHER INFORMATION: Obtained from environmental sample

<400> SEQUENCE: 70

Met Lys Glu Tyr Phe Pro Glu Ile Gly Lys Ile Gln Phe Glu Gly Pro
1 5 10 15

Glu Ser Lys Asn Pro Met Ala Phe His Tyr Tyr Asp Ala Glu Arg Val
20 25 30

Val Ala Gly Lys Thr Met Lys Glu Trp Met Arg Phe Ala Met Ala Trp
35 40 45

Trp His Thr Leu Cys Ala Glu Gly Gly Asp Gln Phe Gly Gly Gly Thr
    50                  55                  60

Lys His Phe Pro Trp Asn Glu Gly Ala Asn Ala Leu Glu Ile Ala Lys
65                  70                  75                  80

His Lys Ala Asp Ala Gly Phe Glu Ile Met Gln Lys Leu Gly Ile Pro
                85                  90                  95

Tyr Phe Cys Phe His Asp Val Asp Leu Ile Ala Glu Gly Asp Ser Val
            100                 105                 110

Glu Glu Tyr Glu Ala Asn Pro Ala Ala Ile Thr Asp Tyr Leu Lys Gln
        115                 120                 125

Lys Met Asp Glu Thr Gly Ile Lys Leu Leu Trp Ser Thr Ala Asn Val
    130                 135                 140

Phe Ser Asn Pro Arg Tyr Met Asn Gly Ala Ser Thr Asn Pro Asp Phe
145                 150                 155                 160

Asp Val Val Ala Arg Ala Ile Val Gln Ile Lys Asn Ala Ile Asp Ala
                165                 170                 175

Gly Ile Lys Leu Gly Ala Glu Asn Tyr Val Phe Trp Gly Gly Arg Glu
            180                 185                 190

Gly Tyr Met Ser Leu Leu Asn Thr Asp Gln Arg Arg Glu Lys Glu His
        195                 200                 205

Met Ala Thr Met Leu Arg Met Ala Arg Asp Tyr Ala Arg Ala Lys Gly
    210                 215                 220

Phe Lys Gly Thr Phe Leu Ile Glu Pro Lys Pro Cys Glu Pro Ser Lys
225                 230                 235                 240

His Gln Tyr Asp Val Asp Thr Glu Thr Val Ile Gly Phe Leu Lys Ala
                245                 250                 255

His Gly Leu Asp Lys Asp Phe Lys Val Asn Ile Glu Val Asn His Ala
            260                 265                 270

Thr Leu Ala Gly His Thr Phe Glu His Glu Leu Ala Cys Ala Val Asp
        275                 280                 285

Ala Gly Met Leu Gly Ser Ile Asp Ala Asn Arg Gly Asp Ala Gln Asn
    290                 295                 300

Gly Trp Asp Thr Asp Gln Phe Pro Ile Asp Asn Phe Glu Leu Thr Gln
305                 310                 315                 320

Ala Phe Met Gln Ile Val Arg Asn Gly Gly Phe Gly Thr Gly Gly Thr
                325                 330                 335

Asn Phe Asp Ala Lys Thr Arg Arg Asn Ser Thr Asp Leu Glu Asp Ile
            340                 345                 350

Phe Ile Ala His Ile Ser Gly Met Asp Ala Cys Val Arg Ala Leu Leu
        355                 360                 365

Asn Ala Ile Glu Ile Leu Glu Lys Ser Pro Ile Pro Ala Met Leu Lys
    370                 375                 380

Glu Arg Tyr Ala Ser Phe Asp Gly Gly Ile Gly Lys Asp Phe Glu Asp
385                 390                 395                 400

Gly Lys Leu Thr Phe Glu Gln Val Tyr Glu Tyr Gly Lys Lys Val Gly
                405                 410                 415

Glu Pro Lys Gln Thr Ser Gly Lys Gln Glu Leu Tyr Glu Thr Ile Val
            420                 425                 430

Ala Leu Tyr Ala Lys
        435

<210> SEQ ID NO 71
<211> LENGTH: 1314

-continued

<212> TYPE: DNA
<213> ORGANISM: Unknown
<220> FEATURE:
<223> OTHER INFORMATION: Obtained from environmental sample

<400> SEQUENCE: 71
atgaaagagt atttccctga gatcggaaag atccaattcg aaggcccgga gtccaagaat 60
cctatggcat ttcactacta tgacgcagag cgtgtagtag ccggtaaaac aatgaaagag 120
tggatgcgtt tcgctttggc atggtggcac acgctctgcg cagaaggcgg cgaccagttc 180
ggaggcggca cgaagcattt cccttggaat gaaggtgcaa acgctttgga gatcgccaag 240
cacaaagccg atgcaggctt cgagatcatg cagaaactcg gcatccccta tttctgtttc 300
catgacgtgg atctgatcgc cgagggcggt tcggtagaag agtatgaagc taatttaacg 360
gctatcaccg attacctcaa acagaaaatg gacgagaccg gcatcaaact gctgtggtcc 420
actgcgaacg tgttcggtaa cgcacgttat atgaacggcg cgagcacgaa ccccgatttc 480
gatgtagtgg cacgcgctat cgtgcagatc aagaacgcta tcgacgccgg catcaaactg 540
ggcgcagaga actacgtctt ctggggcggt cgcgagggat atatgtcgct cctgaacacc 600
gaccagaagc gtgagaaaga gcatatggct accatgctcc gtatggcgcg tgactacgcg 660
cgttccaaag gattcaaagg tacgttcctc atcgagccca aaccgtgtga gccgtccaaa 720
catcagtacg acgtggacac tgagaccgtc atcggtttcc tcaaagccca tggtctcggc 780
aaggatttca aagtgaacat cgaggtgaat cacgccaccc tcgcagggca cacgttcgaa 840
cacgaactgg cttgcgccgt agatgccggc atgctcggtt cgatcgacgc caaccgcggt 900
gacgcacaaa acggatggga caccgaccag ttccctattg ataatttcga actcacccag 960
gcattcatgc agatcgtccg caacggcggt ttcggaacag gcggtacgaa cttcgacgcc 1020
aagacacgcc gtaattccac cgacttggag gacatcttca tcgcccatat cagcggcatg 1080
gacgcttgtg cccgtgcgtt gctcaatgct gtcgaaatcc ttgaaaagag cccgatcccg 1140
gcgatgctca aagagcgtta cgcctccttt gacagcggta tgggtaagga ctttgaggag 1200
ggcaagctga ccttcgagca ggtctatgag tacggcaaac aggtcggcga acccaaacag 1260
accagcggca agcaggagct ctacgaaacc atcgtcgccc tctatgccaa atag 1314

<210> SEQ ID NO 72
<211> LENGTH: 437
<212> TYPE: PRT
<213> ORGANISM: Unknown
<220> FEATURE:
<223> OTHER INFORMATION: Obtained from environmental sample

<400> SEQUENCE: 72

Met Lys Glu Tyr Phe Pro Glu Ile Gly Lys Ile Gln Phe Glu Gly Pro
1 5 10 15

Glu Ser Lys Asn Pro Met Ala Phe His Tyr Tyr Asp Ala Glu Arg Val
20 25 30

Val Ala Gly Lys Thr Met Lys Glu Trp Met Arg Phe Ala Leu Ala Trp
35 40 45

Trp His Thr Leu Cys Ala Glu Gly Gly Asp Gln Phe Gly Gly Gly Thr
50 55 60

Lys His Phe Pro Trp Asn Glu Gly Ala Asn Ala Leu Glu Ile Ala Lys
65 70 75 80

His Lys Ala Asp Ala Gly Phe Glu Ile Met Gln Lys Leu Gly Ile Pro
85 90 95

```
Tyr Phe Cys Phe His Asp Val Asp Leu Ile Ala Glu Gly Gly Ser Val
            100                 105                 110

Glu Glu Tyr Glu Ala Asn Leu Thr Ala Ile Thr Asp Tyr Leu Lys Gln
        115                 120                 125

Lys Met Asp Glu Thr Gly Ile Lys Leu Leu Trp Ser Thr Ala Asn Val
    130                 135                 140

Phe Gly Asn Ala Arg Tyr Met Asn Gly Ala Ser Thr Asn Pro Asp Phe
145                 150                 155                 160

Asp Val Val Ala Arg Ala Ile Val Gln Ile Lys Asn Ala Ile Asp Ala
                165                 170                 175

Gly Ile Lys Leu Gly Ala Glu Asn Tyr Val Phe Trp Gly Gly Arg Glu
            180                 185                 190

Gly Tyr Met Ser Leu Leu Asn Thr Asp Gln Lys Arg Glu Lys Glu His
        195                 200                 205

Met Ala Thr Met Leu Arg Met Ala Arg Asp Tyr Ala Arg Ser Lys Gly
    210                 215                 220

Phe Lys Gly Thr Phe Leu Ile Glu Pro Lys Pro Cys Glu Pro Ser Lys
225                 230                 235                 240

His Gln Tyr Asp Val Asp Thr Glu Thr Val Ile Gly Phe Leu Lys Ala
                245                 250                 255

His Gly Leu Gly Lys Asp Phe Lys Val Asn Ile Glu Val Asn His Ala
            260                 265                 270

Thr Leu Ala Gly His Thr Phe Glu His Glu Leu Ala Cys Ala Val Asp
        275                 280                 285

Ala Gly Met Leu Gly Ser Ile Asp Ala Asn Arg Gly Asp Ala Gln Asn
    290                 295                 300

Gly Trp Asp Thr Asp Gln Phe Pro Ile Asp Asn Phe Glu Leu Thr Gln
305                 310                 315                 320

Ala Phe Met Gln Ile Val Arg Asn Gly Gly Phe Gly Thr Gly Gly Thr
                325                 330                 335

Asn Phe Asp Ala Lys Thr Arg Arg Asn Ser Thr Asp Leu Glu Asp Ile
            340                 345                 350

Phe Ile Ala His Ile Ser Gly Met Asp Ala Cys Ala Arg Ala Leu Leu
        355                 360                 365

Asn Ala Val Glu Ile Leu Glu Lys Ser Pro Ile Pro Ala Met Leu Lys
    370                 375                 380

Glu Arg Tyr Ala Ser Phe Asp Ser Gly Met Gly Lys Asp Phe Glu Glu
385                 390                 395                 400

Gly Lys Leu Thr Phe Glu Gln Val Tyr Glu Tyr Gly Lys Gln Val Gly
                405                 410                 415

Glu Pro Lys Gln Thr Ser Gly Lys Gln Glu Leu Tyr Glu Thr Ile Val
            420                 425                 430

Ala Leu Tyr Ala Lys
        435
```

<210> SEQ ID NO 73
<211> LENGTH: 1314
<212> TYPE: DNA
<213> ORGANISM: Unknown
<220> FEATURE:
<223> OTHER INFORMATION: Obtained from environmental sample

<400> SEQUENCE: 73

```
atgaaagagt attttccaca aatcggcaag atcccatttg agggaccaga gtcaaagaac      60

ccaatggcat tccactacta tgacgcagag cgcgtagttg ccggtaagac aatgaaggaa     120
```

```
tggatgcgtt tcgctatggc ctggtggcac actctctgtg ctgagggtag cgatcagttc    180

ggccctggta caaagaagtt cccttggaac gagggcgaga cagcccttga gcgcgctaag    240

cacaaggcag atgctggctt cgaggttatg cagaagctcg gcatcccata tttctgcttc    300

cacgatgtag accttatcga cgagggtgct aacgtggctg agtatgaggc aaacctcgct    360

gctatcactg actacctgaa ggagaagatg gaggagactg gcgtaaagct cctctggtct    420

acagccaacg tgttcggtaa cgctcgctat atgaacggtg cttctacaaa tcctgacttc    480

gacgttgtgg ctcgtgccat cgtacagatt aagaacgcta tcgacgctgg tatcaagctt    540

ggtgctgaga actacgtgtt ctggggcggc cgcgagggct acatgagcct tctgaacact    600

gaccagaagc gcgagaagga gcacatggca actatgctcg gcatggctcg cgactatgcc    660

cgcgctaagg gattcaccgg taccttcctc attgagccaa agccaatgga gccaacaaag    720

catcagtatg atgttgacac agagaccgtt atcggtttcc tcaaggctca cggtctggac    780

aaggacttca aggtgaacat cgaggtgaac cacgctactc tcgccggtca caccttcgag    840

cacgagctcg cttgcgctgt tgacgctggt atgctcggtt ctatcgacgc taaccgcggt    900

gacgctcaga acggatggga taccgaccag ttcccaatcg acaacttcga gctgacacag    960

gcttggatgc agattgttcg caatggcggt cttggcacag gtggtaccaa cttcgacgca   1020

aagacccgtc gtaactctac cgacctcgag gacatcttca tcgctcacat ctccggtatg   1080

gacgcttgtg cacgcgctct cctcaacgca gtagagatac tcgagaactc tccaatccca   1140

acaatgctga aggaccgcta tgcaagcttc gactcaggta tgggtaagga cttcgaggac   1200

ggcaagctca cacttgagca ggtttatgag tatggtaaga aggtcgacga gccaaagcag   1260

acctctggta agcaggaact ctatgagacc atcgttgctc tctatgcaaa ataa         1314
```

<210> SEQ ID NO 74
<211> LENGTH: 437
<212> TYPE: PRT
<213> ORGANISM: Unknown
<220> FEATURE:
<223> OTHER INFORMATION: Obtained from environmental sample

<400> SEQUENCE: 74

```
Met Lys Glu Tyr Phe Pro Gln Ile Gly Lys Ile Pro Phe Glu Gly Pro
1               5                   10                  15

Glu Ser Lys Asn Pro Met Ala Phe His Tyr Tyr Asp Ala Glu Arg Val
            20                  25                  30

Val Ala Gly Lys Thr Met Lys Glu Trp Met Arg Phe Ala Met Ala Trp
        35                  40                  45

Trp His Thr Leu Cys Ala Glu Gly Ser Asp Gln Phe Gly Pro Gly Thr
    50                  55                  60

Lys Lys Phe Pro Trp Asn Glu Gly Glu Thr Ala Leu Glu Arg Ala Lys
65                  70                  75                  80

His Lys Ala Asp Ala Gly Phe Glu Val Met Gln Lys Leu Gly Ile Pro
                85                  90                  95

Tyr Phe Cys Phe His Asp Val Asp Leu Ile Asp Glu Gly Ala Asn Val
            100                 105                 110

Ala Glu Tyr Glu Ala Asn Leu Ala Ala Ile Thr Asp Tyr Leu Lys Glu
        115                 120                 125

Lys Met Glu Glu Thr Gly Val Lys Leu Leu Trp Ser Thr Ala Asn Val
    130                 135                 140

Phe Gly Asn Ala Arg Tyr Met Asn Gly Ala Ser Thr Asn Pro Asp Phe
```

-continued

```
145                 150                 155                 160

Asp Val Val Ala Arg Ala Ile Val Gln Ile Lys Asn Ala Ile Asp Ala
                165                 170                 175

Gly Ile Lys Leu Gly Ala Glu Asn Tyr Val Phe Trp Gly Gly Arg Glu
            180                 185                 190

Gly Tyr Met Ser Leu Leu Asn Thr Asp Gln Lys Arg Glu Lys Glu His
        195                 200                 205

Met Ala Thr Met Leu Gly Met Ala Arg Asp Tyr Ala Arg Ala Lys Gly
    210                 215                 220

Phe Thr Gly Thr Phe Leu Ile Glu Pro Lys Pro Met Glu Pro Thr Lys
225                 230                 235                 240

His Gln Tyr Asp Val Asp Thr Glu Thr Val Ile Gly Phe Leu Lys Ala
                245                 250                 255

His Gly Leu Asp Lys Asp Phe Lys Val Asn Ile Glu Val Asn His Ala
            260                 265                 270

Thr Leu Ala Gly His Thr Phe Glu His Glu Leu Ala Cys Ala Val Asp
        275                 280                 285

Ala Gly Met Leu Gly Ser Ile Asp Ala Asn Arg Gly Asp Ala Gln Asn
    290                 295                 300

Gly Trp Asp Thr Asp Gln Phe Pro Ile Asp Asn Phe Glu Leu Thr Gln
305                 310                 315                 320

Ala Trp Met Gln Ile Val Arg Asn Gly Gly Leu Gly Thr Gly Gly Thr
                325                 330                 335

Asn Phe Asp Ala Lys Thr Arg Arg Asn Ser Thr Asp Leu Glu Asp Ile
            340                 345                 350

Phe Ile Ala His Ile Ser Gly Met Asp Ala Cys Ala Arg Ala Leu Leu
        355                 360                 365

Asn Ala Val Glu Ile Leu Glu Asn Ser Pro Ile Pro Thr Met Leu Lys
    370                 375                 380

Asp Arg Tyr Ala Ser Phe Asp Ser Gly Met Gly Lys Asp Phe Glu Asp
385                 390                 395                 400

Gly Lys Leu Thr Leu Glu Gln Val Tyr Glu Tyr Gly Lys Lys Val Asp
                405                 410                 415

Glu Pro Lys Gln Thr Ser Gly Lys Gln Glu Leu Tyr Glu Thr Ile Val
            420                 425                 430

Ala Leu Tyr Ala Lys
        435


<210> SEQ ID NO 75
<211> LENGTH: 1320
<212> TYPE: DNA
<213> ORGANISM: Unknown
<220> FEATURE:
<223> OTHER INFORMATION: Obtained from environmental sample

<400> SEQUENCE: 75

atggctaaag aatacttccc ctccatcggc aaaatccctt ttgaaggagg cgacagcaaa      60

aatcccctcg ctttccatta ttatgacgcc ggacgcgtgg ttatgggcaa gcccatgaag     120

gaatggctta aattcgccat ggcctggtgg cacacgctgg gccaggcctc cggagacccc     180

ttcggcggcc agacccgcag ctacgaatgg gacaagggcg aatgccccta ctgccgcgcc     240

aaagccaagg ccgacgccgg ttttgaaatc atgcaaaagc tgggtatcga atacttctgc     300

ttccacgatg tggaccttat cgaggattgc gatgacattg ccgaatacga agcccgcatg     360

aaggacatca cggactacct gctggaaaag atgaaggaga ccggcatcaa gaacctctgg     420
```

```
ggcaccgcca atgtcttcgg ccacaagcgc tacatgaacg gcgccggcac caatccgcag    480

ttcgatgtgg tggcccgtgc cgccgtccag atcaagaacg ccctggacgc caccatcaag    540

ctgggcggct ccaactatgt gttctggggc ggccgcgaag gctattacac cctcctcaac    600

acccagatgc agcgggaaaa agaccacctg gccaagttgc tgacggccgc ccgcgactat    660

gcccgcgcca agggcttcaa gggcaccttc ctcattgagc ccaaacccat ggaacccacc    720

aagcaccagt acgacgtgga tacggagacg gtcatcggct tcctccgtgc caacggcctg    780

gacaaggact tcaaggtgaa catcgaggtg aaccacgcca ccctggccgg ccacaccttc    840

gagcatgagc tcaccgtggc ccgcgagaac ggtttcctgg gctccatcgg tgccaaccgc    900

ggcgacgccc agaacggctg ggacacggac cagttccctg tggacccgta cgatcttacc    960

caggccatga tgcaggtgct gctgaacggc ggcttcggca acggcggcac caacttcgac   1020

gccaaactcc gccgctcctc caccgaccct gaggacatct tcatcgccca tatttccgcc   1080

atggatgcca tggcccacgc tttgcttaac gcagctgccg tgctggaaga gagccccctg   1140

tgccagatgg tcaaggagcg ttatgccagc ttcgacggcg gcctcggcaa acagttcgag   1200

gaaggcaagg ctaccctgga agacctgtac gaatacgcca aggtccaggg tgaacccgtt   1260

gtcgcctccg gcaagcagga gctttacgag actctcctga acctgtatgc cgtcaagtaa   1320
```

<210> SEQ ID NO 76
<211> LENGTH: 439
<212> TYPE: PRT
<213> ORGANISM: Unknown
<220> FEATURE:
<223> OTHER INFORMATION: Obtained from environmental sample

<400> SEQUENCE: 76

```
Met Ala Lys Glu Tyr Phe Pro Ser Ile Gly Lys Ile Pro Phe Glu Gly
1               5                   10                  15

Gly Asp Ser Lys Asn Pro Leu Ala Phe His Tyr Tyr Asp Ala Gly Arg
            20                  25                  30

Val Val Met Gly Lys Pro Met Lys Glu Trp Leu Lys Phe Ala Met Ala
        35                  40                  45

Trp Trp His Thr Leu Gly Gln Ala Ser Gly Asp Pro Phe Gly Gly Gln
    50                  55                  60

Thr Arg Ser Tyr Glu Trp Asp Lys Gly Glu Cys Pro Tyr Cys Arg Ala
65                  70                  75                  80

Lys Ala Lys Ala Asp Ala Gly Phe Glu Ile Met Gln Lys Leu Gly Ile
                85                  90                  95

Glu Tyr Phe Cys Phe His Asp Val Asp Leu Ile Glu Asp Cys Asp Asp
            100                 105                 110

Ile Ala Glu Tyr Glu Ala Arg Met Lys Asp Ile Thr Asp Tyr Leu Leu
        115                 120                 125

Glu Lys Met Lys Glu Thr Gly Ile Lys Asn Leu Trp Gly Thr Ala Asn
    130                 135                 140

Val Phe Gly His Lys Arg Tyr Met Asn Gly Ala Gly Thr Asn Pro Gln
145                 150                 155                 160

Phe Asp Val Val Ala Arg Ala Ala Val Gln Ile Lys Asn Ala Leu Asp
                165                 170                 175

Ala Thr Ile Lys Leu Gly Gly Ser Asn Tyr Val Phe Trp Gly Gly Arg
            180                 185                 190

Glu Gly Tyr Tyr Thr Leu Leu Asn Thr Gln Met Gln Arg Glu Lys Asp
        195                 200                 205
```

His Leu Ala Lys Leu Leu Thr Ala Ala Arg Asp Tyr Ala Arg Ala Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Arg
        275                 280                 285

Glu Asn Gly Phe Leu Gly Ser Ile Gly Ala Asn Arg Gly Asp Ala Gln
    290                 295                 300

Asn Gly Trp Asp Thr Asp Gln Phe Pro Val Asp Pro Tyr Asp Leu Thr
305                 310                 315                 320

Gln Ala Met Met Gln Val Leu Leu Asn Gly Gly Phe Gly Asn Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Val Leu Glu Glu Ser Pro Leu Cys Gln Met Val
    370                 375                 380

Lys Glu Arg Tyr Ala Ser Phe Asp Gly Gly Leu Gly Lys Gln Phe Glu
385                 390                 395                 400

Glu Gly Lys Ala Thr Leu Glu Asp Leu Tyr Glu Tyr Ala Lys Val Gln
                405                 410                 415

Gly Glu Pro Val Val Ala Ser Gly Lys Gln Glu Leu Tyr Glu Thr Leu
            420                 425                 430

Leu Asn Leu Tyr Ala Val Lys
        435

<210> SEQ ID NO 77
<211> LENGTH: 1320
<212> TYPE: DNA
<213> ORGANISM: Unknown
<220> FEATURE:
<223> OTHER INFORMATION: Obtained from environmental sample

<400> SEQUENCE: 77
atggcaaaag agtattttcc gtttaccggt aagattcctt tcgaaggaaa ggacagtaag 60
aatgtaatgg ctttccacta ctacgagcct gagaaggtcg tgatgggaaa gaagatgaag 120
gactggctga agttcgctat ggcttggtgg catacactgg gtggcgcttc tgctgaccag 180
tttggtggtc agactcgttc atacgagtgg gacaaggctg gtgacgctgt tcagcgcgct 240
aaggataaga tggacgctgg cttcgagatc atggacaagc tgggcatcga gtacttctgc 300
ttccacgatg ttgacctcgt tgaagagggt gacaccatcg aggagtatga ggctcgcatg 360
aaggccatca ccgactacgc tcaggagaag atgaagcagt tccccaacat caagctgctc 420
tggggtaccg caaacgtatt cggtaacaag cgctatgcta acggtgcttc taccaacccc 480
gacttcgacg tagtggctcg cgccatcgtt cagatcaaga acgctattga tgctaccatc 540
aagctgggtg gtaccaacta tgtgttctgg ggtggtcgtg agggctatat gagtctgctg 600
aacaccgacc agaagcgtga gaaggagcac atggctacta tgctgaccat ggctcgcgac 660
tatgctcgcg ccaagggatt caagggtaca ttcctcattg agccgaagcc catggagccc 720
agcaagcacc agtatgatgt ggatacagag accgttatcg gcttcctgaa ggcacacaac 780
ctggacaagg acttcaaggt gaacatcgag gtgaaccacg ctacactcgc tggtcatacc 840
ttcgagcacg agctggcttg cgctgttgac gctggtatgc ttggttctat cgacgctaac 900
cgtggtgatg ctcagaacgg ttgggatacc gaccagttcc ccatcgacaa ctacgagctg 960
acacaggcta tgctcgagat catccgcaat ggtggtctgg gcaatggtgg taccaacttc 1020
gatgctaaga tccgtcgtaa cagcaccgac ctcgaggatc tcttcatcgc tcacatcagt 1080
ggtatggatg ctatggcacg cgctctgatg aacgctgctg acatccttga gaactctgag 1140
ctgcccgcaa tgaagaaggc tcgctacgca agcttcgacc agggtgttgg taaggacttc 1200
gaagatggca agctgaccct tgagcaggtt tacgagtatg gtaagaaggt gggtgagccc 1260
aagcagactt ctggtaagca ggagaagtac gagaccatcg ttgctctcta tgcaaaataa 1320

<210> SEQ ID NO 78
<211> LENGTH: 439
<212> TYPE: PRT
<213> ORGANISM: Unknown
<220> FEATURE:
<223> OTHER INFORMATION: Obtained from environmental sample

<400> SEQUENCE: 78

Met Ala Lys Glu Tyr Phe Pro Phe Thr Gly Lys Ile Pro Phe Glu Gly
1               5                   10                  15

Lys Asp Ser Lys Asn Val Met Ala Phe His Tyr Tyr Glu Pro Glu Lys
            20                  25                  30

Val Val Met Gly Lys Lys Met Lys Asp Trp Leu Lys Phe Ala Met Ala
        35                  40                  45

Trp Trp His Thr Leu Gly Gly Ala Ser Ala Asp Gln Phe Gly Gly Gln
    50                  55                  60

Thr Arg Ser Tyr Glu Trp Asp Lys Ala Gly Asp Ala Val Gln Arg Ala
65                  70                  75                  80

Lys Asp Lys Met Asp Ala Gly Phe Glu Ile Met Asp Lys Leu Gly Ile
                85                  90                  95

Glu Tyr Phe Cys Phe His Asp Val Asp Leu Val Glu Glu Gly Asp Thr
            100                 105                 110

Ile Glu Glu Tyr Glu Ala Arg Met Lys Ala Ile Thr Asp Tyr Ala Gln
        115                 120                 125

Glu Lys Met Lys Gln Phe Pro Asn Ile Lys Leu Leu Trp Gly Thr Ala
    130                 135                 140

Asn Val Phe Gly Asn Lys Arg Tyr Ala Asn Gly Ala Ser Thr Asn Pro
145                 150                 155                 160

Asp Phe Asp Val Val Ala Arg Ala Ile Val Gln Ile Lys Asn Ala Ile
                165                 170                 175

Asp Ala Thr Ile Lys Leu Gly Gly Thr Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Met Ala Thr Met Leu Thr Met Ala Arg Asp Tyr Ala Arg Ala
    210                 215                 220

Lys Gly Phe Lys Gly Thr Phe Leu Ile Glu Pro Lys Pro Met Glu Pro
225                 230                 235                 240

Ser Lys His Gln Tyr Asp Val Asp Thr Glu Thr Val Ile Gly Phe Leu
                245                 250                 255

```
Lys Ala His Asn Leu Asp Lys Asp Phe Lys Val Asn Ile Glu Val Asn
            260                 265                 270

His Ala Thr Leu Ala Gly His Thr Phe Glu His Glu Leu Ala Cys Ala
        275                 280                 285

Val Asp Ala Gly Met Leu Gly Ser Ile Asp Ala Asn Arg Gly Asp Ala
    290                 295                 300

Gln Asn Gly Trp Asp Thr Asp Gln Phe Pro Ile Asp Asn Tyr Glu Leu
305                 310                 315                 320

Thr Gln Ala Met Leu Glu Ile Ile Arg Asn Gly Gly Leu Gly Asn Gly
                325                 330                 335

Gly Thr Asn Phe Asp Ala Lys Ile Arg Arg Asn Ser Thr Asp Leu Glu
            340                 345                 350

Asp Leu Phe Ile Ala His Ile Ser Gly Met Asp Ala Met Ala Arg Ala
        355                 360                 365

Leu Met Asn Ala Ala Asp Ile Leu Glu Asn Ser Glu Leu Pro Ala Met
    370                 375                 380

Lys Lys Ala Arg Tyr Ala Ser Phe Asp Gln Gly Val Gly Lys Asp Phe
385                 390                 395                 400

Glu Asp Gly Lys Leu Thr Leu Glu Gln Val Tyr Glu Tyr Gly Lys Lys
                405                 410                 415

Val Gly Glu Pro Lys Gln Thr Ser Gly Lys Gln Glu Lys Tyr Glu Thr
            420                 425                 430

Ile Val Ala Leu Tyr Ala Lys
        435
```

<210> SEQ ID NO 79
<211> LENGTH: 1320
<212> TYPE: DNA
<213> ORGANISM: Unknown
<220> FEATURE:
<223> OTHER INFORMATION: Obtained from environmental sample

<400> SEQUENCE: 79

```
atggcaaaag agtattttcc gtttaccggt aagattcctt tcgaaggaaa agagagcaag     60

aacgtaatgg ctttccatta ctatgagcct gaaaaggtgg tcatgggcaa gaaaatgaag    120

gattggctga aattcgccat ggcttggtgg cacaccctcg gtggagccag cgccgaccag    180

ttcggtggac agacccgcag ctatgagtgg gacaaggccg aggatgccgt acagcgtgct    240

aaggacaaga tggacgccgg cttcgagatc atggacaaac tgggcatcga gtatttctgc    300

ttccacgatg tcgacctcgt cgacgagggt gctaccgttg aggagtatga ggctcgcatg    360

aaagccatca ccgactatgc ccaggtcaag atgaaggaat atcccaacat caaactgctc    420

tggggcaccg ccaacgtgtt cggcaacaag cgttatgcca acggcgcttc caccaacccc    480

gacttcgacg tggtggcacg cgctatcgtt cagatcaaga atgccatcga cgctaccatc    540

aagctcggcg gtcagaacta cgtgttctgg ggcggacgcg agggctacat gagcctgctc    600

aataccgatc agaaacgtga gaaggaacac atggccacca tgctcaccat ggcgcgcgac    660

tatgctcgca gcaagggatt caagggcacc ttcctcatcg aacccaaacc catggagcct    720

tccaagcacc agtatgatgt cgacaccgag acggtcatcg gcttcctccg cgcccacaac    780

ctcgacaagg acttcaaggt gaacatcgag gtcaaccacg ccacgctcgc cggccacacc    840

ttcgagcacg aactggcttg cgccgtcgac gccggcatgc tcggcagcat cgacgccaac    900

cgcggcgacg cacagaacgg ctgggatacc gaccagttcc ccatcgacaa ctacgaactg    960

acacaggcca tgctggagat catccgcaat ggcggcctcg gcaatggtgg taccaacttc   1020
```

```
gacgccaaga tccgtcgtaa cagcaccgac ctcgaagatc tcttcatcgc tcacatcagc   1080

ggtatggatg ccatggctcg cgcgctgctc aacgccgccg ccatcctcga ggagagcgaa   1140

ctgcccgcca tgaagaaggc ccgctacgct tccttcgacg aaggtatcgg caaggacttc   1200

gaagacggca aactcaccct cgagcaggtt tacgagtacg gcaagaaggt aggcgagccc   1260

aagcagacct ccggcaagca agagaagtac gagaccatcg tggctctcta cagcaaataa   1320


<210> SEQ ID NO 80
<211> LENGTH: 439
<212> TYPE: PRT
<213> ORGANISM: Unknown
<220> FEATURE:
<223> OTHER INFORMATION: Obtained from environmental sample

<400> SEQUENCE: 80

Met Ala Lys Glu Tyr Phe Pro Phe Thr Gly Lys Ile Pro Phe Glu Gly
1               5                   10                  15

Lys Glu Ser Lys Asn Val Met Ala Phe His Tyr Tyr Glu Pro Glu Lys
            20                  25                  30

Val Val Met Gly Lys Lys Met Lys Asp Trp Leu Lys Phe Ala Met Ala
        35                  40                  45

Trp Trp His Thr Leu Gly Gly Ala Ser Ala Asp Gln Phe Gly Gly Gln
    50                  55                  60

Thr Arg Ser Tyr Glu Trp Asp Lys Ala Glu Asp Ala Val Gln Arg Ala
65                  70                  75                  80

Lys Asp Lys Met Asp Ala Gly Phe Glu Ile Met Asp Lys Leu Gly Ile
                85                  90                  95

Glu Tyr Phe Cys Phe His Asp Val Asp Leu Val Asp Glu Gly Ala Thr
            100                 105                 110

Val Glu Glu Tyr Glu Ala Arg Met Lys Ala Ile Thr Asp Tyr Ala Gln
        115                 120                 125

Val Lys Met Lys Glu Tyr Pro Asn Ile Lys Leu Leu Trp Gly Thr Ala
    130                 135                 140

Asn Val Phe Gly Asn Lys Arg Tyr Ala Asn Gly Ala Ser Thr Asn Pro
145                 150                 155                 160

Asp Phe Asp Val Val Ala Arg Ala Ile Val Gln Ile Lys Asn Ala Ile
                165                 170                 175

Asp Ala Thr Ile Lys Leu Gly Gly Gln Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Met Ala Thr Met Leu Thr Met Ala Arg Asp Tyr Ala Arg Ser
    210                 215                 220

Lys Gly Phe Lys Gly Thr Phe Leu Ile Glu Pro Lys Pro Met Glu Pro
225                 230                 235                 240

Ser Lys His Gln Tyr Asp Val Asp Thr Glu Thr Val Ile Gly Phe Leu
                245                 250                 255

Arg Ala His Asn Leu Asp Lys Asp Phe Lys Val Asn Ile Glu Val Asn
            260                 265                 270

His Ala Thr Leu Ala Gly His Thr Phe Glu His Glu Leu Ala Cys Ala
        275                 280                 285

Val Asp Ala Gly Met Leu Gly Ser Ile Asp Ala Asn Arg Gly Asp Ala
    290                 295                 300

Gln Asn Gly Trp Asp Thr Asp Gln Phe Pro Ile Asp Asn Tyr Glu Leu
```

-continued

```
305                 310                 315                 320

Thr Gln Ala Met Leu Glu Ile Ile Arg Asn Gly Gly Leu Gly Asn Gly
                325                 330                 335

Gly Thr Asn Phe Asp Ala Lys Ile Arg Arg Asn Ser Thr Asp Leu Glu
            340                 345                 350

Asp Leu Phe Ile Ala His Ile Ser Gly Met Asp Ala Met Ala Arg Ala
        355                 360                 365

Leu Leu Asn Ala Ala Ala Ile Leu Glu Glu Ser Glu Leu Pro Ala Met
    370                 375                 380

Lys Lys Ala Arg Tyr Ala Ser Phe Asp Glu Gly Ile Gly Lys Asp Phe
385                 390                 395                 400

Glu Asp Gly Lys Leu Thr Leu Glu Gln Val Tyr Glu Tyr Gly Lys Lys
                405                 410                 415

Val Gly Glu Pro Lys Gln Thr Ser Gly Lys Gln Glu Lys Tyr Glu Thr
            420                 425                 430

Ile Val Ala Leu Tyr Ser Lys
        435
```

<210> SEQ ID NO 81
<211> LENGTH: 1314
<212> TYPE: DNA
<213> ORGANISM: Unknown
<220> FEATURE:
<223> OTHER INFORMATION: Obtained from environmental sample

<400> SEQUENCE: 81

```
atgaaagagt atttcccgca aattggaaag attcccttcg agggaccaga gagcaagagt      60
ccattggcgt tccattatta tgagccggat cgcatggtgc tcggaaagag gatggaggat     120
tggctgaaat tcgccatggc atggtggcac acccttggcc aggccagcgg cgaccagttc     180
ggcggacaga cacgtgagta cgagtgggat aaggctggag atccgataca aagggcaaag     240
gataagatgg acgccggatt cgagatcatg gagaaattgg gtatcaagta cttctgcttc     300
catgatgtgg atctcgtcga ggaagctccc accatcgccg aatatgagga gcgtatgagg     360
atcatcaccg actatgcgct cgagaagatg aaagccactg gcatcaaact cctttggggt     420
acagccaatg ttttcggaca taagagatat atgaatgggg ccgccaccaa cccggagttc     480
ggtgttgtcg ccagggctgc tgtccagatc aagaacgcga tcgacgccac catcaagctg     540
ggaggaacaa actatgtgtt ctggggtggc cgcgagggct acatgagcct gctcaacacc     600
cagatgcaga gggagaagga ccatctcgcc aatatgctca aggctgctcg tgactatgct     660
cgcgccaagg gattcaaggg cacattcctc atcgagccga agccgatgga acctactaag     720
catcagtacg atgtcgacac tgagaccgtg atcggcttcc tccgcgcaaa cggtcttgac     780
aaggatttca aggtcaacat cgaggtcaat cacgccactc ttgcgggtca cactttcgag     840
catgagctcg ccgtggctgt cgacaatggt ctccttggct caatcgatgc gaacagggga     900
gattatcaga acggttggga caccgaccag ttccctgttg atctctttga tttgacccag     960
gccatgctcc agatcatccg taacggaggc ctcggtaatg gtggatccaa cttcgacgcc    1020
aagcttcgcc gtaactccac tgatcctgag gatatattca ttgcccatat ttgcggtatg    1080
gacgctatgg ccagggctct ccttgccgcc gccgcgatcg tggaggagtc tcctatcccg    1140
gctatggtca aagagcgtta cgcatccttc gacgaaggtg agggcaagag attcgaggat    1200
ggtaagatga gtctggagga acttgttgat tacgcgaaga ctcacggaga gcccgcccag    1260
aagagtggca aacaggagct ctacgaaacc cttgtcaaca tgtacatcaa ataa          1314
```

<210> SEQ ID NO 82
<211> LENGTH: 437
<212> TYPE: PRT
<213> ORGANISM: Unknown
<220> FEATURE:
<223> OTHER INFORMATION: Obtained from environmental sample

<400> SEQUENCE: 82

Met Lys Glu Tyr Phe Pro Gln Ile Gly Lys Ile Pro Phe Glu Gly Pro
1               5                   10                  15

Glu Ser Lys Ser Pro Leu Ala Phe His Tyr Tyr Glu Pro Asp Arg Met
            20                  25                  30

Val Leu Gly Lys Arg Met Glu Asp Trp Leu Lys Phe Ala Met Ala Trp
        35                  40                  45

Trp His Thr Leu Gly Gln Ala Ser Gly Asp Gln Phe Gly Gly Gln Thr
    50                  55                  60

Arg Glu Tyr Glu Trp Asp Lys Ala Gly Asp Pro Ile Gln Arg Ala Lys
65                  70                  75                  80

Asp Lys Met Asp Ala Gly Phe Glu Ile Met Glu Lys Leu Gly Ile Lys
                85                  90                  95

Tyr Phe Cys Phe His Asp Val Asp Leu Val Glu Glu Ala Pro Thr Ile
            100                 105                 110

Ala Glu Tyr Glu Glu Arg Met Arg Ile Ile Thr Asp Tyr Ala Leu Glu
        115                 120                 125

Lys Met Lys Ala Thr Gly Ile Lys Leu Leu Trp Gly Thr Ala Asn Val
    130                 135                 140

Phe Gly His Lys Arg Tyr Met Asn Gly Ala Ala Thr Asn Pro Glu Phe
145                 150                 155                 160

Gly Val Val Ala Arg Ala Ala Val Gln Ile Lys Asn Ala Ile Asp Ala
                165                 170                 175

Thr Ile Lys Leu Gly Gly Thr Asn Tyr Val Phe Trp Gly Gly Arg Glu
            180                 185                 190

Gly Tyr Met Ser Leu Leu Asn Thr Gln Met Gln Arg Glu Lys Asp His
        195                 200                 205

Leu Ala Asn Met Leu Lys Ala Ala Arg Asp Tyr Ala Arg Ala Lys Gly
    210                 215                 220

Phe Lys Gly Thr Phe Leu Ile Glu Pro Lys Pro Met Glu Pro Thr Lys
225                 230                 235                 240

His Gln Tyr Asp Val Asp Thr Glu Thr Val Ile Gly Phe Leu Arg Ala
                245                 250                 255

Asn Gly Leu Asp Lys Asp Phe Lys Val Asn Ile Glu Val Asn His Ala
            260                 265                 270

Thr Leu Ala Gly His Thr Phe Glu His Glu Leu Ala Val Ala Val Asp
        275                 280                 285

Asn Gly Leu Leu Gly Ser Ile Asp Ala Asn Arg Gly Asp Tyr Gln Asn
    290                 295                 300

Gly Trp Asp Thr Asp Gln Phe Pro Val Asp Leu Phe Asp Leu Thr Gln
305                 310                 315                 320

Ala Met Leu Gln Ile Ile Arg Asn Gly Gly Leu Gly Asn Gly Gly Ser
                325                 330                 335

Asn Phe Asp Ala Lys Leu Arg Arg Asn Ser Thr Asp Pro Glu Asp Ile
            340                 345                 350

Phe Ile Ala His Ile Cys Gly Met Asp Ala Met Ala Arg Ala Leu Leu
        355                 360                 365

```
Ala Ala Ala Ala Ile Val Glu Glu Ser Pro Ile Pro Ala Met Val Lys
    370                 375                 380

Glu Arg Tyr Ala Ser Phe Asp Glu Gly Glu Gly Lys Arg Phe Glu Asp
385                 390                 395                 400

Gly Lys Met Ser Leu Glu Glu Leu Val Asp Tyr Ala Lys Thr His Gly
                405                 410                 415

Glu Pro Ala Gln Lys Ser Gly Lys Gln Glu Leu Tyr Glu Thr Leu Val
            420                 425                 430

Asn Met Tyr Ile Lys
        435
```

<210> SEQ ID NO 83
<211> LENGTH: 1320
<212> TYPE: DNA
<213> ORGANISM: Unknown
<220> FEATURE:
<223> OTHER INFORMATION: Obtained from environmental sample

<400> SEQUENCE: 83

```
atggcaaaag agtattttcc gtttaccggt aagattcctt tcgagggaaa ggacagtaag     60

aatgtaatgg cgttccacta ctacgagccc gagcgcgtgg taatgggcaa gaagatgaag    120

gagtggctga agtttgccat ggcctggtgg cacacgctgg gtggagccag tgccgaccag    180

tttggcggac agacccgcag ctacgagtgg gacaaggctg aagacgccgt gcagcgtgcc    240

aaggacaaga tggatgccgg cttcgagatc atggacaagc tgggcatcga gtatttctgc    300

ttccatgatg tcgatctcgt tgacgagggt gccactgtcg aggagtatga ggctcgcatg    360

caggccatca ccgactatgc gcaggagaag atgaagcagt atcctgccat caagctgctg    420

tggggtacgg ccaatgtctt tggcaacaag cgttatgcca acggtgcctc taccaatccc    480

gacttcgatg tggtggcccg cgccatcgtg cagattaaga atgccattga tgccaccatc    540

aagctgggcg gcagcaacta tgtgttctgg ggcggtcgcg agggctacat gtcgctgctc    600

aacaccgacc agaagcgtga gaaggaacac atggcccgga tgctgaccat ggcccgcgac    660

tatgcccgct cgaagggctt caagggcaac ttcctgattg agcccaagcc catggagccg    720

tcgaagcatc agtacgacgt ggacaccgag acggttatcg gattcctccg cgcacatggc    780

cttgacaagg acttcaaggt gaacatcgag gtgaaccatg ccacgctggc cggtcatacc    840

ttcgagcacg aactggcttg cgccgtagat gccggcatgc tgggcagcat tgatgccaac    900

cgcggcgacg cacagaacgg atgggacacc gaccagttcc ccatcgacaa ctatgagttg    960

acacaggcca tgatggagat tatccgcaat ggcggtctgg gtcttggcgg taccaatttc   1020

gatgccaaga ttcgccgtaa ctccaccgac ctggaagacc tcttcatcgc ccacatcagt   1080

ggcatggacg ccatggctcg tgcgctcctt aatgctgccg acattctgga gaacagcgaa   1140

ctgcccgcca tgaagaaagc gcgctacgcc tcgttcgaca gtggcatggg caaggacttc   1200

gaggacggca aactgaccct tgagcaggtt tacgaatacg gcaaaaaagt cggcgaacct   1260

aagcagacct ccggcaagca ggagaagtac gagaccatcg tggctctcta tgccaagtaa   1320
```

<210> SEQ ID NO 84
<211> LENGTH: 439
<212> TYPE: PRT
<213> ORGANISM: Unknown
<220> FEATURE:
<223> OTHER INFORMATION: Obtained from environmental sample

<400> SEQUENCE: 84

```
Met Ala Lys Glu Tyr Phe Pro Phe Thr Gly Lys Ile Pro Phe Glu Gly
1               5                   10                  15

Lys Asp Ser Lys Asn Val Met Ala Phe His Tyr Tyr Glu Pro Glu Arg
            20                  25                  30

Val Val Met Gly Lys Lys Met Lys Glu Trp Leu Lys Phe Ala Met Ala
        35                  40                  45

Trp Trp His Thr Leu Gly Gly Ala Ser Ala Asp Gln Phe Gly Gly Gln
    50                  55                  60

Thr Arg Ser Tyr Glu Trp Asp Lys Ala Glu Asp Ala Val Gln Arg Ala
65                  70                  75                  80

Lys Asp Lys Met Asp Ala Gly Phe Glu Ile Met Asp Lys Leu Gly Ile
                85                  90                  95

Glu Tyr Phe Cys Phe His Asp Val Asp Leu Val Asp Glu Gly Ala Thr
            100                 105                 110

Val Glu Glu Tyr Glu Ala Arg Met Gln Ala Ile Thr Asp Tyr Ala Gln
        115                 120                 125

Glu Lys Met Lys Gln Tyr Pro Ala Ile Lys Leu Leu Trp Gly Thr Ala
    130                 135                 140

Asn Val Phe Gly Asn Lys Arg Tyr Ala Asn Gly Ala Ser Thr Asn Pro
145                 150                 155                 160

Asp Phe Asp Val Val Ala Arg Ala Ile Val Gln Ile Lys Asn Ala Ile
                165                 170                 175

Asp Ala Thr Ile Lys Leu Gly Gly Ser Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Met Ala Arg Met Leu Thr Met Ala Arg Asp Tyr Ala Arg Ser
    210                 215                 220

Lys Gly Phe Lys Gly Asn Phe Leu Ile Glu Pro Lys Pro Met Glu Pro
225                 230                 235                 240

Ser Lys His Gln Tyr Asp Val Asp Thr Glu Thr Val Ile Gly Phe Leu
                245                 250                 255

Arg Ala His Gly Leu Asp Lys Asp Phe Lys Val Asn Ile Glu Val Asn
            260                 265                 270

His Ala Thr Leu Ala Gly His Thr Phe Glu His Glu Leu Ala Cys Ala
        275                 280                 285

Val Asp Ala Gly Met Leu Gly Ser Ile Asp Ala Asn Arg Gly Asp Ala
    290                 295                 300

Gln Asn Gly Trp Asp Thr Asp Gln Phe Pro Ile Asp Asn Tyr Glu Leu
305                 310                 315                 320

Thr Gln Ala Met Met Glu Ile Ile Arg Asn Gly Gly Leu Gly Leu Gly
                325                 330                 335

Gly Thr Asn Phe Asp Ala Lys Ile Arg Arg Asn Ser Thr Asp Leu Glu
            340                 345                 350

Asp Leu Phe Ile Ala His Ile Ser Gly Met Asp Ala Met Ala Arg Ala
        355                 360                 365

Leu Leu Asn Ala Ala Asp Ile Leu Glu Asn Ser Glu Leu Pro Ala Met
    370                 375                 380

Lys Lys Ala Arg Tyr Ala Ser Phe Asp Ser Gly Met Gly Lys Asp Phe
385                 390                 395                 400

Glu Asp Gly Lys Leu Thr Leu Glu Gln Val Tyr Glu Tyr Gly Lys Lys
                405                 410                 415
```

Val Gly Glu Pro Lys Gln Thr Ser Gly Lys Gln Glu Lys Tyr Glu Thr
420 425 430

Ile Val Ala Leu Tyr Ala Lys
435

<210> SEQ ID NO 85
<211> LENGTH: 1320
<212> TYPE: DNA
<213> ORGANISM: Unknown
<220> FEATURE:
<223> OTHER INFORMATION: Obtained from environmental sample

<400> SEQUENCE: 85
atggcaaaag agtattttcc gtttacaggt aaaattcctt tcgaaggaaa ggacagtaag 60
aacgtaatgg ctttccacta ctacgagccc gaaaaggtcg tgatgggaaa gaaaatgaaa 120
gactggctga agttcgccat ggcctggtgg cacacactgg gtggcgccag cgccgaccag 180
tttggcggcc agacacgcag ctatgagtgg gacaaggctg ccgatgccgt gcagcgcgca 240
aaggacaaga tggacgccgg cttcgaaatc atggacaagc tgggcatcga gtatttctgc 300
ttccacgacg tggacctcgt tgaggaggga gccaccatcg aggagtatga ggcccgcatg 360
aaggctatca ccgactatgc ccaggagaag atgaaacagt atcccagcat caagctgctc 420
tggggcaccg ccaatgtgtt tggcaacaag cgctacgcca acggcgccag caccaacccc 480
gacttcgacg tcgtggcccg tgccatcgtg cagatcaaga acgccatcga tgccaccatc 540
aagctgggcg gcaccaacta cgtgttctgg ggcggacgcg agggctacat gagcctgctc 600
aacaccgacc agaagcgcga gaaggagcac atggccacca tgctcaccat ggcccgcgac 660
tacgcccgcg caaagggatt caagggcacc ttcctcatcg agcccaagcc catggagccg 720
tcgaagcacc agtacgacgt ggacaccgag accgtcatcg gtttcctgaa ggcccacggt 780
ctggacaagg acttcaaggt gaacatcgag gtgaaccacg ccacgctggc cggccacacc 840
ttcgagcatg agctggcctg cgccgtcgac gccggtatgc tgggcagcat cgatgccaac 900
cgcggcgacg cccagaacgg ctgggacacc gaccagttcc ccatcgacaa cttcgagctc 960
acccaggcca tgatggaaat tatccgcaac ggcggcctcg gcaacggcgg caccaacttc 1020
gacgctaaga tccgccgcaa ctccaccgac ctcgaggacc tcttcatcgc ccacatcagc 1080
ggcatggacg ccatggcccg cgcactgatg aacgctgccg acattatgga gaacagcgag 1140
ctgcccgcca tgaagaaggc acgctacgcc agcttcgacg ccggcatcgg caaggacttt 1200
gaggatggca agctctcgct ggagcaggtc tacgagtatg gcaagaaggt ggaagagccc 1260
aagcagacca gcggcaagca ggagaagtac gagaccatcg tcgccctcta tgccaagtaa 1320

<210> SEQ ID NO 86
<211> LENGTH: 439
<212> TYPE: PRT
<213> ORGANISM: Unknown
<220> FEATURE:
<223> OTHER INFORMATION: Obtained from environmental sample

<400> SEQUENCE: 86

Met Ala Lys Glu Tyr Phe Pro Phe Thr Gly Lys Ile Pro Phe Glu Gly
1 5 10 15

Lys Asp Ser Lys Asn Val Met Ala Phe His Tyr Tyr Glu Pro Glu Lys
20 25 30

Val Val Met Gly Lys Lys Met Lys Asp Trp Leu Lys Phe Ala Met Ala
35 40 45

-continued

```
Trp Trp His Thr Leu Gly Gly Ala Ser Ala Asp Gln Phe Gly Gly Gln
    50                  55                  60

Thr Arg Ser Tyr Glu Trp Asp Lys Ala Ala Asp Ala Val Gln Arg Ala
65                  70                  75                  80

Lys Asp Lys Met Asp Ala Gly Phe Glu Ile Met Asp Lys Leu Gly Ile
                85                  90                  95

Glu Tyr Phe Cys Phe His Asp Val Asp Leu Val Glu Glu Gly Ala Thr
            100                 105                 110

Ile Glu Glu Tyr Glu Ala Arg Met Lys Ala Ile Thr Asp Tyr Ala Gln
        115                 120                 125

Glu Lys Met Lys Gln Tyr Pro Ser Ile Lys Leu Leu Trp Gly Thr Ala
    130                 135                 140

Asn Val Phe Gly Asn Lys Arg Tyr Ala Asn Gly Ala Ser Thr Asn Pro
145                 150                 155                 160

Asp Phe Asp Val Val Ala Arg Ala Ile Val Gln Ile Lys Asn Ala Ile
                165                 170                 175

Asp Ala Thr Ile Lys Leu Gly Gly Thr Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Met Ala Thr Met Leu Thr Met Ala Arg Asp Tyr Ala Arg Ala
    210                 215                 220

Lys Gly Phe Lys Gly Thr Phe Leu Ile Glu Pro Lys Pro Met Glu Pro
225                 230                 235                 240

Ser Lys His Gln Tyr Asp Val Asp Thr Glu Thr Val Ile Gly Phe Leu
                245                 250                 255

Lys Ala His Gly Leu Asp Lys Asp Phe Lys Val Asn Ile Glu Val Asn
            260                 265                 270

His Ala Thr Leu Ala Gly His Thr Phe Glu His Glu Leu Ala Cys Ala
        275                 280                 285

Val Asp Ala Gly Met Leu Gly Ser Ile Asp Ala Asn Arg Gly Asp Ala
    290                 295                 300

Gln Asn Gly Trp Asp Thr Asp Gln Phe Pro Ile Asp Asn Phe Glu Leu
305                 310                 315                 320

Thr Gln Ala Met Met Glu Ile Ile Arg Asn Gly Gly Leu Gly Asn Gly
                325                 330                 335

Gly Thr Asn Phe Asp Ala Lys Ile Arg Arg Asn Ser Thr Asp Leu Glu
            340                 345                 350

Asp Leu Phe Ile Ala His Ile Ser Gly Met Asp Ala Met Ala Arg Ala
        355                 360                 365

Leu Met Asn Ala Ala Asp Ile Met Glu Asn Ser Glu Leu Pro Ala Met
    370                 375                 380

Lys Lys Ala Arg Tyr Ala Ser Phe Asp Ala Gly Ile Gly Lys Asp Phe
385                 390                 395                 400

Glu Asp Gly Lys Leu Ser Leu Glu Gln Val Tyr Glu Tyr Gly Lys Lys
                405                 410                 415

Val Glu Glu Pro Lys Gln Thr Ser Gly Lys Gln Glu Lys Tyr Glu Thr
            420                 425                 430

Ile Val Ala Leu Tyr Ala Lys
        435
```

<210> SEQ ID NO 87
<211> LENGTH: 1320
<212> TYPE: DNA

<213> ORGANISM: Unknown
<220> FEATURE:
<223> OTHER INFORMATION: Obtained from environmental sample

<400> SEQUENCE: 87

```
atggcaaaag agtatttcgc ctttacaggc aagattcctt tcgagggaaa agacagtaag      60

aacgtgatgg ctttccacta ctacgagccg gagcgtgtgg tgatgggcaa gaagatgaag     120

gagtggctga agttcgccat ggcctggtgg cacacactgg gtggcgcatc ggccgaccag     180

ttcggaggcc agacacgcag ctacgagtgg gacaaggccg ccgacgccgt gcagcgcgcc     240

aaggacaaga tggacgccgg cttcgagatt atggacaagc tgggcatcga gtacttctgc     300

ttccacgatg tagacctcgt tgaggagggt gagaccatag ccgagtacga gcgccgcatg     360

aaggaaatca ccgactacgc acaggagaag atgaagcagt tccccaacat caagctgctc     420

tggggcacag ccaacgtgtt cggcaacaag cgctacgcca acggcgcatc gaccaacccc     480

gacttcgacg ttgtggcacg cgccatcgtg cagatcaaga acgccatcga cgccaccatc     540

aagctcggcg gctccaacta tgtgttctgg ggcggacgcg agggctatat gagcctgctc     600

aacaccgacc agaagcgcga gaaggagcac atggccacca tgctcaccat ggcccgcgac     660

tatgcacgcg ccaagggatt caagggcaca ttcctcatcg agccgaagcc catggagccc     720

tcgaagcacc agtacgacgt agacacagag accgtcatcg gcttcctccg tgcacacggg     780

ctggacaagg acttcaaggt gaacatcgag gtaaaccacg ccacactggc cggccacacc     840

ttcgagcacg agctggcttg cgccgtcgac gctggcatgc tgggcagcat cgacgccaac     900

cgtggcgacg cacagaacgg atgggacacc gaccagttcc ccatcgacaa cttcgagctc     960

acacaggcca tgatggaaat catccgcaat ggcggactgg gcaatggcgg caccaacttc    1020

gacgccaaga tccgtcgtaa cagcaccgac ctcgaagacc tcttcatcgc ccacatcagc    1080

ggcatggacg ccatggcacg cgcactgctc aacgctgccg acatcctgga gcacagcgag    1140

ctgcccaaga tgaagaagga gcgctacgcc agcttcgacg caggcatcgg caaggacttc    1200

gaagacggca agctcacact cgagcaggtc tacgagtacg gcaagaaggt cgaagagccc    1260

cgtcagacca gcggcaagca ggagaagtac gagaccatcg tcgccctcta tgccaagtaa    1320
```

<210> SEQ ID NO 88
<211> LENGTH: 439
<212> TYPE: PRT
<213> ORGANISM: Unknown
<220> FEATURE:
<223> OTHER INFORMATION: Obtained from environmental sample

<400> SEQUENCE: 88

```
Met Ala Lys Glu Tyr Phe Ala Phe Thr Gly Lys Ile Pro Phe Glu Gly
1               5                   10                  15

Lys Asp Ser Lys Asn Val Met Ala Phe His Tyr Tyr Glu Pro Glu Arg
            20                  25                  30

Val Val Met Gly Lys Lys Met Lys Glu Trp Leu Lys Phe Ala Met Ala
        35                  40                  45

Trp Trp His Thr Leu Gly Gly Ala Ser Ala Asp Gln Phe Gly Gly Gln
    50                  55                  60

Thr Arg Ser Tyr Glu Trp Asp Lys Ala Ala Asp Ala Val Gln Arg Ala
65                  70                  75                  80

Lys Asp Lys Met Asp Ala Gly Phe Glu Ile Met Asp Lys Leu Gly Ile
                85                  90                  95

Glu Tyr Phe Cys Phe His Asp Val Asp Leu Val Glu Glu Gly Glu Thr
```

```
            100                 105                 110

Ile Ala Glu Tyr Glu Arg Arg Met Lys Glu Ile Thr Asp Tyr Ala Gln
        115                 120                 125

Glu Lys Met Lys Gln Phe Pro Asn Ile Lys Leu Leu Trp Gly Thr Ala
    130                 135                 140

Asn Val Phe Gly Asn Lys Arg Tyr Ala Asn Gly Ala Ser Thr Asn Pro
145                 150                 155                 160

Asp Phe Asp Val Val Ala Arg Ala Ile Val Gln Ile Lys Asn Ala Ile
                165                 170                 175

Asp Ala Thr Ile Lys Leu Gly Gly Ser Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Met Ala Thr Met Leu Thr Met Ala Arg Asp Tyr Ala Arg Ala
    210                 215                 220

Lys Gly Phe Lys Gly Thr Phe Leu Ile Glu Pro Lys Pro Met Glu Pro
225                 230                 235                 240

Ser Lys His Gln Tyr Asp Val Asp Thr Glu Thr Val Ile Gly Phe Leu
                245                 250                 255

Arg Ala His Gly Leu Asp Lys Asp Phe Lys Val Asn Ile Glu Val Asn
            260                 265                 270

His Ala Thr Leu Ala Gly His Thr Phe Glu His Glu Leu Ala Cys Ala
        275                 280                 285

Val Asp Ala Gly Met Leu Gly Ser Ile Asp Ala Asn Arg Gly Asp Ala
    290                 295                 300

Gln Asn Gly Trp Asp Thr Asp Gln Phe Pro Ile Asp Asn Phe Glu Leu
305                 310                 315                 320

Thr Gln Ala Met Met Glu Ile Ile Arg Asn Gly Gly Leu Gly Asn Gly
                325                 330                 335

Gly Thr Asn Phe Asp Ala Lys Ile Arg Arg Asn Ser Thr Asp Leu Glu
            340                 345                 350

Asp Leu Phe Ile Ala His Ile Ser Gly Met Asp Ala Met Ala Arg Ala
        355                 360                 365

Leu Leu Asn Ala Ala Asp Ile Leu Glu His Ser Glu Leu Pro Lys Met
    370                 375                 380

Lys Lys Glu Arg Tyr Ala Ser Phe Asp Ala Gly Ile Gly Lys Asp Phe
385                 390                 395                 400

Glu Asp Gly Lys Leu Thr Leu Glu Gln Val Tyr Glu Tyr Gly Lys Lys
                405                 410                 415

Val Glu Glu Pro Arg Gln Thr Ser Gly Lys Gln Glu Lys Tyr Glu Thr
            420                 425                 430

Ile Val Ala Leu Tyr Ala Lys
        435
```

<210> SEQ ID NO 89
<211> LENGTH: 1320
<212> TYPE: DNA
<213> ORGANISM: Unknown
<220> FEATURE:
<223> OTHER INFORMATION: Obtained from environmental sample

<400> SEQUENCE: 89

```
atggcaaaag agtattttcc gtttactggt aagattcctt tcgagggaaa ggatagtaag      60

aatgtaatgg ctttccacta ttacgagccc gagaaagtcg tgatgggaaa gaagatgaag     120
```

-continued gactggctga agttcgcaat ggcttggtgg catacactgg gtggtgcatc tgcagaccag 180
ttcggtggag agacccgcag ctacgagtgg agcaaggctg ctgatcccgt tcagcgcgcc 240
aaggacaaga tggacgccgg ctttgagatt atggataagc tgggcatcga gtacttctgt 300
ttccacgata tagacctcgt tcaggaggca gataccattg cagaatatga ggagcgcatg 360
aaggcaatta ccgactatgc tctggagaag atgaagcagt tccccaacat caagttgctc 420
tggggtaccg ctaacgtatt tagcaacaag cgctatatga acggtgcttc taccaatccc 480
gacttcgacg tggtggcccg tgccatcgtt cagatcaaga acgctattga tgcaaccatc 540
aaactcggtg gtaccaacta tgtattctgg ggtggtcgtg agggttacat gagcctattg 600
aataccgacc agaagcgtga aaaggagcac atggcaatga tgctcggtat ggctcgcgac 660
tatgcccgca gcaagggatt caagggtacg ttcctcatcg agccgaagcc gatggagccc 720
tctaagcatc agtatgatgt cgatacggag actgtgattg gtttcctgaa ggcacacggt 780
ctggacaagg acttcaaggt gaacatcgag gtgaaccacg ctacactggc tggtcatacc 840
ttcgagcatg agctggcttg cgctgttgac gcaggtatgc tgggctctat cgacgctaac 900
cgcggtgatg cccagaacgg ctgggatacc gaccagttcc ccatcgacaa ctacgagctg 960
acacaggcta tgatggaaat catccgcaac ggtggtctgg gcaatggtgg taccaacttc 1020
gacgctaaga tccgccgtaa ctctaccgac ctcgaggatc tgttcatcgc tcatatcagt 1080
ggtatggatg ctatggcccg tgctttgttg aatgctgccg acattctgga gaactctgaa 1140
ctgcccgcta tgaagaaggc ccgctacgcc agcttcgaca acggtatcgg taaggacttc 1200
gaggatggca agctgacctt cgagcaggtt tacgaatatg gtaagaaagt tgaagagccg 1260
aagcagacct ctggcaagca ggagaaatac gagaccatcg ttgctctgta tgctaaataa 1320

<210> SEQ ID NO 90
<211> LENGTH: 439
<212> TYPE: PRT
<213> ORGANISM: Unknown
<220> FEATURE:
<223> OTHER INFORMATION: Obtained from environmental sample

<400> SEQUENCE: 90

Met Ala Lys Glu Tyr Phe Pro Phe Thr Gly Lys Ile Pro Phe Glu Gly
1 5 10 15

Lys Asp Ser Lys Asn Val Met Ala Phe His Tyr Tyr Glu Pro Glu Lys
20 25 30

Val Val Met Gly Lys Lys Met Lys Asp Trp Leu Lys Phe Ala Met Ala
35 40 45

Trp Trp His Thr Leu Gly Gly Ala Ser Ala Asp Gln Phe Gly Gly Glu
50 55 60

Thr Arg Ser Tyr Glu Trp Ser Lys Ala Ala Asp Pro Val Gln Arg Ala
65 70 75 80

Lys Asp Lys Met Asp Ala Gly Phe Glu Ile Met Asp Lys Leu Gly Ile
85 90 95

Glu Tyr Phe Cys Phe His Asp Ile Asp Leu Val Gln Glu Ala Asp Thr
100 105 110

Ile Ala Glu Tyr Glu Glu Arg Met Lys Ala Ile Thr Asp Tyr Ala Leu
115 120 125

Glu Lys Met Lys Gln Phe Pro Asn Ile Lys Leu Leu Trp Gly Thr Ala
130 135 140

Asn Val Phe Ser Asn Lys Arg Tyr Met Asn Gly Ala Ser Thr Asn Pro
145 150 155 160

```
Asp Phe Asp Val Val Ala Arg Ala Ile Val Gln Ile Lys Asn Ala Ile
                165                 170                 175

Asp Ala Thr Ile Lys Leu Gly Gly Thr Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Met Ala Met Met Leu Gly Met Ala Arg Asp Tyr Ala Arg Ser
    210                 215                 220

Lys Gly Phe Lys Gly Thr Phe Leu Ile Glu Pro Lys Pro Met Glu Pro
225                 230                 235                 240

Ser Lys His Gln Tyr Asp Val Asp Thr Glu Thr Val Ile Gly Phe Leu
                245                 250                 255

Lys Ala His Gly Leu Asp Lys Asp Phe Lys Val Asn Ile Glu Val Asn
            260                 265                 270

His Ala Thr Leu Ala Gly His Thr Phe Glu His Glu Leu Ala Cys Ala
        275                 280                 285

Val Asp Ala Gly Met Leu Gly Ser Ile Asp Ala Asn Arg Gly Asp Ala
    290                 295                 300

Gln Asn Gly Trp Asp Thr Asp Gln Phe Pro Ile Asp Asn Tyr Glu Leu
305                 310                 315                 320

Thr Gln Ala Met Met Glu Ile Ile Arg Asn Gly Gly Leu Gly Asn Gly
                325                 330                 335

Gly Thr Asn Phe Asp Ala Lys Ile Arg Arg Asn Ser Thr Asp Leu Glu
            340                 345                 350

Asp Leu Phe Ile Ala His Ile Ser Gly Met Asp Ala Met Ala Arg Ala
        355                 360                 365

Leu Leu Asn Ala Ala Asp Ile Leu Glu Asn Ser Glu Leu Pro Ala Met
    370                 375                 380

Lys Lys Ala Arg Tyr Ala Ser Phe Asp Asn Gly Ile Gly Lys Asp Phe
385                 390                 395                 400

Glu Asp Gly Lys Leu Thr Phe Glu Gln Val Tyr Glu Tyr Gly Lys Lys
                405                 410                 415

Val Glu Glu Pro Lys Gln Thr Ser Gly Lys Gln Glu Lys Tyr Glu Thr
            420                 425                 430

Ile Val Ala Leu Tyr Ala Lys
        435
```

<210> SEQ ID NO 91
<211> LENGTH: 1320
<212> TYPE: DNA
<213> ORGANISM: Unknown
<220> FEATURE:
<223> OTHER INFORMATION: Obtained from environmental sample

<400> SEQUENCE: 91

```
atggcaaaag agtattttcc gtttaccggt aaaattcctt tcgagggaaa ggacagtaag      60

aatgtaatgg ctttccacta ctacgagcct gagcgcgtag tgatgggaaa gaagatgaag     120

gattggttgc gatttgcaat ggcttggtgg cacacactgg gtggcgcttc tgccgaccag     180

tttggtggtc agacccgcag ttacgaatgg gacaaggctg ctgatgctgt tcagcgtgct     240

aaggacaaga tggatgccgg cttcgagatt atggataagc tgggaatcga gttcttctgc     300

tggcacgata tcgacctcgt tgaagagggt gagaccattg aagagtatga gcgccgcatg     360

aaggctatca ccgactatgc tcttgagaag atgcagcagt atcccaacat caagaacctc     420
```

```
tggggaacag ccaatgtgtt tggcaacaag cgttatgcca acggtgccag cacaaaccca    480

gactttgacg tcgttgctcg tgctatcgta cagattaaga atgctatcga cgctactatc    540

aagttgggtg gtcagaatta tgtgttctgg ggtggccgtg agggctacat gagcctgctc    600

aatactgacc agaagcgtga gaaggagcac atggctacaa tgctgaccat ggcacgcgac    660

tatgcccgca gcaagggatt caagggtaac ttcctcattg agcccaagcc catggagccg    720

tcaaagcacc agtatgatgt tgacaccgag accgtatgcg gtttcctgcg tgcccacaac    780

cttgacaagg atttcaaggt aaatatcgag gttaaccatg ctactctggc tggtcatact    840

ttcgagcacg aactggcatg cgctgttgac gctggtatgc ttggttctat cgatgctaac    900

cgtggtgatg cccagaatgg ctgggatacc gaccagttcc ccatcaacaa ctatgaactc    960

actcaggcta tgcttgagat catccgtaat ggtggtctgg gtcttggcgg cacaaacttc   1020

gatgccaaga ttcgtcgtaa ctcaacagat cttgaggatc tcttcatcgc tcacatcagt   1080

ggtatggatg ccatggcccg tgctctgctg aatgctgctg ctattctgga ggagagcgag   1140

ctgcctaaga tgaagaagga gcgttatgct tctttcgatg ccggtatcgg taaggacttc   1200

gaggatggca agcttaccct tgagcaggct tacgagtatg gtaagaaggt tgaggagccc   1260

aagcagactt caggcaagca ggagaagtac gagaccatcg ttgctctgta tgcaaaataa   1320


<210> SEQ ID NO 92
<211> LENGTH: 439
<212> TYPE: PRT
<213> ORGANISM: Unknown
<220> FEATURE:
<223> OTHER INFORMATION: Obtained from environmental sample

<400> SEQUENCE: 92

Met Ala Lys Glu Tyr Phe Pro Phe Thr Gly Lys Ile Pro Phe Glu Gly
1               5                   10                  15

Lys Asp Ser Lys Asn Val Met Ala Phe His Tyr Tyr Glu Pro Glu Arg
            20                  25                  30

Val Val Met Gly Lys Lys Met Lys Asp Trp Leu Arg Phe Ala Met Ala
        35                  40                  45

Trp Trp His Thr Leu Gly Gly Ala Ser Ala Asp Gln Phe Gly Gly Gln
    50                  55                  60

Thr Arg Ser Tyr Glu Trp Asp Lys Ala Ala Asp Ala Val Gln Arg Ala
65                  70                  75                  80

Lys Asp Lys Met Asp Ala Gly Phe Glu Ile Met Asp Lys Leu Gly Ile
                85                  90                  95

Glu Phe Phe Cys Trp His Asp Ile Asp Leu Val Glu Glu Gly Glu Thr
            100                 105                 110

Ile Glu Glu Tyr Glu Arg Arg Met Lys Ala Ile Thr Asp Tyr Ala Leu
        115                 120                 125

Glu Lys Met Gln Gln Tyr Pro Asn Ile Lys Asn Leu Trp Gly Thr Ala
    130                 135                 140

Asn Val Phe Gly Asn Lys Arg Tyr Ala Asn Gly Ala Ser Thr Asn Pro
145                 150                 155                 160

Asp Phe Asp Val Val Ala Arg Ala Ile Val Gln Ile Lys Asn Ala Ile
                165                 170                 175

Asp Ala Thr Ile Lys Leu Gly Gly Gln Asn Tyr Val Phe Trp Gly Gly
            180                 185                 190

Arg Glu Gly Tyr Met Ser Leu Leu Asn Thr Asp Gln Lys Arg Glu Lys
        195                 200                 205
```

```
Glu His Met Ala Thr Met Leu Thr Met Ala Arg Asp Tyr Ala Arg Ser
    210                 215                 220

Lys Gly Phe Lys Gly Asn Phe Leu Ile Glu Pro Lys Pro Met Glu Pro
225                 230                 235                 240

Ser Lys His Gln Tyr Asp Val Asp Thr Glu Thr Val Cys Gly Phe Leu
                245                 250                 255

Arg Ala His Asn Leu Asp Lys Asp Phe Lys Val Asn Ile Glu Val Asn
            260                 265                 270

His Ala Thr Leu Ala Gly His Thr Phe Glu His Glu Leu Ala Cys Ala
        275                 280                 285

Val Asp Ala Gly Met Leu Gly Ser Ile Asp Ala Asn Arg Gly Asp Ala
    290                 295                 300

Gln Asn Gly Trp Asp Thr Asp Gln Phe Pro Ile Asn Asn Tyr Glu Leu
305                 310                 315                 320

Thr Gln Ala Met Leu Glu Ile Ile Arg Asn Gly Gly Leu Gly Leu Gly
                325                 330                 335

Gly Thr Asn Phe Asp Ala Lys Ile Arg Arg Asn Ser Thr Asp Leu Glu
            340                 345                 350

Asp Leu Phe Ile Ala His Ile Ser Gly Met Asp Ala Met Ala Arg Ala
        355                 360                 365

Leu Leu Asn Ala Ala Ala Ile Leu Glu Glu Ser Glu Leu Pro Lys Met
    370                 375                 380

Lys Lys Glu Arg Tyr Ala Ser Phe Asp Ala Gly Ile Gly Lys Asp Phe
385                 390                 395                 400

Glu Asp Gly Lys Leu Thr Leu Glu Gln Ala Tyr Glu Tyr Gly Lys Lys
                405                 410                 415

Val Glu Glu Pro Lys Gln Thr Ser Gly Lys Gln Glu Lys Tyr Glu Thr
            420                 425                 430

Ile Val Ala Leu Tyr Ala Lys
        435
```

<210> SEQ ID NO 93
<211> LENGTH: 1317
<212> TYPE: DNA
<213> ORGANISM: Unknown
<220> FEATURE:
<223> OTHER INFORMATION: Obtained from environmental sample

<400> SEQUENCE: 93

```
atgaaacagt attttcccca gattggaaag ataccccttcg agggtgtaga gagcaagaat      60

gtgatggctt tccactatta tgagccagaa agagtagtca tgggcaagcc tatgaaagaa     120

tggctgcgct tcgctatggc gtggtggcac acgctggggc aggcgagcgg cgacccccttc     180

ggcggacaga cccgcagcta cgagtgggac cgtgcggccg acgcgctaca gcgcgccaag     240

gacaagatgg atgcgggctt cgagctgatg gagaagcttg gcattgagta cttctgcttc     300

cacgacgtgg acctcgtaga agagggcgcc acggtggagg aatacgagcg gcggatggct     360

gccatcaccg actacgcggt agagaagatg cgcgagcatc ccgagataca ctgcctgtgg     420

ggcacggcca atgtcttcgg ccacaagcgc tacatgaacg gagccgccac caaccccgac     480

ttcgacgtgg tggcgcgtgc ggtggtgcag ataaagaaca gcatcgacgc cacgatcaag     540

ctgggcggcg agaactatgt gttctggggc ggacgcgagg gatatatgag cctgctcaac     600

accgaccagc gccgcgagaa ggagcacctg gccatgatgc ttgcgaaggc ccgcgactat     660

ggccgcgccc acggcttcaa gggcaccttc ctgatagagc ccaagccgat ggagcccatg     720
```

```
aagcaccagt acgacgtgga caccgagacg gtgataggtt tcctgcgtgc ccacggactg    780

gacaaggact tcaaggtgaa catcgaggtg aaccacgcca cgttggcggg ccacacgttc    840

gagcacgagc tggcctgtgc cgtcgatgcc ggcatgctgg gcagcatcga cgccaaccgt    900

ggcgacgcgc agaacggatg ggatacggac cagttcccca tagactgcta cgagctcacg    960

caggcgtgga tggagatcat tcgtggcggc ggcttcacca ccggcggcac caacttcgac   1020

gctaagctgc gccgcaactc gaccgacccc gaggatatct tcatagctca catcagcggc   1080

atggatgcta tggcccgcgc cctgctctgc gccgccgaca tcttggagca cagcgagctg   1140

ccggagatga agcggaagcg ctatgcctcg ttcgacagcg gcatgggcaa ggagttcgaa   1200

gagggcaatc tcagcttcga gcaaatctat gcctacggca agcaggcggg cgaaccggcc   1260

acgaccagcg gcaagcagga gaaatacgaa gccattgttt cactttatac ccgatga      1317


<210> SEQ ID NO 94
<211> LENGTH: 438
<212> TYPE: PRT
<213> ORGANISM: Unknown
<220> FEATURE:
<223> OTHER INFORMATION: Obtained from environmental sample

<400> SEQUENCE: 94

Met Lys Gln Tyr Phe Pro Gln Ile Gly Lys Ile Pro Phe Glu Gly Val
1               5                   10                  15

Glu Ser Lys Asn Val Met Ala Phe His Tyr Tyr Glu Pro Glu Arg Val
            20                  25                  30

Val Met Gly Lys Pro Met Lys Glu Trp Leu Arg Phe Ala Met Ala Trp
        35                  40                  45

Trp His Thr Leu Gly Gln Ala Ser Gly Asp Pro Phe Gly Gly Gln Thr
    50                  55                  60

Arg Ser Tyr Glu Trp Asp Arg Ala Ala Asp Ala Leu Gln Arg Ala Lys
65                  70                  75                  80

Asp Lys Met Asp Ala Gly Phe Glu Leu Met Glu Lys Leu Gly Ile Glu
                85                  90                  95

Tyr Phe Cys Phe His Asp Val Asp Leu Val Glu Glu Gly Ala Thr Val
            100                 105                 110

Glu Glu Tyr Glu Arg Arg Met Ala Ala Ile Thr Asp Tyr Ala Val Glu
        115                 120                 125

Lys Met Arg Glu His Pro Glu Ile His Cys Leu Trp Gly Thr Ala Asn
    130                 135                 140

Val Phe Gly His Lys Arg Tyr Met Asn Gly Ala Ala Thr Asn Pro Asp
145                 150                 155                 160

Phe Asp Val Val Ala Arg Ala Val Val Gln Ile Lys Asn Ser Ile Asp
                165                 170                 175

Ala Thr Ile Lys Leu Gly Gly Glu Asn Tyr Val Phe Trp Gly Gly Arg
            180                 185                 190

Glu Gly Tyr Met Ser Leu Leu Asn Thr Asp Gln Arg Arg Glu Lys Glu
        195                 200                 205

His Leu Ala Met Met Leu Ala Lys Ala Arg Asp Tyr Gly Arg Ala His
    210                 215                 220

Gly Phe Lys Gly Thr Phe Leu Ile Glu Pro Lys Pro Met Glu Pro Met
225                 230                 235                 240

Lys His Gln Tyr Asp Val Asp Thr Glu Thr Val Ile Gly Phe Leu Arg
                245                 250                 255

Ala His Gly Leu Asp Lys Asp Phe Lys Val Asn Ile Glu Val Asn His
```

-continued

```
            260                 265                 270

Ala Thr Leu Ala Gly His Thr Phe Glu His Glu Leu Ala Cys Ala Val
        275                 280                 285

Asp Ala Gly Met Leu Gly Ser Ile Asp Ala Asn Arg Gly Asp Ala Gln
    290                 295                 300

Asn Gly Trp Asp Thr Asp Gln Phe Pro Ile Asp Cys Tyr Glu Leu Thr
305                 310                 315                 320

Gln Ala Trp Met Glu Ile Ile Arg Gly Gly Gly Phe Thr Thr Gly Gly
                325                 330                 335

Thr Asn Phe Asp Ala Lys Leu Arg Arg Asn Ser Thr Asp Pro Glu Asp
            340                 345                 350

Ile Phe Ile Ala His Ile Ser Gly Met Asp Ala Met Ala Arg Ala Leu
        355                 360                 365

Leu Cys Ala Ala Asp Ile Leu Glu His Ser Glu Leu Pro Glu Met Lys
    370                 375                 380

Arg Lys Arg Tyr Ala Ser Phe Asp Ser Gly Met Gly Lys Glu Phe Glu
385                 390                 395                 400

Glu Gly Asn Leu Ser Phe Glu Gln Ile Tyr Ala Tyr Gly Lys Gln Ala
                405                 410                 415

Gly Glu Pro Ala Thr Thr Ser Gly Lys Gln Glu Lys Tyr Glu Ala Ile
            420                 425                 430

Val Ser Leu Tyr Thr Arg
        435


<210> SEQ ID NO 95
<211> LENGTH: 1320
<212> TYPE: DNA
<213> ORGANISM: Unknown
<220> FEATURE:
<223> OTHER INFORMATION: Obtained from environmental sample

<400> SEQUENCE: 95

atggcaaaag agtattttcc gtttatcggt aaggttcctt tcgaaggaac agagagcaag      60

aacgtgatgg cattccacta ctatgagccc gaaaaggtgg tcatgggtaa gaaaatgaag     120

gactggctga agttcgctat ggcttggtgg cacacactgg gtggtgccag cgccgaccag     180

tttggtggtc agactcgcag ctacgagtgg gacaaggctg ctgatgccgt tcagcgcgcc     240

aaggacaaga tggatgctgg cttcgagatc atggataagc tcggcattga gtacttctgc     300

ttccatgacg tagacctcgt tgaggagggt gaaaccgtcg ctgagtatga ggctcgcatg     360

aaggtcatca ccgactatgc cctggagaag atgcagcagt tccccaacat caaactgctc     420

tggggtactg ctaacgtgtt cggccacaag cgctatgcca acggtgccag caccaatccc     480

gacttcgacg tcgtggcccg tgctatcgtt cagatcaaga atgccatcga tgctaccatt     540

aagctcggcg gtacgaacta tgtgttctgg ggtggtcgtg agggctacat gagccttctc     600

aacaccgacc agaagcgcga gaaggagcac atggcaacga tgctgaccat ggctcgcgac     660

tatgcccgcg ccaagggatt caagggcacg ttcctcatcg agccgaagcc catggagccc     720

tcgaagcatc agtacgacgt cgacaccgag accgtcatcg gcttcctccg tgcccacggt     780

ctggataagg acttcaaggt gaacatcgag gtgaaccacg ccacgctggc cggtcatacc     840

ttcgagcacg aactggcttg cgccgttgat gccggcatgc tcggctctat cgatgccaac     900

cgcggcgacg ctcagaacgg ctgggacacc gaccagttcc ccatcgacaa ctacgagctc     960

actcaggcca tgatggaaat catccgtaat ggcggtctgg gcaacggcgg cacgaacttc    1020
```

gatgccaaga tccgtcgtaa cagcaccgac ctcgaggacc tcttcatcgc tcacatcagc 1080
ggcatggatg ccatggcacg cgctctgatg aacgctgctg ccatcctcga agagagcgag 1140
ctgcccgcca tgaagaaggc ccgctatgct tcgttcgacg agggtatcgg caaggacttc 1200
gaggacggca agttgtcact tgagcaggtc tacgaatatg gtaagaaggt tgaggagccc 1260
aagcagacct cgggcaagca ggagaagtac gagaccatcg tggccctcta tgccaagtaa 1320

<210> SEQ ID NO 96
<211> LENGTH: 439
<212> TYPE: PRT
<213> ORGANISM: Unknown
<220> FEATURE:
<223> OTHER INFORMATION: Obtained from environmental sample

<400> SEQUENCE: 96

Met Ala Lys Glu Tyr Phe Pro Phe Ile Gly Lys Val Pro Phe Glu Gly
1 5 10 15

Thr Glu Ser Lys Asn Val Met Ala Phe His Tyr Tyr Glu Pro Glu Lys
20 25 30

Val Val Met Gly Lys Lys Met Lys Asp Trp Leu Lys Phe Ala Met Ala
35 40 45

Trp Trp His Thr Leu Gly Gly Ala Ser Ala Asp Gln Phe Gly Gly Gln
50 55 60

Thr Arg Ser Tyr Glu Trp Asp Lys Ala Ala Asp Ala Val Gln Arg Ala
65 70 75 80

Lys Asp Lys Met Asp Ala Gly Phe Glu Ile Met Asp Lys Leu Gly Ile
85 90 95

Glu Tyr Phe Cys Phe His Asp Val Asp Leu Val Glu Glu Gly Glu Thr
100 105 110

Val Ala Glu Tyr Glu Ala Arg Met Lys Val Ile Thr Asp Tyr Ala Leu
115 120 125

Glu Lys Met Gln Gln Phe Pro Asn Ile Lys Leu Leu Trp Gly Thr Ala
130 135 140

Asn Val Phe Gly His Lys Arg Tyr Ala Asn Gly Ala Ser Thr Asn Pro
145 150 155 160

Asp Phe Asp Val Val Ala Arg Ala Ile Val Gln Ile Lys Asn Ala Ile
165 170 175

Asp Ala Thr Ile Lys Leu Gly Gly Thr Asn Tyr Val Phe Trp Gly Gly
180 185 190

Arg Glu Gly Tyr Met Ser Leu Leu Asn Thr Asp Gln Lys Arg Glu Lys
195 200 205

Glu His Met Ala Thr Met Leu Thr Met Ala Arg Asp Tyr Ala Arg Ala
210 215 220

Lys Gly Phe Lys Gly Thr Phe Leu Ile Glu Pro Lys Pro Met Glu Pro
225 230 235 240

Ser Lys His Gln Tyr Asp Val Asp Thr Glu Thr Val Ile Gly Phe Leu
245 250 255

Arg Ala His Gly Leu Asp Lys Asp Phe Lys Val Asn Ile Glu Val Asn
260 265 270

His Ala Thr Leu Ala Gly His Thr Phe Glu His Glu Leu Ala Cys Ala
275 280 285

Val Asp Ala Gly Met Leu Gly Ser Ile Asp Ala Asn Arg Gly Asp Ala
290 295 300

Gln Asn Gly Trp Asp Thr Asp Gln Phe Pro Ile Asp Asn Tyr Glu Leu
305 310 315 320

```
Thr Gln Ala Met Met Glu Ile Ile Arg Asn Gly Gly Leu Gly Asn Gly
                325                 330                 335

Gly Thr Asn Phe Asp Ala Lys Ile Arg Arg Asn Ser Thr Asp Leu Glu
            340                 345                 350

Asp Leu Phe Ile Ala His Ile Ser Gly Met Asp Ala Met Ala Arg Ala
        355                 360                 365

Leu Met Asn Ala Ala Ala Ile Leu Glu Glu Ser Glu Leu Pro Ala Met
    370                 375                 380

Lys Lys Ala Arg Tyr Ala Ser Phe Asp Glu Gly Ile Gly Lys Asp Phe
385                 390                 395                 400

Glu Asp Gly Lys Leu Ser Leu Glu Gln Val Tyr Glu Tyr Gly Lys Lys
                405                 410                 415

Val Glu Glu Pro Lys Gln Thr Ser Gly Lys Gln Glu Lys Tyr Glu Thr
            420                 425                 430

Ile Val Ala Leu Tyr Ala Lys
        435
```

<210> SEQ ID NO 97
<211> LENGTH: 1320
<212> TYPE: DNA
<213> ORGANISM: Unknown
<220> FEATURE:
<223> OTHER INFORMATION: Obtained from environmental sample

<400> SEQUENCE: 97

```
atggcaaaag agtattttcc gtttgttggt aagattcctt tcgagggaaa ggatagtaag     60

aatgtaatgg ctttccacta ttacgaacca gagaaggtcg tgatgggaaa gaagatgaag    120

gactggctga agttcgccat ggcatggtgg cacacactgg gacaggccag tgccgacccg    180

tttggaggtc agacccgcag ctacgagtgg gacaaggctg acgatgctgt gcagcgcgca    240

aaggacaaga tggatgccgg atttgagatc atggacaagc tgggcatcga gtacttctgc    300

ttccacgatg tagacctcgt tgaggaggga gcaactgttg aggagtacga ggctcgcatg    360

aaggccatca ccgactatgc attggagaag atgaaagagt atcccaacat caagaacctc    420

tggggtacag ccaatgtatt cagcaacaag cgctatatga acggtgccag caccaacccc    480

gacttcgacg ttgttgcacg tgccatcgta cagataaaga acgccattga cgctaccatc    540

aagctcggcg gtcagaacta cgtgttctgg ggcggacgtg agggatacat gagcctgctc    600

aacaccgacc agaagcgcga gaaggagcac atggcaacca tgctgaccat ggctcgcgac    660

tacgctcgca agaacggttt caagggcaca ttcctcatcg agcctaagcc catggaaccc    720

tcaaagcacc agtacgacgt agacacagag accgtatgcg gtttcctccg cgcccatggt    780

cttgacaagg atttcaaggt gaacattgag gtgaaccacg ctaccctcgc cggccacacc    840

tttgagcatg aactggcttg cgccgtcgac aacggcatgc tcggcagcat cgatgccaac    900

cgcggcgacg ttcagaacgg ctgggacacc gaccagttcc ccatcgacaa ctacgagctg    960

actcaggcca tgctcgaaat catccgcaac ggtggtctgg gcaacggcgg taccaacttc   1020

gacgccaaga tccgtcgtaa ctctaccgac ctcgaggatc tgttcatcgc ccacatcagc   1080

ggtatggacg ccatggcacg tgcactgctc aatgcagcag ccatactgga ggagagcgag   1140

ctgcctgcca tgaagaagga gcgttacgcc agcttcgaca gcggcatcgg caaggacttc   1200

gaggacggca agctcacact tgagcaggcc tatgagtatg gtaagaaggt tgaggagcca   1260

aagcagacct ctggcaagca ggagaagtat gagactatag tagccctcta cgctaagtag   1320
```

<210> SEQ ID NO 98
<211> LENGTH: 439
<212> TYPE: PRT
<213> ORGANISM: Unknown
<220> FEATURE:
<223> OTHER INFORMATION: Obtained from environmental sample

<400> SEQUENCE: 98

```
Met Ala Lys Glu Tyr Phe Pro Phe Val Gly Lys Ile Pro Phe Glu Gly
1               5                   10                  15

Lys Asp Ser Lys Asn Val Met Ala Phe His Tyr Tyr Glu Pro Glu Lys
            20                  25                  30

Val Val Met Gly Lys Lys Met Lys Asp Trp Leu Lys Phe Ala Met Ala
        35                  40                  45

Trp Trp His Thr Leu Gly Gln Ala Ser Ala Asp Pro Phe Gly Gly Gln
    50                  55                  60

Thr Arg Ser Tyr Glu Trp Asp Lys Ala Asp Asp Ala Val Gln Arg Ala
65                  70                  75                  80

Lys Asp Lys Met Asp Ala Gly Phe Glu Ile Met Asp Lys Leu Gly Ile
                85                  90                  95

Glu Tyr Phe Cys Phe His Asp Val Asp Leu Val Glu Glu Gly Ala Thr
            100                 105                 110

Val Glu Glu Tyr Glu Ala Arg Met Lys Ala Ile Thr Asp Tyr Ala Leu
        115                 120                 125

Glu Lys Met Lys Glu Tyr Pro Asn Ile Lys Asn Leu Trp Gly Thr Ala
    130                 135                 140

Asn Val Phe Ser Asn Lys Arg Tyr Met Asn Gly Ala Ser Thr Asn Pro
145                 150                 155                 160

Asp Phe Asp Val Val Ala Arg Ala Ile Val Gln Ile Lys Asn Ala Ile
                165                 170                 175

Asp Ala Thr Ile Lys Leu Gly Gly Gln Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Met Ala Thr Met Leu Thr Met Ala Arg Asp Tyr Ala Arg Lys
    210                 215                 220

Asn Gly Phe Lys Gly Thr Phe Leu Ile Glu Pro Lys Pro Met Glu Pro
225                 230                 235                 240

Ser Lys His Gln Tyr Asp Val Asp Thr Glu Thr Val Cys Gly Phe Leu
                245                 250                 255

Arg Ala His Gly Leu Asp Lys Asp Phe Lys Val Asn Ile Glu Val Asn
            260                 265                 270

His Ala Thr Leu Ala Gly His Thr Phe Glu His Glu Leu Ala Cys Ala
        275                 280                 285

Val Asp Asn Gly Met Leu Gly Ser Ile Asp Ala Asn Arg Gly Asp Val
    290                 295                 300

Gln Asn Gly Trp Asp Thr Asp Gln Phe Pro Ile Asp Asn Tyr Glu Leu
305                 310                 315                 320

Thr Gln Ala Met Leu Glu Ile Ile Arg Asn Gly Gly Leu Gly Asn Gly
                325                 330                 335

Gly Thr Asn Phe Asp Ala Lys Ile Arg Arg Asn Ser Thr Asp Leu Glu
            340                 345                 350

Asp Leu Phe Ile Ala His Ile Ser Gly Met Asp Ala Met Ala Arg Ala
        355                 360                 365
```

Leu Leu Asn Ala Ala Ala Ile Leu Glu Glu Ser Glu Leu Pro Ala Met
    370                 375                 380

Lys Lys Glu Arg Tyr Ala Ser Phe Asp Ser Gly Ile Gly Lys Asp Phe
385                 390                 395                 400

Glu Asp Gly Lys Leu Thr Leu Glu Gln Ala Tyr Glu Tyr Gly Lys Lys
                405                 410                 415

Val Glu Glu Pro Lys Gln Thr Ser Gly Lys Gln Glu Lys Tyr Glu Thr
            420                 425                 430

Ile Val Ala Leu Tyr Ala Lys
        435

<210> SEQ ID NO 99
<211> LENGTH: 1317
<212> TYPE: DNA
<213> ORGANISM: Unknown
<220> FEATURE:
<223> OTHER INFORMATION: Obtained from environmental sample

<400> SEQUENCE: 99
atgactaaag agtatttccc taccattggc aagattccct ttgagggacc tgaaagcaag 60
aacccgcttg cattccatta ctatgagccc gaccgcctgg tcatgggcaa gaagatgaaa 120
gactggctgc gtttcgccat ggcctggtgg cacaccctgg gccaggcctc cggcgaccag 180
ttcggcggcc agacccgcca ctatgcctgg gatgatccgg attgcccgta tgcacgtgcc 240
aaagccaagg ccgacgccgg tttcgaaatc atgcagaaac tgggcattga attcttctgc 300
ttccacgaca tcgacctggt cgaggatgcc gatgaaatcg ccgagtacga ggcccggatg 360
aaggacatca ccgactatct gctcgtcaag atgaaagaga ccggcatcaa gaacctttgg 420
ggaacggcca acgtatttgg ccacaagcgc tacatgaacg gcgccgccac caaccccgat 480
ttcgacgtgc tggcccgtgc cgccgtccag atcaagaacg ccatcgacgc caccatcaag 540
ttgggcggtc agaactatgt gttctggggc ggccgtgaag gctaccagac cctgctcaat 600
acccagatgc agcgcgagaa ggaacacatg ggccgtatgt tggcactggc ccgcgactat 660
ggccgtgcac acggtttcaa gggcacgttc ctcatcgagc ccaaaccgat ggagccgacc 720
aagcaccagt acgatcagga tacggaaacc gtcatcggct tcctgcgccg ccatggcctc 780
gacaaggact tcaaggtcaa catcgaggtg aaccatgcta ccctggcggg ccacaccttc 840
gagcacgagc tggcttgcgc cgtcgaccac ggcatgctgg gcagcatcga cgccaaccgg 900
ggtgatgccc agaacggctg ggacaccgac cagttcccga tcgataacta tgagctgacg 960
ctggccatgc tccagatcat ccgcaacggc ggcctggcac ccggcggctc gaacttcgat 1020
gcgaagctgc gtcgcaactc caccgatccg gaagatatct tcatcgcgca catcagcgcc 1080
atggatgcca tggcccgcgc cctggtcaat gctgtcgcca ttctcgagga atcgcccatc 1140
ccggccatgg tcagggaacg ttacgcctcg ttcgacagcg gaaagggcag ggaatatgag 1200
gaaggcaggc tgtctctcga agacatcgtg gcctatgcca aagcccacgg cgaaccgaaa 1260
cagatttccg gcaagcagga actctacgaa accatcgtgg ctctctattg caagtag 1317

<210> SEQ ID NO 100
<211> LENGTH: 438
<212> TYPE: PRT
<213> ORGANISM: Unknown
<220> FEATURE:
<223> OTHER INFORMATION: Obtained from environmental sample

<400> SEQUENCE: 100

-continued

```
Met Thr Lys Glu Tyr Phe Pro Thr Ile Gly Lys Ile Pro Phe Glu Gly
1               5                   10                  15

Pro Glu Ser Lys Asn Pro Leu Ala Phe His Tyr Tyr Glu Pro Asp Arg
            20                  25                  30

Leu Val Met Gly Lys Lys Met Lys Asp Trp Leu Arg Phe Ala Met Ala
        35                  40                  45

Trp Trp His Thr Leu Gly Gln Ala Ser Gly Asp Gln Phe Gly Gly Gln
    50                  55                  60

Thr Arg His Tyr Ala Trp Asp Asp Pro Asp Cys Pro Tyr Ala Arg Ala
65                  70                  75                  80

Lys Ala Lys Ala Asp Ala Gly Phe Glu Ile Met Gln Lys Leu Gly Ile
                85                  90                  95

Glu Phe Phe Cys Phe His Asp Ile Asp Leu Val Glu Asp Ala Asp Glu
            100                 105                 110

Ile Ala Glu Tyr Glu Ala Arg Met Lys Asp Ile Thr Asp Tyr Leu Leu
        115                 120                 125

Val Lys Met Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Asp
145                 150                 155                 160

Phe Asp Val Leu Ala Arg Ala Ala Val Gln Ile Lys Asn Ala Ile Asp
                165                 170                 175

Ala Thr Ile Lys Leu Gly Gly Gln Asn Tyr Val Phe Trp Gly Gly Arg
            180                 185                 190

Glu Gly Tyr Gln Thr Leu Leu Asn Thr Gln Met Gln Arg Glu Lys Glu
        195                 200                 205

His Met Gly Arg Met Leu Ala Leu Ala Arg Asp Tyr Gly Arg Ala His
    210                 215                 220

Gly Phe Lys Gly Thr Phe Leu Ile Glu Pro Lys Pro Met Glu Pro Thr
225                 230                 235                 240

Lys His Gln Tyr Asp Gln Asp Thr Glu Thr Val Ile Gly Phe Leu Arg
                245                 250                 255

Arg His Gly Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp His Gly Met Leu Gly Ser Ile Asp Ala Asn Arg Gly Asp Ala Gln
    290                 295                 300

Asn Gly Trp Asp Thr Asp Gln Phe Pro Ile Asp Asn Tyr Glu Leu Thr
305                 310                 315                 320

Leu Ala Met Leu Gln Ile Ile Arg Asn Gly Gly Leu Ala Pro Gly Gly
                325                 330                 335

Ser Asn Phe Asp Ala Lys Leu Arg Arg Asn Ser Thr Asp Pro Glu Asp
            340                 345                 350

Ile Phe Ile Ala His Ile Ser Ala Met Asp Ala Met Ala Arg Ala Leu
        355                 360                 365

Val Asn Ala Val Ala Ile Leu Glu Glu Ser Pro Ile Pro Ala Met Val
    370                 375                 380

Arg Glu Arg Tyr Ala Ser Phe Asp Ser Gly Lys Gly Arg Glu Tyr Glu
385                 390                 395                 400

Glu Gly Arg Leu Ser Leu Glu Asp Ile Val Ala Tyr Ala Lys Ala His
                405                 410                 415

Gly Glu Pro Lys Gln Ile Ser Gly Lys Gln Glu Leu Tyr Glu Thr Ile
```

```
            420                 425                 430

Val Ala Leu Tyr Cys Lys
        435


<210> SEQ ID NO 101
<211> LENGTH: 1317
<212> TYPE: DNA
<213> ORGANISM: Unknown
<220> FEATURE:
<223> OTHER INFORMATION: Obtained from environmental sample

<400> SEQUENCE: 101

atggcaaaag agtatttccc gcagatcgga aagatcggct ttgagggtcc tgcaagcaag     60

aacccgctgg cattccatta ttatgacgcc gagcgcgtgg tgatgggtaa acccatgaaa    120

gactggttta aattcgccct cgcgtggtgg cacagcctcg gccaggcctc cggcgacccg    180

ttcggcggcc agacccgctc ctacgagtgg gacaagggcg aatgccccta ctgccgcgcc    240

cgcgccaagg cggacgccgg cttcgagatc atgcaaaagc tcggcatcgg ctatttctgc    300

ttccacgacg tcgacctcat cgaagacacg gacgacatcg ccgaatatga ggcccgcctc    360

aaggacatca cggactacct gctcgaaagg atgcaggaaa ccggcatcaa gaacctctgg    420

ggcacggcca atgtcttcgg tcacaagcgc tacatgaacg gcgccggcac caatccgcag    480

ttcgacatcg tcgcccgcgc tgccgtccag atcaagaacg ccctcgacgc caccatcaag    540

ctcggtggct cgaactacgt cttctggggc ggccgcgaag gttattacac gctgctcaac    600

acccagatgc agcgcgagaa agaccacctc gccaagctcc tcaccgccgc ccgcgactat    660

gcccgcgcca agggcttcca gggcaccttc ctgatcgagc ccaagccgat ggagccgacc    720

aagcaccagt acgatgtcga cacggagact gtaatcggat tcctccgcgc caacggactg    780

gacaaggact tcaaggtcaa catcgaggtc aaccacgcca ccctcgccgg ccataccttc    840

gagcatgagc tgaccgtcgc ccgcgagaac ggattcctcg gcagcatcga cgccaaccgc    900

ggtgacgccc agaacggctg ggacaccgac cagttccccg tggacgccta cgacctcacc    960

caggccatga tgcaggtgct cctgaacggc ggtttcggca acggcggcac caatttcgac   1020

gccaagctcc gtcgcagctc caccgatccc gaggacatct tcatcgccca catcagcgcg   1080

atggacgcca tggcccacgc cctgctgaac gccgcggcca ttctcgagga gagcccgctg   1140

cccgcgatgg tcaaggagcg ttacgcctcc ttcgacagcg gtctcggcaa gcagttcgag   1200

gagggaaagg ccacgctgga ggacctctac gactacgcca aggcccatgg cgagcccgtc   1260

gccgcctccg gcaagcagga actgtgtgaa acttacctga atctgtatgc aaagtaa      1317


<210> SEQ ID NO 102
<211> LENGTH: 438
<212> TYPE: PRT
<213> ORGANISM: Unknown
<220> FEATURE:
<223> OTHER INFORMATION: Obtained from environmental sample

<400> SEQUENCE: 102

Met Ala Lys Glu Tyr Phe Pro Gln Ile Gly Lys Ile Gly Phe Glu Gly
1               5                   10                  15

Pro Ala Ser Lys Asn Pro Leu Ala Phe His Tyr Tyr Asp Ala Glu Arg
            20                  25                  30

Val Val Met Gly Lys Pro Met Lys Asp Trp Phe Lys Phe Ala Leu Ala
        35                  40                  45

Trp Trp His Ser Leu Gly Gln Ala Ser Gly Asp Pro Phe Gly Gly Gln
```

```
    50                  55                  60

Thr Arg Ser Tyr Glu Trp Asp Lys Gly Glu Cys Pro Tyr Cys Arg Ala
65                  70                  75                  80

Arg Ala Lys Ala Asp Ala Gly Phe Glu Ile Met Gln Lys Leu Gly Ile
                85                  90                  95

Gly Tyr Phe Cys Phe His Asp Val Asp Leu Ile Glu Asp Thr Asp Asp
            100                 105                 110

Ile Ala Glu Tyr Glu Ala Arg Leu Lys Asp Ile Thr Asp Tyr Leu Leu
        115                 120                 125

Glu Arg Met Gln Glu Thr Gly Ile Lys Asn Leu Trp Gly Thr Ala Asn
    130                 135                 140

Val Phe Gly His Lys Arg Tyr Met Asn Gly Ala Gly Thr Asn Pro Gln
145                 150                 155                 160

Phe Asp Ile Val Ala Arg Ala Ala Val Gln Ile Lys Asn Ala Leu Asp
                165                 170                 175

Ala Thr Ile Lys Leu Gly Gly Ser Asn Tyr Val Phe Trp Gly Gly Arg
            180                 185                 190

Glu Gly Tyr Tyr Thr Leu Leu Asn Thr Gln Met Gln Arg Glu Lys Asp
        195                 200                 205

His Leu Ala Lys Leu Leu Thr Ala Ala Arg Asp Tyr Ala Arg Ala Lys
    210                 215                 220

Gly Phe Gln Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Arg
        275                 280                 285

Glu Asn Gly Phe Leu Gly Ser Ile Asp Ala Asn Arg Gly Asp Ala Gln
    290                 295                 300

Asn Gly Trp Asp Thr Asp Gln Phe Pro Val Asp Ala Tyr Asp Leu Thr
305                 310                 315                 320

Gln Ala Met Met Gln Val Leu Leu Asn Gly Gly Phe Gly Asn Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Ile Leu Glu Glu Ser Pro Leu Pro Ala Met Val
    370                 375                 380

Lys Glu Arg Tyr Ala Ser Phe Asp Ser Gly Leu Gly Lys Gln Phe Glu
385                 390                 395                 400

Glu Gly Lys Ala Thr Leu Glu Asp Leu Tyr Asp Tyr Ala Lys Ala His
                405                 410                 415

Gly Glu Pro Val Ala Ala Ser Gly Lys Gln Glu Leu Cys Glu Thr Tyr
            420                 425                 430

Leu Asn Leu Tyr Ala Lys
        435
```

<210> SEQ ID NO 103
<211> LENGTH: 1317
<212> TYPE: DNA
<213> ORGANISM: Unknown

<220> FEATURE:
<223> OTHER INFORMATION: Obtained from environmental sample

<400> SEQUENCE: 103

```
atgacaaaag agtatttccc taccatcggc aagatcccct ttgagggacc cgagagcaaa     60
aaccccctcg cttttcatta ctatgagccc gaccgcctgg tcatgggcaa gaagatgaaa    120
gactggctgc gtttcgccat ggcctggtgg cacaccctgg gccaggcctc cggcgaccag    180
tttggcggcc agacccgcca ctatgcctgg gatgatccgg attgcccgta tgcacgtgcc    240
aaagccaagg ccgacgccgg tttcgaaatc atgcagaaac tgggcattga attcttctgc    300
ttccacgaca tcgacctgat cgaggatacc gatgacatcg tcgagtatga ggcccggatg    360
aaggacatca ccgactatct gctggtcaag atgaaagaga ccggcatcaa gaatctctgg    420
ggaacggcca acgtattcgg gcacaagcgc tatatgaacg gcgctgccac caaccccgat    480
ttcgacgtgc tggcccgtgc cgccgtccag atcaagaacg ccatcgacgc caccatcaag    540
ctgggcggcc agaattatgt gttctggggc gggcgtgaag gctaccagag cctgctcaat    600
acccagatgc agcgcgaaaa ggaacacatg ggccgtatgt tggcactagc ccgcgactat    660
ggccgtgcac acggtttcaa gggcacgttc ctcatcgagc ccaaaccgat ggagccgacc    720
aagcaccagt acgatcagga tacggagacc gtcatcggtt ttctgcgccg ccatggcctc    780
gacaaggact tcaaggtcaa catcgaggtg aaccatgcta ccctggcggg ccacaccttc    840
gagcacgagc tggcctgcgc cgtcgaccac ggcatgctgg gcagtattga cgccaaccgc    900
ggtgacgccc agaacggctg ggacaccgac cagttcccga tcgataacta tgagctgacg    960
ctggccatgc tccagatcat ccgcaacggc ggcctggcac ccggcggctc gaacttcgat   1020
gcgaagctgc gtcgcaactc caccgatccg gaagatatct tcatcgcgca catcagcgcc   1080
atggatgcca tggcccgcgc cctggtcaac gctgtcgcca ttcttgagga atcgcccatt   1140
ccggacatgg tcaaggagcg ctacgcttcg ttcgacagcg gaaaaggcag ggagtacgaa   1200
gaggggaaac tttccttcga ggacctcgtg gcctatgcca aagcccacgg cgaaccgaaa   1260
cagatttccg gcaagcagga actctacgaa accatcgtgg ctctctattg caagtag      1317
```

<210> SEQ ID NO 104
<211> LENGTH: 438
<212> TYPE: PRT
<213> ORGANISM: Unknown
<220> FEATURE:
<223> OTHER INFORMATION: Obtained from environmental sample

<400> SEQUENCE: 104

```
Met Thr Lys Glu Tyr Phe Pro Thr Ile Gly Lys Ile Pro Phe Glu Gly
1               5                   10                  15

Pro Glu Ser Lys Asn Pro Leu Ala Phe His Tyr Tyr Glu Pro Asp Arg
            20                  25                  30

Leu Val Met Gly Lys Lys Met Lys Asp Trp Leu Arg Phe Ala Met Ala
        35                  40                  45

Trp Trp His Thr Leu Gly Gln Ala Ser Gly Asp Gln Phe Gly Gly Gln
    50                  55                  60

Thr Arg His Tyr Ala Trp Asp Asp Pro Asp Cys Pro Tyr Ala Arg Ala
65                  70                  75                  80

Lys Ala Lys Ala Asp Ala Gly Phe Glu Ile Met Gln Lys Leu Gly Ile
                85                  90                  95

Glu Phe Phe Cys Phe His Asp Ile Asp Leu Ile Glu Asp Thr Asp Asp
            100                 105                 110
```

```
Ile Val Glu Tyr Glu Ala Arg Met Lys Asp Ile Thr Asp Tyr Leu Leu
        115                 120                 125

Val Lys Met Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Asp
145                 150                 155                 160

Phe Asp Val Leu Ala Arg Ala Ala Val Gln Ile Lys Asn Ala Ile Asp
                165                 170                 175

Ala Thr Ile Lys Leu Gly Gly Gln Asn Tyr Val Phe Trp Gly Gly Arg
            180                 185                 190

Glu Gly Tyr Gln Ser Leu Leu Asn Thr Gln Met Gln Arg Glu Lys Glu
        195                 200                 205

His Met Gly Arg Met Leu Ala Leu Ala Arg Asp Tyr Gly Arg Ala His
    210                 215                 220

Gly Phe Lys Gly Thr Phe Leu Ile Glu Pro Lys Pro Met Glu Pro Thr
225                 230                 235                 240

Lys His Gln Tyr Asp Gln Asp Thr Glu Thr Val Ile Gly Phe Leu Arg
                245                 250                 255

Arg His Gly Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp His Gly Met Leu Gly Ser Ile Asp Ala Asn Arg Gly Asp Ala Gln
    290                 295                 300

Asn Gly Trp Asp Thr Asp Gln Phe Pro Ile Asp Asn Tyr Glu Leu Thr
305                 310                 315                 320

Leu Ala Met Leu Gln Ile Ile Arg Asn Gly Gly Leu Ala Pro Gly Gly
                325                 330                 335

Ser Asn Phe Asp Ala Lys Leu Arg Arg Asn Ser Thr Asp Pro Glu Asp
            340                 345                 350

Ile Phe Ile Ala His Ile Ser Ala Met Asp Ala Met Ala Arg Ala Leu
        355                 360                 365

Val Asn Ala Val Ala Ile Leu Glu Glu Ser Pro Ile Pro Asp Met Val
    370                 375                 380

Lys Glu Arg Tyr Ala Ser Phe Asp Ser Gly Lys Gly Arg Glu Tyr Glu
385                 390                 395                 400

Glu Gly Lys Leu Ser Phe Glu Asp Leu Val Ala Tyr Ala Lys Ala His
                405                 410                 415

Gly Glu Pro Lys Gln Ile Ser Gly Lys Gln Glu Leu Tyr Glu Thr Ile
            420                 425                 430

Val Ala Leu Tyr Cys Lys
        435
```

<210> SEQ ID NO 105
<211> LENGTH: 1317
<212> TYPE: DNA
<213> ORGANISM: Unknown
<220> FEATURE:
<223> OTHER INFORMATION: Obtained from environmental sample

<400> SEQUENCE: 105

```
atgacaaaag agtatttccc taccatcggc aagatcccct ttgagggacc cgagagcaaa      60

aaccccctcg cttttcatta ctatgagccc gaccgcctgg tcatgggcaa gaagatgaaa     120

gactggctgc gtttcgccat ggcctggtgg cacaccctgg gccaggcctc cggcgaccag     180
```

```
tttggcggcc agacccgcca ctatgcctgg gatgatccgg attgcccgta tgcacgtgcc    240

aaagccaagg ccgacgccgg tttcgaaatc atgcagaaac tgggcattga attcttctgc    300

ttccacgaca tcgacctgat cgaggatacc gatgacatcg tcgagtatga ggcccggatg    360

aaggacatca ccgactatct gctggtcaag atgaaagaga ccggcatcaa gaatctctgg    420

ggaacggcca acgtattcgg gcacaagcgc tatatgaacg gcgctgccac caaccccgat    480

ttcgacgtgc tggcccgtgc cgccgcccag atcaagaacg ccatcgacgc caccatcaag    540

ctgggcggcc agaattatgt gttctggggc gggcgtgaag gctaccagag cctgctcaat    600

acccagatgc agcgcgaaaa ggaacacatg ggccgtatgt tggcactagc ccgcgactat    660

ggccgtgcac acggtttcaa gggcacgctc ctcatcgagc ccaaaccgat ggagccgacc    720

aagcaccagt acgatcagga tacggagacc gtcatcggtt ttctgcgccg ccatggcctc    780

gacaaggact tcaaggtcaa catcgaggtg aaccatgcta ccctggcggg ccacaccttc    840

gagcacgagc tggcctgcgc cgtcgaccac ggcatgctgg gcagtattga cgccaaccgc    900

ggtgacgccc aggacggctg ggacaccgac cagttcccga tcgataacta tgagctgacg    960

ctggccatgc tccagatcat ccgcaacggc ggcctggcac ccggcggctc gaacttcgat   1020

gcgaagctgc gtcgcaactc caccgatccg gaagatatct tcatcgcgca catcagcgcc   1080

atggatgcca tggcccgcgc cctggtcaac gctgtcgcca ttcttgagga atcgcccatt   1140

ccggacatgg tcaaggagcg ctacgcttcg ttcgacagcg gaaaaggcag ggagtacgaa   1200

gaggggaaac tttccttcga ggacctcgtg gcctatgcca aagcccacgg cgaaccgaaa   1260

cagatttccg gcaagcagga actctacgaa accatcgtgg ctctctattg caagtag      1317
```

<210> SEQ ID NO 106
<211> LENGTH: 438
<212> TYPE: PRT
<213> ORGANISM: Unknown
<220> FEATURE:
<223> OTHER INFORMATION: Obtained from environmental sample

<400> SEQUENCE: 106

```
Met Thr Lys Glu Tyr Phe Pro Thr Ile Gly Lys Ile Pro Phe Glu Gly
1               5                   10                  15

Pro Glu Ser Lys Asn Pro Leu Ala Phe His Tyr Tyr Glu Pro Asp Arg
            20                  25                  30

Leu Val Met Gly Lys Lys Met Lys Asp Trp Leu Arg Phe Ala Met Ala
        35                  40                  45

Trp Trp His Thr Leu Gly Gln Ala Ser Gly Asp Gln Phe Gly Gly Gln
    50                  55                  60

Thr Arg His Tyr Ala Trp Asp Asp Pro Asp Cys Pro Tyr Ala Arg Ala
65                  70                  75                  80

Lys Ala Lys Ala Asp Ala Gly Phe Glu Ile Met Gln Lys Leu Gly Ile
                85                  90                  95

Glu Phe Phe Cys Phe His Asp Ile Asp Leu Ile Glu Asp Thr Asp Asp
            100                 105                 110

Ile Val Glu Tyr Glu Ala Arg Met Lys Asp Ile Thr Asp Tyr Leu Leu
        115                 120                 125

Val Lys Met Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Asp
145                 150                 155                 160
```

-continued

```
Phe Asp Val Leu Ala Arg Ala Ala Ala Gln Ile Lys Asn Ala Ile Asp
                165                 170                 175

Ala Thr Ile Lys Leu Gly Gly Gln Asn Tyr Val Phe Trp Gly Gly Arg
            180                 185                 190

Glu Gly Tyr Gln Ser Leu Leu Asn Thr Gln Met Gln Arg Glu Lys Glu
        195                 200                 205

His Met Gly Arg Met Leu Ala Leu Ala Arg Asp Tyr Gly Arg Ala His
    210                 215                 220

Gly Phe Lys Gly Thr Leu Leu Ile Glu Pro Lys Pro Met Glu Pro Thr
225                 230                 235                 240

Lys His Gln Tyr Asp Gln Asp Thr Glu Thr Val Ile Gly Phe Leu Arg
                245                 250                 255

Arg His Gly Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp His Gly Met Leu Gly Ser Ile Asp Ala Asn Arg Gly Asp Ala Gln
    290                 295                 300

Asp Gly Trp Asp Thr Asp Gln Phe Pro Ile Asp Asn Tyr Glu Leu Thr
305                 310                 315                 320

Leu Ala Met Leu Gln Ile Ile Arg Asn Gly Gly Leu Ala Pro Gly Gly
                325                 330                 335

Ser Asn Phe Asp Ala Lys Leu Arg Arg Asn Ser Thr Asp Pro Glu Asp
            340                 345                 350

Ile Phe Ile Ala His Ile Ser Ala Met Asp Ala Met Ala Arg Ala Leu
        355                 360                 365

Val Asn Ala Val Ala Ile Leu Glu Glu Ser Pro Ile Pro Asp Met Val
    370                 375                 380

Lys Glu Arg Tyr Ala Ser Phe Asp Ser Gly Lys Gly Arg Glu Tyr Glu
385                 390                 395                 400

Glu Gly Lys Leu Ser Phe Glu Asp Leu Val Ala Tyr Ala Lys Ala His
                405                 410                 415

Gly Glu Pro Lys Gln Ile Ser Gly Lys Gln Glu Leu Tyr Glu Thr Ile
            420                 425                 430

Val Ala Leu Tyr Cys Lys
        435


<210> SEQ ID NO 107
<211> LENGTH: 1317
<212> TYPE: DNA
<213> ORGANISM: Unknown
<220> FEATURE:
<223> OTHER INFORMATION: Obtained from environmental sample

<400> SEQUENCE: 107

atgacaaaag agtatttccc taccatcggc aagatcccct ttgagggacc cgagagcaaa      60

aaccccctcg cttttcatta ctatgagccc gaccgcctgg tcatgggcaa gaagatgaaa     120

gactggctgc gtttcgccat ggcctggtgg cacaccctgg gccaggcctc cggcgaccag     180

tttggcggcc agacccgcca ctatgcctgg gatgatccgg attgcccgta tgcacgtgcc     240

aaagccaagg ccgacgccgg tttcgaaatc atgcagaaac tgggcattga attcttctgc     300

ttccacgaca tcgacctgat cgaggatacc gatgacatcg tcgagtatga ggcccggatg     360

aaggacatca ccgactatct gctggtcaag atgaaagaga ccggcatcaa gaatctctgg     420

ggaacggcca acgtattcgg gcacaagcgc tatatgaacg gcgctgccac caaccccgat     480
```

-continued

```
ttcgacgtgc tggcccgtgc cgccgtccag atcaagaacg ccatcgacgc caccatcaag    540

ctgggcggcc agaattatgt gttctggggc gggcgtgaag gctaccagag cctgctcaat    600

acccagatgc agcgcgaaaa ggaacacatg ggccgtatgt tggcactagc ccgcgactat    660

ggccgtgcac acggtttcaa gggcacgttc ctcatcgagc ccaaaccgat ggagccgacc    720

aagcaccagt acgatcagga tacggagacc gtcatcggtt ttctgcgccg ccatggcctc    780

gacaaggact tcaaggtcaa catcgaggtg aaccatgcta ccctggcggg ccacaccttc    840

gagcacgagc tggcctgcgc cgtcgaccac ggcatgctgg gcagtattga cgccaaccgc    900

ggtgacgccc agaacggctg ggacaccgac cagttcccga tcgataacta tgagctgacg    960

ctggccatgc tccagatcat ccgcaacggc ggcctggcac ccggcggctc gaacttcgat   1020

gcgaagctgc gtcgcaactc caccgatccg gaagatgtct tcatcgcgca catcagcgcc   1080

atggatgcca tggcccgcgc cctggtcaac gctgtcgcca ttcttgagga atcgcccatt   1140

ccggacatgg tcaaggagcg ctacgcttcg ttcgacagcg gaaaaggcag ggagtacgaa   1200

gaggggaaac tttccttcga ggacctcgtg gcctatgcca aagcccacgg cgaaccgaaa   1260

cagatttccg gcaagcagga actctacgaa accatcgtgg ctctctattg caagtag      1317


<210> SEQ ID NO 108
<211> LENGTH: 438
<212> TYPE: PRT
<213> ORGANISM: Unknown
<220> FEATURE:
<223> OTHER INFORMATION: Obtained from environmental sample

<400> SEQUENCE: 108

Met Thr Lys Glu Tyr Phe Pro Thr Ile Gly Lys Ile Pro Phe Glu Gly
1               5                   10                  15

Pro Glu Ser Lys Asn Pro Leu Ala Phe His Tyr Tyr Glu Pro Asp Arg
            20                  25                  30

Leu Val Met Gly Lys Lys Met Lys Asp Trp Leu Arg Phe Ala Met Ala
        35                  40                  45

Trp Trp His Thr Leu Gly Gln Ala Ser Gly Asp Gln Phe Gly Gly Gln
    50                  55                  60

Thr Arg His Tyr Ala Trp Asp Asp Pro Asp Cys Pro Tyr Ala Arg Ala
65                  70                  75                  80

Lys Ala Lys Ala Asp Ala Gly Phe Glu Ile Met Gln Lys Leu Gly Ile
                85                  90                  95

Glu Phe Phe Cys Phe His Asp Ile Asp Leu Ile Glu Asp Thr Asp Asp
            100                 105                 110

Ile Val Glu Tyr Glu Ala Arg Met Lys Asp Ile Thr Asp Tyr Leu Leu
        115                 120                 125

Val Lys Met Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Asp
145                 150                 155                 160

Phe Asp Val Leu Ala Arg Ala Ala Val Gln Ile Lys Asn Ala Ile Asp
                165                 170                 175

Ala Thr Ile Lys Leu Gly Gly Gln Asn Tyr Val Phe Trp Gly Gly Arg
            180                 185                 190

Glu Gly Tyr Gln Ser Leu Leu Asn Thr Gln Met Gln Arg Glu Lys Glu
        195                 200                 205

His Met Gly Arg Met Leu Ala Leu Ala Arg Asp Tyr Gly Arg Ala His
```

```
    210                 215                 220

Gly Phe Lys Gly Thr Phe Leu Ile Glu Pro Lys Pro Met Glu Pro Thr
225                 230                 235                 240

Lys His Gln Tyr Asp Gln Asp Thr Glu Thr Val Ile Gly Phe Leu Arg
                245                 250                 255

Arg His Gly Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp His Gly Met Leu Gly Ser Ile Asp Ala Asn Arg Gly Asp Ala Gln
    290                 295                 300

Asn Gly Trp Asp Thr Asp Gln Phe Pro Ile Asp Asn Tyr Glu Leu Thr
305                 310                 315                 320

Leu Ala Met Leu Gln Ile Ile Arg Asn Gly Gly Leu Ala Pro Gly Gly
                325                 330                 335

Ser Asn Phe Asp Ala Lys Leu Arg Arg Asn Ser Thr Asp Pro Glu Asp
            340                 345                 350

Val Phe Ile Ala His Ile Ser Ala Met Asp Ala Met Ala Arg Ala Leu
        355                 360                 365

Val Asn Ala Val Ala Ile Leu Glu Glu Ser Pro Ile Pro Asp Met Val
    370                 375                 380

Lys Glu Arg Tyr Ala Ser Phe Asp Ser Gly Lys Gly Arg Glu Tyr Glu
385                 390                 395                 400

Glu Gly Lys Leu Ser Phe Glu Asp Leu Val Ala Tyr Ala Lys Ala His
                405                 410                 415

Gly Glu Pro Lys Gln Ile Ser Gly Lys Gln Glu Leu Tyr Glu Thr Ile
            420                 425                 430

Val Ala Leu Tyr Cys Lys
        435
```

<210> SEQ ID NO 109
<211> LENGTH: 1317
<212> TYPE: DNA
<213> ORGANISM: Unknown
<220> FEATURE:
<223> OTHER INFORMATION: Obtained from environmental sample

<400> SEQUENCE: 109

```
atggcaaaag agtatttccc gacaatcgga aagatcccct tcgagggcgt tgagagcaag      60

aatccccttg ctttccatta ttatgacgcc gagcgcgtgg tcatgggcaa gcccatgaag     120

gactggttca agttcgcgat ggcctggtgg cacaccctgg gccaggcttc cgcggacccg     180

ttcggcggcc agacccgctc ctacgagtgg gacaagggcg agtgccccta ctgccgcgcc     240

cgcgccaagg ctgacgccgg cttcgagatc atgcagaagc tcggaatcgg ctactattgc     300

ttccacgaca tcgacctggt ggaggacacc gaggacatcg ccgaatacga ggcccgcatg     360

aaggacatca ccgactacct cgtcgagaag cagaaggaga ccggcatcaa gaacctctgg     420

ggcaccgcga acgtgttcgg caacaagcgc tacatgaacg gcgccgccac gaacccgcag     480

ttcgacatcg tcgcccgcgc ggccctgcag atcaagaacg cgatcgatgc caccatcaag     540

ctcggcggca ccggctacgt gttctggggc ggccgggaag gctactacac cctgctgaac     600

acccagatgc agcgcgagaa ggaccacctc gccaagatgc tcaccgccgc ccgcgactac     660

gcccgcgcca acggcttcaa gggcaccttc ctcatcgagc ccaagccgat ggagcccacc     720

aagcaccaat acgacgtgga cacggagacc gtgatcggct tcctccgcgc caatggcctg     780
```

-continued

```
gacaaggact tcaaggtgaa catcgaggtg aaccacgcca ccctcgccgg ccacaccttc    840

gagcacgagc tcaccgtggc cgttgacaac ggcttcctcg gcagcatcga cgccaaccgc    900

ggcgacgccc agaacggctg ggataccgac cagttcccgg tggatccgta cgatctcacc    960

caggcgatga tccagatcat ccgcaacggc ggcttcaagg acggcggcac caacttcgac   1020

gccaggctcc gccgctcttc caccgacccg gaggacatct tcatcgccca catcagcgcg   1080

atggacgcca tggcccacgc cctgctgaac gccgccgccg tcatcgagga gagcccgctc   1140

tgcgagatgg tcgccaagcg ttacgcttcc ttcgacagcg gcctcggcaa aaagttcgag   1200

gaaggcaagg ccaccctcga ggaactctac gagtatgcca aggcgaacgg tgaggtcaag   1260

gccgaatccg gcaagcagga gctctacgag acccttctga acctctacgc gaaatag      1317
```

```
<210> SEQ ID NO 110
<211> LENGTH: 438
<212> TYPE: PRT
<213> ORGANISM: Unknown
<220> FEATURE:
<223> OTHER INFORMATION: Obtained from environmental sample

<400> SEQUENCE: 110

Met Ala Lys Glu Tyr Phe Pro Thr Ile Gly Lys Ile Pro Phe Glu Gly
1               5                   10                  15

Val Glu Ser Lys Asn Pro Leu Ala Phe His Tyr Tyr Asp Ala Glu Arg
            20                  25                  30

Val Val Met Gly Lys Pro Met Lys Asp Trp Phe Lys Phe Ala Met Ala
        35                  40                  45

Trp Trp His Thr Leu Gly Gln Ala Ser Ala Asp Pro Phe Gly Gly Gln
    50                  55                  60

Thr Arg Ser Tyr Glu Trp Asp Lys Gly Glu Cys Pro Tyr Cys Arg Ala
65                  70                  75                  80

Arg Ala Lys Ala Asp Ala Gly Phe Glu Ile Met Gln Lys Leu Gly Ile
                85                  90                  95

Gly Tyr Tyr Cys Phe His Asp Ile Asp Leu Val Glu Asp Thr Glu Asp
            100                 105                 110

Ile Ala Glu Tyr Glu Ala Arg Met Lys Asp Ile Thr Asp Tyr Leu Val
        115                 120                 125

Glu Lys Gln Lys Glu Thr Gly Ile Lys Asn Leu Trp Gly Thr Ala Asn
    130                 135                 140

Val Phe Gly Asn Lys Arg Tyr Met Asn Gly Ala Ala Thr Asn Pro Gln
145                 150                 155                 160

Phe Asp Ile Val Ala Arg Ala Ala Leu Gln Ile Lys Asn Ala Ile Asp
                165                 170                 175

Ala Thr Ile Lys Leu Gly Gly Thr Gly Tyr Val Phe Trp Gly Gly Arg
            180                 185                 190

Glu Gly Tyr Tyr Thr Leu Leu Asn Thr Gln Met Gln Arg Glu Lys Asp
        195                 200                 205

His Leu Ala Lys Met Leu Thr Ala Ala Arg Asp Tyr Ala Arg Ala Asn
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270
```

```
Ala Thr Leu Ala Gly His Thr Phe Glu His Glu Leu Thr Val Ala Val
        275                 280                 285

Asp Asn Gly Phe Leu Gly Ser Ile Asp Ala Asn Arg Gly Asp Ala Gln
    290                 295                 300

Asn Gly Trp Asp Thr Asp Gln Phe Pro Val Asp Pro Tyr Asp Leu Thr
305                 310                 315                 320

Gln Ala Met Ile Gln Ile Ile Arg Asn Gly Gly Phe Lys Asp Gly Gly
                325                 330                 335

Thr Asn Phe Asp Ala Arg Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Val Ile Glu Glu Ser Pro Leu Cys Glu Met Val
    370                 375                 380

Ala Lys Arg Tyr Ala Ser Phe Asp Ser Gly Leu Gly Lys Lys Phe Glu
385                 390                 395                 400

Glu Gly Lys Ala Thr Leu Glu Glu Leu Tyr Glu Tyr Ala Lys Ala Asn
                405                 410                 415

Gly Glu Val Lys Ala Glu Ser Gly Lys Gln Glu Leu Tyr Glu Thr Leu
            420                 425                 430

Leu Asn Leu Tyr Ala Lys
        435
```

```
<210> SEQ ID NO 111
<211> LENGTH: 1317
<212> TYPE: DNA
<213> ORGANISM: Unknown
<220> FEATURE:
<223> OTHER INFORMATION: Obtained from environmental sample

<400> SEQUENCE: 111

atggcacaag cgtattttcc taccatcggg aaaatcccct tcgagggacc cgaaagcaag      60

aatcccctgg cattccatta ttatgagccc gaccgcctgg tcctgggcaa gaagatgaag     120

gactggctgc gtttcgccat ggcctggtgg cacacgctgg gccaggcttc cggcgaccag     180

ttcggcggcc agacccgcca ctacgcctgg gacgagcccg ccacgcccct ggaacgggcc     240

aaggccaagg cggatgccgg tttcgagatc atgcagaaac tgggcatcga attcttctgc     300

ttccacgatg tggacctcat cgaagagggc gccacgatcg aggaatacga gcagcggatg     360

cagcagatca cggattatct gctggtcaag atgaaagaga ccggcatccg caacctctgg     420

ggtacggcca acgtgttcgg acacgagcgc tacatgaacg gcgcggccac gaaccccgat     480

ttcgatgtcg tggcccgcgc ggccgtgcag atcaagacgg ccatcgacgc caccatcaag     540

ttgggcggcg agaactatgt gttctggggc ggccgggaag gctatatgag cctgctcaat     600

acgcagatgc accgcgagaa gctgcatctg ggcaagatgc tcgccgcggc ccgcgactac     660

ggacgcgccc acggcttcaa ggggaccttc ctcatcgaac ccaagccgat ggaacccacc     720

aagcatcagt atgaccagga tacggagacg gtcatcggtt tcctgcgccg ctacggcctg     780

gacgaagact tcaaggtgaa catcgaggtc aaccacgcta cgctggccgg ccataccttc     840

gaacacgaac tggccacggc ggtcgatgcc ggcctgctgg gcagcatcga cgccaaccgc     900

ggcgacgccc agaacggctg ggataccgac cagttcccga tcgacaacta cgaactgacc     960

ctggcgatgc tgcaggtcat ccgcaacggc ggtctggccc cgggcggctc gaatttcgat    1020

gccaagctcc gccggaactc caccgatccg gaagacatct tcattgccca catcagcgcg    1080
```

-continued

```
atggatgcga tggcgcgggc cctgctcaat gcggccgccc tctgcgagac gtccccgatt   1140

ccggcgatgg tcaaggcgcg ttacgcttcg ttcgacagcg gcgccggcaa ggatttcgaa   1200

gagggaagga tgacgctgga agacctcgtg gcctatgcca ggacccacgg cgagccgaag   1260

cggacctcgg gcaagcagga actctatgag accctcgtgg cgctttattg caaatag      1317
```

```
<210> SEQ ID NO 112
<211> LENGTH: 438
<212> TYPE: PRT
<213> ORGANISM: Unknown
<220> FEATURE:
<223> OTHER INFORMATION: Obtained from environmental sample

<400> SEQUENCE: 112

Met Ala Gln Ala Tyr Phe Pro Thr Ile Gly Lys Ile Pro Phe Glu Gly
1               5                   10                  15

Pro Glu Ser Lys Asn Pro Leu Ala Phe His Tyr Tyr Glu Pro Asp Arg
            20                  25                  30

Leu Val Leu Gly Lys Lys Met Lys Asp Trp Leu Arg Phe Ala Met Ala
        35                  40                  45

Trp Trp His Thr Leu Gly Gln Ala Ser Gly Asp Gln Phe Gly Gly Gln
    50                  55                  60

Thr Arg His Tyr Ala Trp Asp Glu Pro Ala Thr Pro Leu Glu Arg Ala
65                  70                  75                  80

Lys Ala Lys Ala Asp Ala Gly Phe Glu Ile Met Gln Lys Leu Gly Ile
                85                  90                  95

Glu Phe Phe Cys Phe His Asp Val Asp Leu Ile Glu Glu Gly Ala Thr
            100                 105                 110

Ile Glu Glu Tyr Glu Gln Arg Met Gln Gln Ile Thr Asp Tyr Leu Leu
        115                 120                 125

Val Lys Met Lys Glu Thr Gly Ile Arg Asn Leu Trp Gly Thr Ala Asn
    130                 135                 140

Val Phe Gly His Glu Arg Tyr Met Asn Gly Ala Ala Thr Asn Pro Asp
145                 150                 155                 160

Phe Asp Val Val Ala Arg Ala Ala Val Gln Ile Lys Thr Ala Ile Asp
                165                 170                 175

Ala Thr Ile Lys Leu Gly Gly Glu Asn Tyr Val Phe Trp Gly Gly Arg
            180                 185                 190

Glu Gly Tyr Met Ser Leu Leu Asn Thr Gln Met His Arg Glu Lys Leu
        195                 200                 205

His Leu Gly Lys Met Leu Ala Ala Ala Arg Asp Tyr Gly Arg Ala His
    210                 215                 220

Gly Phe Lys Gly Thr Phe Leu Ile Glu Pro Lys Pro Met Glu Pro Thr
225                 230                 235                 240

Lys His Gln Tyr Asp Gln Asp Thr Glu Thr Val Ile Gly Phe Leu Arg
                245                 250                 255

Arg Tyr Gly Leu Asp Glu Asp Phe Lys Val Asn Ile Glu Val Asn His
            260                 265                 270

Ala Thr Leu Ala Gly His Thr Phe Glu His Glu Leu Ala Thr Ala Val
        275                 280                 285

Asp Ala Gly Leu Leu Gly Ser Ile Asp Ala Asn Arg Gly Asp Ala Gln
    290                 295                 300

Asn Gly Trp Asp Thr Asp Gln Phe Pro Ile Asp Asn Tyr Glu Leu Thr
305                 310                 315                 320
```

```
Leu Ala Met Leu Gln Val Ile Arg Asn Gly Gly Leu Ala Pro Gly Gly
                325                 330                 335

Ser Asn Phe Asp Ala Lys Leu Arg Arg Asn Ser Thr Asp Pro Glu Asp
            340                 345                 350

Ile Phe Ile Ala His Ile Ser Ala Met Asp Ala Met Ala Arg Ala Leu
        355                 360                 365

Leu Asn Ala Ala Ala Leu Cys Glu Thr Ser Pro Ile Pro Ala Met Val
    370                 375                 380

Lys Ala Arg Tyr Ala Ser Phe Asp Ser Gly Ala Gly Lys Asp Phe Glu
385                 390                 395                 400

Glu Gly Arg Met Thr Leu Glu Asp Leu Val Ala Tyr Ala Arg Thr His
                405                 410                 415

Gly Glu Pro Lys Arg Thr Ser Gly Lys Gln Glu Leu Tyr Glu Thr Leu
            420                 425                 430

Val Ala Leu Tyr Cys Lys
        435


<210> SEQ ID NO 113
<211> LENGTH: 1317
<212> TYPE: DNA
<213> ORGANISM: Unknown
<220> FEATURE:
<223> OTHER INFORMATION: Obtained from environmental sample

<400> SEQUENCE: 113

atgaccaacg agtattttcc cggaatcggt gtgattccgt ttgaaggaca ggaaagcaag      60

aatcccctgg ctttccatta ttatgacgcc aaccgcgtag tgatgggcaa acccatgaag     120

gaatggttca aatttgccat ggcctggtgg catacgctgg ggcaggcatc ggccgatccc     180

ttcggcggac agacccgctc ctacgcatgg gacaagggcg agtgccctta ctgccgtgcc     240

cgccagaagg ccgacgccgg ctttgaactg atgcagaagc tgggaatcgg ctatttctgc     300

ttccacgatg tgaatatcat cgaggactgc gaggacattg ccgagtatga ggcccgtatg     360

aaggacatca cggactatct gctggtgaag atgaaggaaa cgggcatcaa gaatctgtgg     420

ggcacggcca acgtcttcgg ccacaagcgc tatatgaacg gcgccgccac caacccgcaa     480

ttcgacgtgg tagcccgcgc tgcggtccag atcaagaacg ccctggacgc caccatcaag     540

ctgggcggca gcaattatgt gttctggggc ggccgggaag gctactacac ccttttgaac     600

acgcagatgc agcgggagaa ggaccacctg gcccagatgc tcaaggcggc ccgcgactat     660

gcccgcggca agggattcaa gggcacgttc ctcattgagc ccaagcccat ggagcccacc     720

aagcaccagt acgacgtaga tacggagacc gtgattggtt tcctgcgcgc caacgggctg     780

gacaaggact tcaaggtgaa tatcgaagtg aaccacgcca ccctggccgg ccataccttc     840

gagcacgagc tcaccgtggc ccgcgaaaac ggcttcctgg gcagcatcga cgccaaccgc     900

ggagacgccc agaacggctg ggatacagac cagttccccg tggacgcctt tgacctcacc     960

caggccatga tgcaggtcct gctcaacggc ggattcggca acggcggcac caacttcgac    1020

gccaaactgc gccgttcctc cacggatccc gaggacatct tcatcgccca catcagcgcc    1080

atggacgcca tggcccacgc cctcctgaac gccgccgcca tcctggaaga gagccccatg    1140

ccgggcatgg tgaaggagcg ctacgcttcc ttcgacaatg gccttggcaa gaagttcgag    1200

gaaggaaagg ccacgctgga agagctgtac gactatgcca agaagaacgg cgagcctgtg    1260

gccgcttccg gaaagcagga actgtacgaa acgctgctga acctgtacgc caagtaa      1317
```

```
<210> SEQ ID NO 114
<211> LENGTH: 438
<212> TYPE: PRT
<213> ORGANISM: Unknown
<220> FEATURE:
<223> OTHER INFORMATION: Obtained from environmental sample

<400> SEQUENCE: 114

Met Thr Asn Glu Tyr Phe Pro Gly Ile Gly Val Ile Pro Phe Glu Gly
1               5                   10                  15

Gln Glu Ser Lys Asn Pro Leu Ala Phe His Tyr Tyr Asp Ala Asn Arg
            20                  25                  30

Val Val Met Gly Lys Pro Met Lys Glu Trp Phe Lys Phe Ala Met Ala
        35                  40                  45

Trp Trp His Thr Leu Gly Gln Ala Ser Ala Asp Pro Phe Gly Gly Gln
    50                  55                  60

Thr Arg Ser Tyr Ala Trp Asp Lys Gly Glu Cys Pro Tyr Cys Arg Ala
65                  70                  75                  80

Arg Gln Lys Ala Asp Ala Gly Phe Glu Leu Met Gln Lys Leu Gly Ile
                85                  90                  95

Gly Tyr Phe Cys Phe His Asp Val Asn Ile Ile Glu Asp Cys Glu Asp
            100                 105                 110

Ile Ala Glu Tyr Glu Ala Arg Met Lys Asp Ile Thr Asp Tyr Leu Leu
        115                 120                 125

Val Lys Met Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Gln
145                 150                 155                 160

Phe Asp Val Val Ala Arg Ala Ala Val Gln Ile Lys Asn Ala Leu Asp
                165                 170                 175

Ala Thr Ile Lys Leu Gly Gly Ser Asn Tyr Val Phe Trp Gly Gly Arg
            180                 185                 190

Glu Gly Tyr Tyr Thr Leu Leu Asn Thr Gln Met Gln Arg Glu Lys Asp
        195                 200                 205

His Leu Ala Gln Met Leu Lys Ala Ala Arg Asp Tyr Ala Arg Gly Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Arg
        275                 280                 285

Glu Asn Gly Phe Leu Gly Ser Ile Asp Ala Asn Arg Gly Asp Ala Gln
    290                 295                 300

Asn Gly Trp Asp Thr Asp Gln Phe Pro Val Asp Ala Phe Asp Leu Thr
305                 310                 315                 320

Gln Ala Met Met Gln Val Leu Leu Asn Gly Gly Phe Gly Asn Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Ile Leu Glu Glu Ser Pro Met Pro Gly Met Val
```

370 375 380

Lys Glu Arg Tyr Ala Ser Phe Asp Asn Gly Leu Gly Lys Lys Phe Glu
385 390 395 400

Glu Gly Lys Ala Thr Leu Glu Glu Leu Tyr Asp Tyr Ala Lys Lys Asn
405 410 415

Gly Glu Pro Val Ala Ala Ser Gly Lys Gln Glu Leu Tyr Glu Thr Leu
420 425 430

Leu Asn Leu Tyr Ala Lys
435

<210> SEQ ID NO 115
<211> LENGTH: 1317
<212> TYPE: DNA
<213> ORGANISM: Unknown
<220> FEATURE:
<223> OTHER INFORMATION: Obtained from environmental sample

<400> SEQUENCE: 115
atggcaaaag agtatttccc gactatcggc aagattccct tcgagggcgt cgaatccaag 60
aacccgatgg cattccacta ttatgacgcg aaacgcgtcg tgatgggcaa gcccatgaag 120
gactggctca agttcgcgat ggcctggtgg cacaccctgg gacaggcttc cggcgacccg 180
ttcggcggcc agacccgttc ctacgagtgg gacaagggcg agtgccccta ctgccgcgcc 240
aaggccaagg ccgacgccgg tttcgagatc atgcagaaac tgggcatcga gtactactgc 300
ttccatgaca tcgacctggt ggaggacacc gaggacatcg ccgagtacga ggcccgcatg 360
aaggacatca ccgactacct cgtcgagaag cagaaggaga ccggtatcaa gaacctctgg 420
ggcacggcca acgtgttcgg caacaagcgc tacatgaacg gcgccgccac gaacccgcag 480
ttcgacgtcg tcgcccgcgc cgccgtccag atcaagaacg ccatcgacgc caccatcaaa 540
ctcggcggca cctcttacgt gttctggggc ggccgtgaag gctactacac cctcctgaac 600
acccagatgc agcgcgagaa ggaccacctc gccaagatgc tcaccgccgc ccgcgactac 660
gcccgcgccc acggcttcaa gggcaccttc ctcatcgagc ccaagcccat ggagcccacc 720
aagcaccagt acgacgtgga cacggagacc gtgatcggct tcctccgcgc caacggcctg 780
gacaaggact tcaaggtcaa tatcgaagtg aaccacgcca ccctcgccgg ccacaccttc 840
gagcatgagc tcaccgtggc ggtcgataac ggcttcctcg gctccatcga cgccaaccgt 900
ggcgacgccc agaacggctg ggataccgac cagttcccgg tggatccgta cgacctcacc 960
caggccatga tgcagatcat ccgcaacggc ggcttcaagg acggcggcac caacttcgac 1020
gccaaactcc gccgctcctc caccgacccg gaggacatct tcatcgccca catcagcgcg 1080
atggacgcca tggcccacgc gctcctgaac gccgccgccg tcatcgagga gagcccgctc 1140
tgcaagatgg tcgaggagcg ctacgcttcc ttcgacagcg gtctcggcaa gcagttcgag 1200
gaaggcaagg ccacccttga ggacctctac gagtatgcca agaagaacgg cgagcccgtc 1260
gtcgcttccg gcaagcagga gctctacgag acccttctga acctctacgc gaagtag 1317

<210> SEQ ID NO 116
<211> LENGTH: 438
<212> TYPE: PRT
<213> ORGANISM: Unknown
<220> FEATURE:
<223> OTHER INFORMATION: Obtained from environmental sample

<400> SEQUENCE: 116

Met Ala Lys Glu Tyr Phe Pro Thr Ile Gly Lys Ile Pro Phe Glu Gly

-continued

```
1               5                   10                  15

Val Glu Ser Lys Asn Pro Met Ala Phe His Tyr Tyr Asp Ala Lys Arg
            20                  25                  30

Val Val Met Gly Lys Pro Met Lys Asp Trp Leu Lys Phe Ala Met Ala
        35                  40                  45

Trp Trp His Thr Leu Gly Gln Ala Ser Gly Asp Pro Phe Gly Gly Gln
    50                  55                  60

Thr Arg Ser Tyr Glu Trp Asp Lys Gly Glu Cys Pro Tyr Cys Arg Ala
65                  70                  75                  80

Lys Ala Lys Ala Asp Ala Gly Phe Glu Ile Met Gln Lys Leu Gly Ile
                85                  90                  95

Glu Tyr Tyr Cys Phe His Asp Ile Asp Leu Val Glu Asp Thr Glu Asp
            100                 105                 110

Ile Ala Glu Tyr Glu Ala Arg Met Lys Asp Ile Thr Asp Tyr Leu Val
        115                 120                 125

Glu Lys Gln Lys Glu Thr Gly Ile Lys Asn Leu Trp Gly Thr Ala Asn
    130                 135                 140

Val Phe Gly Asn Lys Arg Tyr Met Asn Gly Ala Ala Thr Asn Pro Gln
145                 150                 155                 160

Phe Asp Val Val Ala Arg Ala Ala Val Gln Ile Lys Asn Ala Ile Asp
                165                 170                 175

Ala Thr Ile Lys Leu Gly Gly Thr Ser Tyr Val Phe Trp Gly Gly Arg
            180                 185                 190

Glu Gly Tyr Tyr Thr Leu Leu Asn Thr Gln Met Gln Arg Glu Lys Asp
        195                 200                 205

His Leu Ala Lys Met Leu Thr Ala Ala Arg Asp Tyr Ala Arg Ala His
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Val
        275                 280                 285

Asp Asn Gly Phe Leu Gly Ser Ile Asp Ala Asn Arg Gly Asp Ala Gln
    290                 295                 300

Asn Gly Trp Asp Thr Asp Gln Phe Pro Val Asp Pro Tyr Asp Leu Thr
305                 310                 315                 320

Gln Ala Met Met Gln Ile Ile Arg Asn Gly Gly Phe Lys Asp Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Val Ile Glu Glu Ser Pro Leu Cys Lys Met Val
    370                 375                 380

Glu Glu Arg Tyr Ala Ser Phe Asp Ser Gly Leu Gly Lys Gln Phe Glu
385                 390                 395                 400

Glu Gly Lys Ala Thr Leu Glu Asp Leu Tyr Glu Tyr Ala Lys Lys Asn
                405                 410                 415

Gly Glu Pro Val Val Ala Ser Gly Lys Gln Glu Leu Tyr Glu Thr Leu
            420                 425                 430
```

Leu Asn Leu Tyr Ala Lys
        435

<210> SEQ ID NO 117
<211> LENGTH: 1317
<212> TYPE: DNA
<213> ORGANISM: Unknown
<220> FEATURE:
<223> OTHER INFORMATION: Obtained from environmental sample

<400> SEQUENCE: 117
atgtcaactg agtatttccc tacaatcggc aagattccct tcgagggacc cgagagcaag 60
aaccccatgg ccttccacta ctatgaaccc gaaaagttgg tgatgggcaa gaagatgaag 120
gactggctgc gtttcgcaat ggcctggtgg cacacccttg gagccgcatc cggcgaccag 180
ttcggcggac agacccgcag ttacgcctgg gacaagggcg actgccctta cagccgcgcc 240
cgcgccaagg tcgacgccgg cttcgagatc atgcagaagc tcggcataga gttcttctgc 300
ttccatgaca tcgacctggt cgaggatacc gacgacatcg ccgagtatga agcccggatg 360
aaagacatca cggactatct gctggaaaag atggaggcta ccggcatcaa gaacctctgg 420
ggcacggcca atgtcttcgg tcacaagcgt tatatgaacg gtgcagccac aaaccccgat 480
ttcgcagtgg tcgcaagggc ggccgtgcag atcaagaacg ccatcgacgc caccatcaag 540
ctgggtggtg agaactatgt gttctggggt ggacgcgagg gttatatgag cctgctcaac 600
acccagatgc agagggagaa ggaacacctt gccaagatgc tcaccgccgc acgtgactat 660
gcacgcgcca aggtttcaa gggcacgttc ctcatcgaac ccaagccgat ggaacccacc 720
aagcaccagt atgaccagga taccgagacc gttatcggat tcctccgcag ccacggcctg 780
gacaaggact tcaaggtcaa catcgaggtg aaccacgcca ccctggcggg ccataccttc 840
gagcacgaac tggccaccgc cgtcgacaac ggcatgctcg gcagcatcga cgccaaccgc 900
ggagacgccc agaacggctg ggacaccgac cagttcccga tcgacaactt cgagctcacg 960
cttgccatga tgcagataat ccgcaacggc ggcctggcac cgggcggttc gaacttcgac 1020
gcaaagctgc gccgcaattc caccgatccc gaggacatct tcatcgccca catcagcgcg 1080
atggacgcca tggcccgcgc cctcgtcaac gccgccgcca tcctcggcga gtcgcccgtt 1140
ccggctatgg tcaaggaccg ctatgcttcg ttcgactgcg gcaagggcaa ggacttcgaa 1200
gacggcaaac tgactctcga agacatcgtc gcctacgcca gggagaatgg cgagccgaaa 1260
cagatttccg gcaagcagga actctacgaa actatcgtcg ctctttactg caagtaa 1317

<210> SEQ ID NO 118
<211> LENGTH: 438
<212> TYPE: PRT
<213> ORGANISM: Unknown
<220> FEATURE:
<223> OTHER INFORMATION: Obtained from environmental sample

<400> SEQUENCE: 118

Met Ser Thr Glu Tyr Phe Pro Thr Ile Gly Lys Ile Pro Phe Glu Gly
1               5                   10                  15

Pro Glu Ser Lys Asn Pro Met Ala Phe His Tyr Tyr Glu Pro Glu Lys
            20                  25                  30

Leu Val Met Gly Lys Lys Met Lys Asp Trp Leu Arg Phe Ala Met Ala
        35                  40                  45

Trp Trp His Thr Leu Gly Ala Ala Ser Gly Asp Gln Phe Gly Gly Gln
    50                  55                  60

```
Thr Arg Ser Tyr Ala Trp Asp Lys Gly Asp Cys Pro Tyr Ser Arg Ala
65                  70                  75                  80

Arg Ala Lys Val Asp Ala Gly Phe Glu Ile Met Gln Lys Leu Gly Ile
                85                  90                  95

Glu Phe Phe Cys Phe His Asp Ile Asp Leu Val Glu Asp Thr Asp Asp
            100                 105                 110

Ile Ala Glu Tyr Glu Ala Arg Met Lys Asp Ile Thr Asp Tyr Leu Leu
        115                 120                 125

Glu Lys Met Glu Ala Thr Gly Ile Lys Asn Leu Trp Gly Thr Ala Asn
    130                 135                 140

Val Phe Gly His Lys Arg Tyr Met Asn Gly Ala Ala Thr Asn Pro Asp
145                 150                 155                 160

Phe Ala Val Val Ala Arg Ala Ala Val Gln Ile Lys Asn Ala Ile Asp
                165                 170                 175

Ala Thr Ile Lys Leu Gly Gly Glu Asn Tyr Val Phe Trp Gly Gly Arg
            180                 185                 190

Glu Gly Tyr Met Ser Leu Leu Asn Thr Gln Met Gln Arg Glu Lys Glu
        195                 200                 205

His Leu Ala Lys Met Leu Thr Ala Ala Arg Asp Tyr Ala Arg Ala Lys
    210                 215                 220

Gly Phe Lys Gly Thr Phe Leu Ile Glu Pro Lys Pro Met Glu Pro Thr
225                 230                 235                 240

Lys His Gln Tyr Asp Gln Asp Thr Glu Thr Val Ile Gly Phe Leu Arg
                245                 250                 255

Ser His Gly Leu Asp Lys Asp Phe Lys Val Asn Ile Glu Val Asn His
            260                 265                 270

Ala Thr Leu Ala Gly His Thr Phe Glu His Glu Leu Ala Thr Ala Val
        275                 280                 285

Asp Asn Gly Met Leu Gly Ser Ile Asp Ala Asn Arg Gly Asp Ala Gln
    290                 295                 300

Asn Gly Trp Asp Thr Asp Gln Phe Pro Ile Asp Asn Phe Glu Leu Thr
305                 310                 315                 320

Leu Ala Met Met Gln Ile Ile Arg Asn Gly Gly Leu Ala Pro Gly Gly
                325                 330                 335

Ser Asn Phe Asp Ala Lys Leu Arg Arg Asn Ser Thr Asp Pro Glu Asp
            340                 345                 350

Ile Phe Ile Ala His Ile Ser Ala Met Asp Ala Met Ala Arg Ala Leu
        355                 360                 365

Val Asn Ala Ala Ala Ile Leu Gly Glu Ser Pro Val Pro Ala Met Val
    370                 375                 380

Lys Asp Arg Tyr Ala Ser Phe Asp Cys Gly Lys Gly Lys Asp Phe Glu
385                 390                 395                 400

Asp Gly Lys Leu Thr Leu Glu Asp Ile Val Ala Tyr Ala Arg Glu Asn
                405                 410                 415

Gly Glu Pro Lys Gln Ile Ser Gly Lys Gln Glu Leu Tyr Glu Thr Ile
            420                 425                 430

Val Ala Leu Tyr Cys Lys
        435
```

<210> SEQ ID NO 119
<211> LENGTH: 1314
<212> TYPE: DNA
<213> ORGANISM: Unknown
<220> FEATURE:

<223> OTHER INFORMATION: Obtained from environmental sample

<400> SEQUENCE: 119

```
atgtcatatt ttcctactat cggtaacatc ccctttgagg gtgtagagag caagaatccc     60
cttgccttcc attattatga cgcttcccgc gtagttatgg gcaagcccat gaaggagtgg    120
ctcaagtttg ccatggcctg gtggcacacg ctgggtcagg catcggccga ccctttcggc    180
ggacaaaccc gcagctatgc ctgggacaaa ggcgagtgcc cctactgccg tgcccgtgcc    240
aaggccgacg ccggcttcga gctcatgcag aaactgggca tcgagtattt ctgctcccac    300
gacattgacc tcatcgagga ctgcgacgac attgcagagt acgaggcccg tctgaaggac    360
attacggact acctcctgga gaagatgaag aagaccggta tcaagaacct gtggggtacg    420
gccaatgtgt tcggtaacaa gcgttacatg aacggtgctg ctaccaaccc tcagtttgac    480
gttgtggccc gcgctgccgt ccagatcaag aacgccattg acgctaccat caagctgggc    540
ggttccaact atgtgttctg ggtggccgt gagggttact acacgcttct gaacacccag    600
atgcagcgtg agaagaatca cctggctgcc atgctcaagg ctgcccgcga ctatgcccgc    660
gccaacggtt tcaagggcac cttcctcatt gagcccaagc ccatggagcc caccaagcac    720
cagtacgacg tagacacgga gaccgtgatt ggattcctcc gcgccaacgg tctggagaag    780
gacttcaagg tgaacattga ggtgaaccac gctactcttg ccggtcacac cttcgagcac    840
gagctcaccg tggcccgtga gaacggcttc ctgggttcca ttgacgccaa ccgcggagat    900
gcccagaacg gctgggacac cgaccagttc ccggtagatg cctttgacct cacccaggcc    960
atgatgcaga ttctcctcaa cggaggctcc ggcaatggcg gtaccaactt tgacgccaag   1020
ctgcgccgtt cctccaccga ccccgaggac atcttcatcg cgcacatcag cgccatggat   1080
gccatggctc acgccctgct caatgcagct gccgtgctgg aggagagccc gctttgcaag   1140
atggtcaagg agcgttacgc ttccttcgac agcggtcttg gcaagcagtt cgaggaagga   1200
aaggctacgc tggaagatct gtatgcctat gccgtcaaga acggtgagcc cgtggtggct   1260
tccggcaagc aggaactgta cgaaaccttc ctgaacctct atgcaaaatg gtaa         1314
```

<210> SEQ ID NO 120
<211> LENGTH: 437
<212> TYPE: PRT
<213> ORGANISM: Unknown
<220> FEATURE:
<223> OTHER INFORMATION: Obtained from environmental sample

<400> SEQUENCE: 120

```
Met Ser Tyr Phe Pro Thr Ile Gly Asn Ile Pro Phe Glu Gly Val Glu
1               5                   10                  15

Ser Lys Asn Pro Leu Ala Phe His Tyr Tyr Asp Ala Ser Arg Val Val
            20                  25                  30

Met Gly Lys Pro Met Lys Glu Trp Leu Lys Phe Ala Met Ala Trp Trp
        35                  40                  45

His Thr Leu Gly Gln Ala Ser Ala Asp Pro Phe Gly Gly Gln Thr Arg
    50                  55                  60

Ser Tyr Ala Trp Asp Lys Gly Glu Cys Pro Tyr Cys Arg Ala Arg Ala
65                  70                  75                  80

Lys Ala Asp Ala Gly Phe Glu Leu Met Gln Lys Leu Gly Ile Glu Tyr
                85                  90                  95

Phe Cys Ser His Asp Ile Asp Leu Ile Glu Asp Cys Asp Asp Ile Ala
            100                 105                 110
```

```
Glu Tyr Glu Ala Arg Leu Lys Asp Ile Thr Asp Tyr Leu Leu Glu Lys
        115                 120                 125

Met Lys Lys Thr Gly Ile Lys Asn Leu Trp Gly Thr Ala Asn Val Phe
    130                 135                 140

Gly Asn Lys Arg Tyr Met Asn Gly Ala Ala Thr Asn Pro Gln Phe Asp
145                 150                 155                 160

Val Val Ala Arg Ala Ala Val Gln Ile Lys Asn Ala Ile Asp Ala Thr
                165                 170                 175

Ile Lys Leu Gly Gly Ser Asn Tyr Val Phe Trp Gly Gly Arg Glu Gly
            180                 185                 190

Tyr Tyr Thr Leu Leu Asn Thr Gln Met Gln Arg Glu Lys Asn His Leu
        195                 200                 205

Ala Ala Met Leu Lys Ala Ala Arg Asp Tyr Ala Arg Ala Asn Gly Phe
    210                 215                 220

Lys Gly Thr Phe Leu Ile Glu Pro Lys Pro Met Glu Pro Thr Lys His
225                 230                 235                 240

Gln Tyr Asp Val Asp Thr Glu Thr Val Ile Gly Phe Leu Arg Ala Asn
                245                 250                 255

Gly Leu Glu Lys Asp Phe Lys Val Asn Ile Glu Val Asn His Ala Thr
            260                 265                 270

Leu Ala Gly His Thr Phe Glu His Glu Leu Thr Val Ala Arg Glu Asn
        275                 280                 285

Gly Phe Leu Gly Ser Ile Asp Ala Asn Arg Gly Asp Ala Gln Asn Gly
    290                 295                 300

Trp Asp Thr Asp Gln Phe Pro Val Asp Ala Phe Asp Leu Thr Gln Ala
305                 310                 315                 320

Met Met Gln Ile Leu Leu Asn Gly Gly Ser Gly Asn Gly Gly Thr Asn
                325                 330                 335

Phe Asp Ala Lys Leu Arg Arg Ser Ser Thr Asp Pro Glu Asp Ile Phe
            340                 345                 350

Ile Ala His Ile Ser Ala Met Asp Ala Met Ala His Ala Leu Leu Asn
        355                 360                 365

Ala Ala Ala Val Leu Glu Glu Ser Pro Leu Cys Lys Met Val Lys Glu
    370                 375                 380

Arg Tyr Ala Ser Phe Asp Ser Gly Leu Gly Lys Gln Phe Glu Glu Gly
385                 390                 395                 400

Lys Ala Thr Leu Glu Asp Leu Tyr Ala Tyr Ala Val Lys Asn Gly Glu
                405                 410                 415

Pro Val Val Ala Ser Gly Lys Gln Glu Leu Tyr Glu Thr Phe Leu Asn
            420                 425                 430

Leu Tyr Ala Lys Trp
        435
```

<210> SEQ ID NO 121
<211> LENGTH: 1317
<212> TYPE: DNA
<213> ORGANISM: Unknown
<220> FEATURE:
<223> OTHER INFORMATION: Obtained from environmental sample

<400> SEQUENCE: 121

```
atgtcaactg agtatttccc tacaatcggc aagattccct tcgagggacc cgagagcaag      60

aaccccatgg ccttccacta ctatgaaccc gaaaagttgg tgatgggcaa gaagatgaag     120

gactggctgc gtttcgcaat ggcctggtgg cacacccttg gagccgcatc cggcgaccag     180
```

-continued

```
ttcggcggac agacccgcag ttacgcctgg gacaagggcg actgccctta cagccgcgcc    240

cgcgccaagg tcgacgccgg cttcgagatc atgcagaagc tcggcataga gttcttctgc    300

ttccatgaca tcgacctggt cgaggatacc gacgacatcg ccgagtatga agcccggatg    360

aaagacatca cggactatct gctggaaaag atggaggtta ccggcatcaa gaacctctgg    420

ggcacggcca atgtcttcgg tcacaagcgt tatatgaacg atgcagccac aaaccccgat    480

ttcgcagtgg tcgcaagggc ggccgtgcag atcaagaacg ccatcgacgc caccatcaag    540

ctgggtggtg agaactatgt gttctggggt ggacgcgagg gttatatgag cctgctcaac    600

acccagatgc agagggagaa ggaacacctt gccaagatgc tcaccgccgc acgtgactat    660

gcacgcgcca aaggtttcaa gggcacgttc ctcatcgaac ccgagccgat ggaacccacc    720

aagcaccagt atgaccagga taccgagacc gttatcggat tcctccgcag ccacggcctg    780

gacaaggact tcaaggtcaa catcgaggtg aaccacgcca ccctggcggg ccataccttc    840

gagcacgaac tggccaccgc cgtcgacaac ggcatgctcg gcagcatcga cgccaaccgc    900

ggagacgccc agaacggctg ggacaccgac cagttcccga tcgacaactt cgagctcacg    960

cttgccatga tgcagataat ccgcaacggc ggcctggcac cgggcggttc gaacttcgac   1020

gcaaagctgc gccgcaattc caccgatccc gaggacatca tcatcgccca catcagcgcg   1080

atggacgcca tggcccgcgc cctcgtcaac gccgccgcca tcctcggcga gtcgcccgtt   1140

ccggctatgg tcaaggaccg ctatgcttcg ttcgactgcg gcaagggcaa ggacttcgaa   1200

gacggcaaac tgactctcga agacatcgtc gcctacgcca gggagaatgg cgagccgaaa   1260

cagatttccg gcaagcagga actctacgaa actatcgtcg ctctttactg caagtaa      1317
```

```
<210> SEQ ID NO 122
<211> LENGTH: 438
<212> TYPE: PRT
<213> ORGANISM: Unknown
<220> FEATURE:
<223> OTHER INFORMATION: Obtained from environmental sample

<400> SEQUENCE: 122

Met Ser Thr Glu Tyr Phe Pro Thr Ile Gly Lys Ile Pro Phe Glu Gly
1               5                   10                  15

Pro Glu Ser Lys Asn Pro Met Ala Phe His Tyr Tyr Glu Pro Glu Lys
            20                  25                  30

Leu Val Met Gly Lys Lys Met Lys Asp Trp Leu Arg Phe Ala Met Ala
        35                  40                  45

Trp Trp His Thr Leu Gly Ala Ala Ser Gly Asp Gln Phe Gly Gly Gln
    50                  55                  60

Thr Arg Ser Tyr Ala Trp Asp Lys Gly Asp Cys Pro Tyr Ser Arg Ala
65                  70                  75                  80

Arg Ala Lys Val Asp Ala Gly Phe Glu Ile Met Gln Lys Leu Gly Ile
                85                  90                  95

Glu Phe Phe Cys Phe His Asp Ile Asp Leu Val Glu Asp Thr Asp Asp
            100                 105                 110

Ile Ala Glu Tyr Glu Ala Arg Met Lys Asp Ile Thr Asp Tyr Leu Leu
        115                 120                 125

Glu Lys Met Glu Val Thr Gly Ile Lys Asn Leu Trp Gly Thr Ala Asn
    130                 135                 140

Val Phe Gly His Lys Arg Tyr Met Asn Asp Ala Ala Thr Asn Pro Asp
145                 150                 155                 160

Phe Ala Val Val Ala Arg Ala Ala Val Gln Ile Lys Asn Ala Ile Asp
```

-continued

```
                165                 170                 175

Ala Thr Ile Lys Leu Gly Gly Glu Asn Tyr Val Phe Trp Gly Gly Arg
            180                 185                 190

Glu Gly Tyr Met Ser Leu Leu Asn Thr Gln Met Gln Arg Glu Lys Glu
        195                 200                 205

His Leu Ala Lys Met Leu Thr Ala Ala Arg Asp Tyr Ala Arg Ala Lys
    210                 215                 220

Gly Phe Lys Gly Thr Phe Leu Ile Glu Pro Glu Pro Met Glu Pro Thr
225                 230                 235                 240

Lys His Gln Tyr Asp Gln Asp Thr Glu Thr Val Ile Gly Phe Leu Arg
                245                 250                 255

Ser His Gly Leu Asp Lys Asp Phe Lys Val Asn Ile Glu Val Asn His
            260                 265                 270

Ala Thr Leu Ala Gly His Thr Phe Glu His Glu Leu Ala Thr Ala Val
        275                 280                 285

Asp Asn Gly Met Leu Gly Ser Ile Asp Ala Asn Arg Gly Asp Ala Gln
    290                 295                 300

Asn Gly Trp Asp Thr Asp Gln Phe Pro Ile Asp Asn Phe Glu Leu Thr
305                 310                 315                 320

Leu Ala Met Met Gln Ile Ile Arg Asn Gly Gly Leu Ala Pro Gly Gly
                325                 330                 335

Ser Asn Phe Asp Ala Lys Leu Arg Arg Asn Ser Thr Asp Pro Glu Asp
            340                 345                 350

Ile Ile Ile Ala His Ile Ser Ala Met Asp Ala Met Ala Arg Ala Leu
        355                 360                 365

Val Asn Ala Ala Ala Ile Leu Gly Glu Ser Pro Val Pro Ala Met Val
    370                 375                 380

Lys Asp Arg Tyr Ala Ser Phe Asp Cys Gly Lys Gly Lys Asp Phe Glu
385                 390                 395                 400

Asp Gly Lys Leu Thr Leu Glu Asp Ile Val Ala Tyr Ala Arg Glu Asn
                405                 410                 415

Gly Glu Pro Lys Gln Ile Ser Gly Lys Gln Glu Leu Tyr Glu Thr Ile
            420                 425                 430

Val Ala Leu Tyr Cys Lys
        435
```

<210> SEQ ID NO 123
<211> LENGTH: 1317
<212> TYPE: DNA
<213> ORGANISM: Unknown
<220> FEATURE:
<223> OTHER INFORMATION: Obtained from environmental sample

<400> SEQUENCE: 123

```
atgaccaacg agtattttcc cggaatcggt gtgattccgt ttgaaggaca ggaaagcaag     60

aatcccctgg ctttccatta ttatgacgcc aaccgcgtag tgatgggcaa acccatgaag    120

gaatggttca aatttgccat ggcctggtgg catacgctgg ggcaggcatc ggccgatccc    180

ttcggcggac agacccgctc ctacgcatgg gacaagggcg agtgccctta ctgccgtgcc    240

cgccagaagg ccgacgccgg ctttgaactg atgcagaagc tgggaatcgg ctatttctgc    300

ttccacgatg tggatatcat cgaggactgc gaggacattg ccgagtatga ggcccgtatg    360

aaggacatca cggactatct gctggtgaag atgaaggaaa cgggcatcaa gaatctgtgg    420

ggcacggcca acgtcttcgg ccacaagcgc tatatgaacg gcgccgccac caacccgcaa    480
```

-continued

```
ttcgacgtgg tagcccgcgc tgcggtccag atcaagaacg ccctggacgc caccatcaag    540

ctgggcggca gcaattatgt gttctggggc ggccgggaag gctactacac ccttttgaac    600

acgcagatgc agcgggagaa ggaccacctg gcccagatgc tcaaggcggc ccgcgactat    660

gcccgcggca agggattcaa gggcacgttc ctcattgagc ccaagcccat ggagcccacc    720

aagcaccagt acgacgtaga tacggagacc gtgattggtt tcctgcgcgc caacgggctg    780

gacaaggact tcaaggtgaa tatcgaagtg aaccacgcca ccctggccgg ccataccttc    840

gagcacgagc tcaccgtggc ccgcgaaaac ggcttcctgg gcagcatcga cgccaaccgc    900

ggagacgccc agaacggctg ggatacagac cagttccccg tggacgcctt tgacctcacc    960

caggccatga tgcaggtcct gctcaacggc ggattcggca acggcggcac caacttcgac   1020

gccaaactgc gccgttcctc cacggatccc gaggacatct tcatcgccca catcagcgcc   1080

atggacgcca tggcccacgc cctcctgaac gccgccgcca tcctggaaga gagccccatg   1140

ccgggcatgg tgaaggagcg ctacgcttcc ttcgacaatg gccttggcaa gaagttcgag   1200

gaaggaaagg ccacgctgga agagctgtac gactatgcca agaagaacgg cgagcctgtg   1260

gccgcttccg gaaagcagga actgtacgaa acgctgctga acctgtacgc caagtaa      1317
```

<210> SEQ ID NO 124
<211> LENGTH: 438
<212> TYPE: PRT
<213> ORGANISM: Unknown
<220> FEATURE:
<223> OTHER INFORMATION: Obtained from environmental sample

<400> SEQUENCE: 124

```
Met Thr Asn Glu Tyr Phe Pro Gly Ile Gly Val Ile Pro Phe Glu Gly
1               5                   10                  15

Gln Glu Ser Lys Asn Pro Leu Ala Phe His Tyr Tyr Asp Ala Asn Arg
            20                  25                  30

Val Val Met Gly Lys Pro Met Lys Glu Trp Phe Lys Phe Ala Met Ala
        35                  40                  45

Trp Trp His Thr Leu Gly Gln Ala Ser Ala Asp Pro Phe Gly Gly Gln
    50                  55                  60

Thr Arg Ser Tyr Ala Trp Asp Lys Gly Glu Cys Pro Tyr Cys Arg Ala
65                  70                  75                  80

Arg Gln Lys Ala Asp Ala Gly Phe Glu Leu Met Gln Lys Leu Gly Ile
                85                  90                  95

Gly Tyr Phe Cys Phe His Asp Val Asp Ile Ile Glu Asp Cys Glu Asp
            100                 105                 110

Ile Ala Glu Tyr Glu Ala Arg Met Lys Asp Ile Thr Asp Tyr Leu Leu
        115                 120                 125

Val Lys Met Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Gln
145                 150                 155                 160

Phe Asp Val Val Ala Arg Ala Ala Val Gln Ile Lys Asn Ala Leu Asp
                165                 170                 175

Ala Thr Ile Lys Leu Gly Gly Ser Asn Tyr Val Phe Trp Gly Gly Arg
            180                 185                 190

Glu Gly Tyr Tyr Thr Leu Leu Asn Thr Gln Met Gln Arg Glu Lys Asp
        195                 200                 205

His Leu Ala Gln Met Leu Lys Ala Ala Arg Asp Tyr Ala Arg Gly Lys
    210                 215                 220
```

```
Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Arg
        275                 280                 285

Glu Asn Gly Phe Leu Gly Ser Ile Asp Ala Asn Arg Gly Asp Ala Gln
    290                 295                 300

Asn Gly Trp Asp Thr Asp Gln Phe Pro Val Asp Ala Phe Asp Leu Thr
305                 310                 315                 320

Gln Ala Met Met Gln Val Leu Leu Asn Gly Gly Phe Gly Asn Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Ile Leu Glu Glu Ser Pro Met Pro Gly Met Val
    370                 375                 380

Lys Glu Arg Tyr Ala Ser Phe Asp Asn Gly Leu Gly Lys Lys Phe Glu
385                 390                 395                 400

Glu Gly Lys Ala Thr Leu Glu Glu Leu Tyr Asp Tyr Ala Lys Lys Asn
                405                 410                 415

Gly Glu Pro Val Ala Ala Ser Gly Lys Gln Glu Leu Tyr Glu Thr Leu
            420                 425                 430

Leu Asn Leu Tyr Ala Lys
        435


<210> SEQ ID NO 125
<211> LENGTH: 1317
<212> TYPE: DNA
<213> ORGANISM: Unknown
<220> FEATURE:
<223> OTHER INFORMATION: Obtained from environmental sample

<400> SEQUENCE: 125

atggcaaaag agtatttccc gcagatcgga aagatcggct ttgagggtct tgagagcaag      60

aacccgatgg cattccatta ttatgacgcc gagcgtgtcg tgctcggaaa gaagatgaag     120

gactggctga agttcgcgat ggcctggtgg catacgctcg gacaggcttc cggcgaccca     180

ttcggcggcc agactcgcag ctatgagtgg gacaagggcg agtgccccta ctgccgtgcc     240

cgcgccaagg ccgacgccgg cttcgagctc atgcagaagc tcggcatcga gtacttctgc     300

ttccacgaca tcgacctcat cgaggactgc gacgacatcg acgagtacga ggcccggatg     360

aaggacatca ccgactacct gctggagaag atgaaggaga ccggaatcaa gaatctctgg     420

ggaacggcca acgtcttcgg tcacaagcgc tacatgaacg gcgccgctac caatccgcag     480

tttgaaatcg tcgcccgcgc tgccgtccag atcaagaacg cgctcgacgc caccatcaag     540

ctcggcggct ccaactacgt cttctggggc ggccgcgagg gctattacac gctgctgaat     600

acccagatgc agcgcgagaa ggaccatctc gccaggctcc ttaccgccgc ccgcgactat     660

gcgcgcgcca aggggttcaa ggggaccttc cccatcgagc cgaagccgat ggagccgacc     720

aagcaccagt atgacgtcga cacggagacc gtcatcggtt tcctccgcca gaatggcctc     780
```

-continued

```
gacaaggact tcaaggtcaa tatcgaggtg aaccacgcca ccctcgccgg ccataccttc    840

gagcacgagc tgaccgcggc ccgggagaac ggcttcctcg gcagcatcga cgccaaccgc    900

ggcgacgccc agaacggctg ggacaccgac cagttcccgg tggacgcctt cgatctcacg    960

cgggccatga tgcagatcct gctcaatggc ggtttcggca acggcggcac caacttcgac   1020

gccaagctgc gccgcagctc caccgatccc gaggacatct tcatcgccca catcagcgcg   1080

atggacgcca tggcccacgc cctgctgaat gcggccgcca tcctcgagga aagcccgctg   1140

ccggccctgg tcaagcagcg ctatgcgtcc ttcgacagcg gtctcggcaa gcagttcgag   1200

gagggtaagg ccacgctcga ggacctgtac gcatacgcga aggagcacgg cgagcccgtc   1260

gcggcctccg gcaagcagga gctctgcgag acctatctca acctctacgc gaaataa      1317
```

<210> SEQ ID NO 126
<211> LENGTH: 438
<212> TYPE: PRT
<213> ORGANISM: Unknown
<220> FEATURE:
<223> OTHER INFORMATION: Obtained from environmental sample

<400> SEQUENCE: 126

```
Met Ala Lys Glu Tyr Phe Pro Gln Ile Gly Lys Ile Gly Phe Glu Gly
1               5                   10                  15

Leu Glu Ser Lys Asn Pro Met Ala Phe His Tyr Tyr Asp Ala Glu Arg
            20                  25                  30

Val Val Leu Gly Lys Lys Met Lys Asp Trp Leu Lys Phe Ala Met Ala
        35                  40                  45

Trp Trp His Thr Leu Gly Gln Ala Ser Gly Asp Pro Phe Gly Gly Gln
    50                  55                  60

Thr Arg Ser Tyr Glu Trp Asp Lys Gly Glu Cys Pro Tyr Cys Arg Ala
65                  70                  75                  80

Arg Ala Lys Ala Asp Ala Gly Phe Glu Leu Met Gln Lys Leu Gly Ile
                85                  90                  95

Glu Tyr Phe Cys Phe His Asp Ile Asp Leu Ile Glu Asp Cys Asp Asp
            100                 105                 110

Ile Asp Glu Tyr Glu Ala Arg Met Lys Asp Ile Thr Asp Tyr Leu Leu
        115                 120                 125

Glu Lys Met Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Gln
145                 150                 155                 160

Phe Glu Ile Val Ala Arg Ala Ala Val Gln Ile Lys Asn Ala Leu Asp
                165                 170                 175

Ala Thr Ile Lys Leu Gly Gly Ser Asn Tyr Val Phe Trp Gly Gly Arg
            180                 185                 190

Glu Gly Tyr Tyr Thr Leu Leu Asn Thr Gln Met Gln Arg Glu Lys Asp
        195                 200                 205

His Leu Ala Arg Leu Leu Thr Ala Ala Arg Asp Tyr Ala Arg Ala Lys
    210                 215                 220

Gly Phe Lys Gly Thr Phe Pro Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Gln Asn Gly Leu Asp Lys Asp Phe Lys Val Asn Ile Glu Val Asn His
            260                 265                 270
```

-continued

```
Ala Thr Leu Ala Gly His Thr Phe Glu His Glu Leu Thr Ala Ala Arg
        275                 280                 285

Glu Asn Gly Phe Leu Gly Ser Ile Asp Ala Asn Arg Gly Asp Ala Gln
    290                 295                 300

Asn Gly Trp Asp Thr Asp Gln Phe Pro Val Asp Ala Phe Asp Leu Thr
305                 310                 315                 320

Arg Ala Met Met Gln Ile Leu Leu Asn Gly Gly Phe Gly Asn Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Ile Leu Glu Glu Ser Pro Leu Pro Ala Leu Val
    370                 375                 380

Lys Gln Arg Tyr Ala Ser Phe Asp Ser Gly Leu Gly Lys Gln Phe Glu
385                 390                 395                 400

Glu Gly Lys Ala Thr Leu Glu Asp Leu Tyr Ala Tyr Ala Lys Glu His
                405                 410                 415

Gly Glu Pro Val Ala Ala Ser Gly Lys Gln Glu Leu Cys Glu Thr Tyr
            420                 425                 430

Leu Asn Leu Tyr Ala Lys
        435
```

<210> SEQ ID NO 127
<211> LENGTH: 1317
<212> TYPE: DNA
<213> ORGANISM: Unknown
<220> FEATURE:
<223> OTHER INFORMATION: Obtained from environmental sample

<400> SEQUENCE: 127

```
atgagtaaag agtattttcc tgggattggc aaaatcccgt atgagggagc cgagagcaag     60

aatgtgatgg cattccacta ttatgatccc gaacgcgtgg tcatgggcaa gaaaatgaaa    120

gactggttca agttcgctat tgcctggtgg catacccctgg ggcaggccag tgctgaccag   180

tttggcggac agacccgttt ctatgaatgg gacaaagccg aggacccctt gcagcgtgcc    240

aaggacaaga tggatgccgg ttttgaaatc atgcagaagc tgggcatcga gtatttctgt    300

ttccatgatg tggacctcat cgaggaggcc gataccatcg aggaatatga agcccgcatg    360

caggcgatta ccgactacgc gctggagaag atgaaggcaa cgggtatcaa gttgctgtgg    420

ggcactgcca acgtgttcgg ccacaagcgt tacatgaacg gcgccgccac caatcccgac    480

ttcaatgtcg tggcacgtgc agccgtgcag atcaagaacg ccctcgatgc taccatcaag    540

ttgggcggaa cgagctacgt cttctggggc ggtcgtgaag gctatcagag cctgctcaac    600

acccagatgc agcgcgagaa gaaccacctg gccaagatgc tcacggcagc ccgtgactat    660

gcccgtgcta agggcttcaa gggcaccttc ctgattgagc ccaagccgat ggaacccacc    720

aagcaccagt atgaccagga caccgagacc gttatcggct tcttgcgtgc caatggcctt    780

gacaaggact ttaaggtcaa cattgaggtc aaccatgcca cgctggctgg ccacaccttt    840

gcacatgagt tggcagtggc tgtggataac ggtatgctgg gcagcatcga tgctaaccgt    900

ggtgaccacc agaacggctg ggatacagac cagttcccca tcaacagtta tgaactcacc    960

aatgctatgc tgcagatcat gcacggcggc ggtttcaagg acggcggtac caactttgac   1020

gccaagctgc gccgcaacag taccgacccc gaggacatct ttaccgctca catcagtggt   1080
```

atggacgctc tggcccgtgc cctgttgagt gctgccgata tccttgagaa gagcgagttg 1140
cctgaaatgc tcaaggaacg ctatgccagc tttgacgcgg gtgaaggcaa gcgctttgag 1200
gatggccaga tgactcttga ggaactggtt gcctatgcca agtcccatgg cgagcctgct 1260
accatcagtg gcaagcagga aaaatatgaa gccatcgtgg ctttgcacgt caagtaa 1317

<210> SEQ ID NO 128
<211> LENGTH: 438
<212> TYPE: PRT
<213> ORGANISM: Unknown
<220> FEATURE:
<223> OTHER INFORMATION: Obtained from environmental sample

<400> SEQUENCE: 128

Met Ser Lys Glu Tyr Phe Pro Gly Ile Gly Lys Ile Pro Tyr Glu Gly
1 5 10 15

Ala Glu Ser Lys Asn Val Met Ala Phe His Tyr Tyr Asp Pro Glu Arg
20 25 30

Val Val Met Gly Lys Lys Met Lys Asp Trp Phe Lys Phe Ala Ile Ala
35 40 45

Trp Trp His Thr Leu Gly Gln Ala Ser Ala Asp Gln Phe Gly Gly Gln
50 55 60

Thr Arg Phe Tyr Glu Trp Asp Lys Ala Glu Asp Pro Leu Gln Arg Ala
65 70 75 80

Lys Asp Lys Met Asp Ala Gly Phe Glu Ile Met Gln Lys Leu Gly Ile
85 90 95

Glu Tyr Phe Cys Phe His Asp Val Asp Leu Ile Glu Glu Ala Asp Thr
100 105 110

Ile Glu Glu Tyr Glu Ala Arg Met Gln Ala Ile Thr Asp Tyr Ala Leu
115 120 125

Glu Lys Met Lys Ala Thr Gly Ile Lys Leu Leu Trp Gly Thr Ala Asn
130 135 140

Val Phe Gly His Lys Arg Tyr Met Asn Gly Ala Ala Thr Asn Pro Asp
145 150 155 160

Phe Asn Val Val Ala Arg Ala Ala Val Gln Ile Lys Asn Ala Leu Asp
165 170 175

Ala Thr Ile Lys Leu Gly Gly Thr Ser Tyr Val Phe Trp Gly Gly Arg
180 185 190

Glu Gly Tyr Gln Ser Leu Leu Asn Thr Gln Met Gln Arg Glu Lys Asn
195 200 205

His Leu Ala Lys Met Leu Thr Ala Ala Arg Asp Tyr Ala Arg Ala Lys
210 215 220

Gly Phe Lys Gly Thr Phe Leu Ile Glu Pro Lys Pro Met Glu Pro Thr
225 230 235 240

Lys His Gln Tyr Asp Gln Asp Thr Glu Thr Val Ile Gly Phe Leu Arg
245 250 255

Ala Asn Gly Leu Asp Lys Asp Phe Lys Val Asn Ile Glu Val Asn His
260 265 270

Ala Thr Leu Ala Gly His Thr Phe Ala His Glu Leu Ala Val Ala Val
275 280 285

Asp Asn Gly Met Leu Gly Ser Ile Asp Ala Asn Arg Gly Asp His Gln
290 295 300

Asn Gly Trp Asp Thr Asp Gln Phe Pro Ile Asn Ser Tyr Glu Leu Thr
305 310 315 320

Asn Ala Met Leu Gln Ile Met His Gly Gly Gly Phe Lys Asp Gly Gly

```
                325                 330                 335

Thr Asn Phe Asp Ala Lys Leu Arg Arg Asn Ser Thr Asp Pro Glu Asp
            340                 345                 350

Ile Phe Thr Ala His Ile Ser Gly Met Asp Ala Leu Ala Arg Ala Leu
        355                 360                 365

Leu Ser Ala Ala Asp Ile Leu Glu Lys Ser Glu Leu Pro Glu Met Leu
    370                 375                 380

Lys Glu Arg Tyr Ala Ser Phe Asp Ala Gly Glu Gly Lys Arg Phe Glu
385                 390                 395                 400

Asp Gly Gln Met Thr Leu Glu Glu Leu Val Ala Tyr Ala Lys Ser His
                405                 410                 415

Gly Glu Pro Ala Thr Ile Ser Gly Lys Gln Glu Lys Tyr Glu Ala Ile
            420                 425                 430

Val Ala Leu His Val Lys
        435
```

<210> SEQ ID NO 129
<211> LENGTH: 1329
<212> TYPE: DNA
<213> ORGANISM: Unknown
<220> FEATURE:
<223> OTHER INFORMATION: Obtained from environmental sample

<400> SEQUENCE: 129

```
atgagtaaag agtattatcc tgagattggc aaaatcccgt ttgagggtcc cgagagcaag      60

aatgtgatgg cgttccatta ctatgaaccc gaacgcgtcg tcatgggtaa gaagatgaaa     120

gactggctca agtttgccat gtgctggtgg cacagcctgg gtcaggccag tgccgaccag     180

ttcggcggac agacacgttt ctacgagtgg gacaaggccg ataccccct gcagcgtgcc     240

aaggacaaaa tggatgccgg atttgaaatc atgcagaagt tgggcatcga gtacttctgc     300

ttccacgatg tggacctcat cgaggaggcc gataccatcg aggaatacga ggcccgcatg     360

aaggccatta ccgactatgc gctggagaag atgcaggcca ccggcatcaa gttgctgtgg     420

ggcactgcca atgtgttcgg ccacaagcgc tacatgaacg gcgccgccac caatcccgat     480

ttcaatgtcg tggcacgtgc cgccgtccaa atcaagaatg ccatcgatgc caccatcaag     540

ctgggcggca cgagttacgt cttctggggt ggtcgtgagg gctatcagag tctgctcaac     600

acgcagatgc agcgcgagaa ggaccatctg gcccgcatgc tggcggcagc ccgcgactat     660

ggccgtgccc atggcttcaa gggcactttc ctgatcgagc ccaaacccat ggagcccacc     720

aagcaccagt atgatgtgga caccgagacc gtgctcggct tcctgcgtgc ccacggcctg     780

gacaaggact tcaaggttaa catcgaggtc aatcatgcta cgctggcggg acacactttc     840

agccacgaac tggctgtggc cgtggacaac ggtatgctgg gcagcatcga cgccaaccgc     900

ggcgattatc agaatggctg ggacaccgac cagttcccca tcgacagctt cgagctcacc     960

caggccatgc tgcagatcat gcgcggcggc ggcttcaagg acggaggtac caacttcgat    1020

gccaagctgc gtcgcaacag taccgaccct gaggacatct tcatcgccca catcagcggt    1080

atggatgcca tggcacgcgg cctgttgagc gctgccgcta tcctcgagga tggcgagttg    1140

cccgcgatgc tcaaggcacg ttatgccagc tttgaccagg gcgagggtaa gcgctttgag    1200

gacggcgaga tgacgctcga gcagctggtg gattatgcaa aggattatgc caaatcgcac    1260

ggcgagcctg atgtcatcag cggcaagcag gagaagtttg aaaccatcgt ggccctttac    1320

gccaagtaa                                                           1329
```

<210> SEQ ID NO 130
<211> LENGTH: 442
<212> TYPE: PRT
<213> ORGANISM: Unknown
<220> FEATURE:
<223> OTHER INFORMATION: Obtained from environmental sample

<400> SEQUENCE: 130

Met Ser Lys Glu Tyr Tyr Pro Glu Ile Gly Lys Ile Pro Phe Glu Gly
1 5 10 15

Pro Glu Ser Lys Asn Val Met Ala Phe His Tyr Tyr Glu Pro Glu Arg
20 25 30

Val Val Met Gly Lys Lys Met Lys Asp Trp Leu Lys Phe Ala Met Cys
35 40 45

Trp Trp His Ser Leu Gly Gln Ala Ser Ala Asp Gln Phe Gly Gly Gln
50 55 60

Thr Arg Phe Tyr Glu Trp Asp Lys Ala Asp Thr Pro Leu Gln Arg Ala
65 70 75 80

Lys Asp Lys Met Asp Ala Gly Phe Glu Ile Met Gln Lys Leu Gly Ile
85 90 95

Glu Tyr Phe Cys Phe His Asp Val Asp Leu Ile Glu Glu Ala Asp Thr
100 105 110

Ile Glu Glu Tyr Glu Ala Arg Met Lys Ala Ile Thr Asp Tyr Ala Leu
115 120 125

Glu Lys Met Gln Ala Thr Gly Ile Lys Leu Leu Trp Gly Thr Ala Asn
130 135 140

Val Phe Gly His Lys Arg Tyr Met Asn Gly Ala Ala Thr Asn Pro Asp
145 150 155 160

Phe Asn Val Val Ala Arg Ala Ala Val Gln Ile Lys Asn Ala Ile Asp
165 170 175

Ala Thr Ile Lys Leu Gly Gly Thr Ser Tyr Val Phe Trp Gly Gly Arg
180 185 190

Glu Gly Tyr Gln Ser Leu Leu Asn Thr Gln Met Gln Arg Glu Lys Asp
195 200 205

His Leu Ala Arg Met Leu Ala Ala Ala Arg Asp Tyr Gly Arg Ala His
210 215 220

Gly Phe Lys Gly Thr Phe Leu Ile Glu Pro Lys Pro Met Glu Pro Thr
225 230 235 240

Lys His Gln Tyr Asp Val Asp Thr Glu Thr Val Leu Gly Phe Leu Arg
245 250 255

Ala His Gly Leu Asp Lys Asp Phe Lys Val Asn Ile Glu Val Asn His
260 265 270

Ala Thr Leu Ala Gly His Thr Phe Ser His Glu Leu Ala Val Ala Val
275 280 285

Asp Asn Gly Met Leu Gly Ser Ile Asp Ala Asn Arg Gly Asp Tyr Gln
290 295 300

Asn Gly Trp Asp Thr Asp Gln Phe Pro Ile Asp Ser Phe Glu Leu Thr
305 310 315 320

Gln Ala Met Leu Gln Ile Met Arg Gly Gly Gly Phe Lys Asp Gly Gly
325 330 335

Thr Asn Phe Asp Ala Lys Leu Arg Arg Asn Ser Thr Asp Pro Glu Asp
340 345 350

Ile Phe Ile Ala His Ile Ser Gly Met Asp Ala Met Ala Arg Gly Leu
355 360 365

```
Leu Ser Ala Ala Ala Ile Leu Glu Asp Gly Glu Leu Pro Ala Met Leu
    370                 375                 380

Lys Ala Arg Tyr Ala Ser Phe Asp Gln Gly Glu Gly Lys Arg Phe Glu
385                 390                 395                 400

Asp Gly Glu Met Thr Leu Glu Gln Leu Val Asp Tyr Ala Lys Asp Tyr
                405                 410                 415

Ala Lys Ser His Gly Glu Pro Asp Val Ile Ser Gly Lys Gln Glu Lys
            420                 425                 430

Phe Glu Thr Ile Val Ala Leu Tyr Ala Lys
        435                 440
```

<210> SEQ ID NO 131
<211> LENGTH: 1317
<212> TYPE: DNA
<213> ORGANISM: Unknown
<220> FEATURE:
<223> OTHER INFORMATION: Obtained from environmental sample

<400> SEQUENCE: 131

```
atgaccaacg agtattttcc cggaatcggt gtgattccgt ttgaaggaca ggaaagcaag     60

aatcccctgg ctttccatta ttatgacgcc aaccgcgtag tgatgggcaa acccatgaag    120

gaatggttca aatttgccat ggcctggtgg catacgctgg ggcaggcatc ggccgatccc    180

ttcggcggac agacccgctc ctacgcatgg gacaagggcg agtgccctta ctgccgtgcc    240

cgccagaagg ccgacgccgg ctttgaactg atgcagaagc tgggaatcgg ctatttctgc    300

ttccacgatg tggatatcat cgaggactgc gaggacattg ccgagtatga ggcccgtatg    360

aaggacatca cggactatct gctggtgaag atgaaggaaa cgggcatcaa gaatctgtgg    420

ggcacggcca acgtcttcgg ccacaagcgc tatatgaacg gcgccgccac caacccgcaa    480

ttcgacgtgg tagcccgcgc tgcggtccag atcaagaacg ccctggacgc caccatcaag    540

ctgggcggca gcaattatgt gttctggggc ggccgggaag gctactacac cctttttgaac    600

acgcagatgc agcgggagaa ggaccacctg gcccagatgc tcaaggcggc ccgcgactat    660

gcccgcggca agggattcaa gggcacgttc ctcattgagc ccaagcccat ggagcccacc    720

aagcaccagt acgacgtaga tacggagacc gtgattggtt tcctgcgcgc caacgggccg    780

gacaaggact tcaaggtgaa tatcgaagtg aaccacgcca ccctggccgg ccataccttc    840

gagcacgagc tcaccgtggc ccgcgaaaac ggcttcctgg gcagcatcga cgccaaccgc    900

ggagacgccc agaacggctg ggatacagac cagttccccg tggacgcctt tgacctcacc    960

caggccatga tgcaggtcct gctcaacggc ggattcggca acggcggcac caacttcgac   1020

gccaaactgc gccgttcctc cacggatccc gaggacatct tcatcgccca catcagcgcc   1080

atggacgcca tggcccacgc cctcctgaac gccgccgcca tcctggaaga gagccccatg   1140

ccgggcatgg tgaaggagcg ctacgcttcc ttcgacaatg gccttggcaa gaagttcgag   1200

gaaggaaagg ccacgctgga agagctgtac gactatgcca agaagaacgg cgagcctgtg   1260

gccgcttccg gaaagcagga actgtacgaa acgctgctga acctgtacgc caagtaa      1317
```

<210> SEQ ID NO 132
<211> LENGTH: 438
<212> TYPE: PRT
<213> ORGANISM: Unknown
<220> FEATURE:
<223> OTHER INFORMATION: Obtained from environmental sample

<400> SEQUENCE: 132

-continued

```
Met Thr Asn Glu Tyr Phe Pro Gly Ile Gly Val Ile Pro Phe Glu Gly
1               5                   10                  15

Gln Glu Ser Lys Asn Pro Leu Ala Phe His Tyr Tyr Asp Ala Asn Arg
            20                  25                  30

Val Val Met Gly Lys Pro Met Lys Glu Trp Phe Lys Phe Ala Met Ala
        35                  40                  45

Trp Trp His Thr Leu Gly Gln Ala Ser Ala Asp Pro Phe Gly Gly Gln
    50                  55                  60

Thr Arg Ser Tyr Ala Trp Asp Lys Gly Glu Cys Pro Tyr Cys Arg Ala
65                  70                  75                  80

Arg Gln Lys Ala Asp Ala Gly Phe Glu Leu Met Gln Lys Leu Gly Ile
                85                  90                  95

Gly Tyr Phe Cys Phe His Asp Val Asp Ile Ile Glu Asp Cys Glu Asp
            100                 105                 110

Ile Ala Glu Tyr Glu Ala Arg Met Lys Asp Ile Thr Asp Tyr Leu Leu
        115                 120                 125

Val Lys Met Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Gln
145                 150                 155                 160

Phe Asp Val Val Ala Arg Ala Ala Val Gln Ile Lys Asn Ala Leu Asp
                165                 170                 175

Ala Thr Ile Lys Leu Gly Gly Ser Asn Tyr Val Phe Trp Gly Gly Arg
            180                 185                 190

Glu Gly Tyr Tyr Thr Leu Leu Asn Thr Gln Met Gln Arg Glu Lys Asp
        195                 200                 205

His Leu Ala Gln Met Leu Lys Ala Ala Arg Asp Tyr Ala Arg Gly Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Pro Asp Lys Asp Phe Lys Val Asn Ile Glu Val Asn His
            260                 265                 270

Ala Thr Leu Ala Gly His Thr Phe Glu His Glu Leu Thr Val Ala Arg
        275                 280                 285

Glu Asn Gly Phe Leu Gly Ser Ile Asp Ala Asn Arg Gly Asp Ala Gln
    290                 295                 300

Asn Gly Trp Asp Thr Asp Gln Phe Pro Val Asp Ala Phe Asp Leu Thr
305                 310                 315                 320

Gln Ala Met Met Gln Val Leu Leu Asn Gly Gly Phe Gly Asn Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Ile Leu Glu Glu Ser Pro Met Pro Gly Met Val
    370                 375                 380

Lys Glu Arg Tyr Ala Ser Phe Asp Asn Gly Leu Gly Lys Lys Phe Glu
385                 390                 395                 400

Glu Gly Lys Ala Thr Leu Glu Glu Leu Tyr Asp Tyr Ala Lys Lys Asn
                405                 410                 415

Gly Glu Pro Val Ala Ala Ser Gly Lys Gln Glu Leu Tyr Glu Thr Leu
```

420 425 430

Leu Asn Leu Tyr Ala Lys
435

<210> SEQ ID NO 133
<211> LENGTH: 1317
<212> TYPE: DNA
<213> ORGANISM: Unknown
<220> FEATURE:
<223> OTHER INFORMATION: Obtained from environmental sample

<400> SEQUENCE: 133
atgactaaag agtatttccc ttccgtcggc aagattgcct ttgaaggacc cgaaagcaag 60
aaccctatgg ccttccatta ttatgacgcc aatcgcgtgg taatgggaaa gccgatgaaa 120
gaatggctta aatttgccat ggcctggtgg cacaccctgg gccaggcctc tgcagacccc 180
ttcggcggtc agacccgctc ctacgagtgg gacaagggcg agtgccccta ctgccgcgcc 240
aaggccaagg ccgatgccgg ctttgaactg atgcagaaac tgggcatcga gtatttctgc 300
ttccacgata tagacctggt ggaagactgc gatgatatcg ccgaatacga ggcccgcatg 360
aaggacatca cggactatct cctggagaag atgaaggaaa ccggcatcaa gaacctctgg 420
ggaaccgcca acgtgttcgg ccacaagcgc tatatgaacg gcgccgccac caaccctcag 480
ttcgacatcg tggcccgtgc cgctgtccag atcaagaacg ccctggatgc caccatcaag 540
ctgggcggct ccaactatgt gttctggggc ggccgtgagg gctactatac cctcctgaac 600
acccagatgc agagagagaa ggaccacctg gccaagatgc tcaccgccgc ccgcgactat 660
gcccgtgcca agggcttcaa gggcaccttc ctcatcgaac ccaagccgat ggagcccacc 720
aagcaccagt acgacgtaga tacggagacc gtgatcggct tcctccgcgc caacggcctg 780
gacaaggact tcaaggtgaa tattgaggtg aaccacgcca ccctggccgg ccacaccttc 840
gagcacgagc tcaccgtggc ccgcgagaac ggcttcctgg gcagcatcga cgccaaccgc 900
ggagacgccc agaacggctg ggatacggac cagttcccgg tggatgcctt cgacctcacc 960
caggctatga tgcagatcct tctgaacgga ggcttcggca acggcggtac caacttcgac 1020
gccaaactgc gccgctcctc cacggacccc gaggacatct tcatcgccca catcagcgct 1080
atggatgcca tggcccacgc cctgctgaat gcagccgcca tcctggagga aagcccgctt 1140
ccgaagatgc tgaaagagcg ttatgccagc tttgacggcg gtctgggcaa gaagttcgaa 1200
gaaggcaagg cctctctgga agaactctac gagtatgcca agagcaacgg agagcccgtg 1260
gccgcttccg gcaagcagga gctctgcgaa acgtacctga acctctacgc taagtaa 1317

<210> SEQ ID NO 134
<211> LENGTH: 438
<212> TYPE: PRT
<213> ORGANISM: Unknown
<220> FEATURE:
<223> OTHER INFORMATION: Obtained from environmental sample

<400> SEQUENCE: 134

Met Thr Lys Glu Tyr Phe Pro Ser Val Gly Lys Ile Ala Phe Glu Gly
1 5 10 15

Pro Glu Ser Lys Asn Pro Met Ala Phe His Tyr Tyr Asp Ala Asn Arg
20 25 30

Val Val Met Gly Lys Pro Met Lys Glu Trp Leu Lys Phe Ala Met Ala
35 40 45

Trp Trp His Thr Leu Gly Gln Ala Ser Ala Asp Pro Phe Gly Gly Gln

-continued

```
    50                  55                  60

Thr Arg Ser Tyr Glu Trp Asp Lys Gly Glu Cys Pro Tyr Cys Arg Ala
65                  70                  75                  80

Lys Ala Lys Ala Asp Ala Gly Phe Glu Leu Met Gln Lys Leu Gly Ile
                85                  90                  95

Glu Tyr Phe Cys Phe His Asp Ile Asp Leu Val Glu Asp Cys Asp Asp
            100                 105                 110

Ile Ala Glu Tyr Glu Ala Arg Met Lys Asp Ile Thr Asp Tyr Leu Leu
        115                 120                 125

Glu Lys Met Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Gln
145                 150                 155                 160

Phe Asp Ile Val Ala Arg Ala Ala Val Gln Ile Lys Asn Ala Leu Asp
                165                 170                 175

Ala Thr Ile Lys Leu Gly Gly Ser Asn Tyr Val Phe Trp Gly Gly Arg
            180                 185                 190

Glu Gly Tyr Tyr Thr Leu Leu Asn Thr Gln Met Gln Arg Glu Lys Asp
        195                 200                 205

His Leu Ala Lys Met Leu Thr Ala Ala Arg Asp Tyr Ala Arg Ala Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Arg
        275                 280                 285

Glu Asn Gly Phe Leu Gly Ser Ile Asp Ala Asn Arg Gly Asp Ala Gln
    290                 295                 300

Asn Gly Trp Asp Thr Asp Gln Phe Pro Val Asp Ala Phe Asp Leu Thr
305                 310                 315                 320

Gln Ala Met Met Gln Ile Leu Leu Asn Gly Gly Phe Gly Asn Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Ile Leu Glu Glu Ser Pro Leu Pro Lys Met Leu
    370                 375                 380

Lys Glu Arg Tyr Ala Ser Phe Asp Gly Gly Leu Gly Lys Lys Phe Glu
385                 390                 395                 400

Glu Gly Lys Ala Ser Leu Glu Glu Leu Tyr Glu Tyr Ala Lys Ser Asn
                405                 410                 415

Gly Glu Pro Val Ala Ala Ser Gly Lys Gln Glu Leu Cys Glu Thr Tyr
            420                 425                 430

Leu Asn Leu Tyr Ala Lys
        435
```

<210> SEQ ID NO 135
<211> LENGTH: 1320
<212> TYPE: DNA
<213> ORGANISM: Unknown

<220> FEATURE:
<223> OTHER INFORMATION: Obtained from environmental sample

<400> SEQUENCE: 135
atggctaaag aatacttccc ctccatcggc aaaatccctt ttgaaggagc cgacagcaaa 60
aatcccctcg ctttccatta ttatgacgcc ggacgcgtgg ttatgggcaa gcccatgaag 120
gaatggctta aattcgccat ggcctggtgg cacacgctgg gccaggcctc cggagacccc 180
ttcggcggcc agacccgcag ctacgaatgg gacaagggcg aatgccccta ctgccgcgcc 240
aaggccaagg ccgacgccgg ttttgaaatc atgcaaaagc tgggcatcga atacttctgc 300
ttccacgatg tggaccttat cgaggattgc gatgacattg ccgaatacga agcccgcatg 360
aaggacatca cggactacct gctggaaaag atgaaggaga ccggcatcaa gaacctctgg 420
ggcaccgcca atgtcttcgg ccacaagcgc tacatgaacg gcgccggcac caatccgcag 480
ttcgatgtgg tggcccgtgc cgccgtccag atcaagaacg ccctggacgc caccatcaag 540
ctgggcggct ccaactatgt gttctggggc ggccgcgaag gctattacac cctcctcaac 600
acacagatgc agcgggaaaa agaccacctg gccaagttgc tgacggccgc ccgcgactat 660
gcccgcgcca agggcttcaa gggcaccttc ctcattgagc ccaaacccat ggaacccacc 720
aagcaccagt acgacgtgga tacggagacg gtcatcggct tcctccgtgc caacggcctg 780
gacaaggact tcaaggtgaa catcgaggtg aaccacgcca ccctggccgg ccacaccttc 840
gagcatgagc tcaccgtggc ccgcgagaac ggtttcctgg gctccatcga tgccaaccgc 900
ggcgacgccc agaacggctg ggacacggac cagttccctg tggacccgta cgatcttacc 960
caggccatga tgcaggtgct gctgaacggc ggcttcggca acggcggcac caacttcgac 1020
gccaaactcc gccgctcctc caccgaccct gaggacatct tcatcgccca tatttccgcc 1080
atggatgcca tggcccacgc tttgcttaac gcagctgccg tgctggaaga gagccccctg 1140
tgccagatgg tcaaggagcg ttatgccagc ttcgacgatg gcctcggcaa acagttcgag 1200
gaaggcaagg ctaccctgga agacctgtac gaatacgcca aggcccaggg tgaacccgtt 1260
gtcgcctccg gcaagcagga gctttacgag actctcctga acctgtatgc cgtcaagtaa 1320

<210> SEQ ID NO 136
<211> LENGTH: 439
<212> TYPE: PRT
<213> ORGANISM: Unknown
<220> FEATURE:
<223> OTHER INFORMATION: Obtained from environmental sample

<400> SEQUENCE: 136

Met Ala Lys Glu Tyr Phe Pro Ser Ile Gly Lys Ile Pro Phe Glu Gly
1               5                   10                  15

Ala Asp Ser Lys Asn Pro Leu Ala Phe His Tyr Tyr Asp Ala Gly Arg
            20                  25                  30

Val Val Met Gly Lys Pro Met Lys Glu Trp Leu Lys Phe Ala Met Ala
        35                  40                  45

Trp Trp His Thr Leu Gly Gln Ala Ser Gly Asp Pro Phe Gly Gly Gln
    50                  55                  60

Thr Arg Ser Tyr Glu Trp Asp Lys Gly Glu Cys Pro Tyr Cys Arg Ala
65                  70                  75                  80

Lys Ala Lys Ala Asp Ala Gly Phe Glu Ile Met Gln Lys Leu Gly Ile
                85                  90                  95

Glu Tyr Phe Cys Phe His Asp Val Asp Leu Ile Glu Asp Cys Asp Asp
            100                 105                 110

```
Ile Ala Glu Tyr Glu Ala Arg Met Lys Asp Ile Thr Asp Tyr Leu Leu
        115                 120                 125

Glu Lys Met Lys Glu Thr Gly Ile Lys Asn Leu Trp Gly Thr Ala Asn
    130                 135                 140

Val Phe Gly His Lys Arg Tyr Met Asn Gly Ala Gly Thr Asn Pro Gln
145                 150                 155                 160

Phe Asp Val Val Ala Arg Ala Ala Val Gln Ile Lys Asn Ala Leu Asp
                165                 170                 175

Ala Thr Ile Lys Leu Gly Gly Ser Asn Tyr Val Phe Trp Gly Gly Arg
            180                 185                 190

Glu Gly Tyr Tyr Thr Leu Leu Asn Thr Gln Met Gln Arg Glu Lys Asp
        195                 200                 205

His Leu Ala Lys Leu Leu Thr Ala Ala Arg Asp Tyr Ala Arg Ala Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Arg
        275                 280                 285

Glu Asn Gly Phe Leu Gly Ser Ile Asp Ala Asn Arg Gly Asp Ala Gln
    290                 295                 300

Asn Gly Trp Asp Thr Asp Gln Phe Pro Val Asp Pro Tyr Asp Leu Thr
305                 310                 315                 320

Gln Ala Met Met Gln Val Leu Leu Asn Gly Gly Phe Gly Asn Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Val Leu Glu Glu Ser Pro Leu Cys Gln Met Val
    370                 375                 380

Lys Glu Arg Tyr Ala Ser Phe Asp Asp Gly Leu Gly Lys Gln Phe Glu
385                 390                 395                 400

Glu Gly Lys Ala Thr Leu Glu Asp Leu Tyr Glu Tyr Ala Lys Ala Gln
                405                 410                 415

Gly Glu Pro Val Val Ala Ser Gly Lys Gln Glu Leu Tyr Glu Thr Leu
            420                 425                 430

Leu Asn Leu Tyr Ala Val Lys
        435
```

<210> SEQ ID NO 137
<211> LENGTH: 1317
<212> TYPE: DNA
<213> ORGANISM: Unknown
<220> FEATURE:
<223> OTHER INFORMATION: Obtained from environmental sample

<400> SEQUENCE: 137

```
atgaccaaag aatatttccc taccgtcggg aagatcccct tcgagggccc cgaaagcaag      60

aaccctatgg cgttccatta ctatgacccc aaccgtctgg tgatgggcaa gaagatgaaa     120

gactggctgc gtttcgccat ggcctggtgg cacaccctcg gccaggcgtc gggcgaccag     180
```

-continued

```
ttcggcggcc agacccgcag ttatgcgtgg gacgagggag aatgcccgta cgagcgcgcc    240

cgtgccaagg ctgacgccgg cttcgagatc atgcagaaac tcggtatcga gttcttctgc    300

ttccacgaca tcgacctgat cgaggatacc gacgacatcg ccgagtatga ggcccgcctg    360

aaagacatca cggactatct gctcgagaag atgaaagcca ctggcatcaa aaatctctgg    420

ggaacggcca acgtgttcgg ccacaagcgt tgcatgaacg gcgccgccac caacccggac    480

ttcgccgtgc tggcccgcgc tgccgtccag atcaagaacg ccatcgacgc caccatcaag    540

ctgggcggcg agaactatgt gttctggggt ggccgcgaag gctacacgag cctgctcaac    600

acccagatgc agcgtgagaa agagcacctg ggccgcctgc tgtccctggc ccgcgactat    660

ggccgcgccc acggcttcaa gggtaccttc ctgatcgagc ccaagccgat gggaccgacg    720

aaacaccagt acgaccagga tacggaaact gtcatcggtt tcctgcgccg ccacggtcta    780

gacaaggact tcaaggtcaa tatcgaggtg aaccatgcca cgctggcggg ccacaccttc    840

gaacacgaac tggcctgcgc cgtggatcac ggtatgctgg gcagcatcga cgccaaccgc    900

ggtgacgcac agaacggctg ggataccgac cagttcccga tcgacaactt cgagctgacc    960

ctttccatgc tccagatcat ccgcaacggt ggcctggcac ccggcggctc gaatttcgat   1020

gccaagctgc gccgcaactc caccgatccc gaagacattt tcatcgcgca catcagcgcc   1080

atggacgcca tggcccgcgc attggtcaat gcggccgcca tcctggagga gagcgctatt   1140

ccgaagatgg tcaaggagcg ttacgcttcg ttcgacagcg gcaaaggcaa ggaatacgag   1200

gaaggcaagc tgacgctcga agacatcgtg gcctatgcca aggcgaacgg agaaccgaag   1260

cagatttccg gcaaacagga actctacgag acgcttgtcg cactctatag caaataa      1317
```

<210> SEQ ID NO 138
<211> LENGTH: 438
<212> TYPE: PRT
<213> ORGANISM: Unknown
<220> FEATURE:
<223> OTHER INFORMATION: Obtained from environmental sample

<400> SEQUENCE: 138

```
Met Thr Lys Glu Tyr Phe Pro Thr Val Gly Lys Ile Pro Phe Glu Gly
1               5                   10                  15

Pro Glu Ser Lys Asn Pro Met Ala Phe His Tyr Tyr Asp Pro Asn Arg
            20                  25                  30

Leu Val Met Gly Lys Lys Met Lys Asp Trp Leu Arg Phe Ala Met Ala
        35                  40                  45

Trp Trp His Thr Leu Gly Gln Ala Ser Gly Asp Gln Phe Gly Gly Gln
    50                  55                  60

Thr Arg Ser Tyr Ala Trp Asp Glu Gly Glu Cys Pro Tyr Glu Arg Ala
65                  70                  75                  80

Arg Ala Lys Ala Asp Ala Gly Phe Glu Ile Met Gln Lys Leu Gly Ile
                85                  90                  95

Glu Phe Phe Cys Phe His Asp Ile Asp Leu Ile Glu Asp Thr Asp Asp
            100                 105                 110

Ile Ala Glu Tyr Glu Ala Arg Leu Lys Asp Ile Thr Asp Tyr Leu Leu
        115                 120                 125

Glu Lys Met Lys Ala Thr Gly Ile Lys Asn Leu Trp Gly Thr Ala Asn
    130                 135                 140

Val Phe Gly His Lys Arg Cys Met Asn Gly Ala Ala Thr Asn Pro Asp
145                 150                 155                 160
```

```
Phe Ala Val Leu Ala Arg Ala Ala Val Gln Ile Lys Asn Ala Ile Asp
                165                 170                 175

Ala Thr Ile Lys Leu Gly Gly Glu Asn Tyr Val Phe Trp Gly Gly Arg
            180                 185                 190

Glu Gly Tyr Thr Ser Leu Leu Asn Thr Gln Met Gln Arg Glu Lys Glu
        195                 200                 205

His Leu Gly Arg Leu Leu Ser Leu Ala Arg Asp Tyr Gly Arg Ala His
    210                 215                 220

Gly Phe Lys Gly Thr Phe Leu Ile Glu Pro Lys Pro Met Gly Pro Thr
225                 230                 235                 240

Lys His Gln Tyr Asp Gln Asp Thr Glu Thr Val Ile Gly Phe Leu Arg
                245                 250                 255

Arg His Gly Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp His Gly Met Leu Gly Ser Ile Asp Ala Asn Arg Gly Asp Ala Gln
    290                 295                 300

Asn Gly Trp Asp Thr Asp Gln Phe Pro Ile Asp Asn Phe Glu Leu Thr
305                 310                 315                 320

Leu Ser Met Leu Gln Ile Ile Arg Asn Gly Gly Leu Ala Pro Gly Gly
                325                 330                 335

Ser Asn Phe Asp Ala Lys Leu Arg Arg Asn Ser Thr Asp Pro Glu Asp
            340                 345                 350

Ile Phe Ile Ala His Ile Ser Ala Met Asp Ala Met Ala Arg Ala Leu
        355                 360                 365

Val Asn Ala Ala Ala Ile Leu Glu Glu Ser Ala Ile Pro Lys Met Val
    370                 375                 380

Lys Glu Arg Tyr Ala Ser Phe Asp Ser Gly Lys Gly Lys Glu Tyr Glu
385                 390                 395                 400

Glu Gly Lys Leu Thr Leu Glu Asp Ile Val Ala Tyr Ala Lys Ala Asn
                405                 410                 415

Gly Glu Pro Lys Gln Ile Ser Gly Lys Gln Glu Leu Tyr Glu Thr Leu
            420                 425                 430

Val Ala Leu Tyr Ser Lys
        435
```

<210> SEQ ID NO 139
<211> LENGTH: 1317
<212> TYPE: DNA
<213> ORGANISM: Unknown
<220> FEATURE:
<223> OTHER INFORMATION: Obtained from environmental sample

<400> SEQUENCE: 139

```
atgaccaaag ggtatttccc taccatcggc aggattccct tcgagggaac tgaaagcaag      60

aatcccctcg cattccatta ctatgagccc gaccggctcg tactgggcaa gaaaatgaaa     120

gactggctgc gtttcgcgat ggcctggtgg cacaccctgg gccaggcgtc cggcgaccag     180

ttcggcggcc agacccgcag ctatgcctgg gacaaggccg agtgccccta tgagcgcgcc     240

aaggccaaag ccgacgccgg cttcgagatc atgcagaaac tcggcatcga gttcttctgt     300

ttccacgaca ttgacctcgt tgaggatacc gacgacatcg ccgagtatga ggcccggatg     360

aaggacatta ccgactatct cctggtcaag atgaaggaga ccggaatcaa gaacctctgg     420

ggtacggcca atgtcttcgg ccacaagcgc tatatgaacg gcgccgccac caatcccgac     480
```

```
ttcgacgtgg tggcccgcgc cgccgtccag atcaagaacg ccctcgatgc caccatcaag    540

ctgggcggtg aaaactatgt gttctggggc ggccgcgaag gctatatgag cctgctcaac    600

acgcagatgc agcgtgagaa ggagcacctg ggccggatgc tggtcgccgc ccgcgactac    660

gcccgcgccc acggcttcaa gggtaccttc ctcatcgagc ccaaaccgat ggaaccgacc    720

aagcaccagt acgaccagga tacggaaacc gtgatcggct tccttcgccg ccacggcctg    780

gacaaggatt tcaaggtgaa catcgaagtg aaccacgcca cgctggccgg ccacaccttc    840

gagcacgaac tggccaccgc cgtcgactgc ggcctgctgg gcagcatcga cgccaatcgc    900

ggcgacgctc agaacggctg ggataccgac cagttcccga tcgacaactt cgaactcacg    960

ctggccatgc tgcagattat ccgcaacggc ggtctggcac ccggcggctc gaacttcgac   1020

gccaaactgc gccgtaactc caccgatccg gaagatatct tcatcgccca catcagtgcg   1080

atggacgcga tggcccgtgc gctggtcaac gccgccgcaa tctgggaaga gtctcccatc   1140

ccgcagatga agaaagaacg ctacgcgtcg ttcgacagcg gcaagggcaa ggaattcgaa   1200

gagggcaagc tctgcctcga agacctcgtg gcctatgcca aggcgaacgg agaaccgaaa   1260

cagatctccg gcaggcagga actatatgag accatcgtcg ccctttattg caaatag      1317
```

<210> SEQ ID NO 140
<211> LENGTH: 438
<212> TYPE: PRT
<213> ORGANISM: Unknown
<220> FEATURE:
<223> OTHER INFORMATION: Obtained from environmental sample

<400> SEQUENCE: 140

```
Met Thr Lys Gly Tyr Phe Pro Thr Ile Gly Arg Ile Pro Phe Glu Gly
1               5                   10                  15

Thr Glu Ser Lys Asn Pro Leu Ala Phe His Tyr Tyr Glu Pro Asp Arg
            20                  25                  30

Leu Val Leu Gly Lys Lys Met Lys Asp Trp Leu Arg Phe Ala Met Ala
        35                  40                  45

Trp Trp His Thr Leu Gly Gln Ala Ser Gly Asp Gln Phe Gly Gly Gln
    50                  55                  60

Thr Arg Ser Tyr Ala Trp Asp Lys Ala Glu Cys Pro Tyr Glu Arg Ala
65                  70                  75                  80

Lys Ala Lys Ala Asp Ala Gly Phe Glu Ile Met Gln Lys Leu Gly Ile
                85                  90                  95

Glu Phe Phe Cys Phe His Asp Ile Asp Leu Val Glu Asp Thr Asp Asp
            100                 105                 110

Ile Ala Glu Tyr Glu Ala Arg Met Lys Asp Ile Thr Asp Tyr Leu Leu
        115                 120                 125

Val Lys Met Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Asp
145                 150                 155                 160

Phe Asp Val Val Ala Arg Ala Ala Val Gln Ile Lys Asn Ala Leu Asp
                165                 170                 175

Ala Thr Ile Lys Leu Gly Gly Glu Asn Tyr Val Phe Trp Gly Gly Arg
            180                 185                 190

Glu Gly Tyr Met Ser Leu Leu Asn Thr Gln Met Gln Arg Glu Lys Glu
        195                 200                 205

His Leu Gly Arg Met Leu Val Ala Ala Arg Asp Tyr Ala Arg Ala His
```

```
    210                 215                 220

Gly Phe Lys Gly Thr Phe Leu Ile Glu Pro Lys Pro Met Glu Pro Thr
225                 230                 235                 240

Lys His Gln Tyr Asp Gln Asp Thr Glu Thr Val Ile Gly Phe Leu Arg
                245                 250                 255

Arg His Gly Leu Asp Lys Asp Phe Lys Val Asn Ile Glu Val Asn His
            260                 265                 270

Ala Thr Leu Ala Gly His Thr Phe Glu His Glu Leu Ala Thr Ala Val
        275                 280                 285

Asp Cys Gly Leu Leu Gly Ser Ile Asp Ala Asn Arg Gly Asp Ala Gln
    290                 295                 300

Asn Gly Trp Asp Thr Asp Gln Phe Pro Ile Asp Asn Phe Glu Leu Thr
305                 310                 315                 320

Leu Ala Met Leu Gln Ile Ile Arg Asn Gly Gly Leu Ala Pro Gly Gly
                325                 330                 335

Ser Asn Phe Asp Ala Lys Leu Arg Arg Asn Ser Thr Asp Pro Glu Asp
            340                 345                 350

Ile Phe Ile Ala His Ile Ser Ala Met Asp Ala Met Ala Arg Ala Leu
        355                 360                 365

Val Asn Ala Ala Ala Ile Trp Glu Glu Ser Pro Ile Pro Gln Met Lys
    370                 375                 380

Lys Glu Arg Tyr Ala Ser Phe Asp Ser Gly Lys Gly Lys Glu Phe Glu
385                 390                 395                 400

Glu Gly Lys Leu Cys Leu Glu Asp Leu Val Ala Tyr Ala Lys Ala Asn
                405                 410                 415

Gly Glu Pro Lys Gln Ile Ser Gly Arg Gln Glu Leu Tyr Glu Thr Ile
            420                 425                 430

Val Ala Leu Tyr Cys Lys
        435
```

<210> SEQ ID NO 141
<211> LENGTH: 1317
<212> TYPE: DNA
<213> ORGANISM: Unknown
<220> FEATURE:
<223> OTHER INFORMATION: Obtained from environmental sample

<400> SEQUENCE: 141

```
atgaccaacg agtattttcc cggaatcggt gtgattccgt ttgaaggaca ggaaagcaag      60

aatcccatgg ctttccatta ttatgacgcc aaccgcgtag tgatgggcaa acccatgaag     120

gaatggttca aatttgccat ggcctggtgg catacgctgg ggcaggcatc ggccgatccc     180

ttcggcggac agacccgctc ctacgcatgg gacaagggcg agtgccctta ctgccgtgcc     240

cgccagaagg ccgacgccgg ctttgaactg atgcagaagc tgggtatcgg ctatttctgc     300

ttccacgatg tggatatcat cgaggactgc gaagacattg ccgagtatga ggcccgtatg     360

aaggacatca cggactatct gctggtgaag atgaaggaaa cgggcatcaa gaacctgtgg     420

ggcacggcca acgtcttcgg ccacaagcgc tatatgaacg gcgctgccac caacccgcag     480

ttcgacgtgg tggcccgcgc tgcggtccag atcaagaacg ccctggacgc caccatcaag     540

ctgggcggca gcaattacgt gttctggggc ggccgcgaag gctattatac cctttggaac     600

acgcagatgc ggcgggagaa ggaccacctg gcccagatgc tcaaggcagc ccgtgactat     660

gcccgcggca agggattcaa gggcacgttc ctcattgagc ccaagcccat ggagcccacc     720

aagcaccagt acgacgtaga tacggagacc gtgattggct tcctgcgcgc aaacggactg     780
```

```
gacaaggact tcaaggtgaa tatcgaagtg aaccacgcca ccctggccgg ccacaccttc    840

gagcacgaac tcaccgtggc ccgcgaaaac ggcttcctgg gcagcatcga cgccaaccgc    900

ggagacgccc agaacggttg ggatacagac cagttcccca tagatgcctt tgacctcacc    960

caggccatga tgcaggtcct gctcaacggc ggattcggca acggcggcac caacttcgac   1020

gccaaactgc gccgttcctc cacggatccc gaggacatct tcatcgccca catcggcgcc   1080

atggacgcca tggcccacgc cctcctgaac gccgccgcca tcctggaaga gagccccatg   1140

ccgggcatgg tgaaggagcg ctacgcttcc ttcgacaatg gccttggcaa gaagttcgag   1200

gaaggaaagg ccacgctgga agagctgtac gactatgcca agaagaacgg cgagcctgtg   1260

gccgcttccg gcaagcagga actgtacgaa acgctgctga acctgtacgc caagtaa      1317


<210> SEQ ID NO 142
<211> LENGTH: 438
<212> TYPE: PRT
<213> ORGANISM: Unknown
<220> FEATURE:
<223> OTHER INFORMATION: Obtained from environmental sample

<400> SEQUENCE: 142

Met Thr Asn Glu Tyr Phe Pro Gly Ile Gly Val Ile Pro Phe Glu Gly
1               5                   10                  15

Gln Glu Ser Lys Asn Pro Met Ala Phe His Tyr Tyr Asp Ala Asn Arg
            20                  25                  30

Val Val Met Gly Lys Pro Met Lys Glu Trp Phe Lys Phe Ala Met Ala
        35                  40                  45

Trp Trp His Thr Leu Gly Gln Ala Ser Ala Asp Pro Phe Gly Gly Gln
    50                  55                  60

Thr Arg Ser Tyr Ala Trp Asp Lys Gly Glu Cys Pro Tyr Cys Arg Ala
65                  70                  75                  80

Arg Gln Lys Ala Asp Ala Gly Phe Glu Leu Met Gln Lys Leu Gly Ile
                85                  90                  95

Gly Tyr Phe Cys Phe His Asp Val Asp Ile Ile Glu Asp Cys Glu Asp
            100                 105                 110

Ile Ala Glu Tyr Glu Ala Arg Met Lys Asp Ile Thr Asp Tyr Leu Leu
        115                 120                 125

Val Lys Met Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Gln
145                 150                 155                 160

Phe Asp Val Val Ala Arg Ala Ala Val Gln Ile Lys Asn Ala Leu Asp
                165                 170                 175

Ala Thr Ile Lys Leu Gly Gly Ser Asn Tyr Val Phe Trp Gly Gly Arg
            180                 185                 190

Glu Gly Tyr Tyr Thr Leu Trp Asn Thr Gln Met Arg Arg Glu Lys Asp
        195                 200                 205

His Leu Ala Gln Met Leu Lys Ala Ala Arg Asp Tyr Ala Arg Gly Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270
```

Ala Thr Leu Ala Gly His Thr Phe Glu His Glu Leu Thr Val Ala Arg
275 280 285

Glu Asn Gly Phe Leu Gly Ser Ile Asp Ala Asn Arg Gly Asp Ala Gln
290 295 300

Asn Gly Trp Asp Thr Asp Gln Phe Pro Ile Asp Ala Phe Asp Leu Thr
305 310 315 320

Gln Ala Met Met Gln Val Leu Leu Asn Gly Gly Phe Gly Asn Gly Gly
325 330 335

Thr Asn Phe Asp Ala Lys Leu Arg Arg Ser Ser Thr Asp Pro Glu Asp
340 345 350

Ile Phe Ile Ala His Ile Gly Ala Met Asp Ala Met Ala His Ala Leu
355 360 365

Leu Asn Ala Ala Ala Ile Leu Glu Glu Ser Pro Met Pro Gly Met Val
370 375 380

Lys Glu Arg Tyr Ala Ser Phe Asp Asn Gly Leu Gly Lys Lys Phe Glu
385 390 395 400

Glu Gly Lys Ala Thr Leu Glu Glu Leu Tyr Asp Tyr Ala Lys Lys Asn
405 410 415

Gly Glu Pro Val Ala Ala Ser Gly Lys Gln Glu Leu Tyr Glu Thr Leu
420 425 430

Leu Asn Leu Tyr Ala Lys
435

<210> SEQ ID NO 143
<211> LENGTH: 1314
<212> TYPE: DNA
<213> ORGANISM: Unknown
<220> FEATURE:
<223> OTHER INFORMATION: Obtained from environmental sample

<400> SEQUENCE: 143
atgaaagaat acttccctac catcggaaaa atccctttcg agggccctca gagcaagaat 60
ccgctcgcat tccattacta tgacgccaac cgcgttgtcg ccggcaaacc catgaaggac 120
tggctcaagt tcgccatggc ttggtggcac accctgggcg cagcatcggc agaccccttc 180
ggcggccaga cccgcagcta cgagtgggac aaagccgagt gcccttactg ccgtgcccgt 240
gaaaaggccg acgccggctt cgagatcatg cagaaacttg gaatcgagta cttctgcttc 300
catgacatcg accttgtgga agactgcgag gacattgccg agtacgaggc ccgcatgaag 360
gacatcacgg actacctcct ggagaagatg aaggccaccg gcatcaagaa cctgtggggc 420
accgccaacg tctttggcaa caagcgctac atgaacggcg cagccaccaa ccctcagttc 480
gacatcgttg cccgtgcagc tgtccagatc aagaacgcca tcgacgcaac aatcaagctg 540
ggcggtaccg gttacgtatt ctggggcggc cgcgagggct actacaccct cctgaacacc 600
cagatgcagc gcgagaagga ccaccttgcc aagatgctca ccgcagcccg cgactacgcc 660
cgcgccaagg gattcaaggg cacattcctc atcgagccca agcccatgga gcccaccaag 720
caccagtacg atgttgacac ggaaaccgtc atcggcttcc tccgcgccaa cggcctggac 780
aaggacttca aggtgaacat cgaggtgaac cacgccaccc tggccggcca caccttcgag 840
cacgagctca ccgtggccgt ggacaacggc ttcctgggca gcatcgacgc aaaccgcggc 900
gacgcccaga acggctggga cactgaccag ttccctgtgg atccttacga cctcacccag 960
gcaatgatgc agattatccg caacggcggc ttcaaggacg gcggcaccaa cttcgacgcc 1020
aaactccgcc gcagctccac ggaccccgag gacatcttca tcgcccacat cagcgcaatg 1080

```
gatgcaatgg cacacgccct catcaacgct gctgcagtgc ttgaggaaag ccctctgtgc   1140

gagatggttg caaagcgcta cgccagcttt gacagcggtc ttggcaagaa gttcgaggaa   1200

ggcaaagcca ctctcgagga gatctacgag tatgccaaga aggccccggc acccgtcgcc   1260

gcctccggca agcaggagct ctacgagaca ctgctcaatc tgtacgctaa ataa         1314


<210> SEQ ID NO 144
<211> LENGTH: 437
<212> TYPE: PRT
<213> ORGANISM: Unknown
<220> FEATURE:
<223> OTHER INFORMATION: Obtained from environmental sample

<400> SEQUENCE: 144

Met Lys Glu Tyr Phe Pro Thr Ile Gly Lys Ile Pro Phe Glu Gly Pro
1               5                   10                  15

Gln Ser Lys Asn Pro Leu Ala Phe His Tyr Tyr Asp Ala Asn Arg Val
            20                  25                  30

Val Ala Gly Lys Pro Met Lys Asp Trp Leu Lys Phe Ala Met Ala Trp
        35                  40                  45

Trp His Thr Leu Gly Ala Ala Ser Ala Asp Pro Phe Gly Gly Gln Thr
    50                  55                  60

Arg Ser Tyr Glu Trp Asp Lys Ala Glu Cys Pro Tyr Cys Arg Ala Arg
65                  70                  75                  80

Glu Lys Ala Asp Ala Gly Phe Glu Ile Met Gln Lys Leu Gly Ile Glu
                85                  90                  95

Tyr Phe Cys Phe His Asp Ile Asp Leu Val Glu Asp Cys Glu Asp Ile
            100                 105                 110

Ala Glu Tyr Glu Ala Arg Met Lys Asp Ile Thr Asp Tyr Leu Leu Glu
        115                 120                 125

Lys Met Lys Ala Thr Gly Ile Lys Asn Leu Trp Gly Thr Ala Asn Val
    130                 135                 140

Phe Gly Asn Lys Arg Tyr Met Asn Gly Ala Ala Thr Asn Pro Gln Phe
145                 150                 155                 160

Asp Ile Val Ala Arg Ala Ala Val Gln Ile Lys Asn Ala Ile Asp Ala
                165                 170                 175

Thr Ile Lys Leu Gly Gly Thr Gly Tyr Val Phe Trp Gly Gly Arg Glu
            180                 185                 190

Gly Tyr Tyr Thr Leu Leu Asn Thr Gln Met Gln Arg Glu Lys Asp His
        195                 200                 205

Leu Ala Lys Met Leu Thr Ala Ala Arg Asp Tyr Ala Arg Ala Lys Gly
    210                 215                 220

Phe Lys Gly Thr Phe Leu Ile Glu Pro Lys Pro Met Glu Pro Thr Lys
225                 230                 235                 240

His Gln Tyr Asp Val Asp Thr Glu Thr Val Ile Gly Phe Leu Arg Ala
                245                 250                 255

Asn Gly Leu Asp Lys Asp Phe Lys Val Asn Ile Glu Val Asn His Ala
            260                 265                 270

Thr Leu Ala Gly His Thr Phe Glu His Glu Leu Thr Val Ala Val Asp
        275                 280                 285

Asn Gly Phe Leu Gly Ser Ile Asp Ala Asn Arg Gly Asp Ala Gln Asn
    290                 295                 300

Gly Trp Asp Thr Asp Gln Phe Pro Val Asp Pro Tyr Asp Leu Thr Gln
305                 310                 315                 320
```

```
Ala Met Met Gln Ile Ile Arg Asn Gly Gly Phe Lys Asp Gly Gly Thr
                325                 330                 335

Asn Phe Asp Ala Lys Leu Arg Arg Ser Ser Thr Asp Pro Glu Asp Ile
            340                 345                 350

Phe Ile Ala His Ile Ser Ala Met Asp Ala Met Ala His Ala Leu Ile
        355                 360                 365

Asn Ala Ala Ala Val Leu Glu Glu Ser Pro Leu Cys Glu Met Val Ala
    370                 375                 380

Lys Arg Tyr Ala Ser Phe Asp Ser Gly Leu Gly Lys Lys Phe Glu Glu
385                 390                 395                 400

Gly Lys Ala Thr Leu Glu Glu Ile Tyr Glu Tyr Ala Lys Lys Ala Pro
                405                 410                 415

Ala Pro Val Ala Ala Ser Gly Lys Gln Glu Leu Tyr Glu Thr Leu Leu
            420                 425                 430

Asn Leu Tyr Ala Lys
        435
```

<210> SEQ ID NO 145
<211> LENGTH: 1317
<212> TYPE: DNA
<213> ORGANISM: Unknown
<220> FEATURE:
<223> OTHER INFORMATION: Obtained from environmental sample

<400> SEQUENCE: 145

```
atgaccaaag agtatttccc tacaatcgga aagattccct tcgaaggccc ggagagcaag      60

aatccgctgg cattccatta ctatgaaccc gacagaatca tcctcggcag gaagatgaag     120

gactggctgc gcttcgccgt ggcctggtgg cacaccctcg gccaggcgtc cggcgaccag     180

ttcggaggcc agacccgcaa ctatgcgtgg gacgagcccg aatgcccggt agagcgcgcg     240

aaagccaagg ccgacgccgg cttcgagctg atgcagaagc tgggcatcga gtatttctgc     300

ttccacgacg tagacctcat agaggaggcc gcaaccatcg aagaatatga ggagcgcatg     360

ggcatcataa ccgactacct gctcgggaag atgaaggaga caggtatcaa gaacctctgg     420

ggcaccgcca acgtgttcgg ccacaagcgt tacatgaacg gagccgccac caaccccgac     480

ttcgacgtgg tggcccgtgc ggccgtgcag atcaagaacg ccatcgacgc caccatcaag     540

ctgggcggcg agaattacgt attctggggc ggacgcgagg gctatgcaag cctgctcaac     600

actcagatgc agcgcgagaa agaccacctg ggacgcatgc tggctgcagc ccgcgactat     660

ggccgcgccc acggattcaa gggcactttc ctcatcgagc ccaaacccat ggagcctacc     720

aagcaccagt acgaccagga taccgagacc gttatcgcct tcctgcgcag gaacggcctc     780

gacaaggatt tcaaggtaaa catcgaggtg aaccacgcca ccctggcggg ccacaccttc     840

gagcacgaac tggcggtggc agtggacaac ggcctgcttg gcagcatcga cgccaaccgc     900

ggcgacgcgc agaacggatg ggacaccgac cagttcccca tcgacaactt cgagctcacc     960

caggccatgc tgcagataat ccgcaacggc ggactgggaa ccggcggatc gaacttcgac    1020

gccaagctgc gccgcaattc caccgaccct gaggatatct tcatcgccca catcagtgcg    1080

atggacgcca tggcacgcgc gctggcaaac gccgccgcaa tcatcgaaga gagccccatc    1140

cccgcaatgc tgaaggagcg ctacgcatcg ttcgacagcg gcaagggcaa ggagttcgag    1200

gacggcaaac tgagcctcga agaactggta gcctacgcca aggcgaacgg cgagccgaag    1260

cagatttccg gcaagcagga actctacgaa accatagtgg ccctctattg caagtaa       1317
```

<210> SEQ ID NO 146
<211> LENGTH: 438
<212> TYPE: PRT
<213> ORGANISM: Unknown
<220> FEATURE:
<223> OTHER INFORMATION: Obtained from environmental sample

<400> SEQUENCE: 146

```
Met Thr Lys Glu Tyr Phe Pro Thr Ile Gly Lys Ile Pro Phe Glu Gly
1               5                   10                  15

Pro Glu Ser Lys Asn Pro Leu Ala Phe His Tyr Tyr Glu Pro Asp Arg
            20                  25                  30

Ile Ile Leu Gly Arg Lys Met Lys Asp Trp Leu Arg Phe Ala Val Ala
        35                  40                  45

Trp Trp His Thr Leu Gly Gln Ala Ser Gly Asp Gln Phe Gly Gly Gln
    50                  55                  60

Thr Arg Asn Tyr Ala Trp Asp Glu Pro Glu Cys Pro Val Glu Arg Ala
65                  70                  75                  80

Lys Ala Lys Ala Asp Ala Gly Phe Glu Leu Met Gln Lys Leu Gly Ile
                85                  90                  95

Glu Tyr Phe Cys Phe His Asp Val Asp Leu Ile Glu Glu Ala Ala Thr
            100                 105                 110

Ile Glu Glu Tyr Glu Glu Arg Met Gly Ile Ile Thr Asp Tyr Leu Leu
        115                 120                 125

Gly Lys Met Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Asp
145                 150                 155                 160

Phe Asp Val Val Ala Arg Ala Ala Val Gln Ile Lys Asn Ala Ile Asp
                165                 170                 175

Ala Thr Ile Lys Leu Gly Gly Glu Asn Tyr Val Phe Trp Gly Gly Arg
            180                 185                 190

Glu Gly Tyr Ala Ser Leu Leu Asn Thr Gln Met Gln Arg Glu Lys Asp
        195                 200                 205

His Leu Gly Arg Met Leu Ala Ala Ala Arg Asp Tyr Gly Arg Ala His
    210                 215                 220

Gly Phe Lys Gly Thr Phe Leu Ile Glu Pro Lys Pro Met Glu Pro Thr
225                 230                 235                 240

Lys His Gln Tyr Asp Gln Asp Thr Glu Thr Val Ile Ala Phe Leu Arg
                245                 250                 255

Arg Asn Gly Leu Asp Lys Asp Phe Lys Val Asn Ile Glu Val Asn His
            260                 265                 270

Ala Thr Leu Ala Gly His Thr Phe Glu His Glu Leu Ala Val Ala Val
        275                 280                 285

Asp Asn Gly Leu Leu Gly Ser Ile Asp Ala Asn Arg Gly Asp Ala Gln
    290                 295                 300

Asn Gly Trp Asp Thr Asp Gln Phe Pro Ile Asp Asn Phe Glu Leu Thr
305                 310                 315                 320

Gln Ala Met Leu Gln Ile Ile Arg Asn Gly Gly Leu Gly Thr Gly Gly
                325                 330                 335

Ser Asn Phe Asp Ala Lys Leu Arg Arg Asn Ser Thr Asp Pro Glu Asp
            340                 345                 350

Ile Phe Ile Ala His Ile Ser Ala Met Asp Ala Met Ala Arg Ala Leu
        355                 360                 365

Ala Asn Ala Ala Ala Ile Ile Glu Glu Ser Pro Ile Pro Ala Met Leu
```

-continued

```
    370                 375                 380

Lys Glu Arg Tyr Ala Ser Phe Asp Ser Gly Lys Gly Lys Glu Phe Glu
385                 390                 395                 400

Asp Gly Lys Leu Ser Leu Glu Glu Leu Val Ala Tyr Ala Lys Ala Asn
                405                 410                 415

Gly Glu Pro Lys Gln Ile Ser Gly Lys Gln Glu Leu Tyr Glu Thr Ile
            420                 425                 430

Val Ala Leu Tyr Cys Lys
        435


<210> SEQ ID NO 147
<211> LENGTH: 1317
<212> TYPE: DNA
<213> ORGANISM: Unknown
<220> FEATURE:
<223> OTHER INFORMATION: Obtained from environmental sample

<400> SEQUENCE: 147

atggcacaag aatacttccc taccattggg aaaatcccct tcgagggcac tgagagcaag      60

aatcccccttg ctttccatta ctatgagccg gagcgcattg tctgcggcaa acccatgaaa    120

gaatggctca agtttgccat ggcctggtgg cacacgctgg ggcaggcatc ggccgatccc    180

ttcggcggcc aaacccgcag ctatgcctgg gataagggcg aatgccccta ctgccgtgcc    240

cgcgccaagg cggacgccgg cttcgagatt atgcaaaagc tgggcatcga gtacttctgc    300

ttccacgata tcgacctggt agaagactgt gacgatattg cggaatacga agcccgcatg    360

aaggacatca cggactacct cctggagaag atgaaggaaa ccggtatcaa gaacctctgg    420

ggcaccgcca atgtgtttgg tcacaagcgc tacatgaacg gcgccgccac caacccgcag    480

tttgacgtag tggcccgtgc cgctgttcag attaagaacg ccattgacgc caccatcaag    540

ttgggcggtg ccaattacgt gttctggggc ggccgcgagg gctattacag cctcctgaac    600

acccagatgc agcgggagaa ggaccacctg gccaagctgc tcacggcagc ccgcgactat    660

gcccgcgcca acggcttcaa gggaaccttc ctgattgagc ccaagcccat ggagcccacc    720

aagcaccagt acgacgtgga tacggagacg gtcattggct tcctccgcgc caacggcctg    780

gacaaggact tcaaggtgaa tatcgaggtg aaccacgcca cgttggccgg ccacaccttt    840

gagcacgagc tcaccgtggc ccgcgagaac ggcttcctgg gcagcatcga cgccaaccgc    900

ggcgatgccc agaacggctg ggatacggac cagttcccgg tagacgctta tgagctcacc    960

caggccatga tgcaggtgct cctgaacgga ggcttcggca acggcggcac caacttcgac   1020

gccaagctgc gccgctcctc cacggacccg gaggacatct tcatcgccca tatcagtgcg   1080

atggatgcca tggcccacgc cctgctcaac gccgccgccg tgctggagga aagccccctg   1140

tgccagatgg tgaaggagcg ctacgccagc tttgacagcg gtccgggcaa gcagttcgag   1200

gaaggaaagg ccaccctgga ggacctgtac aactacgcca aagccaccgg tgaacccgtg   1260

gttgcctccg gcaagcagga actttacgag accctcctga acctctatgc aaagtag       1317


<210> SEQ ID NO 148
<211> LENGTH: 438
<212> TYPE: PRT
<213> ORGANISM: Unknown
<220> FEATURE:
<223> OTHER INFORMATION: Obtained from environmental sample

<400> SEQUENCE: 148

Met Ala Gln Glu Tyr Phe Pro Thr Ile Gly Lys Ile Pro Phe Glu Gly
```

-continued

```
1               5                   10                  15

Thr Glu Ser Lys Asn Pro Leu Ala Phe His Tyr Tyr Glu Pro Glu Arg
            20                  25                  30

Ile Val Cys Gly Lys Pro Met Lys Glu Trp Leu Lys Phe Ala Met Ala
        35                  40                  45

Trp Trp His Thr Leu Gly Gln Ala Ser Ala Asp Pro Phe Gly Gly Gln
    50                  55                  60

Thr Arg Ser Tyr Ala Trp Asp Lys Gly Glu Cys Pro Tyr Cys Arg Ala
65                  70                  75                  80

Arg Ala Lys Ala Asp Ala Gly Phe Glu Ile Met Gln Lys Leu Gly Ile
                85                  90                  95

Glu Tyr Phe Cys Phe His Asp Ile Asp Leu Val Glu Asp Cys Asp Asp
            100                 105                 110

Ile Ala Glu Tyr Glu Ala Arg Met Lys Asp Ile Thr Asp Tyr Leu Leu
        115                 120                 125

Glu Lys Met Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Gln
145                 150                 155                 160

Phe Asp Val Val Ala Arg Ala Ala Val Gln Ile Lys Asn Ala Ile Asp
                165                 170                 175

Ala Thr Ile Lys Leu Gly Gly Ala Asn Tyr Val Phe Trp Gly Gly Arg
            180                 185                 190

Glu Gly Tyr Tyr Ser Leu Leu Asn Thr Gln Met Gln Arg Glu Lys Asp
        195                 200                 205

His Leu Ala Lys Leu Leu Thr Ala Ala Arg Asp Tyr Ala Arg Ala Asn
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Arg
        275                 280                 285

Glu Asn Gly Phe Leu Gly Ser Ile Asp Ala Asn Arg Gly Asp Ala Gln
    290                 295                 300

Asn Gly Trp Asp Thr Asp Gln Phe Pro Val Asp Ala Tyr Glu Leu Thr
305                 310                 315                 320

Gln Ala Met Met Gln Val Leu Leu Asn Gly Gly Phe Gly Asn Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Val Leu Glu Glu Ser Pro Leu Cys Gln Met Val
    370                 375                 380

Lys Glu Arg Tyr Ala Ser Phe Asp Ser Gly Pro Gly Lys Gln Phe Glu
385                 390                 395                 400

Glu Gly Lys Ala Thr Leu Glu Asp Leu Tyr Asn Tyr Ala Lys Ala Thr
                405                 410                 415

Gly Glu Pro Val Val Ala Ser Gly Lys Gln Glu Leu Tyr Glu Thr Leu
            420                 425                 430
```

Leu Asn Leu Tyr Ala Lys
        435

<210> SEQ ID NO 149
<211> LENGTH: 1317
<212> TYPE: DNA
<213> ORGANISM: Unknown
<220> FEATURE:
<223> OTHER INFORMATION: Obtained from environmental sample

<400> SEQUENCE: 149
atggcacaag aatacttccc taccattggg aaaatcccct tcgagggcac tgagagcaag 60
aatccccttg ctttccatta ctatgagccg gagcgcattg tctgcggcaa acccatgaaa 120
gaatggctca agtttgccat ggcctggtgg cacacgctgg ggcaggcatc ggccgatccc 180
ttcggcggcc aaacccgcag ctatgcctgg gataagggcg aatgccccta ctgccgtgcc 240
cgtgccaagg cggacgccgg ttttgagatt atgcaaaagc tgggcatcga gtacttctgc 300
ttccacgata tcgacctggt agaagactgt gacgatattg cggaatacga agcccgcatg 360
aaggacatca cggactacct cctggagaag atgaaggaaa ccggcatcaa gaacctctgg 420
ggcaccgcca atgtgtttgg tcacaagcgc tacatgaacg gcgccggcac caatccgcag 480
tttgacgtgg tggcccgtgc tgccgtgcaa atcaagaacg ccattgacgc caccatcaag 540
ttgggcggtg ccaattacgt gttctggggc ggccgcgagg gctattacag cctcctgaac 600
acccagatgc agcgggagaa ggaccacctg gccaagctgc tcacggcagc ccgcgactat 660
gcccgcgcca acggcttcaa gggaaccttc ctgattgagc ccaagcccat ggagcccacc 720
aagcaccagt acgacgtgga tacggagacg gtcattggct tcctccgcgc caacggcctg 780
gacaaggact tcaaggtgaa tatcgaggtg aaccacgcca cgctggccgg ccacaccttt 840
gagcacgaac tcaccgtggc ccgcgagaac ggcttcctgg gcagcatcga cgccaaccgc 900
ggcgatgccc agaacggctg ggatacggac cagttcccgg tagacgctta tgagctcacc 960
caggccatga tgcaggtgct cctgaacgga ggcttcggca acggcggcac caacttcgac 1020
gccaagctgc gccgctcctc cacggacctg gaggacatct tcatcgccca tatcagtgcg 1080
atggatgcca tggcccacgc cctgctcaac gccgccgccg tgctggagga aagccccctg 1140
tgccagatgg tgaaggagcg ctacgccagc tttgacagcg gtccgggcaa gcagttcgag 1200
gaaggaaagg ccaccctgga ggacctgtac aactacgcca aagccaacgg tgaacccgtg 1260
gttgcctccg gcaagcagga actttacgag accctcctga acctctatgc aaagtag 1317

<210> SEQ ID NO 150
<211> LENGTH: 438
<212> TYPE: PRT
<213> ORGANISM: Unknown
<220> FEATURE:
<223> OTHER INFORMATION: Obtained from environmental sample

<400> SEQUENCE: 150

Met Ala Gln Glu Tyr Phe Pro Thr Ile Gly Lys Ile Pro Phe Glu Gly
1               5                   10                  15

Thr Glu Ser Lys Asn Pro Leu Ala Phe His Tyr Tyr Glu Pro Glu Arg
            20                  25                  30

Ile Val Cys Gly Lys Pro Met Lys Glu Trp Leu Lys Phe Ala Met Ala
        35                  40                  45

Trp Trp His Thr Leu Gly Gln Ala Ser Ala Asp Pro Phe Gly Gly Gln
    50                  55                  60

```
Thr Arg Ser Tyr Ala Trp Asp Lys Gly Glu Cys Pro Tyr Cys Arg Ala
65                  70                  75                  80

Arg Ala Lys Ala Asp Ala Gly Phe Glu Ile Met Gln Lys Leu Gly Ile
                85                  90                  95

Glu Tyr Phe Cys Phe His Asp Ile Asp Leu Val Glu Asp Cys Asp Asp
            100                 105                 110

Ile Ala Glu Tyr Glu Ala Arg Met Lys Asp Ile Thr Asp Tyr Leu Leu
        115                 120                 125

Glu Lys Met Lys Glu Thr Gly Ile Lys Asn Leu Trp Gly Thr Ala Asn
    130                 135                 140

Val Phe Gly His Lys Arg Tyr Met Asn Gly Ala Gly Thr Asn Pro Gln
145                 150                 155                 160

Phe Asp Val Val Ala Arg Ala Ala Val Gln Ile Lys Asn Ala Ile Asp
                165                 170                 175

Ala Thr Ile Lys Leu Gly Gly Ala Asn Tyr Val Phe Trp Gly Gly Arg
            180                 185                 190

Glu Gly Tyr Tyr Ser Leu Leu Asn Thr Gln Met Gln Arg Glu Lys Asp
        195                 200                 205

His Leu Ala Lys Leu Leu Thr Ala Ala Arg Asp Tyr Ala Arg Ala Asn
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Arg
        275                 280                 285

Glu Asn Gly Phe Leu Gly Ser Ile Asp Ala Asn Arg Gly Asp Ala Gln
    290                 295                 300

Asn Gly Trp Asp Thr Asp Gln Phe Pro Val Asp Ala Tyr Glu Leu Thr
305                 310                 315                 320

Gln Ala Met Met Gln Val Leu Leu Asn Gly Gly Phe Gly Asn Gly Gly
                325                 330                 335

Thr Asn Phe Asp Ala Lys Leu Arg Arg Ser Ser Thr Asp Leu Glu Asp
            340                 345                 350

Ile Phe Ile Ala His Ile Ser Ala Met Asp Ala Met Ala His Ala Leu
        355                 360                 365

Leu Asn Ala Ala Ala Val Leu Glu Glu Ser Pro Leu Cys Gln Met Val
    370                 375                 380

Lys Glu Arg Tyr Ala Ser Phe Asp Ser Gly Pro Gly Lys Gln Phe Glu
385                 390                 395                 400

Glu Gly Lys Ala Thr Leu Glu Asp Leu Tyr Asn Tyr Ala Lys Ala Asn
                405                 410                 415

Gly Glu Pro Val Val Ala Ser Gly Lys Gln Glu Leu Tyr Glu Thr Leu
            420                 425                 430

Leu Asn Leu Tyr Ala Lys
        435
```

<210> SEQ ID NO 151
<211> LENGTH: 1317
<212> TYPE: DNA
<213> ORGANISM: Unknown
<220> FEATURE:

<223> OTHER INFORMATION: Obtained from environmental sample

<400> SEQUENCE: 151
atggcaaaag aatatttccc taccatcggc aagattcctt ttgaaggaac cgacagcaag 60
agtcccctcg ccttccatta ctatgacgcc cagcgcgttg tgatgggcaa acccatgaag 120
gaatggctca agttcgccat ggcctggtgg cacaccctgg gccaggcatc ggccgacccc 180
ttcggcggtc agacccgcca ctatgcctgg gatgaaggcg aatgccccta ctgccgcgcc 240
aaagccaagg ccgacgccgg cttcgagatc atgcagaaac tgggcatcga gtacttctgc 300
ttccacgatg tggacctggt ggaagactgc gacgacatcg ccgagtacga agcccgcatg 360
aaggacatca cggactacct gctggagaag atgaaggaaa ccggcatcaa gaacctctgg 420
ggcacggcca atgtgttcgg ccacaagcgt tacatgaacg gcgccgggac caacccgcag 480
tttgacattg tggcccgcgc tgccgtccag atcaaaaacg ccctggacgc caccatcaag 540
ctgggcggtt ccaactacgt gttctggggc agccgcgaag gctactacac cctcctgaac 600
acccagatgc agcgggagaa agaccacctg gccaagctcc tgaccgccgc ccgcgactac 660
gcccgcgcca aaggcttcaa gggaaccttc ctcatcgagc ccaaacccat ggagcccacc 720
aagcaccagt acgacgtgga caccgagacc gtaatcggct tcctgcgtgc caacggcctg 780
gacaaggact tcaaggtgaa catcgaggtg aaccacgcca ccctggctgg ccacaccttc 840
gagcacgaac tcaccgtcgc ccgtgaaaac ggcttcctcg gatcgatcga cgccaaccgc 900
ggcgacgccc agaacggctg ggacaccgac cagttccccg tagacgccta tgacctcacc 960
caggccatga tgcaggtgct gctgaacggc ggtttcggca atggcggtac caacttcgac 1020
gccaagctcc gccgctcctc cacggatccg gaagacatct tcatcgccca catcagcgcc 1080
atggacgcca tggcccacgc cctgctgaac gccgccgccg tgctggaaga aagcccgctt 1140
cccgccatgg cgaaagagcg ctacgcctcc tttgacagcg gacttggcaa gaagttcgaa 1200
gagggaaagg ccaccctcga agagctgtac gactatgcca aggctaacga cgcccctgtc 1260
gccgcctccg gcaagcagga actttacgaa accttcttga acctctatgc aaaatag 1317

<210> SEQ ID NO 152
<211> LENGTH: 438
<212> TYPE: PRT
<213> ORGANISM: Unknown
<220> FEATURE:
<223> OTHER INFORMATION: Obtained from environmental sample

<400> SEQUENCE: 152

Met Ala Lys Glu Tyr Phe Pro Thr Ile Gly Lys Ile Pro Phe Glu Gly
1 5 10 15

Thr Asp Ser Lys Ser Pro Leu Ala Phe His Tyr Tyr Asp Ala Gln Arg
20 25 30

Val Val Met Gly Lys Pro Met Lys Glu Trp Leu Lys Phe Ala Met Ala
35 40 45

Trp Trp His Thr Leu Gly Gln Ala Ser Ala Asp Pro Phe Gly Gly Gln
50 55 60

Thr Arg His Tyr Ala Trp Asp Glu Gly Glu Cys Pro Tyr Cys Arg Ala
65 70 75 80

Lys Ala Lys Ala Asp Ala Gly Phe Glu Ile Met Gln Lys Leu Gly Ile
85 90 95

Glu Tyr Phe Cys Phe His Asp Val Asp Leu Val Glu Asp Cys Asp Asp
100 105 110

```
Ile Ala Glu Tyr Glu Ala Arg Met Lys Asp Ile Thr Asp Tyr Leu Leu
        115                 120                 125

Glu Lys Met Lys Glu Thr Gly Ile Lys Asn Leu Trp Gly Thr Ala Asn
    130                 135                 140

Val Phe Gly His Lys Arg Tyr Met Asn Gly Ala Gly Thr Asn Pro Gln
145                 150                 155                 160

Phe Asp Ile Val Ala Arg Ala Ala Val Gln Ile Lys Asn Ala Leu Asp
                165                 170                 175

Ala Thr Ile Lys Leu Gly Gly Ser Asn Tyr Val Phe Trp Gly Ser Arg
            180                 185                 190

Glu Gly Tyr Tyr Thr Leu Leu Asn Thr Gln Met Gln Arg Glu Lys Asp
        195                 200                 205

His Leu Ala Lys Leu Leu Thr Ala Ala Arg Asp Tyr Ala Arg Ala Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Arg
        275                 280                 285

Glu Asn Gly Phe Leu Gly Ser Ile Asp Ala Asn Arg Gly Asp Ala Gln
    290                 295                 300

Asn Gly Trp Asp Thr Asp Gln Phe Pro Val Asp Ala Tyr Asp Leu Thr
305                 310                 315                 320

Gln Ala Met Met Gln Val Leu Leu Asn Gly Gly Phe Gly Asn Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Val Leu Glu Glu Ser Pro Leu Pro Ala Met Ala
    370                 375                 380

Lys Glu Arg Tyr Ala Ser Phe Asp Ser Gly Leu Gly Lys Lys Phe Glu
385                 390                 395                 400

Glu Gly Lys Ala Thr Leu Glu Glu Leu Tyr Asp Tyr Ala Lys Ala Asn
                405                 410                 415

Asp Ala Pro Val Ala Ala Ser Gly Lys Gln Glu Leu Tyr Glu Thr Phe
            420                 425                 430

Leu Asn Leu Tyr Ala Lys
        435
```

<210> SEQ ID NO 153
<211> LENGTH: 1317
<212> TYPE: DNA
<213> ORGANISM: Unknown
<220> FEATURE:
<223> OTHER INFORMATION: Obtained from environmental sample

<400> SEQUENCE: 153

```
atggcaaaac agtattttcc gcaaatcgga aagattaaat tcgaaggaac agagagcaag      60

aatccgcttg cgttccatta ttatgacgca aacagggtag tcctcggaaa ggcaatggag     120

gagtggctca agttcgcaat ggcttggtgg catactctcg gacaggcttc cggagaccag     180
```

```
ttcggcggcc agacccgcag ctacgagtgg gatcttgcag ccacccccga gcagcgcgca    240

aaggacaagc tcgacgccgg cttcgaaata atggagaaac ttggaatcaa gtatttctgt    300

ttccacgatg ttgaccttat cgaagacagc gacgatattg cgacatatga ggctcgtctc    360

aaggacctta cagactacgc tgcagagcag atgaagctcc acgacatcaa gctcctctgg    420

ggtacagcga atgtattcgg caacaagcgc tacatgaacg gtgcggctac aaaccctgat    480

ttcgatgtag ttgcccgcgc agccgttcag attaagaacg ctatcgacgc gaccatcaag    540

ctcggtggta ccagctatgt attctggggc ggtcgtgagg gatatcagag cctgctcaac    600

actcagatgc agcgtgagaa ggaccacctc gcaaccatgc ttacaatcgc tcgcgactat    660

gctcgcagca agggctttac cggaaccttc cttatcgagc ctaagccgat ggagcctaca    720

aaacaccagt acgacgtaga tacagagact gttgtcggct tcctcaaggc acacggcctg    780

gacaaggact tcaaggtaaa tatcgaggtt aaccacgcaa ctctcgcagg ccacaccttc    840

gagcacgaac tcaccgttgc tgtggataac ggaatgctcg gttctatcga cgctaaccgc    900

ggtgatgcac agaacggctg ggatacagac cagttccctg taagcgctga ggagcttacc    960

ctcgctatga tgcagattat ccgtaatggt ggccttggca acggaggatc caacttcgac   1020

gcaaagcttc gccgcaactc taccgatcct gaagacatct tcatcgcaca catctgcggt   1080

atggatgcaa tggcacacgc tctcctcaat gcagctgcaa ttatcgagga gtctcctatc   1140

cctacaatgg ttaaggagcg ttacgcttcc ttcgacagcg gtatgggtaa ggacttcgag   1200

gatggaaagc ttaccctcga ggatctctac agctacggcg tgaagaacgg agagccaaag   1260

cagaccagcg caaagcagga gctctatgag actctcatga atatctattg caagtaa      1317
```

```
<210> SEQ ID NO 154
<211> LENGTH: 438
<212> TYPE: PRT
<213> ORGANISM: Unknown
<220> FEATURE:
<223> OTHER INFORMATION: Obtained from environmental sample

<400> SEQUENCE: 154

Met Ala Lys Gln Tyr Phe Pro Gln Ile Gly Lys Ile Lys Phe Glu Gly
1               5                   10                  15

Thr Glu Ser Lys Asn Pro Leu Ala Phe His Tyr Tyr Asp Ala Asn Arg
            20                  25                  30

Val Val Leu Gly Lys Ala Met Glu Glu Trp Leu Lys Phe Ala Met Ala
        35                  40                  45

Trp Trp His Thr Leu Gly Gln Ala Ser Gly Asp Gln Phe Gly Gly Gln
    50                  55                  60

Thr Arg Ser Tyr Glu Trp Asp Leu Ala Ala Thr Pro Glu Gln Arg Ala
65                  70                  75                  80

Lys Asp Lys Leu Asp Ala Gly Phe Glu Ile Met Glu Lys Leu Gly Ile
                85                  90                  95

Lys Tyr Phe Cys Phe His Asp Val Asp Leu Ile Glu Asp Ser Asp Asp
            100                 105                 110

Ile Ala Thr Tyr Glu Ala Arg Leu Lys Asp Leu Thr Asp Tyr Ala Ala
        115                 120                 125

Glu Gln Met Lys Leu His Asp Ile Lys Leu Leu Trp Gly Thr Ala Asn
    130                 135                 140

Val Phe Gly Asn Lys Arg Tyr Met Asn Gly Ala Ala Thr Asn Pro Asp
145                 150                 155                 160

Phe Asp Val Val Ala Arg Ala Ala Val Gln Ile Lys Asn Ala Ile Asp
```

```
                165                 170                 175

Ala Thr Ile Lys Leu Gly Gly Thr Ser Tyr Val Phe Trp Gly Gly Arg
            180                 185                 190

Glu Gly Tyr Gln Ser Leu Leu Asn Thr Gln Met Gln Arg Glu Lys Asp
        195                 200                 205

His Leu Ala Thr Met Leu Thr Ile Ala Arg Asp Tyr Ala Arg Ser Lys
    210                 215                 220

Gly Phe Thr Gly Thr Phe Leu Ile Glu Pro Lys Pro Met Glu Pro Thr
225                 230                 235                 240

Lys His Gln Tyr Asp Val Asp Thr Glu Thr Val Val Gly Phe Leu Lys
                245                 250                 255

Ala His Gly Leu Asp Lys Asp Phe Lys Val Asn Ile Glu Val Asn His
            260                 265                 270

Ala Thr Leu Ala Gly His Thr Phe Glu His Glu Leu Thr Val Ala Val
        275                 280                 285

Asp Asn Gly Met Leu Gly Ser Ile Asp Ala Asn Arg Gly Asp Ala Gln
    290                 295                 300

Asn Gly Trp Asp Thr Asp Gln Phe Pro Val Ser Ala Glu Glu Leu Thr
305                 310                 315                 320

Leu Ala Met Met Gln Ile Ile Arg Asn Gly Gly Leu Gly Asn Gly Gly
                325                 330                 335

Ser Asn Phe Asp Ala Lys Leu Arg Arg Asn Ser Thr Asp Pro Glu Asp
            340                 345                 350

Ile Phe Ile Ala His Ile Cys Gly Met Asp Ala Met Ala His Ala Leu
        355                 360                 365

Leu Asn Ala Ala Ala Ile Ile Glu Glu Ser Pro Ile Pro Thr Met Val
    370                 375                 380

Lys Glu Arg Tyr Ala Ser Phe Asp Ser Gly Met Gly Lys Asp Phe Glu
385                 390                 395                 400

Asp Gly Lys Leu Thr Leu Glu Asp Leu Tyr Ser Tyr Gly Val Lys Asn
                405                 410                 415

Gly Glu Pro Lys Gln Thr Ser Ala Lys Gln Glu Leu Tyr Glu Thr Leu
            420                 425                 430

Met Asn Ile Tyr Cys Lys
        435
```

<210> SEQ ID NO 155
<211> LENGTH: 1317
<212> TYPE: DNA
<213> ORGANISM: Unknown
<220> FEATURE:
<223> OTHER INFORMATION: Obtained from environmental sample

<400> SEQUENCE: 155

```
atggcaaaag aatttttttcc acaagtaggc aagattccat ttgagggtcc tgaaagtact     60

aacgtactcg cattccacta ctatgatcca gaacgcgaag ttcttggtaa gaaaatgaaa    120

gattggctga agtatgctat ggcttggtgg cacacactcg gtcaggcaag tggcgaccaa    180

ttcggtggtc aaactcgttc gtatgaatgg gatgaagccg acgatgttct tcaacgcgca    240

aaggataaaa tggatgctgg ttttgaattg atgaccaaac ttggcattga atactactgc    300

ttccatgatg tcgaccttat tgaagaaggt gcaacaattg aagaatatga agctcgtatg    360

caagctatca ccgactacgc attagaaaaa caaaaagaaa ccggcattaa gctcctttgg    420

ggtactgcta atgtgtttgg tcataagcgt tatatgaatg gtgcggcaac aaaccctgac    480
```

```
tttgatgtag tggctcgcgc tgctgtacaa atcaagaacg ctatcgatgc aactatcaag    540

cttggtggtc aaaactatgt attctggggt ggccgcgaag gttatatgag tttgctcaac    600

actcaaatgc aacgcgaaaa agaccacttg gcaaagatgc ttaccgcagc tcgcgactat    660

gctcgtgcta agggcttcaa gggtacattc ctcgttgaac ctaagcctat ggaaccaact    720

aagcatcaat atgataccga tacagaaact gtgattggtt tcctccgtgc aaatggtctt    780

gaaaaagact tcaaggtgaa cattgaagtg aaccatgcta ctctcgctca gcacactttc    840

gaacacgaac tcgctgtggc tgtcgacaat ggcatgctcg gttctatcga cgctaaccgt    900

ggcgatgctc aaaatggctg ggataccgac caattcccaa tcgacaacta cgaactcacc    960

ctcgctatgc tccaaatcat tcgcaatggt ggtcttggca atggcggtag caacctcgac   1020

gctaagattc gtcgtaatag caccgacctt gaagacctct ttatcgctca catcagtggt   1080

atggatgcta tggctcgtgc acttctcaat gctgctgcaa tcgttgaaaa gagcgaaatt   1140

cctgctatgt tgaagcagcg ttatgcaagc tctgatgcag gtatgggtaa ggacttcgaa   1200

gaaggaaaac tcactctcga acaactcgta gactatgcta aggctaacgg cgaacctgct   1260

acagtaagcg gcaagcaaga aaagtatgaa actctcgttg ctctctacgc taagtaa      1317
```

```
<210> SEQ ID NO 156
<211> LENGTH: 438
<212> TYPE: PRT
<213> ORGANISM: Unknown
<220> FEATURE:
<223> OTHER INFORMATION: Obtained from environmental sample

<400> SEQUENCE: 156

Met Ala Lys Glu Phe Phe Pro Gln Val Gly Lys Ile Pro Phe Glu Gly
1               5                   10                  15

Pro Glu Ser Thr Asn Val Leu Ala Phe His Tyr Tyr Asp Pro Glu Arg
            20                  25                  30

Glu Val Leu Gly Lys Lys Met Lys Asp Trp Leu Lys Tyr Ala Met Ala
        35                  40                  45

Trp Trp His Thr Leu Gly Gln Ala Ser Gly Asp Gln Phe Gly Gly Gln
    50                  55                  60

Thr Arg Ser Tyr Glu Trp Asp Glu Ala Asp Asp Val Leu Gln Arg Ala
65                  70                  75                  80

Lys Asp Lys Met Asp Ala Gly Phe Glu Leu Met Thr Lys Leu Gly Ile
                85                  90                  95

Glu Tyr Tyr Cys Phe His Asp Val Asp Leu Ile Glu Glu Gly Ala Thr
            100                 105                 110

Ile Glu Glu Tyr Glu Ala Arg Met Gln Ala Ile Thr Asp Tyr Ala Leu
        115                 120                 125

Glu Lys Gln Lys Glu Thr Gly Ile Lys Leu Leu Trp Gly Thr Ala Asn
    130                 135                 140

Val Phe Gly His Lys Arg Tyr Met Asn Gly Ala Ala Thr Asn Pro Asp
145                 150                 155                 160

Phe Asp Val Val Ala Arg Ala Ala Val Gln Ile Lys Asn Ala Ile Asp
                165                 170                 175

Ala Thr Ile Lys Leu Gly Gly Gln Asn Tyr Val Phe Trp Gly Gly Arg
            180                 185                 190

Glu Gly Tyr Met Ser Leu Leu Asn Thr Gln Met Gln Arg Glu Lys Asp
        195                 200                 205

His Leu Ala Lys Met Leu Thr Ala Ala Arg Asp Tyr Ala Arg Ala Lys
    210                 215                 220
```

```
Gly Phe Lys Gly Thr Phe Leu Val Glu Pro Lys Pro Met Glu Pro Thr
225                 230                 235                 240

Lys His Gln Tyr Asp Thr Asp Thr Glu Thr Val Ile Gly Phe Leu Arg
                245                 250                 255

Ala Asn Gly Leu Glu Lys Asp Phe Lys Val Asn Ile Glu Val Asn His
            260                 265                 270

Ala Thr Leu Ala Gln His Thr Phe Glu His Glu Leu Ala Val Ala Val
        275                 280                 285

Asp Asn Gly Met Leu Gly Ser Ile Asp Ala Asn Arg Gly Asp Ala Gln
    290                 295                 300

Asn Gly Trp Asp Thr Asp Gln Phe Pro Ile Asp Asn Tyr Glu Leu Thr
305                 310                 315                 320

Leu Ala Met Leu Gln Ile Ile Arg Asn Gly Gly Leu Gly Asn Gly Gly
                325                 330                 335

Ser Asn Leu Asp Ala Lys Ile Arg Arg Asn Ser Thr Asp Leu Glu Asp
            340                 345                 350

Leu Phe Ile Ala His Ile Ser Gly Met Asp Ala Met Ala Arg Ala Leu
        355                 360                 365

Leu Asn Ala Ala Ala Ile Val Glu Lys Ser Glu Ile Pro Ala Met Leu
    370                 375                 380

Lys Gln Arg Tyr Ala Ser Ser Asp Ala Gly Met Gly Lys Asp Phe Glu
385                 390                 395                 400

Glu Gly Lys Leu Thr Leu Glu Gln Leu Val Asp Tyr Ala Lys Ala Asn
                405                 410                 415

Gly Glu Pro Ala Thr Val Ser Gly Lys Gln Glu Lys Tyr Glu Thr Leu
            420                 425                 430

Val Ala Leu Tyr Ala Lys
        435
```

<210> SEQ ID NO 157
<211> LENGTH: 1317
<212> TYPE: DNA
<213> ORGANISM: Unknown
<220> FEATURE:
<223> OTHER INFORMATION: Obtained from environmental sample

<400> SEQUENCE: 157

```
atgactaaag agtatttccc gggaatcgga aagattccgt ttgaaggaac caagagcaag     60

aaccccctgg ccttccatta ttataacgcc tcccaggtag cgatgggcaa gcccatgaag    120

gactggctca agtatgccat ggcctggtgg cacaccctgg gccaggcctc tgcagacccc    180

tttggcggcc agacccgctc ctacgaatgg gacaagggcg agtgccctta ttgccgcgcc    240

aagcagaagg ccgatgccgg ctttgagctc atgcagaagc tgggcatcga gtactactgc    300

ttccacgacg tggacatcat cgaggactgc gaggacattg ccgagtacga ggcccgcatg    360

aaggacatca cggactacct gctggagaag cagaaagaga ccggcatcaa gaacctctgg    420

ggcaccgcca acgtgtttgg ccacaagcgc tacatgaacg gcgccgccac caaccctcag    480

tttgacattg tggcccgtgc cgccgtccag atcaagaacg ccctggatgc caccatcaag    540

ctgggtggta ccaactacgt gttctggggt ggccgcgaag gctactacac gctgctcaac    600

acccagatgc agcgggagaa gaaccacctg gccaagatgc tcaccgccgc ccgcgactac    660

gcccgcgcca agggcttcaa gggcaccttc ctcattgagc ccaaacccat ggagcccacc    720

aagcaccagt acgacgtgga caccgagacc gtgattggtt tcatccgcgc caacggcctg    780
```

```
gacaaggact tcaaggtaaa cattgaggta aaccacgcca ccctggccgg ccacaccttt    840

gagcacgagc tcaccgtggc ccgcgagaac ggcttcctgg gctccatcga cgccaaccgc    900

ggagatgccc agaacggctg ggatacggac cagttcccca tcgacgccct ggatctcacc    960

caggctatga tgcaggtcat cctcaacggt ggcttcggca atggcggcac caactttgac   1020

gccaagctcc gccgctcctc caccgatccc gaggacatct tcatcgccca catcagcgcc   1080

atggatgcca tggcacacgc cctcctgaac gcagccgcca tcctggaaga gagccccctg   1140

cccgccatgg tcaaggagcg ttacgcttcc ttcgacagcg gtctgggcaa gaagttcgaa   1200

gaaggcaagg cctccctgga agaactttac gaatatgcca agaagaatgg agagcccgtg   1260

gccgcttccg gcaaacagga gctctgcgaa acttacttga acctctatgc aaagtag      1317
```

<210> SEQ ID NO 158
<211> LENGTH: 438
<212> TYPE: PRT
<213> ORGANISM: Unknown
<220> FEATURE:
<223> OTHER INFORMATION: Obtained from environmental sample

<400> SEQUENCE: 158

```
Met Thr Lys Glu Tyr Phe Pro Gly Ile Gly Lys Ile Pro Phe Glu Gly
1               5                   10                  15

Thr Lys Ser Lys Asn Pro Leu Ala Phe His Tyr Tyr Asn Ala Ser Gln
            20                  25                  30

Val Ala Met Gly Lys Pro Met Lys Asp Trp Leu Lys Tyr Ala Met Ala
        35                  40                  45

Trp Trp His Thr Leu Gly Gln Ala Ser Ala Asp Pro Phe Gly Gly Gln
    50                  55                  60

Thr Arg Ser Tyr Glu Trp Asp Lys Gly Glu Cys Pro Tyr Cys Arg Ala
65                  70                  75                  80

Lys Gln Lys Ala Asp Ala Gly Phe Glu Leu Met Gln Lys Leu Gly Ile
                85                  90                  95

Glu Tyr Tyr Cys Phe His Asp Val Asp Ile Ile Glu Asp Cys Glu Asp
            100                 105                 110

Ile Ala Glu Tyr Glu Ala Arg Met Lys Asp Ile Thr Asp Tyr Leu Leu
        115                 120                 125

Glu Lys Gln Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Gln
145                 150                 155                 160

Phe Asp Ile Val Ala Arg Ala Ala Val Gln Ile Lys Asn Ala Leu Asp
                165                 170                 175

Ala Thr Ile Lys Leu Gly Gly Thr Asn Tyr Val Phe Trp Gly Gly Arg
            180                 185                 190

Glu Gly Tyr Tyr Thr Leu Leu Asn Thr Gln Met Gln Arg Glu Lys Asn
        195                 200                 205

His Leu Ala Lys Met Leu Thr Ala Ala Arg Asp Tyr Ala Arg Ala Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Ile Arg
                245                 250                 255

Ala Asn Gly Leu Asp Lys Asp Phe Lys Val Asn Ile Glu Val Asn His
            260                 265                 270
```

-continued

```
Ala Thr Leu Ala Gly His Thr Phe Glu His Glu Leu Thr Val Ala Arg
        275                 280                 285

Glu Asn Gly Phe Leu Gly Ser Ile Asp Ala Asn Arg Gly Asp Ala Gln
    290                 295                 300

Asn Gly Trp Asp Thr Asp Gln Phe Pro Ile Asp Ala Leu Asp Leu Thr
305                 310                 315                 320

Gln Ala Met Met Gln Val Ile Leu Asn Gly Gly Phe Gly Asn Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Ile Leu Glu Glu Ser Pro Leu Pro Ala Met Val
    370                 375                 380

Lys Glu Arg Tyr Ala Ser Phe Asp Ser Gly Leu Gly Lys Lys Phe Glu
385                 390                 395                 400

Glu Gly Lys Ala Ser Leu Glu Glu Leu Tyr Glu Tyr Ala Lys Lys Asn
                405                 410                 415

Gly Glu Pro Val Ala Ala Ser Gly Lys Gln Glu Leu Cys Glu Thr Tyr
            420                 425                 430

Leu Asn Leu Tyr Ala Lys
        435
```

<210> SEQ ID NO 159
<211> LENGTH: 1317
<212> TYPE: DNA
<213> ORGANISM: Unknown
<220> FEATURE:
<223> OTHER INFORMATION: Obtained from environmental sample

<400> SEQUENCE: 159

```
atgactaaag agtatttccc gggaatcgga aagattccgt ttgaaggaac caagagcaag      60

aaccccctgg ccttccatta ttataacgcc tcccaggtag tgatgggcaa gcccatgaag     120

gactggctca agtatgccat ggcctggtgg cacaccctgg gccaggcctc tgcagacccc     180

tttggcggcc agacccgctc ctacgaatgg gacaagggcg agtgcccgta ctgccgcgcc     240

aagcagaagg ccgatgccgg ctttgagctc atgcagaagc tgggcatcga gtactactgc     300

ttccacgacg tggacatcat cgaggactgc gaggacattg ccgagtacga ggcccgcatg     360

aaggacatca cggactacct gctggagaag cagaaagaga ccggcatcaa gaacctctgg     420

ggcaccgcca acgtgtttgg ccacaagcgc tacatgaacg gcgccgccac caaccctcag     480

tttgacattg tggcccgtgc cgccgtccag atcaagaacg ccctggatgc caccatcaaa     540

ctgggtggta ccaactacgt gttctggggt ggccgcgaag gctactacac gctgctcaac     600

acccagatgc agcgggagaa gaaccacctg gccaagatgc tcaccgccgc ccgcgactac     660

gcccgcgcca agggcttcaa gggcaccttc ctcattgagc ccaaacccat ggagcccacc     720

aagcaccagt acgacgtgga caccgagacc gtgattggtt tcatccgcgc caacggcctg     780

gacaaggact tcaaggtaaa cattgaggta aaccacgcca ccctggccgg ccacaccttt     840

gagcacgagc tcaccgtggc ccgcgagaac ggcttcctgg gctccatcga cgccaaccgc     900

ggagatgccc agaacggctg ggatacggac cagttcccca tcgacgccct ggatctcacc     960

caggctatga tgcaggtcat cctcaacggt ggcttcggca atggcggcac caactttgac    1020

gccaagctcc gccgctcctc caccgatccc gaggacatct tcatcgccca catcagcgcc    1080
```

atggatgcca tggcacacgc cctcctgaac gcagccgcca tcctggaaga gagccccctg 1140
cccgccatgg tcaaggagcg ttacgcttcc ttcgacagcg gtctgggcaa gaagttcgaa 1200
gaaggcaagg cctccctgga agaactttac gaatatgcca agaagaatgg agagcccgtg 1260
gccgcttccg gcaaacagga gctctgcgaa acttacttga acctctatgc aaagtag 1317

<210> SEQ ID NO 160
<211> LENGTH: 438
<212> TYPE: PRT
<213> ORGANISM: Unknown
<220> FEATURE:
<223> OTHER INFORMATION: Obtained from environmental sample

<400> SEQUENCE: 160

Met Thr Lys Glu Tyr Phe Pro Gly Ile Gly Lys Ile Pro Phe Glu Gly
1 5 10 15

Thr Lys Ser Lys Asn Pro Leu Ala Phe His Tyr Tyr Asn Ala Ser Gln
20 25 30

Val Val Met Gly Lys Pro Met Lys Asp Trp Leu Lys Tyr Ala Met Ala
35 40 45

Trp Trp His Thr Leu Gly Gln Ala Ser Ala Asp Pro Phe Gly Gly Gln
50 55 60

Thr Arg Ser Tyr Glu Trp Asp Lys Gly Glu Cys Pro Tyr Cys Arg Ala
65 70 75 80

Lys Gln Lys Ala Asp Ala Gly Phe Glu Leu Met Gln Lys Leu Gly Ile
85 90 95

Glu Tyr Tyr Cys Phe His Asp Val Asp Ile Ile Glu Asp Cys Glu Asp
100 105 110

Ile Ala Glu Tyr Glu Ala Arg Met Lys Asp Ile Thr Asp Tyr Leu Leu
115 120 125

Glu Lys Gln Lys Glu Thr Gly Ile Lys Asn Leu Trp Gly Thr Ala Asn
130 135 140

Val Phe Gly His Lys Arg Tyr Met Asn Gly Ala Ala Thr Asn Pro Gln
145 150 155 160

Phe Asp Ile Val Ala Arg Ala Ala Val Gln Ile Lys Asn Ala Leu Asp
165 170 175

Ala Thr Ile Lys Leu Gly Gly Thr Asn Tyr Val Phe Trp Gly Gly Arg
180 185 190

Glu Gly Tyr Tyr Thr Leu Leu Asn Thr Gln Met Gln Arg Glu Lys Asn
195 200 205

His Leu Ala Lys Met Leu Thr Ala Ala Arg Asp Tyr Ala Arg Ala Lys
210 215 220

Gly Phe Lys Gly Thr Phe Leu Ile Glu Pro Lys Pro Met Glu Pro Thr
225 230 235 240

Lys His Gln Tyr Asp Val Asp Thr Glu Thr Val Ile Gly Phe Ile Arg
245 250 255

Ala Asn Gly Leu Asp Lys Asp Phe Lys Val Asn Ile Glu Val Asn His
260 265 270

Ala Thr Leu Ala Gly His Thr Phe Glu His Glu Leu Thr Val Ala Arg
275 280 285

Glu Asn Gly Phe Leu Gly Ser Ile Asp Ala Asn Arg Gly Asp Ala Gln
290 295 300

Asn Gly Trp Asp Thr Asp Gln Phe Pro Ile Asp Ala Leu Asp Leu Thr
305 310 315 320

Gln Ala Met Met Gln Val Ile Leu Asn Gly Gly Phe Gly Asn Gly Gly 325 330 335

Thr Asn Phe Asp Ala Lys Leu Arg Arg Ser Ser Thr Asp Pro Glu Asp
340 345 350

Ile Phe Ile Ala His Ile Ser Ala Met Asp Ala Met Ala His Ala Leu
355 360 365

Leu Asn Ala Ala Ala Ile Leu Glu Glu Ser Pro Leu Pro Ala Met Val
370 375 380

Lys Glu Arg Tyr Ala Ser Phe Asp Ser Gly Leu Gly Lys Lys Phe Glu
385 390 395 400

Glu Gly Lys Ala Ser Leu Glu Glu Leu Tyr Glu Tyr Ala Lys Lys Asn
405 410 415

Gly Glu Pro Val Ala Ala Ser Gly Lys Gln Glu Leu Cys Glu Thr Tyr
420 425 430

Leu Asn Leu Tyr Ala Lys
435

<210> SEQ ID NO 161
<211> LENGTH: 1317
<212> TYPE: DNA
<213> ORGANISM: Unknown
<220> FEATURE:
<223> OTHER INFORMATION: Obtained from environmental sample

<400> SEQUENCE: 161
atggcaaaag agtatttccc gactatcggc aagattccct tcgagggcgt cgaatccaag 60
aacccgatgg cattccacta ctatgacgcg aaccgcgtcg tgatgggcaa gcccatgaag 120
gactggctca agttcgcgat ggcctggtgg cacaccctgg gacaggcttc cggcgacccg 180
ttcggcggcc agacccgttc ctacgagtgg gacaagggcg agtgccccta ctgccgcgcc 240
aaggccaagg ccgacgccgg cttcgagatc atgcagaagc tcggtatcga gtactactgc 300
ttccatgaca tcgacctcgt ggaggacacc gaggacatcg ccgagtacga ggcccgcatg 360
aaggacatca ccgactacct cgtcgagaag cagaaggaaa ccggcatcaa gaacctctgg 420
ggcacggcca acgtgttcgg caacaagcgc tacatgaacg gcgccgccac gaacccgcag 480
ttcgacgtcg tcgcccgcgc cgccgtccag atcaagaacg ccatcgacgc caccatcaag 540
ctcggcggta ccggttacgt gttctggggc ggccgtgaag gctactacac cctcctgaac 600
acccagatgc agcgcgagaa ggaccacctc gccaagatgc tcaccgccgc ccgcgactac 660
gcccgcgccc acggcttcca gggcaccttc ctcatcgagc ccaagcccat ggagcccacc 720
aagcaccagt acgacgtgga cacggagacc gtgatcggct tcctgcgcgc caacggtctg 780
gacaaggact tcaaggtcaa tatcgaggtg aaccacgcca ccctcgccgg ccacaccttc 840
gagcacgagc tcaccgtggc tgtcgataac ggcttcctcg gctccatcga cgccaaccgc 900
ggcgacgccc agaacggctg ggacaccgac cagttccccg tggacccgta cgacctcacc 960
caggccatga tgcagatcat ccgcaacggc ggtttcaagg acggcggcac caacttcgac 1020
gccaagctcc gccgctcttc caccgacccg gaggacatct tcatcgccca catcagcgcg 1080
atggacgcca tggcccacgc cctgctgaac gccgccgccg tcatcgagga gagcccgctc 1140
tgcaagatgg tcgaggagcg ctacgcttcc ttcgacagcg gcctcggcaa gcagttcgag 1200
gaaggcaagg ccaccctcga ggacctctac gagtatgcca agaagaatgg cgagcccgtc 1260
gtcgcctccg gcaagcagga gctctacgag acgctgctga acctttacgc gaagtag 1317

<210> SEQ ID NO 162

<211> LENGTH: 438
<212> TYPE: PRT
<213> ORGANISM: Unknown
<220> FEATURE:
<223> OTHER INFORMATION: Obtained from environmental sample

<400> SEQUENCE: 162

Met Ala Lys Glu Tyr Phe Pro Thr Ile Gly Lys Ile Pro Phe Glu Gly
1               5                   10                  15

Val Glu Ser Lys Asn Pro Met Ala Phe His Tyr Tyr Asp Ala Asn Arg
            20                  25                  30

Val Val Met Gly Lys Pro Met Lys Asp Trp Leu Lys Phe Ala Met Ala
        35                  40                  45

Trp Trp His Thr Leu Gly Gln Ala Ser Gly Asp Pro Phe Gly Gly Gln
    50                  55                  60

Thr Arg Ser Tyr Glu Trp Asp Lys Gly Glu Cys Pro Tyr Cys Arg Ala
65                  70                  75                  80

Lys Ala Lys Ala Asp Ala Gly Phe Glu Ile Met Gln Lys Leu Gly Ile
                85                  90                  95

Glu Tyr Tyr Cys Phe His Asp Ile Asp Leu Val Glu Asp Thr Glu Asp
            100                 105                 110

Ile Ala Glu Tyr Glu Ala Arg Met Lys Asp Ile Thr Asp Tyr Leu Val
        115                 120                 125

Glu Lys Gln Lys Glu Thr Gly Ile Lys Asn Leu Trp Gly Thr Ala Asn
    130                 135                 140

Val Phe Gly Asn Lys Arg Tyr Met Asn Gly Ala Ala Thr Asn Pro Gln
145                 150                 155                 160

Phe Asp Val Val Ala Arg Ala Ala Val Gln Ile Lys Asn Ala Ile Asp
                165                 170                 175

Ala Thr Ile Lys Leu Gly Gly Thr Gly Tyr Val Phe Trp Gly Gly Arg
            180                 185                 190

Glu Gly Tyr Tyr Thr Leu Leu Asn Thr Gln Met Gln Arg Glu Lys Asp
        195                 200                 205

His Leu Ala Lys Met Leu Thr Ala Ala Arg Asp Tyr Ala Arg Ala His
    210                 215                 220

Gly Phe Gln Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Val
        275                 280                 285

Asp Asn Gly Phe Leu Gly Ser Ile Asp Ala Asn Arg Gly Asp Ala Gln
    290                 295                 300

Asn Gly Trp Asp Thr Asp Gln Phe Pro Val Asp Pro Tyr Asp Leu Thr
305                 310                 315                 320

Gln Ala Met Met Gln Ile Ile Arg Asn Gly Gly Phe Lys Asp Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Val Ile Glu Glu Ser Pro Leu Cys Lys Met Val
    370                 375                 380

Glu Glu Arg Tyr Ala Ser Phe Asp Ser Gly Leu Gly Lys Gln Phe Glu
385 390 395 400

Glu Gly Lys Ala Thr Leu Glu Asp Leu Tyr Glu Tyr Ala Lys Lys Asn
405 410 415

Gly Glu Pro Val Val Ala Ser Gly Lys Gln Glu Leu Tyr Glu Thr Leu
420 425 430

Leu Asn Leu Tyr Ala Lys
435

<210> SEQ ID NO 163
<211> LENGTH: 1317
<212> TYPE: DNA
<213> ORGANISM: Unknown
<220> FEATURE:
<223> OTHER INFORMATION: Obtained from environmental sample

<400> SEQUENCE: 163
atggcaaaag agtatttccc gacaatcggt aagatcccct tcgagggacc cgagtccaag 60
aacccgatgg cattccacta ctatgacgcg gagcgcgtgg tgatgggcaa gaagatgaag 120
gactggttca agttcgcgat ggcctggtgg cacaccctgg gccaggcttc cgccgacccg 180
ttcggcggcc agacccgctc ctacgagtgg gacaagggcg aaggcccctg ctcccgcgcc 240
cgcgccaagg ctgacgccgg tttcgagatc atgcagaaac tgggcatcgg ctactactgc 300
ttccacgaca tcgacctggt ggaggacacc gaggacatcg ccgagtatga agcccgcatg 360
aaggacatca ccgactacct cgtggagaag cagaaggaga ccggcatcaa gaacctctgg 420
ggcacggcca acgtattcgg caacaagccc tacatgaacg gcgccgccac gaacccgcag 480
ttcgacatcg ccgcccgcgc ggccctgcag accaagaacg ccatcgatgc caccatcaag 540
ctgggcggca ccggttacgt gttctggggc ggccgtgaag gctactacac cctcctgaac 600
acccagatgc agcgcgagaa ggaccacctt gccaagatgc tcaccgcggc tcgcgactat 660
gcccgcgccc acggcttcaa gggcaccttc ttcatcgagc cgaaaccgat ggagcccacc 720
aagcaccagt acgacgtgga cacggagacc gtgatcggct tcctccgcgc caacggcctg 780
gacaaggact tcaaggtgaa catcgaagtg aaccacgcca ccctcgccgg ccacaccttc 840
gagcacgggc tcaccgtggc cgttgacaac ggcttcctcg gcagcatcga cgccaaccgc 900
ggagacgccc agaacggctg ggataccgac cagttcccgg tggatccgta cgacctcacc 960
caggcgatga tccagatcat ccgcaatggc ggcttcaagg acggcggtac caacttcgac 1020
gccaagctcc gccgctcttc caccgacccg gaggacatct tcatcgccca catcagcgcg 1080
atggacgcca tggcccacgc cctgctgaac gccgccgccg tgctcgagga gagcccgctc 1140
tgcgagatgg ttgcaaagcg ttacgcttcc ttcgacagcg gtctcggcaa gaagttcgag 1200
gaaggcaacg ccaccctcga ggaactctac gagtacgcca aggcgaaggg cgaggtcgtt 1260
gccgaatccg gcaagcagga actctacgag accctgctga acctctacgc gaagtag 1317

<210> SEQ ID NO 164
<211> LENGTH: 438
<212> TYPE: PRT
<213> ORGANISM: Unknown
<220> FEATURE:
<223> OTHER INFORMATION: Obtained from environmental sample

<400> SEQUENCE: 164

Met Ala Lys Glu Tyr Phe Pro Thr Ile Gly Lys Ile Pro Phe Glu Gly
1 5 10 15

-continued

```
Pro Glu Ser Lys Asn Pro Met Ala Phe His Tyr Tyr Asp Ala Glu Arg
            20                  25                  30

Val Val Met Gly Lys Lys Met Lys Asp Trp Phe Lys Phe Ala Met Ala
        35                  40                  45

Trp Trp His Thr Leu Gly Gln Ala Ser Ala Asp Pro Phe Gly Gly Gln
    50                  55                  60

Thr Arg Ser Tyr Glu Trp Asp Lys Gly Glu Gly Pro Cys Ser Arg Ala
65                  70                  75                  80

Arg Ala Lys Ala Asp Ala Gly Phe Glu Ile Met Gln Lys Leu Gly Ile
                85                  90                  95

Gly Tyr Tyr Cys Phe His Asp Ile Asp Leu Val Glu Asp Thr Glu Asp
            100                 105                 110

Ile Ala Glu Tyr Glu Ala Arg Met Lys Asp Ile Thr Asp Tyr Leu Val
        115                 120                 125

Glu Lys Gln Lys Glu Thr Gly Ile Lys Asn Leu Trp Gly Thr Ala Asn
    130                 135                 140

Val Phe Gly Asn Lys Pro Tyr Met Asn Gly Ala Ala Thr Asn Pro Gln
145                 150                 155                 160

Phe Asp Ile Ala Ala Arg Ala Ala Leu Gln Thr Lys Asn Ala Ile Asp
                165                 170                 175

Ala Thr Ile Lys Leu Gly Gly Thr Gly Tyr Val Phe Trp Gly Gly Arg
            180                 185                 190

Glu Gly Tyr Tyr Thr Leu Leu Asn Thr Gln Met Gln Arg Glu Lys Asp
        195                 200                 205

His Leu Ala Lys Met Leu Thr Ala Ala Arg Asp Tyr Ala Arg Ala His
    210                 215                 220

Gly Phe Lys Gly Thr Phe Phe Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Gly Leu Thr Val Ala Val
        275                 280                 285

Asp Asn Gly Phe Leu Gly Ser Ile Asp Ala Asn Arg Gly Asp Ala Gln
    290                 295                 300

Asn Gly Trp Asp Thr Asp Gln Phe Pro Val Asp Pro Tyr Asp Leu Thr
305                 310                 315                 320

Gln Ala Met Ile Gln Ile Ile Arg Asn Gly Gly Phe Lys Asp Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Val Leu Glu Glu Ser Pro Leu Cys Glu Met Val
    370                 375                 380

Ala Lys Arg Tyr Ala Ser Phe Asp Ser Gly Leu Gly Lys Lys Phe Glu
385                 390                 395                 400

Glu Gly Asn Ala Thr Leu Glu Glu Leu Tyr Glu Tyr Ala Lys Ala Lys
                405                 410                 415

Gly Glu Val Val Ala Glu Ser Gly Lys Gln Glu Leu Tyr Glu Thr Leu
            420                 425                 430
```

Leu Asn Leu Tyr Ala Lys
435

<210> SEQ ID NO 165
<211> LENGTH: 1317
<212> TYPE: DNA
<213> ORGANISM: Unknown
<220> FEATURE:
<223> OTHER INFORMATION: Obtained from environmental sample

<400> SEQUENCE: 165
atggcaaaag agtatttccc gacaatcgga aagatcccct tcgagggcgc tgagagcaag 60
aatccccttg ctttccacta ttatgacgcc gagcgtgtgg tcatgggcaa gcccatgaag 120
gactggttca agttcgcgat ggcctggtgg cacaccctgg gccaggcttc cgccgacccg 180
ttcggcggcc agacccgctc ctacgagtgg gacaagggcg agtgccccta ctgccgcgcc 240
cgccagaagg ctgacgccgg tttcgagatc atgcagaagc tcggcatcgg ctactactgc 300
ttccacgaca tcgacctggt cgaggacacc gaggacatcg ccgagtacga ggcccgcatg 360
aaggacatca ccgactacct cgtcgagaag cagaaggaga ccggcatcaa gaacctctgg 420
ggcacggcca acgtgttcgg caacaagcgc tacatgaacg gcgccgccac gaacccgcag 480
ttcgacatcg tcgcccacgc ggccctgcag atcaagaacg cgatcggcgc caccatcaag 540
ctcggcggca ccggttacgt gttctggggc ggccgtgaag gttactacac cctcctgaac 600
acccagatgc agcgcgagaa ggaccacctc gccaagatgc tcaccgccgc ccgcgactac 660
gcccgcgcca acggcttcaa gggcaccttc ctcatcgagc cgaagccgat ggagcccacc 720
aagcaccagt atgacgtgga cacggagacc gtgatcggct tcctccgcgc caacggcctg 780
gacaaggact tcaaggtgaa catcgaggtg aaccacgcca ccctcgccgg ccacaccttc 840
gagcacgagc tcaccgtggc ggtcgacaac ggcttcctcg gcagcatcga cgccaaccgc 900
ggtgacgccc agaacggctg ggataccgac cagttccccg tggatccgta cgatctcacc 960
caggcgatga tccagatcat ccgcaacggc ggcttcaagg atggcggcac caacttcgac 1020
gccaagctcc gccgctcttc caccgacccg gaggacatct tcatcgccca catcagcgcg 1080
atggacgcca tggcccacgc cctgctgaac gccgccgccg tcatcgagga gagcccgctc 1140
tgcgagatgg tcgccaagcg ctacgcttcc ttcgacagcg gtctcggcaa gaagttcgag 1200
gaaggcaacg ccaccctcga ggaactctac gagtacgcca aggcgaacgg tgaggtcaag 1260
gccgaatccg gcaagcagga gctctacgag acccttctga acctctacgc gaaatag 1317

<210> SEQ ID NO 166
<211> LENGTH: 438
<212> TYPE: PRT
<213> ORGANISM: Unknown
<220> FEATURE:
<223> OTHER INFORMATION: Obtained from environmental sample

<400> SEQUENCE: 166

Met Ala Lys Glu Tyr Phe Pro Thr Ile Gly Lys Ile Pro Phe Glu Gly
1 5 10 15

Ala Glu Ser Lys Asn Pro Leu Ala Phe His Tyr Tyr Asp Ala Glu Arg
20 25 30

Val Val Met Gly Lys Pro Met Lys Asp Trp Phe Lys Phe Ala Met Ala
35 40 45

Trp Trp His Thr Leu Gly Gln Ala Ser Ala Asp Pro Phe Gly Gly Gln
50 55 60

Thr Arg Ser Tyr Glu Trp Asp Lys Gly Glu Cys Pro Tyr Cys Arg Ala
65 70 75 80

Arg Gln Lys Ala Asp Ala Gly Phe Glu Ile Met Gln Lys Leu Gly Ile
85 90 95

Gly Tyr Tyr Cys Phe His Asp Ile Asp Leu Val Glu Asp Thr Glu Asp
100 105 110

Ile Ala Glu Tyr Glu Ala Arg Met Lys Asp Ile Thr Asp Tyr Leu Val
115 120 125

Glu Lys Gln Lys Glu Thr Gly Ile Lys Asn Leu Trp Gly Thr Ala Asn
130 135 140

Val Phe Gly Asn Lys Arg Tyr Met Asn Gly Ala Ala Thr Asn Pro Gln
145 150 155 160

Phe Asp Ile Val Ala His Ala Ala Leu Gln Ile Lys Asn Ala Ile Gly
165 170 175

Ala Thr Ile Lys Leu Gly Gly Thr Gly Tyr Val Phe Trp Gly Gly Arg
180 185 190

Glu Gly Tyr Tyr Thr Leu Leu Asn Thr Gln Met Gln Arg Glu Lys Asp
195 200 205

His Leu Ala Lys Met Leu Thr Ala Ala Arg Asp Tyr Ala Arg Ala Asn
210 215 220

Gly Phe Lys Gly Thr Phe Leu Ile Glu Pro Lys Pro Met Glu Pro Thr
225 230 235 240

Lys His Gln Tyr Asp Val Asp Thr Glu Thr Val Ile Gly Phe Leu Arg
245 250 255

Ala Asn Gly Leu Asp Lys Asp Phe Lys Val Asn Ile Glu Val Asn His
260 265 270

Ala Thr Leu Ala Gly His Thr Phe Glu His Glu Leu Thr Val Ala Val
275 280 285

Asp Asn Gly Phe Leu Gly Ser Ile Asp Ala Asn Arg Gly Asp Ala Gln
290 295 300

Asn Gly Trp Asp Thr Asp Gln Phe Pro Val Asp Pro Tyr Asp Leu Thr
305 310 315 320

Gln Ala Met Ile Gln Ile Ile Arg Asn Gly Gly Phe Lys Asp Gly Gly
325 330 335

Thr Asn Phe Asp Ala Lys Leu Arg Arg Ser Ser Thr Asp Pro Glu Asp
340 345 350

Ile Phe Ile Ala His Ile Ser Ala Met Asp Ala Met Ala His Ala Leu
355 360 365

Leu Asn Ala Ala Ala Val Ile Glu Glu Ser Pro Leu Cys Glu Met Val
370 375 380

Ala Lys Arg Tyr Ala Ser Phe Asp Ser Gly Leu Gly Lys Lys Phe Glu
385 390 395 400

Glu Gly Asn Ala Thr Leu Glu Glu Leu Tyr Glu Tyr Ala Lys Ala Asn
405 410 415

Gly Glu Val Lys Ala Glu Ser Gly Lys Gln Glu Leu Tyr Glu Thr Leu
420 425 430

Leu Asn Leu Tyr Ala Lys
435

<210> SEQ ID NO 167
<211> LENGTH: 1317
<212> TYPE: DNA
<213> ORGANISM: Unknown
<220> FEATURE:
<223> OTHER INFORMATION: Obtained from environmental sample

<400> SEQUENCE: 167

```
atggcaaaag agtatttccc cactatcggg aagattcctt tcgaaggagt cgagagcaag      60
aacccccttg cattccatta ttatgacgca aaccgcatgg tcatgggcaa gcccatgaag     120
gactggttca agttcgccat ggcatggtgg cacaccctgg gacaggcctc cgcagacccg     180
ttcggcggcc agacccgctc ctacgaatgg gacaagggcg aatgccccta ctgccgcgcc     240
agggcaaagg ccgatgccgg cttcgagatc atgcagaaac tgggtatcga gtatttctgc     300
ttccatgaca tcgacctggt agaggactgc gacgacatcg ccgagtacga ggcccgcatg     360
aaggacatca cggactatct cctggagaag atgaaggaaa ccggcatcaa gaacctctgg     420
ggcaccgcca acgtgttcgg caacaagcgt tacatgaacg gcgccggcac caatccgcag     480
ttcgacgtag tggcccgcgc tgccgtccag atcaagaacg ccatcgacgc caccatcaag     540
ctcggcggtt ccaactatgt gttctggggc ggccgtgaag gatactacac cctgctgaac     600
acccagatgc agcgcgagaa ggaccacctc ggcaaactgc tcaccgccgc ccgcgactat     660
gcccgcaaga acggcttcaa gggcaccttc ctcatcgagc ccaagccgat ggagcccacc     720
aagcaccagt acgacgtaga cacggagacc gtgatcggct tcctccgcgc caacggcctg     780
gagaaagact tcaaggtgaa catcgaggtg aaccacgcca ccctggccgg ccataccttc     840
gagcatgaac tcaccgtggc cgtggacaac ggcttcctgg gatccatcga cgccaaccgc     900
ggcgacgccc agaacggctg ggatacggac cagttcccgg tagacccgta cgacctcacc     960
caggccatga tgcagatcat ccgcaacggc ggcctcggca acggcggtac caacttcgac    1020
gccaaactgc gccgttcctc caccgatcct gaggacatct tcatcgccca catcagcgcc    1080
atggacgcca tggcccacgc cctgctcaac gcagccgccg tgctggaaga aagtccgctc    1140
tgtgagatgg tcaaggagcg ctacgcttcc ttcgacagcg gtctcggcaa gaagttcgaa    1200
gagggcaagg ctaccctgga agaaatctac gagtatgcca agaagagcgg cgaacccgtg    1260
gtcgcttccg gcaagcagga gctctacgaa accctgctga acctctacgc caagtag       1317
```

<210> SEQ ID NO 168
<211> LENGTH: 438
<212> TYPE: PRT
<213> ORGANISM: Unknown
<220> FEATURE:
<223> OTHER INFORMATION: Obtained from environmental sample

<400> SEQUENCE: 168

```
Met Ala Lys Glu Tyr Phe Pro Thr Ile Gly Lys Ile Pro Phe Glu Gly
1               5                   10                  15

Val Glu Ser Lys Asn Pro Leu Ala Phe His Tyr Tyr Asp Ala Asn Arg
            20                  25                  30

Met Val Met Gly Lys Pro Met Lys Asp Trp Phe Lys Phe Ala Met Ala
        35                  40                  45

Trp Trp His Thr Leu Gly Gln Ala Ser Ala Asp Pro Phe Gly Gly Gln
    50                  55                  60

Thr Arg Ser Tyr Glu Trp Asp Lys Gly Glu Cys Pro Tyr Cys Arg Ala
65                  70                  75                  80

Arg Ala Lys Ala Asp Ala Gly Phe Glu Ile Met Gln Lys Leu Gly Ile
                85                  90                  95

Glu Tyr Phe Cys Phe His Asp Ile Asp Leu Val Glu Asp Cys Asp Asp
            100                 105                 110

Ile Ala Glu Tyr Glu Ala Arg Met Lys Asp Ile Thr Asp Tyr Leu Leu
```

```
        115                 120                 125

Glu Lys Met Lys Glu Thr Gly Ile Lys Asn Leu Trp Gly Thr Ala Asn
    130                 135                 140

Val Phe Gly Asn Lys Arg Tyr Met Asn Gly Ala Gly Thr Asn Pro Gln
145                 150                 155                 160

Phe Asp Val Val Ala Arg Ala Ala Val Gln Ile Lys Asn Ala Ile Asp
                165                 170                 175

Ala Thr Ile Lys Leu Gly Gly Ser Asn Tyr Val Phe Trp Gly Gly Arg
            180                 185                 190

Glu Gly Tyr Tyr Thr Leu Leu Asn Thr Gln Met Gln Arg Glu Lys Asp
        195                 200                 205

His Leu Gly Lys Leu Leu Thr Ala Ala Arg Asp Tyr Ala Arg Lys Asn
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Leu Glu Lys Asp Phe Lys Val Asn Ile Glu Val Asn His
            260                 265                 270

Ala Thr Leu Ala Gly His Thr Phe Glu His Glu Leu Thr Val Ala Val
        275                 280                 285

Asp Asn Gly Phe Leu Gly Ser Ile Asp Ala Asn Arg Gly Asp Ala Gln
    290                 295                 300

Asn Gly Trp Asp Thr Asp Gln Phe Pro Val Asp Pro Tyr Asp Leu Thr
305                 310                 315                 320

Gln Ala Met Met Gln Ile Ile Arg Asn Gly Gly Leu Gly Asn Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Val Leu Glu Glu Ser Pro Leu Cys Glu Met Val
    370                 375                 380

Lys Glu Arg Tyr Ala Ser Phe Asp Ser Gly Leu Gly Lys Lys Phe Glu
385                 390                 395                 400

Glu Gly Lys Ala Thr Leu Glu Glu Ile Tyr Glu Tyr Ala Lys Lys Ser
                405                 410                 415

Gly Glu Pro Val Val Ala Ser Gly Lys Gln Glu Leu Tyr Glu Thr Leu
            420                 425                 430

Leu Asn Leu Tyr Ala Lys
        435
```

<210> SEQ ID NO 169
<211> LENGTH: 1317
<212> TYPE: DNA
<213> ORGANISM: Unknown
<220> FEATURE:
<223> OTHER INFORMATION: Obtained from environmental sample

<400> SEQUENCE: 169

```
atggctaaag aatacttccc ctccatcggc aaaatccctt ttgaaggagg cgacagcaaa      60

aatcccctcg ctttccatta ttatgacgcc ggacgcgtgg ttatgggcaa gcccatgaag     120

gaatggctta aattcgccat ggcctggtgg cacacgctgg gccaggcctc cggagacccc     180

ttcggcggcc agacccgcag ctacgaatgg gacaagggcg aatgccccta ctgccgcgcc     240
```

```
aaagccaagg ccgacgccgg ttttgaaatc atgcaaaagc tgggtatcga atacttctgc    300
ttccacgatg tggaccttat cgaggattgc gatgacattg ccgaatacga agcccgcatg    360
aaggacatca cggactacct gctggaaaag atgaaggaga ccggcatcaa gaacctctgg    420
ggcaccgcca atgtcttcgg ccacaagcgc tacatgaacg gcgccgccac gaacccgcag    480
ttcgacgtgg tcgcccgcgc cgccgtccag atcaagaacg cgattgacgc caccatcaag    540
ctcggcggta ccagttatgt attctggggc ggccgcgagg gctactacac cctcctgaac    600
acccagatgc agcgtgagaa agaccacctg gccaagatgc tcaccgcagc ccgcgactac    660
gcccgcgcca agggcttcaa gggcaccttc ctcatcgagc ccaagccgat ggagcccacc    720
aagcaccagt acgacgttga cacggagacc gtgatcggct ccctgcgcgc caacggcctg    780
gacaaggact tcaaggtgaa catcgaggtg aaccacgcca ccctggccgg ccacaccttc    840
gagcacgaac tcaccgtggc tgttgacaac ggcttcctgg gctccatcga cgccaaccgc    900
ggcgacgccc agaacggctg ggatacggac cagttcccgg tagacccgta cgacctcacc    960
caggccatga tgcagattat ccgcaacggc ggcttcaagg acggcggcac caacttcgat   1020
gccaaactgc gccgctcttc caccgatccg gaagacatct tcatcgccca catcagcgct   1080
atggatgcca tggcacacgc cctgctcaac gccgccgccg tgctggaaga gagcccgctg   1140
tgcaacatgg tcaaggagcg ttacgccggc ttcgacagcg gccttggcaa gaagttcgag   1200
gaagggaagg caacgctgga ggaaatctat gactatgcca agaagagcgg cgaacccgtc   1260
gtggcttccg gcaagcagga actctacgaa accatcctga acctctatgc caagtag      1317
```

```
<210> SEQ ID NO 170
<211> LENGTH: 438
<212> TYPE: PRT
<213> ORGANISM: Unknown
<220> FEATURE:
<223> OTHER INFORMATION: Obtained from environmental sample

<400> SEQUENCE: 170

Met Ala Lys Glu Tyr Phe Pro Ser Ile Gly Lys Ile Pro Phe Glu Gly
1               5                   10                  15

Gly Asp Ser Lys Asn Pro Leu Ala Phe His Tyr Tyr Asp Ala Gly Arg
            20                  25                  30

Val Val Met Gly Lys Pro Met Lys Glu Trp Leu Lys Phe Ala Met Ala
        35                  40                  45

Trp Trp His Thr Leu Gly Gln Ala Ser Gly Asp Pro Phe Gly Gly Gln
    50                  55                  60

Thr Arg Ser Tyr Glu Trp Asp Lys Gly Glu Cys Pro Tyr Cys Arg Ala
65                  70                  75                  80

Lys Ala Lys Ala Asp Ala Gly Phe Glu Ile Met Gln Lys Leu Gly Ile
                85                  90                  95

Glu Tyr Phe Cys Phe His Asp Val Asp Leu Ile Glu Asp Cys Asp Asp
            100                 105                 110

Ile Ala Glu Tyr Glu Ala Arg Met Lys Asp Ile Thr Asp Tyr Leu Leu
        115                 120                 125

Glu Lys Met Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Gln
145                 150                 155                 160

Phe Asp Val Val Ala Arg Ala Ala Val Gln Ile Lys Asn Ala Ile Asp
                165                 170                 175
```

```
Ala Thr Ile Lys Leu Gly Gly Thr Ser Tyr Val Phe Trp Gly Gly Arg
            180                 185                 190

Glu Gly Tyr Tyr Thr Leu Leu Asn Thr Gln Met Gln Arg Glu Lys Asp
        195                 200                 205

His Leu Ala Lys Met Leu Thr Ala Ala Arg Asp Tyr Ala Arg Ala Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Ser Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Val
        275                 280                 285

Asp Asn Gly Phe Leu Gly Ser Ile Asp Ala Asn Arg Gly Asp Ala Gln
    290                 295                 300

Asn Gly Trp Asp Thr Asp Gln Phe Pro Val Asp Pro Tyr Asp Leu Thr
305                 310                 315                 320

Gln Ala Met Met Gln Ile Ile Arg Asn Gly Gly Phe Lys Asp Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Val Leu Glu Glu Ser Pro Leu Cys Asn Met Val
    370                 375                 380

Lys Glu Arg Tyr Ala Gly Phe Asp Ser Gly Leu Gly Lys Lys Phe Glu
385                 390                 395                 400

Glu Gly Lys Ala Thr Leu Glu Glu Ile Tyr Asp Tyr Ala Lys Lys Ser
                405                 410                 415

Gly Glu Pro Val Val Ala Ser Gly Lys Gln Glu Leu Tyr Glu Thr Ile
            420                 425                 430

Leu Asn Leu Tyr Ala Lys
        435
```

<210> SEQ ID NO 171
<211> LENGTH: 1317
<212> TYPE: DNA
<213> ORGANISM: Unknown
<220> FEATURE:
<223> OTHER INFORMATION: Obtained from environmental sample

<400> SEQUENCE: 171

```
atgtcaaaag agtatttccc tacaatcggc agggtcccct tcgagggacc tgagagcaag      60

aatccgctgg cgttccacta ttacgagccg gaccggctcg tcctgggcag gaaaatgaag     120

gactggctgc gcttcgcaat ggcctggtgg catacgctcg ggcaggcttc cggcgaccag     180

ttcggcggac agacctgcac atacgcctgg gatgaaggcg agtgtcccgt ctgccgggca     240

aaggccaagg ctgacgccgg ctttgaactg atgcagaaac tgggcatcgg gtatttctgc     300

ttccacgacg tggacctggt cgaggaggcc gacaccattg aagaatacga ggagcggatg     360

cggatcatca ccgactacct gctcgagaag atggaagaga ccggcatccg caatctctgg     420

ggaaccgcca atgtcttcgg acacaagcgc tatatgaacg gcgccgccac caatcccgac     480

ttcgacgtcg tggcccgtgc cgcggtccag atcaagaatg ccatcgatgc caccatcaaa     540
```

```
ctgggtggtg agaactatgt gttctggggt ggccgcgagg gctatacgag cctgctcaac    600

acgcagatgc accgggaaaa acaccacctc ggaaatatgc tcagggcagc ccgcgactat    660

ggccgtgccc acggtttcaa gggaacgttc ctgatcgagc ccaagccgat ggagccgacc    720

aagcatcagt acgaccagga tacggagacg gtcatcggtt tcctgcgctg tcacggcctg    780

gacaaggatt tcaaggtgaa catcgaggtg aaccacgcca cgctcgccgg acacaccttc    840

gagcacgaac tggccactgc ggtcgatgcc ggcctgctgg gcagcatcga tgccaaccgc    900

ggcgacgccc agaacggctg ggataccgac cagttcccga tcgacaacta cgaactcacg    960

ctggcgatgc tgcagatcat ccgcaatggc ggactcgcac ccggcggatc gaacttcgat   1020

gccaagttgc gccgcaattc caccgatccg gaagacatct tcatcgccca catcagcgcg   1080

atggacgcga tggcccgtgc cctgctcaat gcggcggcca tctggaccga atcgccgatt   1140

caggatatgg tcagggaccg ctatgcttcc ttcgacagcg gaaagggcag ggagttcgag   1200

gaaggcagac tcagtctgga agacctcgtg gcctatgcga aggagcacgg tgagccgcgc   1260

cagatctccg gcaggcagga actttatgaa accatcgtag cgctttactg caggtaa      1317
```

<210> SEQ ID NO 172
<211> LENGTH: 438
<212> TYPE: PRT
<213> ORGANISM: Unknown
<220> FEATURE:
<223> OTHER INFORMATION: Obtained from environmental sample

<400> SEQUENCE: 172

```
Met Ser Lys Glu Tyr Phe Pro Thr Ile Gly Arg Val Pro Phe Glu Gly
1               5                   10                  15

Pro Glu Ser Lys Asn Pro Leu Ala Phe His Tyr Tyr Glu Pro Asp Arg
            20                  25                  30

Leu Val Leu Gly Arg Lys Met Lys Asp Trp Leu Arg Phe Ala Met Ala
        35                  40                  45

Trp Trp His Thr Leu Gly Gln Ala Ser Gly Asp Gln Phe Gly Gly Gln
    50                  55                  60

Thr Cys Thr Tyr Ala Trp Asp Glu Gly Glu Cys Pro Val Cys Arg Ala
65                  70                  75                  80

Lys Ala Lys Ala Asp Ala Gly Phe Glu Leu Met Gln Lys Leu Gly Ile
                85                  90                  95

Gly Tyr Phe Cys Phe His Asp Val Asp Leu Val Glu Glu Ala Asp Thr
            100                 105                 110

Ile Glu Glu Tyr Glu Glu Arg Met Arg Ile Ile Thr Asp Tyr Leu Leu
        115                 120                 125

Glu Lys Met Glu Glu Thr Gly Ile Arg Asn Leu Trp Gly Thr Ala Asn
    130                 135                 140

Val Phe Gly His Lys Arg Tyr Met Asn Gly Ala Ala Thr Asn Pro Asp
145                 150                 155                 160

Phe Asp Val Val Ala Arg Ala Ala Val Gln Ile Lys Asn Ala Ile Asp
                165                 170                 175

Ala Thr Ile Lys Leu Gly Gly Glu Asn Tyr Val Phe Trp Gly Gly Arg
            180                 185                 190

Glu Gly Tyr Thr Ser Leu Leu Asn Thr Gln Met His Arg Glu Lys His
        195                 200                 205

His Leu Gly Asn Met Leu Arg Ala Ala Arg Asp Tyr Gly Arg Ala His
    210                 215                 220
```

-continued

```
Gly Phe Lys Gly Thr Phe Leu Ile Glu Pro Lys Pro Met Glu Pro Thr
225                 230                 235                 240

Lys His Gln Tyr Asp Gln Asp Thr Glu Thr Val Ile Gly Phe Leu Arg
                245                 250                 255

Cys His Gly Leu Asp Lys Asp Phe Lys Val Asn Ile Glu Val Asn His
            260                 265                 270

Ala Thr Leu Ala Gly His Thr Phe Glu His Glu Leu Ala Thr Ala Val
        275                 280                 285

Asp Ala Gly Leu Leu Gly Ser Ile Asp Ala Asn Arg Gly Asp Ala Gln
    290                 295                 300

Asn Gly Trp Asp Thr Asp Gln Phe Pro Ile Asp Asn Tyr Glu Leu Thr
305                 310                 315                 320

Leu Ala Met Leu Gln Ile Ile Arg Asn Gly Gly Leu Ala Pro Gly Gly
                325                 330                 335

Ser Asn Phe Asp Ala Lys Leu Arg Arg Asn Ser Thr Asp Pro Glu Asp
            340                 345                 350

Ile Phe Ile Ala His Ile Ser Ala Met Asp Ala Met Ala Arg Ala Leu
        355                 360                 365

Leu Asn Ala Ala Ala Ile Trp Thr Glu Ser Pro Ile Gln Asp Met Val
    370                 375                 380

Arg Asp Arg Tyr Ala Ser Phe Asp Ser Gly Lys Gly Arg Glu Phe Glu
385                 390                 395                 400

Glu Gly Arg Leu Ser Leu Glu Asp Leu Val Ala Tyr Ala Lys Glu His
                405                 410                 415

Gly Glu Pro Arg Gln Ile Ser Gly Arg Gln Glu Leu Tyr Glu Thr Ile
            420                 425                 430

Val Ala Leu Tyr Cys Arg
        435
```

<210> SEQ ID NO 173
<211> LENGTH: 1317
<212> TYPE: DNA
<213> ORGANISM: Unknown
<220> FEATURE:
<223> OTHER INFORMATION: Obtained from environmental sample

<400> SEQUENCE: 173

```
atgactaaag agtatttccc gggaatcgga acgattccgt ttgaaggaac caagagcaag     60

aaccccctgg ccttccatta ttataacgcc tcccaggtag tgatgggcaa gcccatgaag    120

gactggctca agtatgccat ggcctggtgg cacaccctgg gccaggcctc tgcagacccc    180

tttggcggcc agacccgctc ctacgaatgg gacaagggcg agtgcccgta ctgccgcgcc    240

aagcagaagg ccgatgccgg ctttgagctc atgcagaagc tgggcatcga gtactactgc    300

ttccacgacg tggacatcat cgaggactgc gaggacattg ccgagtacga ggcccgcatg    360

aaggacatca cggactacct gctggagaag cagaaagaga ccggcatcaa gaacctctgg    420

ggcaccgcca acgtgtttgg ccacaagcgc tacatgaacg gcgccgccac caaccctcag    480

tttgacattg tggcccgtgc cgccgtccag atcaagaacg ccctggatgc cgccatcaaa    540

ctgggtggta ccaactacgt gttctggggt ggccgcgaag gctactacac gctgctcaac    600

acccagatgc agcgggagaa gaaccacctg gccaagatgc tcaccgccgc ccgcgactac    660

gcccgcgcca agggcttcaa gggcaccttc ctcattgagc ccaaacccat ggagcccacc    720

aagcaccagt acgacgtgga caccgagacc gtgattggtt tcatccgcgc caacggcctg    780

gacaaggact tcaaggtaaa cattgaggta aaccacgcca ccctggccgg ccacaccttt    840
```

gagcacgagc tcaccgtggc ccgcgagaac ggcttcctgg gctccatcga cgccaaccgc 900
ggagatgccc agaacggctg ggatacggac cagttcccca tcgacgccct ggatctcacc 960
caggctatga tgcaggtcat cctcaacggt ggcttcggca atggcggcac caactttgac 1020
gccaagctcc gccgctcctc caccgatccc gaggacatct tcatcgccca catcagcgcc 1080
atggatgcca tggcacacgc cctcctgaac gcagccgcca tcctggaaga gagccccctg 1140
cccgccatgg tcaaggagcg ttacgcttcc ttcgacagcg gtctgggcaa gaagttcgaa 1200
gaaggcaagg cctccctgga agaactttac gaatatgcca agaagaatgg agagcccgtg 1260
gccgcttccg gcaaacagga gctctgcgaa acttacttga acctctatgc aaagtag 1317

<210> SEQ ID NO 174
<211> LENGTH: 438
<212> TYPE: PRT
<213> ORGANISM: Unknown
<220> FEATURE:
<223> OTHER INFORMATION: Obtained from environmental sample

<400> SEQUENCE: 174

Met Thr Lys Glu Tyr Phe Pro Gly Ile Gly Thr Ile Pro Phe Glu Gly
1 5 10 15

Thr Lys Ser Lys Asn Pro Leu Ala Phe His Tyr Tyr Asn Ala Ser Gln
20 25 30

Val Val Met Gly Lys Pro Met Lys Asp Trp Leu Lys Tyr Ala Met Ala
35 40 45

Trp Trp His Thr Leu Gly Gln Ala Ser Ala Asp Pro Phe Gly Gly Gln
50 55 60

Thr Arg Ser Tyr Glu Trp Asp Lys Gly Glu Cys Pro Tyr Cys Arg Ala
65 70 75 80

Lys Gln Lys Ala Asp Ala Gly Phe Glu Leu Met Gln Lys Leu Gly Ile
85 90 95

Glu Tyr Tyr Cys Phe His Asp Val Asp Ile Ile Glu Asp Cys Glu Asp
100 105 110

Ile Ala Glu Tyr Glu Ala Arg Met Lys Asp Ile Thr Asp Tyr Leu Leu
115 120 125

Glu Lys Gln Lys Glu Thr Gly Ile Lys Asn Leu Trp Gly Thr Ala Asn
130 135 140

Val Phe Gly His Lys Arg Tyr Met Asn Gly Ala Ala Thr Asn Pro Gln
145 150 155 160

Phe Asp Ile Val Ala Arg Ala Ala Val Gln Ile Lys Asn Ala Leu Asp
165 170 175

Ala Ala Ile Lys Leu Gly Gly Thr Asn Tyr Val Phe Trp Gly Gly Arg
180 185 190

Glu Gly Tyr Tyr Thr Leu Leu Asn Thr Gln Met Gln Arg Glu Lys Asn
195 200 205

His Leu Ala Lys Met Leu Thr Ala Ala Arg Asp Tyr Ala Arg Ala Lys
210 215 220

Gly Phe Lys Gly Thr Phe Leu Ile Glu Pro Lys Pro Met Glu Pro Thr
225 230 235 240

Lys His Gln Tyr Asp Val Asp Thr Glu Thr Val Ile Gly Phe Ile Arg
245 250 255

Ala Asn Gly Leu Asp Lys Asp Phe Lys Val Asn Ile Glu Val Asn His
260 265 270

Ala Thr Leu Ala Gly His Thr Phe Glu His Glu Leu Thr Val Ala Arg

```
        275                 280                 285

Glu Asn Gly Phe Leu Gly Ser Ile Asp Ala Asn Arg Gly Asp Ala Gln
    290                 295                 300

Asn Gly Trp Asp Thr Asp Gln Phe Pro Ile Asp Ala Leu Asp Leu Thr
305                 310                 315                 320

Gln Ala Met Met Gln Val Ile Leu Asn Gly Gly Phe Gly Asn Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Ile Leu Glu Glu Ser Pro Leu Pro Ala Met Val
    370                 375                 380

Lys Glu Arg Tyr Ala Ser Phe Asp Ser Gly Leu Gly Lys Lys Phe Glu
385                 390                 395                 400

Glu Gly Lys Ala Ser Leu Glu Glu Leu Tyr Glu Tyr Ala Lys Lys Asn
                405                 410                 415

Gly Glu Pro Val Ala Ala Ser Gly Lys Gln Glu Leu Cys Glu Thr Tyr
            420                 425                 430

Leu Asn Leu Tyr Ala Lys
        435


<210> SEQ ID NO 175
<211> LENGTH: 1308
<212> TYPE: DNA
<213> ORGANISM: Unknown
<220> FEATURE:
<223> OTHER INFORMATION: Obtained from environmental sample

<400> SEQUENCE: 175

gtgactgatt tcttcaaggg catcgcgccc gtcaagtttg aggggccgca gagctccaat     60

ccgctggcct atcgccacta taacaaggac gaaatcgtcc tcggcaagcg gatggaagac    120

catatccgtc ccggcgttgc ctattggcac accttcgcct atgagggcgg cgatccgttt    180

ggcggccgca ccttcgatcg cccctggttc gacaagggta tggacggcgc ccgcctcaag    240

gccgacgtgg ccttcgaact gttcgacctg ctcgacgttc ctttcttctg tttccacgat    300

gctgatatcg ctcccgaagg cgcaacgctg gccgagagca accgcaatgt gcgcgagatt    360

ggcgagatct tcgctcgcaa gatggaaacc agccgcacca agctgctctg ggtacggca     420

aacctgttct ccaatcgccg ctacatggcc ggcgccgcca ccaacccgga cccggaaatc    480

ttcgcctatg ccgctgggca ggtgaagaac gtgctggaac tgacccacga actgggcggc    540

gccaactatg tgctgtgggg cggtcgcgag ggttatgaaa ccctgctcaa caccaagatc    600

ggccaggaaa tggaccagat gggccgtttt ctgtcgatgg tcgtcgagca tgccgaaaag    660

atcggcttca agggccagat cctgatcgag cccaagccgc aggagccgag caagcaccag    720

tatgacttcg acgttgcaac cgtttacggc ttcctcaaga agtatggtct cgaaaccaag    780

gtgaagtgca atatcgaggt cggccatgcc ttcctcgcca atcactcctt cgagcatgaa    840

ctggctttgg ccgcatcgct gggcattctc ggctcggtcg acgccaatcg caacgatcta    900

cagtccggct gggataccga ccagttcccc aataatgtcc ccgaaaccgc actcgccttc    960

tatcagattc tcaaggcggg cggactgggc aatggcggct ggaacttcga cgcccgcgtg   1020

cgccgccagt cacttgatcc ggccgacctg ctgcacggcc atatcggcgg cctcgacgtg   1080

ctggcgcgcg gcctcaaggc cgccgcggcg ctgatcgagg acggcaccta tgacaaggtc   1140
```

gtcgacgccc gctatgccgg ctggaaccag ggcctgggca aggatatcct tggtggcaag 1200
ctgaaccttg ccgacctggc tgccaaggtc gacgccgaaa acctcaaccc gcagcctagg 1260
tccggccagc aggaatatct cgaaaacctg atcaaccggt tcgtttag 1308

<210> SEQ ID NO 176
<211> LENGTH: 435
<212> TYPE: PRT
<213> ORGANISM: Unknown
<220> FEATURE:
<223> OTHER INFORMATION: Obtained from environmental sample

<400> SEQUENCE: 176

Met Thr Asp Phe Phe Lys Gly Ile Ala Pro Val Lys Phe Glu Gly Pro
1 5 10 15

Gln Ser Ser Asn Pro Leu Ala Tyr Arg His Tyr Asn Lys Asp Glu Ile
20 25 30

Val Leu Gly Lys Arg Met Glu Asp His Ile Arg Pro Gly Val Ala Tyr
35 40 45

Trp His Thr Phe Ala Tyr Glu Gly Gly Asp Pro Phe Gly Gly Arg Thr
50 55 60

Phe Asp Arg Pro Trp Phe Asp Lys Gly Met Asp Gly Ala Arg Leu Lys
65 70 75 80

Ala Asp Val Ala Phe Glu Leu Phe Asp Leu Leu Asp Val Pro Phe Phe
85 90 95

Cys Phe His Asp Ala Asp Ile Ala Pro Glu Gly Ala Thr Leu Ala Glu
100 105 110

Ser Asn Arg Asn Val Arg Glu Ile Gly Glu Ile Phe Ala Arg Lys Met
115 120 125

Glu Thr Ser Arg Thr Lys Leu Leu Trp Gly Thr Ala Asn Leu Phe Ser
130 135 140

Asn Arg Arg Tyr Met Ala Gly Ala Ala Thr Asn Pro Asp Pro Glu Ile
145 150 155 160

Phe Ala Tyr Ala Ala Gly Gln Val Lys Asn Val Leu Glu Leu Thr His
165 170 175

Glu Leu Gly Gly Ala Asn Tyr Val Leu Trp Gly Gly Arg Glu Gly Tyr
180 185 190

Glu Thr Leu Leu Asn Thr Lys Ile Gly Gln Glu Met Asp Gln Met Gly
195 200 205

Arg Phe Leu Ser Met Val Val Glu His Ala Glu Lys Ile Gly Phe Lys
210 215 220

Gly Gln Ile Leu Ile Glu Pro Lys Pro Gln Glu Pro Ser Lys His Gln
225 230 235 240

Tyr Asp Phe Asp Val Ala Thr Val Tyr Gly Phe Leu Lys Lys Tyr Gly
245 250 255

Leu Glu Thr Lys Val Lys Cys Asn Ile Glu Val Gly His Ala Phe Leu
260 265 270

Ala Asn His Ser Phe Glu His Glu Leu Ala Leu Ala Ala Ser Leu Gly
275 280 285

Ile Leu Gly Ser Val Asp Ala Asn Arg Asn Asp Leu Gln Ser Gly Trp
290 295 300

Asp Thr Asp Gln Phe Pro Asn Asn Val Pro Glu Thr Ala Leu Ala Phe
305 310 315 320

Tyr Gln Ile Leu Lys Ala Gly Gly Leu Gly Asn Gly Gly Trp Asn Phe
325 330 335

Asp Ala Arg Val Arg Arg Gln Ser Leu Asp Pro Ala Asp Leu Leu His
340 345 350

Gly His Ile Gly Gly Leu Asp Val Leu Ala Arg Gly Leu Lys Ala Ala
355 360 365

Ala Ala Leu Ile Glu Asp Gly Thr Tyr Asp Lys Val Val Asp Ala Arg
370 375 380

Tyr Ala Gly Trp Asn Gln Gly Leu Gly Lys Asp Ile Leu Gly Gly Lys
385 390 395 400

Leu Asn Leu Ala Asp Leu Ala Ala Lys Val Asp Ala Glu Asn Leu Asn
405 410 415

Pro Gln Pro Arg Ser Gly Gln Gln Glu Tyr Leu Glu Asn Leu Ile Asn
420 425 430

Arg Phe Val
435

<210> SEQ ID NO 177
<211> LENGTH: 23
<212> TYPE: PRT
<213> ORGANISM: Unknown
<220> FEATURE:
<223> OTHER INFORMATION: Obtained from environmental sample

<400> SEQUENCE: 177

Gly Cys Ile Gly Cys Ile Cys Ala Arg Gly Ala Arg Gly Gly Asn Ala
1 5 10 15

Thr Tyr Gly Thr Val Thr Thr
20

<210> SEQ ID NO 178
<211> LENGTH: 8
<212> TYPE: PRT
<213> ORGANISM: Unknown
<220> FEATURE:
<223> OTHER INFORMATION: Obtained from environmental sample

<400> SEQUENCE: 178

Ala Ala Gln Glu Gly Ile Val Phe
1 5

<210> SEQ ID NO 179
<211> LENGTH: 23
<212> TYPE: PRT
<213> ORGANISM: Unknown
<220> FEATURE:
<223> OTHER INFORMATION: Obtained from environmental sample

<400> SEQUENCE: 179

Gly Cys Asp Ala Thr Tyr Thr Cys Asn Gly Cys Arg Ala Thr Arg Thr
1 5 10 15

Ala Cys Ala Thr Ser Gly Gly
20

<210> SEQ ID NO 180
<211> LENGTH: 8
<212> TYPE: PRT
<213> ORGANISM: Unknown
<220> FEATURE:
<223> OTHER INFORMATION: Obtained from environmental sample

<400> SEQUENCE: 180

Pro Met Tyr Ile Ala Glu Ile Ala
1 5

<210> SEQ ID NO 181
<211> LENGTH: 60
<212> TYPE: DNA
<213> ORGANISM: Unknown
<220> FEATURE:
<223> OTHER INFORMATION: Obtained from environmental sample

<400> SEQUENCE: 181
ggcgcgcctc tagaaagctt acgcgtgagc tccctgcagg gatatcggta ccgcggccgc 60

<210> SEQ ID NO 182
<211> LENGTH: 53
<212> TYPE: DNA
<213> ORGANISM: Unknown
<220> FEATURE:
<223> OTHER INFORMATION: Obtained from environmental sample

<400> SEQUENCE: 182
caccattaat taaagctttg taaatatgat gagagaataa tataaatcaa acg 53

<210> SEQ ID NO 183
<211> LENGTH: 57
<212> TYPE: DNA
<213> ORGANISM: Unknown
<220> FEATURE:
<223> OTHER INFORMATION: Obtained from environmental sample

<400> SEQUENCE: 183
ggcgcgcctc tagaaagctt aatcgacaag aacacttcta tttatatagg tatgaaa 57

<210> SEQ ID NO 184
<211> LENGTH: 57
<212> TYPE: DNA
<213> ORGANISM: Unknown
<220> FEATURE:
<223> OTHER INFORMATION: Obtained from environmental sample

<400> SEQUENCE: 184
gcagggatat cggtacccac cagcggccgc tgaagaaggt ttatttcgtt tcgctgt 57

<210> SEQ ID NO 185
<211> LENGTH: 38
<212> TYPE: DNA
<213> ORGANISM: Unknown
<220> FEATURE:
<223> OTHER INFORMATION: Obtained from environmental sample

<400> SEQUENCE: 185
caccattaat taacccaggt gagactggat gctccata 38

<210> SEQ ID NO 186
<211> LENGTH: 60
<212> TYPE: DNA
<213> ORGANISM: Unknown
<220> FEATURE:
<223> OTHER INFORMATION: Obtained from environmental sample

<400> SEQUENCE: 186
gcctctagaa agcttacgcg tgagctccct gcagggatat cggtacccac cagcggccgc 60

<210> SEQ ID NO 187
<211> LENGTH: 60
<212> TYPE: DNA
<213> ORGANISM: Unknown
<220> FEATURE:

<223> OTHER INFORMATION: Obtained from environmental sample

<400> SEQUENCE: 187
cgctggtggg taccgatatc cctgcaggga gctcacgcgt aagctttcta gaggcgcgcc 60

<210> SEQ ID NO 188
<211> LENGTH: 200
<212> TYPE: DNA
<213> ORGANISM: Unknown
<220> FEATURE:
<223> OTHER INFORMATION: Obtained from environmental sample

<400> SEQUENCE: 188
tgcgtgtgcc gcgagtccac gtctactcgc gaaccgagtg caggcgggtc ttcggccagg 60
acggccgtgc gtgaccccgg ccgccagacg aaacggaccg cgctcgccag acgctaccca 120
gcccgttcat gccggccgcg agccgacctg tctcggtcgc ttcgacgcac gcgcggtcct 180
ttcgggtact cgcctaagac 200

<210> SEQ ID NO 189
<211> LENGTH: 39
<212> TYPE: DNA
<213> ORGANISM: Unknown
<220> FEATURE:
<223> OTHER INFORMATION: Obtained from environmental sample

<400> SEQUENCE: 189
caatagcggc cgcggtacct gcgtgtgccg cgagtccac 39

<210> SEQ ID NO 190
<211> LENGTH: 34
<212> TYPE: DNA
<213> ORGANISM: Unknown
<220> FEATURE:
<223> OTHER INFORMATION: Obtained from environmental sample

<400> SEQUENCE: 190
tgttaggatc cgtcttaggc gagtacccga aagg 34

<210> SEQ ID NO 191
<211> LENGTH: 37
<212> TYPE: DNA
<213> ORGANISM: Unknown
<220> FEATURE:
<223> OTHER INFORMATION: Obtained from environmental sample

<400> SEQUENCE: 191
caataggatc caggcatatt tatggtgaag aataagt 37

<210> SEQ ID NO 192
<211> LENGTH: 35
<212> TYPE: DNA
<213> ORGANISM: Unknown
<220> FEATURE:
<223> OTHER INFORMATION: Obtained from environmental sample

<400> SEQUENCE: 192
tgttactcga gaaatcatta cgaccgagat tcccg 35

<210> SEQ ID NO 193
<211> LENGTH: 31
<212> TYPE: DNA
<213> ORGANISM: Unknown
<220> FEATURE:
<223> OTHER INFORMATION: Obtained from environmental sample

<400> SEQUENCE: 193
caatactcga gtgcgtgtgc cgcgagtcca c 31

<210> SEQ ID NO 194
<211> LENGTH: 36
<212> TYPE: DNA
<213> ORGANISM: Unknown
<220> FEATURE:
<223> OTHER INFORMATION: Obtained from environmental sample

<400> SEQUENCE: 194
tgttagcggc cgcgtcttag gcgagtaccc gaaagg 36

<210> SEQ ID NO 195
<211> LENGTH: 32
<212> TYPE: DNA
<213> ORGANISM: Unknown
<220> FEATURE:
<223> OTHER INFORMATION: Obtained from environmental sample

<400> SEQUENCE: 195
actagtggat ccctcgaggt cgacgtttaa ac 32

<210> SEQ ID NO 196
<211> LENGTH: 64
<212> TYPE: DNA
<213> ORGANISM: Unknown
<220> FEATURE:
<223> OTHER INFORMATION: Obtained from environmental sample

<400> SEQUENCE: 196
caccaggcgc gcctctagaa agcttacgcg tagtttatca ttatcaatac tgccatttca 60
aaga 64

<210> SEQ ID NO 197
<211> LENGTH: 57
<212> TYPE: DNA
<213> ORGANISM: Unknown
<220> FEATURE:
<223> OTHER INFORMATION: Obtained from environmental sample

<400> SEQUENCE: 197
aacgtcgacc tcgagggatc cactagttcg aaactaagtt cttggtgttt taaaact 57

<210> SEQ ID NO 198
<211> LENGTH: 58
<212> TYPE: DNA
<213> ORGANISM: Unknown
<220> FEATURE:
<223> OTHER INFORMATION: Obtained from environmental sample

<400> SEQUENCE: 198
gtggatccct cgaggtcgac gtttaaacat tgaattgaat tgaaatcgat agatcaat 58

<210> SEQ ID NO 199
<211> LENGTH: 69
<212> TYPE: DNA
<213> ORGANISM: Unknown
<220> FEATURE:
<223> OTHER INFORMATION: Obtained from environmental sample

<400> SEQUENCE: 199
caccagcggc cgcggtaccg atatccctgc agggagctcg aaatatcgaa tgggaaaaaa 60
aaactggat 69

<210> SEQ ID NO 200
<211> LENGTH: 25
<212> TYPE: DNA
<213> ORGANISM: Unknown
<220> FEATURE:
<223> OTHER INFORMATION: Obtained from environmental sample

<400> SEQUENCE: 200
acagggataa caaagtttct ccagc 25

<210> SEQ ID NO 201
<211> LENGTH: 25
<212> TYPE: DNA
<213> ORGANISM: Unknown
<220> FEATURE:
<223> OTHER INFORMATION: Obtained from environmental sample

<400> SEQUENCE: 201
cataccaagt catgcgttac cagag 25

<210> SEQ ID NO 202
<211> LENGTH: 25
<212> TYPE: DNA
<213> ORGANISM: Unknown
<220> FEATURE:
<223> OTHER INFORMATION: Obtained from environmental sample

<400> SEQUENCE: 202
tttcccattc gatatttcga gctcc 25

<210> SEQ ID NO 203
<211> LENGTH: 25
<212> TYPE: DNA
<213> ORGANISM: Unknown
<220> FEATURE:
<223> OTHER INFORMATION: Obtained from environmental sample

<400> SEQUENCE: 203
cataccaagt catgcgttac cagag 25

<210> SEQ ID NO 204
<211> LENGTH: 7
<212> TYPE: PRT
<213> ORGANISM: Artificial Sequence
<220> FEATURE:
<223> OTHER INFORMATION: Sequence Motif
<220> FEATURE:
<221> NAME/KEY: MISC_FEATURE
<222> LOCATION: (1)..(1)
<223> OTHER INFORMATION: Can be either Leu or Ile
<220> FEATURE:
<221> NAME/KEY: MISC_FEATURE
<222> LOCATION: (6)..(6)
<223> OTHER INFORMATION: Can be any two amino acids

<400> SEQUENCE: 204

Xaa Glu Pro Lys Pro Xaa Pro
1               5

<210> SEQ ID NO 205
<211> LENGTH: 10
<212> TYPE: PRT
<213> ORGANISM: Artificial Sequence
<220> FEATURE:
<223> OTHER INFORMATION: Sequence Motif
<220> FEATURE:

<221> NAME/KEY: MISC_FEATURE
<222> LOCATION: (1)..(1)
<223> OTHER INFORMATION: Can be either Phe or Leu
<220> FEATURE:
<221> NAME/KEY: MISC_FEATURE
<222> LOCATION: (4)..(4)
<223> OTHER INFORMATION: Can be any amino acid but Lys
<220> FEATURE:
<221> NAME/KEY: MISC_FEATURE
<222> LOCATION: (6)..(6)
<223> OTHER INFORMATION: Can be either Leu, Ile, or Val
<220> FEATURE:
<221> NAME/KEY: MISC_FEATURE
<222> LOCATION: (7)..(7)
<223> OTHER INFORMATION: Can be any amino acid
<220> FEATURE:
<221> NAME/KEY: MISC_FEATURE
<222> LOCATION: (8)..(8)
<223> OTHER INFORMATION: Can be either Asp or Pro
<220> FEATURE:
<221> NAME/KEY: MISC_FEATURE
<222> LOCATION: (9)..(9)
<223> OTHER INFORMATION: Can be any amino acid
<220> FEATURE:
<221> NAME/KEY: MISC_FEATURE
<222> LOCATION: (10)..(10)
<223> OTHER INFORMATION: Can be either Asp, Gly, or Glu

<400> SEQUENCE: 205

```
Xaa His Asp Xaa Asp Xaa Xaa Xaa Xaa Xaa
1               5                   10
```

<210> SEQ ID NO 206
<211> LENGTH: 12
<212> TYPE: PRT
<213> ORGANISM: Artificial Sequence
<220> FEATURE:
<223> OTHER INFORMATION: Sequence Motif
<220> FEATURE:
<221> NAME/KEY: MISC_FEATURE
<222> LOCATION: (2)..(2)
<223> OTHER INFORMATION: Can be either Phe or Tyr
<220> FEATURE:
<221> NAME/KEY: MISC_FEATURE
<222> LOCATION: (3)..(3)
<223> OTHER INFORMATION: Can be either Ala, Ser, or Thr
<220> FEATURE:
<221> NAME/KEY: MISC_FEATURE
<222> LOCATION: (4)..(4)
<223> OTHER INFORMATION: Can be either Met, Leu, Val, or Ile
<220> FEATURE:
<221> NAME/KEY: MISC_FEATURE
<222> LOCATION: (5)..(5)
<223> OTHER INFORMATION: Can be either Ala or Ser
<220> FEATURE:
<221> NAME/KEY: MISC_FEATURE
<222> LOCATION: (6)..(6)
<223> OTHER INFORMATION: Can be either Trp, Tyr, Phe, or Leu
<220> FEATURE:
<221> NAME/KEY: MISC_FEATURE
<222> LOCATION: (8)..(8)
<223> OTHER INFORMATION: Can be either His or Thr
<220> FEATURE:
<221> NAME/KEY: MISC_FEATURE
<222> LOCATION: (10)..(10)
<223> OTHER INFORMATION: Can be either Leu, Phe, Met, or Gly

<400> SEQUENCE: 206

```
Pro Xaa Xaa Xaa Xaa Xaa Trp Xaa Asn Xaa Gly Ala
1               5                   10
```

<210> SEQ ID NO 207
<211> LENGTH: 11
<212> TYPE: PRT
<213> ORGANISM: Artificial Sequence

```
<220> FEATURE:
<223> OTHER INFORMATION: Sequence Motif
<220> FEATURE:
<221> NAME/KEY: MISC_FEATURE
<222> LOCATION: (2)..(2)
<223> OTHER INFORMATION: Can be either Phe or Tyr
<220> FEATURE:
<221> NAME/KEY: MISC_FEATURE
<222> LOCATION: (3)..(3)
<223> OTHER INFORMATION: Can be either Ala or Ser
<220> FEATURE:
<221> NAME/KEY: MISC_FEATURE
<222> LOCATION: (4)..(4)
<223> OTHER INFORMATION: Can be any two amino acids
<220> FEATURE:
<221> NAME/KEY: MISC_FEATURE
<222> LOCATION: (5)..(5)
<223> OTHER INFORMATION: Can be either Trp, Tyr, Phe, or Leu
<220> FEATURE:
<221> NAME/KEY: MISC_FEATURE
<222> LOCATION: (7)..(7)
<223> OTHER INFORMATION: Can be either His or Thr
<220> FEATURE:
<221> NAME/KEY: MISC_FEATURE
<222> LOCATION: (8)..(8)
<223> OTHER INFORMATION: Can be any amino acid but Thr or Val
<220> FEATURE:
<221> NAME/KEY: MISC_FEATURE
<222> LOCATION: (9)..(9)
<223> OTHER INFORMATION: Can be any amino acid

<400> SEQUENCE: 207

Pro Xaa Xaa Xaa Xaa Trp Xaa Xaa Xaa Gly Ala
1               5                   10


<210> SEQ ID NO 208
<211> LENGTH: 11
<212> TYPE: PRT
<213> ORGANISM: Artificial Sequence
<220> FEATURE:
<223> OTHER INFORMATION: Sequence Motif
<220> FEATURE:
<221> NAME/KEY: MISC_FEATURE
<222> LOCATION: (1)..(1)
<223> OTHER INFORMATION: Can be either Gly, Ser, or Asn
<220> FEATURE:
<221> NAME/KEY: MISC_FEATURE
<222> LOCATION: (2)..(2)
<223> OTHER INFORMATION: Can be either Ile, Val, or Ala
<220> FEATURE:
<221> NAME/KEY: MISC_FEATURE
<222> LOCATION: (4)..(4)
<223> OTHER INFORMATION: Can be either Tyr, Phe, His, or Gly
<220> FEATURE:
<221> NAME/KEY: MISC_FEATURE
<222> LOCATION: (5)..(5)
<223> OTHER INFORMATION: Can be either Phe, Tyr, Leu, Ile, or Val
<220> FEATURE:
<221> NAME/KEY: MISC_FEATURE
<222> LOCATION: (7)..(7)
<223> OTHER INFORMATION: Can be either Phe or Trp
<220> FEATURE:
<221> NAME/KEY: MISC_FEATURE
<222> LOCATION: (10)..(10)
<223> OTHER INFORMATION: Can be any amino acid

<400> SEQUENCE: 208

Xaa Xaa Arg Xaa Xaa Cys Xaa His Asp Xaa Asp
1               5                   10


<210> SEQ ID NO 209
<211> LENGTH: 11
<212> TYPE: PRT
<213> ORGANISM: Artificial Sequence
<220> FEATURE:
```

```
<223> OTHER INFORMATION: Sequence Motif
<220> FEATURE:
<221> NAME/KEY: MISC_FEATURE
<222> LOCATION: (2)..(2)
<223> OTHER INFORMATION: Can be either Ala, Ser, Thr, or Cys
<220> FEATURE:
<221> NAME/KEY: MISC_FEATURE
<222> LOCATION: (3)..(3)
<223> OTHER INFORMATION: Can be either Asn or Lys
<220> FEATURE:
<221> NAME/KEY: MISC_FEATURE
<222> LOCATION: (4)..(4)
<223> OTHER INFORMATION: Can be any amino acid but Leu
<220> FEATURE:
<221> NAME/KEY: MISC_FEATURE
<222> LOCATION: (6)..(6)
<223> OTHER INFORMATION: Can be any amino acid
<220> FEATURE:
<221> NAME/KEY: MISC_FEATURE
<222> LOCATION: (7)..(7)
<223> OTHER INFORMATION: Can be either Asn, Asp, or His
<220> FEATURE:
<221> NAME/KEY: MISC_FEATURE
<222> LOCATION: (8)..(8)
<223> OTHER INFORMATION: Can be either Pro, Arg, Lys, Ala, or Gly
<220> FEATURE:
<221> NAME/KEY: MISC_FEATURE
<222> LOCATION: (9)..(9)
<223> OTHER INFORMATION: Can be either Arg, Val, or Ala
<220> FEATURE:
<221> NAME/KEY: MISC_FEATURE
<222> LOCATION: (10)..(10)
<223> OTHER INFORMATION: Can be either Phe or Tyr

<400> SEQUENCE: 209

Thr Xaa Xaa Xaa Phe Xaa Xaa Xaa Xaa Xaa Cys
1               5                   10


<210> SEQ ID NO 210
<211> LENGTH: 13
<212> TYPE: PRT
<213> ORGANISM: Artificial Sequence
<220> FEATURE:
<223> OTHER INFORMATION: Sequence Motif
<220> FEATURE:
<221> NAME/KEY: MISC_FEATURE
<222> LOCATION: (1)..(1)
<223> OTHER INFORMATION: Can be either Trp, Phe, or Tyr
<220> FEATURE:
<221> NAME/KEY: MISC_FEATURE
<222> LOCATION: (3)..(3)
<223> OTHER INFORMATION: Can be either Thr, Gln, Val, or Ile
<220> FEATURE:
<221> NAME/KEY: MISC_FEATURE
<222> LOCATION: (5)..(5)
<223> OTHER INFORMATION: Can be any amino acid
<220> FEATURE:
<221> NAME/KEY: MISC_FEATURE
<222> LOCATION: (6)..(6)
<223> OTHER INFORMATION: Can be either Phe or Tyr
<220> FEATURE:
<221> NAME/KEY: MISC_FEATURE
<222> LOCATION: (7)..(7)
<223> OTHER INFORMATION: Can be either Pro or Phe
<220> FEATURE:
<221> NAME/KEY: MISC_FEATURE
<222> LOCATION: (8)..(8)
<223> OTHER INFORMATION: Can be any amino acid but Thr
<220> FEATURE:
<221> NAME/KEY: MISC_FEATURE
<222> LOCATION: (9)..(9)
<223> OTHER INFORMATION: Can be any combination of 2, 3 or 4 amino acids
<220> FEATURE:
<221> NAME/KEY: MISC_FEATURE
<222> LOCATION: (10)..(10)
<223> OTHER INFORMATION: Can be either Tyr, Phe, or His
<220> FEATURE:
```

<221> NAME/KEY: MISC_FEATURE
<222> LOCATION: (12)..(12)
<223> OTHER INFORMATION: Can be either Ala, Thr, or Leu

<400> SEQUENCE: 210

Xaa Asp Xaa Asp Xaa Xaa Xaa Xaa Xaa Xaa Ser Xaa Thr
1               5                   10

<210> SEQ ID NO 211
<211> LENGTH: 9
<212> TYPE: PRT
<213> ORGANISM: Artificial Sequence
<220> FEATURE:
<223> OTHER INFORMATION: Sequence Motif
<220> FEATURE:
<221> NAME/KEY: MISC_FEATURE
<222> LOCATION: (3)..(3)
<223> OTHER INFORMATION: Can be either Asn or His
<220> FEATURE:
<221> NAME/KEY: MISC_FEATURE
<222> LOCATION: (6)..(6)
<223> OTHER INFORMATION: Can be either Ser or Ala

<400> SEQUENCE: 211

Gly Phe Xaa Phe Asp Xaa Lys Thr Arg
1               5

<210> SEQ ID NO 212
<211> LENGTH: 13
<212> TYPE: PRT
<213> ORGANISM: Artificial Sequence
<220> FEATURE:
<223> OTHER INFORMATION: Sequence Motif
<220> FEATURE:
<221> NAME/KEY: MISC_FEATURE
<222> LOCATION: (3)..(3)
<223> OTHER INFORMATION: Can be any amino acid
<220> FEATURE:
<221> NAME/KEY: MISC_FEATURE
<222> LOCATION: (6)..(6)
<223> OTHER INFORMATION: Can be either Arg or Lys
<220> FEATURE:
<221> NAME/KEY: MISC_FEATURE
<222> LOCATION: (7)..(7)
<223> OTHER INFORMATION: Can be any 2 amino acids
<220> FEATURE:
<221> NAME/KEY: MISC_FEATURE
<222> LOCATION: (9)..(9)
<223> OTHER INFORMATION: Can be either Trp, Tyr, or Phe
<220> FEATURE:
<221> NAME/KEY: MISC_FEATURE
<222> LOCATION: (10)..(10)
<223> OTHER INFORMATION: Can be either Asp, Asn, or Gly
<220> FEATURE:
<221> NAME/KEY: MISC_FEATURE
<222> LOCATION: (11)..(11)
<223> OTHER INFORMATION: Can be any 2 or 3 amino acids
<220> FEATURE:
<221> NAME/KEY: MISC_FEATURE
<222> LOCATION: (12)..(12)
<223> OTHER INFORMATION: Can be either Asp, Asn, Glu, Gly, or Thr
<220> FEATURE:
<221> NAME/KEY: MISC_FEATURE
<222> LOCATION: (13)..(13)
<223> OTHER INFORMATION: Can be either Ala or Thr

<400> SEQUENCE: 212

Phe Gly Xaa Gln Thr Xaa Xaa Glu Xaa Xaa Xaa Xaa Xaa
1               5                   10

<210> SEQ ID NO 213
<211> LENGTH: 13
<212> TYPE: PRT

<213> ORGANISM: Artificial Sequence
<220> FEATURE:
<223> OTHER INFORMATION: Sequence Motif
<220> FEATURE:
<221> NAME/KEY: MISC_FEATURE
<222> LOCATION: (3)..(3)
<223> OTHER INFORMATION: Can be any amino acid
<220> FEATURE:
<221> NAME/KEY: MISC_FEATURE
<222> LOCATION: (6)..(6)
<223> OTHER INFORMATION: Can be either Arg or Lys
<220> FEATURE:
<221> NAME/KEY: MISC_FEATURE
<222> LOCATION: (7)..(7)
<223> OTHER INFORMATION: Can be any 2 amino acids
<220> FEATURE:
<221> NAME/KEY: MISC_FEATURE
<222> LOCATION: (9)..(9)
<223> OTHER INFORMATION: Can be either Trp, Tyr, or Phe
<220> FEATURE:
<221> NAME/KEY: MISC_FEATURE
<222> LOCATION: (10)..(10)
<223> OTHER INFORMATION: Can be either Asp, Asn, or Gly
<220> FEATURE:
<221> NAME/KEY: MISC_FEATURE
<222> LOCATION: (11)..(11)
<223> OTHER INFORMATION: Can be any 3 amino acids
<220> FEATURE:
<221> NAME/KEY: MISC_FEATURE
<222> LOCATION: (12)..(12)
<223> OTHER INFORMATION: Can be any amino acid but Cys
<220> FEATURE:
<221> NAME/KEY: MISC_FEATURE
<222> LOCATION: (13)..(13)
<223> OTHER INFORMATION: Can be any amino acid but Pro

<400> SEQUENCE: 213

Phe Gly Xaa Gln Thr Xaa Xaa Glu Xaa Xaa Xaa Xaa Xaa
1 5 10

<210> SEQ ID NO 214
<211> LENGTH: 15
<212> TYPE: PRT
<213> ORGANISM: Artificial Sequence
<220> FEATURE:
<223> OTHER INFORMATION: Sequence Motif
<220> FEATURE:
<221> NAME/KEY: MISC_FEATURE
<222> LOCATION: (1)..(1)
<223> OTHER INFORMATION: Can be either Phe or Trp
<220> FEATURE:
<221> NAME/KEY: MISC_FEATURE
<222> LOCATION: (4)..(4)
<223> OTHER INFORMATION: Can be any amino acid
<220> FEATURE:
<221> NAME/KEY: MISC_FEATURE
<222> LOCATION: (6)..(6)
<223> OTHER INFORMATION: Can be either Leu, Val, or Ile
<220> FEATURE:
<221> NAME/KEY: MISC_FEATURE
<222> LOCATION: (7)..(7)
<223> OTHER INFORMATION: Can be any amino acid
<220> FEATURE:
<221> NAME/KEY: MISC_FEATURE
<222> LOCATION: (8)..(8)
<223> OTHER INFORMATION: Can be either Asp or Glu
<220> FEATURE:
<221> NAME/KEY: MISC_FEATURE
<222> LOCATION: (11)..(11)
<223> OTHER INFORMATION: Can be any amino acid but Pro
<220> FEATURE:
<221> NAME/KEY: MISC_FEATURE
<222> LOCATION: (12)..(12)
<223> OTHER INFORMATION: Can be either Thr, Ser, or Asp
<220> FEATURE:
<221> NAME/KEY: MISC_FEATURE
<222> LOCATION: (13)..(13)

<223> OTHER INFORMATION: Can be either Ile or Val
<220> FEATURE:
<221> NAME/KEY: MISC_FEATURE
<222> LOCATION: (14)..(14)
<223> OTHER INFORMATION: Can be either Glu or Ala

<400> SEQUENCE: 214

Xaa His Asp Xaa Asp Xaa Xaa Xaa Glu Gly Xaa Xaa Xaa Xaa Glu
1 5 10 15

<210> SEQ ID NO 215
<211> LENGTH: 1008
<212> TYPE: DNA
<213> ORGANISM: Saccharomyces cerevisiae

<400> SEQUENCE: 215
atgtctgaac cagctcaaaa gaaacaaaag gttgctaaca actctctaga acaattgaaa 60
gcctccggca ctgtcgttgt tgccgacact ggtgatttcg gctctattgc caagtttcaa 120
cctcaagact ccacaactaa cccatcattg atcttggctg ctgccaagca accaacttac 180
gccaagttga tcgatgttgc cgtggaatac ggtaagaagc atggtaagac caccgaagaa 240
caagtcgaaa atgctgtgga cagattgtta gtcgaattcg gtaaggagat cttaaagatt 300
gttccaggca gagtctccac cgaagttgat gctagattgt cttttgacac tcaagctacc 360
attgaaaagg ctagacatat cattaaattg tttgaacaag aaggtgtctc caaggaaaga 420
gtccttatta aaattgcttc cacttgggaa ggtattcaag ctgccaaaga attggaagaa 480
aaggacggta tccactgtaa tttgactcta ttattctcct tcgttcaagc agttgcctgt 540
gccgaggccc aagttacttt gatttcccca tttgttggta gaattctaga ctggtacaaa 600
tccagcactg gtaaagatta caagggtgaa gccgacccag gtgttatttc cgtcaagaaa 660
atctacaact actacaagaa gtacggttac aagactattg ttatgggtgc ttctttcaga 720
agcactgacg aaatcaaaaa cttggctggt gttgactatc taacaatttc tccagcttta 780
ttggacaagt tgatgaacag tactgaacct ttcccaagag ttttggaccc tgtctccgct 840
aagaaggaag ccggcgacaa gatttcttac atcagcgacg aatctaaatt cagattcgac 900
ttgaatgaag acgctatggc cactgaaaaa ttgtccgaag gtatcagaaa attctctgcc 960
gatattgtta ctctattcga cttgattgaa aagaaagtta ccgcttaa 1008

<210> SEQ ID NO 216
<211> LENGTH: 1803
<212> TYPE: DNA
<213> ORGANISM: Saccharomyces cerevisiae

<400> SEQUENCE: 216
atgttgtgtt cagtaattca gagacagaca agagaggttt ccaacacaat gtctttagac 60
tcatactatc ttgggtttga tctttcgacc caacaactga aatgtctcgc cattaaccag 120
gacctaaaaa ttgtccattc agaaacagtg gaatttgaaa aggatcttcc gcattatcac 180
acaaagaagg gtgtctatat acacggcgac actatcgaat gtcccgtagc catgtggtta 240
gaggctctag atctggttct ctcgaaatat cgcgaggcta aatttccatt gaacaaagtt 300
atggccgtct cagggtcctg ccagcagcac gggtctgtct actggtcctc ccaagccgaa 360
tctctgttag agcaattgaa taagaaaccg gaaaaagatt tattgcacta cgtgagctct 420
gtagcatttg caaggcaaac cgcccccaat tggcaagacc acagtactgc aaagcaatgt 480
caagagtttg aagagtgcat aggtgggcct gaaaaaatgg ctcaattaac agggtccaga 540

```
gcccatttta gatttactgg tcctcaaatt ctgaaaattg cacaattaga accagaagct    600
tacgaaaaaa caaagaccat ttctttagtg tctaattttt tgacttctat cttagtgggc    660
catcttgttg aattagagga ggcagatgcc tgtggtatga acctttatga tatacgtgaa    720
agaaaattca gtgatgagct actacatcta attgatagtt cttctaagga taaaactatc    780
agacaaaaat taatgagagc acccatgaaa aatttgatag cgggtaccat ctgtaaatat    840
tttattgaga agtacggttt caatacaaac tgcaaggtct ctcccatgac tggggataat    900
ttagccacta tatgttcttt acccctgcgg aagaatgacg ttctcgtttc cctaggaaca    960
agtactacag ttcttctggt caccgataag tatcacccct ctccgaacta tcatcttttc   1020
attcatccaa ctctgccaaa ccattatatg ggtatgattt gttattgtaa tggttctttg   1080
gcaagggaga ggataagaga cgagttaaac aaagaacggg aaaataatta tgagaagact   1140
aacgattgga ctctttttaa tcaagctgtg ctagatgact cagaaagtag tgaaaatgaa   1200
ttaggtgtat attttcctct gggggagatc gttcctagcg taaaagccat aaacaaaagg   1260
gttatcttca atccaaaaac gggtatgatt gaaagagagg tggccaagtt caaagacaag   1320
aggcacgatg ccaaaaatat tgtagaatca caggctttaa gttgcagggt aagaatatct   1380
cccctgcttt cggattcaaa cgcaagctca caacagagac tgaacgaaga tacaatcgtg   1440
aagtttgatt acgatgaatc tccgctgcgg gactacctaa ataaaaggcc agaaaggact   1500
ttttttgtag gtggggcttc taaaaacgat gctattgtga agaagtttgc tcaagtcatt   1560
ggtgctacaa agggtaattt taggctagaa acaccaaact catgtgccct tggtggttgt   1620
tataaggcca tgtggtcatt gttatatgac tctaataaaa ttgcagttcc ttttgataaa   1680
tttctgaatg acaattttcc atggcatgta atggaaagca tatccgatgt ggataatgaa   1740
aattgggatc gctataattc caagattgtc cccttaagcg aactggaaaa gactctcatc   1800
taa                                                                 1803
```

<210> SEQ ID NO 217
<211> LENGTH: 2043
<212> TYPE: DNA
<213> ORGANISM: Saccharomyces cerevisiae

<400> SEQUENCE: 217

```
atgactcaat tcactgacat tgataagcta gccgtctcca ccataagaat tttggctgtg     60
gacaccgtat ccaaggccaa ctcaggtcac ccaggtgctc cattgggtat ggcaccagct    120
gcacacgttc tatggagtca aatgcgcatg aacccaacca acccagactg gatcaacaga    180
gatagatttg tcttgtctaa cggtcacgcg gtcgctttgt tgtattctat gctacatttg    240
actggttacg atctgtctat tgaagacttg aaacagttca gacagttggg ttccagaaca    300
ccaggtcatc ctgaatttga gttgccaggt gttgaagtta ctaccggtcc attaggtcaa    360
ggtatctcca acgctgttgg tatggccatg gctcaagcta acctggctgc cacttacaac    420
aagccgggct ttaccttgtc tgacaactac acctatgttt tcttgggtga cggttgtttg    480
caagaaggta tttcttcaga agcttcctcc ttggctggtc atttgaaatt gggtaacttg    540
attgccatct acgatgacaa caagatcact atcgatggtg ctaccagtat ctcattcgat    600
gaagatgttg ctaagagata cgaagcctac ggttgggaag ttttgtacgt agaaaatggt    660
aacgaagatc tagccggtat tgccaaggct attgctcaag ctaagttatc caaggacaaa    720
ccaactttga tcaaaatgac cacaaccatt ggttacggtt ccttgcatgc cggctctcac    780
tctgtgcacg gtgccccatt gaaagcagat gatgttaaac aactaaagag caaattcggt    840
```

ttcaacccag acaagtcctt tgttgttcca caagaagttt acgaccacta ccaaaagaca 900
attttaaagc caggtgtcga agccaacaac aagtggaaca agttgttcag cgaataccaa 960
aagaaattcc cagaattagg tgctgaattg gctagaagat tgagcggcca actacccgca 1020
aattgggaat ctaagttgcc aacttacacc gccaaggact ctgccgtggc cactagaaaa 1080
ttatcagaaa ctgttcttga ggatgtttac aatcaattgc cagagttgat tggtggttct 1140
gccgatttaa caccttctaa cttgaccaga tggaaggaag cccttgactt ccaacctcct 1200
tcttccggtt caggtaacta ctctggtaga tacattaggt acggtattag agaacacgct 1260
atgggtgcca taatgaacgg tatttcagct ttcggtgcca actacaaacc atacggtggt 1320
actttcttga acttcgtttc ttatgctgct ggtgccgtta gattgtccgc tttgtctggc 1380
cacccagtta tttgggttgc tacacatgac tctatcggtg tcggtgaaga tggtccaaca 1440
catcaaccta ttgaaacttt agcacacttc agatccctac caaacattca agtttggaga 1500
ccagctgatg gtaacgaagt ttctgccgcc tacaagaact ctttagaatc caagcatact 1560
ccaagtatca ttgctttgtc cagacaaaac ttgccacaat tggaaggtag ctctattgaa 1620
agcgcttcta agggtggtta cgtactacaa gatgttgcta acccagatat tattttagtg 1680
gctactggtt ccgaagtgtc tttgagtgtt gaagctgcta agactttggc cgcaaagaac 1740
atcaaggctc gtgttgtttc tctaccagat ttcttcactt ttgacaaaca accccctagaa 1800 tacagactat cagtcttacc agacaacgtt ccaatcatgt ctgttgaagt tttggctacc 1860
acatgttggg gcaaatacgc tcatcaatcc ttcggtattg acagatttgg tgcctccggt 1920
aaggcaccag aagtcttcaa gttcttcggt ttcaccccag aaggtgttgc tgaaagagct 1980
caaaagacca ttgcattcta taagggtgac aagctaattt ctcctttgaa aaaagctttc 2040
taa 2043

<210> SEQ ID NO 218
<211> LENGTH: 717
<212> TYPE: DNA
<213> ORGANISM: Saccharomyces cerevisiae

<400> SEQUENCE: 218
atggtcaaac caattatagc tcccagtatc cttgcttctg acttcgccaa cttgggttgc 60
gaatgtcata aggtcatcaa cgccggcgca gattggttac atatcgatgt catggacggc 120
cattttgttc caaacattac tctgggccaa ccaattgtta cctccctacg tcgttctgtg 180
ccacgccctg gcgatgctag caacacagaa aagaagccca ctgcgttctt cgattgtcac 240
atgatggttg aaaatcctga aaaatgggtc gacgattttg ctaaatgtgg tgctgaccaa 300
tttacgttcc actacgaggc cacacaagac cctttgcatt tagttaagtt gattaagtct 360
aagggcatca aagctgcatg cgccatcaaa cctggtactt ctgttgacgt tttatttgaa 420
ctagctcctc atttggatat ggctcttgtt atgactgtgg aacctgggtt tggaggccaa 480
aaattcatgg aagacatgat gccaaaagtg gaaactttga gagccaagtt cccccatttg 540
aatatccaag tcgatggtgg tttgggcaag gagaccatcc cgaaagccgc caaagccggt 600
gccaacgtta ttgtcgctgg taccagtgtt ttcactgcag ctgacccgca cgatgttatc 660
tccttcatga aagaagaagt ctcgaaggaa ttgcgttcta gagatttgct agattag 717

<210> SEQ ID NO 219
<211> LENGTH: 777
<212> TYPE: DNA

<213> ORGANISM: Saccharomyces cerevisiae

<400> SEQUENCE: 219

```
atggctgccg gtgtcccaaa aattgatgcg ttagaatctt tgggcaatcc tttggaggat      60
gccaagagag ctgcagcata cagagcagtt gatgaaaatt taaaatttga tgatcacaaa     120
attattggaa ttggtagtgg tagcacagtg gtttatgttg ccgaaagaat tggacaatat     180
ttgcatgacc ctaaatttta tgaagtagcg tctaaattca tttgcattcc aacaggattc     240
caatcaagaa acttgatttt ggataacaag ttgcaattag gctccattga acagtatcct     300
cgcattgata tagcgtttga cggtgctgat gaagtggatg agaatttaca attaattaaa     360
ggtggtggtg cttgtctatt tcaagaaaaa ttggttagta ctagtgctaa aaccttcatt     420
gtcgttgctg attcaagaaa aaagtcacca aaacatttag gtaagaactg gaggcaaggt     480
gttcccattg aaattgtacc ttcctcatac gtgagggtca agaatgatct attagaacaa     540
ttgcatgctg aaaaagttga catcagacaa ggaggttctg ctaaagcagg tcctgttgta     600
actgacaata ataacttcat tatcgatgcg gatttcggtg aaatttccga tccaagaaaa     660
ttgcatagag aaatcaaact gttagtgggc gtggtggaaa caggtttatt catcgacaac     720
gcttcaaaag cctacttcgg taattctgac ggtagtgttg aagttaccga aaagtga        777
```

<210> SEQ ID NO 220
<211> LENGTH: 1725
<212> TYPE: DNA
<213> ORGANISM: Saccharomyces cerevisiae

<400> SEQUENCE: 220

```
atggcagttg aggagaacaa tatgcctgtt gtttcacagc aaccccaagc tggtgaagac      60
gtgatctctt cactcagtaa agattcccat ttaagcgcac aatctcaaaa gtattctaat     120
gatgaattga aagccggtga gtcagggtct gaaggctccc aaagtgttcc tatagagata     180
cccaagaagc ccatgtctga atatgttacc gtttccttgc tttgtttgtg tgttgccttc     240
ggcggcttca tgtttggctg ggataccggt actatttctg ggtttgttgt ccaaacagac     300
tttttgagaa ggtttggtat gaaacataag gatggtaccc actatttgtc aaacgtcaga     360
acaggtttaa tcgtcgccat tttcaatatt ggctgtgcct ttggtggtat tatactttcc     420
aaaggtggag atatgtatgg ccgtaaaaag ggtctttcga ttgtcgtctc ggtttatata     480
gttggtatta tcattcaaat tgcctctatc aacaagtggt accaatattt cattggtaga     540
atcatatctg gtttgggtgt cggcggcatc gccgtcttat gtcctatgtt gatctctgaa     600
attgctccaa agcacttgag aggcacacta gtttcttgtt atcagctgat gattactgca     660
ggtatctttt tgggctactg tactaattac ggtacaaaga gctattcgaa ctcagttcaa     720
tggagagttc cattagggct atgtttcgct tggtcattat ttatgattgg cgctttgacg     780
ttagttcctg aatccccacg ttatttatgt gaggtgaata aggtagaaga cgccaagcgt     840
tccattgcta agtctaacaa ggtgtcacca gaggatcctg ccgtccaggc agagttagat     900
ctgatcatgg ccggtataga agctgaaaaa ctggctggca atgcgtcctg gggggaatta     960
ttttccacca agaccaaagt atttcaacgt ttgttgatgg gtgtgtttgt tcaaatgttc    1020
caacaattaa ccggtaacaa ttattttttc tactacggta ccgttatttt caagtcagtt    1080
ggcctggatg attcctttga aacatccatt gtcattggtg tagtcaactt tgcctccact    1140
ttctttagtt tgtggactgt cgaaaacttg ggacatcgta aatgtttact tttgggcgct    1200
gccactatga tggcttgtat ggtcatctac gcctctgttg gtgttactag attatatcct    1260
```

cacggtaaaa gccagccatc ttctaaaggt gccggtaact gtatgattgt ctttacctgt 1320
ttttatattt tctgttatgc cacaacctgg gcgccagttg cctgggtcat cacagcagaa 1380
tcattcccac tgagagtcaa gtcgaaatgt atggcgttgg cctctgcttc caattgggta 1440
tgggggttct tgattgcatt tttcacccca ttcatcacat ctgccattaa cttctactac 1500
ggttatgtct tcatgggctg tttggttgcc atgttttttt atgtcttttt ctttgttcca 1560
gaaactaaag gcctatcgtt agaagaaatt caagaattat gggaagaagg tgttttacct 1620
tggaaatctg aaggctggat tccttcatcc agaagaggta ataattacga tttagaggat 1680
ttacaacatg acgacaaacc gtggtacaag gccatgctag aataa 1725

<210> SEQ ID NO 221
<211> LENGTH: 37
<212> TYPE: DNA
<213> ORGANISM: Unknown
<220> FEATURE:
<223> OTHER INFORMATION: Obtained from environmental sample

<400> SEQUENCE: 221
caccattaat taacccgggg cacctgtcac tttggaa 37

<210> SEQ ID NO 222
<211> LENGTH: 51
<212> TYPE: DNA
<213> ORGANISM: Unknown
<220> FEATURE:
<223> OTHER INFORMATION: Obtained from environmental sample

<400> SEQUENCE: 222
cgcgtaagct ttctagaggc gcgccaagct tttacactct tgaccagcgc a 51

<210> SEQ ID NO 223
<211> LENGTH: 57
<212> TYPE: DNA
<213> ORGANISM: Unknown
<220> FEATURE:
<223> OTHER INFORMATION: Obtained from environmental sample

<400> SEQUENCE: 223
ccgctggtgg gtaccgatat ccctgcaggg agctcacgcg taagctttct agaggcg 57

<210> SEQ ID NO 224
<211> LENGTH: 56
<212> TYPE: DNA
<213> ORGANISM: Unknown
<220> FEATURE:
<223> OTHER INFORMATION: Obtained from environmental sample

<400> SEQUENCE: 224
ctgcagggat atcggtaccc accagcggcc gcaggccttg ggtgcttgct ggcgaa 56

<210> SEQ ID NO 225
<211> LENGTH: 48
<212> TYPE: DNA
<213> ORGANISM: Unknown
<220> FEATURE:
<223> OTHER INFORMATION: Obtained from environmental sample

<400> SEQUENCE: 225
acctctgcat gcgaattctt aagacaaata aaatttatag agacttgt 48

<210> SEQ ID NO 226

<211> LENGTH: 36
<212> TYPE: DNA
<213> ORGANISM: Unknown
<220> FEATURE:
<223> OTHER INFORMATION: Obtained from environmental sample

<400> SEQUENCE: 226
gtcttaagaa ttcgcatgca gaggtagttt caaggt 36

<210> SEQ ID NO 227
<211> LENGTH: 39
<212> TYPE: DNA
<213> ORGANISM: Unknown
<220> FEATURE:
<223> OTHER INFORMATION: Obtained from environmental sample

<400> SEQUENCE: 227
caccattaat taatacgtat ttctcgccga gaaaaactt 39

<210> SEQ ID NO 228
<211> LENGTH: 25
<212> TYPE: DNA
<213> ORGANISM: Unknown
<220> FEATURE:
<223> OTHER INFORMATION: Obtained from environmental sample

<400> SEQUENCE: 228
ccccatcgac aactacgagc tcact 25

<210> SEQ ID NO 229
<211> LENGTH: 25
<212> TYPE: DNA
<213> ORGANISM: Unknown
<220> FEATURE:
<223> OTHER INFORMATION: Obtained from environmental sample

<400> SEQUENCE: 229
caacttgccg tcctcgaagt ccttg 25

<210> SEQ ID NO 230
<211> LENGTH: 25
<212> TYPE: DNA
<213> ORGANISM: Unknown
<220> FEATURE:
<223> OTHER INFORMATION: Obtained from environmental sample

<400> SEQUENCE: 230
cgagcctgag aaggtcgtga tggga 25

<210> SEQ ID NO 231
<211> LENGTH: 25
<212> TYPE: DNA
<213> ORGANISM: Unknown
<220> FEATURE:
<223> OTHER INFORMATION: Obtained from environmental sample

<400> SEQUENCE: 231
tacgtcgaag tcggggttgg tagaa 25

<210> SEQ ID NO 232
<211> LENGTH: 21
<212> TYPE: DNA
<213> ORGANISM: Unknown
<220> FEATURE:
<223> OTHER INFORMATION: Obtained from environmental sample

<400> SEQUENCE: 232
agtcacatca agatcgttta t 21

<210> SEQ ID NO 233
<211> LENGTH: 21
<212> TYPE: DNA
<213> ORGANISM: Unknown
<220> FEATURE:
<223> OTHER INFORMATION: Obtained from environmental sample

<400> SEQUENCE: 233
gcacggaata tgggactact t 21

<210> SEQ ID NO 234
<211> LENGTH: 21
<212> TYPE: DNA
<213> ORGANISM: Unknown
<220> FEATURE:
<223> OTHER INFORMATION: Obtained from environmental sample

<400> SEQUENCE: 234
actccacttc aagtaagagt t 21

<210> SEQ ID NO 235
<211> LENGTH: 27
<212> TYPE: DNA
<213> ORGANISM: Unknown
<220> FEATURE:
<223> OTHER INFORMATION: Obtained from environmental sample

<400> SEQUENCE: 235
gaacaaaaac ctgcaggaaa cgaagat 27

<210> SEQ ID NO 236
<211> LENGTH: 31
<212> TYPE: DNA
<213> ORGANISM: Unknown
<220> FEATURE:
<223> OTHER INFORMATION: Obtained from environmental sample

<400> SEQUENCE: 236
gctctaattt gtgagtttag tatacatgca t 31

<210> SEQ ID NO 237
<211> LENGTH: 1338
<212> TYPE: DNA
<213> ORGANISM: Unknown
<220> FEATURE:
<223> OTHER INFORMATION: Obtained from environmental sample

<400> SEQUENCE: 237
ttaattaagt taattacctt ttttgcgagg catatttatg gtgaagaata agttttgacc 60
atcaaagaag gttaatgtgg ctgtggtttc agggtccata aagcttttca attcatcatt 120
ttttttttat tcttttttt gattccggtt tccttgaaat ttttttgatt cggtaatctc 180
cgaacagaag gaagaacgaa ggaaggagca cagacttaga ttggtatata tacgcatatg 240
tagtgttgaa gaaacatgaa attgcccagt attcttaacc caactgcaca gaacaaaaac 300
ctgcaggaaa cgaagataaa tcatgtcgaa agctacatat aaggaacgtg ctgctactca 360
tcctagtcct gttgctgcca agctatttaa tatcatgcac gaaaagcaaa caaacttgtg 420
tgcttcattg gatgttcgta ccaccaagga attactggag ttagttgaag cattaggtcc 480
caaaatttgt ttactaaaaa cacatgtgga tatcttgact gatttttcca tggagggcac 540

-continued

```
agttaagccg ctaaaggcat tatccgccaa gtacaatttt ttactcttcg aagacagaaa    600

atttgctgac attggtaata cagtcaaatt gcagtactct gcgggtgtat acagaatagc    660

agaatgggca gacattacga atgcacacgg tgtggtgggc ccaggtattg ttagcggttt    720

gaagcaggcg gcagaagaag taacaaagga acctagaggc cttttgatgt tagcagaatt    780

gtcatgcaag ggctccctag ctactggaga atatactaag ggtactgttg acattgcgaa    840

gagcgacaaa gattttgtta tcggctttat tgctcaaaga gacatgggtg gaagagatga    900

aggttacgat tggttgatta tgacacccgg tgtgggttta gatgacaagg gagacgcatt    960

gggtcaacag tatagaaccg tggatgatgt ggtctctaca ggatctgaca ttattattgt   1020

tggaagagga ctatttgcaa agggaaggga tgctaaggta gagggtgaac gttacagaaa   1080

agcaggctgg gaagcatatt tgagaagatg cggccagcaa aactaaaaaa ctgtattata   1140

agtaaatgca tgtatactaa actcacaaat tagagcttca atttaattat atcagttatt   1200

acccgggaat ctcggtcgta atgattttta taatgacgaa aaaaaaaaaa ttggaaagaa   1260

aaagcttcat ggcctttata aaaaggaacc atccaatacc tcgccagaac caagtaacag   1320

tattttacgg ttaattaa                                                 1338
```

XYLOSE ISOMERASES AND THEIR USES

This application claims the benefit under 35 U.S.C. §119 (e) of U.S. provisional application No. 61/675,241, filed Jul. 24, 2012, the contents of which are incorporated by reference in their entireties herein.

1. BACKGROUND

The efficient, commercial production of biofuels from plant material, such as sugarcane, requires the fermentation of pentoses, such as xylose. Xylose in plant material typically comes from lignocellulose, which is a matrix composed of cellulose, hemicelluloses, and lignin. Lignocellulose is broken down either by acid hydrolysis or enzymatic reaction, yielding xylose in addition to other monosaccharides, such as glucose (Maki et al., 2009, Int. J. Biol. Sci. 5:500-516).

Fungi, especially *Saccharomyces cerevisiae*, are commercially relevant microorganisms that ferment sugars into biofuels such as ethanol. However, *S. cerevisiae* does not endogenously metabolize xylose, requiring genetic modifications that allow it to convert xylose into xylulose. Other organisms, whose usefulness in ethanol production is limited, are able to metabolize xylose (Nevigot, 2008, Micobiol. Mol. Biol. Rev. 72:379-412).

Two pathways have been identified for the metabolism of xylose to xylulose in microorganisms: the xylose reductase (XR, EC 1.1.1.307)/xylitol dehydrogenase (XDH, EC 1.1.1.9, 1.1.1.10 and 1.1.1.B19) pathway and the xylose isomerase (XI, EC 5.3.1.5) pathway. Use of the XR/XDH pathway for xylose metabolism creates an imbalance of cofactors (excess NADH and NADP+) limiting the potential output of this pathway for the production of ethanol. The XI pathway, on the otherhand, converts xylose to xylulose in a single step and does not create a cofactor imbalance (Young et al., 2010, Biotechnol. Biofuels 3:24-36).

Because *S. cerevisiae* does not possess a native XI, it has been desirable to search for an XI in another organism to insert into *S. cerevisiae* for the purpose of biofuels production. Several XI genes have been discovered, although little or no enzymatic activity upon expression in *S. cerevisiae* has been a common problem. The XI from *Piromyces* sp. E2 was the first heterologously expressed XI in *S. cerevisiae* whose enzymatic activity could be observed (WO 03/062430).

2. SUMMARY

Due to the physiology of *S. cerevisiae* and the process of commercial biofuel production, there are other characteristics besides activity that are valuable in a commercially useful XI. During fermentation, the pH of the yeast cell and its environment can become more acidic (Rosa and Sa-Correia, 1991, Appl. Environ. Microbiol. 57:830-835). The ability of the XI to function in an acidic environment is therefore highly desirable. Therefore, there is a still a need in the art for XI enzymes with enhanced activity to convert xylose to xylulose for biofuels production under a broader range of commercially relevant conditions.

The present disclosure relates to novel xylose isomerases. The xylose isomerases have desirable characteristics for xylose fermentation, such as high activity, tolerance to acidic conditions (i.e., pH levels below 7, e.g., pH 6.5 or pH 6), or both.

The present disclosure has multiple aspects. In one aspect, the disclosure is directed to XI polypeptides. The polypeptides of the disclosure typically comprise amino acid sequences having at least 70%, 75%, 80%, 85%, 90%, 93%, 95%, 96%, 98%, 99% or 100% sequence identity to any of the XI polypeptides of Table 1, or the catalytic domain or dimerization domain thereof, or are encoded by nucleic acid sequences comprising nucleotide sequences having at least 70%, 75%, 80%, 85%, 90%, 93%, 95%, 96%, 98%, 99% or 100% sequence identity to any of the nucleic acids of Table 1:

TABLE 1

| SEQ ID NO: | Clone No. | Organism Classification | Type of Sequence | Catalytic Domain | Dimerization Domain |
|---|---|---|---|---|---|
| 1 | 1754MI2_001 | Bacteroidales | DNA | | |
| 2 | 1754MI2_001 | Bacteroidales | Amino Acid | 2-376 | 377-437 |
| 3 | 5586MI6_004 | Bacteroidales | DNA | | |
| 4 | 5586MI6_004 | Bacteroidales | Amino Acid | 2-376 | 377-437 |
| 5 | 5749MI1_003 | Bacteroidales | DNA | | |
| 6 | 5749MI1_003 | Bacteroidales | Amino Acid | 2-381 | 382-442 |
| 7 | 5750MI1_003 | Bacteroidales | DNA | | |
| 8 | 5750MI1_003 | Bacteroidales | Amino Acid | 2-381 | 382-442 |
| 9 | 5750MI2_003 | Bacteroidales | DNA | | |
| 10 | 5750MI2_003 | Bacteroidales | Amino Acid | 2-381 | 382-442 |
| 11 | 5586MI5_004 | *Bacteroides* | DNA | | |
| 12 | 5586MI5_004 | *Bacteroides* | Amino Acid | 2-375 | 376-435 |
| 13 | 5586MI202_004 | *Bacteroides* | DNA | | |
| 14 | 5586MI202_004 | *Bacteroides* | Amino Acid | 2-377 | 378-438 |
| 15 | 5586MI211_003 | *Bacteroides* | DNA | | |
| 16 | 5586MI211_003 | *Bacteroides* | Amino Acid | 2-376 | 377-437 |
| 17 | 5606MI1_005 | *Bacteroides* | DNA | | |
| 18 | 5606MI1_005 | *Bacteroides* | Amino Acid | 2-377 | 378-438 |
| 19 | 5606MI2_003 | *Bacteroides* | DNA | | |
| 20 | 5606MI2_003 | *Bacteroides* | Amino Acid | 2-378 | 379-439 |
| 21 | 5610MI3_003 | *Bacteroides* | DNA | | |
| 22 | 5610MI3_003 | *Bacteroides* | Amino Acid | 2-377 | 378-439 |
| 23 | 5749MI2_004 | *Bacteroides* | DNA | | |
| 24 | 5749MI2_004 | *Bacteroides* | Amino Acid | 2-377 | 378-438 |
| 25 | 5750MI3_003 | *Bacteroides* | DNA | | |
| 26 | 5750MI3_003 | *Bacteroides* | Amino Acid | 2-377 | 378-438 |
| 27 | 5750MI4_003 | *Bacteroides* | DNA | | |
| 28 | 5750MI4_003 | *Bacteroides* | Amino Acid | 2-377 | 378-438 |
| 29 | 5751MI4_002 | *Bacteroides* | DNA | | |
| 30 | 5751MI4_002 | *Bacteroides* | Amino Acid | 2-376 | 377-437 |
| 31 | 5751MI5_003 | *Bacteroides* | DNA | | |

TABLE 1-continued

| SEQ ID NO: | Clone No. | Organism Classification | Type of Sequence | Catalytic Domain | Dimerization Domain |
|---|---|---|---|---|---|
| 32 | 5751MI5__003 | *Bacteroides* | Amino Acid | 2-377 | 378-438 |
| 33 | 5751MI6__004 | *Bacteroides* | DNA | | |
| 34 | 5751MI6__004 | *Bacteroides* | Amino Acid | 2-377 | 378-438 |
| 35 | 5586MI22__003 | Clostridiales | DNA | | |
| 36 | 5586MI22__003 | Clostridiales | Amino Acid | 2-375 | 376-439 |
| 37 | 1753MI4__001 | Firmicutes | DNA | | |
| 38 | 1753MI4__001 | Firmicutes | Amino Acid | 2-374 | 375-440 |
| 39 | 1753MI6__001 | Firmicutes | DNA | | |
| 40 | 1753MI6__001 | Firmicutes | Amino Acid | 2-374 | 375-440 |
| 41 | 1753MI35__004 | Firmicutes | DNA | | |
| 42 | 1753MI35__004 | Firmicutes | Amino Acid | 2-375 | 376-441 |
| 43 | 1754MI9__004 | Firmicutes | DNA | | |
| 44 | 1754MI9__004 | Firmicutes | Amino Acid | 2-375 | 376-440 |
| 45 | 1754MI22__004 | Firmicutes | DNA | | |
| 46 | 1754MI22__004 | Firmicutes | Amino Acid | 2-375 | 376-440 |
| 47 | 727MI1__002 | Firmicutes | DNA | | |
| 48 | 727MI1__002 | Firmicutes | Amino Acid | 2-372 | 373-436 |
| 49 | 727MI9__005 | Firmicutes | DNA | | |
| 50 | 727MI9__005 | Firmicutes | Amino Acid | 2-374 | 375-438 |
| 51 | 727MI27__002 | Firmicutes | DNA | | |
| 52 | 727MI27__002 | Firmicutes | Amino Acid | 2-374 | 375-439 |
| 53 | 1753MI2__006 | Neocallimastigales | DNA | | |
| 54 | 1753MI2__006 | Neocallimastigales | Amino Acid | 2-376 | 377-437 |
| 55 | 5586MI3__005 | Neocallimastigales | DNA | | |
| 56 | 5586MI3__005 | Neocallimastigales | Amino Acid | 2-376 | 377-437 |
| 57 | 5586MI91__002 | Neocallimastigales | DNA | | |
| 58 | 5586MI91__002 | Neocallimastigales | Amino Acid | 2-376 | 377-437 |
| 59 | 5586MI194__003 | Neocallimastigales | DNA | | |
| 60 | 5586MI194__003 | Neocallimastigales | Amino Acid | 2-376 | 377-438 |
| 61 | 5586MI198__003 | Neocallimastigales | DNA | | |
| 62 | 5586MI198__003 | Neocallimastigales | Amino Acid | 2-375 | 376-437 |
| 63 | 5586MI201__003 | Neocallimastigales | DNA | | |
| 64 | 5586MI201__003 | Neocallimastigales | Amino Acid | 2-376 | 377-438 |
| 65 | 5586MI204__002 | Neocallimastigales | DNA | | |
| 66 | 5586MI204__002 | Neocallimastigales | Amino Acid | 2-375 | 376-437 |
| 67 | 5586MI207__002 | Neocallimastigales | DNA | | |
| 68 | 5586MI207__002 | Neocallimastigales | Amino Acid | 2-375 | 376-437 |
| 69 | 5586MI209__003 | Neocallimastigales | DNA | | |
| 70 | 5586MI209__003 | Neocallimastigales | Amino Acid | 2-375 | 376-437 |
| 71 | 5586MI214__002 | Neocallimastigales | DNA | | |
| 72 | 5586MI214__002 | Neocallimastigales | Amino Acid | 2-375 | 376-437 |
| 73 | 5751MI3__001 | Neocallimastigales | DNA | | |
| 74 | 5751MI3__001 | Neocallimastigales | Amino Acid | 2-375 | 376-437 |
| 75 | 5753MI3__002 | *Prevotella* | DNA | | |
| 76 | 5753MI3__002 | *Prevotella* | Amino Acid | 2-376 | 377-439 |
| 77 | 1754MI1__001 | *Prevotella* | DNA | | |
| 78 | 1754MI1__001 | *Prevotella* | Amino Acid | 2-377 | 378-439 |
| 79 | 1754MI3__007 | *Prevotella* | DNA | | |
| 80 | 1754MI3__007 | *Prevotella* | Amino Acid | 2-377 | 378-439 |
| 81 | 1754MI5__009 | *Prevotella* | DNA | | |
| 82 | 1754MI5__009 | *Prevotella* | Amino Acid | 2-375 | 376-437 |
| 83 | 5586MI1__003 | *Prevotella* | DNA | | |
| 84 | 5586MI1__003 | *Prevotella* | Amino Acid | 2-377 | 378-439 |
| 85 | 5586MI2__006 | *Prevotella* | DNA | | |
| 86 | 5586MI2__006 | *Prevotella* | Amino Acid | 2-377 | 378-439 |
| 87 | 5586MI8__003 | *Prevotella* | DNA | | |
| 88 | 5586MI8__003 | *Prevotella* | Amino Acid | 2-377 | 378-439 |
| 89 | 5586MI14__003 | *Prevotella* | DNA | | |
| 90 | 5586MI14__003 | *Prevotella* | Amino Acid | 2-377 | 378-439 |
| 91 | 5586MI26__003 | *Prevotella* | DNA | | |
| 92 | 5586MI26__003 | *Prevotella* | Amino Acid | 2-377 | 378-439 |
| 93 | 5586MI86__001 | *Prevotella* | DNA | | |
| 94 | 5586MI86__001 | *Prevotella* | Amino Acid | 2-376 | 377-438 |
| 95 | 5586MI108__002 | *Prevotella* | DNA | | |
| 96 | 5586MI108__002 | *Prevotella* | Amino Acid | 2-377 | 378-439 |
| 97 | 5586MI182__004 | *Prevotella* | DNA | | |
| 98 | 5586MI182__004 | *Prevotella* | Amino Acid | 2-377 | 378-439 |
| 99 | 5586MI193__004 | *Prevotella* | DNA | | |
| 100 | 5586MI193__004 | *Prevotella* | Amino Acid | 2-376 | 377-438 |
| 101 | 5586MI195__003 | *Prevotella* | DNA | | |
| 102 | 5586MI195__003 | *Prevotella* | Amino Acid | 2-376 | 377-438 |
| 103 | 5586MI216__003 | *Prevotella* | DNA | | |
| 104 | 5586MI216__003 | *Prevotella* | Amino Acid | 2-376 | 377-438 |
| 105 | 5586MI197__003 | *Prevotella* | DNA | | |
| 106 | 5586MI197__003 | *Prevotella* | Amino Acid | 2-376 | 377-438 |
| 107 | 5586MI199__003 | *Prevotella* | DNA | | |
| 108 | 5586MI199__003 | *Prevotella* | Amino Acid | 2-376 | 377-438 |

TABLE 1-continued

| SEQ ID NO: | Clone No. | Organism Classification | Type of Sequence | Catalytic Domain | Dimerization Domain |
|---|---|---|---|---|---|
| 109 | 5586MI200_003 | *Prevotella* | DNA | | |
| 110 | 5586MI200_003 | *Prevotella* | Amino Acid | 2-376 | 377-438 |
| 111 | 5586MI203_003 | *Prevotella* | DNA | | |
| 112 | 5586MI203_003 | *Prevotella* | Amino Acid | 2-376 | 377-438 |
| 113 | 5586MI205_004 | *Prevotella* | DNA | | |
| 114 | 5586MI205_004 | *Prevotella* | Amino Acid | 2-376 | 377-438 |
| 115 | 5586MI206_004 | *Prevotella* | DNA | | |
| 116 | 5586MI206_004 | *Prevotella* | Amino Acid | 2-376 | 377-438 |
| 117 | 5586MI208_003 | *Prevotella* | DNA | | |
| 118 | 5586MI208_003 | *Prevotella* | Amino Acid | 2-376 | 377-438 |
| 119 | 5586MI210_002 | *Prevotella* | DNA | | |
| 120 | 5586MI210_002 | *Prevotella* | Amino Acid | 2-374 | 375-437 |
| 121 | 5586MI212_002 | *Prevotella* | DNA | | |
| 122 | 5586MI212_002 | *Prevotella* | Amino Acid | 2-376 | 377-438 |
| 123 | 5586MI213_003 | *Prevotella* | DNA | | |
| 124 | 5586MI213_003 | *Prevotella* | Amino Acid | 2-376 | 377-438 |
| 125 | 5586MI215_003 | *Prevotella* | DNA | | |
| 126 | 5586MI215_003 | *Prevotella* | Amino Acid | 2-376 | 377-438 |
| 127 | 5607MI1_003 | *Prevotella* | DNA | | |
| 128 | 5607MI1_003 | *Prevotella* | Amino Acid | 2-376 | 377-438 |
| 129 | 5607MI2_003 | *Prevotella* | DNA | | |
| 130 | 5607MI2_003 | *Prevotella* | Amino Acid | 2-376 | 377-442 |
| 131 | 5607MI3_003 | *Prevotella* | DNA | | |
| 132 | 5607MI3_003 | *Prevotella* | Amino Acid | 2-376 | 377-438 |
| 133 | 5607MI4_005 | *Prevotella* | DNA | | |
| 134 | 5607MI4_005 | *Prevotella* | Amino Acid | 2-376 | 377-438 |
| 135 | 5607MI5_002 | *Prevotella* | DNA | | |
| 136 | 5607MI5_002 | *Prevotella* | Amino Acid | 2-376 | 377-439 |
| 137 | 5607MI6_002 | *Prevotella* | DNA | | |
| 138 | 5607MI6_002 | *Prevotella* | Amino Acid | 2-376 | 377-438 |
| 139 | 5607MI7_002 | *Prevotella* | DNA | | |
| 140 | 5607MI7_002 | *Prevotella* | Amino Acid | 2-376 | 377-438 |
| 141 | 5608MI1_004 | *Prevotella* | DNA | | |
| 142 | 5608MI1_004 | *Prevotella* | Amino Acid | 2-376 | 377-438 |
| 143 | 5608MI2_002 | *Prevotella* | DNA | | |
| 144 | 5608MI2_002 | *Prevotella* | Amino Acid | 2-375 | 376-437 |
| 145 | 5608MI3_004 | *Prevotella* | DNA | | |
| 146 | 5608MI3_004 | *Prevotella* | Amino Acid | 2-376 | 377-438 |
| 147 | 5609MI1_005 | *Prevotella* | DNA | | |
| 148 | 5609MI1_005 | *Prevotella* | Amino Acid | 2-376 | 377-438 |
| 149 | 5610MI1_003 | *Prevotella* | DNA | | |
| 150 | 5610MI1_003 | *Prevotella* | Amino Acid | 2-376 | 377-438 |
| 151 | 5610MI2_004 | *Prevotella* | DNA | | |
| 152 | 5610MI2_004 | *Prevotella* | Amino Acid | 2-376 | 377-438 |
| 153 | 5751MI1_003 | *Prevotella* | DNA | | |
| 154 | 5751MI1_003 | *Prevotella* | Amino Acid | 2-376 | 377-438 |
| 155 | 5751MI2_003 | *Prevotella* | DNA | | |
| 156 | 5751MI2_003 | *Prevotella* | Amino Acid | 2-376 | 377-438 |
| 157 | 5752MI1_003 | *Prevotella* | DNA | | |
| 158 | 5752MI1_003 | *Prevotella* | Amino Acid | 2-376 | 377-438 |
| 159 | 5752MI2_003 | *Prevotella* | DNA | | |
| 160 | 5752MI2_003 | *Prevotella* | Amino Acid | 2-376 | 377-438 |
| 161 | 5752MI3_002 | *Prevotella* | DNA | | |
| 162 | 5752MI3_002 | *Prevotella* | Amino Acid | 2-376 | 377-438 |
| 163 | 5752MI5_003 | *Prevotella* | DNA | | |
| 164 | 5752MI5_003 | *Prevotella* | Amino Acid | 2-376 | 377-438 |
| 165 | 5752MI6_004 | *Prevotella* | DNA | | |
| 166 | 5752MI6_004 | *Prevotella* | Amino Acid | 2-376 | 377-438 |
| 167 | 5753MI1_002 | *Prevotella* | DNA | | |
| 168 | 5753MI1_002 | *Prevotella* | Amino Acid | 2-376 | 377-438 |
| 169 | 5753MI2_002 | *Prevotella* | DNA | | |
| 170 | 5753MI2_002 | *Prevotella* | Amino Acid | 2-376 | 377-438 |
| 171 | 5753MI4_002 | *Prevotella* | DNA | | |
| 172 | 5753MI4_002 | *Prevotella* | Amino Acid | 2-376 | 377-438 |
| 173 | 5752MI4_004 | *Prevotella* | DNA | | |
| 174 | 5752MI4_004 | *Prevotella* | Amino Acid | 2-376 | 377-438 |
| 175 | 727MI4_006 | Rhizobiales | DNA | | |
| 176 | 727MI4_006 | Rhizobiales | Amino Acid | 2-373 | 374-435 |

In specific embodiments, a polypeptide of the disclosure comprises an amino acid sequence having:

(1) (a) at least 97% or 98% sequence identity to SEQ ID NO:78 or the catalytic domain thereof (amino acids 2-377 of SEQ ID NO:78) and/or (b) at least 80%, 85%, 90%, 93% or 95% sequence identity to SEQ ID NO:78 or the catalytic domain thereof (amino acids 2-377 of SEQ ID NO:78) and further comprises (i) SEQ ID NO:212 or SEQ ID NO:213 and/or (ii) SEQ ID NO:214;

(2) (a) at least 95%, 97% or 98% sequence identity to SEQ ID NO:96 or the catalytic domain thereof (amino acids 2-377 of SEQ ID NO:96) and/or (b) at least 80%, 85%, 90%, 93% or 95% sequence identity to SEQ ID NO:96 or the catalytic domain thereof (amino acids 2-377 of SEQ ID NO:96) and further comprises (i) SEQ ID NO:212 or SEQ ID NO:213 and/or (ii) SEQ ID NO:214;

(3) at least 80%, 85%, 90%, 93%, 95%, 97% or 98% sequence identity to SEQ ID NO:38 or the catalytic domain thereof (amino acids 2-374 of SEQ ID NO:38), and optionally further comprises one, two, three, four or all five of (i) SEQ ID NO:206 or SEQ ID NO:207; (ii) SEQ ID NO:208; (iii) SEQ ID NO:209; (iv) SEQ ID NO:210; and (iv) SEQ ID NO:211;

(4) at least 80%, 85%, 90%, 93%, 95%, 97% or 98% sequence identity to SEQ ID NO:2 or the catalytic domain thereof (amino acids 2-374 of SEQ ID NO:2);

(5) at least 93%, 95%, 97% or 98% sequence identity to SEQ ID NO:58 or the catalytic domain thereof (amino acids 2-376 of SEQ ID NO:58), (6) at least 80%, 85%, 90%, 93%, 95%, 97% or 98% sequence identity to SEQ ID NO:42 or the catalytic domain thereof (amino acids 2-375 of SEQ ID NO:42), and optionally further comprises one, two or all three of (i) SEQ ID NO:206 or SEQ ID NO:207; (ii) SEQ ID NO:210; and (iii) SEQ ID NO:211;

(7) (a) at least 97% or 98% sequence identity to SEQ ID NO:84 or the catalytic domain thereof (amino acids 2-376 of SEQ ID NO:84), and/or (b) at least 80%, 85%, 90%, 93% or 95% sequence identity to SEQ ID NO:84 or the catalytic domain thereof (amino acids 2-376 of SEQ ID NO:84) and further comprises (i) SEQ ID NO:212 or SEQ ID NO:213 and/or (ii) SEQ ID NO:214;

(8) (a) at least 97% or 98% sequence identity to SEQ ID NO:80 or the catalytic domain thereof (amino acids 2-377 of SEQ ID NO:80) and/or (b) at least 80%, 85%, 90%, 93% or 95% sequence identity to SEQ ID NO:80 or the catalytic domain thereof (amino acids 2-377 of SEQ ID NO:80) and further comprises (i) SEQ ID NO:212 or SEQ ID NO:213 and/or (ii) SEQ ID NO:214;

(9) at least 93%, 95%, 97% or 98% sequence identity to SEQ ID NO:54 or the catalytic domain thereof (amino acids 2-376 of SEQ ID NO:54);

(10) at least 80%, 85%, 90%, 93%, 95%, 97% or 98% sequence identity to SEQ ID NO:46 or the catalytic domain thereof (amino acids 2-376 of SEQ ID NO:46), and optionally further comprises SEQ ID NO:206 or SEQ ID NO:207;

(11) at least 90%, 93%, 95%, 97% or 98% sequence identity to SEQ ID NO:16 or the catalytic domain thereof (amino acids 2-376 of SEQ ID NO:16);

(12) at least 85%, 90%, 93%, 95%, 97% or 98% sequence identity to SEQ ID NO:82 or the catalytic domain thereof (amino acids 2-375 of SEQ ID NO:82); and/or

(13) at least 90%, 93%, 95%, 97% or 98% sequence identity to SEQ ID NO:32 or the catalytic domain thereof (amino acids 2-377 of SEQ ID NO:32).

The XIs of the disclosure can be characterized in terms of their activity. In some embodiments, a XI of the disclosure has at least 1.3 times the activity of the *Orpinomyces* sp. XI assigned Genbank Accession No. 169733248 ("Op-XI") at pH 7.5, for example using the assay described in any of Examples 4, 6 and 7. In certain specific embodiments, a XI of the disclosure has an activity ranging from 1.25 to 3.0 times, from 1.5 to 3 times, from 1.5 to 2.25 times, or from 1.75 to 3 times the activity of Op-XI at pH 7.5.

The XIs of the disclosure can also be characterized in terms of their tolerance to acidic environments (e.g., at a pH of 6.5 or 6). In some embodiments, a XI of the disclosure has at least 1.9 times the activity of the Op-XI at pH 6, for example using the assay described in Example 7. In certain specific embodiments, a XI of the disclosure has an activity ranging from 1.9 to 4.1 times, from 2.4 to 4.1 times, from 2.4 to 3.9 times, or 2.4 to 4.1 times the activity of Op-XI at pH 6.

Tolerance to acidic environments can also be characterized as a ratio of activity at pH 6 to activity at pH 7.5 ("a pH 6 to pH 7.5 activity ratio"), for example as measured using the assay of Example 7. In some embodiments, the pH 6 to pH 7.5 activity ratio is at least 0.5 or at least 0.6. In various embodiments, the pH 6 to pH 7.5 activity ratio is 0.5-0.9 or 0.6-0.9.

In another aspect, the disclosure is directed to a nucleic acid which encodes a XI polypeptide of the disclosure. In various embodiments, the nucleic acid comprises a nucleotide sequence with at least 70%, 75%, 80%, 85%, 90%, 93%, 95%, 96%, 98%, 99% or 100% sequence identity to the nucleotide sequence of any one of SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, and 175, or the portion of any of the foregoing sequences encoding a XI catalytic domain or dimerization domain.

In other aspects, the disclosure is directed to a vector comprising a XI-encoding nucleotide sequence, for example a vector having an origin of replication and/or a promoter sequence operably linked to the XI-encoding nucleotide sequence. The promoter sequence can be one that is operable in a eukaryotic cell, for example in a fungal cell. In some embodiments, the promoter is operable in yeast (e.g., *S. cerevisiae*) or filamentous fungi.

In yet another aspect, the disclosure is directed to a recombinant cell comprising a nucleic acid that encodes a XI polypeptide. Particularly, the cell is engineered to express any of the XI polypeptides described herein. The recombinant cell may be of any species, and is preferably a eukaryotic cell, for example a yeast cell. Suitable genera of yeast include *Saccharomyces, Kluyveromyces, Candida, Pichia, Schizosaccharomyces, Hansenula, Klockera, Schwanniomyces, Issatchenkia* and *Yarrowia*. In specific embodiments, the recombinant cell is a *S. cerevisiae, S. bulderi, S. barnetti, S. exiguus, S. uvarum, S. diastaticus, K. lactis, I. orientalis, K. marxianus* or *K. fragilis*. Suitable genera of filamentous fungi include *Aspergillus, Penicillium, Rhizopus, Chrysosporium, Myceliophthora, Trichoderma, Humicola, Acremonium* and *Fusarium*. In specific embodiments, the recombinant cell is an *Aspergillus niger, Aspergillus oryzae, Trichoderma reesei, Penicillium chrysogenum, Myceliophthora thermophila*, or *Rhizopus oryzae*.

The recombinant cell may also be mutagenized or engineered to include modifications other than the recombinant expression of XI, particularly those that make the cell more suited to utilize xylose in a fermentation pathway. Exemplary additional modifications create one, two, three, four, five or even more of the following phenotypes: (a) increase in xylose transport into the cell; (b) increase in aerobic growth rate on xylose; (c) increase in xylulose kinase activity; (d) increase in flux through the pentose phosphate pathway into glycolysis, (e) decrease in aldose reductase activity, (f) decrease in sensitivity to catabolite repression, (g) increase in tolerance to biofuels, e.g., ethanol, (h) increase tolerance to intermediate production (e.g., xylitol), (i) increase in temperature tolerance, (j) osmolarity of organic acids, and (k) a reduced production of byproducts.

Increases in activity can be achieved by increased expression levels, for example expression of a hexose or pentose (e.g., xylose) transporter, a xylulose kinase, a glycolytic enzyme, or an ethanologenic enzyme is increased. The increased expression levels are achieved by overexpressing an endogenous protein or by expressing a heterologous protein.

Other modifications to the recombinant cell that are part of the disclosure are modifications that decrease the activity of genes or pathways in the recombinant cell. Preferably, the expression levels of one, two, three or more of the genes for hexose kinase, MIG-1, MIG-2, XR, aldose reductase, and XDH are reduced. Reducing gene activity can be achieved by a targeted deletion or disruption of the gene (and optionally reintroducing the gene under the control of a different promoter that drives lower levels of expression or inducible expression).

In yet other aspects, the disclosure is directed to methods of producing fermentation products, for example one or more of ethanol, butanol, diesel, lactic acid, 3-hydroxy-propionic acid, acrylic acid, acetic acid, succinic acid, citric acid, malic acid, fumaric acid, itaconic acid, an amino acid, 1,3-propanediol, ethylene, glycerol, a β-lactam antibiotic and a cephalosporin. Typically, a cell that recombinantly expresses a XI of the disclosure is cultured in a xylose-containing medium, for example a medium supplemented with a lignocellulosic hydrolysate. The media may also contain glucose, arabinose, or other sugars, particularly those derived from lignocellulose. The media may be of any pH, particularly a pH between 3.0 and 9.0, preferably between 4.0 and 8.0, more preferably between 5.0 and 8.0, even more preferably between 6.0 and 7.5. The culture may occur in any media where the culture is under anaerobic or aerobic conditions, preferably under anaerobic conditions for production of compounds mentioned above and aerobically for biomass/cellular production. Optionally, the methods further comprise recovering the fermentation product produced by the recombinant cell.

3. BRIEF DESCRIPTION OF THE FIGURES

Figure 8:
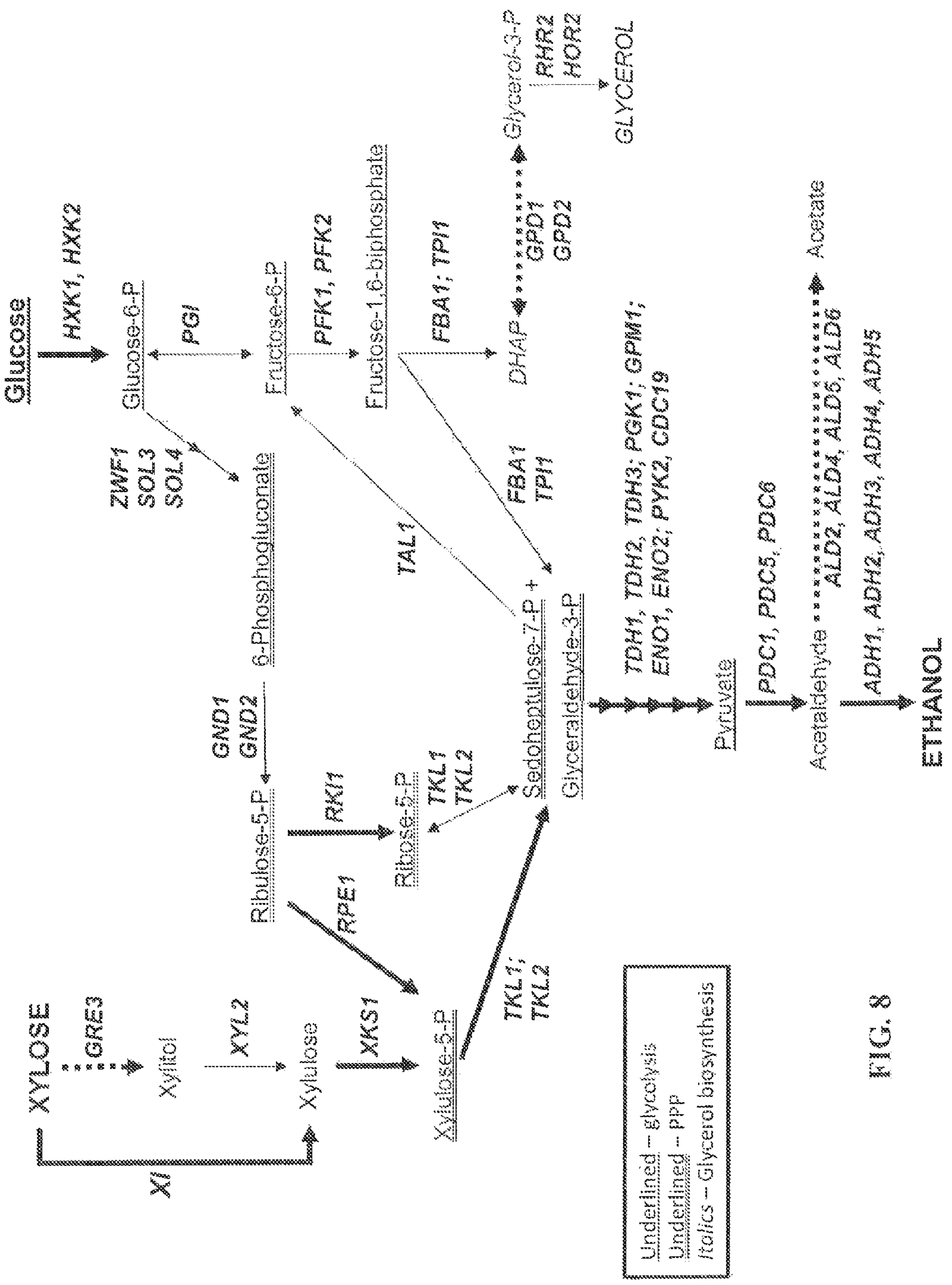

FIG. 8: Production of ethanol from glycolytic and pentose phosphate ("PPP") pathways. Not all steps are shown. For example, glyceraldehyde-3-phosphate is converted to pyruvate via a series of glycolytic steps: (1) glyceraldehyde-3-phosphate to 3-phospho-D-glycerol-phosphate catalyzed by glyceraldehyde-3-phosphate dehydrogenase (TDH1-3); (2) 3-phospho-D-glycerol-phosphate to 3-phosphoglycerate catalyzed by 3-phosphoglycerate kinase (PGK1); (3) 3-phosphoglycerate to 2-phosphoglycerate catalyzed by phosphoglycerate mutase (GPM1); (4) 2-phosphoglycerate to phosphoenolpyruvate catalyzed by enolase (ENO1; ENO2); and (5) phosphoenolpyruvate to pyruvate calatyzed by pyruvate kinase (PYK2; CDC19). Other abbreviations: DHAP=dihydroxy-acetone-phosphate; GPD=Glycerol-3-phosphate dehydrogenase; RHR2/HOR2=DL-glycerol-3-phosphatase; XI=xylose isomerase; GRE=xylose reductase/aldose reductase; XYL=xylitol dehydrogenase; XKS=xylulokinase; PDC=pyruvate decarboxylase; ADH=alcohol dehydrogenase; ALD=aldehyde dehydrogenase; FIXK=hexokinase; PGI=phosphoglucose isomerase; PFK=phosphofructokinase; FBA=aldolase; TPI=triosephosphate isomerase; ZWF=glucose-6 phosphate dehydrogenase; SOL=6-phosphogluconolactonase; GND=6-phosphogluconate dehydrogenase; RPE=D-ribulose-5-Phosphate 3-epimerase; RKI=ribose-5-phosphate ketol-isomerase; TKL=transketolase; TAL=transaldolase. Heavy dashed arrows indicate reactions and corresponding enzymes that can be reduced or eliminated to increase xylose utilization, particularly in the production of ethanol, and heavy solid arrows indicate reactions and corresponding enzymes that can be increased to increase xylose utilization, particularly in the production of ethanol. The enzymes shown in FIG. 8 are encoded by *S. cerevisiae* genes. The *S. cerevisiae* genes are used for exemplification purposes. Analogous enzymes and modifications in other organisms are within the scope of the present disclosure.

4. DETAILED DESCRIPTION

4.1 Xylose Isomerase Polypeptides

A "xylose isomerase" or "XI" is an enzyme that catalyzes the direct isomerisation of D-xylose into D-xylulose and/or vice versa. This class of enzymes is also known as D-xylose ketoisomerases. A xylose isomerase herein may also be capable of catalyzing the conversion between D-glucose and D-fructose (and accordingly may therefore be referred to as a glucose isomerase).

A "XI polypeptide of the disclosure" or a "XI of the disclosure" is a xylose isomerase having an amino acid sequence that is related to any one of SEQ ID NOs:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, or 176. In some embodiments, the xylose isomerase of the disclosure has an amino acid sequence that is at least about 70%, at least 80%, at least 90%, at least 95%, at least 96%, at least 98%, or at least 99% sequence identity thereto, or to a catalytic or dimerization domain thereof. The xylose isomerase of the disclosure can also have 100% sequence identity to one of the foregoing sequences.

The disclosure provides isolated, synthetic or recombinant XI polypeptides comprising an amino acid sequence having at least about 80%, e.g., at least about 81%, 82%, 83%, 84%, 85%, 86%, 87%, 88%, 89%, 90%, 91%, 92%, 93%, 94%, 95%, 96%, 97%, 98%, 99%, or complete (100%) sequence identity to a polypeptide of SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, or 176, over a region of at least about 10, e.g., at least about 15, 20, 25, 30, 35, 40, 45, 50, 55, 60, 65, 70, 75, 80, 85, 90, 95, 100, 125, 150, 175, 200, 225, 250, 275, 300, 325, or 350 residues, or over the full length of the polypeptide, over the length of catalytic domain, or over the length of the dimerization domain.

The XI polypeptides of the disclosure can be encoded by a nucleic acid sequence having at least about 80%, about 85%, about 86%, about 87%, about 88%, about 89%, or about 90% sequence identity to 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, or 175, or by a nucleic acid sequence capable of hybridizing under high stringency conditions to a complement of SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, or 175, or to a fragment thereof. Exemplary nucleic acids of the disclosure are described in Section 4.2 below.

In specific embodiments, a polypeptide of the disclosure comprises an amino acid sequence having:

(1) (a) at least 97% or 98% sequence identity to SEQ ID NO:78 or the catalytic domain thereof (amino acids 2-377 of SEQ ID NO:78) and/or (b) at least 80%, 85%, 90%, 93% or 95% sequence identity to SEQ ID NO:78 or the catalytic domain thereof (amino acids 2-377 of SEQ ID NO:78) and further comprises (i) SEQ ID NO:212 or SEQ ID NO:213 and/or (ii) SEQ ID NO:214;

(2) (a) at least 95%, 97% or 98% sequence identity to SEQ ID NO:96 or the catalytic domain thereof (amino acids 2-377 of SEQ ID NO:96) and/or (b) at least 80%, 85%, 90%, 93% or 95% sequence identity to SEQ ID NO:96 or the catalytic domain thereof (amino acids 2-377 of SEQ ID NO:96) and further comprises (i) SEQ ID NO:212 or SEQ ID NO:213 and/or (ii) SEQ ID NO:214;

(3) at least 80%, 85%, 90%, 93%, 95%, 97% or 98% sequence identity to SEQ ID NO:38 or the catalytic domain thereof (amino acids 2-374 of SEQ ID NO:38), and optionally further comprises one, two, three, four or all five of (i) SEQ ID NO:206 or SEQ ID NO:207; (ii) SEQ ID NO:208; (iii) SEQ ID NO:209; (iv) SEQ ID NO:210; and (iv) SEQ ID NO:211;

(4) at least 80%, 85%, 90%, 93%, 95%, 97% or 98% sequence identity to SEQ ID NO:2 or the catalytic domain thereof (amino acids 2-374 of SEQ ID NO:2);

(5) at least 93%, 95%, 97% or 98% sequence identity to SEQ ID NO:58 or the catalytic domain thereof (amino acids 2-376 of SEQ ID NO:58), (6) at least 80%, 85%, 90%, 93%, 95%, 97% or 98% sequence identity to SEQ ID NO:42 or the catalytic domain thereof (amino acids 2-375 of SEQ ID NO:42), and optionally further comprises one, two or all three of (i) SEQ ID NO:206 or SEQ ID NO:207; (ii) SEQ ID NO:210; and (iii) SEQ ID NO:211;

(7) (a) at least 97% or 98% sequence identity to SEQ ID NO:84 or the catalytic domain thereof (amino acids 2-376 of SEQ ID NO:84), and/or (b) at least 80%, 85%, 90%, 93% or 95% sequence identity to SEQ ID NO:84 or the catalytic domain thereof (amino acids 2-376 of SEQ ID NO:84) and further comprises (i) SEQ ID NO:212 or SEQ ID NO:213 and/or (ii) SEQ ID NO:214;

(8) (a) at least 97% or 98% sequence identity to SEQ ID NO:80 or the catalytic domain thereof (amino acids 2-377 of SEQ ID NO:80) and/or (b) at least 80%, 85%, 90%, 93% or 95% sequence identity to SEQ ID NO:80 or the catalytic domain thereof (amino acids 2-377 of SEQ ID NO:80) and further comprises (i) SEQ ID NO:212 or SEQ ID NO:213 and/or (ii) SEQ ID NO:214;

(9) at least 93%, 95%, 97% or 98% sequence identity to SEQ ID NO:54 or the catalytic domain thereof (amino acids 2-376 of SEQ ID NO:54);

(10) at least 80%, 85%, 90%, 93%, 95%, 97% or 98% sequence identity to SEQ ID NO:46 or the catalytic domain thereof (amino acids 2-376 of SEQ ID NO:46), and optionally further comprises SEQ ID NO:206 or SEQ ID NO:207;

(11) at least 90%, 93%, 95%, 97% or 98% sequence identity to SEQ ID NO:16 or the catalytic domain thereof (amino acids 2-376 of SEQ ID NO:16);

(12) at least 85%, 90%, 93%, 95%, 97% or 98% sequence identity to SEQ ID NO:82 or the catalytic domain thereof (amino acids 2-375 of SEQ ID NO:82); and/or

(13) at least 90%, 93%, 95%, 97% or 98% sequence identity to SEQ ID NO:32 or the catalytic domain thereof (amino acids 2-377 of SEQ ID NO:32).

An example of an algorithm that is suitable for determining sequence similarity is the BLAST algorithm, which is described in Altschul et al., 1990, J. Mol. Biol. 215:403-410. Software for performing BLAST analyses is publicly available through the National Center for Biotechnology Information. This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, 1992, Proc. Nat'l. Acad. Sci. USA 89:10915-10919) alignments (B) of 50, expectation (E) of 10, M'5, N'-4, and a comparison of both strands.

Any of the amino acid sequences described herein can be produced together or in conjunction with at least 1, e.g., at least (or up to) 2, 3, 5, 10, or 20 heterologous amino acids flanking each of the C- and/or N-terminal ends of the specified amino acid sequence, and or deletions of at least 1, e.g., at least (or up to) 2, 3, 5, 10, or 20 amino acids from the C- and/or N-terminal ends of a XI of the disclosure.

The XIs of the disclosure can be characterized in terms of their activity. In some embodiments, a XI of the disclosure has at least 1.3 times the activity of the *Orpinomyces* sp. XI assigned Genbank Accession No. 169733248 ("Op-XI") at pH 7.5, for example using the assay described in any of Examples 4, 6 and 7. In certain specific embodiments, a XI of the disclosure has an activity ranging from 1.25 to 3.0 times, from 1.5 to 3 times, from 1.5 to 2.25 times, or from 1.75 to 3 times the activity of Op-XI at pH 7.5.

The XIs of the disclosure can also be characterized in terms of their tolerance to acidic environments (e.g., at a pH of 6.5 or 6). In some embodiments, a XI of the disclosure has at least 1.9 times the activity of the Op-XI at pH 6, for example using the assay described in Example 7. In certain specific embodiments, a XI of the disclosure has an activity ranging from 1.9 to 4.1 times, from 2.4 to 4.1 times, from 2.4 to 3.9 times, or 2.4 to 4.1 times the activity of Op-XI at pH6.

Tolerance to acidic environments can also be characterized as a ratio of activity at pH 6 to activity at pH 7.5 ("a pH 6 to pH 7.5 activity ratio"), for example as measured using the assay of Example 7. In some embodiments, the pH 6 to pH 7.5 activity ratio is at least 0.5 or at least 0.6. In various embodiments, the pH 6 to pH 7.5 activity ratio is 0.5-0.9 or 0.6-0.9.

The xylose isomerases of the disclosure can have one or more (e.g., up to 2, 3, 5, 10, or 20) conservative amino acid substitutions relative to the polypeptide of SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, or 176 or to the portion thereof of discussed above. The conservative substitutions can be chosen from among a group having a similar side chain to the reference amino acid. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Accordingly, exemplary conservative substitutions for each of the naturally occurring amino acids are as follows: ala to ser; arg to lys; asn to gln or his; asp to glu; cys to ser or ala; gln to asn; glu to asp; gly to pro; his to asn or gln; ile to leu or val; leu to ile or val; lys to arg; gln or glu; met to leu or ile; phe to met, leu or tyr; ser to thr; thr to ser; trp to tyr; tyr to trp or phe; and, val to ile or leu.

The present disclosure also provides a fusion protein that includes at least a portion (e.g., a fragment or domain) of a XI polypeptide of the disclosure attached to one or more fusion segments, which are typically heterologous to the XI polypeptide. Suitable fusion segments include, without limitation, segments that can provide other desirable biological activity or facilitate purification of the XI polypeptide (e.g., by affinity chromatography). Fusion segments can be joined to the amino or carboxy terminus of a XI polypeptide. The fusion segments can be susceptible to cleavage.

4.2 Xylose Isomerase Nucleic Acids

A "XI nucleic acid of the disclosure" is a nucleic acid encoding a xylose isomerase of the disclosure. In certain embodiments, the xylose isomerase nucleic acid of the disclosure is encoded by a nucleotide sequence of any one of SEQ ID NOs:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, or 175, or a sequence having at least about 70%, at least 80%, at least 90%, at least 95%, at least 96%, at least 98%, or at least 99% sequence identity thereto. The xylose isomerase nucleic acid of the disclosure can also have 100% sequence identity to one of the foregoing sequences.

The present disclosure provides nucleic acids encoding a polypeptide of the disclosure, for example one described in Section 4.1 above. The disclosure provides isolated, synthetic or recombinant nucleic acids comprising a nucleic acid sequence having at least about 70%, e.g., at least about 71%, 72%, 73%, 74%, 75%, 76%, 77%, 78%, 79%, 80%, 81%, 82%, 83%, 84%, 85%, 86%, 87%, 88%; 89%, 90%, 91%, 92%, 93%, 94%, 95%, 96%, 97%, 98%, or 99%, or complete (100%) sequence identity to a nucleic acid of SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, or 175, over a region of at least about 10, e.g., at least about 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, or 2000 nucleotides.

Nucleic acids of the disclosure also include isolated, synthetic or recombinant nucleic acids encoding a XI polypeptide having the sequence of SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, or 176, and subsequences thereof (e.g., a conserved domain or a catalytic domain), and variants thereof.

To increase the likelihood that a XI polypeptide is recombinantly expressed, a XI nucleic acid may be adapted to optimize its codon usage to that of the chosen cell. Several methods for codon optimization are known in the art. For expression in yeast, an exemplary method to optimize codon usage of the nucleotide sequences to that of the yeast is a codon pair optimization technology as disclosed in WO2006/077258 and/or WO2008/000632. WO2008/000632 addresses codon-pair optimization. Codon-pair optimization is a method wherein the nucleotide sequences encoding a polypeptide are modified with respect to their codon-usage, in particular the codon-pairs that are used, to obtain improved expression of the nucleotide sequence encoding the polypeptide and/or improved production of the encoded polypeptide. Codon pairs are defined as a set of two subsequent triplets (codons) in a coding sequence.

4.3 Host Cells and Recombinant Expression

The disclosure also provides host cells transformed with a XI nucleic acid and recombinant host cells engineered to express XI polypeptides. The XI nucleic acid construct may be extrachromosomal, on a plasmid, which can be a low copy plasmid or a high copy plasmid. The nucleic acid construct may be maintained episomally and thus comprise a sequence for autonomous replication, such as an autosomal replication sequence. Alternatively, a XI nucleic acid may be integrated in one or more copies into the genome of the cell. Integration into the cell's genome may occur at random by non-homologous recombination but preferably, the nucleic acid construct may be integrated into the cell's genome by homologous recombination as is well known in the art. In certain embodiments, the host cell is bacterial or fungal (e.g., a yeast or a filamentous fungus).

Suitable host cells of the bacterial genera include, but are not limited to, cells of *Escherichia, Bacillus, Lactobacillus, Pseudomonas*, and *Streptomyces*. Suitable cells of bacterial species include, but are not limited to, cells of *Escherichia*

*coli, Bacillus subtilis, Bacillus licheniformis, Lactobacillus brevis, Pseudomonas aeruginosa*, and *Streptomyces lividans*.

Suitable host cells of the genera of yeast include, but are not limited to, cells of *Saccharomyces, Kluyveromyces, Candida, Pichia, Schizosaccharomyces, Hansenula, Klockera, Schwanniomyces, Phaffia, Issatchenkia* and *Yarrowia*. In specific embodiments, the recombinant cell is a *S. cerevisiae, C. albicans, S. pombe, S. bulderi, S. barnetti, S. exiguus, S. uvarum, S. diastaticus, H. polymorpha, K. lactis, I. orientalis, K. marxianus, K. fragilis, P. pastoris, P. canadensis, K. marxianus* or *P. rhodozyma*. Exemplary yeast strains that are suitable for recombinant XI expression include, but are not limited to, Lallemand LYCC 6391, Lallemand LYCC 6939, Lallemand LYCC 6469, (all from Lallemand, Inc., Montreal, Canada); NRRL YB-1952 (ARS (NRRL) Collection, U.S. Department of Agriculture); and BY4741.

Suitable host cells of filamentous fungi include all filamentous forms of the subdivision Eumycotina. Suitable cells of filamentous fungal genera include, but are not limited to, cells of *Acremonium, Aspergillus, Aureobasidium, Bjerkandera, Ceriporiopsis, Chrysoporium, Coprinus, Coriolus, Corynascus, Chaetomium, Cryptococcus, Filobasidium, Fusarium, Gibberella, Humicola, Hypocrea, Magnaporthe, Mucor, Myceliophthora, Neocallimastix, Neurospora, Paecilomyces, Penicillium, Phanerochaete, Phlebia, Piromyces, Pleurotus, Scytaldium, Schizophyllum, Sporotrichum, Talaromyces, Thermoascus, Thielavia, Tolypocladium, Trametes*, and *Trichoderma*. In certain aspects, the recombinant cell is a *Trichoderma* sp. (e.g., *Trichoderma reesei*), *Penicillium* sp., *Humicola* sp. (e.g., *Humicola insolens*); *Aspergillus* sp. (e.g., *Aspergillus niger*), *Chrysosporium* sp., *Fusarium* sp., or *Hypocrea* sp. Suitable cells can also include cells of various anamorph and teleomorph forms of these filamentous fungal genera.

Suitable cells of filamentous fungal species include, but are not limited to, cells of *Aspergillus awamori, Aspergillus fumigatus, Aspergillus foetidus, Aspergillus japonicus, Aspergillus nidulans, Aspergillus niger, Aspergillus oryzae, Chrysosporium lucknowense, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Coprinus cinereus, Coriolus hirsutus, Humicola insolens, Humicola lanuginosa, Mucor miehei, Myceliophthora thermophila, Neurospora crassa, Neurospora intermedia, Penicillium purpurogenum, Penicillium canescens, Penicillium solitum, Penicillium funiculosum, Phanerochaete chrysosporium, Phlebia radiate, Pleurotus eryngii, Talaromyces flavus, Thielavia terrestris, Trametes villosa, Trametes versicolor, Trichoderma harzianum, Trichoderma koningii, Trichoderma longibrachiatum, Trichoderma reesei*, and *Trichoderma viride*.

Typically, for recombinant expression, the XI nucleic acid will be operably linked to one or more nucleic acid sequences capable of providing for or aiding the transcription and/or translation of the XI sequence, for example a promoter operable in the organism in which the XI is to be expressed. The promoters can be homologous or heterologous, and constitutive or inducible.

Preferably, the XI polypeptide is expressed in the cytosol and therefore lacks a mitochondrial or peroxisomal targeting signal.

Where recombinant expression in a filamentous fungal host is desired, the promoter can be a fungal promoter (including but not limited to a filamentous fungal promoter), a promoter operable in plant cells, a promoter operable in mammalian cells.

As described in U.S. provisional application No. 61/553,901, filed Oct. 31, 2011, the contents of which are hereby incorporated in their entireties, promoters that are constitutively active in mammalian cells (which can derived from a mammalian genome or the genome of a mammalian virus) are capable of eliciting high expression levels in filamentous fungi such as *Trichoderma reesei*. An exemplary promoter is the cytomegalovirus ("CMV") promoter.

As described in U.S. provisional application No. 61/553,897, filed Oct. 31, 2011, the contents of which are hereby incorporated in their entireties, promoters that are constitutively active in plant cells (which can derived from a plant genome or the genome of a plant virus) are capable of eliciting high expression levels in filamentous fungi such as *Trichoderma reesei*. Exemplary promoters are the cauliflower mosaic virus ("CaMV") 35S promoter or the *Commelina* yellow mottle virus ("CoYMV") promoter.

Mammalian, mammalian viral, plant and plant viral promoters can drive particularly high expression when the associated 5' UTR sequence (i.e., the sequence which begins at the transcription start site and ends one nucleotide (nt) before the start codon), normally associated with the mammalian or mammalian viral promoter is replaced by a fungal 5' UTR sequence.

The source of the 5' UTR can vary provided it is operable in the filamentous fungal cell. In various embodiments, the 5' UTR can be derived from a yeast gene or a filamentous fungal gene. The 5' UTR can be from the same species, one other component in the expression cassette (e.g., the promoter or the XI coding sequence), or from a different species. The 5' UTR can be from the same species as the filamentous fungal cell that the expression construct is intended to operate in. In an exemplary embodiment, the 5' UTR comprises a sequence corresponding to a fragment of a 5' UTR from a *T. reesei* glyceraldehyde-3-phosphate dehydrogenase (gpd). In a specific embodiment, the 5' UTR is not naturally associated with the CMV promoter Examples of other promoters that can be used include, but are not limited to, a cellulase promoter, a xylanase promoter, the 1818 promoter (previously identified as a highly expressed protein by EST mapping *Trichoderma*). For example, the promoter can suitably be a cellobiohydrolase, endoglucanase, or β-glucosidase promoter. A particularly suitable promoter can be, for example, a *T. reesei* cellobiohydrolase, endoglucanase, or β-glucosidase promoter. Non-limiting examples of promoters include a cbh1, cbh2, egl1, egl2, egl3, egl4, egl5, pkil, gpdl, xyn1, or xyn2 promoter.

For recombinant expression in yeast, suitable promoters for *S. cerevisiae* include the MFa1 promoter, galactose inducible promoters such as the GAL1, GAL7 and GAL10 promoters, glycolytic enzyme promoters including the TPI and PGK promoters, the TDH3 promoter, the TEF1 promoter, the TRP1 promoter, the CYCI promoter, the CUP1 promoter, the PHOS promoter, the ADH1 promoter, and the HSP promoter. Promoters that are active at different stage of growth or production (e.g., idiophase or trophophase) can also be used (see, e.g., Puig et al., 1996, Biotechnology Letters 18(8):887-892; Puig and Perez-Ortin, 2000, Systematic and Applied Microbiology 23(2):300-303; Simon et al., 2001, Cell 106:697-

708; Wittenberg and Reed, 2005, Oncogene 24:2746-2755). A suitable promoter in the genus *Pichia* sp. is the AOXI (methanol utilization) promoter.

The engineered host cells can be cultured in conventional nutrient media modified as appropriate for activating promoters, selecting transformants, or amplifying the nucleic acid sequence encoding the XI polypeptide. Culture conditions, such as temperature, pH and the like, are those previously used with the host cell selected for expression, and will be apparent to those skilled in the art. As noted, many references are available for the culture and production of many cells, including cells of bacterial and fungal origin. Cell culture media in general are set forth in Atlas and Parks (eds.), 1993, The Handbook of Microbiological Media, CRC Press, Boca Raton, Fla., which is incorporated herein by reference. For recombinant expression in filamentous fungal cells, the cells are cultured in a standard medium containing physiological salts and nutrients, such as described in Pourquie et al., 1988, Biochemistry and Genetics of Cellulose Degradation, eds. Aubert, et al., Academic Press, pp. 71-86; and Ilmen et al., 1997, Appl. Environ. Microbiol. 63:1298-1306. Culture conditions are also standard, e.g., cultures are incubated at 30° C. in shaker cultures or fermenters until desired levels of XI expression are achieved. Preferred culture conditions for a given filamentous fungus may be found in the scientific literature and/or from the source of the fungi such as the American Type Culture Collection (ATCC). After fungal growth has been established, the cells are exposed to conditions effective to cause or permit the expression of a XI.

In cases where a XI coding sequence is under the control of an inducible promoter, the inducing agent, e.g., a sugar, metal salt or antibiotics, is added to the medium at a concentration effective to induce XI expression.

In addition to recombinant expression of a XI polypeptide, a host cell of the disclosure may further include one or more genetic modifications that increase the cell's ability to utilize xylose as a substrate in a fermentation process. Exemplary additional modifications create one, two, three, four, five or even more of the following phenotypes: (a) increase in xylose transport into the cell; (b) increase in aerobic growth rate on xylose; (c) increase in xylulose kinase activity; (d) increase in flux through the pentose phosphate pathway into glycolysis, (e) modulating in aldose reductase activity, (f) decrease in sensitivity to catabolite repression, (g) increase in tolerance to biofuels, e.g., ethanol, (h) increase tolerance to intermediate production (for example xylitol), (i) increase in temperature tolerance, (j) osmolarity of organic acids, and (k) a reduced production of byproducts.

As illustrated below, a modification that results in one or more of the foregoing phenotypes can be a result of increasing or decreasing expression of an endogenous protein (e.g., by at least a factor of about 1.1, about 1.2, about 1.5, about 2, about 5, about 10 or about 20) or a result of introducing expression of a heterologous polypeptide. For avoidance of doubt, "decreasing" or "reducing" gene expression encompasses eliminating expression. Decreasing (or reducing) the expression of an endogenous protein can be accomplished by inactivating one or more (or all) endogenous copies of a gene in a cell. A gene can be inactivated by deletion of at least part of the gene or by disruption of the gene. This can be achieved by deleting the some or all of a gene coding sequence or regulatory sequence whose deletion results in a reduction of gene expression in the cell. Examples of modifications that increase xylose utilization or yield of fermentation product are described below.

Increasing Xylose Transport:

Xylose transport can be increased directly or indirectly. For example, a recombinant cell may include one or more genetic modifications that result in expression of a xylose transporter. Exemplary transporters include, but are not limited to GXF1, SUT1 and At6g59250 from *Candida intermedia*, *Pichia stipitis* (now renamed *Scheffersomyces stipitis*; the terms are used interchangeably herein) and *Arabidopsis thaliana*, respectively (Runquist et al., 2010, Biotechnol. Biofuels 3:5), as well as HXT4, HXT5, HXT7, GAL2, AGT1, and GXF2 (see, e.g., Matsushika et al., 2009, Appl. Microbiol. Biotechnol. 84:37-53). Other transporters include PsAraT, SUT2-4 and XUT1-5 from *P. stiptis*; GXS1 from *Candida intermedia*; Xy1HP and DEHAOD02167 from *Debaryomyces hansenii*; and YALI0C06424 from *Yarrowia lipolytica* (see, e.g., Young et al., 2011, Appl. Environ. Microbiol. 77:3311-3319). Xylose transport can also be increased by (over-) expression of low-affinity hexose transporters, which are capable of non-selectively transporting sugars, including xylose, into the cell once glucose levels are low (e.g., 0.2-1.0 g/l); and includes CgHXT1-CgHXTS from *Colletotrichum graminicola*. The foregoing modifications can be made singly or in combinations of two, three or more modifications.

Increasing Xylulose Kinase Activity:

Xylulose kinase activity can be increased by overexpression of a xylulose kinase, e.g., xylulose kinase (XKS1; *Saccharomyces* genome database ("SGD") accession no. YGR194C) of *S. cerevisiae*, particularly where the recombinant cell is a yeast cell. In one embodiment, a *S. cerevisiae* cell is engineered to include at least 2 additional copies of xylulose kinase under the control of a strong constitutive promoter such as TDH3, TEF1 or PGK1. In another embodiment, overexpression of an endogenous xylulose kinase was engineered. This xylulose kinase having improved kinetic activities through the use of protein engineering techniques known by those skilled in the art.

Increasing Flux Through the Pentose Phosphate Pathway:

This can be achieved by increasing expression of one or more genes in the pentose phosphate pathway, for example *S. cerevisiae* transaldolase TAL1 (SGD accession no. YLR354C), transketolase TKL1 (SGD accession no. YPR074C), ribulose 5-phosphate epimerase RPE1 (SGD accession no. YJL121C) and ribose-5-phosphate ketoisomerase RKI1 (SGD accession no. YOR095C) and/or one or more genes to increase glycolytic flux, for example *S. cerevisiae* pyruvate kinase PYK1/CDC19 (SGD accession no. YAL038W), pyruvate decarboxylase PDC1 (SGD accession no. YLR044C), pyruvate decarboxylase PDC5 (SGD accession no. YLR134W), pyruvate decarboxylase PDC6 (SGD accession no. YGR087C), the alcohol dehydrogenases ADH1-5 (SGD accession nos. YOL086C, YMR303C, YMR083W, YGL256W, and YBR145W, respectively), and hexose kinase HXK1-2 (SGD accession nos. YFR053C and YGL253W, respectively). In one embodiment, the yeast cell has one additional copy each of TAL1, TKL1, RPE1 and RKI1 from *S. cerevisiae* under the control of strong constitutive promoters (e.g., PGK1, TDH3, TEF1); and may also include improvements to glycolytic flux (e.g., increased copies of genes such as PYK1, PDC1, PDC5, PDC6, ADH1-5) and glucose-6-phosphate and hexokinase. The foregoing modifications can be made singly or in combinations of two, three or more modifications.

Modulating Aldose Reductase Activity:

A recombinant cell can include one or more genetic modifications that increase or reduce (unspecific) aldose reductase (sometimes called aldo-keto reductase) activity. Aldose reductase activity can be reduced by one or more genetic modifications that reduce the expression of or inactivate a gene encoding an aldose reductase, for example *S. cerevisiae* GRE3 (SGD accession no. YHR104W).

In certain embodiments, GRE3 expression is reduced. In one aspect, the recombinant cell is a yeast cell in which the GRE3 gene is deleted. Deletion of GRE3 decreased xylitol yield by 49% and biomass production by 31%, but increased ethanol yield by 19% (Traff-Bjerre et al., 2004, Yeast 21:141-150). In another aspect, the recombinant cell is a yeast cell which has a reduction in expression of GRE3. Reducing GRE3 expression has been shown to result in a two-fold decrease in by-product (i.e., xylitol) formation and an associated improvement in ethanol yield (Traff et al., 2001, Appl. Environ. Microbiol. 67:5668-5674).

In another embodiment, the recombinant cell is a cell (optionally but not necessarily a yeast cell) in which GRE3 is overexpressed. In a study analyzing the effect of GRE3 overexpression in *S. cerevisiae* to investigate the effect on xylose utilization, an increase of about 30% in xylose consumption and about 120% in ethanol production was noted (Traff-Bjerre et al., 2004, Yeast 21:141-150).

Decreasing Xylose Reductase Activity:

A recombinant cell may include one or more genetic modifications that reduce xylose reductase activity. Xylose reductase activity can be reduced by one or more genetic modifications that reduce the expression of or inactivate a gene encoding a xylose reductase.

Decreasing Sensitivity to Catabolite Repression:

Glucose and other sugars, such as galactose or maltose, are able to cause carbon catabolite repression in Crabtree-positive yeast, such as *S. cerevisiae*. In one study, xylose was found to decrease the derepression of various enzymes of an engineered *S. cerevisiae* strain capable of xylose utilization by at least 10-fold in the presence of ethanol. Xylose also impaired the derepression of galactokinase and invertase (Belinchon & Gancedo, 2003, Arch. Microbiol. 180:293-297). In certain embodiments, in order to reduce catabolite sensitivity, yeast can include one or more genetic modifications that reduce expression of one or more of GRR1 (SGD accession no. YJR090C), the gene assigned SGD accession no. YLR042C, GAT1 (SGD accession no. YKR067W) and/or one or more genetic modifications that decrease expression of one or more of SNF1 (SGD accession no. YDR477W), SNF4 (SGD accession no. YGL115W), MIG1 (SGD accession no. YGL035C) and CRE1 (SGD accession no. YJL127C). In further embodiments, yeast can include one or more genetic modifications that result in overexpression of the pentose phosphate pathway enzymes. In yet further embodiments, yeast can include one or more genetic modifications that reduce expression of hexo-/glucokinase. In yet a further embodiment, yeast can include one or more genetic modifications that modulate the activity of one or more GATA factors, for example GAT1, DAL80 (SGD accession no. YKR034W), GZF3 (SGD accession no. YJL110C) and GLN3 (SGD accession no. YER040W). The foregoing modifications can be made singly or in combinations of two, three or more modifications.

Increasing Tolerance to Biofuels (e.g., Ethanol), Pathway Intermediates (e.g., Xylitol), Organic Acids and Temperature:

For efficient bioethanol production from lignocellulosic biomass, it is useful to improve cellular tolerance to toxic compounds released during the pretreatment of biomass. In one study, the gene encoding PHO13 (SGD accession no. YDL236W), a protein with alkaline phosphatase activity, was disrupted. This resulted in improved ethanol production from xylose in the presence of three major inhibitors (i.e., acetic acid, formic acid and furfural). Further, the specific ethanol productivity of the mutant in the presence of 90 mM furfural was four fold higher (Fujitomi et al., 2012, Biores. Tech., 111:161-166). Thus, in one embodiment, yeast has one or more genetic modifications that reduce P11013 expression. In other embodiments, yeast, bacterial and fungal cells are evolved under selective conditions to identify strains that can withstand higher temperatures, higher levels of intermediates, higher levels of organic acids and/or higher levels of biofuels (e.g., ethanol). In yet other embodiments, yeast are engineered to reduce expression of FPS1 (SGD accession no. YLL043W); overexpress unsaturated lipid and ergosterol biosynthetic pathways; reduce expression of PHO13 and/or SSK2 (SGD accession no. YNR031C); modulate global transcription factor cAMP receptor protein, through increasing or decreasing expression; increase expression of MSN2 (SGD accession no. YMR037C), RCN1 (SGD accession no. YKL159C), RSA3 (SGD accession no. YLR221C), CDC19 and/or ADH1; or increase expression of Rice ASR1. The foregoing modifications can be made singly or in combinations of two, three or more modifications.

Reducing Production of Byproducts:

Glycerol is one of the main byproducts in C6 ethanol production. Reducing glycerol is desirable for increasing xylose utilization by yeast. Production of glycerol can be reduced by deleting the gene encoding the FPS1 channel protein, which mediates glycerol export, and GPD2 (SGD accession no. YOL059W), which encodes glycerol-3-phosphate dehydrogenase; optionally along with overexpression of GLT1 (SGD accession no. YDL171C) and GLN1 (SGD accession no. YPR035W). In one study, FPS1 and GPD2 were knocked-out in one *S. cerevisiae* strain, and in another were replaced by overexpression of GLT1 and GLN1, which encode glutamate synthase and glutamine synthetase, respectively. When grown under microaerobic conditions, these strains showed ethanol yield improvements of 13.17% and 6.66%, respectively. Conversely, glycerol, acetic acid and pyruvic acid were found to all decrease, with glycerol down 37.4% and 41.7%, respectively (Zhang and Chen, 2008, Chinese J. Chem. Eng. 16:620-625).

Production of glycerol can also be reduced by deleting the NADH-dependent glycerol-3-phosphate dehydrogenase 1 (GPD1; SGD accession no. YDL022W) and/or the NADPH-dependent glutamate dehydrogenase 1 (GDH1; SGD accession no. YOR375C). Sole deletion of GPD1 or GDH1 reduces glycerol production, and double deletion results in a 46.4% reduction of glycerol production as compared to wild-type *S. cerevisiae* (Kim et al., 2012, Bioproc. Biosys. Eng. 35:49-54). Deleting FPS1 can decrease production of glycerol for osmoregulatory reasons.

Reducing production of acetate can also increase xylose utilization. Deleting ALD6 (SGD accession no. YPL061W) can decrease production of acetate.

ADH2 can also be deleted to reduce or eliminate acetyladehyde formation from ethanol and thereby increase ethanol yield.

The foregoing modifications to reduce byproduct formation can be made singly or in combinations of two, three or more modifications.

In addition to ethanol production, a recombinant XI-expressing cell of the disclosure can be suitable for the production of non-ethanolic fermentation products. Such non-ethanolic fermentation products include in principle any bulk or fine chemical that is producible by a eukaryotic microorganism such as a yeast or a filamentous fungus. Such fermentation products may be, for example, butanol, lactic acid, 3-hydroxy-propionic acid, acrylic acid, acetic acid, succinic acid, citric acid, malic acid, fumaric acid, itaconic acid, an amino acid, 1,3-propane-diol, ethylene, glycerol, a β-lactam antibiotic or a cephalosporin. A preferred modified host cell of the disclosure for production of non-ethanolic fermentation products is a host cell that contains a genetic modification that results in decreased alcohol dehydrogenase activity.

Cells expressing the XI polypeptides of the disclosure can be grown under batch, fed-batch or continuous fermentations conditions. Classical batch fermentation is a closed system, wherein the compositions of the medium is set at the beginning of the fermentation and is not subject to artificial alternations during the fermentation. A variation of the batch system is a fed-batch fermentation in which the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth. Continuous fermentation systems strive to maintain steady state growth conditions. Methods for modulating nutrients and growth factors for continuous fermentation processes as well as techniques for maximizing the rate of product formation are well known in the art of industrial microbiology.

4.4 Fermentation Methods

A further aspect the disclosure relates to fermentation processes in which the recombinant XI-expressing cells are used for the fermentation of carbon source comprising a source of xylose. Thus, in certain embodiments, the disclosure provides a process for producing a fermentation product by (a) fermenting a medium containing a source of xylose with a recombinant XI-expressing cell as defined herein above, under conditions in which the cell ferments xylose to the fermentation product, and optionally, (b) recovery of the fermentation product. In some embodiments, the fermentation product is an alcohol (e.g., ethanol, butanol, etc.), a fatty alcohol (e.g., a C8-C20 fatty alcohol), a fatty acid (e.g., a C8-C20 fatty acid), lactic acid, 3-hydroxypropionic acid, acrylic acid, acetic acid, succinic acid, citric acid, malic acid, fumaric acid, an amino acid, 1,3-propanediol, itaconic acid, ethylene, glycerol, and a β-lactam antibiotic such as Penicillin G or Penicillin V and fermentative derivatives thereof and cephalosporins. The fermentation process may be an aerobic or an anaerobic fermentation process.

In addition to a source of xylose the carbon source in the fermentation medium may also comprise a source of glucose. The source of xylose or glucose may be xylose or glucose as such or may be any carbohydrate oligo- or polymer comprising xylose or glucose units, such as e.g., lignocellulose, xylans, cellulose, starch and the like. Most microorganisms possess carbon catabolite repression that results in sequential consumption of mixed sugars derived from the lignocellulose, reducing the efficacy of the overall process. To increase the efficiency of fermentation, microorganisms that are capable of simultaneous consumption of mixed sugars (e.g., glucose and xylose) have been developed, for example by rendering them less sensitive to glucose repression (see, e.g., Kim et al., 2010, Appl. Microbiol. Biotechnol. 88:1077-85 and Ho et al., 1999, Adv. Biochem. Eng. Biotechnol. 65:163-92). Such cells can be used for recombinant XI expression and in the fermentation methods of the disclosure.

The fermentation process is preferably run at a temperature that is optimal for the recombinant XI-expressing cells. Thus, for most yeasts or fungal host cells, the fermentation process is performed at a temperature which is less than 38° C., unless temperature tolerant mutant strains are used, in which case the temperature may be higher. For most yeast or filamentous fungal host cells, the fermentation process is suitably performed at a temperature which is lower than 35° C., 33° C., 30° C. or 28° C. Optionally, the temperature is higher than 20° C., 22° C., or 25° C.

An exemplary process is a process for the production of ethanol, whereby the process comprises the steps of: (a) fermenting a medium containing a source of xylose with a transformed host cell as defined above, whereby the host cell ferments xylose to ethanol; and optionally, (b) recovery of the ethanol. The fermentation medium can also comprise a source of glucose that is also fermented to ethanol. The source of xylose can be sugars produced from biomass or agricultural wastes. Many processes for the production of monomeric sugars such as glucose generated from lignocellulose are well known, and are suitable for use herein. In brief, the cellulolytic material may be enzymatically, chemically, and/or physically hydrolyzed to a glucose and xylose containing fraction. Alternatively, the recombinant XI-expressing cells of the disclosure can be further transformed with one or more genes encoding for enzymes effective for hydrolysis of complex substrates such as lignocellulose, and include but are not limited to cellulases, hemicellulases, peroxidases, laccases, chitinases, proteases, and pectinases. The recombinant cells of the disclosure can then be fermented under anaerobic in the presence of glucose and xylose. Where the recombinant cell is a yeast cell, the fermentation techniques and conditions described for example, by Wyman (1994, Biores. Technol. 50:3-16) and Olsson and Hahn-Hagerdal (1996, Enzyme Microb. Technol. 18:312-331) can be used. After completion of the fermentation, the ethanol may be recovered and optionally purified or distilled. Solid residue containing lignin may be discarded or burned as a fuel.

The fermentation process may be run under aerobic and anaerobic conditions. In some embodiments, the process is carried out under microaerobic or oxygen limited conditions. Fermentation can be carried out in a batch, fed-batch, or continuous configuration within (bio)reactors.

5. EXAMPLES 5.1 Materials and Methods 5.1.1 Yeast Culture

Unless stated otherwise for a particular example, yeast transformants were grown in SC-ura media with about 2% glucose at 30° C. for about 24 hours. The media contains approx. 20 g agar, approx. 134 g BD Difco™ Yeast Nitrogen Base without amino acids (BD, Franklin Lakes, N.J., and approx. 2 g SC amino-acid mix containing about 85 mg of the following amino acids unless noted (quantity listed in parentheses): L-Adenine (21.0), L-Alanine, L-Arginine, L-Asparagine, L-Aspartic Acid, L-Cysteine, Glutamine, L-Glutamic Acid, Glycine, L-Histidine, Myo-Inositol, L-Isoleucine, L-Leucine (173.4), L-Lysine, L-Methionine, p-Aminobenzoic Acid (8.6), L-Phenylalanine, L-Proline, L-Serine, L-Threonine, L-Tryptophan, L-Tyrosine, L-Valine).

5.1.2 Xylose Isomerase Activity

XI activity in cell lysates was determined using a method based on that of Kersters-Hilderson et al., 1986, Enzyme Microb. Technol. 9:145-148, in which enzymatic conversion of xylose to xylulose by the XI is coupled with the enzymatic conversion of the product (xylulose) to xylitol via the enzyme sorbitol dehydrogenase (SDH). SDH activity requires the oxidation of NADH to $NAD^+$. The rate of oxidation of NADH is directly proportional to the rate of SDH conversion of D-xylulose to D-xylitol and is measured by the decrease in absorbance at 340 nm. One unit of enzyme activity as measured by this assay is a decrease of 1 μmole of NADH per minute under assay conditions. All reactions, solutions, plates, and spectrophotometer were equilibrated to about 35° C. prior to use. Assays were performed either on fresh lysates immediately after preparation or lysates that had been frozen at −20° C. immediately after preparation. Assays were performed using a BioTek Model: Synergy H1 Hybrid Reader spectrophotometer and 96-well plates (Corning, Model #Costar® #3598). All spectrophotometric readings were performed at 340 nm. A standard curve of NADH was generated with each assay with concentrations ranging from 0 to about 0.6 mM.

The reaction buffer used for experiments at pH 7.5 was about 100 mM Tris-HCl (pH 7.5). The assay mix was prepared as follows: reaction buffer to which was added about 10 mM $MgCl_2$, 0.15 mM NADH and 0.05 mg/ml SDH (Roche, catalog #50-720-3313). For experiments where activity was also measured at pH 6, the buffer was changed to about 100 mM sodium phosphate, pH 6. The assay mix for the entire experiment was then prepared as follows: about 10 mM $MgCl_2$, 1.2 mM NADH and 0.02 mg/ml SDH.

Any sample dilutions were performed using the reaction buffer as diluent. Reactions were set up by aliquotting about 90 μl of assay mix into each well of the plates. About 10 μl of each XI sample was added to the wells. The reactions were started by the addition of about 100 μl substrate solution (about 1 M D-xylose). Reactions were mixed and read immediately using kinetic assay mode for about 10 minutes. Volumetric activity (VA) units are in milli-absorbance (mA) units per minute per ml of lysate added to the reactions (mA/min/ml). Background VA rates of negative control wells (no enzyme added) were subtracted from VA of samples. Determination of fold improvement over positive control (FIOPC) was obtained by dividing the VA of the XI-samples by the VA observed for a control (*Orpinomyces* xylose isomerase, NCBI:169733248 (Op-XI)) expressed using the same host and expression vector. In some characterizations, the slope of an NADH standard curve was used to convert VA (mA/min) to μmole-NADH/min (or Units). If protein quantitation was performed, specific activities (SA) were calculated where the units for SA are (μmole $NADH^+$/min/mg, or U/mg lysate protein). All activities listed (VA or SA) account for any dilutions, volumes of lysate added, and protein concentrations for the lysates assayed.

5.2 Example 2: Activity-Based Discovery Screen for Xylose Isomerases

Libraries used for the activity-based discovery ("ABD") screen were in the format of excised phagemids. These libraries were constructed as described in U.S. Pat. No. 6,280,926. Sources for these libraries were environmental rumen samples collected from the foregut of deceased herbivores.

An *Escherichia coli* screening strain was constructed to identify genes from the environmental libraries encoding xylose isomerase activity. Specifically, *E. coli* strain SEL700, a MG1655 derivative that is $recA^-$, phage lambda resistant and contains an F' plasmid, was complemented with plasmid pJC859, a derivative of pBR322 containing the *E. coli* recA gene (Kokjohn et al., 1987, J. Bacteriol. 169:1499-1508) to generate a wild-type recA phenotype.

Figure 1A:
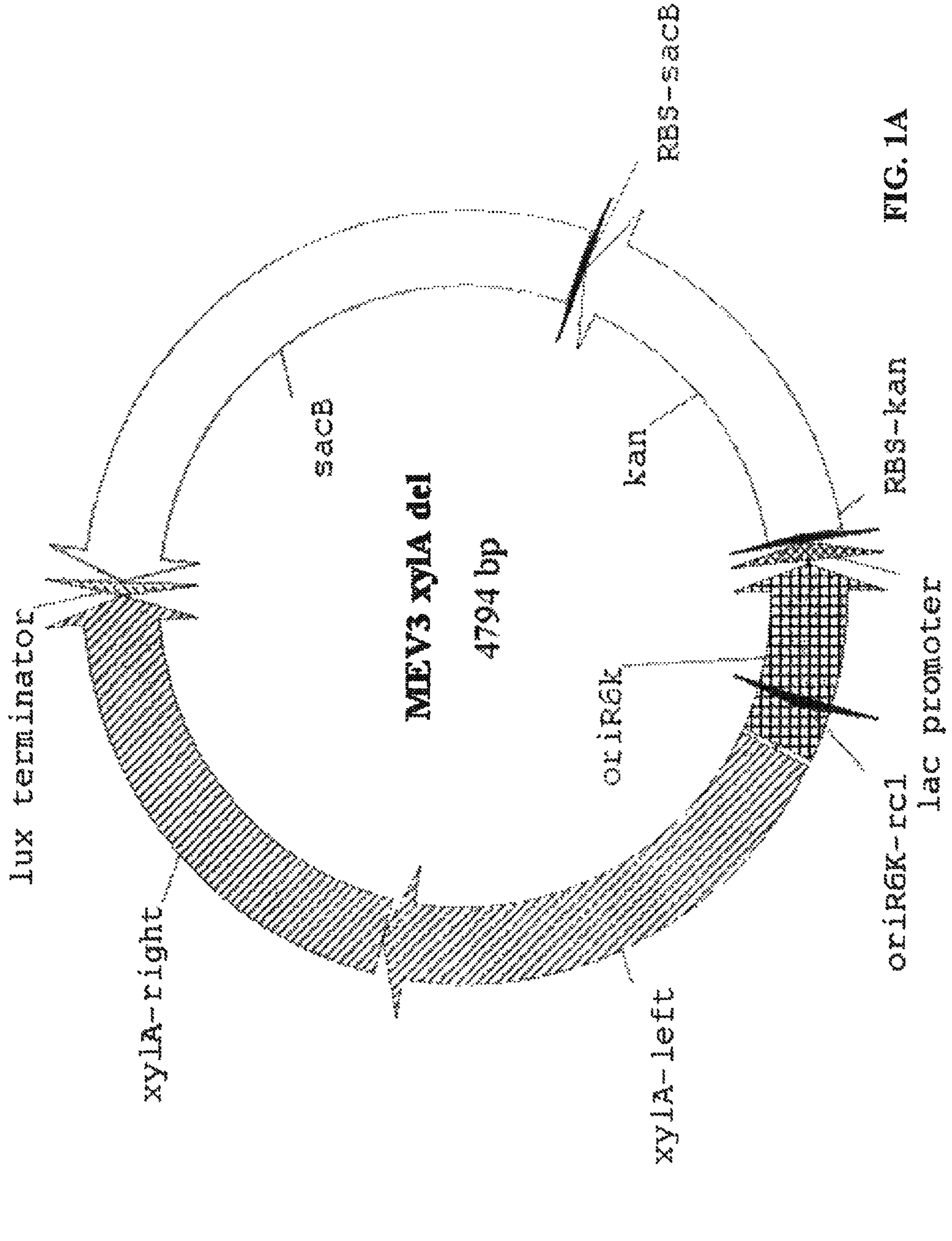
FIGS. 1A-1B are maps for the vector pMEV-ΔxylA (MEV3 xylA del) and PCR-BluntII-TOPO-xylA, respectively, used in the activity-based screen for XIs.

A two-step marker exchange procedure was then used to delete the entire coding sequence of the endogenous xylA xylose isomerase gene. Briefly, pMEV3, a plasmid with a pir-dependent replicon (ori6RK) encoding kanamycin-resistance and the sacB levansucrase, was used as a vector for construction of the xylA deletion plasmid. A fragment of DNA containing the flanking regions of the xylA gene (0.7 kb of sequence 5' and 0.9 kb of sequence 3' of xylA) and containing BsaI restriction sites was generated by overlap extension PCR using primers, ligated to pMEV3 digested with BbsI, and transformed into *E. coli* by electroporation. Clones were confirmed by sequencing, resulting in plasmid pMEV3-ΔxylA (FIG. 1A).

Figure 2:
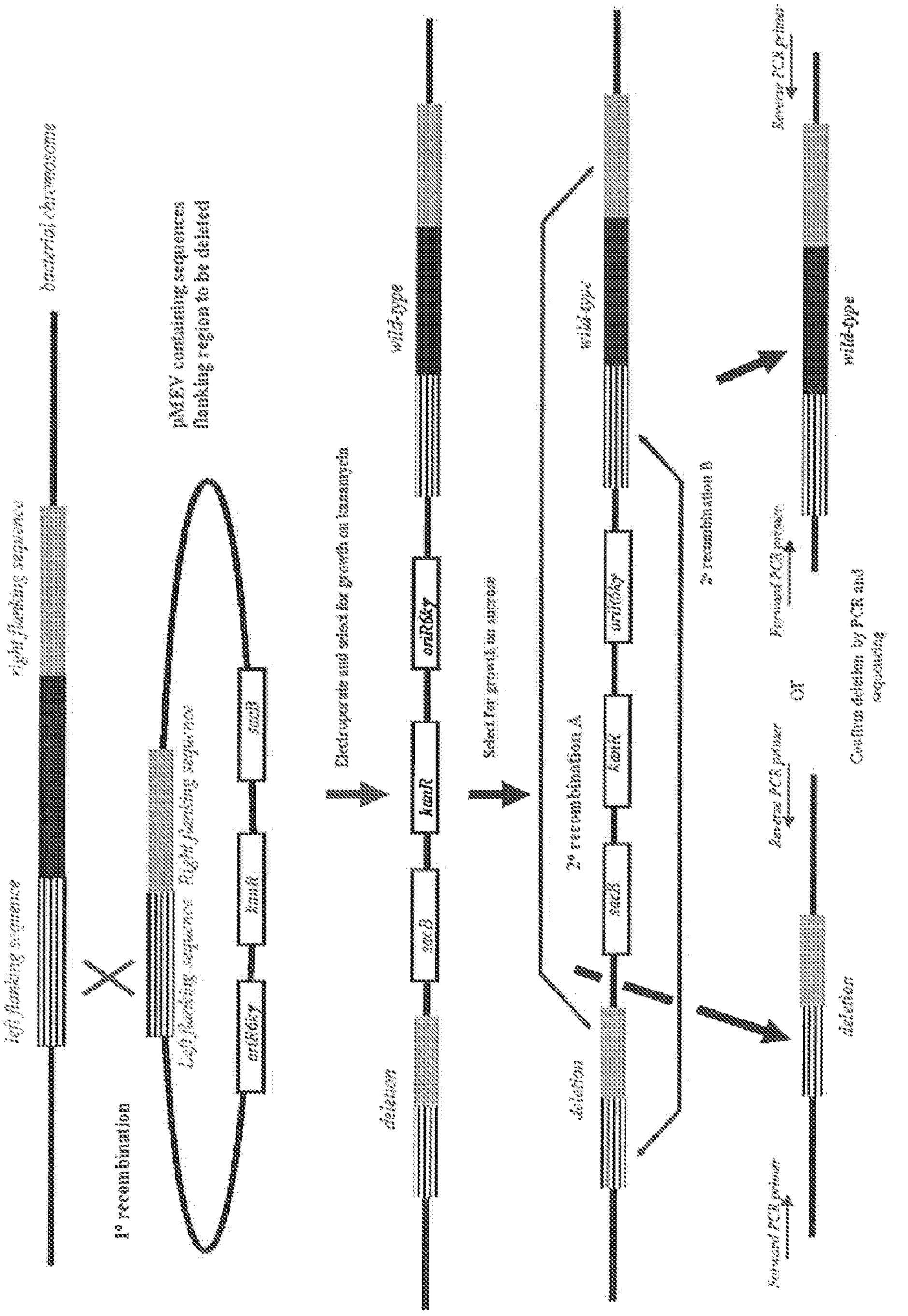
FIG. 2 illustrates the experimental strategy for the two-step marker exchange approach.

The pMEV3-ΔxylA plasmid was then transformed into strain *E. coli* strain SEL700 (MG1655 $\Delta^r$, Δ(recA-srl)306,srl-301::Tn10-84(Tets), [F'proAB, $lacI^q$, ZΔM15, Tn10 ($Tet^r$)] pJC859). Single-crossover events were selected for by plating on LB agar plates containing kanamycin (final concentration, about 50 μg/ml). After confirmation of integration of pMEV3-ΔxylA on the chromosome, a second crossover event was selected for by growth on LB agar media containing sucrose (FIG. 2). Colonies displaying resistance to kanamycin and the ability to grow on sucrose were screened both by PCR characterization with primers flanking the xylA gene to confirm gene deletion and by growth on a modified MacConkey media (ABD media), comprised of: MacConkey Agar Base (Difco™ #281810) (approximate formula per liter: Pancreatic Digest of Gelatin (17.0 g) Peptones (meat and casein) (3.0 g), Bile Salts No. 3 (1.5 g), Sodium Chloride (5.0 g), Agar (13.5 g), Neutral Red (0.03 g), Crystal Violet (1.0 g, Xylose (30.0 g) and Kanamycin (50 mg). The ABD media contained neutral red, a pH indicator that turns red at a pH<6.8. Colonies of mutants lacking xylA appeared white on this media while colonies with restored xylose metabolism ability appeared red in color due to the fermentation of xylose to xylulose, which lowered the pH of the media surrounding those colonies.

Following the successful deletion of xylA, the resulting strain was cured of pJC859 by the following method: The xylA deletion strain was grown for about 24 hours in LB media containing tetracycline at a final concentration, about 20 μg/ml, at around 37° C. The next day the cells were sub-cultured (1:100 dilution) into LB tetracycline (at the same concentration) media and incubated at about three different temperatures (30, 37, and 42° C.). Cells were passaged the same way as above for about two more days. Dilutions of the resulting cultures were plated on LB plates to isolate single colonies. Colonies were replica plated onto LB agar plates with and without Carbenicillin (at about 100 μg/ml, final concentration). Carbenicillin resistant colonies were deemed to still contain vector pJC859 whereas carbenicillin sensitive colonies were cured of pJC859, restoring the recA genotype of strain SEL700. This strain, SEL700 ΔxylA, was used for the ABD screening.

Figure 1B:
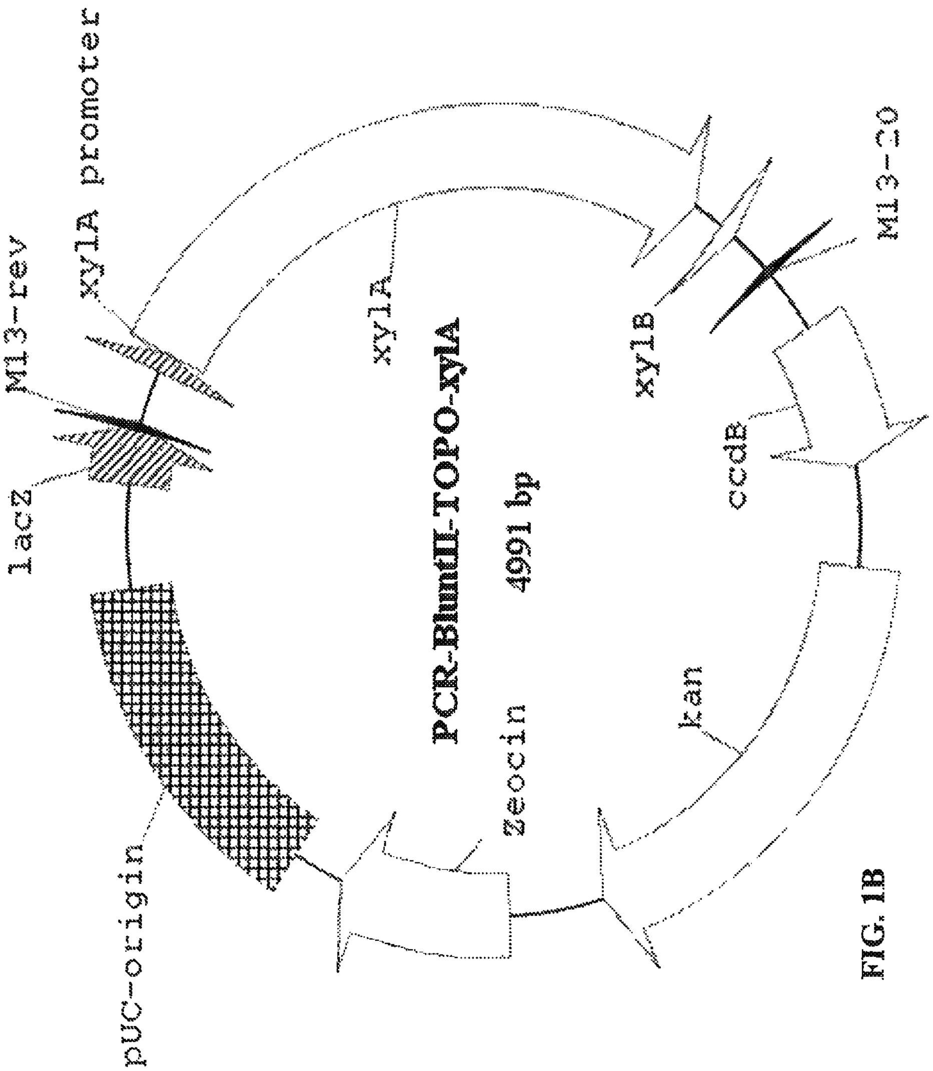

The ABD screening method was verified by creating a positive control strain by PCR amplification of the xylA gene from *E. coli* K12 and cloning into the PCR-BluntII TOPO vector (Invitrogen, Carlsbad, Calif.) using standard procedures. This vector (PCR-BluntII-TOPO-xylA, FIG. 1B) was then transformed into the screening strain (SEL700 ΔxylA). Complementation of the xylose phenotype was verified by growth of transformants on ABD media and appearance of red halos indicating xylose utilization.

The libraries were screened for XI activity by infecting strain SEL700 ΔxylA with the excised phagemid libraries. Infected cells were plated onto ABD media and only colonies with red "halos" (indicating xylose fermentation), were carried forward. Positives were purified to single colonies, and regrown on ABD media to confirm phenotype.

5.3 Example 2: Sequence-Based Discovery for Xylose Isomerases

Libraries used for sequence-based discovery ("SBD") were in the format of genomic DNA (gDNA) extractions.

These libraries were constructed as described in U.S. Pat. No. 6,280,926. Sources for these libraries were samples collected from the guts of deceased herbivores.

XI genes often exist in conserved gene clusters (Dodd et al., 2011, Molecular Microbiol. 79:292-304). In order to obtain full length XI gene sequences from metagenomic samples, primers were designed to both upstream and downstream conserved DNA sequences found in several *Bacteroides* species, typically xylulose kinase and xylose permease, respectively. These flanking DNA sequences were obtained from public databases. Sample genomic DNA was extracted from eleven different animal rumen samples. Left flanking consensus primer has the sequence 5'-GCIGCICARGARGGNATYGTVTT-3' (SEQ ID NO:177) (this primer codes for the amino acid motif AAQEGIV(F) (SEQ ID NO:178)). Right flanking consensus primer has the sequence 5'-GCDATYTCNGCRATRTACATSGG-3' (SEQ ID NO:179) (this primer codes for the amino acid motif PMYIAEIA (SEQ ID NO:180)). PCR reactions were carried out using touchdown cycling conditions, and hot start Platinum® Taq DNA polymerase (Invitrogen, Carlsbad, Calif.). PCR products of expected size were purified and subcloned into pCR4-TOPO vector system (Invitrogen, Carlsbad, Calif.). Positive colonies from the TOPO-based PCR libraries were transformed into TOP10 (Invitrogen, Carlsbad, Calif.) and the transformants grown on LB agar plates with kanamycin (about 25 μg/ml final concentration). Resistant colonies were picked and inoculated into 2 columns each of a 96-deep well plate in about 1.2 ml LB kanamycin (25 μg/ml final concentration) media per well. Cultures were grown overnight at about 30° C. The next day plasmids were purified and inserts sequenced. Sequence analysis revealed multiple full length XI genes. Identification of putative ORFs was done by identifying start and stop codons for the longest protein coding region, and subsequent manual curation based on homology to published xylose isomerase DNA sequences.

5.4 Example 3: XI Sequence Analysis

Plasmids from both ABD and SBD screens were purified and vector inserts were sequenced using an ABI 3730x1 DNA Analyzer and ABI BigDye® v3.1 cycle sequencing chemistry. Identification of putative ORFs was done by identifying start and stop codons for the longest protein coding region, and subsequent manual curation based on homology to published xylose isomerase DNA sequences. The XI ORF identified are set forth in Table 2 below, which indicates the sequences and source organism classification for each XI determined from either the ABD or SBD libraries as well as their assigned sequence identifiers. The putative catalytic domains (based on sequence alignments with other XIs) are underlined.

TABLE 2

| Clone No. | Class of organism | Type of Sequence | SEQ ID NO: | Sequence |
|---|---|---|---|---|
| 1754MI2_001 | *Bacteroidales* | DNA | 1 | ATGGCAGTTAAAGAATATTTCCCGGAGATAGGCAAGATCGCCTTTGAAGGAAAGGAGTCC<br>AAGAACCCTATGGCATTCCACTACTACAATCCAGAGCAGGTAGTAGCCGGAAAGAAAATG<br>AAAGATTGGTTCAAGTTCGCTATGGCATGGTGGCACACCCTCTGCGCTGAAGGTGGCGAC<br>CAGTTCGGTCCTGGTACCAAGAAATTCCCTTGGAACACAGGTGCAACTGCACTCGAAAGA<br>GCAAAGAACAAAATGGACGCAGGTTTCGAGATCATGAGCAAGCTCGGTATCGAGTATTTC<br>TGCTTCCACGATGTTGACCTTATCGACGAGGCTGACACTGTTGAAGAGTACGAGGCTAAC<br>ATGAAGGCTATCACAGCTTACGCAAAGGAGAAAATGGCCGCTACTGGCATCAAACTCCTC<br>TGGGGAACAGCCAATGTATTCGGCAACAAGAGATATATGAACGGCGCTTCTACCAACCCT<br>GACTTCAACGTGGCTGCACGCGCTATGCTCCAGATCAAGAACGCTATCGACGCAACTATC<br>GCTCTCGGTGGTGACTGCTATGTATTCTGGGGCGGCCGTGAGGGTTACATGAGCCTTCTC<br>AACACCGATATGAAGAGAGAGAAAGAGCACATGGCTACCATGCTTACCATGGCACGCGAC<br>TATGCTCGTTCTAAGGGCTTCAAGGGTACCTTCCTTATCGAGCCTAAGCCAATGGAGCCG<br>ATGAAGCACCAGTACGATGTCGATACTGAGACTGTCGTAGGTTTCCTCCGCGCCCATGGT<br>CTTGACAAGGACTTCAAGGTAAACATCGAGGTTAACCACGCTACTCTCGCAGGCCACACC<br>TTCGAGCACGAGCTCCAGTGCGCCGTTGACGCAGGCATGCTCGGAAGCATCGACGCCAAC<br>CGTGGTGACTACCAGAACGGCTGGGATACCGACCAGTTCCCTATCGACCTCTATGAGCTC<br>GTACAGGCTATGATGGTTATCATCAAGGGCGGCGGTCTCGTCGGCGGTACCAACTTCGAC<br>GCCAAGACCCGTCGTAACTCAACAGACCTCGAGGATATCTTCATCGCTCATGTATCCGGC<br>ATGGATGTCATGGCACGCGCTCTCCTCATCGCTGCTGACCTTCTCGAGAAATCTCCTATT<br>CCTGCAATGGTCAAGGAGCGTTACGCTTCCTACGACTCAGGCATGGGCAAGGACTTCGAG<br>AACGGCAAGCTTACTCTCGAGCAGGTTGTCGATTTCGCAAGAAAGAACGGCGAGCCTAAG<br>AGCACCAGCGGAAAGCAGGAGCTCTACGAGTCTATCGTCAATCTCTACATCTAA |
| 1754MI2_001 | *Bacteroidales* | Amino Acid | 2 | MAVKEYFPEIGKIAFEGKESKNPMAFHYYNPEQVVAGKKMKDWFKFAMAWWHTLCAEGGD<br>QFGPGTKKFPWNTGATALERAKNKMDAGFEIMSKLGIEYFCFHDVDLIDEADTVEEYEAN<br>MKAITAYAKEKMAATGIKLLWGTANVFGNKRYMNGASTNPDFNVAARAMLQIKNAIDATI<br>ALGGDCYVFWGGREGYMSLLNTDMKREKEHMATMLTMARDYARSKGFKGTFLIEPKPMEP<br>MKHQYDVDTETVVGFLRAHGLDKDFKVNIEVNHATLAGHTFEHELQCAVDAGMLGSIDAN<br>RGDYQNGWDTDQFPIDLYELVQAMMVIIKGGGLVGGTNFDAKTRRNSTDLEDIFIAHVSG<br>MDVMARALLIAADLLEKSPIPAMVKERYASYDSGMGKDFENGKLTLEQVVDFARKNGEPK<br>STSGKQELYESIVNLYI |
| 5586MI6_004 | *Bacteroidales* | DNA | 3 | ATGGCAAACAAAGAGTACTTCCCGGAGATCGGGAAAATCAAATTCGAAGGCAAGGATTCC<br>AAGAACCCGCTTGCATTCCATTATTACAATCCTGAGCAGGTCGTCTGCGGCAAGCCGATG<br>AAGGACTGGCTCAAGTTCGCTATGGCATGGTGGCACACCCTCTGCGCAGAGGGTAGCGAC<br>CAGTTCGGCGGACCCACCAAGTCATTCCCTTGGAACAAAGCTTCGGATCCCATCGCAAAG<br>GCCAAGCAGAAAGTCGACGCCGGTTTCGAGATCATGCAGAAGCTCGGTATCGGATACTAT<br>TGCTTCCACGATGTAGACCTCATCGACGAGCCCGCCACCATCGAGGAGTATGAGGCCGAT<br>CTCAAGGAGATCGTCGCTTACCTCAAGGAGAAGCAGGCCCAGACCGGCATCAAGCTCCTT<br>TGGGGCACCGCCAACGTCTTCGGTCACAAGCGGTACATGAACGGCGCCTCCACCAACCCT<br>GATTTCGACGTCGCAGCCCGCGCCATGGTCCAGATCAAGAACGCCATGGACGCCACCATC<br>GAGCTCGGCGGCGAGTGCTATGTCTTCTGGGGCGGCCGCGAGGGCTACATGAGCCTCCTC<br>AACACCGACATGAAGCGTGAGAAGCAGCATATGGCCACCATGCTCGGCATGGCCCGCGAC<br>TATGCACGCGGCAAGGGCTTCAAGGGCACCTTCCTCATCGAGCCCAAGCCCATGGAGCCG |

TABLE 2-continued

| Clone No. | Class of organism | Type of Sequence | SEQ ID NO: | Sequence |
|---|---|---|---|---|
| | | | | ACCAAGCACCAGTATGACGTCGACACCGAGACCGTCATCGGTTTCCTCCGTGCCAACGGT<br>CTTGACAAGGACTTCAAGGTCAACATCGAGGTCAATCACGCCACCCTCGCCGGCCACACC<br>TTCGAGCATGAGCTCCAGTGCGCCGCCGATGCCGGTCTCCTCGGATCCATCGACGCCAAC<br>CGCGGCGACTATCAGAACGGCTGGGATACCGACCAGTTCCCGATCGACCTCTATGAGCTC<br>ACCCAGGCCATGATGGTCATCCTCAAGAATGGCGGCCTCGTCGGCGGTACCAACTTCGAC<br>GCCAAGACCCGTCGCAACTCCACCGACCTGGACGACATCATCATCGCCCACGTCAGCGGT<br>ATGGACATCATGGCACGCGCACTCCTCGTCGCTGCCGACGTCCTCACCAAGTCCGAGCTT<br>CCCAAGATGCTCAAGGAGCGTTACGCTTCCTTCGACTCCGGCAAGGGCAAGGAGTTCGAA<br>GAGGGCAAGCTCACTCTCGAGCAGGTCGTAGAGTACGCCAAGACCAAGGGCGAGCCCAAG<br>GCCACCAGCGGCAAGCAGGAGCTCTACGAGACCATCGTCAACATGTACATCTAA |
| 5586MI6_004 | *Bacteroidales* | Amino Acid | 4 | MANKEYFPEIGKIKFEGKDSKNPLAFHYYNPEQVVCGKPMKDWLKFAMAWWHTLCAEGSD<br>QFGGPTKSFPWNKASDPIAKAKQKVDAGFEIMQKLGIGYYCFHDVDLIDEPATIEEYEAD<br>LKEIVAYLKEKQAQTGIKLLWGTANVFGHKRYMNGASTNPDFDVAARAMVQIKNAMDATI<br>ELGGECYVFWGGREGYMSLLNTDMKREKQHMATMLGMARDYARGKGFKGTFLIEPKPMEP<br>TKHQYDVDTETVIGFLRANGLDKDFKVNIEVNHATLAGHTFEHELQCAADAGLLGSIDAN<br>RGDYQNGWDTDQFPIDLYELTQAMMVILKNGGLVGGTNFDAKTRRNSTDLDDIIIAHVSG<br>MDIMARALLVAADVLTKSELPKMLKERYASFDSGKGKEFEEGKLTLEQVVEYAKTKGEPK<br>ATSGKQELYETIVNMYI |
| 5749MI1_003 | *Bacteroidales* | DNA | 5 | ATGAATTTTTATAAAGGCGAAAAAGAATTCTTCCCCGGAATAGGAAAGATTCAGTTTGAA<br>GGACGCGAGTCAAAGAACCCGATGGCGTTTCATTATTATGACGAAAACAAGGTGGTGATG<br>GGTAAAACACTGAAGGATCATCTTCGTTTTGCAATGGCTTACTGGCATACGCTTTGTGCC<br>GAAGGGGGCGACCAGTTTGGCGGTGGTACGAAAACATTCCCCTGGAATGCTGCTGCCGAC<br>CCGATCAGCCGTGCCAAATATAAGATGGATGCAGCGTTCGAGTTTATGACAAAATGCAGC<br>ATCCCTTATTACTGTTTCCATGATGTGGACGTGGTGGACGAAGCTCCCACGCTGGCTCAG<br>TTTGAAAAAGACCTTCATACGATGGTAGGCCATGCCAAAGGGCTTCAGCAGGCAACCGGA<br>AAAAAACTGTTATGGTCTACTGCCAACGTGTTCAGCAACAAACGCTATATGAACGGGGCT<br>GCCACTAATCCTGACTTCTCGGCCGTGGCTTGTGCCGGTACGCAGATCAAGAATGCGATC<br>GATGCCTGTATCGCGCTGGACGGTGAAAACTATGTGTTCTGGGGCGGACGTGAAGGATAT<br>ATGGGCTTGCTCAATACCGATATGAAACGCGAAAAAGACCATCTGGCCATGATGCTGACG<br>ATGGCACGCGACTATGGCCGCAAGAACGGTTTCAAAGGTACTTTCCTGATCGAGCCGAAA<br>CCGATGGAACCGACCAAGCATCAATATGATGTCGACTCGGAAACTGTAATCGGCTTCCTA<br>CGTCATTATGGCCTGGATAAAGACTTCGCCCTGAATATCGAAGTAAATCATGCAACCCTG<br>GCCGGACATACGTTCGAGCACGAATTGCAGGCTGCTGTCGATGCCGGTATGCTGTGCAGT<br>ATCGATGCCAACCGTGGTGACTACCAGAATGGCTGGGATACCGACCAATTCCCGATGGAC<br>ATCTACGAACTGACTCAGGCTTGGCTGGTCATTCTGCAAGGTGGTGGTCTGACAACCGGC<br>GGAACGAACTTCGATGCCAAGACCCGCCGCAACTCGACCGACCTGGACGATATCTTCCTG<br>GCTCATATAGGTGGTATGGATGCGTTTGCCCGTGCCCTGATCACGGCTGCTGCCATCCTT<br>GAAAACTCCGATTACACGAAGATGCGTGCCGAACGTTACACCAGCTTCGATGGTGGCGAA<br>GGCAAAGCGTTTGAAGACGGTAAACTTTCTCTGGAAGACCTGCGTACGATCGCTCTCCGC<br>GACGGAGAACCGAAGATGGTCAGCGGCAAACAGGAATTATATGAGATGATTCTCAATTTA<br>TACATATAA |
| 5749MI1_003 | *Bacteroidales* | Amino Acid | 6 | MNFYKGEKEFFPGIGKIQFEGRESKNPMAFHYYDENKVVMGKTLKDHLRFAMAYWHTLCA<br>EGGDQFGGGTKTFPWNAAADPISRAKYKMDAAFEFMTKCSIPYYCFHDVDVVDEAPTLAQ<br>FEKDLHTMVGHAKGLQQATGKKLLWSTANVFSNKRYMNGAATNPDFSAVACAGTQIKNAI<br>DACIALDGENYVFWGGREGYMGLLNTDMKREKDHLAMMLTMARDYGRKNGFKGTFLIEPK<br>PMEPTKHQYDVDSETVIGFLRHYGLDKDFALNIEVNHATLAGHTFEHELQAAVDAGMLCS<br>IDANRGDYQNGWDTDQFPMDIYELTQAWLVILQGGGLTTGGTNFDAKTRRNSTDLDDIFL<br>AHIGGMDAFARALITAAAILENSDYTKMRAERYTSFDGGEGKAFEDGKLSLEDLRTIALR<br>DGEPKMVSGKQELYEMILNLYI |
| 5750MI1_003 | *Bacteroidales* | DNA | 7 | ATGAATTACTTTAAAGGTGAGAAAGAGTTCTTCCCGGGAATCGGGAAAATAGAGTTTGAA<br>GGACGTGAATCGAAGAATCCGATGGCTTTTCATTACTATGACGAGAACAAGGTTGTCATG<br>GGGAAGACCTTGAAGGACCATCTGCGTTTTGCGATGGCTTATTGGCATACGCTGTGTGCG<br>GAAGGCGCCGACCAGTTCGGCGGCGGGACGAAGGCATTTCCCTGGAATACCGGGGCGGAT<br>CGTATTTCCCGTGCCAAGTATAAGATGGATGCTGCTTTTGAGTTTATGACGAAATGTAAC<br>ATCCCGTACTATTGTTTCCATGATGTGGATGTGGTGGATGAAGCTCCGACACTGGCCGAA<br>TTTGAAAAAGACTTGCATACGATGGTCGAATATGCCAAGCAGCATCAGGAGGCAACCGGG<br>AAAAAACTGTTGTGGTCTACCGCCAATGTGTTCAGCAATAAACGTTATATGAACGGGGCT<br>GCCACAAATCCGTATTTCCCTGCTGTCGCTTGTGCGGGTACGCAGATCAAGAATGCTATC<br>GACGCTTGTATTGCCCTGGGCGGCGAAAACTATGTGTTCTGGGGCGGTCGTGAAGGGTAT<br>ATGAGCTTGTTGAACACCAATATGAAACGCGAAAAGGAACATCTCGCCATGATGTTGACG<br>ATGGCTCGCGATTATGCGCGTAAGAACGGCTTCAAAGGTACTTTCCTGGTAGAGCCTAAA<br>CCGATGGAACCGACCAAACATCAGTATGATGTGGACACAGAAACTGTTATCGGCTTCCTG<br>CGTCATTACGGCCTTGACAAGGACTTTGCCATCAACATCGAAGTGAATCATGCTACATTG<br>GCTGGACATACATTCGAACATGAGCTTCAGGCGGCTGCCGATGCCGGTATGCTGTGCAGC<br>ATCGACGCCAACCGCGGCGATTACCAGAATGGTTGGGACACGGATCAGTTCCCGGTCGAC<br>ATCTACGAACTGACACAGGCGTGGCTGGTTATCCTCGAAGCGGGTGGCCTGACTACCGGT<br>GGTACGAACTTCGACGCCAAGACGCGCCGCAACTCGACTGACCTGGACGATATCTTCCTG<br>GCACACATCGGTGGTATGGATTCGTTTGCCCGTGCTTTGATGGCGGCTGCCGATATATTG<br>GAACACTCCGATTACAAAAAGATGCGTGCCGAACGTTATGCCAGCTTCGATCAAGGCGAC<br>GGCAAGAAGTTCGAAGATGGTAAACTCCTTCTCGAGGACCTCCGCACCATCGCTCTTGCC<br>TCCGGCGAACCGAAGCAAATCAGCGGGAAACAGGAATTGTATGAAATGATTATCAACCAG<br>TACATTTAA |

TABLE 2-continued

| Clone No. | Class of organism | Type of Sequence | SEQ ID NO: | Sequence |
|---|---|---|---|---|
| 5750MI1_003 | *Bacteroidales* | Amino Acid | 8 | MNYFKGEKEFFPGIGKIEFEGRESKNPMAFHYYDENKVVMGKTLKDHLRFAMAYWHTLCA<br>EGADQFGGGTKAFPWNTGADRISRAKYKMDAAFEFMTKCNIPYYCFHDVDVVDEAPTLAE<br>FEKDLHTMVEYAKQHQEATGKKLLWSTANVFSNKRYMNGAATNPYFPAVACAGTQIKNAI<br>DACIALGGENYVFWGGREGYMSLLNTNMKREKEHLAMMLTMARDYARKNGFKGTFLVEPK<br>PMEPTKHQYDVDTETVIGFLRHYGLDKDFAINIEVNHATLAGHTFEHELQAAADAGMLCS<br>IDANRGDYQNGWDTDQFPVDIYELTQAWLVILEAGGLTTGGTNFDAKTRRNSTDLDDIFL<br>AHIGGMDSFARALMAAADILEHSDYKKMRAERYASFDQGDGKKFEDGKLLLEDLRTIALA<br>SGEPKQISGKQELYEMIINQYI |
| 5750MI2_003 | *Bacteroidales* | DNA | 9 | ATGAATTATTTTAAAGGTGAAAAAGAGTTTTTCCCTGGAATCGGGAAAATAGAGTTTGAA<br>GGACGTGAGTCGAAGAATCCGATGGCTTTTCATTATTATGATGAAAACAAGGTCGTAATG<br>GGCAAGACCTTGAAAGATCACCTCCGCTTTGCAATGGCTTACTGGCATACGTTGTGCGCG<br>GAAGGCGCAGACCAGTTTGGCGGTGGCACAAAATCATTCCCCTGGAATACCGCAGCGGAT<br>CGTATTTCCCGCGCTAAATATAAAATGGATGCTGCTTTCGAGTTTATGACCAAGTGCAGT<br>ATCCCGTACTATTGTTTCCATGATGTGGACGTGGTGGACGAAGCTCCGGCACTGGCCGAA<br>TTTGAAAAGGACCTGCATACGATGGTGGGATTCGCCAAACAACACCAGGAAGCAACCGGA<br>AAGAAACTGTTGTGGTCTACAGCCAATGTATTCGGGCATAAACGTTATATGAACGGAGCG<br>GCTACCAATCCTTATTTCCCGGCTGTCGCTTGTGCCGGTACGCAGATCAAGAATGCAATC<br>GACGCCTGTATCGAGCTGGGTGGAGAGAACTATGTATTCTGGGGCGGACGCGAAGGCTAC<br>ATGAGCCTGCTGAACACCAATATGAAACGTGAAAAGGATCATTTGGCCATGATGCTGACA<br>ATGGCACGCGATTATGCCCGCAAGAATGGTTTCAAGGGTACTTTCCTGGTGGAATCTAAG<br>CCGATGGAACCGACCAAACATCAGTATGACGCAGATACGGAAACCGTGATCGGCTTCCTG<br>CGCCACTATGGCCTCGACAAGGATTTCGCTATCAACATTGAAGTGAACCATGCTACATTG<br>GCCGGCCATACATTCGAACATGAACTTCAGGCTGCTGCCGATGCCGGTATGCTGTGCAGC<br>ATCGATGCAAATAGAGGCGACTATCAGAATGGTTGGGATACGGATCAGTTCCCCGTAGAC<br>ATTTACGAACTGACACAGGCCTGGCTGGTTATCCTGGAAGCGGGCGGACTGACAACCGGA<br>GGTACGAACTTCGATGCGAAGACCCGTCGTAACTCGACTGACCTCGACGATATCTTCCTG<br>GCCCATATCGGCGGTATGGATTCGTTTGCACGTGCCTTGATGGCAGCTGCCGATATCCTG<br>GAACATTCTGATTACAAGAAGATGCGTGCCGAACGTTACGCCAGCTTCGACCAGGGCGAC<br>GGCAAGAAGTTCGAAGACGGCAAACTCCTTCTCGAAGACCTGCGCACAATTGCCCTTGCC<br>GGCGACGAACCGAAGCAGATCAGCGGCAAGCAGGAGTTGTATGAGATGATTATCAATCAG<br>TATATTTAA |
| 5750MI2_003 | *Bacteroidales* | Amino Acid | 10 | MNYFKGEKEFFPGIGKIEFEGRESKNPMAFHYYDENKVVMGKTLKDHLRFAMAYWHTLCA<br>EGADQFGGGTKSFPWNTAADRISRAKYKMDAAFEFMTKCSIPYYCFHDVDVVDEAPALAE<br>FEKDLHTMVGFAKQHQEATGKKLLWSTANVFGHKRYMNGAATNPYFPAVACAGTQIKNAI<br>DACIELGGENYVFWGGREGYMSLLNTNMKREKDHLAMMLTMARDYARKNGFKGTFLVESK<br>PMEPTKHQYDADTETVIGFLRHYGLDKDFAINIEVNHATLAGHTFEHELQAAADAGMLCS<br>IDANRGDYQNGWDTDQFPVDIYELTQAWLVILEAGGLTTGGTNFDAKTRRNSTDLDDIFL<br>AHIGGMDSFARALMAAADILEHSDYKKMRAERYASFDQGDGKKFEDGKLLLEDLRTIALA<br>GDEPKQISGKQELYEMIINQYI |
| 5586MI5_004 | *Bacteroides* | DNA | 11 | ATGAAACAGTATTTCCCGAACATCTCCGCCATCAAGTTTGAGGGCGTCGAGAGCAAGAAT<br>CCCCTGGCTTACCGCTACTACGACCGCGACCGCGTCGTCATGGGTAAGAAGATGAGCGAA<br>TGGTTTAAGTTCGCTATGTGCTGGTGGCACACCCTCTGCGCCGAGGGCTCCGATCAGTTC<br>GGTCCCGGCACAAAGACCTTCCCCTGGAACGCCGCCGCCGACCCCGTGCAGGCTGCCAAG<br>GACAAGGCCGACGCTGGCTTCGAGATCATGCAGAAACTCGGCATCGAGTACTACTGCTTC<br>CACGACGTTGACCTCGTGGCCGAGGCTCCCGACGTGGAGACCTACGAGAAGAACCTCAAG<br>GAGATCGTGGCTTATCTCAAGCAGAAACAGGCTGAGACGGGCATCAAGCTGCTCTGGGGC<br>ACTGCCAACGTCTTCGGACACAAGCGCTACATGAACGGAGCCTCCACGAACCCCGACTTC<br>GATGTCGTGGCACGCGCTATCGTGCAGATCAAGAACGCCATCGATGCTACCATCGAGCTG<br>GGCGGCACCAACTACGTCTTCTGGGGCGGTCGCGAAGGCTACATGAGCCTGCTCAACACC<br>GATATGAAGCGCGAGAAGGAGCACATGGCTACGATGTTGACGATGGCACGCGACTATGCC<br>CGTTCTAAGGGATTCAAGGGCACGTTCCTCATCGAACCCAAACCCATGGAACCCACGAAG<br>CATCAGTACGATGCGGACACCGAGACGGTCATCGGATTCCTCCGTGCTCATGGTCTCGAC<br>AAGGATTTCAAGGTCAACATCGAGGTCAACCACGCCACGCTGGCCGGACACACGTTCGAG<br>CATGAGCTGGCCTGCGCCGTAGACGCCGATATGCTCGGCAGCATCGATGCCAATCGCGGC<br>GACTATCAGAACGGATGGGACACCGACCAGTTCCCCATCGACCACTACGAACTCACGCAG<br>GCTATGCTGCAGATCATCCGCAACGGAGGTTTCAAGGACGGTGGCACCAATTTTGACGCT<br>AAGACGCGCCGCAACAGCACCGACCTCGAGGATATCTTCATCGCTCACGTAGCAGCCATG<br>GACGCCATGGCCCACGCCCTGTTGTCGGCTGCCGATATCATCGAGAAGTCGCCCATCTGC<br>ACGATGGTCAAGGAGCGTTACGCCAGCTTCGATGCCGGCGAAGGCAAGCGCTTCGAAGAA<br>GGCAAGATGACCCTCGAGGAAGCCTACGAGTATGGCAAGAAGGTCGGGGAGCCCAAGCAG<br>ACCAGCGGAAAGCAGGAGCTCTACGAAGCCATTGTCAATATGTATTGA |
| 5586MI5_004 | *Bacteroides* | Amino Acid | 12 | MKQYFPNISAIKFEGVESKNPLAYRYYDRDRVVMGKKMSEWFKFAMCWWHTLCAEGSDQF<br>GPGTKTFPWNAAADPVQAAKDKADAGFEIMQKLGIEYYCFHDVDLVAEAPDVETYEKNLK<br>EIVAYLKQKQAETGIKLLWGTANVFGHKRYMNGASTNPDFDVVARAIVQIKNAIDATIEL<br>GGTNYVFWGGREGYMSLLNTDMKREKEHMATMLTMARDYARSKGFKGTFLIEPKPMEPTK<br>HQYDADTETVIGFLRAHGLDKDFKVNIEVNHATLAGHTFEHELACAVDADMLGSIDANRG<br>DYQNGWDTDQFPIDHYELTQAMLQIIRNGGFKDGGTNFDAKTRRNSTDLEDIFIAHVAAM<br>DAMAHALLSAADIIEKSPICTMVKERYASFDAGEGKRFEEGKMTLEEAYEYGKKVGEPKQ<br>TSGKQELYEAIVNMY |

TABLE 2-continued

| Clone No. | Class of organism | Type of Sequence | SEQ ID NO: | Sequence |
|---|---|---|---|---|
| 5586MI202_004 | *Bacteroides* | DNA | 13 | ATGGCAACAAAAGAGTATTTTCCCGGAATAGGAAAGATTAAATTCGAAGGTAAAGAGAGT<br>ATGAACCCGATGGCATATCGTTACTACGATGCTGAGAAGGTAATCATGGGTAAGAAGATG<br>AAAGATTGGTTGAAGTTTGCTATGGCTTGGTGGCACACTCTCTGCGCAGAAGGTGGTGAC<br>CAATTCGGTGGCGGAACGAAACAATTCCCTTGGAATGGTGACTCTGACGCTTTGCAAGCA<br>GCTAAAAATAAATTGGATGCAGGTTTCGAATTCATGCAGAAGATGGGTATCGAATACTAT<br>TGCTTCCACGATGTAGACCTGATTTCTGAAGGTGCAAGCATCGAAGAATACGAAGCTAAC<br>TTGAAAGCTATCGTAGCTTATGCAAAAGAAAAACAGGCTGAAACTGGTATCAAGCTGTTG<br>TGGGGTACTGCTAACGTATTCGGTCATGCACGTTATATGAACGGTGCTGCTACCAATCCT<br>GATTTCGACGTTGTAGCACGCGCTGCTGTTCAGATCAAGAACGCTATTGACGCTACTATC<br>GAACTGGGTGGTTCAAACTATGTATTCTGGGGCGGTCGCGAAGGTTACATGTCTTTGCTG<br>AACACTGACCAGAAACGTGAAAAAGAACACCTTGCAAAGATGTTGACTATCGCTCGTGAC<br>TATGCACGTGCTCGTGGCTTCAAAGGTACTTTCCTGATTGAGCCGAAACCGATGGAACCG<br>ACAAAACATCAGTATGATGTAGATACTGAAACAGTTATCGGCTTCCTGAAAGCTCACGGT<br>TTGGATAAGGATTTCAAAGTAAACATCGAGGTTAATCACGCAACTTTGGCTGGCCATACT<br>TTCGAACACGAACTGGCTGTAGCTGTTGACAACGGCATGTTAGGTTCTATCGACGCTAAC<br>CGTGGTGACTACCAGAACGGTTGGGATACTGACCAATTCCCTATCGATAACTACGAACTG<br>ACTCAAGCTATGATGCAGATCATCCGCAACGGTGGTTTGGGTAATGGCGGTACTAACTTC<br>GACGCTAAGACCCGTCGTAACTCTACCGACCTGGAAGATATCTTCATCGCTCACATTGCA<br>GGTATGGATGCTATGGCACGTGCTCTGGAAAGTGCAGCTAAATTACTGGAAGAATCTCCT<br>TATAAGAAAATGTTGGCTGATCGTTACGCATCATTCGACGGTGGCAAGGGTAAGGAATTC<br>GAAGAAGGCAAATTGTCTTTGGAAGATGTTGTAGCTTATGCGAAAGCTAACGGCGAACCG<br>AAGCAAACCAGCGGCAAGCAAGAATTGTATGAAGCAATCGTGAATATGTATTGCTAA |
| 5586MI202_004 | *Bacteroides* | Amino Acid | 14 | MATKEYFPGIGKIKFEGKESMNPMAYRYYDAEKVIMGKKMKDWLKFAMAWWHTLCAEGGD<br>QFGGGTKQFPWNGDSDALQAAKNKLDAGFEFMQKMGIEYYCFHDVDLISEGASIEEYEAN<br>LKAIVAYAKEKQAETGIKLLWGTANVFGHARYMNGAATNPDFDVVARAAVQIKNAIDATI<br>ELGGSNYVFWGGREGYMSLLNTDQKREKEHLAKMLTIARDYARARGFKGTFLIEPKPMEP<br>TKHQYDVDTETVIGFLKAHGLDKDFKVNIEVNHATLAGHTFEHELAVAVDNGMLGSIDAN<br>RGDYQNGWDTDQFPIDNYELTQAMMQIIRNGGLGNGGTNFDAKTRRNSTDLEDIFIAHIA<br>GMDAMARALESAAKLLEESPYKKMLADRYASFDGGKGKEFEEGKLSLEDVVAYAKANGEP<br>KQTSGKQELYEAIVNMYC |
| 5586MI211_003 | *Bacteroides* | DNA | 15 | ATGGCAAAAGAGTATTTTCCTGGCGTGAAAAAAATCCAGTTCGAGGGTAAGGACAGTAAG<br>AATCCAATGGCTTACCGTTATTATGATGCAGAGAAGGTCATCATGGGTAAGAAGATGAAG<br>GATTGGTTGAAGTTCGCTATGGCTTGGTGGCACACTTTGTGCGCTGAGGGCGCAGACCAG<br>TTCGGTGGCGGTACTAAGACTTTCCCTTGGAACGAAGGTGCAAACGCTTTGGAAGTTGCT<br>AAGAATAAGGCTGATGCTGGTTTCGAGATTATGGAGAAGCTTGGCATCGAGTACTACTGT<br>TTCCACGATGTAGACCTCGTTGAGGAGGCTGCAACTATCGAGGAGTATGAGGCTAACATG<br>AAGGCTATCGTTGCTTATCTTAAGGAGAAGCAGGCTGCTACTGGCAAGAAGCTTCTTTGG<br>GGTACTGCTAACGTATTCGGCAACAAGCGCTATATGAACGGTGCTTCTACAAACCCTGAC<br>TTCGACGTTGTTGCTCGCGCTTGTGTTCAGATTAAGAACGCTATCGACGCTACTATCGAA<br>CTTGGTGGTACAAACTACGTATTCTGGGGTGGCCGCGAGGGTTATATGAGCCTTCTTAAC<br>ACAGATATGAAGCGTGAGAAGGAGCACATGGCAACTATGCTTACTAAGGCTCGCGACTAC<br>GCTCGTTCAAAGGGCTTTACTGGTACATTCCTTATCGAGCCAAAGCCAATGGAACCATCA<br>AAGCATCAGTATGATGTTGATACTGAGACTGTTTGTGGTTTCTTGAGGGCTCACGGTCTT<br>GACAAGGACTTCAAGGTAAACATCGAGGTTAACCACGCTACTTTGGCTGGTCACACATTC<br>GAGCACGAGTTGGCTGCTGCTGTTGATAACGGTATGCTTGGCTCTATCGACGCTAACCGC<br>GGTGACTACCAGAACGGTTGGGATACTGACCAGTTCCCTATCGACAACTTCGAGCTTATT<br>CAGGCTATGATGCAGATTATCCGCAACGGTGGTCTTGGCAACGGTGGTACAAACTTCGAC<br>GCTAAGACTCGTCGTAACTCAACTGACCTTGAGGATATCTTCATCGCACACATCGCTGGT<br>ATGGATGCAATGGCTCGCGCTCTTGAGAACGCAGCAGACCTTTTGGAGAACTCTCCAATC<br>AAGAAGATGGTTGCTGAGCGTTACGCTTCATTCGACAGCGGCAAGGGTAAGGAGTTCGAG<br>GAAGGCAAGTTGAGCCTTGGGGACATCGTTGCTTATGCTAAGCAGAACGGTGAGCCTAAG<br>CAGACAAGCGGTAAGCAGGAGCTTTACGAGGCTATCGTAAACATGTACTGCTAA |
| 5586MI211_003 | *Bacteroides* | Amino Acid | 16 | MAKEYFPGVKKIQFEGKDSKNPMAYRYYDAEKVIMGKKMKDWLKFAMAWWHTLCAEGADQ<br>FGGGTKTFPWNEGANALEVAKNKADAGFEIMEKLGIEYYCFHDVDLVEEAATIEEYEANM<br>KAIVAYLKEKQAATGKKLLWGTANVFGNKRYMNGASTNPDFDVVARACVQIKNAIDATIE<br>LGGTNYVFWGGREGYMSLLNTDMKREKEHMATMLTKARDYARSKGFTGTFLIEPKPMEPS<br>KHQYDVDTETVCGFLRAHGLDKDFKVNIEVNHATLAGHTFEHELAAAVDNGMLGSIDANR<br>GDYQNGWDTDQFPIDNFELIQAMMQIIRNGGLGNGGTNFDAKTRRNSTDLEDIFIAHIAG<br>MDAMARALENAADLLENSPIKKMVAERYASFDSGKGKEFEEGKLSLGDIVAYAKQNGEPK<br>QTSGKQELYEAIVNMYC |
| 5606MI1_005 | *Bacteroides* | DNA | 17 | ATGGCGACAAAAGAATACTTTCCCGGAATAGGGAAAATCAAGTTTGAGGGTGTGAATAGC<br>TATAATCCGCTGGCATACAGATATTACGATGCCGAGCGCATAGTCCTTGGCAAGCCGATG<br>AAGGAGTGGCTCAAGTTTGCCATGGCATGGTGGCACACACTCTGCGCAGAGGGTGGCGAC<br>CAGTTTGGCGGCGGTACGAAGAATTTTCCCTGGAATGGAGATCCCGATCCGGTACAGGCC<br>GCAAAAAACAAAGTAGACGCCGGCTTCGAATTCATGACCAAGATGGGAATAGAGTATTTC<br>TGTTTCCACGACGTGGATCTCGTCAGCGAGGCAGCAACCATCGAGGAGTATGAGGCCAAC<br>CTGAAGGAAGTGGTGGGCTACATCAAGGAAAAGCAGGCCGAGACGGGGATCAAAAACCTC<br>TGGGGCACTGCCAACGTGTTCAGCCACGCGCGCTACATGAACGGAGCCGCCACCAACCCC<br>GACTTCGATGTAGTGGCCCGCGCAGCCGTGCAGATCAAGAATGCTATCGACGCCACGATA<br>GCCTTAGGTGGCACCAACTACGTGTTCTGGGGTGGCCGTGAAGGTTACATGAGCCTGCTC<br>AACACCGACCAGAAGCGCGAGAAGGAGCATCTGGCAATGATGCTCCGCATGGCCCGCGAC |

TABLE 2-continued

| Clone No. | Class of organism | Type of Sequence | SEQ ID NO: | Sequence |
|---|---|---|---|---|
| | | | | TATGCGCGTGCAAAAGGCTTCACCGGCACCTTCCTTATCGAGCCCAAGCCGATGGAGCCC<br>ACCAAGCACCAGTATGATGTAGACACCGAGACTGTGATAGGCTTCCTCCGTGCCCACGGC<br>CTCGACAAGGACTTCAAGGTCAACATAGAGGTGAACCACGCCACCCTGGCCGGCCATACC<br>TTCGAGCATGAGCTGGCAGTGGCCGTGGACAACGGTATGCTCGGCAGCATCGACGCCAAC<br>CGCGGTGACTACCAGAACGGCTGGGATACCGACCAGTTCCCCATCGACAACTACGAGCTG<br>ACCCAGGCCATGATGCAGATAATACGCAACGGCGGCTTCGGCAACGGCGGATGCAACTTC<br>GACGCCAAGACACGCCGCAACTCCACCGACCTGGAGGATATCTTCATAGCCCACATAGCA<br>GGCATGGACGCCATGGCCCGCGCCCTGCTCAGCGCAGCAGAAGTGCTGGAGAAATCGCCC<br>TACAGGAAGATGCTCGCCGAGCGCTACGCACCGTTTGATGCCGGCCAGGGAAAGGCATTT<br>GAAGAGGGCGCAATGTCGCTCACCGACCTTGTGGAGTATGCCAAGGAGCATGGCGAGCCC<br>ACACAGACTTCCGGCAAGCAGGAACTCTATGAGGCAATCGTCAATATGTATTGCTAA |
| 5606MI1_005 | *Bacteroides* | Amino Acid | 18 | MATKEYFPGIGKIKFEGVNSYNPLAYRYYDAERIVLGKPMKEWLKFAMAWWHTLCAEGGD<br>QFGGGTKNFPWNGDPDPVQAAKNKVDAGFEFMTKMGIEYFCFHDVDLVSEAATIEEYEAN<br>LKEVVGYIKEKQAETGIKNLWGTANVFSHARYMNGAATNPDFDVVARAAVQIKNAIDATI<br>ALGGTNYVFWGGREGYMSLLNTDQKREKEHLAMMLRMARDYARAKGFTGTFLIEPKPMEP<br>TKHQYDVDTETVIGFLRAHGLDKDFKVNIEVNHATLAGHTFEHELAVAVDNGMLGSIDAN<br>RGDYQNGWDTDQFPIDNYELTQAMMQIIRNGGFGNGGCNFDAKTRRNSTDLEDIFIAHIA<br>GMDAMARALLSAAEVLEKSPYRKMLAERYAPFDAGQGKAFEEGAMSLTDLVEYAKEHGEP<br>TQTSGKQELYEAIVNMYC |
| 5606MI2_003 | *Bacteroides* | DNA | 19 | ATGGCAACAAAGGAATATTTTCCCCATATAGGGAAGATCCAGTTCAAAGGCACGGAATCG<br>TACGATCCGATGTCGTATCGTTACTATGACGCCGAGCGCGTAGTTCTGGGCAAGCCCATG<br>AAGGAATGGCTGAAATTCGCCATGGCATGGTGGCACACATTGTGCGCCGAGGGCGGCGAC<br>CAGTTCGGCGGCGGAACGAAGAAGTTCCCCTGGAACGAGGGCGAGGACGCCATGACCATC<br>GCCAAGCAGAAGGCTGACGCCGGCTTCGAGATCATGCAGAAGCTCGGCATCGAGTATTTC<br>TGCTTCCACGACATCGACCTGATCGGCGACCTGGGCGACGACATCGAGGACTATGAGAAC<br>CGTATGCACGAAATCACCGCACACCTGAAGGAGAAGATGGCCGCCACGGGCATCAAGAAC<br>CTGTGGGGCACTGCCAACGTGTTCGGCCACGCACGCTATATGAACGGCGCCGCCACCAAC<br>CCCGACTTCGACGTTGTGGCACGCGCATGTGTGCAGATCAAGAACGCCATCGACGCCACC<br>ATCGCTCTAGGCGGTACAAACTATGTATTCTGGGGCGGCCGCGAGGGCTACATGAGCCTG<br>CTGAACACCGACCAGAAGCGCGAGAAAGAGCACTTGGCTACCATGCTGACCATGGCACGC<br>GACTATGCCCGCGCCAATGGCTTCACCGGAACGTTCCTGATCGAGCCCAAACCCATGGAG<br>CCCAGCAAGCATCAGTATGATGTGGATACCGAGACCGTAATCGGCTTCCTGAAGGCCCAC<br>AACCTGGACAAGGACTTCAAGGTGAACATCGAGGTGAACCATGCCACTCTGGCCGGCCAC<br>ACATTCGAGCATGAGCTGGCAGTAGCCGTGGACAACGGCATGCTGGGCAGCATCGACGCC<br>AACCGCGGCGACTATCAGAACGGCTGGGACACCGACCAGTTCCCCATCGACAACTATGAG<br>CTGACCCAGGCCATGATGCAGATAATCCGCAACGGTGGCCTCGGCAACGGCGGTACCAAC<br>TTCGACGCCAAGACACGTCGCAACTCCACCGACCTGGACGACATCTTCATCGCTCACATC<br>GCCGGTATGGACGCTATGGCCCGCGCTCCGCTCAGCGCAGCCGACGTGCTTGAGAAGTCG<br>CCTTACAAGAAGATGCTGGCCGACCGCTACGCTTCATTCGACAGCGGCGAGGGCAAGAAG<br>TTCGAGGAAGGCAAGATGACTCTGGAGGATGTCGTGGCCTACGCCAAGAAGAATCCCGAA<br>CCCGCTCAGACCAGCGGCAAGCAGGAACTCTACGAGGCCATCATCAACATGTACGCCTGA |
| 5606MI2_003 | *Bacteroides* | Amino Acid | 20 | MATKEYFPHIGKIQFKGTESYDPMSYRYYDAERVVLGKPMKEWLKFAMAWWHTLCAEGGD<br>QFGGGTKKFPWNEGEDANTIAKQKADAGFEIMQKLGIEYFCFHDIDLIGDLGDDIEDYEN<br>RMHEITAHLKEKMAATGIKNLWGTANVFGHARYMNGAATNPDFDVVARACVQIKNAIDAT<br>IALGGTNYVFWGGREGYMSLLNTDQKREKEHLATMLTMARDYARANGFTGTFLIEPKPME<br>PSKHQYDVDTETVIGFLKAHNLDKDFKVNIEVNHATLAGHTFEHELAVAVDNGMLGSIDA<br>NRGDYQNGWDTDQFPIDNYELTQAMMQIIRNGGLGNGGTNFDAKTRRNSTDLDDIFIAHI<br>AGMDAMARAPLSAADVLEKSPYKKMLADRYASFDSGEGKKFEEGKMTLEDVVAYAKKNPE<br>PAQTSGKQELYEAIINMYA |
| 5610MI3_003 | *Bacteroides* | DNA | 21 | ATGGCAACAAAAGAATTTTTTCCCGAGATTGGTAAAATCAAGTTTGAGGGCCGCGAAAGC<br>CGCAATCCCCTCGCATTCCGCTACTACGGCCCCGAGAAAGTCGTTCTTGGCAAGAAGATG<br>AAAGACTGGTTCAAGTTTGCGATGGCTTGGTGGCACACACTGTGCGCCCAGGGCACCGAC<br>CAGTTTGGTGGCGACACCAAGCAGTTTCCGTGGAACACTGCCAGTGACCCCATGCAGGCC<br>GCCAAGGATAAGGTGGATGCCGGATTTGAATTCATGACCAAGATGGGCATTGAGTACTTC<br>TGCTTCCACGATGTGGATCTCGTCGCCGAGGCCGCCACTGTCGAGGAGTATGAGGCTAAC<br>CTCAAGACCATCGTCGCCTACATCAAAGAGAAACAAGCCGAGACCGGCATCAAGAACCTG<br>TGGGGCACAGCCAACGTATTCGGACACAAACGCTACATGAACGGTGCCGCCACCAACCCC<br>GACTTTGATGTCGTGGCACGCGCCATCGTGCAAATCAAGAACGCCATCGACGCCACCATC<br>GAGTTGGGCGGCACGAGTTACGTCTTTTGGGGCGGCCGCGAGGGCCACATGAGCCTGCTC<br>AACACCGACCAGAAGCGCGAGAAGGAGCACCTTGCACGCATGCTGACCATGGCACGCGAC<br>TATGCCCGCGCACGTGGTTTCAACGGCACCTTCCTCATCGAGCCCAAGCCCATGGAGCCG<br>ACCAAGCACCAATATGATGTGGACACCGAGACCGTCATCGGTTTCCTGCGTGCCCATGGT<br>CTGGACAAGGACTTCAAGGTCAACATCGAGGTGAACCACGCTACACTGGCCGGACACACC<br>TTCGAGCGCGAACTGGCAGTGGCCGTCGACAACGGTCTACTCGGCTCAATCGACGCCAAC<br>CGTGGTGACTATCAGAATGGTTGGGACACCGATCAGTTCCCCATCGACCACTATGAGTTG<br>GTTCAGGGCATGTTGCAGATTATCCGCAATGGTGGTTTCACCGACGGTGGCACCAACTTC<br>GATGCCAAGACCCGCCGCAACTCGACCGACCTCGAGGACATCTTCATCGCCCACATCGCC<br>GCGATGGATGCCATGGCTCATGCGCTGGAGAGTGCTGCCTCCATCATCGAGGAGTCGCCC<br>TACTGCCAGATGGTCAAGGATCGCTATGCCTCATTTGACTCCGGCATCGGCAAGGACTTT<br>GAGGACGGCAAGTTGACACTGGAACAAGCCTACGAGTACGGTAAGCAAGTGGGCGAACCC<br>AAGCAGACCAGTGGCAAGCAAGAACTGTACGAGTCAATCATCAATATGTATTCCATTTAA |

TABLE 2-continued

| Clone No. | Class of organism | Type of Sequence | SEQ ID NO: | Sequence |
|---|---|---|---|---|
| 5610MI3_003 | *Bacteroides* | Amino Acid | 22 | MATKEFFPEIGKIKFEGRESRNPLAFRYYGPEKVVLGKKMKDWFKFAMAWWHTLCAQGTD<br>QFGGDTKQFPWNTASDPMQAAKDKVDAGFEFMTKMGIEYFCFHDVDLVAEAATVEEYEAN<br>LKTIVAYIKEKQAETGIKNLWGTANVFGHKRYMNGAATNPDFDVVARAIVQIKNAIDATI<br>ELGGTSYVFWGGREGHMSLLNTDQKREKEHLARMLTMARDYARARGFNGTFLIEPKPMEP<br>TKHQYDVDTETVIGFLRAHGLDKDFKVNIEVNHATLAGHTFERELAVAVDNGLLGSIDAN<br>RGDYQNGWDTDQFPIDHYELVQGMLQIIRNGGFTDGGTNFDAKTRRNSTDLEDIFIAHIA<br>AMDAMAHALESAASIIEESPYCQMVKDRYASFDSGIGKDFEDGKLTLEQAYEYGKQVGEP<br>KQTSGKQELYESIINMYSI |
| 5749MI2_004 | *Bacteroides* | DNA | 23 | ATGGCAACAAAAGAGTATTTTCCTGGTATAGGAAAGATTAAATTTGAAGGTAAAGAGAGT<br>AAGAATCCGATGGCATTCCGCTATTATGATGCCAATAAAGTAATCATGGGCAAGAAGATG<br>AGCGAGTGGCTGAAGTTTGCCATGGCTTGGTGGCACACATTGTGCGCCGAAGGTGGTGAC<br>CAGTTTGGTGGTGGAACAAAGACTTTCCCGTGGAACGATTCGGACAACGCCGTAGAAGCA<br>GCCAACCATAAAGTAGATGCCGGTTTTGAATTTATGCAGAAAATGGGCATCGAATACTAT<br>TGCTTCCATGATGTAGACCTCTGCACTGAAGCTGCTACCATTGAAGAATATGAAGCCAAT<br>CTGAAGGAAATAGTAGCCTATCCGAAACAGAAACAGGCTGAAACAGGTATCAAACTTCTG<br>TGGGGTACGGCAAATGTATTTGGTCACAAACGCTATATGAATGGTGCTGCTACCAATCCG<br>GATTTTGATGTAGTGGCTCGTGCTGCTGTACAGATTAAGAATGCGATAGACGCTACAATT<br>GAACTCGGTGGTAGCAACTACGTGTTCTGGGGCGGCCGTGAAGGTTATATGAGCTTGCTC<br>AATACAGACCAGAAACGTGAGAAAGAGCATTTGGCACAAATGTTGACCATGGCTCGTGAC<br>TATGCTCGTGCCAAAGGATTCAAGGGTACCTTCCTGGTTGAACCCAAACCGATGGAACCA<br>ACTAAACACCAGTATGATGTAGATACGGAAACTGTAATCGGCTTCCTCAAGGCTCATAAT<br>TTGGATAAGGATTTCAAGGTAAATATTGAAGTAAACCATGCTACATTGGCCGGTCATACT<br>TTTGAACACGAATTGGCTGTTGCCGTAGACAACGATATGCTTGGCTCTATCGATGCCAAC<br>CGCGGTGACTATCAGAACGGTTGGGATACTGACCAGTTCCCCATTGACAACTTCGAGCTT<br>ATCCAAGCCATGATGCAGATTATTCGCGGTGGTGGCTTCAAAGATGGTGGTACAAACTTC<br>GACGCTAAGACTCGTCGTAACTCTACCGACCTGGAAGATATTTTCATTGCACACATCGCT<br>GGTATGGATGCTATGGCACGTGCTTTGGAAAGTGCAGCCAAGTTGCTTGAGGAATCTCCT<br>TATAAGAAAATGTTGGCTGACCGCTATGCATCGTTCGATAGTGGCAAAGGTAAGGAGTTT<br>GAAGAAGGCAAGCTGACATTGGAAGACGTTGTAGTTTATGCCAAGCAGAATGGCGAGCCT<br>AAACAGACCAGCGGTAAGCAGGAATTGTATGAGGCAATTGTAAATATGTATGCCTGA |
| 5749MI2_004 | *Bacteroides* | Amino Acid | 24 | MATKEYFPGIGKIKFEGKESKNPMAFRYYDANKVIMGKKMSEWLKFAMAWWHTLCAEGGD<br>QFGGGTKTFPWNDSDNAVEAANHKVDAGFEFMQKMGIEYYCFHDVDLCTEAATIEEYEAN<br>LKEIVAYPKQKQAETGIKLLWGTANVFGHKRYMNGAATNPDFDVVARAAVQIKNAIDATI<br>ELGGSNYVFWGGREGYMSLLNTDQKREKEHLAQMLTMARDYARAKGFKGTFLVEPKPMEP<br>TKHQYDVDTETVIGFLKAHNLDKDFKVNIEVNHATLAGHTFEHELAVAVDNDMLGSIDAN<br>RGDYQNGWDTDQFPIDNFELIQAMMQIIRGGGFKDGGTNFDAKTRRNSTDLEDIFIAHIA<br>GMDAMARALESAAKLLEESPYKKMLADRYASFDSGKGKEFEEGKLTLEDVVVYAKQNGEP<br>KQTSGKQELYEAIVNMYA |
| 5750MI3_003 | *Bacteroides* | DNA | 25 | ATGGCAACAAAAGAGTATTTTCCTGGAATAGGAAAGATTAAATTTGAAGGAAAAGAGAGT<br>AAGAACCCGATGGCATTCCGTTGCTACGATGCAGAAAAAGTTATCATGGGTAAGAGAATG<br>AAAGATTGGTTGAAGTTTGCAATGGCGTGGTGGCATACACTTTGTGCAGAAGGCGGTGAC<br>CAATTCGGTGGCGGTACAAAGAGTTTCCCCCGGAACGACTATACTGATAAAATTCAGGCT<br>GCTAAAAACAAGATGGATGCCGGTTTTGAGTTTATGCAGAAGATGGGGATCGAATACTAT<br>TGTTTTCACGATGTAGACCTCTGCACGGAAGCTGATACCATTGAAGAATACGAAGCTAAT<br>TTGAAAGAAATCGTAGTTTACGCAAAGCAAAAGCAGGTAGAAACAGGTATCAAATTATTG<br>TGGGGTACTGCCAATGTATTCGGTCATGAACGCTATATGAATGGTGCGGCTACCAACCCA<br>GATTTTGATGTTGTAGCCCGTGCTGCTGTTCAGATTAAGAATGCAATTGATGCTACCATT<br>GAACTAGGTGGCTTAAACTATGTGTTCTGGGGTGGACGCGAAGGTTATATGTCTTTGCTG<br>AACACTGATCAGAAACGTGAGAAAGAACATCTTGCACAAATGCTGACCATTGCCCGTGAC<br>TATGCCCGTGCCCGTGGCTTCAAAGGTACATTCTTGGTTGAACCGAAACCGATGGAACCA<br>ACCAAACATCAATATGACGTAGATACAGAAACAGTTATCGGTTTTTTGAAAGCTCATGCT<br>TTGGATAAAGACTTTAAAGTAAATATTGAAGTAAATCATGCAACATTAGCCGGTCATACA<br>TTTGAACACGAACTGGCAGTGGCTGTCGACAACGGTATGCTGGGTTCTATTGACGCTAAT<br>CGTGGTGATTGTCAAAACGGTTGGGATACAGACCAATTTCCCATTGATAACTATGAACTG<br>ACTCAAGCCATGATGCAGATTATTCGTAACGGTGGTTTGGGCAATGGTGGTACGAATTTT<br>GACGCTAAAACTCGCCGTAATTCTACTGATCTTGGAGATATCTTCATTGCTCACATCGCA<br>GGTATGGATGCTATGGCACGTGCATTGGAAAGTGCGGCCAAGTTGTTGGAAGAATCTCCC<br>TATAAGAAGATGCTGGCAGAACGTTATGCATCCTTTGACAGCGGTAAGGGTAAAGAGTTT<br>GAAGAGGGTAAGTTGACCTTGGAGGATCTTGTTGCTTATGCAAAAGTCAATGGCGAACCG<br>AAACAAATCAGTGGTAAACAAGAATTGTATGAGGCAATTGTGAATATGTATTGCTAA |
| 5750MI3_003 | *Bacteroides* | Amino Acid | 26 | MATKEYFPGIGKIKFEGKESKNPMAFRCYDAEKVIMGKRMKDWLKFAMAWWHTLCAEGGD<br>QFGGGTKSFPRNDYTDKIQAAKNKMDAGFEFMQKMGIEYYCFHDVDLCTEADTIEEYEAN<br>LKEIVVYAKQKQVETGIKLLWGTANVEGHERYMNGAATNPDFDVVARAAVQIKNAIDATI<br>ELGGLNYVFWGGREGYMSLLNTDQKREKEHLAQMLTIARDYARARGFKGTFLVEPKPMEP<br>TKHQYDVDTETVIGFLKAHALDKDFKVNIEVNHATLAGHTFEHELAVAVDNGMLGSIDAN<br>RGDCQNGWDTDQFPIDNYELTQAMMQIIRNGGLGNGGTNFDAKTRRNSTDLGDIFIAHIA<br>GMDAMARALESAAKLLEESPYKKMLAERYASFDSGKGKEFEEGKLTLEDLVAYAKVNGEP<br>KQISGKQELYEAIVNMYC |
| 5750MI4_003 | *Bacteroides* | DNA | 27 | ATGGCAACAAAAGAGTATTTTCCCGGAATAGGAAAGATTAAATTCGAAGGTAAAGAGAGC<br>AAGAACCCGATGGCATTCCGTTATTACGATGCCGATAAAGTAATCATGGGTAAGAAAATG<br>AGCGAATGGCTGAAGTTCGCCATGGCATGGTGGCACACTCTTTGCGCAGAAGGTGGTGAC |

TABLE 2-continued

| Clone No. | Class of organism | Type of Sequence | SEQ ID NO: | Sequence |
|---|---|---|---|---|
| | | | | CAGTTCGGTGGCGGAACAAAGAAATTCCCCTGGAACGGTGAGGCTGACAAGGTTCAGGCT<br>GCCAAGAACAAAATGGACGCCGGCTTTGAATTCATGCAGAAAATGGGTATCGAATACTAC<br>TGCTTCCACGATGTAGACCTCTGCGAAGAAGCCGAGACCATTGAAGAATACGAAGCCAAC<br>TTGAAGGAAATCGTAGCGTATGCCAAGCAGAAACAAGCAGAAACCGGCATCAAGCTGTTG<br>TGGGGTACTGCCAACGTATTCGGCCATGCCCGCTACATGAATGGTGCAGCCACCAACCCC<br>GATTTCGATGTTGTGGCACGTGCAGCCGTCCAAATCAAAAGCGCCATCGACGCTACTATC<br>GAGCTGGGAGGTTCGAACTATGTGTTCTGGGGCGGTCGCGAAGGCTACATGTCATTGCTG<br>AATACAGACCAGAAGCGTGAGAAAGAGCACCTCGCACAGATGTTGACCATCGCCCGCGAC<br>TATGCCCGTGCCCGTGGCTTCAAAGGTACCTTCCTGATTGAACCGAAACCGATGGAACCT<br>ACAAAACACCAGTATGATGTAGACACCGAAACCGTTATCGGCTTCTTGAAGGCCCACAAT<br>CTGGACAAAGATTTCAAGGTAAACATCGAAGTGAACCACGCTACTTTGGCGGGCCACACC<br>TTCGAGCACGAACTCGCAGTAGCCGTAGACAACGGTATGCTCGGCTCCATCGATGCCAAC<br>CGTGGTGACTACCAGAACGGCTGGGATACAGACCAGTTCCCCATTGACAACTTCGAACTG<br>ACCCAGGCAATGATGCAAATCATCCGTAACGGCGGCTTTGGCAATGGCGGTACAAACTTC<br>GATGCCAAGACCCGTCGTAACTCCACCGACCTGGAAGACATCTTGATTGCCCACATCGCC<br>GGTATGGACGTGATGGCACGTGCACTGGAAAGTGCAGCCAAATTGCTTGAAGAGTCTCCT<br>TACAAGAAGATGCTTGCCGACCGCTATGCTTCCTTCGACAGTGGTAAAGGCAAGGAATTC<br>GAAGACGGCAAGCTGACACTGGAGGATTTGGCAGCTTACGCAAAAGCCAACGGTGAGCCG<br>AAACAGACCAGCGGCAAGCAGGGATTGTATGAGGCAATCGTAAATATGTACTGCTGA |
| 5750MI4_003 | *Bacteroides* | Amino Acid | 28 | MATKEYFPGIGKIKFEGKESKNPMAFRYYDADKVIMGKKMSEWLKFAMAWWHTLCAEGGD<br>QFGGGTKKFPWNGEADKVQAAKNKMDAGFEFMQKMGIEYYCFHDVDLCEEAETIEEYEAN<br>LKEIVAYAKQKQAETGIKLLWGTANVFGHARYMNGAATNPDFDVVARAAVQIKSAIDATI<br>ELGGSNYVFWGGREGYMSLLNTDQKREKEHLAQMLTIARDYARARGFKGTFLIEPKPMEP<br>TKHQYDVDTETVIGFLKAHNLDKDFKVNIEVNHATLAGHTFEHELAVAVDNGMLGSIDAN<br>RGDYQNGWDTDQFPIDNFELTQAMMQIIRNGGFGNGGTNFDAKTRRNSTDLEDIFIAHIA<br>GMDVMARALESAAKLLEESPYKKMLADRYASFDSGKGKEFEDGKLTLEDLAAYAKANGEP<br>KQTSGKQGLYEAIVNMYC |
| 5751MI4_002 | *Bacteroides* | DNA | 29 | ATGACAAAAGAGTATTTTCCAACCATTGGTAAAATTCAGTTTGAAGGTAAAGAGAGTAAG<br>AATCCATTAGCATATCGTTATTACGATGCTAACAAAGTAATAATGGGTAAAAAGATGAGC<br>GAATGGCTCAAGTTTGCAATGGCATGGTGGCACACTTTGTGTGCTGAGGGTAGCGACCAG<br>TTTGGTCCTGGCACCAAGTCATTCCCATGGAACGCATCAACCGACCGTATGCAGGCTGCA<br>AAAGATAAGGCTGACGCAGGCTTCGAAATCATGCAAAAACTGGGCATCGAATACTACTGT<br>TTCCATGATGTTGACCTCATCGACCCAGCAGACGATATTCCAACATACGAAAAGAATCTC<br>AAGGAAATCGTTGCATACCTCAAGCAAAAACAGGCCGAGACAGGTATCAAATTGCTATGG<br>GGTACAGCTAACGTATTTGGCCACAAGCGTTATATGAACGGTGCATCTACCAATCCTGAC<br>TTTGACGTTGTTGCACGAGCTATCGTGCAAATCAAGAATGCTATCGATGCAACAATCGAA<br>CTGGGCGGCACGAACTACGTATTCTGGGGTGGTCGCGAAGGTTACATGTCACTGCTCAAC<br>ACCGACCAAAAGCGCGAGAAAGAGCACATGGCTACCATGTTAGGAATGGCACGTGACTAT<br>GCACGTTCTAAAGGCTTTACTGGTACTCTCCTTATCGAGCCAAAGCCTATGGAACCAACT<br>AAGCATCAATACGACGTCGATACAGAAACTGTTATTGGTTTCCTCAAAGCTCACGGATTA<br>GACAAGGACTTCAAGGTAAATATCGAAGTGAACCACGCTACATTGGCTGGCCATACCTTC<br>GAACATGAATTAGCATGTGCTGTTGATGCAGGTATGCTTGGTTCCATCGATGCTAACCGT<br>GGTGATATGCAGAATGGCTGGGATACAGATCAGTTCCCTATCAACAATTACGAGCTCGTT<br>CAGGCCATGATGCAGATTATCCGCAATGGTGGTTTCGGTAACGGTGGTACAAACTTCGAC<br>GCTAAGACACGTCGTAATTCAACCGATTTGGAAGACATCATCATTGCTCACGTTTCAGCT<br>ATGGATGCTATGGCACGTGCTCTTGAATGTGCTGCAGACATTCTTCAAAACTCACCTATT<br>CCACAGATGGTGGCCAACCGTTATGCAAGTTTTGACAAGGGTATAGGTAAAGATTTCGAA<br>GACGGCAAGCTCACCCTCGAGCAAGTATACGAATATGGTAAGACCGTCGGCGAACCAGCT<br>ATTACAAGCGGCAAACAGGAGCTCTACGAAGCTATCGTTAATATGTATTGCTGA |
| 5751MI4_002 | *Bacteroides* | Amino Acid | 30 | MTKEYFPTIGKIQFEGKESKNPLAYRYYDANKVIMGKKMSEWLKFAMAWWHTLCAEGSDQ<br>FGPGTKSFPWNASTDRMQAAKDKADAGFEIMQKLGIEYYCFHDVDLIDPADDIPTYEKNL<br>KEIVAYLKQKQAETGIKLLWGTANVFGHKRYMNGASTNPDFDVVARAIVQIKNAIDATIE<br>LGGTNYVFWGGREGYMSLLNTDQKREKEHMATMLGMARDYARSKGFTGTLLIEPKPMEPT<br>KHQYDVDTETVIGFLKAHGLDKDFKVNIEVNHATLAGHTFEHELACAVDAGMLGSIDANR<br>GDMQNGWDTDQFPINNYELVQAMMQIIRNGGFGNGGTNFDAKTRRNSTDLEDIIIAHVSA<br>MDAMARALECAADILQNSPIPQMVANRYASFDKGIGKDFEDGKLTLEQVYEYGKTVGEPA<br>ITSGKQELYEAIVNMYC |
| 5751MI5_003 | *Bacteroides* | DNA | 31 | ATGGCTAACAAAGAATTTTTCCCCGGTATTGGTAAAATCAAATTCGAAGGTAAAGAGAGC<br>AAGAACCCCATGGCATATCGTTACTACGATGCTGAGAAGGTAGTCCTTGGCAAGAATATG<br>AAAGACTGGTTCAAGTTTGCGATGGCTTGGTGGCACACATTGTGCGCCGAGGGTAGCGAC<br>CAGTTTGGTCCCGGCACTAAGTCTTTCCCCTGGAACACCGCAGAGTGCCCCATGCAGGCA<br>GCTAAGGACAAGGTTGACGCTGGCTTCGAGTTCATGACCAAGATGGGTATTGAATACTTC<br>TGCTTCCACGATGTAGACCTCGTTGCCGAGGCCGACACTGTTGAGGAGTACGAGGCTCGC<br>ATGAAGGAAATCGTTGCTTACATCAAGGAGAAGGTGGCCGAGACTGGCATCAAGAACCTG<br>TGGGGTACAGCTAACGTATTTGGCAACAAGCGCTACATGAACGGTGCTGCTACTAACCCC<br>GACTTTGACGTTGTGGCTCGCGCTATCGTTCAAATCAAGAACGCTATCGACGCTACTATC<br>GAGCTCGGTGGTACGTCATACGTATTCTGGGGCGGCCGCGAGGGTTACATGAGCCTCTTG<br>AACACCGACCAGAAGCGTGAGAAAGAGCACCTGGCTACTATGCTCACTATGGCACGCGAC<br>TACGCTCGCGCTAAGGGTTTCAAGGGTACATTCCTCATCGAGCCCAAGCCCATGGAGCCC<br>ACAAAGCACCAGTACGATGTTGACACTGAGACTGTAATCGGCTTCCTTAAGGCACACAAC<br>CTTGACAAGGACTTCAAGGTTAACATTGAGGTTAACCACGCAACTCTCGCTGGTCACACA<br>TTTGAGCACGAGCTCGCTTGTGCTGTTGACGCTGGCATGCTTGGCAGCATCGACGCTAAC |

TABLE 2-continued

| Clone No. | Class of organism | Type of Sequence | SEQ ID NO: | Sequence |
|---|---|---|---|---|
| | | | | CGCGGTGACTACCAGAACGGCTGGGATACTGACCAATTCCCCATCGACAACTTCGACCTC<br>ACTCAAGCTATGCTCGAGATCATCCGCAACGATGGTTTCAAGGATGGTGGTACAAACTTC<br>GACGCTAAGACTCGCCGCAACAGCACCGACCTCGAGGATATCTTCATCGCACACATCGCT<br>GCTATGGACGCTATGGCACGTGCTCTCGAGAGCGCTGCTGCAGTACTCGAGGAGTCAGCT<br>CTGCCCCAAATGAAGAAGGACCGCTATGCATCGTTCGACGCTGGCATGGGTAAGGACTTC<br>GAGGACGGCAAGCTCACCCTGGAGCAAGTTTACGAGTATGGTAAGAAGGTGGGCGAGCCC<br>AAGCAGACTAGCGGCAAGCAAGAGCTGTATGAGGCTATCCTCAACATGTACGTATAA |
| 5751MI5_003 | *Bacteroides* | Amino Acid | 32 | MANKEFFPGIGKIKFEGKESKNPMAYRYYDAEKVVLGKNMKDWFKFAMAWWHTLCAEGSD<br>QFGPGTKSFPWNTAECPMQAAKDKVDAGFEFMTKMGIEYFCFHDVDLVAEADTVEEYEAR<br>MKEIVAYIKEKVAETGIKNLWGTANVFGNKRYMNGAATNPDFDVVARAIVQIKNAIDATI<br>ELGGTSYVFWGGREGYMSLLNTDQKREKEHLATMLTMARDYARAKGFKGTFLIEPKPMEP<br>TKHQYDVDTETVIGFLKAHNLDKDFKVNIEVNHATLAGHTFEHELACAVDAGMLGSIDAN<br>RGDYQNGWDTDQFPIDNFDLTQAMLEIIRNDGFKDGGTNFDAKTRRNSTDLEDIFIAHIA<br>AMDAMARALESAAAVLEESALPQMKKDRYASFDAGMGKDFEDGKLTLEQVYEYGKKVGEP<br>KQTSGKQELYEAILNMYV |
| 5751MI6_004 | *Bacteroides* | DNA | 33 | ATGGCTAACAAAGAATTTTTCCCAGGTATTGGTAAAATCAAATTCGAAGGCAAAGAAAGC<br>AAGAACCCCATGGCATATCGTCACTACGATGCCGAGAAGGTAGTCCTTGGTAAGAAGATG<br>AAGGACTGGTTCAAGTTTGCGATGGCTTGGTGGCACACTCTGTGCGCCGAGGGTAGCGAC<br>CAGTTCGGCCCCGTGACCAAGTCTTTCCCCTGGAACCAGGCCGAGTGCCCCATGCAGGCT<br>GCTAAGGACAAGGTTGACGCCGGCTTCGAGTTCATGACCAAGATGGGTATCGAATACTTC<br>TGTTTCCACGATGTAGACCTCGTTGCCGAGGCCGACACCGTTGAGGAGTACGAAGCTCGC<br>ATGAAGGAAATCGTGGCTTACATCAAGGAGAAGATGGCCGAGACCGGCATCAAGAACCTG<br>TGGGGTACAGCCAACGTATTCGGCAACAAGCGCTACATGAACGGTGCTGCCACCAACCCC<br>GACTTTGACGTTGTGGCTCGCGCAATCGTTCAGATCAAGAACGCCATCGACGCTACTATC<br>GAGCTCGGCGGTACCTCTTACGTGTTCTGGGGCGGCCGCGAGGGTTACATGACTCTCTTG<br>AACACCGACCAGAAGCGCGAGAAGGAGCACCTGGCTACCATGCTCACCATGGCTCGCGAC<br>TATGCTCGCGCTAAGGGCTTCAAGGGTACATTCCTTATCGAGCCCAAGCCCATGGAGCCC<br>ACCAAGCACCAGTATGACGTGGATACCGAGACCGTTATCGGCTTCCTCAAGGCTCACGGC<br>CTGGACAAGGACTTCAAGGTGAACATCGAGGTTAACCATGCAACTCTCGCCGGCCACACA<br>TTCGAGCACGAACTCGCTTGCGCTGTTGACGCTGGCATGCTGGGCAGCATCGACGCTAAC<br>CGCGGCGACTACCAGAACGGCTGGGATACCGACCAGTTCCCCATCGACAACTTCGACCTC<br>ACTCAGGCTATGCTCGAGATCATCCGCAACGGTGGTTTCAAGGACGGTGGTACAAACTTC<br>GACGCTAAGACCCGTCGCAACAGCACCGATCTTGAGGACATCTTCATCGCTCACATCGCT<br>GCTATGGACGCAATGGCACGCGCGCTCGAGAGCGCTGCCGCTGTGCTCGAGCAGAGCCCC<br>CTTCCCCAGATGAAGAAAGACCGCTACGCATCGTTCGATGCCGGCATGGGCAAGGACTTC<br>GAGGACGGCAAGCTCACTCTGGAGCAGGTTTACGAGTATGGTAAGAAGGTAGGCGAGCCC<br>AAGCAGACCAGCGGCAAGCAGGAACTGTACGAGGCTATCCTCAACATGTATGTATAA |
| 5751MI6_004 | *Bacteroides* | Amino Acid | 34 | MANKEFFPGIGKIKFEGKESKNPMAYRHYDAEKVVLGKKMKDWFKFAMAWWHTLCAEGSD<br>QFGPVTKSFPWNQAECPMQAAKDKVDAGFEFMTKMGIEYFCFHDVDLVAEADTVEEYEAR<br>MKEIVAYIKEKMAETGIKNLWGTANVFGNKRYMNGAATNPDFDVVARAIVQIKNAIDATI<br>ELGGTSYVFWGGREGYMTLLNTDQKREKEHLATMLTMARDYARAKGFKGTFLIEPKPMEP<br>TKHQYDVDTETVIGFLKAHGLDKDFKVNIEVNHATLAGHTFEHELACAVDAGMLGSIDAN<br>RGDYQNGWDTDQFPIDNFDLTQAMLEIIRNGGFKDGGTNFDAKTRRNSTDLEDIFIAHIA<br>AMDAMARALESAAAVLEQSPLPQMKKDRYASFDAGMGKDFEDGKLTLEQVYEYGKKVGEP<br>KQTSGKQELYEAILNMYV |
| 5586MI22_003 | *Clostridiales* | DNA | 35 | ATGAAAGAATATTTTCCTATGACAAAAAAAGTTGAATATGAGGGCGCAGCATCTAAAAAT<br>CCATTTGCGTTTAAATACTATGATGCCGAAAGAATTATAGCAGGCAAGCCTATGAAAGAA<br>CATCTTAAATTTGCTATGAGTTGGTGGCATACACTTTGTGCGGGCGGTGCAGACCCATTT<br>GGCACAACAACTATGGACAGAACATACGGCGGACTTACCGACCCAATGGAAATTGCAAAG<br>GCAAAAGTAGATGCAGGCTTTGAGTTTATGCAAAAACTCGGTATAGAGTATTTTTGTTTT<br>CACGATGCGGATATTGCACCGGAAGGAAGCAGTTTTGTTGAAACAAAGAAAAACTTTTGG<br>GAAATAGTAGATTATATACAGCAAAAGATGAATGAAACAGGCATAAAGTTGCTTTGGGGT<br>ACTGCAAACTGCTTTAATGCTCCACGTTATATGCACGGTGCAGGAACATCATGCAATGCG<br>CACAGTTTTGCATATGCAGCCGCACAGATAAAAAATGCAATTGAAGCTACCGTTAAACTG<br>GGTGGAAAAGGCTATGTTTTCTGGGGCGGAAGAGAGGGTTATGAAACACTTCTCAATACG<br>GATATGGCACTTGAACTTGACAATATGGCAAGACTTATGCATATGGCAGTTGATTATGGC<br>AGAAGCATTGGTTTTGACGGTGATTTTTATATCGAACCAAAGCCAAAGGAACCAACAAAA<br>CATCAATATGACTTTGACTCGGCAACTGTTTTGGGATTTTTGAGAAAGTACGGTTTAGAT<br>AAGGATTTTAAACTTAATATAGAGGCAAATCATGCGACACTTGCAGGTCATACATTTGAA<br>CATGAATTGACTGTAGCGCGTATAAACGGTGCATTTGGCAGCATAGATGCAAATAGCGGC<br>GATCCCAATCTTGGCTGGGATACCGACCAATTCCCAACAGATGTTTATTCGGCAACCCTT<br>TGTATGCTTGAAGTGATAAGAGCAGGCGGCTTTACAAACGGAGGTCTTAATTTTGATGCA<br>AAGGTCAGAAGAGGCTCATTTACGTTTGATGACATTGTTTATGCATATATCAGCGGTATG<br>GACACTTTTGCGCTGGGTTTTATAAAGGCATATGAAATAATTGAGGACGGCAGAATAGAT<br>GAATTTGTAAAAGAAAGATACGCAAGCTATAATACAGGCATAGGCAAAGATATTATAGAT<br>GGAAAGGCAAGCCTTGAAAGTTTGGAAGAATATATTCTTTCAAATGATAATGTTGTAATG<br>CAAAGCGGCAGACAGGAATATCTTGAAACAGTTTTGAATAATATTTTGTTTAAAGCATAA |
| 5586MI22_003 | *Clostridiales* | Amino Acid | 36 | MKEYFPMTKKVEYEGAASKNPFAFKYYDAERIIAGKPMKEHLKFAMSWWHTLCAGGADPF<br>GTTTMDRTYGGLTDPMEIAKAKVDAGFEFMQKLGIEYFCFHDADIAPEGSSFVETKKNFW<br>EIVDYIQQKMNETGIKLLWGTANCFNAPRYMHGAGTSCNAHSFAYAAAQIKNAIEATVKL<br>GGKGYVFWGGREGYETLLNTDMALELDNMARLMHMAVDYGRSIGEDGDFYIEPKPKEPTK |

TABLE 2-continued

| Clone No. | Class of organism | Type of Sequence | SEQ ID NO: | Sequence |
|---|---|---|---|---|
| | | | | HQYDFDSATVLGELRKYGLDKDFKLNIEANHATLAGHTFEHELTVARINGAFGSIDANSG<br>DPNLGWDTDQFPTDVYSATLCMLEVIRAGGFTNGGLNFDAKVRRGSFTFDDIVYAYISGM<br>DTFALGFIKAYEIIEDGRIDEFVKERYASYNTGIGKDIIDGKASLESLEEYILSNDNVVM<br>QSGRQEYLETVLNNILFKA |
| 1753MI4_001 | *Firmicutes* | DNA | 37 | ATGAAAGAAATTTTCCCAAATATTCCTGAGATTAAATTCGAAGGAAAAGACAGCAAAAAT<br>CCTTTTGCTTTCCATTACTACAACCCAGACCAAATCATCTTAGGCAAACCAATGAAAGAA<br>CACCTCCCATTCGCTATGGCTTGGTGGCACAATCTTGGTGCAACAGGTGTTGATATGTTT<br>GGCGCTGGCCCAGCTGATAAGAGTTTCGGTGCTAAAGTTGGCACAATGGAACACGCTAAG<br>GCCAAAGTCGATGCCGGTTTCGAATTCATGAAGAAACTCGGTATCAGATATTTCTGCTTC<br>CATGATGTTGACTTAGTTCCAGAATGTGCAGATATCAAAGATACAAACAAAGAATTAGAT<br>GAAATCAGTGACTACATCTTAGAAAAGATGAAAGGCACAGATATTAAGTGTTTATGGGGC<br>ACCGCCAATATGTTCTCTAACCCACGCTTCTGCAATGGTGCGGGTTCCACAAACAGTGCG<br>GATGTCTTCGCTTTCGCCGCTGCTCAAGTTAAGAAAGCCTTAGATATCACCGTTAAATTA<br>GGTGGTAGGGGTTACGTCTTCTGGGGTGGTCGTGAAGGTTACGAAACATTACTCAATACA<br>GACGTTAAATTCGAACAAGAAAACATTGCTCGTTTAATGAAGATGGCTGTTGAATATGGC<br>CGTTCCATCGGTTTCAAAGGCGATTTCTATATCGAACCAAAACCAAAAGAACCAATGAAA<br>CACCAATATGACTTCGACGCCGCTACAGCTATTGGCTTCTTAAGAGCCCACGGCTTAGAC<br>AAAGACTTCAAGTTGAACATCGAAGCTAACCACGCTACATTAGCGGGTCATACATTCCAA<br>CACGATTTAAGAATCTCCGCCATTAATGGTATGTTAGGTTCTATCGATGCTAACCAAGGC<br>GATATGCTCTTAGGTTGGGATACAGACGAATTCCCATTTGATGTCTACAGTGCGACACAA<br>TGTATGTACGAAGTCTTAAAGAATGGTGGTCTTACAGGTGGTTTCAACTTTGACTCCAAA<br>ACACGTCGTCCATCCTACACAATGGAAGATATGTTCTTAGCCTATATCTTAGGTATGGAT<br>ACATTCGCTTTAGGTTTAATCAAAGCTGCTCAAATCATCGAAGATGGCCGTATTGATCAA<br>TTCATCGAAAAGAAATATTCTTCCTTCCGTGAAACAGAAATCGGTCAAAAGATCTTAAAC<br>AACAAGACAAGCTTAAAAGAATTATCCGATTACGCTTGCAAGATGGGTGCTCCAGAACTT<br>CCAGGTAGTGGTCGTCAAGAAATGCTCGAAGCCATCGTTAACGATGTCTTATTCGGCAAG<br>TAA |
| 1753MI4_001 | *Firmicutes* | Amino Acid | 38 | MKEIFPNIPEIKFEGKDSKNPFAFHYYNPDQIILGKPMKEHLPFAMAWWHNLGATGVDMF<br>GAGPADKSFGAKVGTMEHAKAKVDAGFEFMKKLGIRYFCFHDVDLVPECADIKDTNKELD<br>ETSDYILEKMKGTDIKCLWGTANMESNPRECNGAGSTNSADVFAFAAAQVKKALDITVKL<br>GGRGYVFWGGREGYETLLNTDVKFEQENIARLMKMAVEYGRSIGFKGDFYIEPKPKEPMK<br>HQYDFDAATAIGFLRAHGLDKDFKLNIEANHATLAGHTFQHDLRISAINGMLGSIDANQG<br>DMLLGWDTDEFPFDVYSATQCMYEVLKNGGLTGGFNFDSKTRRPSYTMEDMFLAYILGMD<br>TFALGLIKAAQIIEDGRIDQFIEKKYSSFRETEIGQKILNNKTSLKELSDYACKMGAPEL<br>PGSGRQEMLEAIVNDVLFGK |
| 1753MI6_001 | *Firmicutes* | DNA | 39 | ATGAAAGAAATTTTCCCAAATATTCCTGAGATTAAATTCGAAGGAAAAGACAGCAAAAAT<br>CCTTTTGCTTTCCATTACTACAACCCAGACCAAATCATCTTAGGTAAACCAATGAAAGAA<br>CACCTCCCATTCGCTATGGCTTGGTGGCACAATCTTGGTGCAACAGGTGTTGATATGTTT<br>GGCGCTGGCCCAGCTGATAAGAGTTTCGGTGCTAAAGTTGGCACAATGGAACACGCTAAG<br>GCCAAAGTCGATGCCGGTTTCGAATTCATGAAGAAACTTGGTATCAGATATTTCTGCTTC<br>CATGATGTTGACTTAGTTCCAGAATGTGCAGATATCAAAGATACAAACAAAGAATTAGAT<br>GAAATCAGTGACTACATCTTAGAAAAGATGAAAGGCACAGATATCAAGTGTTTATGGGGC<br>ACCGCCAATATGTTCTCTAACCCACGTTTCTGCAATGGTGCGGGTTCCACAAACAGTGCG<br>GATGTCTTCGCTTTCGCCGCTGCTCAAGTTAAGAAAGCCTTAGATATCACCGTTAAATTA<br>GGTGGTAGGGGTTACGTCTTCTGGGGTGGTCGTGAAGGTTACGAAACATTACTCAATACA<br>GACGTTAAATTCGAACAAGAAAACATTGCTCGTTTAATGAAGATGGCTGTTGAATATGGC<br>CGTTCCATCGGTTTCAAAGGCGATTTCTATATCGAACCAAAACCAAAAGAACCAATGAAA<br>CACCAATATGACTTCGACGCCGCTACAGCTATTGGCTTCTTAAGAGCCCACGGCTTAGAC<br>AAAGACTTCAAGTTGAACATCGAAGCTAACCACGCTACATTAGCGGGTCATACATTCCAA<br>CACGATTTAAGAATCTCCGCCATTAATGGTATGTTAGGTTCTATCGATGCTAACCAAGGC<br>GATATGCTCTTAGGTTGGGATACAGACGAATTCCCATTTGATGTCTACAGTGCGACACAA<br>TGTATGTACGAAGTCTTAAAGAATGGTGGTCTTACAGGTGGTTTCAACTTTGACTCCAAA<br>ACACGTCGTCCATCCTACACAATGGAAGATATGTTCTTAGCCTATATCTTAGGTATGGAT<br>ACATTCGCTTTAGGTTTAATCAAAGCTGCTCAAATCATCGAAGATGGCCGTATTGATCAA<br>TTCATCGAAAAGAAATATTCTTCCTTCCGTGAAACAGAAATCGGTCAAAAGATCTTAAAC<br>AACAAGACAAGCTTAAAAGAATTATCCGATTACGCTTGCAAGATGGGTGCTCCAGAACTT<br>CCAGGTAGTGGTCGTCAAGAAATGCTCGAAGCCATCGTTAACGATGTCTTATTCGGCAAG<br>TAA |
| 1753MI6_001 | *Firmicutes* | Amino Acid | 40 | MKEIFPNIPEIKFEGKDSKNPFAFHYYNPDQIILGKPMKEHLPFAMAWWHNLGATGVDMF<br>GAGPADKSFGAKVGTMEHAKAKVDAGFEFMKKLGIRYFCFHDVDLVPECADIKDTNKELD<br>EISDYILEKMKGTDIKCLWGTANMFSNPRFCNGAGSTNSADVFAFAAAQVKKALDITVKL<br>GGRGYVFWGGREGYETLLNTDVKFEQENIARLMKMAVEYGRSIGFKGDFYIEPKPKEPMK<br>HQYDFDAATAIGFLRAHGLDKDFKLNIEANHATLAGHTFQHDLRISAINGMLGSIDANQG<br>DMLLGWDTDEFPFDVYSATQCMYEVLKNGGLTGGFNFDSKTRRPSYTMEDMFLAYILGMD<br>TFALGLIKAAQIIEDGRIDQFIEKKYSSFRETEIGQKILNNKTSLKELSDYACKMGAPEL<br>PGSGRQEMLEAIVNDVLFGK |
| 1753MI35_004 | *Firmicutes* | DNA | 41 | ATGGAATATTTCCCTTTCGTCAAATCGGTCCAATACAAGGGACCAACCTCAACTGAACCA<br>TTCGCTTTCAAGTACTACGATGCCAACCGTGTCGTTCTTGGAAAACCAATGAAAGAATGG<br>ATGCCATTCGCTATGGCTTGGTGGCACAACCTCGGCGCTGCCGGTACCGACATGTTCGGC<br>GGCAACACCATGGACAAGTCCTGGGGAGTCGATAAAGAAAAAGACCCAATGGGCTATGCC<br>AAAGCCAAAGTTGATGCCGGCTTCGAATTCATGCAGAAGATGGGCATCGAATACTACTGC |

TABLE 2-continued

| Clone No. | Class of organism | Type of Sequence | SEQ ID NO: | Sequence |
|---|---|---|---|---|
| | | | | TTCCACGATGTCGACCTCGTCCCAGAGTGCGACGACATCACCGTTATGTACCAGAGACTC<br>GATGAGATCGGTGATTACCTTCTCAAGAAACAGAAGGAAACCGGTATCAAGCTTCTTTGG<br>TCAACCGCCAATGCCTTCGGACACCGCCGTTTCATGAACGGTGCTGGTTCCAGCAACTCC<br>GCCGAAGTCTATTGCTTCGCCGCCGCCCAGATCAAGAAAGCTCTTGAGCTCTGCGTCAAA<br>CTCGGTGGCAAAGGCTATGTCTTCTGGGGTGGACGTGAAGGCTACGAAACCCTTCTCAAC<br>ACCGACATGAAGTTCGAACAAGAGAACATCGCCAACCTTATGAGATGCGCCCGTGACTAC<br>GGCCGCAAGATCGGTTTCAAAGGCGACTTCTACATCGAACCAAAACCAAAAGAGCCAACA<br>AAGCATCAGTATGACTTCGACGCCGCTACCGCCATCGGATTCCTCCGTCAGTACGGTCTC<br>GACAAAGACTTCAAGATGAACATCGAAGCCAACCACGCTACCTTAGCTGGCCACACCTTC<br>GAACACGAACTCCGCGTCTCCGCCATGAACGGCATGCTCGGTTCCATCGACGCCAACGAA<br>GGCGATATGCTCCTCGGATGGGATGTCGACCGTTTCCCAGCCAACGTCTATAGCGCCACC<br>TTCGCCATGCTCGAAGTCATCAAAGCCGGTGGACTTACCGGTGGCTTCAACTTCGACGCC<br>AAGACCCGCCGCGCTTCCAACACCTATGAAGATATGTTCAAGGCTTTCGTCCTTGGTATG<br>GATACCTTCGCTTTAGGTCTTCTCAATGCCGAAGCCATCATCAAAGACGGCCGCATCGAC<br>AAGTTCGTCGAGGATAGATATGCCAGCTTCAAGACCGGCATCGGTGCTAAGGTCCGCGAT<br>CACTCCGCTACCCTTGAGGATTTAGCTGCCCACGCCCTTGAGACCAAGGTTTGCCCAGAT<br>CCAGGCAGCGGCGACGAGGAAGAACTCCAGGAAATCCTCAACCAGTTAATGTTCGGTAAG<br>AAATAA |
| 1753MI35_004 | *Firmicutes* | Amino Acid | 42 | MEYFPEVESVQYKGPTSTEPFAFKYYDANRVVLGKPMKEWMPFAMAWWHNLGAAGTDMFG<br>GNTMDKSWGVDKEKDPMGYAKAKVDAGFEFMQKMGIEYYCFHDVDLVPECDDITVMYQRL<br>DEIGDYLLKKQKETGIKLLWSTANAFGHRRFMNGAGSSNSAEVYCFAAAQIKKALELCVK<br>LGGKGYVFWGGREGYETLLNTDMKFEQENIANLMRCARDYGRKIGFKGDFYIEPKPKEPT<br>KHQYDFDAATAIGFLRQYGLDKDFKMNIEANHATLAGHTFEHELRVSAMNGMLGSIDANE<br>GDMLLGWDVDRFPANVYSATFAMLEVIKAGGLTGGFNFDAKTRRASNTYEDMFKAFVLGM<br>DTFALGLLNAEAIIKDGRIDKFVEDRYASFKTGIGAKVRDHSATLEDLAAHALETKVCPD<br>PGSGDEEELQEILNQLMFGKK |
| 1754MI9_004 | *Firmicutes* | DNA | 43 | ATGAGCGAATTTTTTAAGAATATTCCAGAGATTAAATTCGAAGGAAAAGATAGTAAAAAT<br>CCATGGGCATTCAAGTATTACAATCCTGAATTGACCATTATGGGTAAAAAAATGTCTGAA<br>CATCTTCCTTTTGCAATGGCCTGGTGGCATAACCTTGGCGCAAATGGAGTTGATATGTTC<br>GGTTCGGGAACCGCCGATAAATCTTTCGGTCAGGCTCCGGGAACTATGGAGCACGCAAAG<br>GCTAAGGTAGATGCAGGTATCGAGTTTATGAAGAAACTCGGAATCAAGTACTACTGCTGG<br>CATGATGTAGACCTTGTTCCTGAAGATCCAAACGATATCAACGTAACAAACAAGCGCCTT<br>GATGAGATTTCAGATTATATCCTTGAAAAAACAAAGGGAACTGACATCAAGTGTCTCTGG<br>GGAACTGCTAACATGTTCAGTAATCCCCGCTTTATGAACGGGGCAGGCTCAACAAACTCT<br>GCTGACGTTTACTGCTTTGCAGCTGCCCAGGTTAAAAAGGCTCTTGAGATTACCGTAAAG<br>CTTGGTGGCCGCGGTTATGTATTCTGGGGTGGACGCGAAGGTTATGAAACTCTTCTTAAT<br>ACAGATGTAAAGCTTGAACAGGAAAATATTGCAAACCTTATGCACATGGCAGTTGATTAT<br>GGCCGTTCAATCGGTTTCAAGGGAGACTTCTACATCGAGCCTAAGCCAAAGGAGCCGATG<br>AGTCATCAGTATGATTTTGATGCCGCAACTGCAATCGGCTTCCTCCGCCAGTATGGCCTC<br>GACAAAGACTTTAAGATGAACATTGAGGCTAACCACGCTTCTCTTGCAAATCATACCTTC<br>CAGCATGAGCTTTATATCAGCCGCATTAACGGAATGCTTGGTTCTGTAGATGCTAACCAG<br>GGAAATCCAATTCTCGGCTGGGATACAGATAACTTCCCTTGGAATGTCTACGACGCAACT<br>CTTGCAATGTACGAAGTACTCAAGGCTGGTGGACTTACAGGTGGCTTCAACTTTGACTCA<br>AAGAACCGCCGCCCATCAAATACATTTGAAGATATGTTCCACGCTTACATCATGGGAATG<br>GACACTTTTGCTCTTGGTCTTATTAAGGCTGCAGAAATTATTGAAGACGGAAGAATCGAT<br>GGCTTCATTAAAGAAAAGTATTCAAGCTACGAAAGTGGAATTGGTAAGAAGATCCGCGAC<br>AAGCAGACAACTTTGGAAGAGCTTGCTGCCCGTGCCGCAGAAATGAAAAAGCCATCTGAT<br>CCAGGTTCAGGCCGCGAGGAATATCTGGAAGGAGTTGTTAACAATATCCTCTTTCGCGGA<br>TAA |
| 1754MI9_004 | *Firmicutes* | Amino Acid | 44 | MSEFFKNIPEIKFEGKDSKNPWAFKYYNPELTIMGKKMSEHLPFAMAWWHNLGANGVDMF<br>GSGTADKSFGQAPGTMEHAKAKVDAGIEFMKKLGIKYYCWHDVDLVPEDPNDINVTNKRL<br>DEISDYILEKTKGTDIKCLWGTANMFSNPRFMNGAGSTNSADVYCFAAAQVKKALEITVK<br>LGGRGYVFWGGREGYETLLNTDVKLEQENIANLMHMAVDYGRSIGFKGDFYIEPKPKEPM<br>SHQYDFDAATAIGFLRQYGLDKDFKMNIEANHASLANHTFQHELYISRINGMLGSVDANQ<br>GNPILGWDTDNFPWNVYDATLAMYEVLKAGGLTGGFNFDSKNRRPSNTFEDMFHAYIMGM<br>DTFALGLIKAAEIIEDGRIDGFIKEKYSSYESGIGKKIRDKQTTLEELAARAAEMKKPSD<br>PGSGREEYLEGVVNNILFRG |
| 1754MI22_004 | *Firmicutes* | DNA | 45 | ATGAGCGAGTTTTTTAAGAATATTCCTCAAATAAAATACGAAGGAAAAGATAGCAAAAAT<br>CCCTGGGCATTCAAGTATTACAATCCTGAATTGACAATCATGGGTAAAAAGATGAGCGAA<br>CATCTTCCATTCGCAATGGCATGGTGGCATAACCTTGGCGCAAACGGCGTTGATATGTTT<br>GGTCAGGGAACAGCAGACAAGTCTTTCGGACAGATTCCTGGAACTATGGAGCATGCAAAG<br>GCTAAGGTTGATGCTGGTATAGAGTTTATGAAGAAGCTCGGAATCAAATATTACTGCTGG<br>CACGATGTTGACCTTGTTCCTGAGGATCCAAACGATATCAACGTAACTAACAAACGTCTG<br>GACGAAATTTCAGATTACATCCTTGAAAAGACAAAAGGAACAGACATTAAGTGTCTCTGG<br>GGAACTGCAAACATGTTCGGTAACCCTCGCTTTATGAACGGTGCAGGCTCTACAAACTCT<br>GCTGACGTTTACTGTTTTGCTGCCGCTCAGGTAAAAAAGGCTCTTGAGATTACTGTAAAG<br>CTTGGTGGCCGAGGTTATGTTTTCTGGGGTGGCCGCGAAGGTTACGAAACTCTTCTCAAT<br>ACAGACGTAAAACTTGAACAGGAAAATATCGCAAACCTCATGCATATGGCTGTTGATTAT<br>GGCCGCTCAATCGGTTTCAAGGGAGACTTCTACATCGAGCCTAAGCCAAAGGAGCCAATG<br>AGCCATCAGTATGATTTTGATGCTGCAACAGCAATCGGCTTCCTCCGCCAGTATGGCCTC<br>GACAAAGATTTTAAGATGAACATCGAAGCTAACCATGCCTCACTTGCAAATCACACCTTC<br>CAGCACGAGCTTTGTATCAGCCGCATAAACGGAATGCTTGGTTCTGTAGATGCAAATCAG |

TABLE 2-continued

| Clone No. | Class of organism | Type of Sequence | SEQ ID NO: | Sequence |
|---|---|---|---|---|
| | | | | GGAAATCCAATTCTTGGCTGGGATACAGATAACTTCCCATGGAATGTTTACGATGCAACT<br>CTGGCAATGTACGAAGTTCTCAAGGCTGGCGGTCTAACAGGTGGCTTCAACTTTGACTCA<br>AAGAACCGTCGCCCATCAAATACTTTTGAAGATATGTTCCACGCTTATATCATGGGTATG<br>GATACTTTTGCCCTTGGCCTTATTAAGGCTGCAGAAATTATTGAAGACGGCAGAATTGAC<br>GGCTTCATCAAAGAAAAGTATTCAAGCTTTGAAAGTGGAATTGGTAAGAAGATTCGTGAC<br>AAGCAGACAAGTTTGGAAGAGCTTGCAGCTCGTGCCGCTGAAATGAAAAAGCCATCTGAT<br>CCAGGTTCAGGCCGCGAGGAATACCTCGAAGGAGTTGTTAACAACATCCTCTTTCGCGGA<br>TAA |
| 1754MI22_004 | *Firmicutes* | Amino Acid | 46 | MSEFFKNIPQIKYEGKDSKNPWAFKYYNPELTIMGKKMSEHLPFAMAWWHNLGANGVDMF<br>GQGTADKSFGQIPGTMEHAKAKVDAGIEFMKKLGIKYYCWHDVDLVPEDPNDINVTNKRL<br>DEISDYILEKTKGTDIKCLWGTANMEGNPRFMNGAGSTNSADVYCFAAAQVKKALEITVK<br>LGGRGYVFWGGREGYETLLNTDVKLEQENIANLMHMAVDYGRSIGFKGDFYIEPKPKEPM<br>SHQYDFDAATAIGFLRQYGLDKDFKMNIEANHASLANHTFQHELCISRINGMLGSVDANQ<br>GNPILGWDTDNFPWNVYDATLAMYEVLKAGGLTGGENFDSKNRRPSNTFEDMFHAYIMGM<br>DTFALGLIKAAEIIEDGRIDGFIKEKYSSFESGIGKKIRDKQTSLEELAARAAEMKKPSD<br>PGSGREEYLEGVVNNILFRG |
| 727MI1_002 | *Firmicutes* | DNA | 47 | ATGATATTTGAAAATATTCCCGCAATTCCTTATGAGGGTCCGAAGAGCACAAATCCGCTG<br>GCGTTTAAATTCTATGATCCGGACAAGATCGTTATGGGAAAGCCCATGAAGGAGCATCTG<br>CCCTTTGCAATGGCCTGGTGGCACAACCTTGGCGCGGCCGGAACCGATATGTTCGGGCGC<br>GATACCGCCGACAAATCCTTCGGTGCGGTAAAAGGCACAATGGAGCATGCCAAAGCGAAA<br>GTCGATGCCGGCTTTGAGTTCATGCAGAAGCTGGGGATCCGCTATTTCTGCTTCCATGAT<br>GTGGATCTTGTTCCGGAGGCGGATGATATAAAGGAGACCAACCGCCGTCTGGACGAGATC<br>AGCGATTACATCCTTGAAAAGATGAAGGGCACCGATATCAAGTGCCTTTGGGGCACGGCC<br>AATATGTTCTCAAATCCGCGCTTTATGAACGGCGCAGGCTCCTCCAATTCTGCCGATGTA<br>TTCGCTTTTGCGGCAGCACAGGCCAAGAAGGCCTTGGATCTGACCGTCAAACTCGGCGGG<br>CGCGGCTATGTCTTCTGGGGCGGACGTGAGGGCTATGAGACACTTCTCAATACCGACATG<br>AAGTTCGAGCAGGAGAATATCGCGAAGCTCATGCATATGGCTGTCGATTACGGCCGCAGC<br>ATAGGCTTTACCGGTGATTTCTATATCGAGCCCAAACCGAAAGAGCCGATGAAACACCAG<br>TATGATTTCGATGCAGCCACTGCGATAGGCTTCCTCCGCCAGTACGGACTCGATAAGGAC<br>TTCAAGCTCAACATCGAGGCAAACCACGCCACACTGGCAGGTCACACTTTCCAGCACGAT<br>CTGCGTGTTTCCGCAATAAACGGAATGCTGGGCAGCATTGACGCCAACCAGGGCGATATG<br>CTCCTCGGCTGGGATACCGACGAGTTCCCGTTCAATGTATATGATGCGACCATGTGCATG<br>TATGAGGTGCTCAAGTCAGACGGGCTCACCGGCGGCTTTAACTTCGACTCCAAATCACGC<br>CGCCCGAGCTATACGGTCGAGGATATGTTTACAAGCTATATCCTCGGCATGGACACTTTT<br>GCCCTCGGCCTTCTGAAAGCGGCCGAGCTTATCGAAGACGGAAGGCTTGACGCCTTCGTC<br>AAAGAACGCTATTCAAGCTATGAGAGCGGCATCGGCGCAAAGATCCGCAGCGGAGAAACC<br>GATTTGAAGGAATTGGCGGAATATGCGGACTCCCTCGGAGCCCCCGAACTTCCGGGCAGC<br>GGAAAACAGGAACAGCTCGAGAGCATAGTAAATCAGATACTTTTCGGATAA |
| 727MI1_002 | *Firmicutes* | Amino Acid | 48 | MIFENIPAIPYEGPKSTNPLAFKFYDPDKIVMGKPMKEHLPFAMAWWHNLGAAGTDMFGR<br>DTADKSFGAVKGTMEHAKAKVDAGFEFMQKLGIRYFCFHDVDLVPEADDIKETNRRLDEI<br>SDYILEKMKGTDIKCLWGTANMFSNPRFMNGAGSSNSADVFAFAAAQAKKALDLTVKLGG<br>RGYVFWGGREGYETLLNTDMKFEQENIAKLMHMAVDYGRSIGFTGDFYIEPKPKEPMKHQ<br>YDFDAATAIGFLRQYGLDKDFKLNIEANHATLAGHTFQHDLRVSAINGMLGSIDANQGDM<br>LLGWDTDEFPFNVYDATMCMYEVLKSDGLTGGFNFDSKSRRPSYTVEDMFTSYILGMDTF<br>ALGLLKAAELIEDGRLDAFVKERYSSYESGIGAKIRSGETDLKELAEYADSLGAPELPGS<br>GKQEQLESIVNQILFG |
| 727MI9_005 | *Firmicutes* | DNA | 49 | ATGAGCGAGTTTTTTGCCAGCATTCCCAAAATTCCCTTTGAAGGCAAGGACAGCGCCAAT<br>CCCCTGGCGTTCAAATACTACGACGCCGACAGGATGATACTGGGCAAGCCCATGAAGGAG<br>CACCTTCCCTTCGCCATGGCCTGGTGGCACAACCTGTGCGCCGCGGGCACCGATATGTTT<br>GGCCGGGACACCGCCGACAAGTCCTTCGGCCAGGTCAAGGGCACCATGGAACACGCCAAG<br>GCCAAGGTGGACGCGGGCTTTGAGTTCATGAAGAAGCTGGGCATCCGCTACTTCTGCTTC<br>CACGACGTGGACATCGTGCCCGAAGCCGACGACATCAAGGAAACCAACCGCCGTCTGGAC<br>GAGATCTCCGACTATATCCTGGAGAAAATGAAAGGCACCGACATCCAGTGCCTGTGGGGC<br>ACCGCCAACATGTTCGGCAACCCCCGCTATATGAACGGCGCGGGCAGCTCCAACTCCGCC<br>GACGTATACTGCTTCGCCGCGGCCCAGATCAAAAAGGCCCTGGACATCACCGTGAAGCTG<br>GGCGGCAAGGGCTACGTGTTCTGGGGCGGCCGCGAGGGCTACGAGACCCTGCTGAACACC<br>GATATGAAGTTCGAGCAGGAGAACATCGCCCGCCTGATGCACATGGCCGTGGACTACGGC<br>CGCAGCATCGGCTTCACCGGCGATTTCTACATCGAGCCCAAGCCCAAGGAGCCCATGAAG<br>CACCAGTACGACTTCGACGCCGCCACCGCCATAGGCTTTTTGCGCCAGTACGGCCTGGAC<br>AAGGATTTCAAGCTGAACATCGAGTCCAACCACGCCACCCTGGCGGGCCATACCTTCCAG<br>CACGACCTGCGCGTTTCCGCCATCAACGGCATGCTGGGCTCCATCGACGCCAACCAGGGC<br>GACTACCTGCTGGGCTGGGATACCGACGAGTTCCCCTACAGCGTATACGAGACCACCATG<br>TGCATGTACGAGGTGCTCAAGGCCGGAGGTCTCACCGGCGGCTTCAATTTCGACGCCAAG<br>AACCGCCGTCCCAGCTACACCCCCGAGGATATGTTCCACGCCTACATCCTTGGGATGGAC<br>AGCTTCGCCCTGGGCCTGATCAAGGCCGCCGAGCTCATCGAGGACGGTCGCCTGGACGCC<br>TTCGTCCGGGACCGCTACCAGAGCTGGGAGACCGGCATCGGCGATAAGATCCGCAAGGGC<br>GAGACCACACTGGCCGAGCTGGCCGAGTACGCCGCCCGGATGGGCGCGCCCGCGCTGCCC<br>GGCAGCGGCCGCCAGGAATACCTGGAGGGCGTGGTCAACAATATCCTGTTCAAATAA |
| 727MI9_005 | *Firmicutes* | Amino Acid | 50 | MSEFFASIPKIPFEGKDSANPLAFKYYDADRMILGKPMKEHLPFAMAWWHNLCAAGTDMF<br>GRDTADKSFGQVKGTMEHAKAKVDAGFEFMKKLGIRYFCFHDVDIVPEADDIKETNRRLD<br>EISDYILEKMKGTDIQCLWGTANMFGNPRYMNGAGSSNSADVYCFAAAQIKKALDITVKL |

TABLE 2-continued

| Clone No. | Class of organism | Type of Sequence | SEQ ID NO: | Sequence |
|---|---|---|---|---|
| | | | | GGKGYVFWGGREGYETLLNTDMKFEQENIARLMHMAVDYGRSIGFTGDFYIEPKPKEPMK<br>HQYDFDAATAIGFLRQYGLDKDFKLNIESNHATLAGHTFQHDLRVSAINGMLGSIDANQG<br>DYLLGWDTDEFPYSVYETTMCMYEVLKAGGLTGGFNFDAKNRRPSYTPEDMFHAYILGMD<br>SFALGLIKAAELIEDGRLDAFVRDRYQSWETGIGDKIRKGETTLAELAEYAARMGAPALP<br>GSGRQEYLEGVVNNILFK |
| 727MI27_002 | *Firmicutes* | DNA | 51 | ATGAAGACCTATTTCAAAAAAATCCCCGTGATCCCCTACGAGGGACCGAAGTCCCAGAAT<br>CCGCTGTCGTTCAAATTCTATGACGCGGACCGCATCGTTCTCGGCAAGCCCATGAAGGAG<br>CATCTGCCCTTCGCCATGGCCTGGTGGCACAATCTGGGTGCTGCCGGAACGGACATGTTC<br>GGCCGCGATACCGCCGACAAGTCCTTCGGAGCGGAGAAGGGCACCATGGAGCATGCCAAG<br>GCCAAGGTGGACGCTGGCTTCGAGTTTATGAAGAAGGTGGGCATCCGGTATTTCTGCTTC<br>CATGACGTGGATCTGGTCCCGGAAGCGGACGACATCAAGGAGACCAACCGCCGTCTCGAT<br>GAGATCAGCGACTACATCCTCAAGAAGATGAAGGGCACGGATATCAAGTGCCTCTGGGGC<br>ACCGCCAACATGTTCGGCAATCCCCGGTTCATGAACGGCGCGGGCAGCTCCAACAGCGCG<br>GACGTGTTCTGCTTTGCCGCGGCCCAGGTGAAGAAGGCCTTGGACATCACCGTCAAGCTG<br>GGCGGCCGGGGCTATGTGTTCTGGGGCGGCCGTGAGGGGTATGAGTCCCTGCTGAACACG<br>GACGTGAAGTTTGAGCAGGAGAACATCGCCAAGCTCATGCACCTTGCCGTGGACTACGGC<br>CGCAGCATCGGCTTCACCGGCGATTTCTACATCGAGCCCAAGCCCAAGGAGCCCATGAAG<br>CACCAGTACGACTTCGATGCCGCCACCGCCATCGGCTTCCTCAGGCAGTACGGCCTCGAT<br>AAGGACTTCAAGATGAACATTGAAGCCAACCACGCGACCCTGGCCGGCCACACCTTCCAG<br>CACGACCTCAGGATCAGCGCCATCAACGGGATGCTGGGCTCCATCGACGCCAACCAGGGC<br>GACCTCCTGCTGGGATGGGACACCGACGAATTCCCCTTCAACGTCTATGAGGCCACCATG<br>TGCATGTACGAGGTCCTCAAGGCCGGCGGCCTCACCGGCGGCTTCAACTTCGACTCAAAG<br>AACCGCCGTCCCTCCTACACCATGGAGGATATGTTCCACGCCTACATCCTGGGCATGGAC<br>ACCTTCGCCCTGGGTCTTCTCAAGGCCGCGGAGCTCATCGAGGACGGTCGGATCGACAAA<br>TTCGTGGAGGAGCGCTACGCCAGCTACAAGACCGGCATCGGCGCCAAGATCCGTTCCGGC<br>GAGACCACGCTTCAGGAGCTGGCCGCCTATGCCGACAAGTTGGGCGCGCCTGCCCTTCCC<br>GGCAGCGGCCGTCAGGAGTACCTGGAGAGCATCGTCAACCAGGTGCTCTTCGGGATGTGA |
| 727MI27_002 | *Firmicutes* | Amino Acid | 52 | MKTYFKKIPVIPYEGPKSQNPLSFKFYDADRIVLGKPMKEHLPFAMAWWHNLGAAGTDMF<br>GRDTADKSFGAEKGTMEHAKAKVDAGFEFMKKVGIRYFCFHDVDLVPEADDIKETNRRLD<br>EISDYILKKMKGTDIKCLWGTANMFGNPRFMNGAGSSNSADVFCFAAAQVKKALDITVKL<br>GGRGYVFWGGREGYESLLNTDVKFEQENIAKLMHLAVDYGRSIGFTGDFYIEPKPKEPMK<br>HQYDFDAATAIGFLRQYGLDKDFKMNIEANHATLAGHTFQHDLRISAINGMLGSIDANQG<br>DLLLGWDTDEFPFNVYEATMCMYEVLKAGGLTGGFNFDSKNRRPSYTMEDMFHAYILGMD<br>TFALGLLKAAELIEDGRIDKFVEERYASYKTGIGAKIRSGETTLQELAAYADKLGAPALP<br>GSGRQEYLESIVNQVLFGM |
| 1753MI2_006 | *Neocallimastigales* | DNA | 53 | ATGGCTAAAGAGTATTTTCCAGAGATTGGCAAAATCAAGTTTGAAGGCAAGGACAGCAAA<br>AACCCAATGGCTTTCCACTACTATGACCCCGAGAAGGTGATCATGGGCAAGCCTATGAAA<br>GACTGGCTCCGCTTCGCTATGGCATGGTGGCACACCCTCTGCGCAGAAGGTGGCGACCAG<br>TTCGGTGGCGGCACTAAGAAGTTCCCTTGGAACAACGGCGCTGACGCTGTAGAAATCGCA<br>AAACAGAAGGCTGACGCAGGTTTCGAAATCATGCAGAAGCTCGGCATCCCATATTTCTGC<br>TTCCACGACGTGGACCTCGTGTCTGAGGGCGCATCTGTAGAAGAGTATGAGGCTAACCTC<br>AAGGCTATCACAGACTACCTCGCTGTGAAGATGAAGGAAACAGGCATCAAGCTCCTGTGG<br>TCTACTGCCAACGTATTCGGCAACGGCCGCTACATGAACGGTGCTTCTACCAACCCTGAC<br>TTCGACGTCGTTGCTCGCGCTATCGTGCAGATTAAGAACGCTATCGACGCTGGTATCAAG<br>CTCGGCGCTGAGAACTACGTGTTCTGGGGCGGACGCGAAGGCTACATGAGCCTCCTCAAC<br>ACCGACCAGAAGCGTGAGAAGGAGCACATGGCCACTATGCTCACTATGGCTCGCGACTAC<br>GCTCGCGCTAAGGGCTTCAAGGGCACATTCCTCATCGAGCCTAAGCCAATGGAGCCTTCT<br>AAGCACCAGTATGACGTTGACACTGAGACTGTCATCGGCTTCCTCAAGGCACACAACCTC<br>GACAAGGACTTCAAGGTGAACATCGAGGTGAACCACGCAACTCTCGCTGGCCACACCTTC<br>GAGCACGAGCTCGCAGTGGCAGTGGACAACAACATGCTCGGCTCTATCGACGCTAACCGT<br>GGTGACTACCAGAATGGCTGGGATACTGACCAGTTCCCAATCGACCAGTACGAACTCGTT<br>CAGGCTTGGATGGAAATCATCCGTGGCGGCGGTCTCGGCACTGGCGGCACGAACTTCGAC<br>GCTAAGACTCGTCGTAACTCTACCGACCTCGAAGACATCTTCATCGCACACATCGCAGGC<br>ATGGACGCTATGGCACGCGCACTCGAATCAGCTGCTAAGCTCCTCGAAGAGTCTCCATAC<br>AAGGCAATGAAGGCAGCTCGCTACGCTTCATTCGACAACGGTATCGGTAAGGACTTCGAA<br>GATGGCAAGCTCACTCTCGAGCAGGCTTACGAATACGGTAAGAAGGTTGGTGAGCCTAAG<br>CAGACTTCTGGCAAGCAGGAGCTCTACGAAGCCATCGTTGCAATGTACGCTTAA |
| 1753MI2_006 | *Neocallimastigales* | Amino Acid | 54 | MAKEYFPEIGKIKFEGKDSKNPMAFHYYDPEKVIMGKPMKDWLRFAMAWWHTLCAEGGDQ<br>FGGGTKKFPWNNGADAVEIAKQKADAGFEIMQKLGIPYFCFHDVDLVSEGASVEEYEANL<br>KATTDYLAVKMKETGIKLLWSTANVFGNGRYMNGASTNPDFDVVARAIVQIKNAIDAGIK<br>LGAENYVFWGGREGYMSLLNTDQKREKEHMATMLTMARDYARAKGFKGTFLIEPKPMEPS<br>KHQYDVDTETVIGFLKAHNLDKDFKVNIEVNHATLAGHTFEHELAVAVDNNMLGSIDANR<br>GDYQNGWDTDQFPIDQYELVQAWMEIIRGGGLGTGGTNFDAKTRRNSTDLEDIFIAHIAG<br>MDAMARALESAAKLLEESPYKAMKAARYASFDNGIGKDFEDGKLTLEQAYEYGKKVGEPK<br>QTSGKQELYEAIVAMYA |
| 5586MI3_005 | *Neocallimastigales* | DNA | 55 | ATGGCTAAAGAATTTTTCCCAGAGATTGGTAAAATCAAGTTCGAAGGCAAGGATTCAAAG<br>AATCCAATGGCTTTCCATTACTATGATGCAGAGAAGGTAATCATGGGCAAACCCATGAAG<br>GACTGGCTCCGTTTCGCTATGGCATGGTGGCACACACTCTGTGCAGAGGGCGGCGACCAG<br>TTCGGTGGCGGTACGAAGAAGTTCCCTTGGAACGAGGGTGCTAATGCTGTCGAGATTGCT<br>AAGCAGAAGGCTGACGCTGGTTTCGAAATCATGCAGAAGCTTGGCATTCCTTACTTCTGC<br>TTCCACGATGTTGACCTCGTTTCTGAAGGCGCATCTGTTGAGGAGTATGAGGCCAACCTC |

TABLE 2-continued

| Clone No. | Class of organism | Type of Sequence | SEQ ID NO: | Sequence |
|---|---|---|---|---|
| | | | | AAGGCTATCACTGACTATCTCGCGGTGAAGATGAAGGAGACTGGCATTAAGCTCCTGTGG<br>TCTACTGCCAACGTGTTCGGCAATGGCCGTTACATGAATGGTGCTTCCACCAACCCTGAC<br>TTCGACGTTGTTGCTCGCGCCATCGTTCAGATTAAGAACGCTATCGATGCAGGTATCAAG<br>CTCGGTGCTGAGAACTATGTGTTCTGGGGCGGTCGTGAAGGTTACATGAGCCTCCTGAAC<br>ACAGACCAGAAGCGTGAGAAGGAGCACATGGCTACTATGCTCACTATGGCTCGCGACTAC<br>GCTCGCAGCAAGGGCTTCAAGGGTACTTTCCTCATCGAGCCTAAGCCAATGGAGCCATCT<br>AAGCACCAGTACGACGTTGACACAGAGACTGTTATCGGCTTCCTGAAGGCACACAACCTT<br>GACAAGGACTTCAAGGTGAACATCGAGGTGAACCACGCAACACTCGCTGGTCACACCTTC<br>GAGCACGAGCTCGCTGTGGCTGTCGACAACAATATGCTTGGTTCTATCGATGCTAACCGC<br>GGTGACTACCAGAATGGTTGGGATACGGACCAGTTCCCAATTGACCAGTACGAGCTCGTT<br>CAGGCTTGGATGGAGATCATCCGTGGTGGCGGTCTCGGCACAGGTGGTACAAACTTCGAC<br>GCTAAGACTCGTCGTAACTCTACCGACCTCGAGGACATTTTCATTGCTCACATCGCTGGT<br>ATGGACGCTATGGCTCGCGCTCTTGAGTCAGCAGCTAAGCTCCTTGAGGAGTCTCCATAC<br>AAGAAGATGAAGGCTGCCCGTTATGCTTCTTTCGACAGCGGCATGGGTAAGGACTTTGAG<br>AACGGCAAGCTCACACTCGAACAGGTTTATGAGTATGGTAAGAAGGTAGGTGAGCCCAAG<br>CAGACTTCTGGCAAGCAGGAGCTCTTCGAGGCAATCGTGGCCATGTACGCATAA |
| 5586MI3_005 | *Neocallimastigales* | Amino Acid | 56 | MAKEFFPEIGKIKFEGKDSKNPMAFHYYDAEKVIMGKPMKDWLRFAMAWWHTLCAEGGDQ<br>FGGGTKKFPWNEGANAVEIAKQKADAGFEIMQKLGIPYFCFHDVDLVSEGASVEEYEANL<br>KAITDYLAVKMKETGIKLLWSTANVFGNGRYMNGASTNPDFDVVARAIVQIKNAIDAGIK<br>LGAENYVFWGGREGYMSLLNTDQKREKEHMATMLTMARDYARSKGFKGTFLIEPKPMEPS<br>KHQYDVDTETVIGFLKAHNLDKDFKVNIEVNHATLAGHTFEHELAVAVDNNMLGSIDANR<br>GDYQNGWDTDQFPIDQYELVQAWMEIIRGGGLGTGGTNFDAKTRRNSTDLEDIFIAHIAG<br>MDAMARALESAAKLLEESPYKKMKAARYASFDSGMGKDFENGKLTLEQVYEYGKKVGEPK<br>QTSGKQELFEAIVAMYA |
| 5586MI91_002 | *Neocallimastigales* | DNA | 57 | ATGGCTAAAGAGTATTTTCCAGAGATTGGTAAAATCAAGTTTGAAGGCAAGGATTCCAAG<br>AATCCAATGGCATTCCACTATTATGATGCAGAGAAAGTGATTATGGGTAAGCCTATGAAG<br>GAGTGGCTCCGCTTTGCAATGGCATGGTGGCACACACTCTGTGCAGAGGGTGGCGACCAG<br>TTTGGTGGTGGCACTAAGAAATTCCCATGGAACGAGGGCACTGACGCTGTGACGATTGCT<br>AAGCAGAAGGCTGATGCAGGTTTCGAAATCATGCAGAAACTCGGTTTCCCATATTTTTGC<br>TTCCACGACATTGACCTCGTTTCCGAAGGCAACAGCATTGAAGAGTATGAGGCTAACCTC<br>CAGGCAATCACTGATTATCTGAAAGTGAAGATGGAAGAGACAGGCATCAAACTCTTGTGG<br>TCAACTGCCAACGTATTCGGCAATGGTCGCTACATGAATGGTGCTTCCACAAACCCAGAC<br>TTTGACGTGGTGGCTCGTGCCATCGTTCAGATTAAGAACGCAATTGACGCTGGTATCAAA<br>CTCGGTGCTGAGAACTATGTATTCTGGGGCGGTCGCGAAGGCTACATGAGCCTTCTGAAC<br>ACTGACCAGAAGCGTGAGAAGGAGCACATGGCAACCATGCTCACTATGGCTCGCGACTAC<br>GCTCGCAGCAAGGGTTTCAAGGGCACTTTCCTCATTGAGCCAAAGCCAATGGAGCCATCT<br>AAGCACCAGTATGACGTTGACACGGAGACTGTCATCGGCTTCCTCAAGGCACACAACCTC<br>GACAAGGATTTCAAGGTGAACATCGAAGTGAACCACGCTACACTTGCAGGTCATACTTTC<br>GAGCACGAACTTGCTGTGGCTGTTGACAATGGCATGCTCGGTTCTATCGACGCTAACCGT<br>GGTGACTATCAGAACGGTTGGGACACTGACCAGTTCCCAATCGACCAGTACGAACTCGTT<br>CAGGCTTGGATGGAAATCATCCGTGGTGGTGGTCTCGGCACAGGTGGTACTAACTTCGAT<br>GCTAAGACTCGTCGTAACTCAACTGACCTCGAGGACATCTTCATCGCACACATCTCTGGT<br>ATGGATGCAATGGCACGTGCTCTCGAATCGGCGGCTAAACTTCTTGAGGAGTCTCCATAC<br>TGCGCTATGAAGAAGGCTCGTTACGCTTCCTTCGACAGCGGCATCGGTAAGGACTTCGAG<br>GACGGCAAACTCACGCTCGAGCAGGCTTACGAGTACGGCAAGAAAGTCGGCGAACCCAAG<br>CAGACTTCTGGCAAGCAGGAACTCTACGAGGCAATCGTTGCCATGTACGCATAA |
| 5586MI91_002 | *Neocallimastigales* | Amino Acid | 58 | MAKEYFPEIGKIKFEGKDSKNEMAFHYYDAEKVIMGKPMKEWLRFAMAWWHTLCAEGGDQ<br>FGGGTKKFPWNEGTDAVTIAKQKADAGFEIMQKLGFPYFCFHDIDLVSEGNSIEEYEANL<br>QAITDYLKVKMEETGIKLLWSTANVFGNGRYMNGASTNPDFDVVARAIVQIKNAIDAGIK<br>LGAENYVFWGGREGYMSLLNTDQKREKEHMATMLTMARDYARSKGFKGTFLIEPKPMEPS<br>KHQYDVDTETVIGFLKAHNLDKDFKVNIEVNHATLAGHTFEHELAVAVDNGMLGSIDANR<br>GDYQNGWDTDQFPIDQYELVQAWMEIIRGGGLGTGGTNFDAKTRRNSTDLEDIFIAHISG<br>MDAMARALESAAKLLEESPYCAMKKARYASFDSGIGKDFEDGKLTLEQAYEYGKKVGEPK<br>QTSGKQELYEAIVAMYA |
| 5586MI194_003 | *Neocallimastigales* | DNA | 59 | ATGGCAAAAGAGTATTTCCCTACGATCGGTAAGATCGTTTATGAAGGACCGGAGTCCAAG<br>AACCCTATGGCATTTCATTACTATGACGCAGAGCGCGTAGTAGCTGGTAAAAAAATGAAA<br>GATTGGATGCGTTTCGCTATGGCATGGTGGCACACCCTCTGTGCAGAAGGTGCAGACCAG<br>TTCGGTGGAGGCACCAAACACTTCCCGTGGAGTGAAGGTCCCGATGCCGTAACCATCGCC<br>AAGCAGAAAGCAGACGCAGGTTTTGAGATCATGCAGAAACTCGGCTTCCCGTATTTCTGT<br>TTCCATGACGTGGATCTGGTCAGCGAAGGCAGCAGCGTAGAAGAGTACGAGGCGAACCTC<br>GCAGCCATCACCGATTATCTCAAGCAGAAAATGGACGAGTCGGGTATCAAACTCCTTTGG<br>TCCACTGCTAACGTATTCGGTCACGCCCGTTACATGAACGGTGCCAGCACCAATCCTGAC<br>TTTGATGTCGTTGCCCGTGCGATTGTGCAGATCAAGAATGCTATCGACGCAGGTATCAAA<br>CTCGGCGCAGAGAACTACGTCTTCTGGGGCGGTCGTGAAGGTTATATGAGCCTGCTCAAT<br>ACCGACCAGAAACGCGAGAAAGAGCATACGGCAATGATGCTGCGTATGGCGCGTGACTAT<br>GCCCGCAGCAAAGGTTTCAAAGGTACCTTCCTCATCGAACCCAAACCCATGGAGCCGTCC<br>AAGCACCAGTATGACGTAGATACCGAGACGGTGATAGGTTTCCTCAAAGCACACGGTTTG<br>GAGAAAGACTTTAAGGTAAACATCGAAGTGAACCACGCTACCCTCGCCGGTCACACTTTC<br>GAGCACGAACTGGCAGTAGCCGTAGATAACGGCATGCTCGGTTCGATCGATGCCAACCGC<br>GGTGACTATCAGAACGGATGGGATACCGACCAGTTCCCCATCGATAACTTCGAACTGACC<br>CAAGCATGGATGCAGATCGTACGTAACGGTGGTCTCGGCACAGGCGGAACGAACTTCGAC<br>TCCAAGACCCGTCGTAACTCCACCGATCTCGAGGATATCTTCATCGCTCACATCAGTGGT |

TABLE 2-continued

| Clone No. | Class of organism | Type of Sequence | SEQ ID NO: | Sequence |
|---|---|---|---|---|
| | | | | ATGGACGCTTGTGCCCGTGCCCTATTGAATGCCGTAGAGATCATGGAGAAATCACCGATC<br>CCTGCTATGCTCAAAGAGCGTTACGCTTCCTTCGATAGCGGTCTGGGTAAAGATTTCGAG<br>GACGGCAAACTGACCCTTGAGCAAGTCTATGAGTACGGTAAGAAAGTAGGCGAACCCAAA<br>CAAACCAGCGGCAAACAAGAACTCTATGAGGCTATCGTTGCCCTCTACGCTAAATAA |
| 5586MI194_003 | *Neocallimastigales* | Amino Acid | 60 | MAKEYFPTIGKIVYEGPESKNPMAFHYYDAERVVAGKKMKDWMRFAMAWWHTLCAEGADQ<br>FGGGTKHFPWSEGPDAVTIAKQKADAGFEIMQKLGFPYFCFHDVDLVSEGSSVEEYEANL<br>AAITDYLKQKMDESGIKLLWSTANVFGHARYMNGASTNPDFDVVARAIVQIKNAIDAGIK<br>LGAENYVFWGGREGYMSLLNTDQKREKEHTAMMLRMARDYARSKGFKGTFLIEPKPMEPS<br>KHQYDVDTETVIGFLKAHGLEKDFKVNIEVNHATLAGHTFEHELAVAVDNGMLGSIDANR<br>GDYQNGWDTDQFPIDNFELTQAWMQIVRNGGLGTGGTNFDSKTRRNSTDLEDIFIAHISG<br>MDACARALLNAVEIMEKSPIPAMLKERYASFDSGLGKDFEDGKLTLEQVYEYGKKVGEPK<br>QTSGKQELYEAIVALYAK |
| 5586MI198_003 | *Neocallimastigales* | DNA | 61 | ATGAAAGAGTATTTCCCTGAGATCGGTAAGATCCAATTTGAAGGCCCGGAGTCCAAGAAC<br>CCGATGGCATTTCACTACTATGACGCAGAGCGCGTCGTAGCCGGTAAAACAATGAAAGAG<br>TGGATGCGTTTCGCTATGGCTTGGTGGCACACCCTCTGTGCGGAAGGCGGCGACCAGTTC<br>GGAGGCGGAACGAAGAAGTTCCCCTGGAACGAAGGCGCTAACGCTTTGGAGATCGCCAAG<br>CACAAAGCCGATGCGGGATTTGAGATCATGCAGAAACTCGGCATCCCTTATTTCTGTTTC<br>CATGACGTGGATCTCATCGCCGAGGGCGGTTCGGTAGAAGAGTACGAAGCCAACCTCGCT<br>GCCATCACCGATTACCTCAAACAGAAAATGGACGAGACTGGCATCAAACTGCTGTGGTCC<br>ACGGCGAACGTCTTCAGCAACCCCCGTTATATGAACGGCGCCAGCACGAACCCCGATTTC<br>GATGTAGTAGCGCGTGCCATCGTCCAGATCAAGAACGCTATCGACGCCGGTATCAAACTC<br>GGAGCAGAGAACTATGTCTTCTGGGGTGGTCGCGAGGGCTATATGAGCCTCCTCAACACT<br>GACCAGCGCCGAGAGAAAGAGCATATGGCTACCATGCTCCGTATGGCGCGTGACTACGCG<br>CGTGCCAAAGGATTCAAGGGCACCTTCCTCATCGAACCCAAACCATGTGAGCCGTCCAAA<br>CATCAGTATGATGTCGATACCGAGACCGTCATCGGTTTCCTCAAAGCGCATGGACTCGAC<br>AAGGATTTCAAAGTCAATATCGAGGTCAACCACGCCACCCTCGCAGGCCACACGTTCGAA<br>CACGAACTGGCTTGCGCTGTAGATGCCGGCATGCTCGGTTCGATTGACGCCAACCGCGGT<br>GACGCCCAGAACGGATGGGACACCGACCAGTTCCCTATTGATAACTTCGAACTCACACAG<br>GCTTTCATGCAGATCGTCCGCAACGGCGGTTTCGGAACAGGCGGTACGAACTTCGACGCC<br>AAGACACGCCGTAACTCCACCGACTTGGAGGACATCTTCATCGCCCATATCAGCGGCATG<br>GACGCTTGCGCACGTGCGTTACTCAATGCTGTCGAAATCCTCGAGAAGAGCCCGATTCCG<br>GCGATGCTCAAAGAGCGTTATGCTTCCTTTGACGGCGGCATCGGAAAGGACTTCGAGGAG<br>GGAAAACTGACTTTCGAGCAGGTCTATGAGTACGGCAAGAAAGTCGGCGAACCCAAACAG<br>ACCAGCGGCAAACAGGAGCTCTACGAAACCATCGTCGCCCTCTATGCCAAATAG |
| 5586MI198_003 | *Neocallimastigales* | Amino Acid | 62 | MKEYFPEIGKIQFEGPESKNPMAFHYYDAERVVAGKTMKEWMRFAMAWWHTLCAEGGDQF<br>GGGTKKFPWNEGANALEIAKHKADAGFEIMQKLGIPYFCFHDVDLIAEGGSVEEYEANLA<br>AITDYLKQKMDETGIKLLWSTANVFSNPRYMNGASTNPDFDVVARAIVQIKNAIDAGIKL<br>GAENYVFWGGREGYMSLLNTDQRREKEHMATMLRMARDYARAKGFKGTFLIEPKPCEPSK<br>HQYDVDTETVIGFLKAHGLDKDFKVNIEVNHATLAGHTFEHELACAVDAGMLGSIDANRG<br>DAQNGWDTDQFPIDNFELTQAFMQIVRNGGEGTGGTNEDAKTRRNSTDLEDIFIAHISGM<br>DACARALLNAVEILEKSPIPAMLKERYASFDGGIGKDFEEGKLTFEQVYEYGKKVGEPKQ<br>TSGKQELYETIVALYAK |
| 5586MI201_003 | *Neocallimastigales* | DNA | 63 | ATGGCAAAAGAGTATTTCCCTACGATCGGTAAGATCGTTTATGAAGGACCGGAATCCAAG<br>AACCCTATGGCATTTCATTACTATGACGCAGAGCGCGTAGTAGCTGGTAAAAAAATGAAA<br>GATTGGATGCGTTTCGCTATGGCATGGTGGCACACCCTCTGTGCAGAAGGTGCAGACCAG<br>TTCGGTGGAGGCACCAAACACTTCCCGTGGAATGAAGGTCCCGATGCCGTAACCATCGCC<br>AAGCAGAAAGCAGACGCAGGTTTTGAGATCATGCAGAAACTCGGCTTCCCGTATTTCTGT<br>TTCCATGACGTGGATCTGGTCGGCGAAGGCAGCAGCGTAGAAGAGTACGAGGCGAACCTC<br>GCAGCCATCACCGATTATCTCAAGCAGAAAATGGACGAGTCGGGTATCAAACTCCTTTGG<br>TCCACTGCTAACGTATTCGGTCACGCCCGTTACATGAACGGTGCCAGCACCAATCCTGAC<br>TTTGATGTCGTTGCCCGTGCGATTGTGCAGATCAAGAATGCTATCGACGCAGGTATCAAA<br>CTCGGCGCAGAGAACTACGTCTTCTGGGGCGGTCGTGAAGGTTATATGAGCCTGCTCAAC<br>ACCGACCAGAAACGCGAGAAAGAGCATACGGCAATGATGCTGCGTATGGCGCGTGACTAT<br>GCCCGCAGCAAAGGTTTCAAAGGTACCTTCCTCATCGAACCCAAACCCATGGAGCCGTCC<br>AAGCACCAGTATGACGTAGATACCGAGACGGTGATAGGTTTCCTCAAAGCACACGGTTTG<br>GAGAAAGACTTTAAGGTAAACATCGAAGTGAACCACGCTACCCTCGCCGGTCACACTTTC<br>GAGCACGAACTGGCAGTAGCCGTAGATAACGGCATGCTCGGTTCGATCGATGCCAACCGC<br>GGTGACTATCAGAACGGATGGGATACCGACCAGTTCCCCATCGATAACTTCGAACTGACC<br>CAAGCATGGATGCAGATCGTACGTAACGGTGGTCTCGGCACAGGCGGAACGAACTTCGAC<br>TCCAAGACCCGTCGTAACTCCACCGATCTCGAGGATATCTTCATCGCTCACATCAGTGGT<br>ATGGACGCTTGTGCCCGTGCCCTATTGAATGCCGTAGAGATCATGGAGAAATCACCGATC<br>CCTGCTATGCTCAAAGAGCGTTACGCTTCCTTCGATAGCGGTCTGGGTAAAGATTTCGAG<br>GACGGCAAACTGACCCTTGAGCAAGTCTATGAGTACGGTAAGAAAGTAGGCGAACCCAAA<br>CAAACCAGCGGCAAACAAGAACTCTATGAGGCTATCGTTGCCCTCTACGCTAAATAA |
| 5586MI201_003 | *Neocallimastigales* | Amino Acid | 64 | MAKEYFPTIGKIVYEGPESKNPMAFHYYDAERVVAGKKMKDWMRFAMAWWHTLCAEGADQ<br>FGGGTKHFPWNEGPDAVTIAKQKADAGFEIMQKLGFPYFCFHDVDLVGEGSSVEEYEANL<br>AAITDYLKQKMDESGIKLLWSTANVFGHARYMNGASTNPDFDVVARAIVQIKNAIDAGIK<br>LGAENYVFWGGREGYMSLLNTDQKREKEHTAMMLRMARDYARSKGFKGTFLIEPKPMEPS<br>KHQYDVDTETVIGFLKAHGLEKDFKVNIEVNHATLAGHTFEHELAVAVDNGMLGSIDANR |

TABLE 2-continued

| Clone No. | Class of organism | Type of Sequence | SEQ ID NO: | Sequence |
|---|---|---|---|---|
| | | | | GDYQNGWDTDQFPIDNFELTQAWMQIVRNGGLGTGGTNFDSKTRRNSTDLEDIFIAHISG<br>MDACARALLNAVEIMEKSPIPAMLKERYASFDSGLGKDFEDGKLTLEQVYEYGKKVGEPK<br>QTSGKQELYEAIVALYAK |
| 5586MI204_002 | *Neocallimastigales* | DNA | 65 | ATGAAAGAGTATTTCCCTGAGGTCGGTAAGATCCAATTTGAAGGCCCGGAGTCTAAGAAC<br>CCGATGGCATTTCACTACTATGACGCAGAGCGCGTCGTAGCCGGTAAAACAATGAAAGAG<br>TGGATGCGTTTCGCTATGGCTTGGTGGCACACCCTCTGTGCAGAAGGCGGCGACCAGTTC<br>GGAGGCGGAACGAAGCATTTCCCGTGGAATGAAGGCGCTAACGCTTTGGAGATCGCCAAA<br>CACAAAGCCGATGCGGGATTCGAGATCATGCAGAAACTCGGCATCCCCTATTTCTGTTTC<br>CATGACGTGGATCTCATCGCCGAGGGCGGTTCGGTAGAAGAGTACGAAACCAACCTCGCT<br>GCTATCACCGACTACCTCAAGCAGAAAATGGACGAGACCGGCATCAAACTGCTGTGGTCC<br>ACGGCGAACGTGTTCAGCAACCCCCGTTATATGAACGGCGCGAGCACGAACCCCGATTTC<br>GATGTAGTAGCGCGTGCCATCGTGCAGATCAAGAATGCCATCGACGCCGGCATCAAACTG<br>GGCGCAGAGAACTATGTCTTCTGGGGCGGTCGCGAGGGCTACATGAGCCTGCTCAACACC<br>GACCAGCGCCGCGAGAAAGAGCATATGGCTACTATGCTCCGTATGGCGCGTGACTACGCG<br>CGTGCCAAAGGATTCAAGGGCACCTTTCTCATCGAACCCAAACCGTGTGAGCCGTCCAAA<br>CATCAGTATGATGTCGATACCGAGACCGTCATCGGTTTCCTCAAAGCGCATGGACTCGAC<br>AAGGATTTCAAGGTTAATATCGAGGTCAACCACGCCACCCTCGCAGGCCACACGTTCGAA<br>CACGAACTGGCTTGCGCTGTAGATGCCGGCATGCTCGGTTCGATTGACGCCAACCGCGGT<br>GACGCCCAGAACGGATGGGACACCGACCAGTTCCCTATTGATAACTTCGAACTCACACAG<br>GCTTTCATGCAGATCGTCCGCAACGGCGGTTTCGGAACAGGCGGTACGAACTTCGACGCC<br>AAGACACGCCGTAACTCCACCGACTTGGAGGACATCTTCATCGCCCATATCAGCGGCATG<br>GACGCTTGCGCACGTGCGTTGCTCAACGCCATCGAAATCCTCGAGAAGAGCCCGATCCCG<br>GCTATGCTCAAAGACCGTTATGCCTCCTTTGATGGCGGCATCGGAAAGGACTTTGAGGAG<br>GGCAAACTGACTTTCGAGCAGGTCTATGAGTACGGCAAGAAGGTCGGAGAACCCAAACAG<br>ACCAGCGGCAAACAGGAGCTCTACGAAACCATCGTCGCCCTCTATGCCAAATAG |
| 5586MI204_002 | *Neocallimastigales* | Amino Acid | 66 | MKEYFPEVGKIQFEGPESKNPMAFHYYDAERVVAGKTMKEWMRFAMAWWHTLCAEGGDQF<br>GGGTKHFPWNEGANALEIAKHKADAGFEIMQKLGIPYFCFHDVDLIAEGGSVEEYETNLA<br>AITDYLKQKMDETGIKLLWSTANVFSNPRYMNGASTNPDFDVVARAIVQIKNAIDAGIKL<br>GAENYVFWGGREGYMSLLNTDQRREKEHMATMLRMARDYARAKGFKGTFLIEPKPCEPSK<br>HQYDVDTETVIGFLKAHGLDKDFKVNIEVNHATLAGHTFEHELACAVDAGMLGSIDANRG<br>DAQNGWDTDQFPIDNFELTQAFMQIVRNGGFGTGGTNFDAKTRRNSTDLEDIFIAHISGM<br>DACARALLNAIEILEKSPIPAMLKDRYASFDGGIGKDFEEGKLTFEQVYEYGKKVGEPKQ<br>TSGKQELYETIVALYAK |
| 5586MI207_002 | *Neocallimastigales* | DNA | 67 | ATGAAAGAGTATTTCCCTGAGATCGGTAAGATGCAATTTGAAGGCCCGGAGTCCAAGAAC<br>CCGATGGCGTTTCACTACTATGACGCTGAGCGCGTCGTAGCCGGTAAAACAATGAAAGAG<br>TGGATGCGTTTCGCTATGGCTTGGTGGCACACCCTCTGTGCGGAAGGCGGCGACCAGTTC<br>GGAGGAGGAACGAAGAAATTCCCCTGGAACGAAGGGGCAAACGCTTTGGAGATCGCCAAG<br>CACAAAGCCGATGCGGGATTCGAGATCATGCAGAAACTCGGCATCCCTTATTTCTGTTTC<br>CATGACGTGGATCTCATCGCCGAGGGCGAATCGGTAGAAGAGTACGAAGCCAACCTCGCT<br>GCCATCACCGATTACCTCAAACAGAAAATGGACGAGACCGGCATCAAACTGCTGTGGTCC<br>ACGGCGAACGTGTTCAGCAACCCCCGTTATATGAACGGCGCCAGCACGAACCCCGATTTC<br>GATGTAGTGGCACGCGCTATCGTACAAATCAAGAACGCTATCGACGCCGGTATCAAACTC<br>GGAGCAGAGAACTATGTCTTCTGGGGCGGTCGCGAGGGCTATATGTCGCTCCTCAACACC<br>GACCAGCGCCGAGAGAAAGAGCATATGGCTACTATGCTCCGTATGGCGCGTGACTACGCG<br>CGTTCCAAAGGATTCAAGGGCACCTTCCTCATCGAACCCAAACCGTGTGAGCCGTCCAAA<br>CATCAGTACGATGTGGACACAGAGACCGTCATCGGTTTCCTTAAAGCGCATGGACTCGAC<br>AAGGATTTCAAAGTCAATATCGAGGTCAACCACGCCACCCTCGCAGGCCACACGTTCGAA<br>CACGAACTGGCTTGCGCTGTAGATGCCGGCATGCTCGGTTCGATTGACGCCAACCGCGGT<br>GACGCCCAGAACGGATGGGACACCGACCAATTCCCTATTGATAACTTCGAACTCACTCAG<br>GCTTTCATGCAGATCGTCCGCAACGGCGGTTTCGGAACAGGCGGTACGAACTTCGACGCC<br>AAGACACGCCGTAACTCCACCGACTTGGAGGACATCTTCATCGCCCATATCAGCGGCATG<br>GACGCTTGCGCTCGTGCGTTGCTCAATGCTGTCGAAATCCTCGAGAAGAGCCCGATCCCG<br>GCTATGCTCAAAGAGCGTTATGCTTCCTTTGACGGCGGCATCGGAAAGGACTTTGAGGAG<br>GGCAAACTGACTTTCGAGCAGGTCTATGAGTACGGCAAGAAGGTCGGAGAACCCAAACAG<br>ACCAGCGGCAAACAGGAGCTCTACGAAACCATCGTCGCCCTCTATGCCAAATGA |
| 5586MI207_002 | *Neocallimastigales* | Amino Acid | 68 | MKEYFPEIGKIQFEGPESKNPMAFHYYDAERVVAGKTMKEWMRFAMAWWHTLCAEGGDQF<br>GGGTKKFPWNEGANALEIAKHKADAGFEIMQKLGIPYFCFHDVDLIAEGESVEEYEANLA<br>AITDYLKQKMDETGIKLLWSTANVFSNPRYMNGASTNPDFDVVARAIVQIKNAIDAGIKL<br>GAENYVFWGGREGYMSLLNTDQRREKEHMATMLRMARDYARSKGFKGTFLIEPKPCEPSK<br>HQYDVDTETVIGFLKAHGLDKDFKVNIEVNHATLAGHTFEHELACAVDAGMLGSIDANRG<br>DAQNGWDTDQFPIDNFELTQAFMQIVRNGGFGTGGTNFDAKTRRNSTDLEDIFIAHISGM<br>DACARALLNAVEILEKSPIPAMLKERYASFDGGIGKDFEEGKLTFEQVYEYGKKVGEPKQ<br>TSGKQELYETIVALYAK |
| 5586MI209_003 | *Neocallimastigales* | DNA | 69 | ATGAAAGAGTATTTCCCTGAGATCGGTAAGATCCAATTTGAAGGCCCGGAGTCCAAGAAC<br>CCGATGGCGTTTCACTACTATGACGCAGAGCGCGTAGTAGCCGGTAAAACAATGAAAGAA<br>TGGATGCGTTTCGCCATGGCATGGTGGCACACCCTCTGTGCAGAAGGCGGCGACCAGTTC<br>GGAGGAGGAACGAAGCATTTCCCGTGGAATGAAGGCGCTAACGCTTTGGAGATCGCCAAA<br>CACAAAGCCGATGCGGGATTCGAGATCATGCAGAAACTCGGCATCCCCTATTTCTGTTTC<br>CATGACGTGGATCTCATCGCCGAGGGCGATTCGGTGGAGGAGTACGAAGCTAACCCCGCT<br>GCCATCACCGATTACCTCAAACAGAAAATGGACGAGACCGGCATCAAACTGCTGTGGTCC<br>ACGGCGAACGTCTTCAGCAACCCCCGTTACATGAACGGTGCGAGCACGAACCCGGATTTC |

TABLE 2-continued

| Clone No. | Class of organism | Type of Sequence | SEQ ID NO: | Sequence |
|---|---|---|---|---|
| | | | | GATGTAGTGGCACGCGCTATCGTACAAATCAAGAACGCTATCGACGCCGGTATCAAACTC<br>GGAGCAGAGAACTATGTCTTCTGGGGCGGTCGCGAGGGCTATATGTCGCTCCTCAACACC<br>GACCAGCGTCGCGAGAAAGAGCATATGGCTACTATGCTCCGTATGGCGCGTGACTACGCG<br>CGTGCCAAAGGATTCAAGGGCACCTTCCTCATCGAACCCAAACCATGTGAGCCGTCCAAA<br>CATCAGTACGATGTGGACACAGAGACTGTCATCGGTTTCCTCAAAGCGCATGGACTCGAC<br>AAGGATTTCAAAGTCAACATCGAGGTCAACCACGCCACCCTCGCAGGTCACACGTTCGAA<br>CACGAACTGGCTTGCGCTGTAGATGCCGGCATGCTCGGTTCGATTGACGCCAACCGCGGT<br>GACGCCCAGAACGGATGGGACACTGACCAGTTCCCTATTGATAACTTCGAACTCACACAG<br>GCTTTCATGCAGATCGTCCGCAACGGCGGTTTCGGAACAGGCGGTACGAACTTCGACGCC<br>AAGACACGCCGTAACTCCACCGACTTGGAGGACATCTTCATCGCCCATATCAGCGGCATG<br>GACGCTTGTGTCCGTGCGTTGCTCAACGCCATCGAAATCCTCGAGAAGAGCCCGATCCCG<br>GCTATGCTCAAAGAGCGTTACGCTTCCTTTGACGGCGGCATCGGAAAGGACTTTGAGGAT<br>GGTAAACTGACTTTCGAGCAGGTCTATGAGTACGGCAAGAAGGTCGGAGAACCCAAACAG<br>ACCAGCGGCAAACAGGAGCTCTACGAAACCATCGTCGCCCTCTATGCCAAGTAA |
| 5586MI209_003 | *Neocallimastigales* | Amino Acid | 70 | MKEYFPEIGKIQFEGPESKNPMAFHYYDAERVVAGKTMKEWMRFAMAWWHTLCAEGGDQF<br>GGGTKHFPWNEGANALEIAKHKADAGFEIMQKLGIPYFCFHDVDLIAEGDSVEEYEANPA<br>AITDYLKQKMDETGIKLLWSTANVFSNPRYMNGASTNPDFDVVARAIVQIKNAIDAGIKL<br>GAENYVFWGGREGYMSLLNTDQRREKEHMATMLRMARDYARAKGFKGTFLIEPKPCEPSK<br>HQYDVDTETVIGFLKAHGLDKDFKVNIEVNHATLAGHTFEHELACAVDAGMLGSIDANRG<br>DAQNGWDTDQFPIDNFELTQAFMQIVRNGGFGTGGTNFDAKTRRNSTDLEDIFIAHISGM<br>DACVRALLNAIEILEKSPIPAMLKERYASFDGGIGKDFEDGKLTFEQVYEYGKKVGEPKQ<br>TSGKQELYETIVALYAK |
| 5586MI214_002 | *Neocallimastigales* | DNA | 71 | ATGAAAGAGTATTTCCCTGAGATCGGAAAGATCCAATTCGAAGGCCCGGAGTCCAAGAAT<br>CCTATGGCATTTCACTACTATGACGCAGAGCGTGTAGTAGCCGGTAAAACAATGAAAGAG<br>TGGATGCGTTTCGCTTTGGCATGGTGGCACACGCTCTGCGCAGAAGGCGGCGACCAGTTC<br>GGAGGCGGCACGAAGCATTTCCCTTGGAATGAAGGTGCAAACGCTTTGGAGATCGCCAAG<br>CACAAAGCCGATGCAGGCTTCGAGATCATGCAGAAACTCGGCATCCCCTATTTCTGTTTC<br>CATGACGTGGATCTGATCGCCGAGGGCGGTTCGGTAGAAGAGTATGAAGCTAATTTAACG<br>GCTATCACCGATTACCTCAAACAGAAAATGGACGAGACCGGCATCAAACTGCTGTGGTCC<br>ACTGCGAACGTGTTCGGTAACGCACGTTATATGAACGGCGCGAGCACGAACCCCGATTTC<br>GATGTAGTGGCACGCGCTATCGTGCAGATCAAGAACGCTATCGACGCCGGCATCAAACTG<br>GGCGCAGAGAACTACGTCTTCTGGGGCGGTCGCGAGGGATATATGTCGCTCCTGAACACC<br>GACCAGAAGCGTGAGAAAGAGCATATGGCTACCATGCTCCGTATGGCGCGTGACTACGCG<br>CGTTCCAAAGGATTCAAAGGTACGTTCCTCATCGAGCCCAAACCGTGTGAGCCGTCCAAA<br>CATCAGTACGACGTGGACACTGAGACCGTCATCGGTTTCCTCAAAGCCCATGGTCTCGGC<br>AAGGATTTCAAAGTGAACATCGAGGTGAATCACGCCACCCTCGCAGGGCACACGTTCGAA<br>CACGAACTGGCTTGCGCCGTAGATGCCGGCATGCTCGGTTCGATCGACGCCAACCGCGGT<br>GACGCACAAAACGGATGGGACACCGACCAGTTCCCTATTGATAATTTCGAACTCACCCAG<br>GCATTCATGCAGATCGTCCGCAACGGCGGTTTCGGAACAGGCGGTACGAACTTCGACGCC<br>AAGACACGCCGTAATTCCACCGACTTGGAGGACATCTTCATCGCCCATATCAGCGGCATG<br>GACGCTTGTGCCCGTGCGTTGCTCAATGCTGTCGAAATCCTTGAAAAGAGCCCGATCCCG<br>GCGATGCTCAAAGAGCGTTACGCCTCCTTTGACAGCGGTATGGGTAAGGACTTTGAGGAG<br>GGCAAGCTGACCTTCGAGCAGGTCTATGAGTACGGCAAACAGGTCGGCGAACCCAAACAG<br>ACCAGCGGCAAGCAGGAGCTCTACGAAACCATCGTCGCCCTCTATGCCAAATAG |
| 5586MI214_002 | *Neocallimastigales* | Amino Acid | 72 | MKEYFPEIGKIQFEGPESKNPMAFHYYDAERVVAGKTMKEWMRFALAWWHTLCAEGGDQF<br>GGGTKHFPWNEGANALEIAKHKADAGFEIMQKLGIPYFCFHDVDLIAEGGSVEEYEANLT<br>AITDYLKQKMDETGIKLLWSTANVFGNARYMNGASTNPDFDVVARAIVQIKNAIDAGIKL<br>GAENYVFWGGREGYMSLLNTDQKREKEHMATMLRMARDYARSKGFKGTFLIEPKPCEPSK<br>HQYDVDTETVIGFLKAHGLGKDFKVNIEVNHATLAGHTFEHELACAVDAGMLGSIDANRG<br>DAQNGWDTDQFPIDNFELTQAFMQIVRNGGFGTGGTNFDAKTRRNSTDLEDIFIAHISGM<br>DACARALLNAVEILEKSPIPAMLKERYASFDSGMGKDFEEGKLTFEQVYEYGKQVGEPKQ<br>TSGKQELYETIVALYAK |
| 5751MI3_001 | *Neocallimastigales* | DNA | 73 | ATGAAAGAGTATTTTCCACAAATCGGCAAGATCCCATTTGAGGGACCAGAGTCAAAGAAC<br>CCAATGGCATTCCACTACTATGACGCAGAGCGCGTAGTTGCCGGTAAGACAATGAAGGAA<br>TGGATGCGTTTCGCTATGGCCTGGTGGCACACTCTCTGTGCTGAGGGTAGCGATCAGTTC<br>GGCCCTGGTACAAAGAAGTTCCCTTGGAACGAGGGCGAGACAGCCCTTGAGCGCGCTAAG<br>CACAAGGCAGATGCTGGCTTCGAGGTTATGCAGAAGCTCGGCATCCCATATTTCTGCTTC<br>CACGATGTAGACCTTATCGACGAGGGTGCTAACGTGGCTGAGTATGAGGCAAACCTCGCT<br>GCTATCACTGACTACCTGAAGGAGAAGATGGAGGAGACTGGCGTAAAGCTCCTCTGGTCT<br>ACAGCCAACGTGTTCGGTAACGCTCGCTATATGAACGGTGCTTCTACAAATCCTGACTTC<br>GACGTTGTGGCTCGTGCCATCGTACAGATTAAGAACGCTATCGACGCTGGTATCAAGCTT<br>GGTGCTGAGAACTACGTGTTCTGGGGCGGCCGCGAGGGCTACATGAGCCTTCTGAACACT<br>GACCAGAAGCGCGAGAAGGAGCACATGGCAACTATGCTCGGCATGGCTCGCGACTATGCC<br>CGCGCTAAGGGATTCACCGGTACCTTCCTCATTGAGCCAAAGCCAATGGAGCCAACAAAG<br>CATCAGTATGATGTTGACACAGAGACCGTTATCGGTTTCCTCAAGGCTCACGGTCTGGAC<br>AAGGACTTCAAGGTGAACATCGAGGTGAACCACGCTACTCTCGCCGGTCACACCTTCGAG<br>CACGAGCTCGCTTGCGCTGTTGACGCTGGTATGCTCGGTTCTATCGACGCTAACCGCGGT<br>GACGCTCAGAACGGATGGGATACCGACCAGTTCCCAATCGACAACTTCGAGCTGACACAG<br>GCTTGGATGCAGATTGTTCGCAATGGCGGTCTTGGCACAGGTGGTACCAACTTCGACGCA<br>AAGACCCGTCGTAACTCTACCGACCTCGAGGACATCTTCATCGCTCACATCTCCGGTATG<br>GACGCTTGTGCACGCGCTCTCCTCAACGCAGTAGAGATACTCGAGAACTCTCCAATCCCA<br>ACAATGCTGAAGGACCGCTATGCAAGCTTCGACTCAGGTATGGGTAAGGACTTCGAGGAC |

TABLE 2-continued

| Clone No. | Class of organism | Type of Sequence | SEQ ID NO: | Sequence |
|---|---|---|---|---|
| | | | | GGCAAGCTCACACTTGAGCAGGTTTATGAGTATGGTAAGAAGGTCGACGAGCCAAAGCAG<br>ACCTCTGGTAAGCAGGAACTCTATGAGACCATCGTTGCTCTCTATGCAAAATAA |
| 5751MI3_001 | Neocallimastigales | Amino Acid | 74 | MKEYFPQIGKIPFEGPESKNPMAFHYYDAERVVAGKTMKEWMRFAMAWWHTLCAEGSDQF<br>GPGTKKFPWNEGETALERAKHKADAGFEVMQKLGIPYFCFHDVDLIDEGANVAEYEANLA<br>AITDYLKEKMEETGVKLLWSTANVFGNARYMNGASTNPDFDVVARAIVQIKNAIDAGIKL<br>GAENYVFWGGREGYMSLLNTDQKREKEHMATMLGMARDYARAKGFTGTFLIEPKPMEPTK<br>HQYDVDTETVIGFLKAHGLDKDFKVNIEVNHATLAGHTFEHELACAVDAGMLGSIDANRG<br>DAQNGWDTDQFPIDNFELTQAWMQIVRNGGLGTGGTNFDAKTRRNSTDLEDIFIAHISGM<br>DACARALLNAVEILENSPIPTMLKDRYASFDSGMGKDFEDGKLTLEQVYEYGKKVDEPKQ<br>TSGKQELYETIVALYAK |
| 5753MI3_002 | *Prevotella* | DNA | 75 | ATGCCTAAAGAATACTTCCCCTCCATCGGCAAAATCCCTTTTGAAGGAGGCGACAGCAAA<br>AATCCCCTCGCTTTCCATTATTATGACGCCGGACGCGTGGTTATGGGCAAGCCCATGAAG<br>GAATGGCTTAAATTCGCCATGGCCTGGTGGCACACGCTGGGCCAGGCCTCCGGAGACCCC<br>TTCGGCGGCCAGACCCGCAGCTACGAATGGGACAAGGGCGAATGCCCCTACTGCCGCGCC<br>AAAGCCAAGGCCGACGCCGGTTTTGAAATCATGCAAAAGCTGGGTATCGAATACTTCTGC<br>TTCCACGATGTGGACCTTATCGAGGATTGCGATGACATTGCCGAATACGAAGCCCGCATG<br>AAGGACATCACGGACTACCTGCTGGAAAAGATGAAGGAGACCGGCATCAAGAACCTCTGG<br>GGCACCGCCAATGTCTTCGGCCACAAGCGCTACATGAACGGCGCCGGCACCAATCCGCAG<br>TTCGATGTGGTGGCCCGTGCCGCCGTCCAGATCAAGAACGCCCTGGACGCCACCATCAAG<br>CTGGGCGGCTCCAACTATGTGTTCTGGGGCGGCCGCGAAGGCTATTACACCCTCCTCAAC<br>ACCCAGATGCAGCGGGAAAAAGACCACCTGGCCAAGTTGCTGACGGCCGCCCGCGACTAT<br>GCCCGCGCCAAGGGCTTCAAGGGCACCTTCCTCATTGAGCCCAAACCCATGGAACCCACC<br>AAGCACCAGTACGACGTGGATACGGAGACGGTCATCGGCTTCCTCCGTGCCAACGGCCTG<br>GACAAGGACTTCAAGGTGAACATCGAGGTGAACCACGCCACCCTGGCCGGCCACACCTTC<br>GAGCATGAGCTCACCGTGGCCCGCGAGAACGGTTTCCTGGGCTCCATCGGTGCCAACCGC<br>GGCGACGCCCAGAACGGCTGGGACACGGACCAGTTCCCTGTGGACCCGTACGATCTTACC<br>CAGGCCATGATGCAGGTGCTGCTGAACGGCGGCTTCGGCAACGGCGGCACCAACTTCGAC<br>GCCAAACTCCGCCGCTCCTCCACCGACCCTGAGGACATCTTCATCGCCCATATTTCCGCC<br>ATGGATGCCATGGCCCACGCTTTGCTTAACGCAGCTGCCGTGCTGGAAGAGAGCCCCCTG<br>TGCCAGATGGTCAAGGAGCGTTATGCCAGCTTCGACGGCGGCCTCGGCAAACAGTTCGAG<br>GAAGGCAAGGCTACCCTGGAAGACCTGTACGAATACGCCAAGGTCCAGGGTGAACCCGTT<br>GTCGCCTCCGGCAAGCAGGAGCTTTACGAGACTCTCCTGAACCTGTATGCCGTCAAGTAA |
| 5753MI3_002 | *Prevotella* | Amino Acid | 76 | MAKEYFPSIGKIPFEGGDSKNPLAFHYYDAGRVVMGKPMKEWLKFAMAWWHTLGQASGDP<br>FGGQTRSYEWDKGECPYCRAKAKADAGFEIMQKLGIEYFCFHDVDLIEDCDDIAEYEARM<br>KDITDYLLEKMKETGIKNLWGTANVFGHKRYMNGAGTNPQFDVVARAAVQIKNALDATIK<br>LGGSNYVFWGGREGYYTLLNTQMQREKDHLAKLLTAARDYARAKGFKGTFLIEPKPMEPT<br>KHQYDVDTETVIGFLRANGLDKDFKVNIEVNHATLAGHTFEHELTVARENGFLGSIGANR<br>GDAQNGWDTDQFPVDPYDLTQAMMQVLLNGGFGNGGTNFDAKLRRSSTDPEDIFIAHISA<br>MDAMAHALLNAAAVLEESPLCQMVKERYASFDGGLGKQFEEGKATLEDLYEYAKVQGEPV<br>VASGKQELYETLLNLYAVK |
| 1754MI1_001 | *Prevotella* | DNA | 77 | ATGGCAAAAGAGTATTTTCCGTTTACCGGTAAGATTCCTTTCGAAGGAAAGGACAGTAAG<br>AATGTAATGGCTTTCCACTACTACGAGCCTGAGAAGGTCGTGATGGGAAAGAAGATGAAG<br>GACTGGCTGAAGTTCGCTATGGCTTGGTGGCATACACTGGGTGGCGCTTCTGCTGACCAG<br>TTTGGTGGTCAGACTCGTTCATACGAGTGGGACAAGGCTGGTGACGCTGTTCAGCGCGCT<br>AAGGATAAGATGGACGCTGGCTTCGAGATCATGGACAAGCTGGGCATCGAGTACTTCTGC<br>TTCCACGATGTTGACCTCGTTGAAGAGGGTGACACCATCGAGGAGTATGAGGCTCGCATG<br>AAGGCCATCACCGACTACGCTCAGGAGAAGATGAAGCAGTTCCCCAACATCAAGCTGCTC<br>TGGGGTACCGCAAACGTATTCGGTAACAAGCGCTATGCTAACGGTGCTTCTACCAACCCC<br>GACTTCGACGTAGTGGCTCGCGCCATCGTTCAGATCAAGAACGCTATTGATGCTACCATC<br>AAGCTGGGTGGTACCAACTATGTGTTCTGGGGTGGTCGTGAGGGCTATATGAGTCTGCTG<br>AACACCGACCAGAAGCGTGAGAAGGAGCACATGGCTACTATGCTGACCATGGCTCGCGAC<br>TATGCTCGCGCCAAGGGATTCAAGGGTACATTCCTCATTGAGCCGAAGCCCATGGAGCCC<br>AGCAAGCACCAGTATGATGTGGATACAGAGACCGTTATCGGCTTCCTGAAGGCACACAAC<br>CTGGACAAGGACTTCAAGGTGAACATCGAGGTGAACCACGCTACACTCGCTGGTCATACC<br>TTCGAGCACGAGCTGGCTTGCGCTGTTGACGCTGGTATGCTTGGTTCTATCGACGCTAAC<br>CGTGGTGATGCTCAGAACGGTTGGGATACCGACCAGTTCCCCATCGACAACTACGAGCTG<br>ACACAGGCTATGCTCGAGATCATCCGCAATGGTGGTCTGGGCAATGGTGGTACCAACTTC<br>GATGCTAAGATCCGTCGTAACAGCACCGACCTCGAGGATCTCTTCATCGCTCACATCAGT<br>GGTATGGATGCTATGGCACGCGCTCTGATGAACGCTGCTGACATCCTTGAGAACTCTGAG<br>CTGCCCGCAATGAAGAAGGCTCGCTACGCAAGCTTCGACCAGGGTGTTGGTAAGGACTTC<br>GAAGATGGCAAGCTGACCCTTGAGCAGGTTTACGAGTATGGTAAGAAGGTGGGTGAGCCC<br>AAGCAGACTTCTGGTAAGCAGGAGAAGTACGAGACCATCGTTGCTCTCTATGCAAAATAA |
| 1754MI1_001 | *Prevotella* | Amino Acid | 78 | MAKEYFPFTGKIPFEGKDSKNVMAFHYYEPEKVVMGKKMKDWLKFAMAWWHTLGGASADQ<br>FGGQTRSYEWDKAGDAVQRAKDKMDAGFEIMDKLGIEYFCFHDVDLVEEGDTIEEYEARM<br>KAITDYAQEKMKQFPNIKLLWGTANVFGNKRYANGASTNPDFDVVARAIVQIKNAIDATI<br>KLGGTNYVFWGGREGYMSLLNTDQKREKEHMATMLTMARDYARAKGFKGTFLIEPKPMEP<br>SKHQYDVDTETVIGFLKAHNLDKDFKVNIEVNHATLAGHTFEHELACAVDAGMLGSIDAN<br>RGDAQNGWDTDQFPIDNYELTQAMLEIIRNGGLGNGGTNFDAKIRRNSTDLEDLFIAHIS<br>GMDAMARALMNAADILENSELPAMKKARYASFDQGVGKDFEDGKLTLEQVYEYGKKVGEP<br>KQTSGKQEKYETIVALYAK |

TABLE 2-continued

| Clone No. | Class of organism | Type of Sequence | SEQ ID NO: | Sequence |
|---|---|---|---|---|
| 1754MI3_007 | *Prevotella* | DNA | 79 | ATGGCAAAAGAGTATTTTCCGTTTACCGGTAAGATTCCTTTCGAAGGAAAAGAGAGCAAG<br>AACGTAATGGCTTTCCATTACTATGAGCCTGAAAAGGTGGTCATGGGCAAGAAAATGAAG<br>GATTGGCTGAAATTCGCCATGGCTTGGTGGCACACCCTCGGTGGAGCCAGCGCCGACCAG<br>TTCGGTGGACAGACCCGCAGCTATGAGTGGGACAAGGCCGAGGATGCCGTACAGCGTGCT<br>AAGGACAAGATGGACGCCGGCTTCGAGATCATGGACAAACTGGGCATCGAGTATTTCTGC<br>TTCCACGATGTCGACCTCGTCGACGAGGGTGCTACCGTTGAGGAGTATGAGGCTCGCATG<br>AAAGCCATCACCGACTATGCCCAGGTCAAGATGAAGGAATATCCCAACATCAAACTGCTC<br>TGGGGCACCGCCAACGTGTTCGGCAACAAGCGTTATGCCAACGGCGCTTCCACCAACCCC<br>GACTTCGACGTGGTGGCACGCGCTATCGTTCAGATCAAGAATGCCATCGACGCTACCATC<br>AAGCTCGGCGGTCAGAACTACGTGTTCTGGGGCGGACGCGAGGGCTACATGAGCCTGCTC<br>AATACCGATCAGAAACGTGAGAAGGAACACATGGCCACCATGCTCACCATGGCGCGCGAC<br>TATGCTCGCAGCAAGGGATTCAAGGGCACCTTCCTCATCGAACCCAAACCCATGGAGCCT<br>TCCAAGCACCAGTATGATGTCGACACCGAGACGGTCATCGGCTTCCTCCGCGCCCACAAC<br>CTCGACAAGGACTTCAAGGTGAACATCGAGGTCAACCACGCCACGCTCGCCGGCCACACC<br>TTCGAGCACGAACTGGCTTGCGCCGTCGACGCCGGCATGCTCGGCAGCATCGACGCCAAC<br>CGCGGCGACGCACAGAACGGCTGGGATACCGACCAGTTCCCCATCGACAACTACGAACTG<br>ACACAGGCCATGCTGGAGATCATCCGCAATGGCGGCCTCGGCAATGGTGGTACCAACTTC<br>GACGCCAAGATCCGTCGTAACAGCACCGACCTCGAAGATCTCTTCATCGCTCACATCAGC<br>GGTATGGATGCCATGGCTCGCGCGCTGCTCAACGCCGCCGCCATCCTCGAGGAGAGCGAA<br>CTGCCCGCCATGAAGAAGGCCCGCTACGCTTCCTTCGACGAAGGTATCGGCAAGGACTTC<br>GAAGACGGCAAACTCACCCTCGAGCAGGTTTACGAGTACGGCAAGAAGGTAGGCGAGCCC<br>AAGCAGACCTCCGGCAAGCAAGAGAAGTACGAGACCATCGTGGCTCTCTACAGCAAATAA |
| 1754MI3_007 | *Prevotella* | Amino Acid | 80 | MAKEYFPFTGKIPFEGKESKNVMAFHYYEPEKVVMGKKMKDWLKFAMAWWHTLGGASADQ<br>FGGQTRSYEWDKAEDAVQRAKDKMDAGFEIMDKLGIEYFCFHDVDLVDEGATVEEYEARM<br>KAITDYAQVKMKEYPNIKLLWGTANVFGNKRYANGASTNPDFDVVARAIVQIKNAIDATI<br>KLGGQNYVFWGGREGYMSLLNTDQKREKEHMATMLTMARDYARSKGFKGTFLIEPKPMEP<br>SKHQYDVDTETVIGFLRAHNLDKDFKVNIEVNHATLAGHTFEHELACAVDAGMLGSIDAN<br>RGDAQNGWDTDQFPIDNYELTQAMLEIIRNGGLGNGGTNFDAKIRRNSTDLEDLFIAHIS<br>GMDAMARALLNAAAILEESELPAMKKARYASFDEGIGKDFEDGKLTLEQVYEYGKKVGEP<br>KQTSGKQEKYETIVALYSK |
| 1754MI5_009 | *Prevotella* | DNA | 81 | ATGAAAGAGTATTTCCCGCAAATTGGAAAGATTCCCTTCGAGGGACCAGAGAGCAAGAGT<br>CCATTGGCGTTCCATTATTATGAGCCGGATCGCATGGTGCTCGGAAAGAGGATGGAGGAT<br>TGGCTGAAATTCGCCATGGCATGGTGGCACACCCTTGGCCAGGCCAGCGGCGACCAGTTC<br>GGCGGACAGACACGTGAGTACGAGTGGGATAAGGCTGGAGATCCGATACAAAGGGCAAAG<br>GATAAGATGGACGCCGGATTCGAGATCATGGAGAAATTGGGTATCAAGTACTTCTGCTTC<br>CATGATGTGGATCTCGTCGAGGAAGCTCCCACCATCGCCGAATATGAGGAGCGTATGAGG<br>ATCATCACCGACTATGCGCTCGAGAAGATGAAAGCCACTGGCATCAAACTCCTTTGGGGT<br>ACAGCCAATGTTTTCGGACATAAGAGATATATGAATGGGGCCGCCACCAACCCGGAGTTC<br>GGTGTTGTCGCCAGGGCTGCTGTCCAGATCAAGAACGCGATCGACGCCACCATCAAGCTG<br>GGAGGAACAAACTATGTGTTCTGGGGTGGCCGCGAGGGCTACATGAGCCTGCTCAACACC<br>CAGATGCAGAGGGAGAAGGACCATCTCGCCAATATGCTCAAGGCTGCTCGTGACTATGCT<br>CGCGCCAAGGGATTCAAGGGCACATTCCTCATCGAGCCGAAGCCGATGGAACCTACTAAG<br>CATCAGTACGATGTCGACACTGAGACCGTGATCGGCTTCCTCCGCGCAAACGGTCTTGAC<br>AAGGATTTCAAGGTCAACATCGAGGTCAATCACGCCACTCTTGCGGGTCACACTTTCGAG<br>CATGAGCTCGCCGTGGCTGTCGACAATGGTCTCCTTGGCTCAATCGATGCGAACAGGGGA<br>GATTATCAGAACGGTTGGGACACCGACCAGTTCCCTGTTGATCTCTTTGATTTGACCCAG<br>GCCATGCTCCAGATCATCCGTAACGGAGGCCTCGGTAATGGTGGATCCAACTTCGACGCC<br>AAGCTTCGCCGTAACTCCACTGATCCTGAGGATATATTCATTGCCCATATTTGCGGTATG<br>GACGCTATGGCCAGGGCTCTCCTTGCCGCCGCCGCGATCGTGGAGGAGTCTCCTATCCCG<br>GCTATGGTCAAAGAGCGTTACGCATCCTTCGACGAAGGTGAGGGCAAGAGATTCGAGGAT<br>GGTAAGATGAGTCTGGAGGAACTTGTTGATTACGCGAAGACTCACGGAGAGCCCGCCCAG<br>AAGAGTGGCAAACAGGAGCTCTACGAAACCCTTGTCAACATGTACATCAAATAA |
| 1754MI5_009 | *Prevotella* | Amino Acid | 82 | MKEYFPQIGKIPFEGPESKSPLAFHYYEPDRMVLGKRMEDWLKFAMAWWHTLGQASGDQF<br>GGQTREYEWDKAGDPIQRAKDKMDAGFEIMEKLGIKYFCFHDVDLVEEAPTIAEYEERMR<br>IITDYALEKMKATGIKLLWGTANVFGHKRYMNGAATNPEFGVVARAAVQIKNAIDATIKL<br>GGTNYVFWGGREGYMSLLNTQMQREKDHLANMLKAARDYARAKGFKGTFLIEPKPMEPTK<br>HQYDVDTETVIGFLRANGLDKDFKVNIEVNHATLAGHTFEHELAVAVDNGLLGSIDANRG<br>DYQNGWDTDQFPVDLFDLTQAMLQIIRNGGLGNGGSNFDAKLRRNSTDPEDIFIAHICGM<br>DAMARALLAAAAIVEESPIPAMVKERYASFDEGEGKRFEDGKMSLEELVDYAKTHGEPAQ<br>KSGKQELYETLVNMYIK |
| 5586MI1_003 | *Prevotella* | DNA | 83 | ATGGCAAAAGAGTATTTTCCGTTTACCGGTAAGATTCCTTTCGAGGGAAAGGACAGTAAG<br>AATGTAATGGCGTTCCACTACTACGAGCCCGAGCGCGTGGTAATGGGCAAGAAGATGAAG<br>GAGTGGCTGAAGTTTGCCATGGCCTGGTGGCACACGCTGGGTGGAGCCAGTGCCGACCAG<br>TTTGGCGGACAGACCCGCAGCTACGAGTGGGACAAGGCTGAAGACGCCGTGCAGCGTGCC<br>AAGGACAAGATGGATGCCGGCTTCGAGATCATGGACAAGCTGGGCATCGAGTATTTCTGC<br>TTCCATGATGTCGATCTCGTTGACGAGGGTGCCACTGTCGAGGAGTATGAGGCTCGCATG<br>CAGGCCATCACCGACTATGCGCAGGAGAAGATGAAGCAGTATCCTGCCATCAAGCTGCTG<br>TGGGGTACGGCCAATGTCTTTGGCAACAAGCGTTATGCCAACGGTGCCTCTACCAATCCC<br>GACTTCGATGTGGTGGCCCGCGCCATCGTGCAGATTAAGAATGCCATTGATGCCACCATC<br>AAGCTGGGCGGCAGCAACTATGTGTTCTGGGGCGGTCGCGAGGGCTACATGTCGCTGCTC<br>AACACCGACCAGAAGCGTGAGAAGGAACACATGGCCCGGATGCTGACCATGGCCCGCGAC<br>TATGCCCGCTCGAAGGGCTTCAAGGGCAACTTCCTGATTGAGCCCAAGCCCATGGAGCCG |

TABLE 2-continued

| Clone No. | Class of organism | Type of Sequence | SEQ ID NO: | Sequence |
|---|---|---|---|---|
| | | | | TCGAAGCATCAGTACGACGTGGACACCGAGACGGTTATCGGATTCCTCCGCGCACATGGC<br>CTTGACAAGGACTTCAAGGTGAACATCGAGGTGAACCATGCCACGCTGGCCGGTCATACC<br>TTCGAGCACGAACTGGCTTGCGCCGTAGATGCCGGCATGCTGGGCAGCATTGATGCCAAC<br>CGCGGCGACGCACAGAACGGATGGGACACCGACCAGTTCCCCATCGACAACTATGAGTTG<br>ACACAGGCCATGATGGAGATTATCCGCAATGGCGGTCTGGGTCTTGGCGGTACCAATTTC<br>GATGCCAAGATTCGCCGTAACTCCACCGACCTGGAAGACCTCTTCATCGCCCACATCAGT<br>GGCATGGACGCCATGGCTCGTGCGCTCCTTAATGCTGCCGACATTCTGGAGAACAGCGAA<br>CTGCCCGCCATGAAGAAAGCGCGCTACGCCTCGTTCGACAGTGGCATGGGCAAGGACTTC<br>GAGGACGGCAAACTGACCCTTGAGCAGGTTTACGAATACGGCAAAAAAGTCGGCGAACCT<br>AAGCAGACCTCCGGCAAGCAGGAGAAGTACGAGACCATCGTGGCTCTCTATGCCAAGTAA |
| 5586MI1_003 | *Prevotella* | Amino Acid | 84 | MAKEYFPFTGKIPFEGKDSKNVMAFHYYEPERVVMGKKMKEWLKFAMAWWHTLGGASADQ<br>FGGQTRSYEWDKAEDAVQRAKDKMDAGFEIMDKLGIEYFCFHDVDLVDEGATVEEYEARM<br>QAITDYAQEKMKQYPAIKLLWGTANVFGNKRYANGASTNPDFDVVARAIVQIKNAIDATI<br>KLGGSNYVFWGGREGYMSLLNTDQKREKEHMARMLTMARDYARSKGFKGNFLIEPKPMEP<br>SKHQYDVDTETVIGFLRAHGLDKDEKVNIEVNHATLAGHTFEHELACAVDAGMLGSIDAN<br>RGDAQNGWDTDQFPIDNYELTQAMMEIIRNGGLGLGGTNFDAKIRRNSTDLEDLFIAHIS<br>GMDAMARALLNAADILENSELPAMKKARYASFDSGMGKDFEDGKLTLEQVYEYGKKVGEP<br>KQTSGKQEKYETIVALYAK |
| 5586MI2_006 | *Prevotella* | DNA | 85 | ATGGCAAAAGAGTATTTTCCGTTTACAGGTAAAATTCCTTTCGAAGGAAAGGACAGTAAG<br>AACGTAATGGCTTTCCACTACTACGAGCCCGAAAAGGTCGTGATGGGAAAGAAAATGAAA<br>GACTGGCTGAAGTTCGCCATGGCCTGGTGGCACACACTGGGTGGCGCCAGCGCCGACCAG<br>TTTGGCGGCCAGACACGCAGCTATGAGTGGGACAAGGCTGCCGATGCCGTGCAGCGCGCA<br>AAGGACAAGATGGACGCCGGCTTCGAAATCATGGACAAGCTGGGCATCGAGTATTTCTGC<br>TTCCACGACGTGGACCTCGTTGAGGAGGGAGCCACCATCGAGGAGTATGAGGCCCGCATG<br>AAGGCTATCACCGACTATGCCCAGGAGAAGATGAAACAGTATCCCAGCATCAAGCTGCTC<br>TGGGGCACCGCCAATGTGTTTGGCAACAAGCGCTACGCCAACGGCGCCAGCACCAACCCC<br>GACTTCGACGTCGTGGCCCGTGCCATCGTGCAGATCAAGAACGCCATCGATGCCACCATC<br>AAGCTGGGCGGCACCAACTACGTGTTCTGGGGCGGACGCGAGGGCTACATGAGCCTGCTC<br>AACACCGACCAGAAGCGCGAGAAGGAGCACATGGCCACCATGCTCACCATGGCCCGCGAC<br>TACGCCCGCGCAAAGGGATTCAAGGGCACCTTCCTCATCGAGCCCAAGCCCATGGAGCCG<br>TCGAAGCACCAGTACGACGTGGACACCGAGACCGTCATCGGTTTCCTGAAGGCCCACGGT<br>CTGGACAAGGACTTCAAGGTGAACATCGAGGTGAACCACGCCACGCTGGCCGGCCACACC<br>TTCGAGCATGAGCTGGCCTGCGCCGTCGACGCCGGTATGCTGGGCAGCATCGATGCCAAC<br>CGCGGCGACGCCCAGAACGGCTGGGACACCGACCAGTTCCCCATCGACAACTTCGAGCTC<br>ACCCAGGCCATGATGGAAATTATCCGCAACGGCGGCCTCGGCAACGGCGGCACCAACTTC<br>GACGCTAAGATCCGCCGCAACTCCACCGACCTCGAGGACCTCTTCATCGCCCACATCAGC<br>GGCATGGACGCCATGGCCCGCGCACTGATGAACGCTGCCGACATTATGGAGAACAGCGAG<br>CTGCCCGCCATGAAGAAGGCACGCTACGCCAGCTTCGACGCCGGCATCGGCAAGGACTTT<br>GAGGATGGCAAGCTCTCGCTGGAGCAGGTCTACGAGTATGGCAAGAAGGTGGAAGAGCCC<br>AAGCAGACCAGCGGCAAGCAGGAGAAGTACGAGACCATCGTCGCCCTCTATGCCAAGTAA |
| 5586MI2_006 | *Prevotella* | Amino Acid | 86 | MAKEYFPFTGKIPFEGKDSKNVMAFHYYEPEKVVMGKKMKDWLKFAMAWWHTLGGASADQ<br>FGGQTRSYEWDKAADAVQRAKDKMDAGFEIMDKLGIEYFCFHDVDLVEEGATIEEYEARM<br>KAITDYAQEKMKQYPSIKLLWGTANVFGNKRYANGASTNPDFDVVARAIVQIKNAIDATI<br>KLGGTNYVFWGGREGYMSLLNTDQKREKEHMATMLTMARDYARAKGFKGTFLIEPKPMEP<br>SKHQYDVDTETVIGFLKAHGLDKDFKVNIEVNHATLAGHTFEHELACAVDAGMLGSIDAN<br>RGDAQNGWDTDQFPIDNFELTQAMMEIIRNGGLGNGGTNFDAKIRRNSTDLEDLFIAHIS<br>GMDAMARALMNAADIMENSELPAMKKARYASFDAGIGKDFEDGKLSLEQVYEYGKKVEEP<br>KQTSGKQEKYETIVALYAK |
| 5586MI8_003 | *Prevotella* | DNA | 87 | ATGGCAAAAGAGTATTTCGCCTTTACAGGCAAGATTCCTTTCGAGGGAAAAGACAGTAAG<br>AACGTGATGGCTTTCCACTACTACGAGCCGGAGCGTGTGGTGATGGGCAAGAAGATGAAG<br>GAGTGGCTGAAGTTCGCCATGGCCTGGTGGCACACACTGGGTGGCGCATCGGCCGACCAG<br>TTCGGAGGCCAGACACGCAGCTACGAGTGGGACAAGGCCGCCGACGCCGTGCAGCGCGCC<br>AAGGACAAGATGGACGCCGGCTTCGAGATTATGGACAAGCTGGGCATCGAGTACTTCTGC<br>TTCCACGATGTAGACCTCGTTGAGGAGGGTGAGACCATAGCCGAGTACGAGCGCCGCATG<br>AAGGAAATCACCGACTACGCACAGGAGAAGATGAAGCAGTTCCCCAACATCAAGCTGCTC<br>TGGGGCACAGCCAACGTGTTCGGCAACAAGCGCTACGCCAACGGCGCATCGACCAACCCC<br>GACTTCGACGTTGTGGCACGCGCCATCGTGCAGATCAAGAACGCCATCGACGCCACCATC<br>AAGCTCGGCGGCTCCAACTATGTGTTCTGGGGCGGACGCGAGGGCTATATGAGCCTGCTC<br>AACACCGACCAGAAGCGCGAGAAGGAGCACATGGCCACCATGCTCACCATGGCCCGCGAC<br>TATGCACGCGCCAAGGGATTCAAGGGCACATTCCTCATCGAGCCGAAGCCCATGGAGCCC<br>TCGAAGCACCAGTACGACGTAGACACAGAGACCGTCATCGGCTTCCTCCGTGCACACGGG<br>CTGGACAAGGACTTCAAGGTGAACATCGAGGTAAACCACGCCACACTGGCCGGCCACACC<br>TTCGAGCACGAGCTGGCTTGCGCCGTCGACGCTGGCATGCTGGGCAGCATCGACGCCAAC<br>CGTGGCGACGCACAGAACGGATGGGACACCGACCAGTTCCCCATCGACAACTTCGAGCTC<br>ACACAGGCCATGATGGAAATCATCCGCAATGGCGGACTGGGCAATGGCGGCACCAACTTC<br>GACGCCAAGATCCGTCGTAACAGCACCGACCTCGAAGACCTCTTCATCGCCCACATCAGC<br>GGCATGGACGCCATGGCACGCGCACTGCTCAACGCTGCCGACATCCTGGAGCACAGCGAG<br>CTGCCCAAGATGAAGAAGGAGCGCTACGCCAGCTTCGACGCAGGCATCGGCAAGGACTTC<br>GAAGACGGCAAGCTCACACTCGAGCAGGTCTACGAGTACGGCAAGAAGGTCGAAGAGCCC<br>CGTCAGACCAGCGGCAAGCAGGAGAAGTACGAGACCATCGTCGCCCTCTATGCCAAGTAA |

TABLE 2-continued

| Clone No. | Class of organism | Type of Sequence | SEQ ID NO: | Sequence |
|---|---|---|---|---|
| 5586MI8_003 | *Prevotella* | Amino Acid | 88 | MAKEYFAFTGKIPFEGKDSKNVMAFHYYEPERVVMGKKMKEWLKFAMAWWHTLGGASADQ<br>FGGQTRSYEWDKAADAVQRAKDKMDAGFEIMDKLGIEYFCFHDVDLVEEGETIAEYERRM<br>KEITDYAQEKMKQFPNIKLLWGTANVFGNKRYANGASTNPDFDVVARAIVQIKNAIDATI<br>KLGGSNYVFWGGREGYMSLLNTDQKREKEHMATMLTMARDYARAKGFKGTFLIEPKPMEP<br>SKHQYDVDTETVIGFLRAHGLDKDFKVNIEVNHATLAGHTFEHELACAVDAGMLGSIDAN<br>RGDAQNGWDTDQFPIDNFELTQAMMEIIRNGGLGNGGTNFDAKIRRNSTDLEDLFIAHIS<br>GMDAMARALLNAADILEHSELPKMKKERYASFDAGIGKDFEDGKLTLEQVYEYGKKVEEP<br>RQTSGKQEKYETIVALYAK |
| 5586MI14_003 | *Prevotella* | DNA | 89 | ATGGCAAAAGAGTATTTTCCGTTTACTGGTAAGATTCCTTTCGAGGGAAAGGATAGTAAG<br>AATGTAATGGCTTTCCACTATTACGAGCCCGAGAAAGTCGTGATGGGAAAGAAGATGAAG<br>GACTGGCTGAAGTTCGCAATGGCTTGGTGGCATACACTGGGTGGTGCATCTGCAGACCAG<br>TTCGGTGGAGAGACCCGCAGCTACGAGTGGAGCAAGGCTGCTGATCCCGTTCAGCGCGCC<br>AAGGACAAGATGGACGCCGGCTTTGAGATTATGGATAAGCTGGGCATCGAGTACTTCTGT<br>TTCCACGATATAGACCTCGTTCAGGAGGCAGATACCATTGCAGAATATGAGGAGCGCATG<br>AAGGCAATTACCGACTATGCTCTGGAGAAGATGAAGCAGTTCCCCAACATCAAGTTGCTC<br>TGGGGTACCGCTAACGTATTTAGCAACAAGCGCTATATGAACGGTGCTTCTACCAATCCC<br>GACTTCGACGTGGTGGCCCGTGCCATCGTTCAGATCAAGAACGCTATTGATGCAACCATC<br>AAACTCGGTGGTACCAACTATGTATTCTGGGGTGGTCGTGAGGGTTACATGAGCCTATTG<br>AATACCGACCAGAAGCGTGAAAAGGAGCACATGGCAATGATGCTCGGTATGGCTCGCGAC<br>TATGCCCGCAGCAAGGGATTCAAGGGTACGTTCCTCATCGAGCCGAAGCCGATGGAGCCC<br>TCTAAGCATCAGTATGATGTCGATACGGAGACTGTGATTGGTTTCCTGAAGGCACACGGT<br>CTGGACAAGGACTTCAAGGTGAACATCGAGGTGAACCACGCTACACTGGCTGGTCATACC<br>TTCGAGCATGAGCTGGCTTGCGCTGTTGACGCAGGTATGCTGGGCTCTATCGACGCTAAC<br>CGCGGTGATGCCCAGAACGGCTGGGATACCGACCAGTTCCCCATCGACAACTACGAGCTG<br>ACACAGGCTATGATGGAAATCATCCGCAACGGTGGTCTGGGCAATGGTGGTACCAACTTC<br>GACGCTAAGATCCGCCGTAACTCTACCGACCTCGAGGATCTGTTCATCGCTCATATCAGT<br>GGTATGGATGCTATGGCCCGTGCTTTGTTGAATGCTGCCGACATTCTGGAGAACTCTGAA<br>CTGCCCGCTATGAAGAAGGCCCGCTACGCCAGCTTCGACAACGGTATCGGTAAGGACTTC<br>GAGGATGGCAAGCTGACCTTCGAGCAGGTTTACGAATATGGTAAGAAAGTTGAAGAGCCG<br>AAGCAGACCTCTGGCAAGCAGGAGAAATACGAGACCATCGTTGCTCTGTATGCTAAATAA |
| 5586MI14_003 | *Prevotella* | Amino Acid | 90 | MAKEYFPFTGKIPFEGKDSKNVMAFHYYEPEKVVMGKKMKDWLKFAMAWWHTLGGASADQ<br>FGGETRSYEWSKAADPVQRAKDKMDAGFEIMDKLGIEYFCFHDIDLVQEADTIAEYEERM<br>KAITDYALEKMKQFPNIKLLWGTANVFSNKRYMNGASTNPDFDVVARAIVQIKNAIDATI<br>KLGGTNYVFWGGREGYMSLLNTDQKREKEHMAMMLGMARDYARSKGFKGTFLIEPKPMEP<br>SKHQYDVDTETVIGFLKAHGLDKDFKVNIEVNHATLAGHTFEHELACAVDAGMLGSIDAN<br>RGDAQNGWDTDQFPIDNYELTQAMMEIIRNGGLGNGGTNFDAKIRRNSTDLEDLFIAHIS<br>GMDAMARALLNAADILENSELPAMKKARYASFDNGIGKDFEDGKLTFEQVYEYGKKVEEP<br>KQTSGKQEKYETIVALYAK |
| 5586MI26_003 | *Prevotella* | DNA | 91 | ATGGCAAAAGAGTATTTTCCGTTTACCGGTAAAATTCCTTTCGAGGGAAAGGACAGTAAG<br>AATGTAATGGCTTTCCACTACTACGAGCCTGAGCGCGTAGTGATGGGAAAGAAGATGAAG<br>GATTGGTTGCGATTTGCAATGGCTTGGTGGCACACACTGGGTGGCGCTTCTGCCGACCAG<br>TTTGGTGGTCAGACCCGCAGTTACGAATGGGACAAGGCTGCTGATGCTGTTCAGCGTGCT<br>AAGGACAAGATGGATGCCGGCTTCGAGATTATGGATAAGCTGGGAATCGAGTTCTTCTGC<br>TGGCACGATATCGACCTCGTTGAAGAGGGTGAGACCATTGAAGAGTATGAGCGCCGCATG<br>AAGGCTATCACCGACTATGCTCTTGAGAAGATGCAGCAGTATCCCAACATCAAGAACCTC<br>TGGGGAACAGCCAATGTGTTTGGCAACAAGCGTTATGCCAACGGTGCCAGCACAAACCCA<br>GACTTTGACGTCGTTGCTCGTGCTATCGTACAGATTAAGAATGCTATCGACGCTACTATC<br>AAGTTGGGTGGTCAGAATTATGTGTTCTGGGGTGGCCGTGAGGGCTACATGAGCCTGCTC<br>AATACTGACCAGAAGCGTGAGAAGGAGCACATGGCTACAATGCTGACCATGGCACGCGAC<br>TATGCCCGCAGCAAGGGATTCAAGGGTAACTTCCTCATTGAGCCCAAGCCCATGGAGCCG<br>TCAAAGCACCAGTATGATGTTGACACCGAGACCGTATGCGGTTTCCTGCGTGCCCACAAC<br>CTTGACAAGGATTTCAAGGTAAATATCGAGGTTAACCATGCTACTCTGGCTGGTCATACT<br>TTCGAGCACGAACTGGCATGCGCTGTTGACGCTGGTATGCTTGGTTCTATCGATGCTAAC<br>CGTGGTGATGCCCAGAATGGCTGGGATACCGACCAGTTCCCCATCAACAACTATGAACTC<br>ACTCAGGCTATGCTTGAGATCATCCGTAATGGTGGTCTGGGTCTTGGCGGCACAAACTTC<br>GATGCCAAGATTCGTCGTAACTCAACAGATCTTGAGGATCTCTTCATCGCTCACATCAGT<br>GGTATGGATGCCATGGCCCGTGCTCTGCTGAATGCTGCTGCTATTCTGGAGGAGAGCGAG<br>CTGCCTAAGATGAAGAAGGAGCGTTATGCTTCTTTCGATGCCGGTATCGGTAAGGACTTC<br>GAGGATGGCAAGCTTACCCTTGAGCAGGCTTACGAGTATGGTAAGAAGGTTGAGGAGCCC<br>AAGCAGACTTCAGGCAAGCAGGAGAAGTACGAGACCATCGTTGCTCTGTATGCAAAATAA |
| 5586MI26_003 | *Prevotella* | Amino Acid | 92 | MAKEYFPFTGKIPFEGKDSKNVMAFHYYEPERVVMGKKMKDWLRFAMAWWHTLGGASADQ<br>FGGQTRSYEWDKAADAVQRAKDKMDAGFEIMDKLGIEFFCWHDIDLVEEGETIEEYERRM<br>KAITDYALEKMQQYPNIKNLWGTANVFGNKRYANGASTNPDFDVVARAIVQIKNAIDATI<br>KLGGQNYVFWGGREGYMSLLNTDQKREKEHMATMLTMARDYARSKGEKGNFLIEPKPMEP<br>SKHQYDVDTETVCGFLRAHNLDKDFKVNIEVNHATLAGHTFEHELACAVDAGMLGSIDAN<br>RGDAQNGWDTDQFPINNYELTQAMLEIIRNGGLGLGGTNFDAKIRRNSTDLEDLFIAHIS<br>GMDAMARALLNAAAILEESELPKMKKERYASFDAGIGKDFEDGKLTLEQAYEYGKKVEEP<br>KQTSGKQEKYETIVALYAK |

TABLE 2-continued

| Clone No. | Class of organism | Type of Sequence | SEQ ID NO: | Sequence |
|---|---|---|---|---|
| 5586MI86_001 | *Prevotella* | DNA | 93 | ATGAAACAGTATTTTCCCCAGATTGGAAAGATACCCTTCGAGGGTGTAGAGAGCAAGAAT<br>GTGATGGCTTTCCACTATTATGAGCCAGAAAGAGTAGTCATGGGCAAGCCTATGAAAGAA<br>TGGCTGCGCTTCGCTATGGCGTGGTGGCACACGCTGGGGCAGGCGAGCGGCGACCCCTTC<br>GGCGGACAGACCCGCAGCTACGAGTGGGACCGTGCGGCCGACGCGCTACAGCGCGCCAAG<br>GACAAGATGGATGCGGGCTTCGAGCTGATGGAGAAGCTTGGCATTGAGTACTTCTGCTTC<br>CACGACGTGGACCTCGTAGAAGAGGGCGCCACGGTGGAGGAATACGAGCGGCGGATGGCT<br>GCCATCACCGACTACGCGGTAGAGAAGATGCGCGAGCATCCCGAGATACACTGCCTGTGG<br>GGCACGGCCAATGTCTTCGGCCACAAGCGCTACATGAACGGAGCCGCCACCAACCCCGAC<br>TTCGACGTGGTGGCGCGTGCGGTGGTGCAGATAAAGAACAGCATCGACGCCACGATCAAG<br>CTGGGCGGCGAGAACTATGTGTTCTGGGGCGGACGCGAGGGATATATGAGCCTGCTCAAC<br>ACCGACCAGCGCCGCGAGAAGGAGCACCTGGCCATGATGCTTGCGAAGGCCCGCGACTAT<br>GGCCGCGCCCACGGCTTCAAGGGCACCTTCCTGATAGAGCCCAAGCCGATGGAGCCCATG<br>AAGCACCAGTACGACGTGGACACCGAGACGGTGATAGGTTTCCTGCGTGCCCACGGACTG<br>GACAAGGACTTCAAGGTGAACATCGAGGTGAACCACGCCACGTTGGCGGGCCACACGTTC<br>GAGCACGAGCTGGCCTGTGCCGTCGATGCCGGCATGCTGGGCAGCATCGACGCCAACCGT<br>GGCGACGCGCAGAACGGATGGGATACGGACCAGTTCCCCATAGACTGCTACGAGCTCACG<br>CAGGCGTGGATGGAGATCATTCGTGGCGGCGGCTTCACCACCGGCGGCACCAACTTCGAC<br>GCTAAGCTGCGCCGCAACTCGACCGACCCCGAGGATATCTTCATAGCTCACATCAGCGGC<br>ATGGATGCTATGGCCCGCGCCCTGCTCTGCGCCGCCGACATCTTGGAGCACAGCGAGCTG<br>CCGGAGATGAAGCGGAAGCGCTATGCCTCGTTCGACAGCGGCATGGGCAAGGAGTTCGAA<br>GAGGGCAATCTCAGCTTCGAGCAAATCTATGCCTACGGCAAGCAGGCGGGCGAACCGGCC<br>ACGACCAGCGGCAAGCAGGAGAAATACGAAGCCATTGTTTCACTTTATACCCGATGA |
| 5586MI86_001 | *Prevotella* | Amino Acid | 94 | MKQYFPQIGKIPFEGVESKNVMAFHYYEPERVVMGKPMKEWLRFAMAWWHTLGQASGDPF<br>GGQTRSYEWDRAADALQRAKDKMDAGFELMEKLGIEYFCFHDVDLVEEGATVEEYERRMA<br>AITDYAVEKMREHPEIHCLWGTANVFGHKRYMNGAATNPDFDVVARAVVQIKNSIDATIK<br>LGGENYVFWGGREGYMSLLNTDQRREKEHLAMMLAKARDYGRAHGFKGTFLIEPKPMEPM<br>KHQYDVDTETVIGFLRAHGLDKDFKVNIEVNHATLAGHTFEHELACAVDAGMLGSIDANR<br>GDAQNGWDTDQFPIDCYELTQAWMEIIRGGGFTTGGTNFDAKLRRNSTDPEDIFIAHISG<br>MDAMARALLCAADILEHSELPEMKRKRYASFDSGMGKEFEEGNLSFEQIYAYGKQAGEPA<br>TTSGKQEKYEAIVSLYTR |
| 5586MI108_002 | *Prevotella* | DNA | 95 | ATGGCAAAAGAGTATTTTCCGTTTATCGGTAAGGTTCCTTTCGAAGGAACAGAGAGCAAG<br>AACGTGATGGCATTCCACTACTATGAGCCCGAAAAGGTGGTCATGGGTAAGAAAATGAAG<br>GACTGGCTGAAGTTCGCTATGGCTTGGTGGCACACACTGGGTGGTGCCAGCGCCGACCAG<br>TTTGGTGGTCAGACTCGCAGCTACGAGTGGGACAAGGCTGCTGATGCCGTTCAGCGCGCC<br>AAGGACAAGATGGATGCTGGCTTCGAGATCATGGATAAGCTCGGCATTGAGTACTTCTGC<br>TTCCATGACGTAGACCTCGTTGAGGAGGGTGAAACCGTCGCTGAGTATGAGGCTCGCATG<br>AAGGTCATCACCGACTATGCCCTGGAGAAGATGCAGCAGTTCCCCAACATCAAACTGCTC<br>TGGGGTACTGCTAACGTGTTCGGCCACAAGCGCTATGCCAACGGTGCCAGCACCAATCCC<br>GACTTCGACGTCGTGGCCCGTGCTATCGTTCAGATCAAGAATGCCATCGATGCTACCATT<br>AAGCTCGGCGGTACGAACTATGTGTTCTGGGGTGGTCGTGAGGGCTACATGAGCCTTCTC<br>AACACCGACCAGAAGCGCGAGAAGGAGCACATGGCAACGATGCTGACCATGGCTCGCGAC<br>TATGCCCGCGCCAAGGGATTCAAGGGCACGTTCCTCATCGAGCCGAAGCCCATGGAGCCC<br>TCGAAGCATCAGTACGACGTCGACACCGAGACCGTCATCGGCTTCCTCCGTGCCCACGGT<br>CTGGATAAGGACTTCAAGGTGAACATCGAGGTGAACCACGCCACGCTGGCCGGTCATACC<br>TTCGAGCACGAACTGGCTTGCGCCGTTGATGCCGGCATGCTCGGCTCTATCGATGCCAAC<br>CGCGGCGACGCTCAGAACGGCTGGGACACCGACCAGTTCCCCATCGACAACTACGAGCTC<br>ACTCAGGCCATGATGGAAATCATCCGTAATGGCGGTCTGGGCAACGGCGGCACGAACTTC<br>GATGCCAAGATCCGTCGTAACAGCACCGACCTCGAGGACCTCTTCATCGCTCACATCAGC<br>GGCATGGATGCCATGGCACGCGCTCTGATGAACGCTGCTGCCATCCTCGAAGAGAGCGAG<br>CTGCCCGCCATGAAGAAGGCCCGCTATGCTTCGTTCGACGAGGGTATCGGCAAGGACTTC<br>GAGGACGGCAAGTTGTCACTTGAGCAGGTCTACGAATATGGTAAGAAGGTTGAGGAGCCC<br>AAGCAGACCTCGGGCAAGCAGGAGAAGTACGAGACCATCGTGGCCCTCTATGCCAAGTAA |
| 5586MI108_002 | *Prevotella* | Amino Acid | 96 | MAKEYFPFIGKVPFEGTESKNVMAFHYYEPEKVVMGKKMKDWLKFAMAWWHTLGGASADQ<br>FGGQTRSYEWDKAADAVQRAKDKMDAGFEIMDKLGIEYFCFHDVDLVEEGETVAEYEARM<br>KVITDYALEKMQQFPNIKLLWGTANVFGHKRYANGASTNPDFDVVARAIVQIKNAIDATI<br>KLGGTNYVFWGGREGYMSLLNTDQKREKEHMATMLTMARDYARAKGFKGTFLIEPKPMEP<br>SKHQYDVDTETVIGFLRAHGLDKDFKVNIEVNHATLAGHTFEHELACAVDAGMLGSIDAN<br>RGDAQNGWDTDQFPIDNYELTQAMMEIIRNGGLGNGGTNFDAKIRRNSTDLEDLFIAHIS<br>GMDAMARALMNAAAILEESELPAMKKARYASFDEGIGKDFEDGKLSLEQVYEYGKKVEEP<br>KQTSGKQEKYETIVALYAK |
| 5586MI182_004 | *Prevotella* | DNA | 97 | ATGGCAAAAGAGTATTTTCCGTTTGTTGGTAAGATTCCTTTCGAGGGAAAGGATAGTAAG<br>AATGTAATGGCTTTCCACTATTACGAACCAGAGAAGGTCGTGATGGGAAAGAAGATGAAG<br>GACTGGCTGAAGTTCGCCATGGCATGGTGGCACACACTGGGACAGGCCAGTGCCGACCCG<br>TTTGGAGGTCAGACCCGCAGCTACGAGTGGGACAAGGCTGACGATGCTGTGCAGCGCGCA<br>AAGGACAAGATGGATGCCGGATTTGAGATCATGGACAAGCTGGGCATCGAGTACTTCTGC<br>TTCCACGATGTAGACCTCGTTGAGGAGGGAGCAACTGTTGAGGAGTACGAGGCTCGCATG<br>AAGGCCATCACCGACTATGCATTGGAGAAGATGAAAGAGTATCCCAACATCAAGAACCTC<br>TGGGGTACAGCCAATGTATTCAGCAACAAGCGCTATATGAACGGTGCCAGCACCAACCCC<br>GACTTCGACGTTGTTGCACGTGCCATCGTACAGATAAAGAACGCCATTGACGCTACCATC<br>AAGCTCGGCGGTCAGAACTACGTGTTCTGGGGCGGACGTGAGGGATACATGAGCCTGCTC<br>AACACCGACCAGAAGCGCGAGAAGGAGCACATGGCAACCATGCTGACCATGGCTCGCGAC |

TABLE 2-continued

| Clone No. | Class of organism | Type of Sequence | SEQ ID NO: | Sequence |
|---|---|---|---|---|
| | | | | TACGCTCGCAAGAACGGTTTCAAGGGCACATTCCTCATCGAGCCTAAGCCCATGGAACCC<br>TCAAAGCACCAGTACGACGTAGACACAGAGACCGTATGCGGTTTCCTCCGCGCCCATGGT<br>CTTGACAAGGATTTCAAGGTGAACATTGAGGTGAACCACGCTACCCTCGCCGGCCACACC<br>TTTGAGCATGAACTGGCTTGCGCCGTCGACAACGGCATGCTCGGCAGCATCGATGCCAAC<br>CGCGGCGACGTTCAGAACGGCTGGGACACCGACCAGTTCCCCATCGACAACTACGAGCTG<br>ACTCAGGCCATGCTCGAAATCATCCGCAACGGTGGTCTGGGCAACGGCGGTACCAACTTC<br>GACGCCAAGATCCGTCGTAACTCTACCGACCTCGAGGATCTGTTCATCGCCCACATCAGC<br>GGTATGGACGCCATGGCACGTGCACTGCTCAATGCAGCAGCCATACTGGAGGAGAGCGAG<br>CTGCCTGCCATGAAGAAGGAGCGTTACGCCAGCTTCGACAGCGGCATCGGCAAGGACTTC<br>GAGGACGGCAAGCTCACACTTGAGCAGGCCTATGAGTATGGTAAGAAGGTTGAGGAGCCA<br>AAGCAGACCTCTGGCAAGCAGGAGAAGTATGAGACTATAGTAGCCCTCTACGCTAAGTAG |
| 5586MI182_004 | *Prevotella* | Amino Acid | 98 | MAKEYFPFVGKIPFEGKDSKNVMAFHYYEPEKVVMGKKMKDWLKFAMAWWHTLGQASADP<br>FGGQTRSYEWDKADDAVQRAKDKMDAGFEIMDKLGIEYFCFHDVDLVEEGATVEEYEARM<br>KAITDYALEKMKEYPNIKNLWGTANVFSNKRYMNGASTNPDFDVVARAIVQIKNAIDATI<br>KLGGQNYVFWGGREGYMSLLNTDQKREKEHMATMLTMARDYARKNGFKGTFLIEPKPMEP<br>SKHQYDVDTETVCGFLRAHGLDKDFKVNIEVNHATLAGHTFEHELACAVDNGMLGSIDAN<br>RGDVQNGWDTDQFPIDNYELTQAMLEIIRNGGLGNGGTNFDAKIRRNSTDLEDLFIAHIS<br>GMDAMARALLNAAAILEESELPAMKKERYASFDSGIGKDFEDGKLTLEQAYEYGKKVEEP<br>KQTSGKQEKYETIVALYAK |
| 5586MI193_004 | *Prevotella* | DNA | 99 | ATGACTAAAGAGTATTTCCCTACCATTGGCAAGATTCCCTTTGAGGGACCTGAAAGCAAG<br>AACCCGCTTGCATTCCATTACTATGAGCCCGACCGCCTGGTCATGGGCAAGAAGATGAAA<br>GACTGGCTGCGTTTCGCCATGGCCTGGTGGCACACCCTGGGCCAGGCCTCCGGCGACCAG<br>TTCGGCGGCCAGACCCGCCACTATGCCTGGGATGATCCGGATTGCCCGTATGCACGTGCC<br>AAAGCCAAGGCCGACGCCGGTTTCGAAATCATGCAGAAACTGGGCATTGAATTCTTCTGC<br>TTCCACGACATCGACCTGGTCGAGGATGCCGATGAAATCGCCGAGTACGAGGCCCGGATG<br>AAGGACATCACCGACTATCTGCTCGTCAAGATGAAAGAGACCGGCATCAAGAACCTTTGG<br>GGAACGGCCAACGTATTTGGCCACAAGCGCTACATGAACGGCGCCGCCACCAACCCCGAT<br>TTCGACGTGCTGGCCCGTGCCGCCGTCCAGATCAAGAACGCCATCGACGCCACCATCAAG<br>TTGGGCGGTCAGAACTATGTGTTCTGGGGCGGCCGTGAAGGCTACCAGACCCTGCTCAAT<br>ACCCAGATGCAGCGCGAGAAGGAACACATGGGCCGTATGTTGGCACTGGCCCGCGACTAT<br>GGCCGTGCACACGGTTTCAAGGGCACGTTCCTCATCGAGCCCAAACCGATGGAGCCGACC<br>AAGCACCAGTACGATCAGGATACGGAAACCGTCATCGGCTTCCTGCGCCGCCATGGCCTC<br>GACAAGGACTTCAAGGTCAACATCGAGGTGAACCATGCTACCCTGGCGGGCCACACCTTC<br>GAGCACGAGCTGGCTTGCGCCGTCGACCACGGCATGCTGGGCAGCATCGACGCCAACCGG<br>GGTGATGCCCAGAACGGCTGGGACACCGACCAGTTCCCGATCGATAACTATGAGCTGACG<br>CTGGCCATGCTCCAGATCATCCGCAACGGCGGCCTGGCACCCGGCGGCTCGAACTTCGAT<br>GCGAAGCTGCGTCGCAACTCCACCGATCCGGAAGATATCTTCATCGCGCACATCAGCGCC<br>ATGGATGCCATGGCCCGCGCCCTGGTCAATGCTGTCGCCATTCTCGAGGAATCGCCCATC<br>CCGGCCATGGTCAGGGAACGTTACGCCTCGTTCGACAGCGGAAAGGGCAGGGAATATGAG<br>GAAGGCAGGCTGTCTCTCGAAGACATCGTGGCCTATGCCAAAGCCCACGGCGAACCGAAA<br>CAGATTTCCGGCAAGCAGGAACTCTACGAAACCATCGTGGCTCTCTATTGCAAGTAG |
| 5586MI193_004 | *Prevotella* | Amino Acid | 100 | MTKEYFPTIGKIPFEGPESKNPLAFHYYEPDRLVMGKKMKDWLRFAMAWWHTLGQASGDQ<br>FGGQTRHYAWDDPDCPYARAKAKADAGFEIMQKLGIEFFCFHDIDLVEDADEIAEYEARM<br>KDITDYLLVKMKETGIKNLWGTANVFGHKRYMNGAATNPDFDVLARAAVQIKNAIDATIK<br>LGGQNYVFWGGREGYQTLLNTQMQREKEHMGRMLALARDYGRAHGFKGTFLIEPKPMEPT<br>KHQYDQDTETVIGFLRRHGLDKDFKVNIEVNHATLAGHTFEHELACAVDHGMLGSIDANR<br>GDAQNGWDTDQFPIDNYELTLAMLQIIRNGGLAPGGSNFDAKLRRNSTDPEDIFIAHISA<br>MDAMARALVNAVAILEESPIPAMVRERYASFDSGKGREYEEGRLSLEDIVAYAKAHGEPK<br>QISGKQELYETIVALYCK |
| 5586MI195_003 | *Prevotella* | DNA | 101 | ATGGCAAAAGAGTATTTCCCGCAGATCGGAAAGATCGGCTTTGAGGGTCCTGCAAGCAAG<br>AACCCGCTGGCATTCCATTATTATGACGCCGAGCGCGTGGTGATGGGTAAACCCATGAAA<br>GACTGGTTTAAATTCGCCCTCGCGTGGTGGCACAGCCTCGGCCAGGCCTCCGGCGACCCG<br>TTCGGCGGCCAGACCCGCTCCTACGAGTGGGACAAGGGCGAATGCCCCTACTGCCGCGCC<br>CGCGCCAAGGCGGACGCCGGCTTCGAGATCATGCAAAAGCTCGGCATCGGCTATTTCTGC<br>TTCCACGACGTCGACCTCATCGAAGACACGGACGACATCGCCGAATATGAGGCCCGCCTC<br>AAGGACATCACGGACTACCTGCTCGAAAGGATGCAGGAAACCGGCATCAAGAACCTCTGG<br>GGCACGGCCAATGTCTTCGGTCACAAGCGCTACATGAACGGCGCCGGCACCAATCCGCAG<br>TTCGACATCGTCGCCCGCGCTGCCGTCCAGATCAAGAACGCCCTCGACGCCACCATCAAG<br>CTCGGTGGCTCGAACTACGTCTTCTGGGGCGGCCGCGAAGGTTATTACACGCTGCTCAAC<br>ACCCAGATGCAGCGCGAGAAAGACCACCTCGCCAAGCTCCTCACCGCCGCCCGCGACTAT<br>GCCCGCGCCAAGGGCTTCCAGGGCACCTTCCTGATCGAGCCCAAGCCGATGGAGCCGACC<br>AAGCACCAGTACGATGTCGACACGGAGACTGTAATCGGATTCCTCCGCGCCAACGGACTG<br>GACAAGGACTTCAAGGTCAACATCGAGGTCAACCACGCCACCCTCGCCGGCCATACCTTC<br>GAGCATGAGCTGACCGTCGCCCGCGAGAACGGATTCCTCGGCAGCATCGACGCCAACCGC<br>GGTGACGCCCAGAACGGCTGGGACACCGACCAGTTCCCCGTGGACGCCTACGACCTCACC<br>CAGGCCATGATGCAGGTGCTCCTGAACGGCGGTTTCGGCAACGGCGGCACCAATTTCGAC<br>GCCAAGCTCCGTCGCAGCTCCACCGATCCCGAGGACATCTTCATCGCCCACATCAGCGCG<br>ATGGACGCCATGGCCCACGCCCTGCTGAACGCCGCGGCCATTCTCGAGGAGAGCCCGCTG<br>CCCGCGATGGTCAAGGAGCGTTACGCCTCCTTCGACAGCGGTCTCGGCAAGCAGTTCGAG<br>GAGGGAAAGGCCACGCTGGAGGACCTCTACGACTACGCCAAGGCCCATGGCGAGCCCGTC<br>GCCGCCTCCGGCAAGCAGGAACTGTGTGAAACTTACCTGAATCTGTATGCAAAGTAA |

TABLE 2-continued

| Clone No. | Class of organism | Type of Sequence | SEQ ID NO: | Sequence |
|---|---|---|---|---|
| 5586MI195_003 | *Prevotella* | Amino Acid | 102 | MAKEYFPQIGKIGFEGPASKNPLAFHYYDAERVVMGKPMKDWFKFALAWWHSLGQASGDP<br>FGGQTRSYEWDKGECPYCRARAKADAGFEIMQKLGIGYFCFHDVDLIEDTDDIAEYEARL<br>KDITDYLLERMQETGIKNLWGTANVFGHKRYMNGAGTNPQFDIVARAAVQIKNALDATIK<br>LGGSNYVFWGGREGYYTLLNTQMQREKDHLAKLLTAARDYARAKGFQGTFLIEPKPMEPT<br>KHQYDVDTETVIGFLRANGLDKDFKVNIEVNHATLAGHTFEHELTVARENGFLGSIDANR<br>GDAQNGWDTDQFPVDAYDLTQAMMQVLLNGGEGNGGTNEDAKLRRSSTDPEDIFIAHISA<br>MDAMAHALLNAAAILEESPLPAMVKERYASFDSGLGKQFEEGKATLEDLYDYAKAHGEPV<br>AASGKQELCETYLNLYAK |
| 5586MI196_003 | *Prevotella* | DNA | 103 | ATGACAAAAGAGTATTTCCCTACCATCGGCAAGATCCCCTTTGAGGGACCCGAGAGCAAA<br>AACCCCCTCGCTTTTCATTACTATGAGCCCGACCGCCTGGTCATGGGCAAGAAGATGAAA<br>GACTGGCTGCGTTTCGCCATGGCCTGGTGGCACACCCTGGGCCAGGCCTCCGGCGACCAG<br>TTTGGCGGCCAGACCCGCCACTATGCCTGGGATGATCCGGATTGCCCGTATGCACGTGCC<br>AAAGCCAAGGCCGACGCCGGTTTCGAAATCATGCAGAAACTGGGCATTGAATTCTTCTGC<br>TTCCACGACATCGACCTGATCGAGGATACCGATGACATCGTCGAGTATGAGGCCCGGATG<br>AAGGACATCACCGACTATCTGCTGGTCAAGATGAAAGAGACCGGCATCAAGAATCTCTGG<br>GGAACGGCCAACGTATTCGGGCACAAGCGCTATATGAACGGCGCTGCCACCAACCCCGAT<br>TTCGACGTGCTGGCCCGTGCCGCCGTCCAGATCAAGAACGCCATCGACGCCACCATCAAG<br>CTGGGCGGCCAGAATTATGTGTTCTGGGGCGGGCGTGAAGGCTACCAGAGCCTGCTCAAT<br>ACCCAGATGCAGCGCGAAAAGGAACACATGGGCCGTATGTTGGCACTAGCCCGCGACTAT<br>GGCCGTGCACACGGTTTCAAGGGCACGTTCCTCATCGAGCCCAAACCGATGGAGCCGACC<br>AAGCACCAGTACGATCAGGATACGGAGACCGTCATCGGTTTTCTGCGCCGCCATGGCCTC<br>GACAAGGACTTCAAGGTCAACATCGAGGTGAACCATGCTACCCTGGCGGGCCACACCTTC<br>GAGCACGAGCTGGCCTGCGCCGTCGACCACGGCATGCTGGGCAGTATTGACGCCAACCGC<br>GGTGACGCCCAGAACGGCTGGGACACCGACCAGTTCCCGATCGATAACTATGAGCTGACG<br>CTGGCCATGCTCCAGATCATCCGCAACGGCGGCCTGGCACCCGGCGGCTCGAACTTCGAT<br>GCGAAGCTGCGTCGCAACTCCACCGATCCGGAAGATATCTTCATCGCGCACATCAGCGCC<br>ATGGATGCCATGGCCCGCGCCCTGGTCAACGCTGTCGCCATTCTTGAGGAATCGCCCATT<br>CCGGACATGGTCAAGGAGCGCTACGCTTCGTTCGACAGCGGAAAAGGCAGGGAGTACGAA<br>GAGGGGAAACTTTCCTTCGAGGACCTCGTGGCCTATGCCAAAGCCCACGGCGAACCGAAA<br>CAGATTTCCGGCAAGCAGGAACTCTACGAAACCATCGTGGCTCTCTATTGCAAGTAG |
| 5586MI196_003 | *Prevotella* | Amino Acid | 104 | MTKEYFPTIGKIPFEGPESKNPLAFHYYEPDRLVMGKKMKDWLRFAMAWWHTLGQASGDQ<br>FGGQTRHYAWDDPDCPYARAKAKADAGFEIMQKLGIEFFCFHDIDLIEDTDDIVEYEARM<br>KDITDYLLVKMKETGIKNLWGTANVFGHKRYMNGAATNPDFDVLARAAVQIKNAIDATIK<br>LGGQNYVFWGGREGYQSLLNTQMQREKEHMGRMLALARDYGRAHGFKGTFLIEPKPMEPT<br>KHQYDQDTETVIGFLRRHGLDKDFKVNIEVNHATLAGHTFEHELACAVDHGMLGSIDANR<br>GDAQNGWDTDQFPIDNYELTLAMLQIIRNGGLAPGGSNFDAKLRRNSTDPEDIFIAHISA<br>MDAMARALVNAVAILEESPIPDMVKERYASFDSGKGREYEEGKLSFEDLVAYAKAHGEPK<br>QISGKQELYETIVALYCK |
| 5586MI197_003 | *Prevotella* | DNA | 105 | ATGACAAAAGAGTATTTCCCTACCATCGGCAAGATCCCCTTTGAGGGACCCGAGAGCAAA<br>AACCCCCTCGCTTTTCATTACTATGAGCCCGACCGCCTGGTCATGGGCAAGAAGATGAAA<br>GACTGGCTGCGTTTCGCCATGGCCTGGTGGCACACCCTGGGCCAGGCCTCCGGCGACCAG<br>TTTGGCGGCCAGACCCGCCACTATGCCTGGGATGATCCGGATTGCCCGTATGCACGTGCC<br>AAAGCCAAGGCCGACGCCGGTTTCGAAATCATGCAGAAACTGGGCATTGAATTCTTCTGC<br>TTCCACGACATCGACCTGATCGAGGATACCGATGACATCGTCGAGTATGAGGCCCGGATG<br>AAGGACATCACCGACTATCTGCTGGTCAAGATGAAAGAGACCGGCATCAAGAATCTCTGG<br>GGAACGGCCAACGTATTCGGGCACAAGCGCTATATGAACGGCGCTGCCACCAACCCCGAT<br>TTCGACGTGCTGGCCCGTGCCGCCGCCCAGATCAAGAACGCCATCGACGCCACCATCAAG<br>CTGGGCGGCCAGAATTATGTGTTCTGGGGCGGGCGTGAAGGCTACCAGAGCCTGCTCAAT<br>ACCCAGATGCAGCGCGAAAAGGAACACATGGGCCGTATGTTGGCACTAGCCCGCGACTAT<br>GGCCGTGCACACGGTTTCAAGGGCACGCTCCTCATCGAGCCCAAACCGATGGAGCCGACC<br>AAGCACCAGTACGATCAGGATACGGAGACCGTCATCGGTTTTCTGCGCCGCCATGGCCTC<br>GACAAGGACTTCAAGGTCAACATCGAGGTGAACCATGCTACCCTGGCGGGCCACACCTTC<br>GAGCACGAGCTGGCCTGCGCCGTCGACCACGGCATGCTGGGCAGTATTGACGCCAACCGC<br>GGTGACGCCCAGGACGGCTGGGACACCGACCAGTTCCCGATCGATAACTATGAGCTGACG<br>CTGGCCATGCTCCAGATCATCCGCAACGGCGGCCTGGCACCCGGCGGCTCGAACTTCGAT<br>GCGAAGCTGCGTCGCAACTCCACCGATCCGGAAGATATCTTCATCGCGCACATCAGCGCC<br>ATGGATGCCATGGCCCGCGCCCTGGTCAACGCTGTCGCCATTCTTGAGGAATCGCCCATT<br>CCGGACATGGTCAAGGAGCGCTACGCTTCGTTCGACAGCGGAAAAGGCAGGGAGTACGAA<br>GAGGGGAAACTTTCCTTCGAGGACCTCGTGGCCTATGCCAAAGCCCACGGCGAACCGAAA<br>CAGATTTCCGGCAAGCAGGAACTCTACGAAACCATCGTGGCTCTCTATTGCAAGTAG |
| 5586MI197_003 | *Prevotella* | Amino Acid | 106 | MTKEYFPTIGKIPFEGPESKNPLAFHYYEPDRLVMGKKMKDWLRFAMAWWHTLGQASGDQ<br>FGGQTRHYAWDDPDCPYARAKAKADAGFEIMQKLGIEFFCFHDIDLIEDTDDIVEYEARM<br>KDITDYLLVKMKETGIKNLWGTANVFGHKRYMNGAATNPDFDVLARAAAQIKNAIDATIK<br>LGGQNYVFWGGREGYQSLLNTQMQREKEHMGRMLALARDYGRAHGFKGTLLIEPKPMEPT<br>KHQYDQDTETVIGFLRRHGLDKDFKVNIEVNHATLAGHTFEHELACAVDHGMLGSIDANR<br>GDAQDGWDTDQFPIDNYELTLAMLQIIRNGGLAPGGSNFDAKLRRNSTDPEDIFIAHISA<br>MDAMARALVNAVAILEESPIPDMVKERYASFDSGKGREYEEGKLSFEDLVAYAKAHGEPK<br>QISGKQELYETIVALYCK |
| 5586MI199_003 | *Prevotella* | DNA | 107 | ATGACAAAAGAGTATTTCCCTACCATCGGCAAGATCCCCTTTGAGGGACCCGAGAGCAAA<br>AACCCCCTCGCTTTTCATTACTATGAGCCCGACCGCCTGGTCATGGGCAAGAAGATGAAA<br>GACTGGCTGCGTTTCGCCATGGCCTGGTGGCACACCCTGGGCCAGGCCTCCGGCGACCAG |

TABLE 2-continued

| Clone No. | Class of organism | Type of Sequence | SEQ ID NO: | Sequence |
|---|---|---|---|---|
| | | | | TTTGGCGGCCAGACCCGCCACTATGCCTGGGATGATCCGGATTGCCCGTATGCACGTGCC<br>AAAGCCAAGGCCGACGCCGGTTTCGAAATCATGCAGAAACTGGGCATTGAATTCTTCTGC<br>TTCCACGACATCGACCTGATCGAGGATACCGATGACATCGTCGAGTATGAGGCCCGGATG<br>AAGGACATCACCGACTATCTGCTGGTCAAGATGAAAGAGACCGGCATCAAGAATCTCTGG<br>GGAACGGCCAACGTATTCGGGCACAAGCGCTATATGAACGGCGCTGCCACCAACCCCGAT<br>TTCGACGTGCTGGCCCGTGCCGCCGTCCAGATCAAGAACGCCATCGACGCCACCATCAAG<br>CTGGGCGGCCAGAATTATGTGTTCTGGGGCGGGCGTGAAGGCTACCAGAGCCTGCTCAAT<br>ACCCAGATGCAGCGCGAAAAGGAACACATGGGCCGTATGTTGGCACTAGCCCGCGACTAT<br>GGCCGTGCACACGGTTTCAAGGGCACGTTCCTCATCGAGCCCAAACCGATGGAGCCGACC<br>AAGCACCAGTACGATCAGGATACGGAGACCGTCATCGGTTTTCTGCGCCGCCATGGCCTC<br>GACAAGGACTTCAAGGTCAACATCGAGGTGAACCATGCTACCCTGGCGGGCCACACCTTC<br>GAGCACGAGCTGGCCTGCGCCGTCGACCACGGCATGCTGGGCAGTATTGACGCCAACCGC<br>GGTGACGCCCAGAACGGCTGGGACACCGACCAGTTCCCGATCGATAACTATGAGCTGACG<br>CTGGCCATGCTCCAGATCATCCGCAACGGCGGCCTGGCACCCGGCGGCTCGAACTTCGAT<br>GCGAAGCTGCGTCGCAACTCCACCGATCCGGAAGATGTCTTCATCGCGCACATCAGCGCC<br>ATGGATGCCATGGCCCGCGCCCTGGTCAACGCTGTCGCCATTCTTGAGGAATCGCCCATT<br>CCGGACATGGTCAAGGAGCGCTACGCTTCGTTCGACAGCGGAAAAGGCAGGGAGTACGAA<br>GAGGGGAAACTTTCCTTCGAGGACCTCGTGGCCTATGCCAAAGCCCACGGCGAACCGAAA<br>CAGATTTCCGGCAAGCAGGAACTCTACGAAACCATCGTGGCTCTCTATTGCAAGTAG |
| 5586MI199_003 | *Prevotella* | Amino Acid | 108 | MTKEYFPTIGKIPFEGPESKNPLAFHYYEPDRLVMGKKMKDWLRFAMAWWHTLGQASGDQ<br>FGGQTRHYAWDDPDCPYARAKAKADAGFEIMQKLGIEFFCFHDIDLIEDTDDIVEYEARM<br>KDITDYLLVKMKETGIKNLWGTANVFGHKRYMNGAATNPDFDVLARAAVQIKNAIDATIK<br>LGGQNYVFWGGREGYQSLLNTQMQREKEHMGRMLALARDYGRAHGFKGTFLIEPKPMEPT<br>KHQYDQDTETVIGFLRRHGLDKDFKVNIEVNHATLAGHTFEHELACAVDHGMLGSIDANR<br>GDAQNGWDTDQFPIDNYELTLAMLQIIRNGGLAPGGSNFDAKLRRNSTDPEDVFIAHISA<br>MDAMARALVNAVAILEESPIPDMVKERYASFDSGKGREYEEGKLSFEDLVAYAKAHGEPK<br>QISGKQELYETIVALYCK |
| 5586MI200_003 | *Prevotella* | DNA | 109 | ATGGCAAAAGAGTATTTCCCGACAATCGGAAAGATCCCCTTCGAGGGCGTTGAGAGCAAG<br>AATCCCCTTGCTTTCCATTATTATGACGCCGAGCGCGTGGTCATGGGCAAGCCCATGAAG<br>GACTGGTTCAAGTTCGCGATGGCCTGGTGGCACACCCTGGGCCAGGCTTCCGCGGACCCG<br>TTCGGCGGCCAGACCCGCTCCTACGAGTGGGACAAGGGCGAGTGCCCCTACTGCCGCGCC<br>CGCGCCAAGGCTGACGCCGGCTTCGAGATCATGCAGAAGCTCGGAATCGGCTACTATTGC<br>TTCCACGACATCGACCTGGTGGAGGACACCGAGGACATCGCCGAATACGAGGCCCGCATG<br>AAGGACATCACCGACTACCTCGTCGAGAAGCAGAAGGAGACCGGCATCAAGAACCTCTGG<br>GGCACCGCGAACGTGTTCGGCAACAAGCGCTACATGAACGGCGCCGCCACGAACCCGCAG<br>TTCGACATCGTCGCCCGCGCGGCCCTGCAGATCAAGAACGCGATCGATGCCACCATCAAG<br>CTCGGCGGCACCGGCTACGTGTTCTGGGGCGGCCGGGAAGGCTACTACACCCTGCTGAAC<br>ACCCAGATGCAGCGCGAGAAGGACCACCTCGCCAAGATGCTCACCGCCGCCCGCGACTAC<br>GCCCGCGCCAACGGCTTCAAGGGCACCTTCCTCATCGAGCCCAAGCCGATGGAGCCCACC<br>AAGCACCAATACGACGTGGACACGGAGACCGTGATCGGCTTCCTCCGCGCCAATGGCCTG<br>GACAAGGACTTCAAGGTGAACATCGAGGTGAACCACGCCACCCTCGCCGGCCACACCTTC<br>GAGCACGAGCTCACCGTGGCCGTTGACAACGGCTTCCTCGGCAGCATCGACGCCAACCGC<br>GGCGACGCCCAGAACGGCTGGGATACCGACCAGTTCCCGGTGGATCCGTACGATCTCACC<br>CAGGCGATGATCCAGATCATCCGCAACGGCGGCTTCAAGGACGGCGGCACCAACTTCGAC<br>GCCAGGCTCCGCCGCTCTTCCACCGACCCGGAGGACATCTTCATCGCCCACATCAGCGCG<br>ATGGACGCCATGGCCCACGCCCTGCTGAACGCCGCCGCCGTCATCGAGGAGAGCCCGCTC<br>TGCGAGATGGTCGCCAAGCGTTACGCTTCCTTCGACAGCGGCCTCGGCAAAAAGTTCGAG<br>GAAGGCAAGGCCACCCTCGAGGAACTCTACGAGTATGCCAAGGCGAACGGTGAGGTCAAG<br>GCCGAATCCGGCAAGCAGGAGCTCTACGAGACCCTTCTGAACCTCTACGCGAAATAG |
| 5586MI200_003 | *Prevotella* | Amino Acid | 110 | MAKEYFPTIGKIPFEGVESKNPLAFHYYDAERVVMGKPMKDWFKFAMAWWHTLGQASADP<br>FGGQTRSYEWDKGECPYCRARAKADAGFEIMQKLGIGYYCFHDIDLVEDTEDIAEYEARM<br>KDITDYLVEKQKETGIKNLWGTANVFGNKRYMNGAATNPQFDIVARAALQIKNAIDATIK<br>LGGTGYVFWGGREGYYTLLNTQMQREKDHLAKMLTAARDYARANGFKGTFLIEPKPMEPT<br>KHQYDVDTETVIGFLRANGLDKDFKVNIEVNHATLAGHTFEHELTVAVDNGFLGSIDANR<br>GDAQNGWDTDQFPVDPYDLTQAMIQIIRNGGFKDGGTNFDARLRRSSTDPEDIFIAHISA<br>MDAMAHALLNAAAVIEESPLCEMVAKRYASFDSGLGKKFEEGKATLEELYEYAKANGEVK<br>AESGKQELYETLLNLYAK |
| 5586MI203_003 | *Prevotella* | DNA | 111 | ATGGCACAAGCGTATTTTCCTACCATCGGGAAAATCCCCTTCGAGGGACCCGAAAGCAAG<br>AATCCCCTGGCATTCCATTATTATGAGCCCGACCGCCTGGTCCTGGGCAAGAAGATGAAG<br>GACTGGCTGCGTTTCGCCATGGCCTGGTGGCACACGCTGGGCCAGGCTTCCGGCGACCAG<br>TTCGGCGGCCAGACCCGCCACTACGCCTGGGACGAGCCCGCCACGCCCCTGGAACGGGCC<br>AAGGCCAAGGCGGATGCCGGTTTCGAGATCATGCAGAAACTGGGCATCGAATTCTTCTGC<br>TTCCACGATGTGGACCTCATCGAAGAGGGCGCCACGATCGAGGAATACGAGCAGCGGATG<br>CAGCAGATCACGGATTATCTGCTGGTCAAGATGAAAGAGACCGGCATCCGCAACCTCTGG<br>GGTACGGCCAACGTGTTCGGACACGAGCGCTACATGAACGGCGCGGCCACGAACCCCGAT<br>TTCGATGTCGTGGCCCGCGCGGCCGTGCAGATCAAGACGGCCATCGACGCCACCATCAAG<br>TTGGGCGGCGAGAACTATGTGTTCTGGGGCGGCCGGGAAGGCTATATGAGCCTGCTCAAT<br>ACGCAGATGCACCGCGAGAAGCTGCATCTGGGCAAGATGCTCGCCGCGGCCCGCGACTAC<br>GGACGCGCCCACGGCTTCAAGGGGACCTTCCTCATCGAACCCAAGCCGATGGAACCCACC<br>AAGCATCAGTATGACCAGGATACGGAGACGGTCATCGGTTTCCTGCGCCGCTACGGCCTG<br>GACGAAGACTTCAAGGTGAACATCGAGGTCAACCACGCTACGCTGGCCGGCCATACCTTC<br>GAACACGAACTGGCCACGGCGGTCGATGCCGGCCTGCTGGGCAGCATCGACGCCAACCGC |

TABLE 2-continued

| Clone No. | Class of organism | Type of Sequence | SEQ ID NO: | Sequence |
|---|---|---|---|---|
| | | | | GGCGACGCCCAGAACGGCTGGGATACCGACCAGTTCCCGATCGACAACTACGAACTGACC<br>CTGGCGATGCTGCAGGTCATCCGCAACGGCGGTCTGGCCCCGGGCGGCTCGAATTTCGAT<br>GCCAAGCTCCGCCGGAACTCCACCGATCCGGAAGACATCTTCATTGCCCACATCAGCGCG<br>ATGGATGCGATGGCGCGGGCCCTGCTCAATGCGGCCGCCCTCTGCGAGACGTCCCCGATT<br>CCGGCGATGGTCAAGGCGCGTTACGCTTCGTTCGACAGCGGCGCCGGCAAGGATTTCGAA<br>GAGGGAAGGATGACGCTGGAAGACCTCGTGGCCTATGCCAGGACCCACGGCGAGCCGAAG<br>CGGACCTCGGGCAAGCAGGAACTCTATGAGACCCTCGTGGCGCTTTATTGCAAATAG |
| 5586MI203_003 | *Prevotella* | Amino Acid | 112 | MAQAYFPTIGKIPFEGPESKNPLAFHYYEPDRLVLGKKMKDWLRFAMAWWHTLGQASGDQ<br>FGGQTRHYAWDEPATPLERAKAKADAGFEIMQKLGIEFFCFHDVDLIEEGATIEEYEQRM<br>QQITDYLLVKMKETGIRNLWGTANVFGHERYMNGAATNPDFDVVARAAVQIKTAIDATIK<br>LGGENYVFWGGREGYMSLLNTQMHREKLHLGKMLAAARDYGRAHGFKGTFLIEPKPMEPT<br>KHQYDQDTETVIGFLRRYGLDEDFKVNIEVNHATLAGHTFEHELATAVDAGLLGSIDANA<br>GDAQNGWDTDQFPIDNYELTLAMLQVIRKGGLAPGGSNFDAKLRRNSTDPEDIFIAHISA<br>MDAMARALLNAAALCETSPIPAMVKARYASFDSGAGKDFEEGRMTLEDLVAYARTHGEPK<br>RTSGKQELYETLVALYCK |
| 5586MI205_004 | *Prevotella* | DNA | 113 | ATGACCAACGAGTATTTTCCCGGAATCGGTGTGATTCCGTTTGAAGGACAGGAAAGCAAG<br>AATCCCCTGGCTTTCCATTATTATGACGCCAACCGCGTAGTGATGGGCAAACCCATGAAG<br>GAATGGTTCAAATTTGCCATGGCCTGGTGGCATACGCTGGGGCAGGCATCGGCCGATCCC<br>TTCGGCGGACAGACCCGCTCCTACGCATGGGACAAGGGCGAGTGCCCTTACTGCCGTGCC<br>CGCCAGAAGGCCGACGCCGGCTTTGAACTGATGCAGAAGCTGGGAATCGGCTATTTCTGC<br>TTCCACGATGTGAATATCATCGAGGACTGCGAGGACATTGCCGAGTATGAGGCCCGTATG<br>AAGGACATCACGGACTATCTGCTGGTGAAGATGAAGGAAACGGGCATCAAGAATCTGTGG<br>GGCACGGCCAACGTCTTCGGCCACAAGCGCTATATGAACGGCGCCGCCACCAACCCGCAA<br>TTCGACGTGGTAGCCCGCGCTGCGGTCCAGATCAAGAACGCCCTGGACGCCACCATCAAG<br>CTGGGCGGCAGCAATTATGTGTTCTGGGGCGGCCGGGAAGGCTACTACACCCTTTTGAAC<br>ACGCAGATGCAGCGGGAGAAGGACCACCTGGCCCAGATGCTCAAGGCGGCCCGCGACTAT<br>GCCCGCGGCAAGGGATTCAAGGGCACGTTCCTCATTGAGCCCAAGCCCATGGAGCCCACC<br>AAGCACCAGTACGACGTAGATACGGAGACCGTGATTGGTTTCCTGCGCGCCAACGGGCTG<br>GACAAGGACTTCAAGGTGAATATCGAAGTGAACCACGCCACCCTGGCCGGCCATACCTTC<br>GAGCACGAGCTCACCGTGGCCCGCGAAAACGGCTTCCTGGGCAGCATCGACGCCAACCGC<br>GGAGACGCCCAGAACGGCTGGGATACAGACCAGTTCCCCGTGGACGCCTTTGACCTCACC<br>CAGGCCATGATGCAGGTCCTGCTCAACGGCGGATTCGGCAACGGCGGCACCAACTTCGAC<br>GCCAAACTGCGCCGTTCCTCCACGGATCCCGAGGACATCTTCATCGCCCACATCAGCGCC<br>ATGGACGCCATGGCCCACGCCCTCCTGAACGCCGCCGCCATCCTGGAAGAGAGCCCCATG<br>CCGGGCATGGTGAAGGAGCGCTACGCTTCCTTCGACAATGGCCTTGGCAAGAAGTTCGAG<br>GAAGGAAAGGCCACGCTGGAAGAGCTGTACGACTATGCCAAGAAGAACGGCGAGCCTGTG<br>GCCGCTTCCGGAAAGCAGGAACTGTACGAAACGCTGCTGAACCTGTACGCCAAGTAA |
| 5586MI205_004 | *Prevotella* | Amino Acid | 114 | MTNEYFPGIGVIPFEGQESKNPLAFHYYDANRVVMGKPMKEWFKFAMAWWHTLGQASADP<br>FGGQTRSYAWDKGECPYCRARQKADAGFELMQKLGIGYFCFHDVNIIEDCEDIAEYEARM<br>KDITDYLLVKMKETGIKNLWGTANVFGHKRYMNGAATNPQFDVVARAAVQIKNALDATIK<br>LGGSNYVFWGGREGYYTLLNTQMQREKDHLAQMLKAARDYARGKGFKGTFLIEPKPMEPT<br>KHQYDVDTETVIGFLRANGLDKDEKVNIEVNHATLAGHTFEHELTVARENGFLGSIDANR<br>GDAQNGWDTDQFPVDAFDLTQAMMQVLLNGGFGNGGTNFDAKLRRSSTDPEDIFIAHISA<br>MDAMAHALLNAAAILEESPMPGMVKERYASFDNGLGKKFEEGKATLEELYDYAKKNGEPV<br>AASGKQELYETLLNLYAK |
| 5586MI206_004 | *Prevotella* | DNA | 115 | ATGGCAAAAGAGTATTTCCCGACTATCGGCAAGATTCCCTTCGAGGGCGTCGAATCCAAG<br>AACCCGATGGCATTCCACTATTATGACGCGAAACGCGTCGTGATGGGCAAGCCCATGAAG<br>GACTGGCTCAAGTTCGCGATGGCCTGGTGGCACACCCTGGGACAGGCTTCCGGCGACCCG<br>TTCGGCGGCCAGACCCGTTCCTACGAGTGGGACAAGGGCGAGTGCCCCTACTGCCGCGCC<br>AAGGCCAAGGCCGACGCCGGTTTCGAGATCATGCAGAAACTGGGCATCGAGTACTACTGC<br>TTCCATGACATCGACCTGGTGGAGGACACCGAGGACATCGCCGAGTACGAGGCCCGCATG<br>AAGGACATCACCGACTACCTCGTCGAGAAGCAGAAGGAGACCGGTATCAAGAACCTCTGG<br>GGCACGGCCAACGTGTTCGGCAACAAGCGCTACATGAACGGCGCCGCCACGAACCCGCAG<br>TTCGACGTCGTCGCCCGCGCCGCCGTCCAGATCAAGAACGCCATCGACGCCACCATCAAA<br>CTCGGCGGCACCTCTTACGTGTTCTGGGGCGGCCGTGAAGGCTACTACACCCTCCTGAAC<br>ACCCAGATGCAGCGCGAGAAGGACCACCTCGCCAAGATGCTCACCGCCGCCCGCGACTAC<br>GCCCGCGCCCACGGCTTCAAGGGCACCTTCCTCATCGAGCCCAAGCCCATGGAGCCCACC<br>AAGCACCAGTACGACGTGGACACGGAGACCGTGATCGGCTTCCTCCGCGCCAACGGCCTG<br>GACAAGGACTTCAAGGTCAATATCGAAGTGAACCACGCCACCCTCGCCGGCCACACCTTC<br>GAGCATGAGCTCACCGTGGCGGTCGATAACGGCTTCCTCGGCTCCATCGACGCCAACCGT<br>GGCGACGCCCAGAACGGCTGGGATACCGACCAGTTCCCGGTGGATCCGTACGACCTCACC<br>CAGGCCATGATGCAGATCATCCGCAACGGCGGCTTCAAGGACGGCGGCACCAACTTCGAC<br>GCCAAACTCCGCCGCTCCTCCACCGACCCGGAGGACATCTTCATCGCCCACATCAGCGCG<br>ATGGACGCCATGGCCCACGCGCTCCTGAACGCCGCCGCCGTCATCGAGGAGAGCCCGCTC<br>TGCAAGATGGTCGAGGAGCGCTACGCTTCCTTCGACAGCGGTCTCGGCAAGCAGTTCGAG<br>GAAGGCAAGGCCACCCTTGAGGACCTCTACGAGTATGCCAAGAAGAACGGCGAGCCCGTC<br>GTCGCTTCCGGCAAGCAGGAGCTCTACGAGACCCTTCTGAACCTCTACGCGAAGTAG |
| 5586MI206_004 | *Prevotella* | Amino Acid | 116 | MAKEYFPTIGKIPFEGVESKNPMAFHYYDAKRVVMGKPMKDWLKFAMAWWHTLGQASGDP<br>FGGQTRSYEWDKGECPYCRAKAKADAGFEIMQKLGIEYYCFHDIDLVEDTEDIAEYEARM<br>KDITDYLVEKQKETGIKNLWGTANVFGNKRYMNGAATNPQFDVVARAAVQIKNAIDATIK<br>LGGTSYVFWGGREGYYTLLNTQMQREKDHLAKMLTAARDYARAHGEKGTFLIEPKPMEPT |

TABLE 2-continued

| Clone No. | Class of organism | Type of Sequence | SEQ ID NO: | Sequence |
|---|---|---|---|---|
| | | | | KHQYDVDTETVIGFLRANGLDKDFKVNIEVNHATLAGHTFEHELTVAVDNGFLGSIDANR<br>GDAQNGWDTDQFPVDPYDLTQAMMQIIRNGGFKDGGTNFDAKLRRSSTDPEDIFIAHISA<br>MDAMAHALLNAAAVIEESPLCKMVEERYASFDSGLGKQFEEGKATLEDLYEYAKKNGEPV<br>VASGKQELYETLLNLYAK |
| 5586MI208_003 | *Prevotella* | DNA | 117 | ATGTCAACTGAGTATTTCCCTACAATCGGCAAGATTCCCTTCGAGGGACCCGAGAGCAAG<br>AACCCCATGGCCTTCCACTACTATGAACCCGAAAAGTTGGTGATGGGCAAGAAGATGAAG<br>GACTGGCTGCGTTTCGCAATGGCCTGGTGGCACACCCTTGGAGCCGCATCCGGCGACCAG<br>TTCGGCGGACAGACCCGCAGTTACGCCTGGGACAAGGGCGACTGCCCTTACAGCCGCGCC<br>CGCGCCAAGGTCGACGCCGGCTTCGAGATCATGCAGAAGCTCGGCATAGAGTTCTTCTGC<br>TTCCATGACATCGACCTGGTCGAGGATACCGACGACATCGCCGAGTATGAAGCCCGGATG<br>AAAGACATCACGGACTATCTGCTGGAAAAGATGGAGGCTACCGGCATCAAGAACCTCTGG<br>GGCACGGCCAATGTCTTCGGTCACAAGCGTTATATGAACGGTGCAGCCACAAACCCCGAT<br>TTCGCAGTGGTCGCAAGGGCGGCCGTGCAGATCAAGAACGCCATCGACGCCACCATCAAG<br>CTGGGTGGTGAGAACTATGTGTTCTGGGGTGGACGCGAGGGTTATATGAGCCTGCTCAAC<br>ACCCAGATGCAGAGGGAGAAGGAACACCTTGCCAAGATGCTCACCGCCGCACGTGACTAT<br>GCACGCGCCAAAGGTTTCAAGGGCACGTTCCTCATCGAACCCAAGCCGATGGAACCCACC<br>AAGCACCAGTATGACCAGGATACCGAGACCGTTATCGGATTCCTCCGCAGCCACGGCCTG<br>GACAAGGACTTCAAGGTCAACATCGAGGTGAACCACGCCACCCTGGCGGGCCATACCTTC<br>GAGCACGAACTGGCCACCGCCGTCGACAACGGCATGCTCGGCAGCATCGACGCCAACCGC<br>GGAGACGCCCAGAACGGCTGGGACACCGACCAGTTCCCGATCGACAACTTCGAGCTCACG<br>CTTGCCATGATGCAGATAATCCGCAACGGCGGCCTGGCACCGGGCGGTTCGAACTTCGAC<br>GCAAAGCTGCGCCGCAATTCCACCGATCCCGAGGACATCTTCATCGCCCACATCAGCGCG<br>ATGGACGCCATGGCCCGCGCCCTCGTCAACGCCGCCGCCATCCTCGGCGAGTCGCCCGTT<br>CCGGCTATGGTCAAGGACCGCTATGCTTCGTTCGACTGCGGCAAGGGCAAGGACTTCGAA<br>GACGGCAAACTGACTCTCGAAGACATCGTCGCCTACGCCAGGGAGAATGGCGAGCCGAAA<br>CAGATTTCCGGCAAGCAGGAACTCTACGAAACTATCGTCGCTCTTTACTGCAAGTAA |
| 5586MI208_003 | *Prevotella* | Amino Acid | 118 | MSTEYFPTIGKIPFEGPESKNPMAFHYYEPEKLVMGKKMKDWLRFAMAWWHTLGAASGDQ<br>FGGQTRSYAWDKGDCPYSRARAKVDAGFEIMQKLGIEFFCFHDIDLVEDTDDIAEYEARM<br>KDITDYLLEKMEATGIKNLWGTANVFGHKRYMNGAATNPDFAVVARAAVQIKNAIDATIK<br>LGGENYVFWGGREGYMSLLNTQMQREKEHLAKMLTAARDYARAKGFKGTFLIEPKPMEPT<br>KHQYDQDTETVIGFLRSHGLDKDFKVNIEVNHATLAGHTFEHELATAVDNGMLGSIDANR<br>GDAQNGWDTDQFPIDNFELTLAMMQIIRNGGLAPGGSNFDAKLRRNSTDPEDIFIAHISA<br>MDAMARALVNAAAILGESPVPAMVKDRYASFDCGKGKDFEDGKLTLEDIVAYARENGEPK<br>QISGKQELYETIVALYCK |
| 5586MI210_002 | *Prevotella* | DNA | 119 | ATGTCATATTTTCCTACTATCGGTAACATCCCCTTTGAGGGTGTAGAGAGCAAGAATCCC<br>CTTGCCTTCCATTATTATGACGCTTCCCGCGTAGTTATGGGCAAGCCCATGAAGGAGTGG<br>CTCAAGTTTGCCATGGCCTGGTGGCACACGCTGGGTCAGGCATCGGCCGACCCTTTCGGC<br>GGACAAACCCGCAGCTATGCCTGGGACAAAGGCGAGTGCCCCTACTGCCGTGCCCGTGCC<br>AAGGCCGACGCCGGCTTCGAGCTCATGCAGAAACTGGGCATCGAGTATTTCTGCTCCCAC<br>GACATTGACCTCATCGAGGACTGCGACGACATTGCAGAGTACGAGGCCCGTCTGAAGGAC<br>ATTACGGACTACCTCCTGGAGAAGATGAAGAAGACCGGTATCAAGAACCTGTGGGGTACG<br>GCCAATGTGTTCGGTAACAAGCGTTACATGAACGGTGCTGCTACCAACCCTCAGTTTGAC<br>GTTGTGGCCCGCGCTGCCGTCCAGATCAAGAACGCCATTGACGCTACCATCAAGCTGGGC<br>GGTTCCAACTATGTGTTCTGGGGTGGCCGTGAGGGTTACTACACGCTTCTGAACACCCAG<br>ATGCAGCGTGAGAAGAATCACCTGGCTGCCATGCTCAAGGCTGCCCGCGACTATGCCCGC<br>GCCAACGGTTTCAAGGGCACCTTCCTCATTGAGCCCAAGCCCATGGAGCCCACCAAGCAC<br>CAGTACGACGTAGACACGGAGACCGTGATTGGATTCCTCCGCGCCAACGGTCTGGAGAAG<br>GACTTCAAGGTGAACATTGAGGTGAACCACGCTACTCTTGCCGGTCACACCTTCGAGCAC<br>GAGCTCACCGTGGCCCGTGAGAACGGCTTCCTGGGTTCCATTGACGCCAACCGCGGAGAT<br>GCCCAGAACGGCTGGGACACCGACCAGTTCCCGGTAGATGCCTTTGACCTCACCCAGGCC<br>ATGATGCAGATTCTCCTCAACGGAGGCTCCGGCAATGGCGGTACCAACTTTGACGCCAAG<br>CTGCGCCGTTCCTCCACCGACCCCGAGGACATCTTCATCGCGCACATCAGCGCCATGGAT<br>GCCATGGCTCACGCCCTGCTCAATGCAGCTGCCGTGCTGGAGGAGAGCCCGCTTTGCAAG<br>ATGGTCAAGGAGCGTTACGCTTCCTTCGACAGCGGTCTTGGCAAGCAGTTCGAGGAAGGA<br>AAGGCTACGCTGGAAGATCTGTATGCCTATGCCGTCAAGAACGGTGAGCCCGTGGTGGCT<br>TCCGGCAAGCAGGAACTGTACGAAACCTTCCTGAACCTCTATGCAAAATGGTAA |
| 5586MI210_002 | *Prevotella* | Amino Acid | 120 | MSYFPTIGNIPFEGVESKNPLAFHYYDASRVVMGKPMKEWLKFAMAWWHTLGQASADPFG<br>GQTRSYAWDKGECPYCRARAKADAGFELMQKLGIEYFCSHDIDLIEDCDDIAEYEARLKD<br>ITDYLLEKMKKTGIKNLWGTANVFGNKRYMNGAATNPQFDVVARAAVQIKNAIDATIKLG<br>GSNYVFWGGREGYYTLLNTQMQREKNHLAAMLKAARDYARANGFKGTFLIEPKPMEPTKH<br>QYDVDTETVIGFLRANGLEKDFKVNIEVNHATLAGHTFEHELTVARENGFLGSIDANRGD<br>AQNGWDTDQFPVDAFDLTQAMMQILLNGGSGNGGTNFDAKLRRSSTDPEDIFIAHISAMD<br>AMAHALLNAAAVLEESPLCKMVKERYASFDSGLGKQFEEGKATLEDLYAYAVKNGEPVVA<br>SGKQELYETFLNLYAKW |
| 5586MI212_002 | *Prevotella* | DNA | 121 | ATGTCAACTGAGTATTTCCCTACAATCGGCAAGATTCCCTTCGAGGGACCCGAGAGCAAG<br>AACCCCATGGCCTTCCACTACTATGAACCCGAAAAGTTGGTGATGGGCAAGAAGATGAAG<br>GACTGGCTGCGTTTCGCAATGGCCTGGTGGCACACCCTTGGAGCCGCATCCGGCGACCAG<br>TTCGGCGGACAGACCCGCAGTTACGCCTGGGACAAGGGCGACTGCCCTTACAGCCGCGCC<br>CGCGCCAAGGTCGACGCCGGCTTCGAGATCATGCAGAAGCTCGGCATAGAGTTCTTCTGC<br>TTCCATGACATCGACCTGGTCGAGGATACCGACGACATCGCCGAGTATGAAGCCCGGATG<br>AAAGACATCACGGACTATCTGCTGGAAAAGATGGAGGTTACCGGCATCAAGAACCTCTGG |

TABLE 2-continued

| Clone No. | Class of organism | Type of Sequence | SEQ ID NO: | Sequence |
|---|---|---|---|---|
| | | | | GGCACGGCCAATGTCTTCGGTCACAAGCGTTATATGAACGATGCAGCCACAAACCCCGAT<br>TTCGCAGTGGTCGCAAGGGCGGCCGTGCAGATCAAGAACGCCATCGACGCCACCATCAAG<br>CTGGGTGGTGAGAACTATGTGTTCTGGGGTGGACGCGAGGGTTATATGAGCCTGCTCAAC<br>ACCCAGATGCAGAGGGAGAAGGAACACCTTGCCAAGATGCTCACCGCCGCACGTGACTAT<br>GCACGCGCCAAAGGTTTCAAGGGCACGTTCCTCATCGAACCCGAGCCGATGGAACCCACC<br>AAGCACCAGTATGACCAGGATACCGAGACCGTTATCGGATTCCTCCGCAGCCACGGCCTG<br>GACAAGGACTTCAAGGTCAACATCGAGGTGAACCACGCCACCCTGGCGGGCCATACCTTC<br>GAGCACGAACTGGCCACCGCCGTCGACAACGGCATGCTCGGCAGCATCGACGCCAACCGC<br>GGAGACGCCCAGAACGGCTGGGACACCGACCAGTTCCCGATCGACAACTTCGAGCTCACG<br>CTTGCCATGATGCAGATAATCCGCAACGGCGGCCTGGCACCGGGCGGTTCGAACTTCGAC<br>GCAAAGCTGCGCCGCAATTCCACCGATCCCGAGGACATCATCATCGCCCACATCAGCGCG<br>ATGGACGCCATGGCCCGCGCCCTCGTCAACGCCGCCGCCATCCTCGGCGAGTCGCCCGTT<br>CCGGCTATGGTCAAGGACCGCTATGCTTCGTTCGACTGCGGCAAGGGCAAGGACTTCGAA<br>GACGGCAAACTGACTCTCGAAGACATCGTCGCCTACGCCAGGGAGAATGGCGAGCCGAAA<br>CAGATTTCCGGCAAGCAGGAACTCTACGAAACTATCGTCGCTCTTTACTGCAAGTAA |
| 5586MI212_002 | *Prevotella* | Amino Acid | 122 | MSTEYFPTIGKIPFEGPESKNPMAFHYYEPEKLVMGKKMKDWLRFAMAWWHTLGAASGDQ<br>FGGQTRSYAWDKGDCPYSRARAKVDAGFEIMQKLGIEFFCFHDIDLVEDTDDIAEYEARM<br>KDITDYLLEKMEVTGIKNLWGTANVFGHKRYMNDAATNPDFAVVARAAVQIKNAIDATIK<br>LGGENYVFWGGREGYMSLLNTQMQREKEHLAKMLTAARDYARAKGFKGTFLIEPEPMEPT<br>KHQYDQDTETVIGFLRSHGLDKDFKVNIEVNHATLAGHTFEHELATAVDNGMLGSIDANR<br>GDAQNGWDTDQFPIDNFELTLAMMQIIRNGGLAPGGSNFDAKLRRNSTDPEDIIIAHISA<br>MDAMARALVNAAAILGESPVPAMVKDRYASFDCGKGKDFEDGKLTLEDIVAYARENGEPK<br>QISGKQELYETIVALYCK |
| 5586MI213_003 | *Prevotella* | DNA | 123 | ATGACCAACGAGTATTTTCCCGGAATCGGTGTGATTCCGTTTGAAGGACAGGAAAGCAAG<br>AATCCCCTGGCTTTCCATTATTATGACGCCAACCGCGTAGTGATGGGCAAACCCATGAAG<br>GAATGGTTCAAATTTGCCATGGCCTGGTGGCATACGCTGGGGCAGGCATCGGCCGATCCC<br>TTCGGCGGACAGACCCGCTCCTACGCATGGGACAAGGGCGAGTGCCCTTACTGCCGTGCC<br>CGCCAGAAGGCCGACGCCGGCTTTGAACTGATGCAGAAGCTGGGAATCGGCTATTTCTGC<br>TTCCACGATGTGGATATCATCGAGGACTGCGAGGACATTGCCGAGTATGAGGCCCGTATG<br>AAGGACATCACGGACTATCTGCTGGTGAAGATGAAGGAAACGGGCATCAAGAATCTGTGG<br>GGCACGGCCAACGTCTTCGGCCACAAGCGCTATATGAACGGCGCCGCCACCAACCCGCAA<br>TTCGACGTGGTAGCCCGCGCTGCGGTCCAGATCAAGAACGCCCTGGACGCCACCATCAAG<br>CTGGGCGGCAGCAATTATGTGTTCTGGGGCGGCCGGGAAGGCTACTACACCCTTTTGAAC<br>ACGCAGATGCAGCGGGAGAAGGACCACCTGGCCCAGATGCTCAAGGCGGCCCGCGACTAT<br>GCCCGCGGCAAGGGATTCAAGGGCACGTTCCTCATTGAGCCCAAGCCCATGGAGCCCACC<br>AAGCACCAGTACGACGTAGATACGGAGACCGTGATTGGTTTCCTGCGCGCCAACGGGCTG<br>GACAAGGACTTCAAGGTGAATATCGAAGTGAACCACGCCACCCTGGCCGGCCATACCTTC<br>GAGCACGAGCTCACCGTGGCCCGCGAAAACGGCTTCCTGGGCAGCATCGACGCCAACCGC<br>GGAGACGCCCAGAACGGCTGGGATACAGACCAGTTCCCCGTGGACGCCTTTGACCTCACC<br>CAGGCCATGATGCAGGTCCTGCTCAACGGCGGATTCGGCAACGGCGGCACCAACTTCGAC<br>GCCAAACTGCGCCGTTCCTCCACGGATCCCGAGGACATCTTCATCGCCCACATCAGCGCC<br>ATGGACGCCATGGCCCACGCCCTCCTGAACGCCGCCGCCATCCTGGAAGAGAGCCCCATG<br>CCGGGCATGGTGAAGGAGCGCTACGCTTCCTTCGACAATGGCCTTGGCAAGAAGTTCGAG<br>GAAGGAAAGGCCACGCTGGAAGAGCTGTACGACTATGCCAAGAAGAACGGCGAGCCTGTG<br>GCCGCTTCCGGAAAGCAGGAACTGTACGAAACGCTGCTGAACCTGTACGCCAAGTAA |
| 5586MI213_003 | *Prevotella* | Amino Acid | 124 | MTNEYFPGIGVIPFEGQESKNPLAFHYYDANRVVMGKPMKEWFKFAMAWWHTLGQASADP<br>FGGQTRSYAWDKGECPYCRARQKADAGFELMQKLGIGYFCFHDVDIIEDCEDIAEYEARM<br>KDITDYLLVKMKETGIKNLWGTANVFGHKRYMNGAATNPQEDVVARAAVQIKNALDATIK<br>LGGSNYVFWGGREGYYTLLNTQMQREKDHLAQMLKAARDYARGKGFKGTFLIEPKPMEPT<br>KHQYDVDTETVIGELRANGLDKDEKVNIEVNHATLAGHTFEHELTVARENGFLGSIDANR<br>GDAQNGWDTDQFPVDAFDLTQAMMQVLLNGGFGNGGTNFDAKLRRSSTDPEDIFIAHISA<br>MDAMAHALLNAAAILEESPMPGMVKERYASFDNGLGKKFEEGKATLEELYDYAKKNGEPV<br>AASGKQELYETLLNLYAK |
| 5586MI215_003 | *Prevotella* | DNA | 125 | ATGGCAAAAGAGTATTTCCCGCAGATCGGAAAGATCGGCTTTGAGGGTCTTGAGAGCAAG<br>AACCCGATGGCATTCCATTATTATGACGCCGAGCGTGTCGTGCTCGGAAAGAAGATGAAG<br>GACTGGCTGAAGTTCGCGATGGCCTGGTGGCATACGCTCGGACAGGCTTCCGGCGACCCA<br>TTCGGCGGCCAGACTCGCAGCTATGAGTGGGACAAGGGCGAGTGCCCCTACTGCCGTGCC<br>CGCGCCAAGGCCGACGCCGGCTTCGAGCTCATGCAGAAGCTCGGCATCGAGTACTTCTGC<br>TTCCACGACATCGACCTCATCGAGGACTGCGACGACATCGACGAGTACGAGGCCCGGATG<br>AAGGACATCACCGACTACCTGCTGGAGAAGATGAAGGAGACCGGAATCAAGAATCTCTGG<br>GGAACGGCCAACGTCTTCGGTCACAAGCGCTACATGAACGGCGCCGCTACCAATCCGCAG<br>TTTGAAATCGTCGCCCGCGCTGCCGTCCAGATCAAGAACGCGCTCGACGCCACCATCAAG<br>CTCGGCGGCTCCAACTACGTCTTCTGGGGCGGCCGCGAGGGCTATTACACGCTGCTGAAT<br>ACCCAGATGCAGCGCGAGAAGGACCATCTCGCCAGGCTCCTTACCGCCGCCCGCGACTAT<br>GCGCGCGCCAAGGGGTTCAAGGGGACCTTCCCCATCGAGCCGAAGCCGATGGAGCCGACC<br>AAGCACCAGTATGACGTCGACACGGAGACCGTCATCGGTTTCCTCCGCCAGAATGGCCTC<br>GACAAGGACTTCAAGGTCAATATCGAGGTGAACCACGCCACCCTCGCCGGCCATACCTTC<br>GAGCACGAGCTGACCGCGGCCCGGGAGAACGGCTTCCTCGGCAGCATCGACGCCAACCGC<br>GGCGACGCCCAGAACGGCTGGGACACCGACCAGTTCCCGGTGGACGCCTTCGATCTCACG<br>CGGGCCATGATGCAGATCCTGCTCAATGGCGGTTTCGGCAACGGCGGCACCAACTTCGAC<br>GCCAAGCTGCGCCGCAGCTCCACCGATCCCGAGGACATCTTCATCGCCCACATCAGCGCG<br>ATGGACGCCATGGCCCACGCCCTGCTGAATGCGGCCGCCATCCTCGAGGAAAGCCCGCTG |

TABLE 2-continued

| Clone No. | Class of organism | Type of Sequence | SEQ ID NO: | Sequence |
|---|---|---|---|---|
| | | | | CCGGCCCTGGTCAAGCAGCGCTATGCGTCCTTCGACAGCGGTCTCGGCAAGCAGTTCGAG<br>GAGGGTAAGGCCACGCTCGAGGACCTGTACGCATACGCGAAGGAGCACGGCGAGCCCGTC<br>GCGGCCTCCGGCAAGCAGGAGCTCTGCGAGACCTATCTCAACCTCTACGCGAAATAA |
| 5586MI215_003 | *Prevotella* | Amino Acid | 126 | MAKEYFPQIGKIGFEGLESKNPMAFHYYDAERVVLGKKMKDWLKFAMANWHTLGQASGDP<br>FGGQTRSYENDKGECPYCRARAKADAGFELMQKLGIEYFCFHDIDLIEDCDDIDEYEARM<br>KDITDYLLEKMKETGIKNLWGTANVFGHKRYMNGAATNPQFEIVARAAVQIKNALDATIK<br>LGGSNYVFWGGREGYYTLLNTQMQREKDHLARLLTAARDYARAKGFKGTFPIEPKPMEPT<br>KHQYDVDTETVIGFLRQNGLDKDEKVNIEVNHATLAGHTFEHELTAARENGFLGSIDANR<br>GDAQNGWDTDQFPVDAFDLTRAMMQILLNGGFGNGGTNFDAKLRRSSTDPEDIFIAHISA<br>MDAMAHALLNAAAILEESPLPALVKQRYASFDSGLGKQFEEGKATLEDLYAYAKEHGEPV<br>AASGKQELCETYLNLYAK |
| 5607MI1_003 | *Prevotella* | DNA | 127 | ATGAGTAAAGAGTATTTTCCTGGGATTGGCAAAATCCCGTATGAGGGAGCCGAGAGCAAG<br>AATGTGATGGCATTCCACTATTATGATCCCGAACGCGTGGTCATGGGCAAGAAAATGAAA<br>GACTGGTTCAAGTTCGCTATTGCCTGGTGGCATACCCTGGGGCAGGCCAGTGCTGACCAG<br>TTTGGCGGACAGACCCGTTTCTATGAATGGGACAAAGCCGAGGACCCCTTGCAGCGTGCC<br>AAGGACAAGATGGATGCCGGTTTTGAAATCATGCAGAAGCTGGGCATCGAGTATTTCTGT<br>TTCCATGATGTGGACCTCATCGAGGAGGCCGATACCATCGAGGAATATGAAGCCCGCATG<br>CAGGCGATTACCGACTACGCGCTGGAGAAGATGAAGGCAACGGGTATCAAGTTGCTGTGG<br>GGCACTGCCAACGTGTTCGGCCACAAGCGTTACATGAACGGCGCCGCCACCAATCCCGAC<br>TTCAATGTCGTGGCACGTGCAGCCGTGCAGATCAAGAACGCCCTCGATGCTACCATCAAG<br>TTGGGCGGAACGAGCTACGTCTTCTGGGGCGGTCGTGAAGGCTATCAGAGCCTGCTCAAC<br>ACCCAGATGCAGCGCGAGAAGAACCACCTGGCCAAGATGCTCACGGCAGCCCGTGACTAT<br>GCCCGTGCTAAGGGCTTCAAGGGCACCTTCCTGATTGAGCCCAAGCCGATGGAACCCACC<br>AAGCACCAGTATGACCAGGACACCGAGACCGTTATCGGCTTCTTGCGTGCCAATGGCCTT<br>GACAAGGACTTTAAGGTCAACATTGAGGTCAACCATGCCACGCTGGCTGGCCACACCTTT<br>GCACATGAGTTGGCAGTGGCTGTGGATAACGGTATGCTGGGCAGCATCGATGCTAACCGT<br>GGTGACCACCAGAACGGCTGGGATACAGACCAGTTCCCCATCAACAGTTATGAACTCACC<br>AATGCTATGCTGCAGATCATGCACGGCGGCGGTTTCAAGGACGGCGGTACCAACTTTGAC<br>GCCAAGCTGCGCCGCAACAGTACCGACCCCGAGGACATCTTTACCGCTCACATCAGTGGT<br>ATGGACGCTCTGGCCCGTGCCCTGTTGAGTGCTGCCGATATCCTTGAGAAGAGCGAGTTG<br>CCTGAAATGCTCAAGGAACGCTATGCCAGCTTTGACGCGGGTGAAGGCAAGCGCTTTGAG<br>GATGGCCAGATGACTCTTGAGGAACTGGTTGCCTATGCCAAGTCCCATGGCGAGCCTGCT<br>ACCATCAGTGGCAAGCAGGAAAAATATGAAGCCATCGTGGCTTTGCACGTCAAGTAA |
| 5607MI1_003 | *Prevotella* | Amino Acid | 128 | MSKEYFPGIGKIPYEGAESKNVMAFHYYDPERVVMGKKMKDWFKFAIAWWHTLGQASADQ<br>FGGQTREYEWDKAEDPLQRAKDKMDAGFEIMQKLGIEYFCFHDVDLIEEADTIEEYEARM<br>QAITDYALEKMKATGIKLLWGTANVFGHKRYMNGAATNPDFNVVARAAVQIKNALDATIK<br>LGGTSYVFWGGREGYQSLLNTQMQREKNHLAKMLTAARDYARAKGFKGTFLIEPKPMEPT<br>KHQYDQDTETVIGFLRANGLDKDEKVNIEVNHATLAGHTFAHELAVAVDNGMLGSIDANR<br>GDHQNGWDTDQFPINSYELTNAMLQIMHGGGFKDGGTNFDAKLRRNSTDPEDIFTAHISG<br>MDALARALLSAADILEKSELPEMLKERYASFDAGEGKRFEDGQMTLEELVAYAKSHGEPA<br>TISGKQEKYEAIVALHVK |
| 5607MI2_003 | *Prevotella* | DNA | 129 | ATGAGTAAAGAGTATTATCCTGAGATTGGCAAAATCCCGTTTGAGGGTCCCGAGAGCAAG<br>AATGTGATGGCGTTCCATTACTATGAACCCGAACGCGTCGTCATGGGTAAGAAGATGAAA<br>GACTGGCTCAAGTTTGCCATGTGCTGGTGGCACAGCCTGGGTCAGGCCAGTGCCGACCAG<br>TTCGGCGGACAGACACGTTTCTACGAGTGGGACAAGGCCGATACCCCCCTGCAGCGTGCC<br>AAGGACAAAATGGATGCCGGATTTGAAATCATGCAGAAGTTGGGCATCGAGTACTTCTGC<br>TTCCACGATGTGGACCTCATCGAGGAGGCCGATACCATCGAGGAATACGAGGCCCGCATG<br>AAGGCCATTACCGACTATGCGCTGGAGAAGATGCAGGCCACCGGCATCAAGTTGCTGTGG<br>GGCACTGCCAATGTGTTCGGCCACAAGCGCTACATGAACGGCGCCGCCACCAATCCCGAT<br>TTCAATGTCGTGGCACGTGCCGCCGTCCAAATCAAGAATGCCATCGATGCCACCATCAAG<br>CTGGGCGGCACGAGTTACGTCTTCTGGGGTGGTCGTGAGGGCTATCAGAGTCTGCTCAAC<br>ACGCAGATGCAGCGCGAGAAGGACCATCTGGCCCGCATGCTGGCGGCAGCCCGCGACTAT<br>GGCCGTGCCCATGGCTTCAAGGGCACTTTCCTGATCGAGCCCAAACCCATGGAGCCCACC<br>AAGCACCAGTATGATGTGGACACCGAGACCGTGCTCGGCTTCCTGCGTGCCCACGGCCTG<br>GACAAGGACTTCAAGGTTAACATCGAGGTCAATCATGCTACGCTGGCGGGACACACTTTC<br>AGCCACGAACTGGCTGTGGCCGTGGACAACGGTATGCTGGGCAGCATCGACGCCAACCGC<br>GGCGATTATCAGAATGGCTGGGACACCGACCAGTTCCCCATCGACAGCTTCGAGCTCACC<br>CAGGCCATGCTGCAGATCATGCGCGGCGGCGGCTTCAAGGACGGAGGTACCAACTTCGAT<br>GCCAAGCTGCGTCGCAACAGTACCGACCCTGAGGACATCTTCATCGCCCACATCAGCGGT<br>ATGGATGCCATGGCACGCGGCCTGTTGAGCGCTGCCGCTATCCTCGAGGATGGCGAGTTG<br>CCCGCGATGCTCAAGGCACGTTATGCCAGCTTTGACCAGGGCGAGGGTAAGCGCTTTGAG<br>GACGGCGAGATGACGCTCGAGCAGCTGGTGGATTATGCAAAGGATTATGCCAAATCGCAC<br>GGCGAGCCTGATGTCATCAGCGGCAAGCAGGAGAAGTTTGAAACCATCGTGGCCCTTTAC<br>GCCAAGTAA |
| 5607MI2_003 | *Prevotella* | Amino Acid | 130 | MSKEYYPEIGKIPFEGPESKNVMAFHYYEPERVVMGKKMKDWLKFAMCWWHSLGQASADQ<br>FGGQTRFYEWDKADTPLQRAKDKMDAGFEIMQKLGIEYFCFHDVDLIEEADTIEEYEARM<br>KAITDYALEKMQATGIKLLWGTANVFGHKRYMNGAATNPDFNVVARAAVQIKNAIDATIK<br>LGGTSYVFWGGREGYQSLLNTQMQREKDHLARMLAAARDYGRAHGFKGTFLIEPKPMEPT<br>KHQYDVDTETVLGFLRAHGLDKDFKVNIEVNHATLAGHTFSHELAVAVDNGMLGSIDANR |

TABLE 2-continued

| Clone No. | Class of organism | Type of Sequence | SEQ ID NO: | Sequence |
|---|---|---|---|---|
| | | | | GDYQNGWDTDQFPIDSFELTQAMLQIMRGGGFKDGGTNFDAKLRRNSTDPEDIFIAHISG<br>MDAMARGLLSAAAILEDGELPAMLKARYASFDQGEGKRFEDGEMTLEQLVDYAKDYAKSH<br>GEPDVISGKQEKFETIVALYAK |
| 5607M13_003 | *Prevotella* | DNA | 131 | ATGACCAACGAGTATTTTCCCGGAATCGGTGTGATTCCGTTTGAAGGACAGGAAAGCAAG<br>AATCCCCTGGCTTTCCATTATTATGACGCCAACCGCGTAGTGATGGGCAAACCCATGAAG<br>GAATGGTTCAAATTTGCCATGGCCTGGTGGCATACGCTGGGGCAGGCATCGGCCGATCCC<br>TTCGGCGGACAGACCCGCTCCTACGCATGGGACAAGGGCGAGTGCCCTTACTGCCGTGCC<br>CGCCAGAAGGCCGACGCCGGCTTTGAACTGATGCAGAAGCTGGGAATCGGCTATTTCTGC<br>TTCCACGATGTGGATATCATCGAGGACTGCGAGGACATTGCCGAGTATGAGGCCCGTATG<br>AAGGACATCACGGACTATCTGCTGGTGAAGATGAAGGAAACGGGCATCAAGAATCTGTGG<br>GGCACGGCCAACGTCTTCGGCCACAAGCGCTATATGAACGGCGCCGCCACCAACCCGCAA<br>TTCGACGTGGTAGCCCGCGCTGCGGTCCAGATCAAGAACGCCCTGGACGCCACCATCAAG<br>CTGGGCGGCAGCAATTATGTGTTCTGGGGCGGCCGGGAAGGCTACTACACCCTTTTGAAC<br>ACGCAGATGCAGCGGGAGAAGGACCACCTGGCCCAGATGCTCAAGGCGGCCCGCGACTAT<br>GCCCGCGGCAAGGGATTCAAGGGCACGTTCCTCATTGAGCCCAAGCCCATGGAGCCCACC<br>AAGCACCAGTACGACGTAGATACGGAGACCGTGATTGGTTTCCTGCGCGCCAACGGGCCG<br>GACAAGGACTTCAAGGTGAATATCGAAGTGAACCACGCCACCCTGGCCGGCCATACCTTC<br>GAGCACGAGCTCACCGTGGCCCGCGAAAACGGCTTCCTGGGCAGCATCGACGCCAACCGC<br>GGAGACGCCCAGAACGGCTGGGATACAGACCAGTTCCCCGTGGACGCCTTTGACCTCACC<br>CAGGCCATGATGCAGGTCCTGCTCAACGGCGGATTCGGCAACGGCGGCACCAACTTCGAC<br>GCCAAACTGCGCCGTTCCTCCACGGATCCCGAGGACATCTTCATCGCCCACATCAGCGCC<br>ATGGACGCCATGGCCCACGCCCTCCTGAACGCCGCCGCCATCCTGGAAGAGAGCCCCATG<br>CCGGGCATGGTGAAGGAGCGCTACGCTTCCTTCGACAATGGCCTTGGCAAGAAGTTCGAG<br>GAAGGAAAGGCCACGCTGGAAGAGCTGTACGACTATGCCAAGAAGAACGGCGAGCCTGTG<br>GCCGCTTCCGGAAAGCAGGAACTGTACGAAACGCTGCTGAACCTGTACGCCAAGTAA |
| 5607M13_003 | *Prevotella* | Amino Acid | 132 | MTNEYFPGIGVIPFEGQESKNPLAFHYYDANRVVMGKPMKEWFKFAMAWWHTLGQASADP<br>FGGQTRSYAWDKGECPYCRARQKADAGFELMQKLGIGYFCFHDVDIIEDCEDIAEYEARM<br>KDITDYLLVKMKETGIKNLWGTANVFGHKRYMNGAATNPQFDVVARAAVQIKNALDATIK<br>LGGSNYVFWGGREGYYTLLNTQMQREKDHLAQMLKAARDYARGKGFKGTFLIEPKPMEPT<br>KHQYDVDTETVIGFLRANGPDKDFKVNIEVNHATLAGHTFEHELTVARENGFLGSIDANR<br>GDAQNGWDTDQFPVDAFDLTQAMMQVLLNGGFGNGGTNFDAKLRRSSTDPEDIFIAHISA<br>MDAMAHALLNAAAILEESPMPGMVKERYASFDNGLGKKFEEGKATLEELYDYAKKNGEPV<br>AASGKQELYETLLNLYAK |
| 5607M14_005 | *Prevotella* | DNA | 133 | ATGACTAAAGAGTATTTCCCTTCCGTCGGCAAGATTGCCTTTGAAGGACCCGAAAGCAAG<br>AACCCTATGGCCTTCCATTATTATGACGCCAATCGCGTGGTAATGGGAAAGCCGATGAAA<br>GAATGGCTTAAATTTGCCATGGCCTGGTGGCACACCCTGGGCCAGGCCTCTGCAGACCCC<br>TTCGGCGGTCAGACCCGCTCCTACGAGTGGGACAAGGGCGAGTGCCCCTACTGCCGCGCC<br>AAGGCCAAGGCCGATGCCGGCTTTGAACTGATGCAGAAACTGGGCATCGAGTATTTCTGC<br>TTCCACGATATAGACCTGGTGGAAGACTGCGATGATATCGCCGAATACGAGGCCCGCATG<br>AAGGACATCACGGACTATCTCCTGGAGAAGATGAAGGAAACCGGCATCAAGAACCTCTGG<br>GGAACCGCCAACGTGTTCGGCCACAAGCGCTATATGAACGGCGCCGCCACCAACCCTCAG<br>TTCGACATCGTGGCCCGTGCCGCTGTCCAGATCAAGAACGCCCTGGATGCCACCATCAAG<br>CTGGGCGGCTCCAACTATGTGTTCTGGGGCGGCCGTGAGGGCTACTATACCCTCCTGAAC<br>ACCCAGATGCAGAGAGAGAAGGACCACCTGGCCAAGATGCTCACCGCCGCCCGCGACTAT<br>GCCCGTGCCAAGGGCTTCAAGGGCACCTTCCTCATCGAACCCAAGCCGATGGAGCCCACC<br>AAGCACCAGTACGACGTAGATACGGAGACCGTGATCGGCTTCCTCCGCGCCAACGGCCTG<br>GACAAGGACTTCAAGGTGAATATTGAGGTGAACCACGCCACCCTGGCCGGCCACACCTTC<br>GAGCACGAGCTCACCGTGGCCCGCGAGAACGGCTTCCTGGGCAGCATCGACGCCAACCGC<br>GGAGACGCCCAGAACGGCTGGGATACGGACCAGTTCCCGGTGGATGCCTTCGACCTCACC<br>CAGGCTATGATGCAGATCCTTCTGAACGGAGGCTTCGGCAACGGCGGTACCAACTTCGAC<br>GCCAAACTGCGCCGCTCCTCCACGGACCCCGAGGACATCTTCATCGCCCACATCAGCGCT<br>ATGGATGCCATGGCCCACGCCCTGCTGAATGCAGCCGCCATCCTGGAGGAAAGCCCGCTT<br>CCGAAGATGCTGAAAGAGCGTTATGCCAGCTTTGACGGCGGTCTGGGCAAGAAGTTCGAA<br>GAAGGCAAGGCCTCTCTGGAAGAACTCTACGAGTATGCCAAGAGCAACGGAGAGCCCGTG<br>GCCGCTTCCGGCAAGCAGGAGCTCTGCGAAACGTACCTGAACCTCTACGCTAAGTAA |
| 5607M14_005 | *Prevotella* | Amino Acid | 134 | MTKEYFPSVGKIAFEGPESKNPMAFHYYDANRVVMGKPMKEWLKFAMAWWHTLGQASADP<br>FGGQTRSYEWDKGECPYCRAKAKADAGFELMQKLGIEYFCFHDIDLVEDCDDIAEYEARM<br>KDITDYLLEKMKETGIKNLWGTANVFGHKRYMNGAATNPQFDIVARAAVQIKNALDATIK<br>LGGSNYVFWGGREGYYTLLNTQMQREKDHLAKMLTAARDYARAKGFKGTFLIEPKPMEPT<br>KHQYDVDTETVIGFLRANGLDKDFKVNIEVNHATLAGHTFEHELTVARENGFLGSIDANR<br>GDAQNGWDTDQFPVDAFDLTQAMMQILLNGGFGNGGTNFDAKLRRSSTDPEDIFIAHISA<br>MDAMAHALLNAAAILEESPLPKMLKERYASFDGGLGKKFEEGKASLEELYEYAKSNGEPV<br>AASGKQELCETYLNLYAK |
| 5607M15_002 | *Prevotella* | DNA | 135 | ATGGCTAAAGAATACTTCCCCTCCATCGGCAAAATCCCTTTTGAAGGAGCCGACAGCAAA<br>AATCCCCTCGCTTTCCATTATTATGACGCCGGACGCGTGGTTATGGGCAAGCCCATGAAG<br>GAATGGCTTAAATTCGCCATGGCCTGGTGGCACACGCTGGGCCAGGCCTCCGGAGACCCC<br>TTCGGCGGCCAGACCCGCAGCTACGAATGGGACAAGGGCGAATGCCCCTACTGCCGCGCC<br>AAGGCCAAGGCCGACGCCGGTTTTGAAATCATGCAAAAGCTGGGCATCGAATACTTCTGC<br>TTCCACGATGTGGACCTTATCGAGGATTGCGATGACATTGCCGAATACGAAGCCCGCATG<br>AAGGACATCACGGACTACCTGCTGGAAAAGATGAAGGAGACCGGCATCAAGAACCTCTGG<br>GGCACCGCCAATGTCTTCGGCCACAAGCGCTACATGAACGGCGCCGGCACCAATCCGCAG |

TABLE 2-continued

| Clone No. | Class of organism | Type of Sequence | SEQ ID NO: | Sequence |
|---|---|---|---|---|
| | | | | TTCGATGTGGTGGCCCGTGCCGCCGTCCAGATCAAGAACGCCCTGGACGCCACCATCAAG<br>CTGGGCGGCTCCAACTATGTGTTCTGGGGCGGCCGCGAAGGCTATTACACCCTCCTCAAC<br>ACACAGATGCAGCGGGAAAAAGACCACCTGGCCAAGTTGCTGACGGCCGCCCGCGACTAT<br>GCCCGCGCCAAGGGCTTCAAGGGCACCTTCCTCATTGAGCCCAAACCCATGGAACCCACC<br>AAGCACCAGTACGACGTGGATACGGAGACGGTCATCGGCTTCCTCCGTGCCAACGGCCTG<br>GACAAGGACTTCAAGGTGAACATCGAGGTGAACCACGCCACCCTGGCCGGCCACACCTTC<br>GAGCATGAGCTCACCGTGGCCCGCGAGAACGGTTTCCTGGGCTCCATCGATGCCAACCGC<br>GGCGACGCCCAGAACGGCTGGGACACGGACCAGTTCCCTGTGGACCCGTACGATCTTACC<br>CAGGCCATGATGCAGGTGCTGCTGAACGGCGGCTTCGGCAACGGCGGCACCAACTTCGAC<br>GCCAAACTCCGCCGCTCCTCCACCGACCCTGAGGACATCTTCATCGCCCATATTTCCGCC<br>ATGGATGCCATGGCCCACGCTTTGCTTAACGCAGCTGCCGTGCTGGAAGAGAGCCCCCTG<br>TGCCAGATGGTCAAGGAGCGTTATGCCAGCTTCGACGATGGCCTCGGCAAACAGTTCGAG<br>GAAGGCAAGGCTACCCTGGAAGACCTGTACGAATACGCCAAGGCCCAGGGTGAACCCGTT<br>GTCGCCTCCGGCAAGCAGGAGCTTTACGAGACTCTCCTGAACCTGTATGCCGTCAAGTAA |
| 5607M15_002 | *Prevotella* | Amino Acid | 136 | MAKEYFPSIGKIPFEGADSKNPLAFHYYDAGRVVMGKPMKEWLKFAMAWWHTLGQASGDP<br>FGGQTRSYEWDKGECPYCRAKAKADAGFEIMQKLGIEYFCFHDVDLIEDCDDIAEYEARM<br>KDITDYLLEKMKETGIKNLWGTANVFGHKRYMNGAGTNPQFDVVARAAVQIKNALDATIK<br>LGGSNYVFWGGREGYYTLLNTQMQREKDHLAKLLTAARDYARAKGFKGTFLIEPKPMEPT<br>KHQYDVDTETVIGFLRANGLDKDFKVNIEVNHATLAGHTFEHELTVARENGFLGSIDANR<br>GDAQNGWDTDQFPVDPYDLTQAMMQVLLNGGFGNGGTNFDAKLRRSSTDPEDIFIAHISA<br>MDAMAHALLNAAAVLEESPLCQMVKERYASFDDGLGKQFEEGKATLEDLYEYAKAQGEPV<br>VASGKQELYETLLNLYAVK |
| 5607M16_002 | *Prevotella* | DNA | 137 | ATGACCAAAGAATATTTCCCTACCGTCGGGAAGATCCCCTTCGAGGGCCCCGAAAGCAAG<br>AACCCTATGGCGTTCCATTACTATGACCCCAACCGTCTGGTGATGGGCAAGAAGATGAAA<br>GACTGGCTGCGTTTCGCCATGGCCTGGTGGCACACCCTCGGCCAGGCGTCGGGCGACCAG<br>TTCGGCGGCCAGACCCGCAGTTATGCGTGGGACGAGGGAGAATGCCCGTACGAGCGCGCC<br>CGTGCCAAGGCTGACGCCGGCTTCGAGATCATGCAGAAACTCGGTATCGAGTTCTTCTGC<br>TTCCACGACATCGACCTGATCGAGGATACCGACGACATCGCCGAGTATGAGGCCCGCCTG<br>AAAGACATCACGGACTATCTGCTCGAGAAGATGAAAGCCACTGGCATCAAAAATCTCTGG<br>GGAACGGCCAACGTGTTCGGCCACAAGCGTTGCATGAACGGCGCCGCCACCAACCCGGAC<br>TTCGCCGTGCTGGCCCGCGCTGCCGTCCAGATCAAGAACGCCATCGACGCCACCATCAAG<br>CTGGGCGGCGAGAACTATGTGTTCTGGGGTGGCCGCGAAGGCTACACGAGCCTGCTCAAC<br>ACCCAGATGCAGCGTGAGAAAGAGCACCTGGGCCGCCTGCTGTCCCTGGCCCGCGACTAT<br>GGCCGCGCCCACGGCTTCAAGGGTACCTTCCTGATCGAGCCCAAGCCGATGGGACCGACG<br>AAACACCAGTACGACCAGGATACGGAAACTGTCATCGGTTTCCTGCGCCGCCACGGTCTA<br>GACAAGGACTTCAAGGTCAATATCGAGGTGAACCATGCCACGCTGGCGGGCCACACCTTC<br>GAACACGAACTGGCCTGCGCCGTGGATCACGGTATGCTGGGCAGCATCGACGCCAACCGC<br>GGTGACGCACAGAACGGCTGGGATACCGACCAGTTCCCGATCGACAACTTCGAGCTGACC<br>CTTTCCATGCTCCAGATCATCCGCAACGGTGGCCTGGCACCCGGCGGCTCGAATTTCGAT<br>GCCAAGCTGCGCCGCAACTCCACCGATCCCGAAGACATTTTCATCGCGCACATCAGCGCC<br>ATGGACGCCATGGCCCGCGCATTGGTCAATGCGGCCGCCATCCTGGAGGAGAGCGCTATT<br>CCGAAGATGGTCAAGGAGCGTTACGCTTCGTTCGACAGCGGCAAAGGCAAGGAATACGAG<br>GAAGGCAAGCTGACGCTCGAAGACATCGTGGCCTATGCCAAGGCGAACGGAGAACCGAAG<br>CAGATTTCCGGCAAACAGGAACTCTACGAGACGCTTGTCGCACTCTATAGCAAATAA |
| 5607M16_002 | *Prevotella* | Amino Acid | 138 | MTKEYFPTVGKIPFEGPESKNPMAFHYYDPNRLVMGKKMKDWLRFAMAWWHTLGQASGDQ<br>FGGQTRSYAWDEGECPYERARAKADAGFEIMQKLGIEFFCFHDIDLIEDTDDIAEYEARL<br>KDITDYLLEKMKATGIKNLWGTANVFGHKRCMNGAATNPDFAVLARAAVQIKNAIDATIK<br>LGGENYVFWGGREGYTSLLNTQMQREKEHLGRLLSLARDYGRAHGFKGTFLIEPKPMGPT<br>KHQYDQDTETVIGFLRRHGLDKDFKVNIEVNHATLAGHTFEHELACAVDHGMLGSIDANR<br>GDAQNGWDTDQFPIDNFELTLSMLQIIRNGGLAPGGSNFDAKLRRNSTDPEDIFIAHISA<br>MDAMARALVNAAAILEESAIPKMVKERYASFDSGKGKEYEEGKLTLEDIVAYAKANGEPK<br>QISGKQELYETLVALYSK |
| 5607M17_002 | *Prevotella* | DNA | 139 | ATGACCAAAGGGTATTTCCCTACCATCGGCAGGATTCCCTTCGAGGGAACTGAAAGCAAG<br>AATCCCCTCGCATTCCATTACTATGAGCCCGACCGGCTCGTACTGGGCAAGAAAATGAAA<br>GACTGGCTGCGTTTCGCGATGGCCTGGTGGCACACCCTGGGCCAGGCGTCCGGCGACCAG<br>TTCGGCGGCCAGACCCGCAGCTATGCCTGGGACAAGGCCGAGTGCCCCTATGAGCGCGCC<br>AAGGCCAAAGCCGACGCCGGCTTCGAGATCATGCAGAAACTCGGCATCGAGTTCTTCTGT<br>TTCCACGACATTGACCTCGTTGAGGATACCGACGACATCGCCGAGTATGAGGCCCGGATG<br>AAGGACATTACCGACTATCTCCTGGTCAAGATGAAGGAGACCGGAATCAAGAACCTCTGG<br>GGTACGGCCAATGTCTTCGGCCACAAGCGCTATATGAACGGCGCCGCCACCAATCCCGAC<br>TTCGACGTGGTGGCCCGCGCCGCCGTCCAGATCAAGAACGCCCTCGATGCCACCATCAAG<br>CTGGGCGGTGAAAACTATGTGTTCTGGGGCGGCCGCGAAGGCTATATGAGCCTGCTCAAC<br>ACGCAGATGCAGCGTGAGAAGGAGCACCTGGGCCGGATGCTGGTCGCCGCCCGCGACTAC<br>GCCCGCGCCCACGGCTTCAAGGGTACCTTCCTCATCGAGCCCAAACCGATGGAACCGACC<br>AAGCACCAGTACGACCAGGATACGGAAACCGTGATCGGCTTCCTTCGCCGCCACGGCCTG<br>GACAAGGATTTCAAGGTGAACATCGAAGTGAACCACGCCACGCTGGCCGGCCACACCTTC<br>GAGCACGAACTGGCCACCGCCGTCGACTGCGGCCTGCTGGGCAGCATCGACGCCAATCGC<br>GGCGACGCTCAGAACGGCTGGGATACCGACCAGTTCCCGATCGACAACTTCGAACTCACG<br>CTGGCCATGCTGCAGATTATCCGCAACGGCGGTCTGGCACCCGGCGGCTCGAACTTCGAC<br>GCCAAACTGCGCCGTAACTCCACCGATCCGGAAGATATCTTCATCGCCCACATCAGTGCG<br>ATGGACGCGATGGCCCGTGCGCTGGTCAACGCCGCCGCAATCTGGGAAGAGTCTCCCATC<br>CCGCAGATGAAGAAAGAACGCTACGCGTCGTTCGACAGCGGCAAGGGCAAGGAATTCGAA |

TABLE 2-continued

| Clone No. | Class of organism | Type of Sequence | SEQ ID NO: | Sequence |
|---|---|---|---|---|
| | | | | GAGGGCAAGCTCTGCCTCGAAGACCTCGTGGCCTATGCCAAGGCGAACGGAGAACCGAAA<br>CAGATCTCCGGCAGGCAGGAACTATATGAGACCATCGTCGCCCTTTATTGCAAATAG |
| 5607M17_002 | *Prevotella* | Amino Acid | 140 | MTKGYFPTIGRIPFEGTESKNPLAFHYYEPDRLVLGKKMKDWLRFAMAWWHTLGQASGDQ<br>FGGQTRSYAWDKAECPYERAKAKADAGFEIMQKLGIEFFCFHDIDLVEDTDDIAEYEARM<br>KDITDYLLVKMKETGIKNLWGTANVFGHKRYMNGAATNPDFDVVARAAVQIKNALDATIK<br>LGGENYVFWGGREGYMSLLNTQMQREKEHLGRMLVAARDYARAHGFKGTFLIEPKPMEPT<br>KHQYDQDTETVIGFLRRHGLDKDFKVNIEVNHATLAGHTFERELATAVDCGLLGSIDANR<br>GDAQNGWDTDQFPIDNFELTLAMLQIIRNGGLAPGGSNFDAKLRRNSTDPEDIFIAHISA<br>MDAMARALVNAAAIWEESPIPQMKKERYASFDSGKGKEFEEGKLCLEDLVAYAKANGEPK<br>QISGRQELYETIVALYCK |
| 5608MI1_004 | *Prevotella* | DNA | 141 | ATGACCAACGAGTATTTTCCCGGAATCGGTGTGATTCCGTTTGAAGGACAGGAAAGCAAG<br>AATCCCATGGCTTTCCATTATTATGACGCCAACCGCGTAGTGATGGGCAAACCCATGAAG<br>GAATGGTTCAAATTTGCCATGGCCTGGTGGCATACGCTGGGGCAGGCATCGGCCGATCCC<br>TTCGGCGGACAGACCCGCTCCTACGCATGGGACAAGGGCGAGTGCCCTTACTGCCGTGCC<br>CGCCAGAAGGCCGACGCCGGCTTTGAACTGATGCAGAAGCTGGGTATCGGCTATTTCTGC<br>TTCCACGATGTGGATATCATCGAGGACTGCGAAGACATTGCCGAGTATGAGGCCCGTATG<br>AAGGACATCACGGACTATCTGCTGGTGAAGATGAAGGAAACGGGCATCAAGAACCTGTGG<br>GGCACGGCCAACGTCTTCGGCCACAAGCGCTATATGAACGGCGCTGCCACCAACCCGCAG<br>TTCGACGTGGTGGCCCGCGCTGCGGTCCAGATCAAGAACGCCCTGGACGCCACCATCAAG<br>CTGGGCGGCAGCAATTACGTGTTCTGGGGCGGCCGCGAAGGCTATTATACCCTTTGGAAC<br>ACGCAGATGCGGCGGGAGAAGGACCACCTGGCCCAGATGCTCAAGGCAGCCCGTGACTAT<br>GCCCGCGGCAAGGGATTCAAGGGCACGTTCCTCATTGAGCCCAAGCCCATGGAGCCCACC<br>AAGCACCAGTACGACGTAGATACGGAGACCGTGATTGGCTTCCTGCGCGCAAACGGACTG<br>GACAAGGACTTCAAGGTGAATATCGAAGTGAACCACGCCACCCTGGCCGGCCACACCTTC<br>GAGCACGAACTCACCGTGGCCCGCGAAAACGGCTTCCTGGGCAGCATCGACGCCAACCGC<br>GGAGACGCCCAGAACGGTTGGGATACAGACCAGTTCCCCATAGATGCCTTTGACCTCACC<br>CAGGCCATGATGCAGGTCCTGCTCAACGGCGGATTCGGCAACGGCGGCACCAACTTCGAC<br>GCCAAACTGCGCCGTTCCTCCACGGATCCCGAGGACATCTTCATCGCCCACATCGGCGCC<br>ATGGACGCCATGGCCCACGCCCTCCTGAACGCCGCCGCCATCCTGGAAGAGAGCCCCATG<br>CCGGGCATGGTGAAGGAGCGCTACGCTTCCTTCGACAATGGCCTTGGCAAGAAGTTCGAG<br>GAAGGAAAGGCCACGCTGGAAGAGCTGTACGACTATGCCAAGAAGAACGGCGAGCCTGTG<br>GCCGCTTCCGGCAAGCAGGAACTGTACGAAACGCTGCTGAACCTGTACGCCAAGTAA |
| 5608MI1_004 | *Prevotella* | Amino Acid | 142 | MTNEYFPGIGVIPFEGQESKNPMAFHYYDANRVVMGKPMKEWFKFAMAWWHTLGQASADP<br>FGGQTRSYAWDKGECPYCRARQKADAGFELMQKLGIGYFCFHDVDIIEDCEDIAEYEARM<br>KDITDYLLVKMKETGIKNLWGTANVFGHKRYMNGAATNPQFDVVARAAVQIKNALDATIK<br>LGGSNYVFWGGREGYYTLWNTQMRREKDHLAQMLKAARDYARGKGFKGTFLIEPKPMEPT<br>KHQYDVDTETVIGFLRANGLDKDFKVNIEVNHATLAGHTFEHELTVARENGFLGSIDANR<br>GDAQNGWDTDQFPIDAFDLTQAMMQVLLNGGFGNGGTNFDAKLRRSSTDPEDIFIAHIGA<br>MDAMAHALLNAAAILEESPMPGMVKERYASFDNGLGKKFEEGKATLEELYDYAKKNGEPV<br>AASGKQELYETLLNLYAK |
| 5608MI2_002 | *Prevotella* | DNA | 143 | ATGAAAGAATACTTCCCTACCATCGGAAAAATCCCTTTCGAGGGCCCTCAGAGCAAGAAT<br>CCGCTCGCATTCCATTACTATGACGCCAACCGCGTTGTCGCCGGCAAACCCATGAAGGAC<br>TGGCTCAAGTTCGCCATGGCTTGGTGGCACACCCTGGGCGCAGCATCGGCAGACCCCTTC<br>GGCGGCCAGACCCGCAGCTACGAGTGGGACAAAGCCGAGTGCCCTTACTGCCGTGCCCGT<br>GAAAAGGCCGACGCCGGCTTCGAGATCATGCAGAAACTTGGAATCGAGTACTTCTGCTTC<br>CATGACATCGACCTTGTGGAAGACTGCGAGGACATTGCCGAGTACGAGGCCCGCATGAAG<br>GACATCACGGACTACCTCCTGGAGAAGATGAAGGCCACCGGCATCAAGAACCTGTGGGGC<br>ACCGCCAACGTCTTTGGCAACAAGCGCTACATGAACGGCGCAGCCACCAACCCTCAGTTC<br>GACATCGTTGCCCGTGCAGCTGTCCAGATCAAGAACGCCATCGACGCAACAATCAAGCTG<br>GGCGGTACCGGTTACGTATTCTGGGGCGGCCGCGAGGGCTACTACACCCTCCTGAACACC<br>CAGATGCAGCGCGAGAAGGACCACCTTGCCAAGATGCTCACCGCAGCCCGCGACTACGCC<br>CGCGCCAAGGGATTCAAGGGCACATTCCTCATCGAGCCCAAGCCCATGGAGCCCACCAAG<br>CACCAGTACGATGTTGACACGGAAACCGTCATCGGCTTCCTCCGCGCCAACGGCCTGGAC<br>AAGGACTTCAAGGTGAACATCGAGGTGAACCACGCCACCCTGGCCGGCCACACCTTCGAG<br>CACGAGCTCACCGTGGCCGTGGACAACGGCTTCCTGGGCAGCATCGACGCAAACCGCGGC<br>GACGCCCAGAACGGCTGGGACACTGACCAGTTCCCTGTGGATCCTTACGACCTCACCCAG<br>GCAATGATGCAGATTATCCGCAACGGCGGCTTCAAGGACGGCGGCACCAACTTCGACGCC<br>AAACTCCGCCGCAGCTCCACGGACCCCGAGGACATCTTCATCGCCCACATCAGCGCAATG<br>GATGCAATGGCACACGCCCTCATCAACGCTGCTGCAGTGCTTGAGGAAAGCCCTCTGTGC<br>GAGATGGTTGCAAAGCGCTACGCCAGCTTTGACAGCGGTCTTGGCAAGAAGTTCGAGGAA<br>GGCAAAGCCACTCTCGAGGAGATCTACGAGTATGCCAAGAAGGCCCCGGCACCCGTCGCC<br>GCCTCCGGCAAGCAGGAGCTCTACGAGACACTGCTCAATCTGTACGCTAAATAA |
| 5608MI2_002 | *Prevotella* | Amino Acid | 144 | MKEYFPTIGKIPFEGPQSKNPLAFHYYDANRVVAGKPMKDWLKFAMAWWHTLGAASADPF<br>GGQTRSYEWDKAECPYCRAREKADAGFEIMQKLGIEYFCFHDIDLVEDCEDIAEYEARMK<br>DITDYLLEKMKATGIKNLWGTANVFGNKRYMNGAATNPQFDIVARAAVQIKNAIDATIKL<br>GGTGYVFWGGREGYYTLLNTQMQREKDHLAKMLTAARDYARAKGFKGTFLIEPKPMEPTK<br>HQYDVDTETVIGFLRANGLDKDFKVNIEVNHATLAGHTFEHELTVAVDNGFLGSIDANRG<br>DAQNGWDTDQFPVDPYDLTQAMMQIIRNGGFKDGGTNFDAKLRRSSTDPEDIFIAHISAM<br>DAMAHALINAAAVLEESPLCEMVAKRYASFDSGLGKKFEEGKATLEEIYEYAKKAPAPVA<br>ASGKQELYETLLNLYAK |

TABLE 2-continued

| Clone No. | Class of organism | Type of Sequence | SEQ ID NO: | Sequence |
|---|---|---|---|---|
| 5608MI3_004 | *Prevotella* | DNA | 145 | ATGACCAAAGAGTATTTCCCTACAATCGGAAAGATTCCCTTCGAAGGCCCGGAGAGCAAG<br>AATCCGCTGGCATTCCATTACTATGAACCCGACAGAATCATCCTCGGCAGGAAGATGAAG<br>GACTGGCTGCGCTTCGCCGTGGCCTGGTGGCACACCCTCGGCCAGGCGTCCGGCGACCAG<br>TTCGGAGGCCAGACCCGCAACTATGCGTGGGACGAGCCCGAATGCCCGGTAGAGCGCGCG<br>AAAGCCAAGGCCGACGCCGGCTTCGAGCTGATGCAGAAGCTGGGCATCGAGTATTTCTGC<br>TTCCACGACGTAGACCTCATAGAGGAGGCCGCAACCATCGAAGAATATGAGGAGCGCATG<br>GGCATCATAACCGACTACCTGCTCGGGAAGATGAAGGAGACAGGTATCAAGAACCTCTGG<br>GGCACCGCCAACGTGTTCGGCCACAAGCGTTACATGAACGGAGCCGCCACCAACCCCGAC<br>TTCGACGTGGTGGCCCGTGCGGCCGTGCAGATCAAGAACGCCATCGACGCCACCATCAAG<br>CTGGGCGGCGAGAATTACGTATTCTGGGGCGGACGCGAGGGCTATGCAAGCCTGCTCAAC<br>ACTCAGATGCAGCGCGAGAAAGACCACCTGGGACGCATGCTGGCTGCAGCCCGCGACTAT<br>GGCCGCGCCCACGGATTCAAGGGCACTTTCCTCATCGAGCCCAAACCCATGGAGCCTACC<br>AAGCACCAGTACGACCAGGATACCGAGACCGTTATCGCCTTCCTGCGCAGGAACGGCCTC<br>GACAAGGATTTCAAGGTAAACATCGAGGTGAACCACGCCACCCTGGCGGGCCACACCTTC<br>GAGCACGAACTGGCGGTGGCAGTGGACAACGGCCTGCTTGGCAGCATCGACGCCAACCGC<br>GGCGACGCGCAGAACGGATGGGACACCGACCAGTTCCCCATCGACAACTTCGAGCTCACC<br>CAGGCCATGCTGCAGATAATCCGCAACGGCGGACTGGGAACCGGCGGATCGAACTTCGAC<br>GCCAAGCTGCGCCGCAATTCCACCGACCCTGAGGATATCTTCATCGCCCACATCAGTGCG<br>ATGGACGCCATGGCACGCGCGCTGGCAAACGCCGCCGCAATCATCGAAGAGAGCCCCATC<br>CCCGCAATGCTGAAGGAGCGCTACGCATCGTTCGACAGCGGCAAGGGCAAGGAGTTCGAG<br>GACGGCAAACTGAGCCTCGAAGAACTGGTAGCCTACGCCAAGGCGAACGGCGAGCCGAAG<br>CAGATTTCCGGCAAGCAGGAACTCTACGAAACCATAGTGGCCCTCTATTGCAAGTAA |
| 5608MI3_004 | *Prevotella* | Amino Acid | 146 | MTKEYFPTIGKIPFEGPESKNPLAFHYYEPDRIILGRKMKDWLRFAVAWWHTLGQASGDQ<br>FGGQTRNYAWDEPECPVERAKAKADAGFELMQKLGIEYFCFHDVDLIEEAATIEEYEERM<br>GIITDYLLGKMKETGIKNLWGTANVFGHKRYMNGAATNPDFDVVARAAVQIKNAIDATIK<br>LGGENYVFWGGREGYASLLNTQMQREKDHLGRMLAAARDYGRAHGFKGTFLIEPKPMEPT<br>KHQYDQDTETVIAFLRRNGLDKDFKVNIEVNHATLAGHTFEHELAVAVDNGLLGSIDANR<br>GDAQNGWDTDQFPIDNFELTQAMLQIIRNGGLGTGGSNFDAKLRRNSTDPEDIFIAHISA<br>MDAMARALANAAAIIEESPIPAMLKERYASFDSGKGKEFEDGKLSLEELVAYAKANGEPK<br>QISGKQELYETIVALYCK |
| 5609MI1_005 | *Prevotella* | DNA | 147 | ATGGCACAAGAATACTTCCCTACCATTGGGAAAATCCCCTTCGAGGGCACTGAGAGCAAG<br>AATCCCCTTGCTTTCCATTACTATGAGCCGGAGCGCATTGTCTGCGGCAAACCCATGAAA<br>GAATGGCTCAAGTTTGCCATGGCCTGGTGGCACACGCTGGGGCAGGCATCGGCCGATCCC<br>TTCGGCGGCCAAACCCGCAGCTATGCCTGGGATAAGGGCGAATGCCCCTACTGCCGTGCC<br>CGCGCCAAGGCGGACGCCGGCTTCGAGATTATGCAAAAGCTGGGCATCGAGTACTTCTGC<br>TTCCACGATATCGACCTGGTAGAAGACTGTGACGATATTGCGGAATACGAAGCCCGCATG<br>AAGGACATCACGGACTACCTCCTGGAGAAGATGAAGGAAACCGGTATCAAGAACCTCTGG<br>GGCACCGCCAATGTGTTTGGTCACAAGCGCTACATGAACGGCGCCGCCACCAACCCGCAG<br>TTTGACGTAGTGGCCCGTGCCGCTGTTCAGATTAAGAACGCCATTGACGCCACCATCAAG<br>TTGGGCGGTGCCAATTACGTGTTCTGGGGCGGCCGCGAGGGCTATTACAGCCTCCTGAAC<br>ACCCAGATGCAGCGGGAGAAGGACCACCTGGCCAAGCTGCTCACGGCAGCCCGCGACTAT<br>GCCCGCGCCAACGGCTTCAAGGGAACCTTCCTGATTGAGCCCAAGCCCATGGAGCCCACC<br>AAGCACCAGTACGACGTGGATACGGAGACGGTCATTGGCTTCCTCCGCGCCAACGGCCTG<br>GACAAGGACTTCAAGGTGAATATCGAGGTGAACCACGCCACGTTGGCCGGCCACACCTTT<br>GAGCACGAGCTCACCGTGGCCCGCGAGAACGGCTTCCTGGGCAGCATCGACGCCAACCGC<br>GGCGATGCCCAGAACGGCTGGGATACGGACCAGTTCCCGGTAGACGCTTATGAGCTCACC<br>CAGGCCATGATGCAGGTGCTCCTGAACGGAGGCTTCGGCAACGGCGGCACCAACTTCGAC<br>GCCAAGCTGCGCCGCTCCTCCACGGACCCGGAGGACATCTTCATCGCCCATATCAGTGCG<br>ATGGATGCCATGGCCCACGCCCTGCTCAACGCCGCCGCCGTGCTGGAGGAAAGCCCCCTG<br>TGCCAGATGGTGAAGGAGCGCTACGCCAGCTTTGACAGCGGTCCGGGCAAGCAGTTCGAG<br>GAAGGAAAGGCCACCCTGGAGGACCTGTACAACTACGCCAAAGCCACCGGTGAACCCGTG<br>GTTGCCTCCGGCAAGCAGGAACTTTACGAGACCCTCCTGAACCTCTATGCAAAGTAG |
| 5609MI1_005 | *Prevotella* | Amino Acid | 148 | MAQEYFPTIGKIPFEGTESKNPLAFHYYEPERIVCGKPMKEWLKFAMAWWHTLGQASADP<br>FGGQTRSYAWDKGECPYCRARAKADAGFEIMQKLGIEYFCFHDIDLVEDCDDIAEYEARM<br>KDITDYLLEKMKETGIKNLWGTANVFGHKRYMNGAATNPQFDVVARAAVQIKNAIDATIK<br>LGGANYVFWGGREGYYSLLNTQMQREKDHLAKLLTAARDYARANGFKGTFLIEPKPMEPT<br>KHQYDVDTETVIGFLRANGLDKDFKVNIEVNHATLAGHTFEHELTVARENGFLGSIDANR<br>GDAQNGWDTDQFPVDAYELTQAMMQVLLNGGFGNGGTNFDAKLRRSSTDPEDIFIAHISA<br>MDAMAHALLNAAAVLEESPLCQMVKERYASFDSGPGKQFEEGKATLEDLYNYAKATGEPV<br>VASGKQELYETLLNLYAK |
| 5610MI1_003 | *Prevotella* | DNA | 149 | ATGGCACAAGAATACTTCCCTACCATTGGGAAAATCCCCTTCGAGGGCACTGAGAGCAAG<br>AATCCCCTTGCTTTCCATTACTATGAGCCGGAGCGCATTGTCTGCGGCAAACCCATGAAA<br>GAATGGCTCAAGTTTGCCATGGCCTGGTGGCACACGCTGGGGCAGGCATCGGCCGATCCC<br>TTCGGCGGCCAAACCCGCAGCTATGCCTGGGATAAGGGCGAATGCCCCTACTGCCGTGCC<br>CGTGCCAAGGCGGACGCCGGTTTTGAGATTATGCAAAAGCTGGGCATCGAGTACTTCTGC<br>TTCCACGATATCGACCTGGTAGAAGACTGTGACGATATTGCGGAATACGAAGCCCGCATG<br>AAGGACATCACGGACTACCTCCTGGAGAAGATGAAGGAAACCGGCATCAAGAACCTCTGG<br>GGCACCGCCAATGTGTTTGGTCACAAGCGCTACATGAACGGCGCCGGCACCAATCCGCAG<br>TTTGACGTGGTGGCCCGTGCTGCCGTGCAAATCAAGAACGCCATTGACGCCACCATCAAG<br>TTGGGCGGTGCCAATTACGTGTTCTGGGGCGGCCGCGAGGGCTATTACAGCCTCCTGAAC<br>ACCCAGATGCAGCGGGAGAAGGACCACCTGGCCAAGCTGCTCACGGCAGCCCGCGACTAT<br>GCCCGCGCCAACGGCTTCAAGGGAACCTTCCTGATTGAGCCCAAGCCCATGGAGCCCACC |

TABLE 2-continued

| Clone No. | Class of organism | Type of Sequence | SEQ ID NO: | Sequence |
|---|---|---|---|---|
| | | | | AAGCACCAGTACGACGTGGATACGGAGACGGTCATTGGCTTCCTCCGCGCCAACGGCCTG<br>GACAAGGACTTCAAGGTGAATATCGAGGTGAACCACGCCACGCTGGCCGGCCACACCTTT<br>GAGCACGAACTCACCGTGGCCCGCGAGAACGGCTTCCTGGGCAGCATCGACGCCAACCGC<br>GGCGATGCCCAGAACGGCTGGGATACGGACCAGTTCCCGGTAGACGCTTATGAGCTCACC<br>CAGGCCATGATGCAGGTGCTCCTGAACGGAGGCTTCGGCAACGGCGGCACCAACTTCGAC<br>GCCAAGCTGCGCCGCTCCTCCACGGACCTGGAGGACATCTTCATCGCCCATATCAGTGCG<br>ATGGATGCCATGGCCCACGCCCTGCTCAACGCCGCCGCCGTGCTGGAGGAAAGCCCCCTG<br>TGCCAGATGGTGAAGGAGCGCTACGCCAGCTTTGACAGCGGTCCGGGCAAGCAGTTCGAG<br>GAAGGAAAGGCCACCCTGGAGGACCTGTACAACTACGCCAAAGCCAACGGTGAACCCGTG<br>GTTGCCTCCGGCAAGCAGGAACTTTACGAGACCCTCCTGAACCTCTATGCAAAGTAG |
| 5610MI1_003 | *Prevotella* | Amino Acid | 150 | MAQEYFPTIGKIPFEGTESKNPLAFHYYEPERIVCGKPMKEWLKFAMAWWHTLGQASADP<br>FGGQTRSYAWDKGECPYCRARAKADAGFEIMQKLGIEYFCFHDIDLVEDCDDIAEYEARM<br>KDITDYLLEKMKETGIKNLWGTANVFGHKRYMNGAGTNPQFDVVARAAVQIKNAIDATIK<br>LGGANYVFWGGREGYYSLLNTQMQREKDHLAKLLTAARDYARANGFKGTFLIEPKPMEPT<br>KHQYDVDTETVIGFLRANGLDKDFKVNIEVNHATLAGHTFEHELTVARENGFLGSIDANR<br>GDAQNGWDTDQFPVDAYELTQAMMQVLLNGGFGNGGTNFDAKLRRSSTDLEDIFIAHISA<br>MDAMAHALLNAAAVLEESPLCQMVKERYASFDSGPGKQFEEGKATLEDLYNYAKANGEPV<br>VASGKQELYETLLNLYAK |
| 5610MI2_004 | *Prevotella* | DNA | 151 | ATGGCAAAAGAATATTTCCCTACCATCGGCAAGATTCCTTTTGAAGGAACCGACAGCAAG<br>AGTCCCCTCGCCTTCCATTACTATGACGCCCAGCGCGTTGTGATGGGCAAACCCATGAAG<br>GAATGGCTCAAGTTCGCCATGGCCTGGTGGCACACCCTGGGCCAGGCATCGGCCGACCCC<br>TTCGGCGGTCAGACCCGCCACTATGCCTGGGATGAAGGCGAATGCCCCTACTGCCGCGCC<br>AAAGCCAAGGCCGACGCCGGCTTCGAGATCATGCAGAAACTGGGCATCGAGTACTTCTGC<br>TTCCACGATGTGGACCTGGTGGAAGACTGCGACGACATCGCCGAGTACGAAGCCCGCATG<br>AAGGACATCACGGACTACCTGCTGGAGAAGATGAAGGAAACCGGCATCAAGAACCTCTGG<br>GGCACGGCCAATGTGTTCGGCCACAAGCGTTACATGAACGGCGCCGGGACCAACCCGCAG<br>TTTGACATTGTGGCCCGCGCTGCCGTCCAGATCAAAAACGCCCTGGACGCCACCATCAAG<br>CTGGGCGGTTCCAACTACGTGTTCTGGGGCAGCCGCGAAGGCTACTACACCCTCCTGAAC<br>ACCCAGATGCAGCGGGAGAAAGACCACCTGGCCAAGCTCCTGACCGCCGCCCGCGACTAC<br>GCCCGCGCCAAAGGCTTCAAGGGAACCTTCCTCATCGAGCCCAAACCCATGGAGCCCACC<br>AAGCACCAGTACGACGTGGACACCGAGACCGTAATCGGCTTCCTGCGTGCCAACGGCCTG<br>GACAAGGACTTCAAGGTGAACATCGAGGTGAACCACGCCACCCTGGCTGGCCACACCTTC<br>GAGCACGAACTCACCGTCGCCCGTGAAAACGGCTTCCTCGGATCGATCGACGCCAACCGC<br>GGCGACGCCCAGAACGGCTGGGACACCGACCAGTTCCCCGTAGACGCCTATGACCTCACC<br>CAGGCCATGATGCAGGTGCTGCTGAACGGCGGTTTCGGCAATGGCGGTACCAACTTCGAC<br>GCCAAGCTCCGCCGCTCCTCCACGGATCCGGAAGACATCTTCATCGCCCACATCAGCGCC<br>ATGGACGCCATGGCCCACGCCCTGCTGAACGCCGCCGCCGTGCTGGAAGAAAGCCCGCTT<br>CCCGCCATGGCGAAAGAGCGCTACGCCTCCTTTGACAGCGGACTTGGCAAGAAGTTCGAA<br>GAGGGAAAGGCCACCCTCGAAGAGCTGTACGACTATGCCAAGGCTAACGACGCCCCTGTC<br>GCCGCCTCCGGCAAGCAGGAACTTTACGAAACCTTCTTGAACCTCTATGCAAAATAG |
| 5610MI2_004 | *Prevotella* | Amino Acid | 152 | MAKEYFPTIGKIPFEGTDSKSPLAFHYYDAQRVVMGKPMKEWLKFAMAWWHTLGQASADP<br>FGGQTRHYAWDEGECPYCRAKAKADAGFEIMQKLGIEYFCFHDVDLVEDCDDIAEYEARM<br>KDITDYLLEKMKETGIKNLWGTANVFGHKRYMNGAGTNPQFDIVARAAVQIKNALDATIK<br>LGGSNYVFWGSREGYYTLLNTQMQREKDHLAKLLTAARDYARAKGFKGTFLIEPKPMEPT<br>KHQYDVDTETVIGFLRANGLDKDFKVNIEVNHATLAGHTFEHELTVARENGFLGSIDANR<br>GDAQNGWDTDQFPVDAYDLTQAMMQVLLNGGFGNGGTNFDAKLRRSSTDPEDIFIAHISA<br>MDAMAHALLNAAAVLEESPLPAMAKERYASFDSGLGKKFEEGKATLEELYDYAKANDAPV<br>AASGKQELYETFLNLYAK |
| 5751MI1_003 | *Prevotella* | DNA | 153 | ATGGCAAAACAGTATTTTCCGCAAATCGGAAAGATTAAATTCGAAGGAACAGAGAGCAAG<br>AATCCGCTTGCGTTCCATTATTATGACGCAAACAGGGTAGTCCTCGGAAAGGCAATGGAG<br>GAGTGGCTCAAGTTCGCAATGGCTTGGTGGCATACTCTCGGACAGGCTTCCGGAGACCAG<br>TTCGGCGGCCAGACCCGCAGCTACGAGTGGGATCTTGCAGCCACCCCCGAGCAGCGCGCA<br>AAGGACAAGCTCGACGCCGGCTTCGAAATAATGGAGAAACTTGGAATCAAGTATTTCTGT<br>TTCCACGATGTTGACCTTATCGAAGACAGCGACGATATTGCGACATATGAGGCTCGTCTC<br>AAGGACCTTACAGACTACGCTGCAGAGCAGATGAAGCTCCACGACATCAAGCTCCTCTGG<br>GGTACAGCGAATGTATTCGGCAACAAGCGCTACATGAACGGTGCGGCTACAAACCCTGAT<br>TTCGATGTAGTTGCCCGCGCAGCCGTTCAGATTAAGAACGCTATCGACGCGACCATCAAG<br>CTCGGTGGTACCAGCTATGTATTCTGGGGCGGTCGTGAGGGATATCAGAGCCTGCTCAAC<br>ACTCAGATGCAGCGTGAGAAGGACCACCTCGCAACCATGCTTACAATCGCTCGCGACTAT<br>GCTCGCAGCAAGGGCTTTACCGGAACCTTCCTTATCGAGCCTAAGCCGATGGAGCCTACA<br>AAACACCAGTACGACGTAGATACAGAGACTGTTGTCGGCTTCCTCAAGGCACACGGCCTG<br>GACAAGGACTTCAAGGTAAATATCGAGGTTAACCACGCAACTCTCGCAGGCCACACCTTC<br>GAGCACGAACTCACCGTTGCTGTGGATAACGGAATGCTCGGTTCTATCGACGCTAACCGC<br>GGTGATGCACAGAACGGCTGGGATACAGACCAGTTCCCTGTAAGCGCTGAGGAGCTTACC<br>CTCGCTATGATGCAGATTATCCGTAATGGTGGCCTTGGCAACGGAGGATCCAACTTCGAC<br>GCAAAGCTTCGCCGCAACTCTACCGATCCTGAAGACATCTTCATCGCACACATCTGCGGT<br>ATGGATGCAATGGCACACGCTCTCCTCAATGCAGCTGCAATTATCGAGGAGTCTCCTATC<br>CCTACAATGGTTAAGGAGCGTTACGCTTCCTTCGACAGCGGTATGGGTAAGGACTTCGAG<br>GATGGAAAGCTTACCCTCGAGGATCTCTACAGCTACGGCGTGAAGAACGGAGAGCCAAAG<br>CAGACCAGCGCAAAGCAGGAGCTCTATGAGACTCTCATGAATATCTATTGCAAGTAA |

TABLE 2-continued

| Clone No. | Class of organism | Type of Sequence | SEQ ID NO: | Sequence |
|---|---|---|---|---|
| 5751MI1_003 | *Prevotella* | Amino Acid | 154 | MAKQYFPQIGKIKFEGTESKNPLAFHYYDANRVVLGKAMEEWLKFAMAWWHTLGQASGDQ<br>FGGQTRSYEWDLAATPEQRAKDKLDAGFEIMEKLGIKYFCFHDVDLIEDSDDIATYEARL<br>KDLTDYAAEQMKLHDIKLLWGTANVFGNKRYMNGAATNPDFDVVARAAVQIKNAIDATIK<br>LGGTSYVFWGGREGYQSLLNTQMQREKDHLATMLTIARDYARSKGFTGTFLIEPKPMEPT<br>KHQYDVDTETVVGFLKAHGLDKDFKVNIEVNHATLAGHTFEHELTVAVDNGMLGSIDANR<br>GDAQNGWDTDQFPVSAEELTLAMMQIIRNGGLGNGGSNFDAKLRRNSTDPEDIFIAHICG<br>MDAMAHALLNAAAIIEESPIPTMVKERYASFDSGMGKDFEDGKLTLEDLYSYGVKNGEPK<br>QTSAKQELYETLMNIYCK |
| 5751MI2_003 | *Prevotella* | DNA | 155 | ATGGCAAAAGAATTTTTTCCACAAGTAGGCAAGATTCCATTTGAGGGTCCTGAAAGTACT<br>AACGTACTCGCATTCCACTACTATGATCCAGAACGCGAAGTTCTTGGTAAGAAAATGAAA<br>GATTGGCTGAAGTATGCTATGGCTTGGTGGCACACACTCGGTCAGGCAAGTGGCGACCAA<br>TTCGGTGGTCAAACTCGTTCGTATGAATGGGATGAAGCCGACGATGTTCTTCAACGCGCA<br>AAGGATAAAATGGATGCTGGTTTTGAATTGATGACCAAACTTGGCATTGAATACTACTGC<br>TTCCATGATGTCGACCTTATTGAAGAAGGTGCAACAATTGAAGAATATGAAGCTCGTATG<br>CAAGCTATCACCGACTACGCATTAGAAAAACAAAAAGAAACCGGCATTAAGCTCCTTTGG<br>GGTACTGCTAATGTGTTTGGTCATAAGCGTTATATGAATGGTGCGGCAACAAACCCTGAC<br>TTTGATGTAGTGGCTCGCGCTGCTGTACAAATCAAGAACGCTATCGATGCAACTATCAAG<br>CTTGGTGGTCAAAACTATGTATTCTGGGGTGGCCGCGAAGGTTATATGAGTTTGCTCAAC<br>ACTCAAATGCAACGCGAAAAAGACCACTTGGCAAAGATGCTTACCGCAGCTCGCGACTAT<br>GCTCGTGCTAAGGGCTTCAAGGGTACATTCCTCGTTGAACCTAAGCCTATGGAACCAACT<br>AAGCATCAATATGATACCGATACAGAAACTGTGATTGGTTTCCTCCGTGCAAATGGTCTT<br>GAAAAAGACTTCAAGGTGAACATTGAAGTGAACCATGCTACTCTCGCTCAGCACACTTTC<br>GAACACGAACTCGCTGTGGCTGTCGACAATGGCATGCTCGGTTCTATCGACGCTAACCGT<br>GGCGATGCTCAAAATGGCTGGGATACCGACCAATTCCCAATCGACAACTACGAACTCACC<br>CTCGCTATGCTCCAAATCATTCGCAATGGTGGTCTTGGCAATGGCGGTAGCAACCTCGAC<br>GCTAAGATTCGTCGTAATAGCACCGACCTTGAAGACCTCTTTATCGCTCACATCAGTGGT<br>ATGGATGCTATGGCTCGTGCACTTCTCAATGCTGCTGCAATCGTTGAAAAGAGCGAAATT<br>CCTGCTATGTTGAAGCAGCGTTATGCAAGCTCTGATGCAGGTATGGGTAAGGACTTCGAA<br>GAAGGAAAACTCACTCTCGAACAACTCGTAGACTATGCTAAGGCTAACGGCGAACCTGCT<br>ACAGTAAGCGGCAAGCAAGAAAAGTATGAAACTCTCGTTGCTCTCTACGCTAAGTAA |
| 5751MI2_003 | *Prevotella* | Amino Acid | 156 | MAKEFFPQVGKIPFEGPESTNVLAFHYYDPEREVLGKKMKDWLKYAMAWWHTLGQASGDQ<br>FGGQTRSYEWDEADDVLQRAKDKMDAGFELMTKLGIEYYCFHDVDLIEEGATIEEYEARM<br>QAITDYALEKQKETGIKLLWGTANVFGHKRYMNGAATNPDFDVVARAAVQIKNAIDATIK<br>LGGQNYVFWGGREGYMSLLNTQMQREKDHLAKMLTAARDYARAKGFKGTFLVEPKPMEPT<br>KHQYDTDTETVIGFLRANGLEKDFKVNIEVNHATLAQHTFEHELAVAVDNGMLGSIDANR<br>GDAQNGWDTDQFPIDNYELTLAMLQIIRNGGLGNGGSNLDAKIRRNSTDLEDLFIAHISG<br>MDAMARALLNAAAIVEKSEIPAMLKQRYASSDAGMGKDFEEGKLTLEQLVDYAKANGEPA<br>TVSGKQEKYETLVALYAK |
| 5752MI1_003 | *Prevotella* | DNA | 157 | ATGACTAAAGAGTATTTCCCGGGAATCGGAAAGATTCCGTTTGAAGGAACCAAGAGCAAG<br>AACCCCCTGGCCTTCCATTATTATAACGCCTCCCAGGTAGCGATGGGCAAGCCCATGAAG<br>GACTGGCTCAAGTATGCCATGGCCTGGTGGCACACCCTGGGCCAGGCCTCTGCAGACCCC<br>TTTGGCGGCCAGACCCGCTCCTACGAATGGGACAAGGGCGAGTGCCCTTATTGCCGCGCC<br>AAGCAGAAGGCCGATGCCGGCTTTGAGCTCATGCAGAAGCTGGGCATCGAGTACTACTGC<br>TTCCACGACGTGGACATCATCGAGGACTGCGAGGACATTGCCGAGTACGAGGCCCGCATG<br>AAGGACATCACGGACTACCTGCTGGAGAAGCAGAAAGAGACCGGCATCAAGAACCTCTGG<br>GGCACCGCCAACGTGTTTGGCCACAAGCGCTACATGAACGGCGCCGCCACCAACCCTCAG<br>TTTGACATTGTGGCCCGTGCCGCCGTCCAGATCAAGAACGCCCTGGATGCCACCATCAAG<br>CTGGGTGGTACCAACTACGTGTTCTGGGGTGGCCGCGAAGGCTACTACACGCTGCTCAAC<br>ACCCAGATGCAGCGGGAGAAGAACCACCTGGCCAAGATGCTCACCGCCGCCCGCGACTAC<br>GCCCGCGCCAAGGGCTTCAAGGGCACCTTCCTCATTGAGCCCAAACCCATGGAGCCCACC<br>AAGCACCAGTACGACGTGGACACCGAGACCGTGATTGGTTTCATCCGCGCCAACGGCCTG<br>GACAAGGACTTCAAGGTAAACATTGAGGTAAACCACGCCACCCTGGCCGGCCACACCTTT<br>GAGCACGAGCTCACCGTGGCCCGCGAGAACGGCTTCCTGGGCTCCATCGACGCCAACCGC<br>GGAGATGCCCAGAACGGCTGGGATACGGACCAGTTCCCCATCGACGCCCTGGATCTCACC<br>CAGGCTATGATGCAGGTCATCCTCAACGGTGGCTTCGGCAATGGCGGCACCAACTTTGAC<br>GCCAAGCTCCGCCGCTCCTCCACCGATCCCGAGGACATCTTCATCGCCCACATCAGCGCC<br>ATGGATGCCATGGCACACGCCCTCCTGAACGCAGCCGCCATCCTGGAAGAGAGCCCCCTG<br>CCCGCCATGGTCAAGGAGCGTTACGCTTCCTTCGACAGCGGTCTGGGCAAGAAGTTCGAA<br>GAAGGCAAGGCCTCCCTGGAAGAACTTTACGAATATGCCAAGAAGAATGGAGAGCCCGTG<br>GCCGCTTCCGGCAAACAGGAGCTCTGCGAAACTTACTTGAACCTCTATGCAAAGTAG |
| 5752MI1_003 | *Prevotella* | Amino Acid | 158 | MTKEYFPGIGKIPFEGTKSKNPLAFHYYNASQVAMGKPMKDWLKYAMAWWHTLGQASADP<br>FGGQTRSYEWDKGECPYCRAKQKADAGFELMQKLGIEYYCFHDVDIIEDCEDIAEYEARM<br>KDITDYLLEKQKETGIKNLWGTANVFGHKRYMNGAATNPQFDIVARAAVQIKNALDATIK<br>LGGTNYVFWGGREGYYTLLNTQMQREKNHLAKMLTAARDYARAKGFKGTFLIEPKPMEPT<br>KHQYDVDTETVIGFIRANGLDKDFKVNIEVNHATLAGHTFEHELTVARENGFLGSIDANR<br>GDAQNGWDTDQFPIDALDLTQAMMQVILNGGFGNGGTNFDAKLRRSSTDPEDIFIAHISA<br>MDAMAHALLNAAAILEESPLPAMVKERYASFDSGLGKKFEEGKASLEELYEYAKKNGEPV<br>AASGKQELCETYLNLYAK |
| 5752MI2_003 | *Prevotella* | DNA | 159 | ATGACTAAAGAGTATTTCCCGGGAATCGGAAAGATTCCGTTTGAAGGAACCAAGAGCAAG<br>AACCCCCTGGCCTTCCATTATTATAACGCCTCCCAGGTAGTGATGGGCAAGCCCATGAAG |

TABLE 2-continued

| Clone No. | Class of organism | Type of Sequence | SEQ ID NO: | Sequence |
|---|---|---|---|---|
| | | | | GACTGGCTCAAGTATGCCATGGCCTGGTGGCACACCCTGGGCCAGGCCTCTGCAGACCCC<br>TTTGGCGGCCAGACCCGCTCCTACGAATGGGACAAGGGCGAGTGCCCGTACTGCCGCGCC<br>AAGCAGAAGGCCGATGCCGGCTTTGAGCTCATGCAGAAGCTGGGCATCGAGTACTACTGC<br>TTCCACGACGTGGACATCATCGAGGACTGCGAGGACATTGCCGAGTACGAGGCCCGCATG<br>AAGGACATCACGGACTACCTGCTGGAGAAGCAGAAAGAGACCGGCATCAAGAACCTCTGG<br>GGCACCGCCAACGTGTTTGGCCACAAGCGCTACATGAACGGCGCCGCCACCAACCCTCAG<br>TTTGACATTGTGGCCCGTGCCGCCGTCCAGATCAAGAACGCCCTGGATGCCACCATCAAA<br>CTGGGTGGTACCAACTACGTGTTCTGGGGTGGCCGCGAAGGCTACTACACGCTGCTCAAC<br>ACCCAGATGCAGCGGGAGAAGAACCACCTGGCCAAGATGCTCACCGCCGCCCGCGACTAC<br>GCCCGCGCCAAGGGCTTCAAGGGCACCTTCCTCATTGAGCCCAAACCCATGGAGCCCACC<br>AAGCACCAGTACGACGTGGACACCGAGACCGTGATTGGTTTCATCCGCGCCAACGGCCTG<br>GACAAGGACTTCAAGGTAAACATTGAGGTAAACCACGCCACCCTGGCCGGCCACACCTTT<br>GAGCACGAGCTCACCGTGGCCCGCGAGAACGGCTTCCTGGGCTCCATCGACGCCAACCGC<br>GGAGATGCCCAGAACGGCTGGGATACGGACCAGTTCCCCATCGACGCCCTGGATCTCACC<br>CAGGCTATGATGCAGGTCATCCTCAACGGTGGCTTCGGCAATGGCGGCACCAACTTTGAC<br>GCCAAGCTCCGCCGCTCCTCCACCGATCCCGAGGACATCTTCATCGCCCACATCAGCGCC<br>ATGGATGCCATGGCACACGCCCTCCTGAACGCAGCCGCCATCCTGGAAGAGAGCCCCCTG<br>CCCGCCATGGTCAAGGAGCGTTACGCTTCCTTCGACAGCGGTCTGGGCAAGAAGTTCGAA<br>GAAGGCAAGGCCTCCCTGGAAGAACTTTACGAATATGCCAAGAAGAATGGAGAGCCCGTG<br>GCCGCTTCCGGCAAACAGGAGCTCTGCGAAACTTACTTGAACCTCTATGCAAAGTAG |
| 5752MI2_003 | *Prevotella* | Amino Acid | 160 | MTKEYFPGIGKIPFEGTKSKNPLAFHYYNASQVVMGKPMKDWLKYAMAWWHTLGQASADP<br>FGGQTRSYEWDKGECPYCRAKQKADAGFELMQKLGIEYYCFHDVDIIEDCEDIAEYEARM<br>KDITDYLLEKQKETGIKNLWGTANVFGHKRYMNGAATNPQFDIVARAAVQIKNALDATIK<br>LGGTNYVFWGGREGYYTLLNTQMQREKNHLAKMLTAARDYARAKGFKGTFLIEPKPMEPT<br>KHQYDVDTETVIGFIRANGLDKDFKVNIEVNHATLAGHTFEHELTVARENGFLGSIDANR<br>GDAQNGWDTDQFPIDALDLTQAMMQVILNGGFGNGGTNFDAKLRRSSTDPEDIFIAHISA<br>MDAMAHALLNAAAILEESPLPAMVKERYASFDSGLGKKFEEGKASLEELYEYAKKNGEPV<br>AASGKQELCETYLNLYAK |
| 5752MI3_002 | *Prevotella* | DNA | 161 | ATGGCAAAAGAGTATTTCCCGACTATCGGCAAGATTCCCTTCGAGGGCGTCGAATCCAAG<br>AACCCGATGGCATTCCACTACTATGACGCGAACCGCGTCGTGATGGGCAAGCCCATGAAG<br>GACTGGCTCAAGTTCGCGATGGCCTGGTGGCACACCCTGGGACAGGCTTCCGGCGACCCG<br>TTCGGCGGCCAGACCCGTTCCTACGAGTGGGACAAGGGCGAGTGCCCCTACTGCCGCGCC<br>AAGGCCAAGGCCGACGCCGGCTTCGAGATCATGCAGAAGCTCGGTATCGAGTACTACTGC<br>TTCCATGACATCGACCTCGTGGAGGACACCGAGGACATCGCCGAGTACGAGGCCCGCATG<br>AAGGACATCACCGACTACCTCGTCGAGAAGCAGAAGGAAACCGGCATCAAGAACCTCTGG<br>GGCACGGCCAACGTGTTCGGCAACAAGCGCTACATGAACGGCGCCGCCACGAACCCGCAG<br>TTCGACGTCGTCGCCCGCGCCGCCGTCCAGATCAAGAACGCCATCGACGCCACCATCAAG<br>CTCGGCGGTACCGGTTACGTGTTCTGGGGCGGCCGTGAAGGCTACTACACCCTCCTGAAC<br>ACCCAGATGCAGCGCGAGAAGGACCACCTCGCCAAGATGCTCACCGCCGCCCGCGACTAC<br>GCCCGCGCCCACGGCTTCCAGGGCACCTTCCTCATCGAGCCCAAGCCCATGGAGCCCACC<br>AAGCACCAGTACGACGTGGACACGGAGACCGTGATCGGCTTCCTGCGCGCCAACGGTCTG<br>GACAAGGACTTCAAGGTCAATATCGAGGTGAACCACGCCACCCTCGCCGGCCACACCTTC<br>GAGCACGAGCTCACCGTGGCTGTCGATAACGGCTTCCTCGGCTCCATCGACGCCAACCGC<br>GGCGACGCCCAGAACGGCTGGGACACCGACCAGTTCCCCGTGGACCCGTACGACCTCACC<br>CAGGCCATGATGCAGATCATCCGCAACGGCGGTTTCAAGGACGGCGGCACCAACTTCGAC<br>GCCAAGCTCCGCCGCTCTTCCACCGACCCGGAGGACATCTTCATCGCCCACATCAGCGCG<br>ATGGACGCCATGGCCCACGCCCTGCTGAACGCCGCCGCCGTCATCGAGGAGAGCCCGCTC<br>TGCAAGATGGTCGAGGAGCGCTACGCTTCCTTCGACAGCGGCCTCGGCAAGCAGTTCGAG<br>GAAGGCAAGGCCACCCTCGAGGACCTCTACGAGTATGCCAAGAAGAATGGCGAGCCCGTC<br>GTCGCCTCCGGCAAGCAGGAGCTCTACGAGACGCTGCTGAACCTTTACGCGAAGTAG |
| 5752MI3_002 | *Prevotella* | Amino Acid | 162 | MAKEYFPTIGKIPFEGVESKNPMAFHYYDANRVVMGKPMKDWLKFAMAWWHTLGQASGDP<br>FGGQTRSYEWDKGECPYCRAKAKADAGFEIMQKLGIEYYCFHDIDLVEDTEDIAEYEARM<br>KDITDYLVEKQKETGIKNLWGTANVFGNKRYMNGAATNPQEDVVARAAVQIKNAIDATIK<br>LGGTGYVFWGGREGYYTLLNTQMQREKDHLAKMLTAARDYARAHGFQGTFLIEPKPMEPT<br>KHQYDVDTETVIGFLRANGLDKDFKVNIEVNHATLAGHTFEHELTVAVDNGFLGSIDANR<br>GDAQNGWDTDQFPVDPYDLTQAMMQIIRNGGFKDGGTNFDAKLRRSSTDPEDIFIAHISA<br>MDAMAHALLNAAAVIEESPLCKMVEERYASFDSGLGKQFEEGKATLEDLYEYAKKNGEPV<br>VASGKQELYETLLNLYAK |
| 5752MI5_003 | *Prevotella* | DNA | 163 | ATGGCAAAAGAGTATTTCCCGACAATCGGTAAGATCCCCTTCGAGGGACCCGAGTCCAAG<br>AACCCGATGGCATTCCACTACTATGACGCGGAGCGCGTGGTGATGGGCAAGAAGATGAAG<br>GACTGGTTCAAGTTCGCGATGGCCTGGTGGCACACCCTGGGCCAGGCTTCCGCCGACCCG<br>TTCGGCGGCCAGACCCGCTCCTACGAGTGGGACAAGGGCGAAGGCCCCTGCTCCCGCGCC<br>CGCGCCAAGGCTGACGCCGGTTTCGAGATCATGCAGAAACTGGGCATCGGCTACTACTGC<br>TTCCACGACATCGACCTGGTGGAGGACACCGAGGACATCGCCGAGTATGAAGCCCGCATG<br>AAGGACATCACCGACTACCTCGTGGAGAAGCAGAAGGAGACCGGCATCAAGAACCTCTGG<br>GGCACGGCCAACGTATTCGGCAACAAGCCCTACATGAACGGCGCCGCCACGAACCCGCAG<br>TTCGACATCGCCGCCCGCGCGGCCCTGCAGACCAAGAACGCCATCGATGCCACCATCAAG<br>CTGGGCGGCACCGGTTACGTGTTCTGGGGCGGCCGTGAAGGCTACTACACCCTCCTGAAC<br>ACCCAGATGCAGCGCGAGAAGGACCACCTTGCCAAGATGCTCACCGCGGCTCGCGACTAT<br>GCCCGCGCCCACGGCTTCAAGGGCACCTTCTTCATCGAGCCGAAACCGATGGAGCCCACC<br>AAGCACCAGTACGACGTGGACACGGAGACCGTGATCGGCTTCCTCCGCGCCAACGGCCTG<br>GACAAGGACTTCAAGGTGAACATCGAAGTGAACCACGCCACCCTCGCCGGCCACACCTTC |

TABLE 2-continued

| Clone No. | Class of organism | Type of Sequence | SEQ ID NO: | Sequence |
|---|---|---|---|---|
| | | | | GAGCACGGGCTCACCGTGGCCGTTGACAACGGCTTCCTCGGCAGCATCGACGCCAACCGC<br>GGAGACGCCCAGAACGGCTGGGATACCGACCAGTTCCCGGTGGATCCGTACGACCTCACC<br>CAGGCGATGATCCAGATCATCCGCAATGGCGGCTTCAAGGACGGCGGTACCAACTTCGAC<br>GCCAAGCTCCGCCGCTCTTCCACCGACCCGGAGGACATCTTCATCGCCCACATCAGCGCG<br>ATGGACGCCATGGCCCACGCCCTGCTGAACGCCGCCGCCGTGCTCGAGGAGAGCCCGCTC<br>TGCGAGATGGTTGCAAAGCGTTACGCTTCCTTCGACAGCGGTCTCGGCAAGAAGTTCGAG<br>GAAGGCAACGCCACCCTCGAGGAACTCTACGAGTACGCCAAGGCGAAGGGCGAGGTCGTT<br>GCCGAATCCGGCAAGCAGGAACTCTACGAGACCCTGCTGAACCTCTACGCGAAGTAG |
| 5752MI5_003 | *Prevotella* | Amino Acid | 164 | MAKEYFPTIGKIPFEGPESKNPMAFHYYDAERVVMGKKMKDWFKFAMAWWHTLGQASADP<br>FGGQTRSYEWDKGEGPCSRARAKADAGFEIMQKLGIGYYCFHDIDLVEDTEDIAEYEARM<br>KDITDYLVEKQKETGIKNLWGTANVFGNKPYMNGAATNPQFDIAARAALQTKNAIDATIK<br>LGGTGYVFWGGREGYYTLLNTQMQREKDHLAKMLTAARDYARAHGFKGTFFIEPKPMEPT<br>KHQYDVDTETVIGFLRANGLDKDFKVNIEVNHATLAGHTFEHGLTVAVDNGFLGSIDANR<br>GDAQNGWDTDQFPVDPYDLTQAMIQIIRNGGFKDGGTNFDAKLRRSSTDPEDIFIAHISA<br>MDAMAHALLNAAAVLEESPLCEMVAKRYASFDSGLGKKFEEGNATLEELYEYAKAKGEVV<br>AESGKQELYETLLNLYAK |
| 5752MI_6004 | *Prevotella* | DNA | 165 | ATGGCAAAAGAGTATTTCCCGACAATCGGAAAGATCCCCTTCGAGGGCGCTGAGAGCAAG<br>AATCCCCTTGCTTTCCACTATTATGACGCCGAGCGTGTGGTCATGGGCAAGCCCATGAAG<br>GACTGGTTCAAGTTCGCGATGGCCTGGTGGCACACCCTGGGCCAGGCTTCCGCCGACCCG<br>TTCGGCGGCCAGACCCGCTCCTACGAGTGGGACAAGGGCGAGTGCCCCTACTGCCGCGCC<br>CGCCAGAAGGCTGACGCCGGTTTCGAGATCATGCAGAAGCTCGGCATCGGCTACTACTGC<br>TTCCACGACATCGACCTGGTCGAGGACACCGAGGACATCGCCGAGTACGAGGCCCGCATG<br>AAGGACATCACCGACTACCTCGTCGAGAAGCAGAAGGAGACCGGCATCAAGAACCTCTGG<br>GGCACGGCCAACGTGTTCGGCAACAAGCGCTACATGAACGGCGCCGCCACGAACCCGCAG<br>TTCGACATCGTCGCCCACGCGGCCCTGCAGATCAAGAACGCGATCGGCGCCACCATCAAG<br>CTCGGCGGCACCGGTTACGTGTTCTGGGGCGGCCGTGAAGGTTACTACACCCTCCTGAAC<br>ACCCAGATGCAGCGCGAGAAGGACCACCTCGCCAAGATGCTCACCGCCGCCCGCGACTAC<br>GCCCGCGCCAACGGCTTCAAGGGCACCTTCCTCATCGAGCCGAAGCCGATGGAGCCCACC<br>AAGCACCAGTATGACGTGGACACGGAGACCGTGATCGGCTTCCTCCGCGCCAACGGCCTG<br>GACAAGGACTTCAAGGTGAACATCGAGGTGAACCACGCCACCCTCGCCGGCCACACCTTC<br>GAGCACGAGCTCACCGTGGCGGTCGACAACGGCTTCCTCGGCAGCATCGACGCCAACCGC<br>GGTGACGCCCAGAACGGCTGGGATACCGACCAGTTCCCGGTGGATCCGTACGATCTCACC<br>CAGGCGATGATCCAGATCATCCGCAACGGCGGCTTCAAGGATGGCGGCACCAACTTCGAC<br>GCCAAGCTCCGCCGCTCTTCCACCGACCCGGAGGACATCTTCATCGCCCACATCAGCGCG<br>ATGGACGCCATGGCCCACGCCCTGCTGAACGCCGCCGCCGTCATCGAGGAGAGCCCGCTC<br>TGCGAGATGGTCGCCAAGCGCTACGCTTCCTTCGACAGCGGTCTCGGCAAGAAGTTCGAG<br>GAAGGCAACGCCACCCTCGAGGAACTCTACGAGTACGCCAAGGCGAACGGTGAGGTCAAG<br>GCCGAATCCGGCAAGCAGGAGCTCTACGAGACCCTTCTGAACCTCTACGCGAAATAG |
| 5752MI6_004 | *Prevotella* | Amino Acid | 166 | MAKEYFPTIGKIPFEGAESKNPLAFHYYDAERVVMGKPMKDWFKFAMAWWHTLGQASADP<br>FGGQTRSYEWDKGECPYCRARQKADAGFEIMQKLGIGYYCFHDIDLVEDTEDIAEYEARM<br>KDITDYLVEKQKETGIKNLWGTANVEGNKRYMNGAATNPQFDIVAHAALQIKNAIGATIK<br>LGGTGYVFWGGREGYYTLLNTQMQREKDHLAKMLTAARDYARANGFKGTFLIEPKPMEPT<br>KHQYDVDTETVIGFLRANGLDKDFKVNIEVNHATLAGHTFEHELTVAVDNGFLGSIDANR<br>GDAQNGWDTDQFPVDPYDLTQAMIQIIRNGGFKDGGTNFDAKLRRSSTDPEDIFIAHISA<br>MDAMAHALLNAAAVIEESPLCEMVAKRYASFDSGLGKKFEEGNATLEELYEYAKANGEVK<br>AESGKQELYETLLNLYAK |
| 5753MI1_002 | *Prevotella* | DNA | 167 | ATGGCAAAAGAGTATTTCCCCACTATCGGGAAGATTCCTTTCGAAGGAGTCGAGAGCAAG<br>AACCCCCTTGCATTCCATTATTATGACGCAAACCGCATGGTCATGGGCAAGCCCATGAAG<br>GACTGGTTCAAGTTCGCCATGGCATGGTGGCACACCCTGGGACAGGCCTCCGCAGACCCG<br>TTCGGCGGCCAGACCCGCTCCTACGAATGGGACAAGGGCGAATGCCCCTACTGCCGCGCC<br>AGGGCAAAGGCCGATGCCGGCTTCGAGATCATGCAGAAACTGGGTATCGAGTATTTCTGC<br>TTCCATGACATCGACCTGGTAGAGGACTGCGACGACATCGCCGAGTACGAGGCCCGCATG<br>AAGGACATCACGGACTATCTCCTGGAGAAGATGAAGGAAACCGGCATCAAGAACCTCTGG<br>GGCACCGCCAACGTGTTCGGCAACAAGCGTTACATGAACGGCGCCGGCACCAATCCGCAG<br>TTCGACGTAGTGGCCCGCGCTGCCGTCCAGATCAAGAACGCCATCGACGCCACCATCAAG<br>CTCGGCGGTTCCAACTATGTGTTCTGGGGCGGCCGTGAAGGATACTACACCCTGCTGAAC<br>ACCCAGATGCAGCGCGAGAAGGACCACCTCGGCAAACTGCTCACCGCCGCCCGCGACTAT<br>GCCCGCAAGAACGGCTTCAAGGGCACCTTCCTCATCGAGCCCAAGCCGATGGAGCCCACC<br>AAGCACCAGTACGACGTAGACACGGAGACCGTGATCGGCTTCCTCCGCGCCAACGGCCTG<br>GAGAAAGACTTCAAGGTGAACATCGAGGTGAACCACGCCACCCTGGCCGGCCATACCTTC<br>GAGCATGAACTCACCGTGGCCGTGGACAACGGCTTCCTGGGATCCATCGACGCCAACCGC<br>GGCGACGCCCAGAACGGCTGGGATACGGACCAGTTCCCGGTAGACCCGTACGACCTCACC<br>CAGGCCATGATGCAGATCATCCGCAACGGCGGCCTCGGCAACGGCGGTACCAACTTCGAC<br>GCCAAACTGCGCCGTTCCTCCACCGATCCTGAGGACATCTTCATCGCCCACATCAGCGCC<br>ATGGACGCCATGGCCCACGCCCTGCTCAACGCAGCCGCCGTGCTGGAAGAAAGTCCGCTC<br>TGTGAGATGGTCAAGGAGCGCTACGCTTCCTTCGACAGCGGTCTCGGCAAGAAGTTCGAA<br>GAGGGCAAGGCTACCCTGGAAGAAATCTACGAGTATGCCAAGAAGAGCGGCGAACCCGTG<br>GTCGCTTCCGGCAAGCAGGAGCTCTACGAAACCCTGCTGAACCTCTACGCCAAGTAG |
| 5753MI1_002 | *Prevotella* | Amino Acid | 168 | MAKEYFPTIGKIPFEGVESKNPLAFHYYDANRMVMGKPMKDWFKFAMAWWHTLGQASADP<br>FGGQTRSYEWDKGECPYCRARAKADAGFEIMQKLGIEYFCFHDIDLVEDCDDIAEYEARM<br>KDITDYLLEKMKETGIKNLWGTANVFGNKRYMNGAGTNPQEDVVARAAVQIKNAIDATIK |

TABLE 2-continued

| Clone No. | Class of organism | Type of Sequence | SEQ ID NO: | Sequence |
|---|---|---|---|---|
| | | | | LGGSNYVFWGGREGYYTLLNTQMQREKDHLGKLLTAARDYARKNGFKGTFLIEPKPMEPT<br>KHQYDVDTETVIGFLRANGLEKDFKVNIEVNHATLAGHTFEHELTVAVDNGFLGSIDANR<br>GDAQNGWDTDQFPVDPYDLTQAMMQIIRNGGLGNGGTNFDAKLRRSSTDPEDIFIAHISA<br>MDAMAHALLNAAAVLEESPLCEMVKERYASFDSGLGKKFEEGKATLEEIYEYAKKSGEPV<br>VASGKQELYETLLNLYAK |
| 5753MI2_002 | *Prevotella* | DNA | 169 | ATGGCTAAAGAATACTTCCCCTCCATCGGCAAAATCCCTTTTGAAGGAGGCGACAGCAAA<br>AATCCCCTCGCTTTCCATTATTATGACGCCGGACGCGTGGTTATGGGCAAGCCCATGAAG<br>GAATGGCTTAAATTCGCCATGGCCTGGTGGCACACGCTGGGCCAGGCCTCCGGAGACCCC<br>TTCGGCGGCCAGACCCGCAGCTACGAATGGGACAAGGGCGAATGCCCCTACTGCCGCGCC<br>AAAGCCAAGGCCGACGCCGGTTTTGAAATCATGCAAAAGCTGGGTATCGAATACTTCTGC<br>TTCCACGATGTGGACCTTATCGAGGATTGCGATGACATTGCCGAATACGAAGCCCGCATG<br>AAGGACATCACGGACTACCTGCTGGAAAAGATGAAGGAGACCGGCATCAAGAACCTCTGG<br>GGCACCGCCAATGTCTTCGGCCACAAGCGCTACATGAACGGCGCCGCCACGAACCCGCAG<br>TTCGACGTGGTCGCCCGCGCCGCCGTCCAGATCAAGAACGCGATTGACGCCACCATCAAG<br>CTCGGCGGTACCAGTTATGTATTCTGGGGCGGCCGCGAGGGCTACTACACCCTCCTGAAC<br>ACCCAGATGCAGCGTGAGAAAGACCACCTGGCCAAGATGCTCACCGCAGCCCGCGACTAC<br>GCCCGCGCCAAGGGCTTCAAGGGCACCTTCCTCATCGAGCCCAAGCCGATGGAGCCCACC<br>AAGCACCAGTACGACGTTGACACGGAGACCGTGATCGGCTCCCTGCGCGCCAACGGCCTG<br>GACAAGGACTTCAAGGTGAACATCGAGGTGAACCACGCCACCCTGGCCGGCCACACCTTC<br>GAGCACGAACTCACCGTGGCTGTTGACAACGGCTTCCTGGGCTCCATCGACGCCAACCGC<br>GGCGACGCCCAGAACGGCTGGGATACGGACCAGTTCCCGGTAGACCCGTACGACCTCACC<br>CAGGCCATGATGCAGATTATCCGCAACGGCGGCTTCAAGGACGGCGGCACCAACTTCGAT<br>GCCAAACTGCGCCGCTCTTCCACCGATCCGGAAGACATCTTCATCGCCCACATCAGCGCT<br>ATGGATGCCATGGCACACGCCCTGCTCAACGCCGCCGCCGTGCTGGAAGAGAGCCCGCTG<br>TGCAACATGGTCAAGGAGCGTTACGCCGGCTTCGACAGCGGCCTTGGCAAGAAGTTCGAG<br>GAAGGGAAGGCAACGCTGGAGGAAATCTATGACTATGCCAAGAAGAGCGGCGAACCCGTC<br>GTGGCTTCCGGCAAGCAGGAACTCTACGAAACCATCCTGAACCTCTATGCCAAGTAG |
| 5753MI2_002 | *Prevotella* | Amino Acid | 170 | MAKEYFPSIGKIPFEGGDSKNPLAFHYYDAGRVVMGKPMKEWLKFAMAWWHTLGQASGDP<br>FGGQTRSYEWDKGECPYCRAKAKADAGFEIMQKLGIEYFCFHDVDLIEDCDDIAEYEARM<br>KDITDYLLEKMKETGIKNLWGTANVFGHKRYMNGAATNPQFDVVARAAVQIKNAIDATIK<br>LGGTSYVFWGGREGYYTLLNTQMQREKDHLAKMLTAARDYARAKGFKGTFLIEPKPMEPT<br>KHQYDVDTETVIGSLRANGLDKDFKVNIEVNHATLAGHTFEHELTVAVDNGFLGSIDANR<br>GDAQNGWDTDQFPVDPYDLTQAMMQIIRNGGFKDGGTNFDAKLRRSSTDPEDIFIAHISA<br>MDAMAHALLNAAAVLEESPLCNMVKERYAGFDSGLGKKFEEGKATLEEIYDYAKKSGEPV<br>VASGKQELYETILNLYAK |
| 5753MI4_002 | *Prevotella* | DNA | 171 | ATGTCAAAAGAGTATTTCCCTACAATCGGCAGGGTCCCCTTCGAGGGACCTGAGAGCAAG<br>AATCCGCTGGCGTTCCACTATTACGAGCCGGACCGGCTCGTCCTGGGCAGGAAAATGAAG<br>GACTGGCTGCGCTTCGCAATGGCCTGGTGGCATACGCTCGGGCAGGCTTCCGGCGACCAG<br>TTCGGCGGACAGACCTGCACATACGCCTGGGATGAAGGCGAGTGTCCCGTCTGCCGGGCA<br>AAGGCCAAGGCTGACGCCGGCTTTGAACTGATGCAGAAACTGGGCATCGGGTATTTCTGC<br>TTCCACGACGTGGACCTGGTCGAGGAGGCCGACACCATTGAAGAATACGAGGAGCGGATG<br>CGGATCATCACCGACTACCTGCTCGAGAAGATGGAAGAGACCGGCATCCGCAATCTCTGG<br>GGAACCGCCAATGTCTTCGGACACAAGCGCTATATGAACGGCGCCGCCACCAATCCCGAC<br>TTCGACGTCGTGGCCCGTGCCGCGGTCCAGATCAAGAATGCCATCGATGCCACCATCAAA<br>CTGGGTGGTGAGAACTATGTGTTCTGGGGTGGCCGCGAGGGCTATACGAGCCTGCTCAAC<br>ACGCAGATGCACCGGGAAAAACACCACCTCGGAAATATGCTCAGGGCAGCCCGCGACTAT<br>GGCCGTGCCCACGGTTTCAAGGGAACGTTCCTGATCGAGCCCAAGCCGATGGAGCCGACC<br>AAGCATCAGTACGACCAGGATACGGAGACGGTCATCGGTTTCCTGCGCTGTCACGGCCTG<br>GACAAGGATTTCAAGGTGAACATCGAGGTGAACCACGCCACGCTCGCCGGACACACCTTC<br>GAGCACGAACTGGCCACTGCGGTCGATGCCGGCCTGCTGGGCAGCATCGATGCCAACCGC<br>GGCGACGCCCAGAACGGCTGGGATACCGACCAGTTCCCGATCGACAACTACGAACTCACG<br>CTGGCGATGCTGCAGATCATCCGCAATGGCGGACTCGCACCCGGCGGATCGAACTTCGAT<br>GCCAAGTTGCGCCGCAATTCCACCGATCCGGAAGACATCTTCATCGCCCACATCAGCGCG<br>ATGGACGCGATGGCCCGTGCCCTGCTCAATGCGGCGGCCATCTGGACCGAATCGCCGATT<br>CAGGATATGGTCAGGGACCGCTATGCTTCCTTCGACAGCGGAAAGGGCAGGGAGTTCGAG<br>GAAGGCAGACTCAGTCTGGAAGACCTCGTGGCCTATGCGAAGGAGCACGGTGAGCCGCGC<br>CAGATCTCCGGCAGGCAGGAACTTTATGAAACCATCGTAGCGCTTTACTGCAGGTAA |
| 5753MI4_002 | *Prevotella* | Amino Acid | 172 | MSKEYFPTIGRVPFEGPESKNPLAFHYYEPDRLVLGRKMKDWLRFAMAWWHTLGQASGDQ<br>FGGQTCTYAWDEGECPVCRAKAKADAGFELMQKLGIGYFCFHDVDLVEEADTIEEYEERM<br>RIITDYLLEKMEETGIRNLWGTANVFGHKRYMNGAATNPDFDVVARAAVQIKNAIDATIK<br>LGGENYVFWGGREGYTSLLNTQMHREKHHLGNMLRAARDYGRAHGFKGTFLIEPKPMEPT<br>KHQYDQDTETVIGFLRCHGLDKDFKVNIEVNHATLAGHTFEHELATAVDAGLLGSIDANR<br>GDAQNGWDTDQFPIDNYELTLAMLQIIRNGGLAPGGSNFDAKLRRNSTDPEDIFIAHISA<br>MDAMARALLNAAAIWTESPIQDMVRDRYASFDSGKGREFEEGRLSLEDLVAYAKEHGEPR<br>QISGRQELYETIVALYCR |
| 5752MI4_004 | *Prevotella* | DNA | 173 | ATGACTAAAGAGTATTTCCCGGGAATCGGAACGATTCCGTTTGAAGGAACCAAGAGCAAG<br>AACCCCCTGGCCTTCCATTATTATAACGCCTCCCAGGTAGTGATGGGCAAGCCCATGAAG<br>GACTGGCTCAAGTATGCCATGGCCTGGTGGCACACCCTGGGCCAGGCCTCTGCAGACCCC<br>TTTGGCGGCCAGACCCGCTCCTACGAATGGGACAAGGGCGAGTGCCCGTACTGCCGCGCC<br>AAGCAGAAGGCCGATGCCGGCTTTGAGCTCATGCAGAAGCTGGGCATCGAGTACTACTGC<br>TTCCACGACGTGGACATCATCGAGGACTGCGAGGACATTGCCGAGTACGAGGCCCGCATG |

TABLE 2-continued

| Clone No. | Class of organism | Type of Sequence | SEQ ID NO: | Sequence |
|---|---|---|---|---|
| | | | | AAGGACATCACGGACTACCTGCTGGAGAAGCAGAAAGAGACCGGCATCAAGAACCTCTGG<br>GGCACCGCCAACGTGTTTGGCCACAAGCGCTACATGAACGGCGCCGCCACCAACCCTCAG<br>TTTGACATTGTGGCCCGTGCCGCCGTCCAGATCAAGAACGCCCTGGATGCCGCCATCAAA<br>CTGGGTGGTACCAACTACGTGTTCTGGGGTGGCCGCGAAGGCTACTACACGCTGCTCAAC<br>ACCCAGATGCAGCGGGAGAAGAACCACCTGGCCAAGATGCTCACCGCCGCCCGCGACTAC<br>GCCCGCGCCAAGGGCTTCAAGGGCACCTTCCTCATTGAGCCCAAACCCATGGAGCCCACC<br>AAGCACCAGTACGACGTGGACACCGAGACCGTGATTGGTTTCATCCGCGCCAACGGCCTG<br>GACAAGGACTTCAAGGTAAACATTGAGGTAAACCACGCCACCCTGGCCGGCCACACCTTT<br>GAGCACGAGCTCACCGTGGCCCGCGAGAACGGCTTCCTGGGCTCCATCGACGCCAACCGC<br>GGAGATGCCCAGAACGGCTGGGATACGGACCAGTTCCCCATCGACGCCCTGGATCTCACC<br>CAGGCTATGATGCAGGTCATCCTCAACGGTGGCTTCGGCAATGGCGGCACCAACTTTGAC<br>GCCAAGCTCCGCCGCTCCTCCACCGATCCCGAGGACATCTTCATCGCCCACATCAGCGCC<br>ATGGATGCCATGGCACACGCCCTCCTGAACGCAGCCGCCATCCTGGAAGAGAGCCCCCTG<br>CCCGCCATGGTCAAGGAGCGTTACGCTTCCTTCGACAGCGGTCTGGGCAAGAAGTTCGAA<br>GAAGGCAAGGCCTCCCTGGAAGAACTTTACGAATATGCCAAGAAGAATGGAGAGCCCGTG<br>GCCGCTTCCGGCAAACAGGAGCTCTGCGAAACTTACTTGAACCTCTATGCAAAGTAG |
| 5752MI4_004 | *Prevotella* | Amino Acid | 174 | MTKEYFPGIGTIPFEGTKSKNPLAFHYYNASQVVMGKPMKDWLKYAMAWWHTLGQASADP<br>FGGQTRSYEWDKGECPYCRAKQKADAGFELMQKLGIEYYCFHDVDIIEDCEDIAEYEARM<br>KDITDYLLEKQKETGIKNLWGTANVFGHKRYMNGAATNPQFDIVARAAVQIKNALDAAIK<br>LGGTNYVFWGGREGYYTLLNTQMQREKNHLAKMLTAARDYARAKGFKGTFLIEPKPMEPT<br>KHQYDVDTETVIGFIRANGLDKDFKVNIEVNHATLAGHTFEHELTVARENGFLGSIDANR<br>GDAQNGWDTDQFPIDALDLTQAMMQVILNGGFGNGGTNFDAKLRRSSTDPEDIFIAHISA<br>MDAMAHALLNAAAILEESPLPAMVKERYASFDSGLGKKFEEGKASLEELYEYAKKNGEPV<br>AASGKQELCETYLNLYAK |
| 727MI4_006 | Rhizobiales | DNA | 175 | GTGACTGATTTCTTCAAGGGCATCGCGCCCGTCAAGTTTGAGGGGCCGCAGAGCTCCAAT<br>CCGCTGGCCTATCGCCACTATAACAAGGACGAAATCGTCCTCGGCAAGCGGATGGAAGAC<br>CATATCCGTCCCGGCGTTGCCTATTGGCACACCTTCGCCTATGAGGGCGGCGATCCGTTT<br>GGCGGCCGCACCTTCGATCGCCCCTGGTTCGACAAGGGTATGGACGGCGCCCGCCTCAAG<br>GCCGACGTGGCCTTCGAACTGTTCGACCTGCTCGACGTTCCTTTCTTCTGTTTCCACGAT<br>GCTGATATCGCTCCCGAAGGCGCAACGCTGGCCGAGAGCAACCGCAATGTGCGCGAGATT<br>GGCGAGATCTTCGCTCGCAAGATGGAAACCAGCCGCACCAAGCTGCTCTGGGGTACGGCA<br>AACCTGTTCTCCAATCGCCGCTACATGGCCGGCGCCGCCACCAACCCGGACCCGGAAATC<br>TTCGCCTATGCCGCTGGGCAGGTGAAGAACGTGCTGGAACTGACCCACGAACTGGGCGGC<br>GCCAACTATGTGCTGTGGGGCGGTCGCGAGGGTTATGAAACCCTGCTCAACACCAAGATC<br>GGCCAGGAAATGGACCAGATGGGCCGTTTTCTGTCGATGGTCGTCGAGCATGCCGAAAAG<br>ATCGGCTTCAAGGGCCAGATCCTGATCGAGCCCAAGCCGCAGGAGCCGAGCAAGCACCAG<br>TATGACTTCGACGTTGCAACCGTTTACGGCTTCCTCAAGAAGTATGGTCTCGAAACCAAG<br>GTGAAGTGCAATATCGAGGTCGGCCATGCCTTCCTCGCCAATCACTCCTTCGAGCATGAA<br>CTGGCTTTGGCCGCATCGCTGGGCATTCTCGGCTCGGTCGACGCCAATCGCAACGATCTA<br>CAGTCCGGCTGGGATACCGACCAGTTCCCCAATAATGTCCCCGAAACCGCACTCGCCTTC<br>TATCAGATTCTCAAGGCGGGCGGACTGGGCAATGGCGGCTGGAACTTCGACGCCCGCGTG<br>CGCCGCCAGTCACTTGATCCGGCCGACCTGCTGCACGGCCATATCGGCGGCCTCGACGTG<br>CTGGCGCGCGGCCTCAAGGCCGCCGCGGCGCTGATCGAGGACGGCACCTATGACAAGGTC<br>GTCGACGCCCGCTATGCCGGCTGGAACCAGGGCCTGGGCAAGGATATCCTTGGTGGCAAG<br>CTGAACCTTGCCGACCTGGCTGCCAAGGTCGACGCCGAAAACCTCAACCCGCAGCCTAGG<br>TCCGGCCAGCAGGAATATCTCGAAAACCTGATCAACCGGTTCGTTTAG |
| 727MI4_006 | Rhizobiales | Amino Acid | 176 | MTDFFKGIAPVKFEGPQSSNPLAYRHYNKDEIVLGKRMEDHIRPGVAYWHTFAYEGGDPF<br>GGRTFDRPWFDKGMDGARLKADVAFELFDLLDVPFFCFHDADIAPEGATLAESNRNVREI<br>GEIFARKMETSRTKLLWGTANLFSNRRYMAGAATNPDPEIFAYAAGQVKNVLELTHELGG<br>ANYVLWGGREGYETLLNTKIGQEMDQMGRELSMVVEHAEKIGFKGQILIEPKPQEPSKHQ<br>YDFDVATVYGFLKKYGLETKVKCNIEVGHAFLANHSFEHELALAASLGILGSVDANRNDL<br>QSGWDTDQFPNNVPETALAFYQILKAGGLGNGGWNFDARVRRQSLDPADLLHGHIGGLDV<br>LARGLKAAAALIEDGTYDKVVDARYAGWNQGLGKDILGGKLNLADLAAKVDAENLNPQPR<br>SGQQEYLENLINRFV |

5.5 Example 4: Quantification of XI Enzyme Activity

Figure 3:
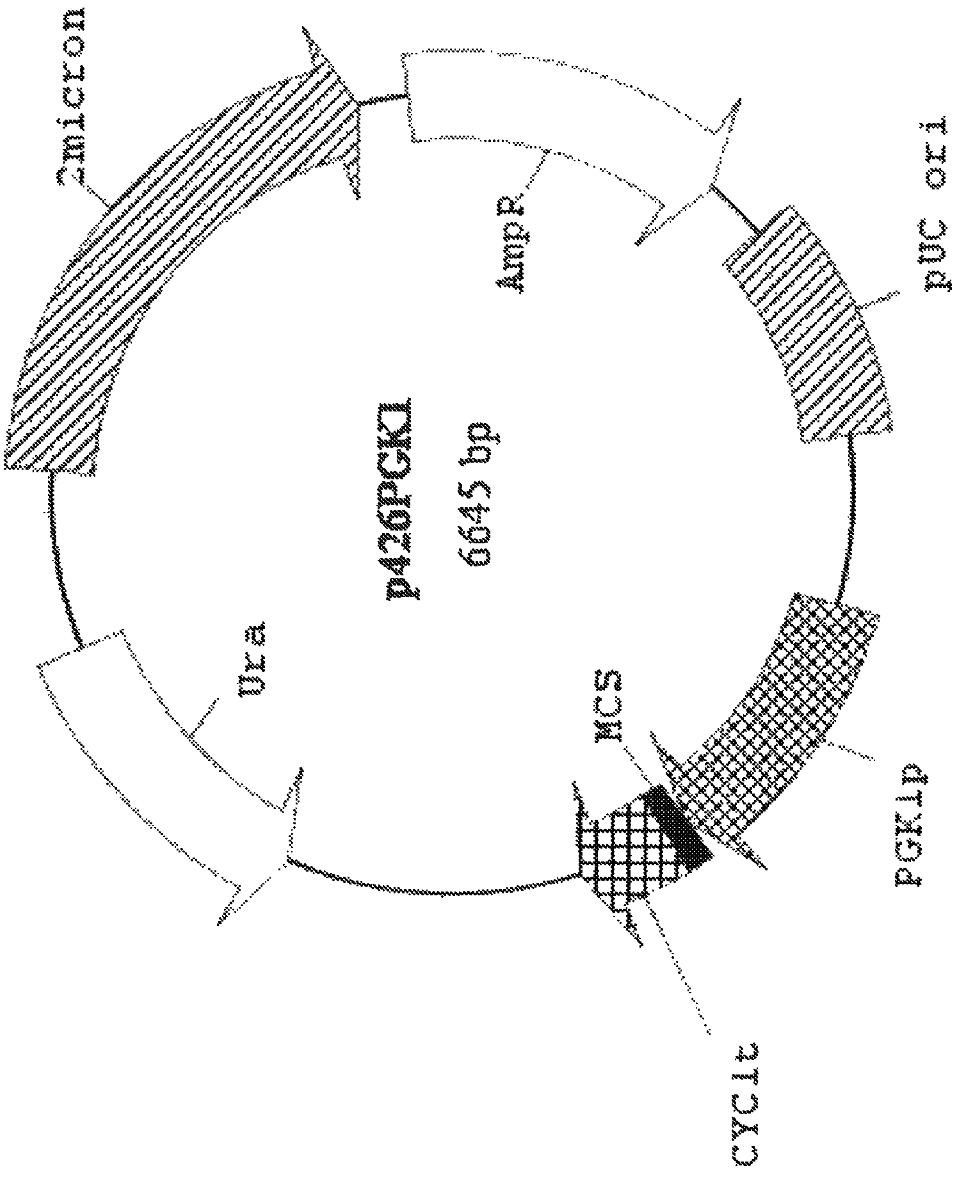
FIG. 3 is a map of the vector p426PGK1 for expressing XI in yeast strain, *Saccharomyces cerevisiae* CEN.PK2-1Ca (ATCC: MYA1108).

The clones identified in the ABD and SBD screens (see Table 2) were subcloned into vector p426PGK1 (FIG. 3), a modified version of p426GPD (ATCC accession number 87361) in which the GPD promoter was replaced with the PGK1 promoter from *Saccharomyces cerevisiae* (ATCC accession number 204501) gDNA. The clones were then transformed into yeast strain MYA11008.

Cells were grown as described in the materials and methods. Cell pellets were resuspended in about 300 μl of lysis buffer: approximate concentrations (50 mM $NaH_2PO_4$ (pH 8.0), 300 mM NaCl, 10 mM imidazole (Sigma, #I5513), to which was added about 2 μl/ml beta-mercaptoethanol (BME)), and protease inhibitor cocktail tablet (Roche, 11836170001) (1 tablet for about 10 ml cell extract). The cell suspension was added to a 2 ml screw-cap microcentrifuge tube that had been pre-aliquotted with about 0.5 ml of acid washed glass beads (425-600 μm). Cells were lysed using a FastPrep-24 (MP Biomedicals, Solon, Ohio) at amplitude setting of about 6 for about 3 repetitions of about 1 minute. Cells were chilled on ice for about 5 minutes between repetitions. Samples were centrifuged at about 10,000×g for about 10 minutes at 4° C. Recovered supernatants were used in the XI enzyme activity assay. XI enzyme activity was performed as described in the materials and methods. Results are shown in Table 3.

TABLE 3

| XI activity at pH 7.5 | | |
|---|---|---|
| SEQ ID NO: | Volumetric Activity | FIOPC |
| 2 | −60.73 | 2.58 |
| 4 | −21.84 | 0.93 |
| 6 | 0.86 | −0.05 |
| 8 | −2.14 | 0.12 |
| 10 | −2.38 | 0.13 |
| 12 | −12.82 | 0.54 |
| 14 | −26.97 | 1.45 |
| 16 | −76.50 | 4.12 |
| 18 | −15.32 | 0.83 |
| 20 | −5.33 | 0.29 |
| 22 | 0.48 | −0.03 |
| 24 | 0.36 | −0.02 |
| 26 | 0.81 | −0.04 |
| 28 | −6.65 | 0.36 |
| 30 | −9.10 | 0.49 |
| 32 | −38.10 | 2.05 |
| 34 | −21.76 | 1.17 |
| 36 | −13.82 | 0.59 |
| 38 | −17.58 | 0.75 |
| 40 | −12.34 | 0.52 |
| 42 | −74.88 | 3.18 |
| 44 | −37.10 | 1.57 |
| 46 | −35.57 | 1.51 |
| 48 | −24.69 | 1.05 |
| 50 | −32.23 | 1.37 |
| 52 | −26.72 | 1.13 |
| 54 | −90.79 | 3.85 |
| 56 | −39.89 | 1.69 |
| 58 | −74.26 | 3.15 |
| 60 | −11.91 | 0.64 |
| 62 | −15.43 | 0.83 |
| 64 | −12.98 | 0.70 |
| 66 | −27.45 | 1.48 |
| 68 | −29.43 | 1.59 |
| 70 | −4.54 | 0.24 |
| 72 | −8.93 | 0.48 |
| 74 | −0.20 | 0.01 |
| 76 | −0.33 | 0.02 |
| 78 | −50.55 | 2.15 |
| 80 | −57.13 | 2.42 |
| 82 | −58.09 | 2.47 |
| 84 | −46.42 | 1.97 |
| 86 | −35.95 | 1.53 |
| 88 | −2.16 | 0.09 |
| 90 | −32.77 | 1.39 |
| 92 | −30.82 | 1.31 |
| 94 | −8.16 | 0.35 |
| 96 | −46.18 | 1.96 |
| 98 | −30.05 | 1.28 |
| 100 | −8.40 | 0.45 |
| 102 | −8.34 | 0.45 |
| 104 | −3.80 | 0.20 |
| 106 | −4.81 | 0.26 |
| 108 | −12.06 | 0.65 |
| 110 | −6.10 | 0.33 |
| 112 | −7.71 | 0.42 |
| 114 | −4.17 | 0.22 |
| 116 | −7.07 | 0.38 |
| 118 | −13.50 | 0.73 |
| 120 | −1.15 | 0.06 |
| 122 | 0.03 | 0.00 |
| 124 | −4.41 | 0.24 |
| 126 | −0.85 | 0.05 |
| 128 | −14.60 | 0.79 |
| 130 | −17.26 | 0.93 |
| 132 | −0.75 | 0.04 |
| 134 | −11.55 | 0.62 |
| 136 | −7.20 | 0.39 |
| 138 | 0.16 | −0.01 |
| 140 | −3.63 | 0.20 |
| 142 | −3.63 | 0.20 |
| 144 | −1.20 | 0.06 |
| 146 | −16.77 | 0.90 |
| 148 | −2.00 | 0.11 |
| 150 | −1.40 | 0.08 |

TABLE 3-continued

| XI activity at pH 7.5 | | |
|---|---|---|
| SEQ ID NO: | Volumetric Activity | FIOPC |
| 152 | −3.63 | 0.20 |
| 154 | −7.09 | 0.38 |
| 156 | −0.96 | 0.05 |
| 158 | −2.79 | 0.15 |
| 160 | −3.23 | 0.17 |
| 162 | −10.17 | 0.55 |
| 164 | −0.51 | 0.03 |
| 166 | −3.43 | 0.19 |
| 168 | −5.65 | 0.30 |
| 170 | −2.35 | 0.13 |
| 172 | −1.20 | 0.06 |
| 174 | −2.29 | 0.12 |
| 176 | −1.92 | 0.08 |
| Op-XI (ABD) | −23.56 | NA |
| Op-XI (SBD) | −18.55 | NA |
| Vo - ctrl | −1.74 | NA |

5.6 Example 5: Growth of Yeast Containing XI Clones on Xylose

Figure 4:
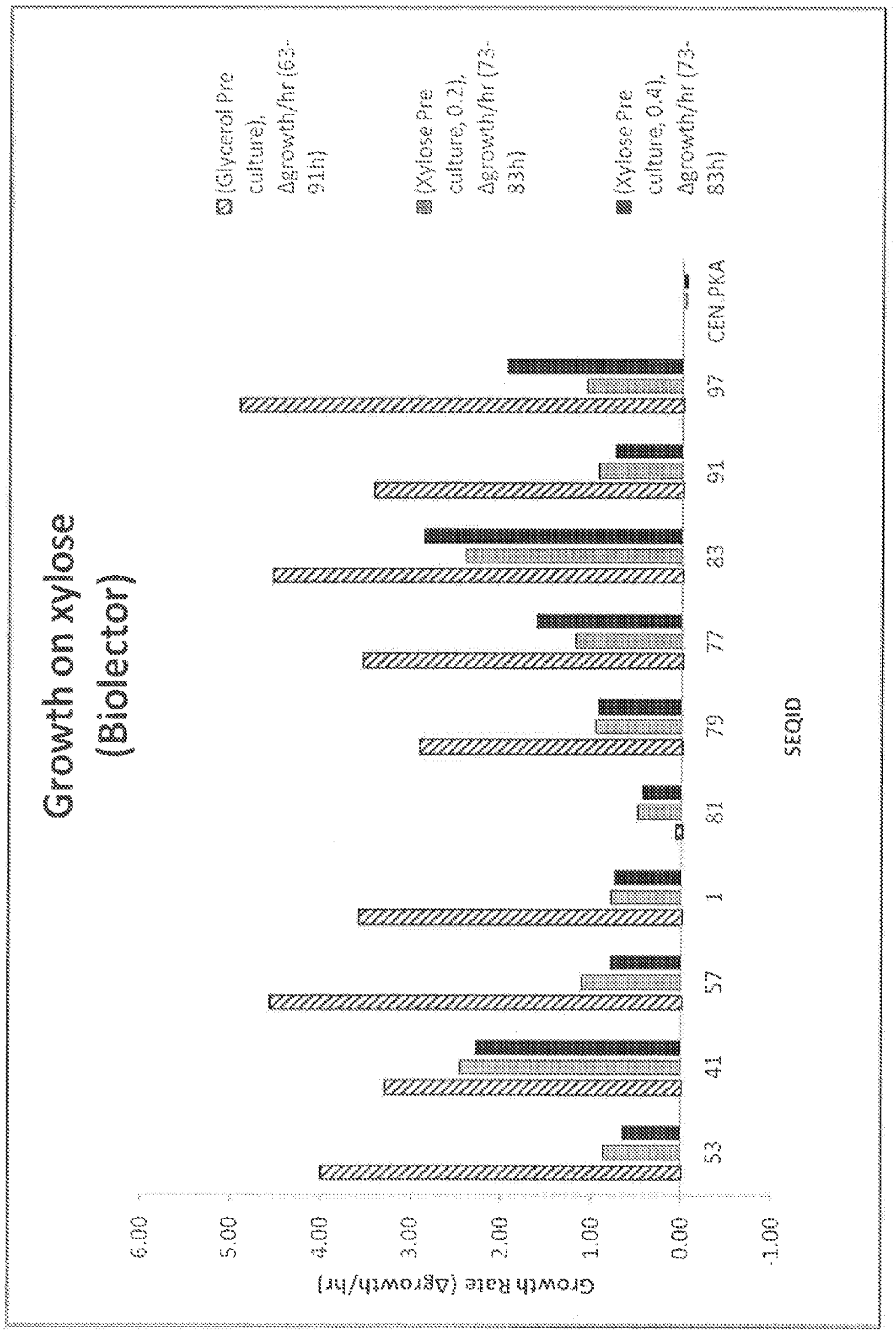
FIG. 4 shows the growth rates on xylose containing media of selected clones expressed in yeast strain, *Saccharomyces cerevisiae* CEN.PK2-1Ca (ATCC: MYA1108).

A subset of the XI genes from Example 3 were expressed in *Saccharomyces cerevisiae* CEN.PK2-1Ca (ATCC: MYA1108) and assayed for ability to confer the ability to grow on xylose. This assay was carried out as follows: colonies were isolated on SC-ura+2% glucose agar plates and inoculated into about 3 ml "pre-cultures" of both SC-ura 2% glycerol and SC-ura 2% xylose media, incubated at about 30° C., about 220 rpm, overnight. Cells were harvested by centrifugation (about 100×g, 5 minutes), supernatant discarded and washed twice and resuspended in about 1 ml of SC-ura 2% xylose. Cells were inoculated into Biolector plates, containing SC-ura, 2% xylose, and inoculums were normalized to two different starting optical densities of about $OD_{600}$ 0.2 and 0.4. Plates were covered using gas permeable seals and incubated in a BioLector microfermentation device (m2p-labs, Model G-BL100) at about 30° C. for about 4 days at 800 rpm and 90% humidity. Growth readings from the Biolector were acquired for 60-100 hours according to manufacturer's recommendations. Results are shown in FIG. 4.

5.7 Example 6: Ethanol Production Under Anaerobic Conditions

A subset of the XI expressing yeast clones in strain *Saccharomyces cerevisiae* CEN.PK2-1Ca (ATCC: MYA1108) were assayed for ability to ferment xylose to ethanol (EtOH). In brief, single colonies were inoculated into about 25 ml of SC-ura medium supplemented with about 0.1% glucose and about 3% xylose. Cultures were incubated under microaerobic conditions at about 30° C. and about 200 rpm. Samples were harvested at about 0, 24, 48, 72 h, and ethanol concentration determined via HPLC standard assays. Ethanol productivity was calculated, and listed in units of grams of EtOH per liter per hour, and FIOPC was generated comparing productivity of the control Op-XI. Results are shown in Table 4.

TABLE 4

| Anaerobic EtOH Production | | | | | | |
|---|---|---|---|---|---|---|
| | Time (h) | | | | EtOH | |
| SEQ ID NO: | 0 | 24 | 48 | 72 | (g/L/h) | FIOPC |
| 6 | 0.28 | 0 | 0 | 0 | −0.004 | −0.5 |
| 8 | 0 | 0 | 0 | 0 | 0.000 | 0.0 |
| 10 | 0 | 0 | 0 | 0 | 0.000 | 0.0 |
| 14 | 0.37 | 0.28 | 0.71 | 1.24 | 0.013 | 1.7 |

TABLE 4-continued

Anaerobic EtOH Production

| SEQ ID NO: | Time (h) 0 | 24 | 48 | 72 | EtOH (g/L/h) | FIOPC |
|---|---|---|---|---|---|---|
| 16 | 0.33 | 0.275 | 0.72 | 1.06 | 0.011 | 1.4 |
| 18 | 0.29 | 0.135 | 0.31 | 0.595 | 0.005 | 0.6 |
| 20 | 0.33 | 0 | 0 | 0 | −0.004 | −0.5 |
| 22 | 0.32 | 0 | 0 | 0 | −0.004 | −0.5 |
| 24 | 0.28 | 0 | 0 | 0 | −0.004 | −0.5 |
| 26 | 0.26 | 0 | 0 | 0 | −0.003 | −0.4 |
| 28 | 0.23 | 0.385 | 1.015 | 1.54 | 0.019 | 2.5 |
| 30 | 0.27 | 0 | 0 | 0.07 | −0.003 | −0.3 |
| 32 | 0 | 0.165 | 0.48 | 0.815 | 0.012 | 1.5 |
| 34 | 0 | 0.125 | 0.33 | 0.615 | 0.009 | 1.1 |
| 36 | 0 | 0 | 0 | 0 | 0.000 | 0.0 |
| 46 | 0 | 0.285 | 0.905 | 1.625 | 0.023 | 3.0 |
| 60 | 0.45 | 0.35 | 0.87 | 1.39 | 0.014 | 1.8 |
| 62 | 0 | 0 | 0 | 0.065 | 0.001 | 0.1 |
| 64 | 0.38 | 0.275 | 0.735 | 1.18 | 0.012 | 1.6 |
| 66 | 0 | 0 | 0.12 | 0.22 | 0.003 | 0.4 |
| 68 | 0 | 0.05 | 0.275 | 0.5 | 0.007 | 0.9 |
| 70 | 0 | 0 | 0 | 0 | 0.000 | 0.0 |
| 72 | 0.119 | 0 | 0.054 | 0.1685 | 0.001 | 0.1 |
| 74 | 0.21 | 0.11 | 0.275 | 0.57 | 0.005 | 0.7 |
| 76 | 0.28 | 0 | 0 | 0 | −0.004 | −0.5 |
| 90 | 0 | 0.24 | 0.69 | 1.09 | 0.016 | 2.0 |
| 100 | 0.104 | 0.642 | 0.141 | 0.366 | 0.001 | 0.2 |
| 102 | 0.185 | 0 | 0 | 0.054 | −0.002 | −0.2 |
| 104 | 0.235 | 0.536 | 0 | 0 | −0.005 | −0.7 |
| 106 | 0.188 | 0.4835 | 0 | 0 | −0.004 | −0.6 |
| 108 | 0.19 | 0.5855 | 0.1455 | 0.313 | 0.000 | 0.0 |
| 110 | 0.3 | 0 | 0 | 0.05 | −0.003 | −0.4 |
| 112 | 0.19 | 0.5535 | 0.106 | 0.1135 | −0.003 | −0.4 |
| 114 | 0.174 | 0 | 0 | 0 | −0.002 | −0.3 |
| 116 | 0.15 | 0 | 0.0515 | 0.211 | 0.001 | 0.1 |
| 118 | 0.177 | 0.7075 | 0.5065 | 0.941 | 0.009 | 1.1 |
| 120 | 0.153 | 0 | 0 | 0 | −0.002 | −0.2 |
| 122 | 0.169 | 0.553 | 0 | 0.074 | −0.003 | −0.5 |
| 124 | 0.125 | 0 | 0 | 0 | −0.002 | −0.2 |
| 126 | 0.32 | 0 | 0 | 0 | −0.004 | −0.5 |
| 128 | 0 | 0 | 0 | 0 | 0.000 | 0.0 |
| 130 | 0 | 0 | 0 | 0 | 0.000 | 0.0 |
| 132 | 0.121 | 0 | 0 | 0 | −0.002 | −0.2 |
| 134 | 0.118 | 0 | 0 | 0.1105 | 0.000 | 0.0 |
| 136 | 0.108 | 0 | 0 | 0 | −0.001 | −0.2 |
| 138 | 0.172 | 0.513 | 0 | 0 | −0.004 | −0.6 |
| 140 | 0.17 | 0.542 | 0 | 0.3135 | 0.000 | −0.1 |
| 142 | 0.102 | 0 | 0 | 0 | −0.001 | −0.2 |
| 144 | 0.28 | 0 | 0 | 0 | −0.004 | −0.5 |
| 146 | 0.103 | 0.635 | 0.263 | 0.563 | 0.004 | 0.5 |
| 150 | 0.27 | 0 | 0 | 0 | −0.003 | −0.4 |
| 149 | 0.27 | 0 | 0 | 0 | −0.003 | −0.4 |
| 152 | 0.17 | 0 | 0 | 0 | −0.002 | −0.3 |
| 154 | 0.23 | 0 | 0 | 0 | −0.003 | −0.4 |
| 156 | 0.23 | 0 | 0 | 0 | −0.003 | −0.4 |
| 158 | 0.4 | 0 | 0.105 | 0.23 | −0.002 | −0.2 |
| 160 | 0.38 | 0 | 0 | 0 | −0.005 | −0.6 |
| 162 | 0.36 | 0.055 | 0.23 | 0.41 | 0.001 | 0.2 |
| 164 | 0.32 | 0 | 0 | 0 | −0.004 | −0.5 |
| 166 | 0.31 | 0 | 0 | 0 | −0.004 | −0.5 |
| 168 | 0.32 | 0 | 0.295 | 0.6 | 0.005 | 0.6 |
| 170 | 0.164 | 0.4995 | 0 | 0 | −0.004 | −0.5 |
| 172 | 0.27 | 0 | 0 | 0 | −0.003 | −0.4 |
| 174 | 0.3 | 0 | 0.17 | 0.345 | 0.001 | 0.2 |
| OP-XI (pos) | 0.2385 | 0.5875 | 0.6965 | 0.81508 | 0.008 | NA |
| Host-(neg) | 0.23625 | 0.088125 | 0 | 0 | −0.003 | NA |

5.8 Example 7: Impact of pH on XI Activity

Extracts from strain *Saccharomyces cerevisiae* CEN.PK2-1 Ca (ATCC: MYA1108, expressing XI gene candidates in vector p426PGK1, were prepared as described in the Materials and Methods and assayed for XI activity at pH 7.5 and pH 6.0. Percent activity listed was calculated by dividing the VA at pH 6 by the VA at pH 7.5 and multiplying by 100. Results are listed in Table 5.

TABLE 5

XI activity at pH 6 and pH 7.5

| SEQ ID NO: | Organism Classification | VA, pH 6 (U/ml) | VA, pH 7.5 (U/ml) | Percent activity (pH 6) |
|---|---|---|---|---|
| 2 | Bacteroidales | 1.92 | 2.59 | 74% |
| 14 | *Bacteroides* | 0.32 | 0.98 | 32% |
| 16 | *Bacteroides* | 1.16 | 2.40 | 48% |
| 32 | *Bacteroides* | 1.17 | 2.21 | 53% |
| 38 | Firmicutes | 2.46 | 2.77 | 89% |
| 42 | Firmicutes | 1.71 | 2.18 | 79% |
| 44 | Firmicutes | 0.19 | 0.25 | 76% |
| 46 | Firmicutes | 1.49 | 1.95 | 76% |
| 50 | Firmicutes | 0.81 | 0.95 | 86% |
| 52 | Firmicutes | 0.02 | 0.08 | 26% |
| 54 | Neocallimastigales | 1.46 | 2.90 | 51% |
| 58 | Neocallimastigales | 1.89 | 3.05 | 62% |
| 68 | Neocallimastigales | 1.50 | 1.97 | 76% |
| 72 | Neocallimastigales | 0.57 | 1.04 | 55% |
| 78 | *Prevotella* | 2.40 | 3.61 | 67% |
| 80 | *Prevotella* | 1.52 | 2.29 | 66% |
| 82 | *Prevotella* | 1.48 | 1.65 | 89% |
| 84 | *Prevotella* | 1.79 | 2.96 | 61% |
| 96 | *Prevotella* | 2.13 | 3.56 | 60% |
| 116 | *Prevotella* | 0.06 | 0.13 | 47% |
| Host-neg | | 0.04 | 0.02 | NA |
| Op-XI | | 0.61 | 1.25 | 49% |

5.9 Example 8: $K_m$ for Selected XI Clones

The $K_m$ and $V_{max}$ at pH 6 were determined for a subset of the XI clones, expressed on p426PGK1 vector in *Saccharomyces cerevisiae* CEN.PK2-1Ca (ATCC: MYA1108), using the XI activity assay described in the Materials and Methods and varying the concentrations of xylose from about 40-600 mM. Results shown are calculated using the Hanes Plot, which rearranges the Michaelis-Menten equation ($v=V_{max}[S]/(K_m+[S])$) as: ($[S]/v=K_m/V_{max}+[S]/V_{max}$), where plotting [S]/v against [S], resulting in a straight line and where the y intercept=$K_m/V_{max}$, the slope=$1/V_{max}$, and the x intercept=$-K_m$. Results are listed in Table 6.

TABLE 6

$K_m$ determination for 3 XIs

| SEQ ID NO: | $K_m$ | $V_{max}$ |
|---|---|---|
| 78 | 35.2 | 27.6 |
| 96 | 33.7 | 28.0 |
| 38 | 28.8 | 28.6 |

Figure 5A:
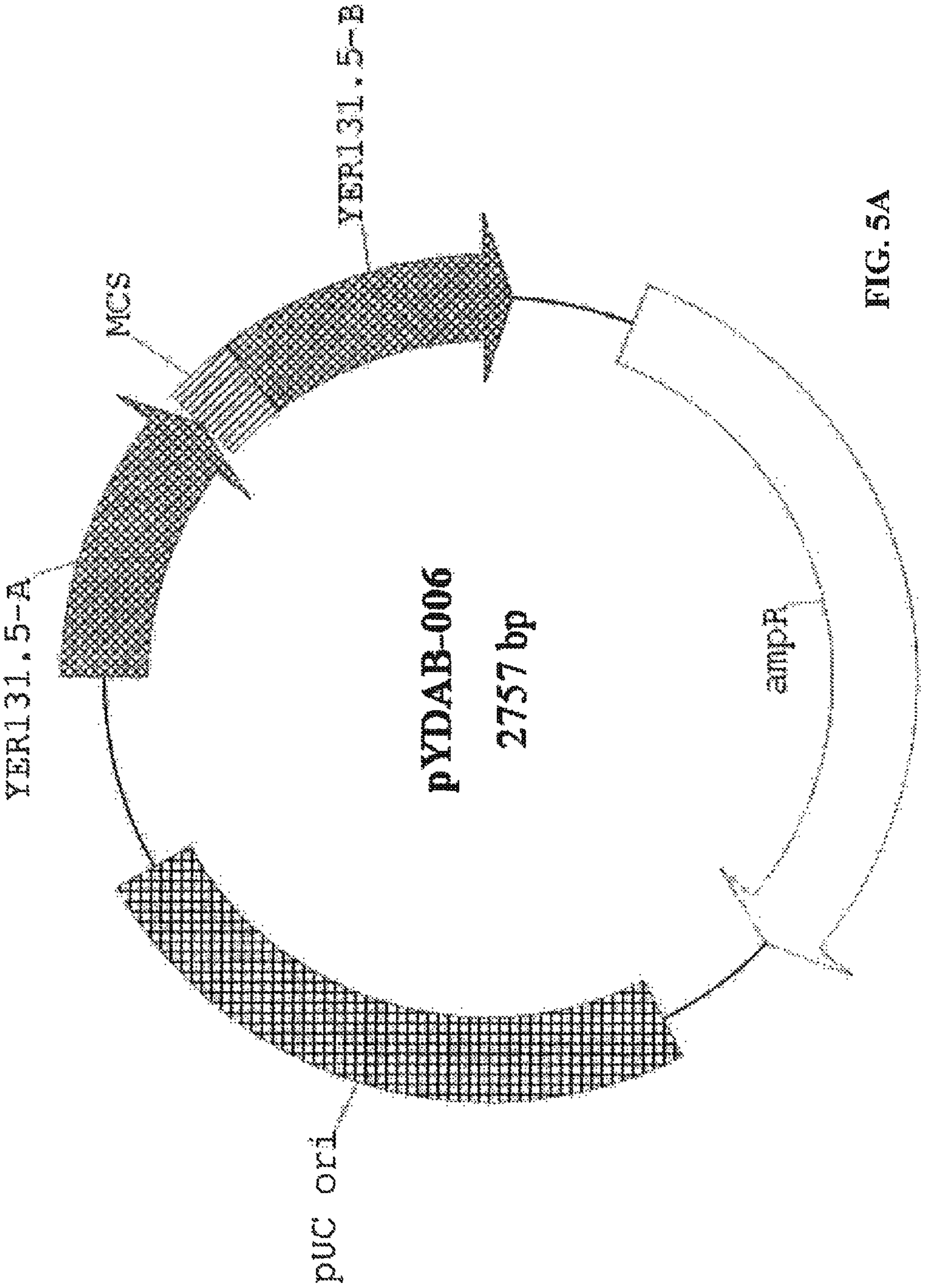
FIGS. 5A-5D are maps for the vectors pYDAB-006, pYDURA01, pYDPt-005 and pYDAB-0006, respectively, all used in creating strains of industrial *S. cerevisiae* strain yBPA130 with a single genomic copy of select XI clones.

5.10 Example 9: Quantification of XI Activity Expressed From Single Genomic Integration Locus A vector named pYDAB006 (FIG. 5A) for integration into locus YER131.5 (between YER131W and YER132C) in the *S. cerevisiae* genome was constructed using conventional cloning methods. The vector backbone with a PacI site at each end was derived from pBluescript II SK (+) (Agilent Technologies, Inc. Santa Clara, Calif.) by standard PCR techniques, which contained only the pUC origin of replication and bla gene encoding ampicillin resistance protein as a selectable marker. Two 300-base pair segments named YER131.5-A and YER 131.5-B were amplified from yeast genomic DNA by standard PCR techniques and connected with a multiple cloning site (MCS 1: 5'-GGCGCGCCTCTAGAAAGCTTACGCGTGAGCTCCCTGCAGG-GATATCGGTACCGCGGCCG C-3' (SEQ ID NO:181)) using the overlapping PCR technique. The PCR primers used in the overlapping PCR are shown in Table 7 below:

TABLE 7

| Primers Used in pYDAB006 Construction | | |
|---|---|---|
| Primer | SEQ ID NO: | Sequence (Pad site is underlined) |
| 131.5AF | 182 | caccattaattaaAGCTTTGTAAATATGATGAGAG AATAATATAAATCAAACG |
| 131.5AR | 183 | GGCGCGCCTCTAGAAAGCTTAATCGACAAGA ACACTTCTATTTATATAGGTATGAAA |
| 131.5BF | 184 | GCAGGGATATCGGTACCCACCAGCGGCCGCT GAAGAAGGTTTATTTCGTTTCGCTGT |
| 131.5BR | 185 | caccattaattaaCCCAGGTGAGACTGGATGCTCCA TA |
| ABMCSF | 186 | GCCTCTAGAAAGCTTACGCGTGAGCTCCCTG CAGGGATATCGGTACCCACCAGCGGCCGC |
| ABMCSR | 187 | CGCTGGTGGGTACCGATATCCCTGCAGGGAG CTCACGCGTAAGCTTTCTAGAGGCGCGCC |

The overlapping PCR product was then ligated with the vector backbone resulting in plasmid pYDAB006.

Figure 5B:
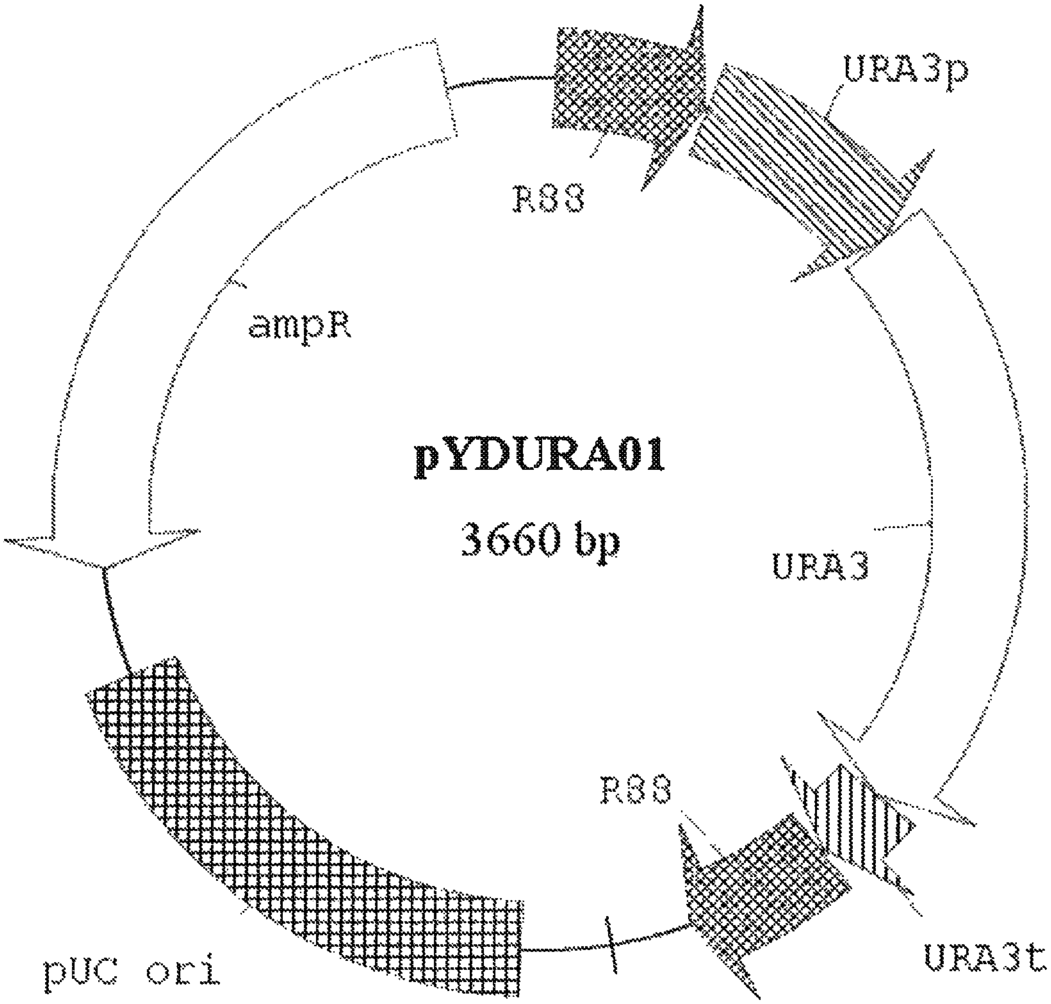

A vector named pYDURA01 (FIG. 5B) for generating yeast selectable and recyclable marker was constructed using similar method as pYDAB006. The URA3 expression cassette was amplified from yeast genomic DNA by standard PCR techniques. The 200 base pair fingerprint sequence (named R88: TGCGTGTGCCGCGAGTCCACGTC-TACTCGCGAACCGAGTGCAGGCGGGTCT-TCGGCCAG GACGGCCGTGCGTGACCCCGGCCGC-CAGACGAAACGGACCGCGCTCGCCAGACGCTACC CAGCCCGTTCATGCCGGCCGCGAGC-CGACCTGTCTCGGTCGCTTCGACGCACGCGCGGTC CTTTCGGGTACTCGCCTAAGAC (SEQ ID NO:188)) at both sides of URA3 cassette was amplified by standard PCR techniques from the genomic DNA of yBPA317, which was a diploid strain having genotypes MATa/MATalpha; URA3/ura3; YDL074.5::P(TDH3)-CBT1-T(CYC1)-R88 YLR388.5::P(TDH3)-StBGL-T(CYC1)-R88/YLR388.5::P(TDH3)-StBGL-T(CYC1)-R88. The primers used in the amplification are described in Table 8 below:

TABLE 8

| Primers Used in pYDURA01 Construction | | |
|---|---|---|
| Primer | SEQ ID NO: | Sequence (KpnI and NotI sites are underlined) |
| NotI-KpnI-R88-F | 189 | caatagcggccgcggtaccTGCGTGT GCCGCGAGTCCAC |
| R88-BamHI-R | 190 | TGTTAGGATCCGTCTTAGGCGAG TACCCGAAAGG |
| BamHI-ura-F | 191 | caataggatccAGGCATATTTATGGTG AAGAATAAGT |
| ura-Xho-R | 192 | TGTTACTCGAGAAATCATTACGAC CGAGATTCCCG |
| XhoI-R88-F | 193 | caatactcgagTGCGTGTGCCGCGAG TCCAC |
| R88-NotI-R | 194 | TGTTAGCGGCCGCGTCTTAGGCG AGTACCCGAAAGG |

Figure 5C:
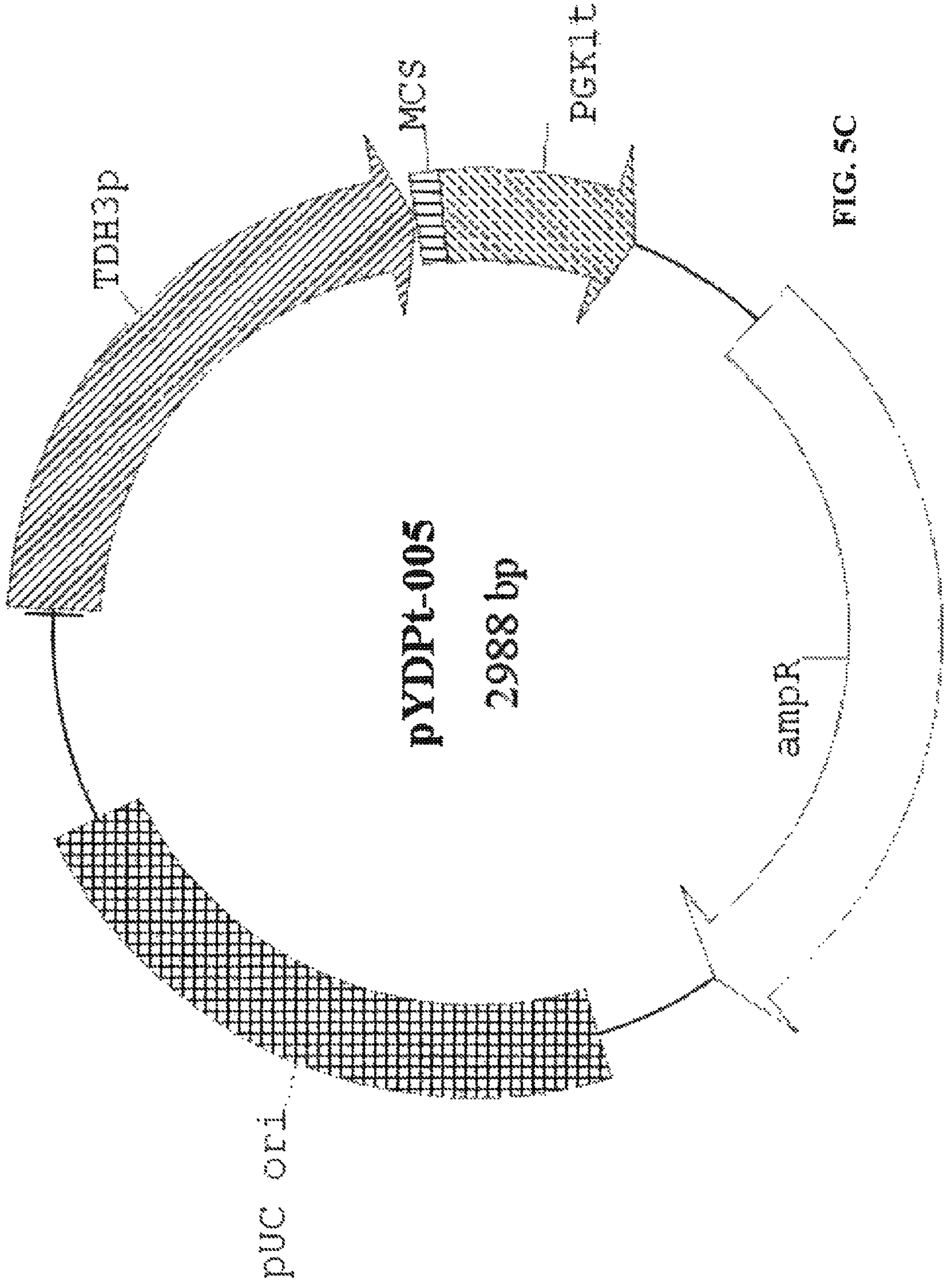

An expression cassette was generated for the XI genes by cloning into a vector named pYDPt005 (FIG. 5C). pYDPt005 was generated using similar method as pYDAB006. It contained a TDH3 promoter and a PGK1 terminator flanking a multiple cloning site (MCS 2: 5'-ACTAGTGGATCCCTCGAGGTCGACGTTTAAAC-3' (SEQ ID NO:195), where single underline is SpeI site, double underline is XhoI site, and jagged underline is PmeI site). The promoter and the terminator were amplified from *S. cerevisiae* genomic DNA; an AscI site was added to the 5' end of the TDH3 promoter while a KpnI site was added to the 3' end of the PGK1 terminator during amplification. Primers used in the amplification are described in Table 9.

TABLE 9

| Primers Used in pYDPt005 Construction | | |
|---|---|---|
| Primer | SEQ ID NO: | Sequence (AscI and KpnI sites are underlined) |
| TDH-F | 196 | CACCAGGCGCGCCTCTAGAAAGCT TACGCGTAGTTTATCATTATCAATA CTGCCATTTCAAAGA |
| overlap-TDH-R | 197 | AACGTCGACCTCGAGGGATCCAC TAGTTCGAAACTAAGTTCTTGGT GTTTTAAAACT |
| overlap-PGK-F | 198 | GTGGATCCCTCGAGGTCGA CGTTTAAACATTGAATTGAA TTGAAATCGATAGATCAAT |
| PGK-R | 199 | CACCAGCGGCCGCGGTACCGATAT CCCTGCAGGGAGCTCGAAATATC GAATGGGAAAAAAAAACTGGAT |

Figure 5D:
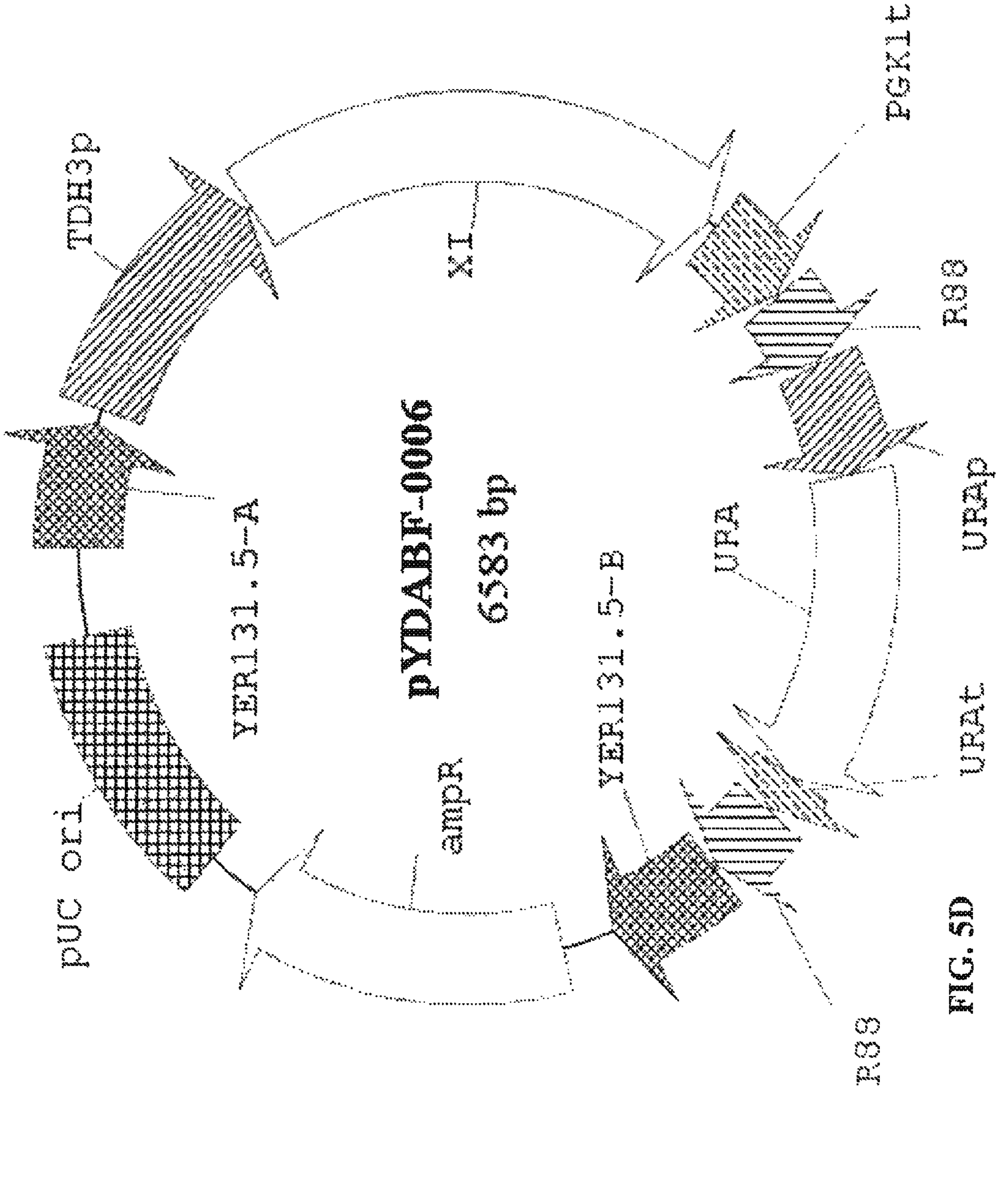

An *Orpinomyces* sp. XI gene (NCBI:169733248) was cloned in this vector between the SpeI and XhoI sites. The *Orpinomyces* sp. XI expression cassette and R88-Ura-R88 fragment were then cloned into vector pYDAB006 using Asa KpnI and Nod sites; the resulting plasmid was named pYDABF006 (FIG. 5D). Subsequently, the *Orpinomyces* sp. XI gene in pYDABF0006 was replaced with a subset of the XI genes of Table 2 by digestion of pYDABF0006 with SpeI and PmeI and ligation to a DNA fragment encoding the appropriate XI sequence which had been amplified from p426PGK1-XI constructs. A SpeI site followed by a Kozak-like sequence (6 consecutive adenines) was added immediately in front of the start codon of the XI genes while a PmeI site was added to the 3' end of the XI genes during amplification.

XI gene integration cassettes were extracted by PacI digestion and used to transform yeast strain yBPA130 using standard techniques. Transformants were selected for growth on SC-Ura (Synthetic Complete, Ura dropout) agar plates. Integration position and existence of XI cassette in transformants was confirmed by PCR using the primers shown in Table 10.

TABLE 10

| Primers Used in Integration Verification | | |
|---|---|---|
| Primer | SEQ ID NO: | Sequence |
| 5' of integration | 200 | ACAGGGATAACAAAGTTTCTCCAGC |
| 3' of integration | 201 | CATACCAAGTCATGCGTTACCAGAG |
| 5' of R88-ura-R88 | 202 | TTTCCCATTCGATATTTCGAGCTCC |
| 3' of integration | 203 | CATACCAAGTCATGCGTTACCAGAG |

Confirmed clones were then grown about 18 hours in liquid YPD to allow looping out of the URA3 marker and were selected for growth on SC+5-FOA agar plate. The absence of the URA3 marker was confirmed by PCR.

Strains containing the confirmed XI expression cassettes were inoculated into about 3 ml of modified YP Media (YP+

0.1% Glucose+3.0% Xylose) and incubated overnight at about 30° C. and about 220 rpm. These overnight cultures were subcultured into about 25 ml of the same media to about $OD_{600}$=0.2. Samples were incubated overnight at about 30° C. and about 220 rpm. Cultures were harvested when $OD_{600}$ was between about 3 and 4. Pellets were collected by centrifugation for about 5 minutes at about 4000 rpm. The supernatant was discarded and pellets washed with about 25 ml of distilled-deionized water and centrifuged again using the same conditions. Supernatant was discarded and the pellet frozen at about −20° C. until lysis and characterization.

Cell pellets were thawed and about 200 mg of each pellet sample was weighed out into 2 ml microcentrifuge tubes. About 50 μl of Complete®, EDTA-free Protease Inhibitor cocktail (Roche Part#11873 580 001) at 5 times the concentration stated in the manufacturer's protocol was added to each sample. To this was added about 0.5 ml of Y-PER Plus® Dialyzable Yeast Protein Extraction Reagent (Thermo Scientific Part#78999) (YP+) to each sample. Samples were incubated at about 25° C. for about 4 hours on rotating mixer. Sample supernatants were collected after centrifugation at about 10,000×g for about 10 minutes for characterization.

Total protein concentrations of the XI sample extracts prepared above were carried out using Bio-Rad Protein Assay Dye Reagent Concentrate (Bio-Rad, cat#500-0006, Hercules Calif.) which is a modified version of the Bradford method (Bradford).

Yeast physiological pH ranges are known to range from about pH 6 to about pH 7.5 (Pena, Ramirez et al., 1995, J. Bacteriology 4:1017-1022). Ranking of XI activity at yeast physiological pH was accomplished using the assay conditions at pH 7.5 and modified for pH 6.0 as described in the materials and methods. The specific activities of 20 XIs when expressed from a single copy integrated into the yeast YER131.5 locus were evaluated. The results are listed in Table 11.

TABLE 11

SA of XI Expressed in an Industrial *S. cerevisiae*

| SEQ ID NO: | Organism Classification | SA, pH 6 (U/mg) | SA, pH 7.5 (U/mg) |
|---|---|---|---|
| 2 | Bacteroidales | 0.86 | 1.08 |
| 14 | *Bacteroides* | 0.33 | 1.07 |
| 16 | *Bacteroides* | 0.57 | 1.05 |
| 32 | *Bacteroides* | 0.53 | 1.00 |
| 38 | Firmicutes | 1.00 | 0.94 |

TABLE 11-continued

SA of XI Expressed in an Industrial *S. cerevisiae*

| SEQ ID NO: | Organism Classification | SA, pH 6 (U/mg) | SA, pH 7.5 (U/mg) |
|---|---|---|---|
| 42 | Firmicutes | 0.79 | 0.82 |
| 44 | Firmicutes | 0.08 | 0.10 |
| 46 | Firmicutes | 0.62 | 0.69 |
| 50 | Firmicutes | 0.35 | 0.41 |
| 52 | Firmicutes | 0.01 | 0.03 |
| 54 | Neocallimastigales | 0.64 | 1.17 |
| 58 | Neocallimastigales | 0.79 | 1.10 |
| 68 | Neocallimastigales | 0.01 | 0.02 |
| 72 | Neocallimastigales | 0.22 | 0.40 |
| 78 | *Prevotella* | 1.10 | 1.45 |
| 80 | *Prevotella* | 0.74 | 1.11 |
| 82 | *Prevotella* | 0.54 | 0.60 |
| 84 | *Prevotella* | 0.76 | 1.06 |
| 96 | *Prevotella* | 1.10 | 1.62 |
| 116 | *Prevotella* | 0.03 | 0.06 |
| Host neg Ctrl | | 0.00 | 0.02 |

5.11 Example 10: Identification of Sequence Motifs in Acid Tolerant XIs

The proposed mechanism of xylose isomerases can be summarized as follows: (i) binding of xylose to xylose isomerase, so that O3 and O4 are coordinated by metal ion I; (ii) enzyme-catalyzed ring opening (the identity of the ring-opening group remains a subject for further investigation; ring opening may be the rate limiting step in the overall isomerization process); (iii) chain extension (sugar binds in a linear extended form) in which O2 and O4 now coordinate metal ion I; (iv) O2 becomes deprotonated causing a shift of metal ion II from position 1 to an adjacent position 2 in which it coordinates O1 and O2 of the sugar together with metal ion I; (v) isomerization via an anionic transition state arises by a hydride shift promoted by electrophilic catalysis provided by both metal ions; (vi) collapse of transition state by return of metal ion II to position 1; (vii) chain contraction to a pseudo-cyclic position with ligands to metal ion I changing from O2/O4 back to O3/O4; (viii) enzyme-catalyzed ring closure; (ix) dissociation of xylulose from xylose isomerase (Lavie et al., 1994, Biochemistry 33(18), 5469-5480).

Many XIs identified contained one or both of two signature sequences characteristic of XIs, [LI]EPKP.{2}P (SEQ ID NO:204) and [FL]HD[^K]D[LIV].[PD].[GDE] (SEQ ID NO:205). Additional sequence motifs present in the top performing *Firmicutes* and *Prevotella* XIs were identified. The motifs are located near the active site including residues in direct contact with the D-xylose and/or the metal ions. The motifs are shown in Table 12 below:

TABLE 12

XI Sequence Motifs

| XI Source | Motif | Sequence | SEQ ID NO: |
|---|---|---|---|
| *Firmicutes* | 1A | P[FY][AST][MLVI][AS][WYFL]W[HT]N[LFMG]GA | 206 |
| *Firmicutes* | 1B | P[FY][AS].{2}[WYFL]W[HT][^TV].GA | 207 |
| *Firmicutes* | 2 | [GSN][IVA]R[YFHG][FYLIV]C[FW]HD.D | 208 |
| *Firmicutes* | 3 | T[ASTC][NK][^L]F. [NDH][PRKAG][RVA][FY]C | 209 |
| *Firmicutes* | 4 | [WFY]D[TQVI]D.[FY][PF][^T].{2,4}[YFH]S[ATL]T | 210 |
| *Firmicutes* | 5 | GF[NH]FD[SA]KTR | 211 |
| *Prevotella* | 1A | FG.QT[RK].{2}E[WYF][DNG].{2,3}[DNEGT][AT] | 212 |

TABLE 12-continued

| XI Sequence Motifs | | | |
|---|---|---|---|
| XI Source | Motif | Sequence | SEQ ID NO: |
| *Prevotella* | 1B | FG.QT[RK].{2}E[WYF][DNG].{3}[^C][AP] | 213 |
| *Prevotella* | 2 | [FW]HD.D[LVI].[DE]EG[^P][TSD][IV][EA]E | 214 |

5.12 Example 11: In Vivo Evaluation of Xylose Isomerase

Haploid *S. cerevisiae* strain yBPA130 (MATa::ura3) and yBPA136 (MATalpha::ura3) were genetically modified to enhance C5 xylose utilization during fermentation. The modification includes the following: the native glucose repressible alcohol dehydrogenase II gene ADH2 was disrupted by inserting an expression cassette of the endogenous transaldolase gene TAL1 (SEQ ID N0:215) and xylulokinase gene XKS1 (SEQ ID NO:216). PHO13 encoding the native alkaline phosphatase specific for p-nitrophenyl phosphate gene was disrupted by inserting the native transketolase-1 gene TKL1 (SEQ ID NO:217). Native aldose reductase gene GRE3 was disrupted by inserting native D-ribulose-5-phosphate 3-epimerase gene RPE1 (SEQ ID NO:218) and Ribose-5-phosphate ketol-isomerase gene RKI1 (SEQ ID NO:219). Also one expression cassette of native galactose permease gene GAL2 (SEQ ID NO: 220) was integrated into the *S. cerevisiae* strain, resulting in haploid strains pBPB007 (MATa::ura3) and pBPB008 (MATalpha::ura3). The genotype of pBPB007 and pBPB008 is adh2::TAL1-XKS1, pho13::TKL1-XKS1, gre3::RPE1-RKI1 and YLR388.5::GAL2. The sequences are shown in Table 13, below:

TABLE 13

| Sequence Name | Type of sequence | SEQ ID NO: | Sequence |
|---|---|---|---|
| TAL1 (*S. cerevisiae*) | DNA | 215 | ATGTCTGAACCAGCTCAAAAGAAACAAAAGGTTGCTAACAACTCT<br>CTAGAACAATTGAAAGCCTCCGGCACTGTCGTTGTTGCCGACACT<br>GGTGATTTCGGCTCTATTGCCAAGTTTCAACCTCAAGACTCCACA<br>ACTAACCCATCATTGATCTTGGCTGCTGCCAAGCAACCAACTTAC<br>GCCAAGTTGATCGATGTTGCCGTGGAATACGGTAAGAAGCATGGT<br>AAGACCACCGAAGAACAAGTCGAAAATGCTGTGGACAGATTGTTA<br>GTCGAATTCGGTAAGGAGATCTTAAAGATTGTTCCAGGCAGAGTC<br>TCCACCGAAGTTGATGCTAGATTGTCTTTTGACACTCAAGCTACC<br>ATTGAAAAGGCTAGACATATCATTAAATTGTTTGAACAAGAAGGT<br>GTCTCCAAGGAAAGAGTCCTTATTAAAATTGCTTCCACTTGGGAA<br>GGTATTCAAGCTGCCAAAGAATTGGAAGAAAAGGACGGTATCCAC<br>TGTAATTTGACTCTATTATTCTCCTTCGTTCAAGCAGTTGCCTGT<br>GCCGAGGCCCAAGTTACTTTGATTTCCCCATTTGTTGGTAGAATT<br>CTAGACTGGTACAAATCCAGCACTGGTAAAGATTACAAGGGTGAA<br>GCCGACCCAGGTGTTATTTCCGTCAAGAAAATCTACAACTACTAC<br>AAGAAGTACGGTTACAAGACTATTGTTATGGGTGCTTCTTTCAGA<br>AGCACTGACGAAATCAAAAACTTGGCTGGTGTTGACTATCTAACA<br>ATTTCTCCAGCTTTATTGGACAAGTTGATGAACAGTACTGAACCT<br>TTCCCAAGAGTTTTGGACCCTGTCTCCGCTAAGAAGGAAGCCGGC<br>GACAAGATTTCTTACATCAGCGACGAATCTAAATTCAGATTCGAC<br>TTGAATGAAGACGCTATGGCCACTGAAAAATTGTCCGAAGGTATC<br>AGAAAATTCTCTGCCGATATTGTTACTCTATTCGACTTGATTGAA<br>AAGAAAGTTACCGCTTAA |
| XKS1 (*S. cerevisiae*) | DNA | 216 | ATGTTGTGTTCAGTAATTCAGAGACAGACAAGAGAGGTTTCCAAC<br>ACAATGTCTTTAGACTCATACTATCTTGGGTTTGATCTTTCGACC<br>CAACAACTGAAATGTCTCGCCATTAACCAGGACCTAAAAATTGTC<br>CATTCAGAAACAGTGGAATTTGAAAAGGATCTTCCGCATTATCAC<br>ACAAAGAAGGGTGTCTATATACACGGCGACACTATCGAATGTCCC<br>GTAGCCATGTGGTTAGAGGCTCTAGATCTGGTTCTCTCGAAATAT<br>CGCGAGGCTAAATTTCCATTGAACAAAGTTATGGCCGTCTCAGGG<br>TCCTGCCAGCAGCACGGGTCTGTCTACTGGTCCTCCCAAGCCGAA<br>TCTCTGTTAGAGCAATTGAATAAGAAACCGGAAAAAGATTTATTG<br>CACTACGTGAGCTCTGTAGCATTTGCAAGGCAAACCGCCCCCAAT<br>TGGCAAGACCACAGTACTGCAAAGCAATGTCAAGAGTTTGAAGAG<br>TGCATAGGTGGGCCTGAAAAAATGGCTCAATTAACAGGGTCCAGA<br>GCCCATTTTAGATTTACTGGTCCTCAAATTCTGAAAATTGCACAA<br>TTAGAACCAGAAGCTTACGAAAAAACAAAGACCATTTCTTTAGTG<br>TCTAATTTTTTGACTTCTATCTTAGTGGGCCATCTTGTTGAATTA<br>GAGGAGGCAGATGCCTGTGGTATGAACCTTTATGATATACGTGAA<br>AGAAAATTCAGTGATGAGCTACTACATCTAATTGATAGTTCTTCT<br>AAGGATAAAACTATCAGACAAAAATTAATGAGAGCACCCATGAAA<br>AATTTGATAGCGGGTACCATCTGTAAATATTTTATTGAGAAGTAC<br>GGTTTCAATACAAACTGCAAGGTCTCTCCCATGACTGGGGATAAT<br>TTAGCCACTATATGTTCTTTACCCCTGCGGAAGAATGACGTTCTC<br>GTTTCCCTAGGAACAAGTACTACAGTTCTTCTGGTCACCGATAAG<br>TATCACCCCTCTCCGAACTATCATCTTTTC<br>ATTCATCCAACTCTGCCAAACCATTATATGGGTATGATTTGTTAT<br>TGTAATGGTTCTTTGGCAAGGGAGAGGATAAGAGACGAGTTAAAC |

TABLE 13-continued

| Sequence Name | Type of sequence | SEQ ID NO: | Sequence |
|---|---|---|---|
| | | | AAAGAACGGGAAAATAATTATGAGAAGACTAACGATTGGACTCTT TTTAATCAAGCTGTGCTAGATGACTCAGAAAGTAGTGAAAATGAA TTAGGTGTATATTTTCCTCTGGGGGAGATCGTTCCTAGCGTAAAA GCCATAAACAAAAGGGTTATCTTCAATCCAAAAACGGGTATGATT GAAAGAGAGGTGGCCAAGTTCAAAGACAAGAGGCACGATGCCAAA AATATTGTAGAATCACAGGCTTTAAGTTGCAGGGTAAGAATATCT CCCCTGCTTTCGGATTCAAACGCAAGCTCACAACAGAGACTGAAC GAAGATACAATCGTGAAGTTTGATTACGATGAATCTCCGCTGCGG GACTACCTAAATAAAAGGCCAGAAAGGACTTTTTTTGTAGGTGGG GCTTCTAAAAACGATGCTATTGTGAAGAAGTTTGCTCAAGTCATT GGTGCTACAAAGGGTAATTTTAGGCTAGAAACACCAAACTCATGT GCCCTTGGTGGTTGTTATAAGGCCATGTGGTCATTGTTATATGAC TCTAATAAAATTGCAGTTCCTTTTGATAAATTTCTGAATGACAAT TTTCCATGGCATGTAATGGAAAGCATATCCGATGTGGATAATGAA AATTGGGATCGCTATAATTCCAAGATTGTCCCCTTAAGCGAACTG GAAAAGACTCTCATCTAA |
| TKL1 (*S. cerevisiae*) | DNA | 217 | ATGACTCAATTCACTGACATTGATAAGCTAGCCGTCTCCACCATA AGAATTTTGGCTGTGGACACCGTATCCAAGGCCAACTCAGGTCAC CCAGGTGCTCCATTGGGTATGGCACCAGCTGCACACGTTCTATGG AGTCAAATGCGCATGAACCCAACCAACCCAGACTGGATCAACAGA GATAGATTTGTCTTGTCTAACGGTCACGCGGTCGCTTTGTTGTAT TCTATGCTACATTTGACTGGTTACGATCTGTCTATTGAAGACTTG AAACAGTTCAGACAGTTGGGTTCCAGAACACCAGGTCATCCTGAA TTTGAGTTGCCAGGTGTTGAAGTTACTACCGGTCCATTAGGTCAA GGTATCTCCAACGCTGTTGGTATGGCCATGGCTCAAGCTAACCTG GCTGCCACTTACAACAAGCCGGGCTTTACCTTGTCTGACAACTAC ACCTATGTTTTCTTGGGTGACGGTTGTTTGCAAGAAGGTATTTCT TCAGAAGCTTCCTCCTTGGCTGGTCATTTGAAATTGGGTAACTTG ATTGCCATCTACGATGACAACAAGATCACTATCGATGGTGCTACC AGTATCTCATTCGATGAAGATGTTGCTAAGAGATACGAAGCCTAC GGTTGGGAAGTTTTGTACGTAGAAAATGGTAACGAAGATCTAGCC GGTATTGCCAAGGCTATTGCTCAAGCTAAGTTATCCAAGGACAAA CCAACTTTGATCAAAATGACCACAACCATTGGTTACGGTTCCTTG CATGCCGGCTCTCACTCTGTGCACGGTGCCCCATTGAAAGCAGAT GATGTTAAACAACTAAAGAGCAAATTCGGTTTCAACCCAGACAAG TCCTTTGTTGTTCCACAAGAAGTTTACGACCACTACCAAAAGACA ATTTTAAAGCCAGGTGTCGAAGCCAACAACAAGTGGAACAAGTTG TTCAGCGAATACCAAAAGAAATTCCCAGAATTAGGTGCTGAATTG GCTAGAAGATTGAGCGGCCAACTACCCGCA AATTGGGAATCTAAGTTGCCAACTTACACCGCCAAGGACTCTGCC GTGGCCACTAGAAAATTATCAGAAACTGTTCTTGAGGATGTTTAC AATCAATTGCCAGAGTTGATTGGTGGTTCTGCCGATTTAACACCT TCTAACTTGACCAGATGGAAGGAAGCCCTTGACTTCCAACCTCCT TCTTCCGGTTCAGGTAACTACTCTGGTAGATACATTAGGTACGGT ATTAGAGAACACGCTATGGGTGCCATAATGAACGGTATTTCAGCT TTCGGTGCCAACTACAAACCATACGGTGGTACTTTCTTGAACTTC GTTTCTTATGCTGCTGGTGCCGTTAGATTGTCCGCTTTGTCTGGC CACCCAGTTATTTGGGTTGCTACACATGACTCTATCGGTGTCGGT GAAGATGGTCCAACACATCAACCTATTGAAACTTTAGCACACTTC AGATCCCTACCAAACATTCAAGTTTGGAGACCAGCTGATGGTAAC GAAGTTTCTGCCGCCTACAAGAACTCTTTAGAATCCAAGCATACT CCAAGTATCATTGCTTTGTCCAGACAAAACTTGCCACAATTGGAA GGTAGCTCTATTGAAAGCGCTTCTAAGGGTGGTTACGTACTACAA GATGTTGCTAACCCAGATATTATTTTAGTGGCTACTGGTTCCGAA GTGTCTTTGAGTGTTGAAGCTGCTAAGACTTTGGCCGCAAAGAAC ATCAAGGCTCGTGTTGTTTCTCTACCAGATTTCTTCACTTTTGAC AAACAACCCCTAGAATACAGACTATCAGTCTTACCAGACAACGTT CCAATCATGTCTGTTGAAGTTTTGGCTACCACATGTTGGGGCAAA TACGCTCATCAATCCTTCGGTATTGACAGATTTGGTGCCTCCGGT AAGGCACCAGAAGTCTTCAAGTTCTTCGGTTTCACCCCAGAAGGT GTTGCTGAAAGAGCTCAAAAGACCATTGCATTCTATAAGGGTGAC AAGCTAATTTCTCCTTTGAAAAAAGCTTTCTAA |
| RPE1 (*S. cerevisiae*) | DNA | 218 | ATGGTCAAACCAATTATAGCTCCCAGTATCCTTGCTTCTGACTTC GCCAACTTGGGTTGCGAATGTCATAAGGTCATCAACGCCGGCGCA GATTGGTTACATATCGATGTCATGGACGGCCATTTTGTTCCAAAC ATTACTCTGGGCCAACCAATTGTTACCTCCCTACGTCGTTCTGTG CCACGCCCTGGCGATGCTAGCAACACAGAAAAGAAGCCCACTGCG TTCTTCGATTGTCACATGATGGTTGAAAATCCTGAAAAATGGGTC GACGATTTTGCTAAATGTGGTGCTGACCAATTTACGTTCCACTAC GAGGCCACACAAGACCCTTTGCATTTAGTTAAGTTGATTAAGTCT AAGGGCATCAAAGCTGCATGCGCCATCAAACCTGGTACTTCTGTT GACGTTTTATTTGAACTAGCTCCTCATTTGGATATGGCTCTTGTT ATGACTGTGGAACCTGGGTTTGGAGGCCAAAAATTCATGGAAGAC ATGATGCCAAAAGTGGAAACTTTGAGAGCCAAGTTCCCCCATTTG AATATCCAAGTCGATGGTGGTTTGGGCAAGGAGACCATCCCGAAA |

TABLE 13-continued

| Sequence Name | Type of sequence | SEQ ID NO: | Sequence |
|---|---|---|---|
| | | | GCCGCCAAAGCCGGTGCCAACGTTATTGTCGCTGGTACCAGTGTT<br>TTCACTGCAGCTGACCCGCACGATGTTATCTCCTTCATGAAAGAA<br>GAAGTCTCGAAGGAATTGCGTTCTAGAGATTTGCTAGATTAG |
| RKI1 (*S. cerevisiae*) | DNA | 219 | ATGGCTGCCGGTGTCCCAAAAATTGATGCGTTAGAATCTTTGGGC<br>AATCCTTTGGAGGATGCCAAGAGAGCTGCAGCATACAGAGCAGTT<br>GATGAAAATTTAAAATTTGATGATCACAAAATTATTGGAATTGGT<br>AGTGGTAGCACAGTGGTTTATGTTGCCGAAAGAATTGGACAATAT<br>TTGCATGACCCTAAATTTTATGAAGTAGCGTCTAAATTCATTTGC<br>ATTCCAACAGGATTCCAATCAAGAAACTTGATTTTGGATAACAAG<br>TTGCAATTAGGCTCCATTGAACAGTATCCTCGCATTGATATAGCG<br>TTTGACGGTGCTGATGAAGTGGATGAGAATTTACAATTAATTAAA<br>GGTGGTGGTGCTTGTCTATTTCAAGAAAAATTGGTTAGTACTAGT<br>GCTAAAACCTTCATTGTCGTTGCTGATTCAAGAAAAAAGTCACCA<br>AAACATTTAGGTAAGAACTGGAGGCAAGGTGTTCCCATTGAAATT<br>GTACCTTCCTCATACGTGAGGGTCAAGAATGATCTATTAGAACAA<br>TTGCATGCTGAAAAAGTTGACATCAGACAAGGAGGTTCTGCTAAA<br>GCAGGTCCTGTTGTAACTGACAATAATAACTTCATTATCGATGCG<br>GATTTCGGTGAAATTTCCGATCCAAGAAAATTGCATAGAGAAATC<br>AAACTGTTAGTGGGCGTGGTGGAAACAGGTTTATTCATCGACAAC<br>GCTTCAAAAGCCTACTTCGGTAATTCTGACGGTAGTGTTGAAGTT<br>ACCGAAAAGTGA |
| GAL2 (*S. cerevisiae*) | DNA | 220 | ATGGCAGTTGAGGAGAACAATATGCCTGTTGTTTCACAGCAACCC<br>CAAGCTGGTGAAGACGTGATCTCTTCACTCAGTAAAGATTCCCAT<br>TTAAGCGCACAATCTCAAAAGTATTCTAATGATGAATTGAAAGCC<br>GGTGAGTCAGGGTCTGAAGGCTCCCAAAGTGTTCCTATAGAGATA<br>CCCAAGAAGCCCATGTCTGAATATGTTACCGTTTCCTTGCTTTGT<br>TTGTGTGTTGCCTTCGGCGGCTTCATGTTTGGCTGGGATACCGGT<br>ACTATTTCTGGGTTTGTTGTCCAAACAGACTTTTTGAGAAGGTTT<br>GGTATGAAACATAAGGATGGTACCCACTATTTGTCAAACGTCAGA<br>ACAGGTTTAATCGTCGCCATTTTCAATATTGGCTGTGCCTTTGGT<br>GGTATTATACTTTCCAAAGGTGGAGATATGTATGGCCGTAAAAAG<br>GGTCTTTCGATTGTCGTCTCGGTTTATATAGTTGGTATTATCATT<br>CAAATTGCCTCTATCAACAAGTGGTACCAATATTTCATTGGTAGA<br>ATCATATCTGGTTTGGGTGTCGGCGGCATCGCCGTCTTATGTCCT<br>ATGTTGATCTCTGAAATTGCTCCAAAGCACTTGAGAGGCACACTA<br>GTTTCTTGTTATCAGCTGATGATTACTGCAGGTATCTTTTTGGGC<br>TACTGTACTAATTACGGTACAAAGAGCTATTCGAACTCAGTTCAA<br>TGGAGAGTTCCATTAGGGCTATGTTTCGCTTGGTCATTATTTATG<br>ATTGGCGCTTTGACGTTAGTTCCTGAATCCCCACGTTATTTATGT<br>GAGGTGAATAAGGTAGAAGACGCCAAGCGTTCCATTGCTAAGTCT<br>AACAAGGTGTCACCAGAGGATCCTGCCGTCCAGGCAGAGTTAGAT<br>CTGATCATGGCCGGTATAGAAGCTGAAAAACTGGCTGGCAATGCG<br>TCCTGGGGGGAATTATTTTCCACCAAGACCAAAGTATTTCAACGT<br>TTGTTGATGGGTGTGTTTGTTCAAATGTTC<br>CAACAATTAACCGGTAACAATTATTTTTTCTACTACGGTACCGTT<br>ATTTTCAAGTCAGTTGGCCTGGATGATTCCTTTGAAACATCCATT<br>GTCATTGGTGTAGTCAACTTTGCCTCCACTTTCTTTAGTTTGTGG<br>ACTGTCGAAAACTTGGGACATCGTAAATGTTTACTTTTGGGCGCT<br>GCCACTATGATGGCTTGTATGGTCATCTACGCCTCTGTTGGTGTT<br>ACTAGATTATATCCTCACGGTAAAAGCCAGCCATCTTCTAAAGGT<br>GCCGGTAACTGTATGATTGTCTTTACCTGTTTTTATATTTTCTGT<br>TATGCCACAACCTGGGCGCCAGTTGCCTGGGTCATCACAGCAGAA<br>TCATTCCCACTGAGAGTCAAGTCGAAATGTATGGCGTTGGCCTCT<br>GCTTCCAATTGGGTATGGGGGTTCTTGATTGCATTTTTCACCCCA<br>TTCATCACATCTGCCATTAACTTCTACTACGGTTATGTCTTCATG<br>GGCTGTTTGGTTGCCATGTTTTTTATGTCTTTTTCTTTGTTCCA<br>GAAACTAAAGGCCTATCGTTAGAAGAAATTCAAGAATTATGGGAA<br>GAAGGTGTTTTACCTTGGAAATCTGAAGGCTGGATTCCTTCATCC<br>AGAAGAGGTAATAATTACGATTTAGAGGATTTACAACATGACGAC<br>AAACCGTGGTACAAGGCCATGCTAGAATAA |

Figure 6:
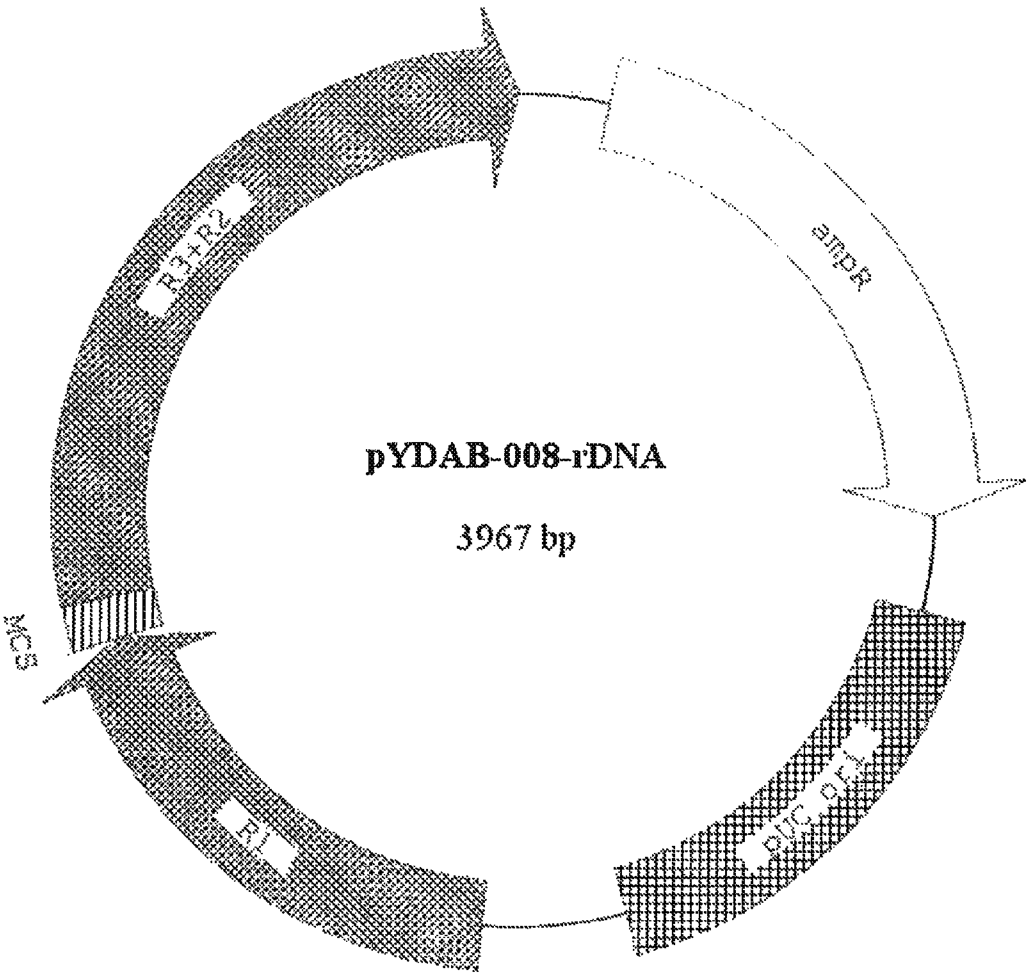
FIG. 6 is a map of vector YDAB008-rDNA for multiple XI integration into *S. cerevisiae* strain yBPB007 and yBPB008.

A vector named pYDAB008 rDNA (FIG. 6) for integration xylose isomerase into ribosomal DNA loci in *S. cerevisiae* genome was constructed using conventional cloning methods. This vector can confer high copy number integration of genes and resulting in high-level expression of proteins. The vector was derived from pBluescript II SK (+) (Agilent Technologies, Inc., Santa Clara, Calif.). The pUC origin of replication and bla gene encoding ampicillin resistance was amplified with specific primer sequences as a selectable marker for cloning. A 741 base-pair segment R1 region, 253 base-pair R3 region and a 874 base-pair R2 region were amplified from yeast genomic DNA by PCR amplifications. A multiple cloning site of SEQ ID NO:181 (: 5'-GGCGCGC-CTCTAGAAAGCTTACGCGTGAGCTCCCT-GCAGGGATATCGGTACCGCGGCCG C-3') was inserted between the R1 and R3/R2 regions by assembly using overlapping PCR. All primers used in above reactions are shown in Table 14. Overlapping PCR products were then ligated in one reaction and result in rDNA integration plasmid named pYDAB008 rDNA (FIG. 6).

TABLE 14

Primers Used in pYDAB008 rDNA vector construction

| Primer | SEQ ID NO: | Sequence (Pac I restriction site is underlined) |
|---|---|---|
| Pac I-rDNA(R1)-R | 221 | CACCATTAATTAACCCGGGGCACCTGTCACTTTGGAA |
| rDNA (R1)-over-R | 222 | CGCGTAAGCTTTCTAGAGGCGCGCCAAGCTTTTACACTCTTGACCAGCGCA |
| AB vector-MCS-R | 223 | CCGCTGGTGGGTACCGATATCCCTGCAGGGAGCTCACGCGTAAGCTTTCTAGAGGCG |
| rDNA(R3)-over-R | 224 | CTGCAGGGATATCGGTACCCACCAGCGGCCGCAGGCCTTGGGTGCTTGCTGGCGAA |
| rDNA(R3)-over-R | 225 | ACCTCTGCATGCGAATTCTTAAGACAAATAAAATTTATAGAGACTTGT |
| rDNA(R2)-over-R | 226 | GTCTTAAGAATTCGCATGCAGAGGTAGTTTCAAGGT |
| Pac I-rDNA(R2)-R | 227 | CACCATTAATTAATACGTATTTCTCGCCGAGAAAAACTT |

pYDABF 0015 (comprising a nucleic acid encoding a xylose isomerase of SEQ ID NO:78) and pYDABF-0026 (comprising a nucleic acid encoding a xylose isomerase of SEQ ID NO:96) (both described in Example 10) were digested with Asc I and Kpn I restriction enzymes (New England Biolabs Inc., MA, USA) and ligated to pYDAB008 rDNA integration vector described above (FIG. 6). The resulting plasmids were named pYDABF-0033 (SEQ ID NO:78) and pYDABF-0036 (SEQ ID NO:96).

The rDNA integration cassette was linearized by Pac I restriction enzyme digestion (New England Biolabs Inc., MA, USA) and purified with DNA column purification kit (Zymo Research, Irvine, Calif., USA). The integration cassette was transformed into modified haploid *S. cerevisiae* strain pBPB007 (MATa::ura3) and pBPB008 (MAT alpha::ura3) using the standard protocol described in previous examples. Transformants were plated on SC-xylose (SC complete+2% xylose) agar plates, about 2-3 days at about 30° C. Colonies that grew on SC-xylose agar plates were then checked by colony PCR analysis with primer sets shown in Table 15 (SEQ ID NOs:228, 229, 230 and 231) to confirm the presence of xylose isomerase in the genome.

TABLE 15

Primers Used in Integration Verification

| Primer | SEQ ID NO: | Sequence |
|---|---|---|
| N16PCR_F | 228 | CCCCATCGACAACTACGAGCTCACT |
| N16PCR_R | 229 | CAACTTGCCGTCCTCGAAGTCCTTG |
| N05PCR_F | 230 | CGAGCCTGAGAAGGTCGTGATGGGA |
| N05PCR_R | 231 | TACGTCGAAGTCGGGGTTGGTAGAA |

Confirmed haploid strains were BD31328 (MATa), BD31336 (MATalpha), BD31526 (MATa) and BD31527 (MATalpha). Diploid strains BD31378 (expressing a xylose isomerase of SEQ ID NO:96) and BD31365 (expressing a xylose isomerase of SEQ ID NO:78) were generated by conventional plate mating on YPXylose (YP+2% xylose) agar plates, about 2 days at about 30° C. Colony PCR with specific primers checking mating types were performed (shown in Table 14) and a single colony, which has both MATa and MATalpha were picked as diploid strains BD 31378 (SEQ ID NO: 96) and BD31365 (SEQ ID NO:78).

A linear fragment encoding the URA3 sequence (SEQ ID NO:237; TTAATTAAGTTAATTACCTTTTTTGC-GAGGCATATTTATGGTGAAGAATAAGTTTTGACCATCAAAGAAGGTTAATGTGGCTGTG-GTTTCAGGGTCCATAAAGCTTTTCAATTCATCATTTTTTTTTTATTCTTTTTTTTGATTCCG-GTTTCCTTGAAATTTTTTTGATTCGGTAATCTCCGAACAGAAGGAAGAACGAAGGAAGGAGCA-CAGACTTAGATTGGTATATATACGCATATGT AGTGT-TGAAGAAACATGAAATTGCCCAGTAT-TCTTAACCCAACTGCACAGAACAAAAACCTGCAGGAAACGAAGATAAATCATGTC-GAAAGCTACATATAAGGAACGTGCTGCTACTC ATC-CTAGTCCTGTTGCTGCCAAGCTATT-TAATATCATGCACGAAAAGCAAACAAACTTGTGTGCTTCATTGGATGTTCGTACCAC-CAAGGAATTACTGGAGTTAGTTGAAGCATTAGGTCCCAAAATTTGTTTACTAAAAACACAT-GTGGATATCTTGACTGATTTTTCCATGGAGGGCACAGTTAAGCCGCTAAAGGCATTATCCGC-CAAGTACAATTTTTTACTCTTCGAAGACAGAAAATTTGCTGACATTGGTAATACAGT-CAAATTGCAGTACTCTGCGGGTGTATACAGAATAGCAGAATGGGCAGACATTACGAATGCA-CACGGTGTGGTGGGCCCAGGTATTGTTAGCGGTTTGAAGCAGGCGGCAGAAGAAGTAA-CAAAGGAACCTAGAGGCCTTTTGATGTTAGCAGAATTGTCATGCAAGGGCTCCCTAGC-TACTGGAGAATATACTAAGGGTACTGTTGACATTGCGAAGAGCGACAAAGATTTTGTTATCG-GCTTTATTGCTCAAAGAGACATGGGTGGAAGAGATGAAGGTTACGATTGGTTGATTATGA-CACCCGGTGTGGGTTTAGATGACAAGGGAGACGCATTGGGTCAACAGTATAGAACCGTG-GATGATGTGGTCTCTACAGGATCTGACATTATTATTGTTGGAAGAGGACTATTTGCAAAGG-GAAGGGATGCTAAGGTAGAGGGTGAACGTTACAGAAAAGCAGGCTGGGAAG-CATATTTGAGAAGATGCGGCCAG-CAAAACTAAAAAACT GTATTATAAGTAAATGCATG-TATACTAAACTCACAAATTAGAGCTTCAATTTAATTA-TAT CAGTTATTACCCGGGAATCTCGGTCG-TAATGATTTTTATAATGACGAAAAAAAAAAAAATTGGAAAGAAAAAGCTTCATGGCCTT-TATAAAAAGGAACCATCCAATACCTCGCCAGAACCAAGTAACAGTATTTTACGGTTAATTAA) was transformed into BD 31378 (SEQ ID NO:96) and BD31365 (SEQ ID NO: 78) by a conventional transformation protocol, and transformants were plated on SCXylose-URA (Synthetic Complete, Uracil dropout) for selection. Colonies were checked by PCR with primers shown in Table 16, SEQ ID NO: 235, SEQ ID NO:236). Confirmed strains are BD31446 (SEQ ID NO: 78) and BD31448 (SEQ ID NO: 96).

TABLE 16

| Primers Used in Mating Type Verification | | |
|---|---|---|
| Primer | SEQ ID NO: | Sequence |
| 1-mating type-R | 232 | AGTCACATCAAGATCGTTTAT |
| 2-mating type alpha-F | 233 | GCACGGAATATGGGACTACTT |
| 3-mating type a-F | 234 | ACTCCACTTCAAGTAAGAGTT |
| Ura fix-F | 235 | GAACAAAAACCTGCAGGAAACG AAGAT |
| Ura fix-R | 236 | GCTCTAATTTGTGAGTTTAGTA TACATGCAT |

Table 17 below shows the genotypes of the resulting yeast strains:

TABLE 17

| Strain Construction | | |
|---|---|---|
| Name | Parent Strain | Description |
| pBPB007 | yBPA130 | MATa, ura3, adh2 :: TAL1-XKS1, pho13:: TKL1-XKS1, gre3:: RPE1-RKI1 and YLR388.5:: GAL2 |
| pBPB008 | yBPA136 | MATalpha, ura3, adh2 :: TAL1-XKS1, pho13:: TKL1-XKS1, gre3:: RPE1-RKI1 and YLR388.5:: GAL2 |
| BD31328 | pBPB007 | MATa, ura3, adh2 :: TAL1-XKS1, pho13:: TKL1-XKS1, gre3:: RPE1-RKI1 and YLR388.5:: GAL2, rDNA::XI (SEQ ID NO: 96) |
| BD31336 | pBPB008 | MATalpha, ura3, adh2 :: TAL1-XKS1, pho13:: TKL1-XKS1, gre3:: RPE1-RKI1 and YLR388.5:: GAL2, rDNA::XI (SEQ ID NO: 96) |
| BD31526 | pBPB007 | MATa, ura3, adh2 :: TAL1-XKS1, pho13:: TKL1-XKS1, gre3:: RPE1-RKI1 and YLR388.5:: GAL2, rDNA::XI (SEQ ID NO: 78) |
| BD31527 | pBPB008 | MATalpha, ura3, adh2 :: TAL1-XKS1, pho13:: TKL1-XKS1, gre3:: RPE1-RKI1 and YLR388.5:: GAL2, rDNA::XI (SEQ ID NO: 78) |
| BD31378 | BD31328 BD31336 | MATa/alpha, ura3, adh2 :: TAL1-XKS1, pho13:: TKL1-XKS1, gre3:: RPE1-RKI1 and YLR388.5:: GAL2, rDNA::XI (SEQ ID NO: 96) |
| BD31365 | BD31526 BD31527 | MATa/alpha, ura3, adh2 :: TAL1-XKS1, pho13:: TKL1-XKS1, gre3:: RPE1-RKI1 and YLR388.5:: GAL2, rDNA::XI (SEQ ID NO: 78) |
| BD31448 | BD31378 | MATa/alpha, adh2 :: TAL1-XKS1, pho13:: TKL1-XKS1, gre3:: RPE1-RKI1 and YLR388.5:: GAL2, rDNA::XI (SEQ ID NO: 96) |
| BD31446 | BD31365 | MATa/alpha. adh2 :: TAL1-XKS1, pho13:: TKL1-XKS1, gre3:: RPE1-RKI1 and YLR388.5:: GAL2, rDNA::XI (SEQ ID NO: 78) |

5.13 Example 12: Fermentation Performance of Yeast Strain Expressing Different Xylose Isomerases Fermentation performances of two different XI-expressing yeast strains were evaluated using the DasGip fermentation systems (Eppendorf, Inc.). DasGip fermenters allowed close control over agitation, pH, and temperature ensuring consistency of the environment during fermentation. DasGip fermenters were used to test performance of the yeast strains expressing the XI genes on hydrolysate (Hz) (neutralized with magnesium bases) as a primary carbon source. Prior to the start of fermentation strains were subjected to propagation testing consisting of two steps as described below.

Seed 1:

About 1 ml of strain glycerol stock was inoculated into about 100 ml of YP (Yeast extract, Peptone) medium containing about 2% glucose and about 1% xylose in the 250 ml bellco baffled flask (Bellco, Inc.). Strains were cultivated at about 30° C. with about 200 rpm agitation for at least 18 hours until at full saturation. Optical density was assessed by measuring light absorbance at wavelength of 600 nm.

Seed 2:

About 20 ml of saturated SEED 1 (see preceding paragraph) was inoculated into 3 L Bioflo unit (New Brunswick, Inc.) containing about 2.1 L of basal medium at pH 6.0 (1% v/v inoculation). Cultivation was conducted at about 30° C. in a fed batch mode with constant air flow of about 2 L/min. Agitation ramp (rpm) was about 200-626 rpm over about 15 hours starting at about 5 hours of elapsed fermentation time (EFT). Feeding profile was about 0-4.8 ml/min over 20 hours. The basal medium contained (per 1 L): about 20% of neutralized hydrolysate (Hz); about 20 g/L sucrose (from cane juice); about 35 ml of nutrients mixture (Table 18), about 1 ml of vitamin mixture (Table 19); about 0.4 ml of antifoam 1410 (Dow Corning, Inc.) and water. Feed medium contained (per 1 L): about 20% neutralized hydrolysate (Hz), about 110 g/L sucrose (from cane juice), about 35 ml of nutrient mixture; about 1 ml of vitamin mixture, about 0.4 ml of antifoam 1410 (Dow Corning, Inc.) and water.

TABLE 18

| Nutrients mixture | | |
|---|---|---|
| Component | FW g/mol | Conc. |
| $KH_2PO_4$ $H_2O$ | 154.1 | 99.1 g/L |
| Urea | 60.06 | 65.6 g/L |
| $MgSO_4$—$7H_2O$ | 192.4 | 14.6 g/L |
| DI Water | NA | To 1.0 L |

TABLE 19

| Vitamin mixture (1000x) | |
|---|---|
| Components | mM |
| $ZnSO_4$ | 100 |
| $H_3BO_3$ | 24 |
| KI | 1.8 |
| $MnSO_4$ | 20 |
| $CuSO_4$ | 10 |
| $Na_2MoO_4$ | 1.5 |
| $CoCl_2$ | 1.5 |
| $FeCl_3$ | 1.23 |

Figure 7A:
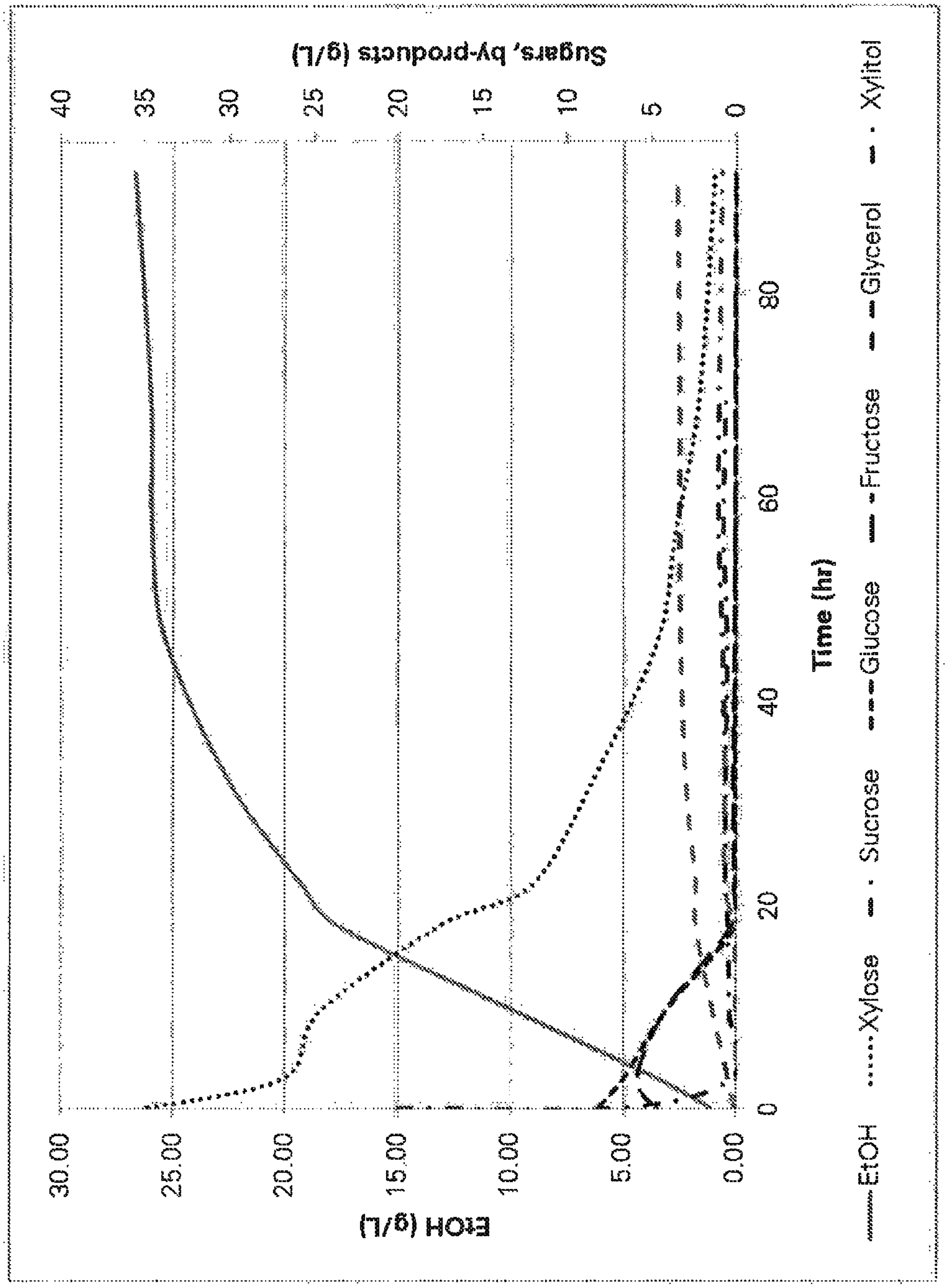
FIGS. 7A-7B show monosaccharide (including xylose) utilization and ethanol production by strains of industrial *S. cerevisiae* with multiple copies of XI clones integrated into ribosomal DNA loci.
Figure 7B:
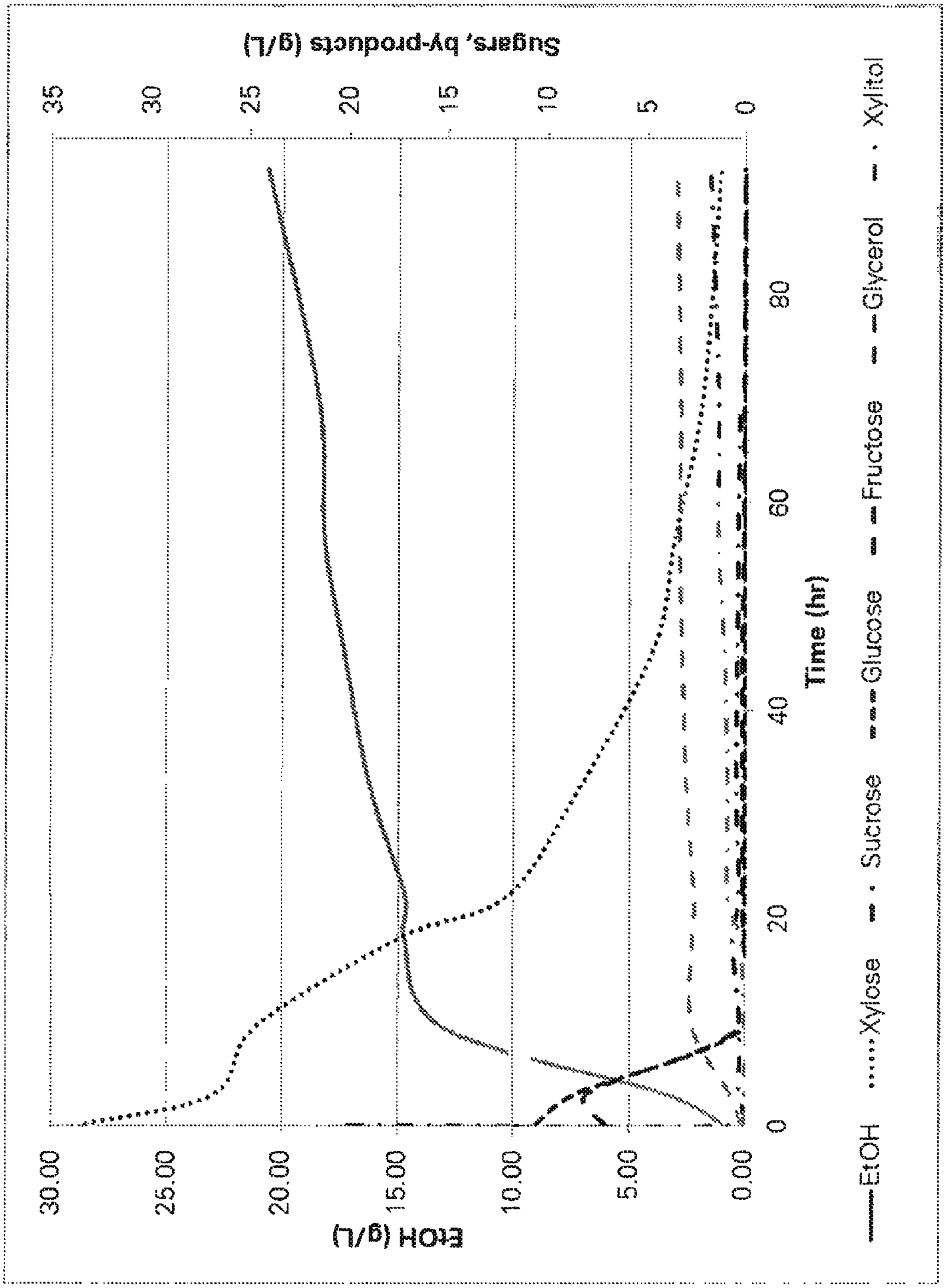

DasGip Fermentation:

Strains were tested in small scale fermentation using the DasGip system in the industrially relevant medium containing detoxified hydrolysate and sucrose. Strains were propagated as described above; DasGip inoculation was performed using the following protocol:

Cell dry weight of SEED 2 was assessed based on the final optical density. Cell dry weight and optical density (600 nm) correlation was used to estimate the volume of the SEED 2 culture needed for fermentation. Targeted inoculation level was about 7% v/v; about 1.5 g/L cell dry weight. Appropriate volume of SEED 2 culture was harvested by centrifugation (about 5000 rpm for 10 min) to pellet the cells and resuspended in about 17.5 ml of PBS. Resuspended cell solution was used to inoculate a 500 ml DasGip unit containing about 250 ml of detoxified hydrolysate and nutrient solution (about 3.5 ml/100 ml of medium). Fermentation was performed at about 32° C. at pH 6.3 with about 200 rpm. The duration of fermentation was about 92 hours with regular sampling. Sampling was conducted by a 25 ml steriological pipette through the port in the head plate of the DasGip unit. About 3 ml of culture were taken out, harvested by centrifugation (about 5000 rpm for 10 min) to pellet the cells and the supernatant was submitted for analysis. Standard analytical techniques such as high-pressure liquid chromatography (HPLC) were used to determine concentration of sugars and ethanol in the medium. Fermentation performances for yeast strains BD31378 (expressing a xylose isomerase of SEQ ID NO:96) and BD31365 (expressing a xylose isomerase of SEQ ID NO:78) are presented in FIG. 7A and FIG. 7B, respectively.

While various specific embodiments have been illustrated and described, it will be appreciated that various changes can be made without departing from the spirit and scope of the invention(s).

What is claimed is:

1. An isolated nucleic acid sequence which encodes a polypeptide comprising an amino acid sequence having at least 95%, 97% or 98% sequence identity to amino acid residues 2-377 of SEQ ID NO:96, wherein the nucleic acid encodes a polypeptide with at least one substitution relative to SEQ ID NO: 96 or at least one heterologous amino acid flanking the N-terminal or the C-terminal.

2. An isolated nucleic acid sequence having at least 90%, 93%, 95%, 96%, 98%, or 99% sequence identity, or having 100% sequence identity, to the nucleotide sequence of SEQ ID NO: 95, or to a portion thereof and encoding a xylose isomerase catalytic or dimerization domain, wherein the nucleic acid comprises at least one substitution relative to SEQ ID NO: 95 or is codon optimized.

3. A vector comprising the nucleic acid sequence of claim 2.

4. The vector of claim 3 which further comprises an origin of replication.

5. The vector of claim 3, which further comprises a promoter sequence operably linked to said nucleic acid sequence.

6. The vector of claim 5, wherein the promoter sequence is operable in yeast.

7. The vector of claim 5, wherein the promoter sequence is operable in filamentous fungi.

8. The nucleic acid sequence of claim 1 or 2, further comprising the amino acid sequence of (a) SEQ ID NO:21.2 or SEQ ID NO:213 and/or (b) SEQ ID NO:214.

9. The nucleic acid sequence of claim 8, wherein the encoded polypeptide comprises an amino acid sequence having at least 95%, 97% or 98% sequence identity to amino acids 2-377 of SEQ ID NO:96.

10. The nucleic acid sequence of claim 8 or 9, wherein the encoded polypeptide comprises an amino acid sequence having at least 95%, 97% or 98% sequence identity to SEQ ID NO:96.

11. A host cell transformed with the vector of claim 3.

12. The host cell of claim 11 which is a prokaryotic cell.

13. The host cell of claim 12 which is a bacterial cell.

14. The host cell of claim 11 which is a eukaryotic cell.

15. A recombinant cell engineered to express the polypeptide encoded by the nucleic acid sequence of any one of claims 1, 2, 8, 9 or 10.

16. The recombinant cell of claim 15 which is a eukaryotic cell.

17. The recombinant cell of claim 15 which is a yeast cell.

18. The recombinant cell of claim 17 which is a yeast cell of the genus *Saccharomyces, Kluyveromyces, Candida, Pichia, Schizosaccharomyces, Hansenula, Klockera, Schwanniomyces, Issatchenkia* or *Yarrowia.*

19. The recombinant cell of claim 18, wherein the yeast cell is of the species *S. cerevisiae, S. bulderi, S. barnetti, S. exiguus, S. uvarum, S. diastaticus, K. lactis, K. marxianus* or *K. fragili*, or *Issatchenkia orientalis.*

20. The recombinant cell of claim 19, which is a *S. cerevisiae* cell.

21. The recombinant cell of claim 20, comprising one or more genetic modifications resulting in at least one of the following phenotypes:

(a) an increase in transport of xylose into the cell;

(b) an increase in xylulose kinase activity;

(c) an increase in aerobic growth rate on xylose;

(d) an increase in flux through the pentose phosphate pathway into glycolysis;

(e) a decrease in aldose reductase activity;

(f) a decrease in sensitivity to catabolite repression;

(g) an increase in tolerance to ethanol, intermediates, osmolarity or organic acids; and (h) a reduced production of byproducts.

22. The recombinant cell of claim 21, wherein one or more genetic modifications result in increased expression levels of one or more of a hexose or pentose transporter, a xylulose kinase, an enzyme from the pentose phosphate pathway, a glycolytic enzyme and an ethanologenic enzyme.

23. The recombinant cell of claim 22, wherein the increased expression levels are achieved by overexpressing an endogenous gene or expressing a heterologous gene in the recombinant cell.

24. The recombinant cell of claim 21, wherein one or more genetic modifications result in decreased expression levels of one or more of a hexose kinase gene, the MIGI gene, and the MIG2 genes.

25. The recombinant cell of claim 21 which is engineered to express the xylose reductase (XR), xylose kinase (XK) and xylitol dehydrogenase (XD) pathway.

26. The recombinant cell of claim 17 in which the nucleic acid is operably linked to a promoter that is insensitive to catabolite repression.

27. The recombinant cell of claim 26 in which the promoter is the TDH3 promoter, the PGK1 promoter, the TEF1 promoter, or the ADH1 promoter.

28. The recombinant cell of claim 15 which is a filamentous fungal cell.

29. The recombinant cell of claim 28, wherein the filamentous fungal cell is of the genus *Aspergillus, Penicillium, Rhizopus, Chrysosporium, Myceliophthora, Trichoderma, Humicola, Acremonium* or *Fusarium.*

30. The recombinant cell of claim 28, wherein the filamentous fungal cell is of the species *Aspergillus niger, Aspergillus oryzae, Trichoderma reesei, Penicillium chrysogenum, Myceliophthora thermophila*, or *Rhizopus oryzae.*

31. A method for producing a fermentation product, comprising culturing the recombinant cell of claim 15 in medium containing xylose under conditions in which the fermentation product is expressed.

32. The method of claim 31, wherein the xylose in the medium is provided by lignocellulosic hydrolysate.

33. The method of claim 31 or claim 32, wherein the fermentation product is ethanol.

34. The method of claim 31 or claim 32, wherein the fermentation product is butanol, diesel, lactic acid, 3-hydroxy-propionic acid, acrylic acid, acetic acid, succinic acid, citric acid, malic acid, fumaric acid, itaconic acid, an amino acid, 1,3-propane-diol, ethylene, glycerol, a β-lactam antibiotic or a cephalosporin.

35. The method of claim 34, wherein the recombinant cell comprises a genetic modification that results in decreased alcohol dehydrogenase activity.

36. The method of claim 34 or claim 35, wherein the recombinant cell expresses one or more enzymes that confers on the cell the ability to produce said fermentation product.

37. The method of any one of claims 31 to 36, wherein the medium further comprises glucose.

38. The method of any One of claims 31 to 36, wherein the recombinant cell is cultured under anaerobic conditions.

39. The method of any one of claims 31 to 38, further comprising recovering the fermentation product.

* * * * *